(12) United States Patent
West et al.

(10) Patent No.: US 10,745,481 B2
(45) Date of Patent: Aug. 18, 2020

(54) ANTI-CD166 ANTIBODIES, ACTIVATABLE ANTI-CD166 ANTIBODIES, AND METHODS OF USE THEREOF

(71) Applicant: CytomX Therapeutics, Inc., South San Francisco, CA (US)

(72) Inventors: James William West, Bend, OR (US); Jason Gary Sagert, San Mateo, CA (US); Jonathan Alexander Terrett, Cupertino, CA (US); Annie Yang Weaver, San Mateo, CA (US); Luc Roland Desnoyers, San Francisco, CA (US); Shweta Singh, Fremont, CA (US)

(73) Assignee: CytomX Therapeutics, Inc., South San Francisco, CA (US)

( * ) Notice: Subject to any disclaimer, the term of this patent is extended or adjusted under 35 U.S.C. 154(b) by 149 days.

(21) Appl. No.: 15/146,603

(22) Filed: May 4, 2016

(65) Prior Publication Data
US 2016/0355587 A1 Dec. 8, 2016

Related U.S. Application Data

(60) Provisional application No. 62/220,805, filed on Sep. 18, 2015, provisional application No. 62/156,835, filed on May 4, 2015.

(51) Int. Cl.
| | | |
|---|---|---|
| *C07K 16/28* | (2006.01) |
| *A61K 31/537* | (2006.01) |
| *A61K 39/00* | (2006.01) |
| *A61K 47/68* | (2017.01) |

(52) U.S. Cl.
CPC ........ *C07K 16/2803* (2013.01); *A61K 31/537* (2013.01); *A61K 47/6873* (2017.08); *A61K 2039/505* (2013.01); *C07K 2317/24* (2013.01); *C07K 2317/73* (2013.01); *C07K 2317/732* (2013.01); *C07K 2317/76* (2013.01); *C07K 2317/92* (2013.01); *C07K 2319/50* (2013.01); *C07K 2319/55* (2013.01)

(58) Field of Classification Search
CPC ...................... A61K 2039/505; C07K 2317/24
See application file for complete search history.

(56) References Cited

U.S. PATENT DOCUMENTS

| | | | |
|---|---|---|---|
| 3,773,919 A | 11/1973 | Boswell et al. |
| 4,485,045 A | 11/1984 | Regen |
| 4,522,811 A | 6/1985 | Eppstein et al. |
| 4,544,545 A | 10/1985 | Ryan et al. |
| 5,013,556 A | 5/1991 | Woodle et al. |
| 5,030,719 A | 7/1991 | Umemoto et al. |
| 5,151,510 A | 9/1992 | Stec et al. |
| 5,998,172 A | 12/1999 | Haynes et al. |
| 6,022,540 A | 2/2000 | Bruder et al. |
| 7,465,790 B2 | 12/2008 | Waldmann et al. |
| 7,582,441 B1 | 9/2009 | Ruben et al. |
| 7,666,817 B2 | 2/2010 | Daugherty et al. |
| 8,003,762 B2 | 8/2011 | Tsukamoto |
| 8,513,390 B2 | 8/2013 | Stagliano et al. |
| 8,518,404 B2 | 8/2013 | Daugherty et al. |
| 8,529,898 B2 | 9/2013 | Daugherty et al. |
| 8,541,203 B2 | 9/2013 | Daugherty et al. |
| 8,563,269 B2 | 10/2013 | Stagliano et al. |
| 8,765,133 B2 | 7/2014 | Tsukamoto |
| 8,809,504 B2 | 8/2014 | Lauermann |
| 9,090,629 B2 | 7/2015 | Chari et al. |
| 9,150,649 B2 | 10/2015 | Singh et al. |
| 9,169,321 B2 | 10/2015 | Daugherty et al. |
| 9,453,078 B2 | 9/2016 | Stagliano et al. |
| 9,593,162 B2 | 3/2017 | Liu et al. |
| 2004/0048319 A1 | 3/2004 | Mather et al. |
| 2004/0109855 A1 | 6/2004 | Waldmann et al. |
| 2009/0070890 A1 | 3/2009 | Stassar et al. |
| 2009/0203538 A1 | 8/2009 | Sugioka et al. |
| 2009/0304719 A1 | 12/2009 | Daugherty et al. |
| 2010/0189651 A1 | 7/2010 | Stagliano et al. |
| 2010/0233165 A1* | 9/2010 | Liu .................... A61K 51/1072 424/133.1 |
| 2012/0149061 A1 | 6/2012 | Stagliano et al. |
| 2012/0207756 A1 | 8/2012 | Stagliano et al. |
| 2012/0237512 A1 | 9/2012 | Daugherty et al. |
| 2012/0237977 A1 | 9/2012 | Daugherty et al. |
| 2012/0244154 A1 | 9/2012 | Daugherty et al. |
| 2013/0309230 A1 | 11/2013 | Stagliano et al. |
| 2014/0024810 A1 | 1/2014 | Stagliano et al. |
| 2014/0045195 A1 | 2/2014 | Daugherty et al. |

(Continued)

FOREIGN PATENT DOCUMENTS

| | | | |
|---|---|---|---|
| EP | 1 523 503 B1 | 4/2009 |
| EP | 1 324 771 B1 | 6/2011 |

(Continued)

OTHER PUBLICATIONS

Carter et al (Xenotransplantation, 1999, vol. 6, pp. 123-130) (Year: 1999).*
Chari et al (Angew. Chem. Int. Ed., 2014, vol. 53, pp. 3796-3827) (Year: 2014).*
Zhao et al (Clinical Cancer Research, 2004, vol. 10, pp. 7994-8004) (Year: 2004).*
Jackman et al (European Journal of Cancer, 1999, vol. 35, Suppl. 1, pp. S3-S8). (Year: 1999).*
Irving, "Probodies Empower a New Generation of Antibody Immunotherapies," presented at Keystone Symposia on Molecular and Cellular Biology, Feb. 2015.

(Continued)

*Primary Examiner* — Karen A. Canella
(74) *Attorney, Agent, or Firm* — Cooley LLP; Ivor Elrifi; Cynthia Kozakiewicz

(57) ABSTRACT

The invention relates generally to antibodies that bind CD166, activatable antibodies that specifically bind to CD166 and methods of making and using these anti-CD166 antibodies and anti-CD166 activatable antibodies in a variety of therapeutic, diagnostic and prophylactic indications.

88 Claims, 26 Drawing Sheets
Specification includes a Sequence Listing.

(56) References Cited

U.S. PATENT DOCUMENTS

| | | |
|---|---|---|
| 2015/0071937 A1 | 3/2015 | Liu et al. |
| 2016/0122425 A1 | 5/2016 | Daugherty et al. |
| 2016/0228546 A1 | 8/2016 | Stagliano et al. |
| 2017/0081397 A1 | 3/2017 | Stagliano et al. |
| 2017/0233488 A1 | 8/2017 | Liu et al. |
| 2017/0362331 A1 | 12/2017 | Lin |
| 2018/0207269 A1 | 7/2018 | Suciu-Foca et al. |
| 2018/0320137 A1 | 11/2018 | Valamehr et al. |
| 2019/0117789 A1 | 4/2019 | Carman et al. |

FOREIGN PATENT DOCUMENTS

| | | |
|---|---|---|
| EP | 1 930 346 B1 | 10/2011 |
| EP | 1 956 032 B1 | 7/2015 |
| EP | 3 325 006 A1 | 5/2018 |
| EP | 3 371 301 A1 | 9/2018 |
| JP | 2009-055899 A | 3/2009 |
| WO | WO 94/11026 A2 | 5/1994 |
| WO | WO 2001/91798 A2 | 12/2001 |
| WO | WO 2002/30460 A2 | 4/2002 |
| WO | WO 2004/009638 A1 | 1/2004 |
| WO | WO 2007/105027 A1 | 9/2007 |
| WO | WO 2008/117049 A1 | 10/2008 |
| WO | WO 2009/025846 A2 | 2/2009 |
| WO | WO 2009/039192 A2 | 3/2009 |
| WO | WO 2009/103113 A1 | 8/2009 |
| WO | WO 2010/081173 A2 | 7/2010 |
| WO | WO 2010/119704 A1 | 10/2010 |
| WO | WO 2010/129609 A2 | 11/2010 |
| WO | WO 2012/155021 A1 | 11/2012 |
| WO | WO 2013/192546 A1 | 12/2013 |
| WO | WO 2014/026136 A2 | 2/2014 |
| WO | WO 2014/107599 A2 | 7/2014 |
| WO | WO 2014/197612 A1 | 12/2014 |
| WO | WO 2017/015227 A1 | 1/2017 |
| WO | WO 2017/078807 A9 | 5/2017 |
| WO | WO 2018/067991 A1 | 4/2018 |
| WO | WO 2018/071058 A1 | 4/2018 |

OTHER PUBLICATIONS

Ke, H. et al., "Derivation, characteriazation, and gene modification of cynomolgus monkey mesenchymal stem cells," Differentiation, 77(3):256-262 (2009).

Erster, O. et al. (2012) "Site-specific targeting of antibody activity in vivo mediated by disease-associated proteases" *J Control Release*, 161(3):804-812.

Piazza, T. et al. (2005) "Internalization and recycling of ALCAM/CD166 detected by a fully human single-chain recombinant antibody" *J Cell Sci*, 118(7):1515-1525.

Polu, K.R. et al. (2014) "Probody therapeutics for targeting antibodies to diseased tissue" *Expert Opin Biol Ther*, 14(8): 1049-1053.

Strassberger, V. et al. (2014 Jan 30) "A comprehensive surface proteome analysis of myeloid leukemia cell lines for therapeutic antibody development" *J Proteomics*, 99:138-151.

Weaver, A.Y. et al. (Dec. 1, 2015) "Abstract C165: Development of a probody drug conjugate (PDC) against CD166 for the treatment of multiple cancers" *Mol Cancer Ther*, 14(12 Supp 2):Abstract nr C165, 4 pages.

Weaver, A.Y. et al. (Nov. 4, 2015) "Development of a Probody™ Drug Conjugate (PDC) Targeting CD166 for the Treatment of Multiple Cancers" CytomX Thereapeutics, Inc. poster [online]. Retrieved from the Internet: URL:http://cytomx.com/wp-content/uploads/2015/11/20151104_CD166_AACR_NCI_EORTC_poster_TO_PRINT_FINAL.pdf [retrieved on Jul. 26, 2016].

Wiiger, M.T. et al. (Jul. 16, 2010) "A novel human recombinant single-chain antibody targeting CD166/ALCAM inhibits cancer cell invasion in vitro and in vivo tumour growth" *Cancer Immunol Immunother*, 59(11):1665-1674.

Cytomx Therapeutics (Jun. 28, 2017) "CytomX Announces the First Patient Treated in Phase 1/2 PROCLAIM-CX-2009 Trial" *GLOBE NEWSWIRE* [online]. Retrieved from the Internet: URL:https://globenewswire.com/news-release/2017/06/28/1029952/0/en/CytomX-Announces-the-First-Patient-Treated-in-Phase-1-2-PROCLAIM-CX-2009-Trial.html [retrieved on Nov. 16, 2018] (3 printed pages).

Cytomx Therapeutics (May 11, 2017) "PROCLAIM-CX-2009: A Trial to Find Safe and Active Doses of an Investigational Drug CX-2009 for Patients With Selected Solid Tumors" www.clinicaltrials.gov[online]. Retrieved from the Internet: URL:https://clinicaltrials.gov/ct2/show/NCT03149549 [retrieved on Nov. 16, 2018] (6 printed pages).

Pauthner, M. et al. (Feb. 24, 2016) Antibody Engineering & Therapeutics. The Annual Meeting of the Antibody Society, Dec. 7-10, 2015, San Diego, CA, USA. *MABS*, 8(3):617-652.

\* cited by examiner

Normal colon

Colon cancer

Normal lung

Lung cancer

FIGURE 8A FIGURE 8B
Normal stomach
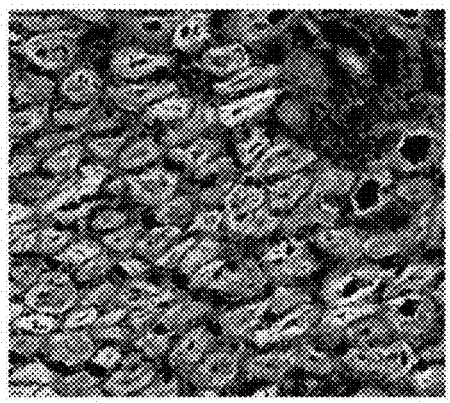 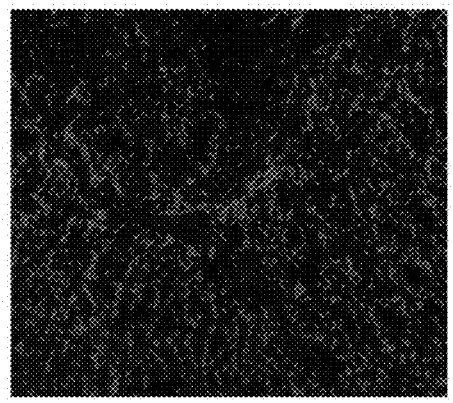
FIGURE 8C FIGURE 8D
Normal bladder
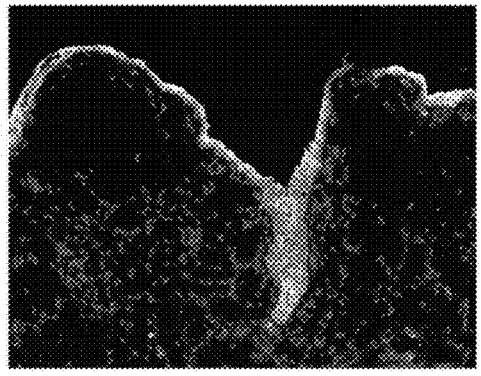 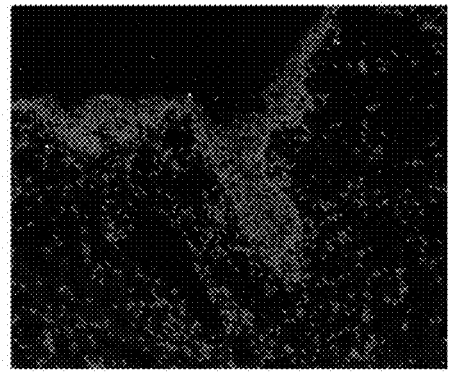

CD166 AADC Beats Benchmark Standard For Efficacy

ELISA – Cyno and human binding are identical

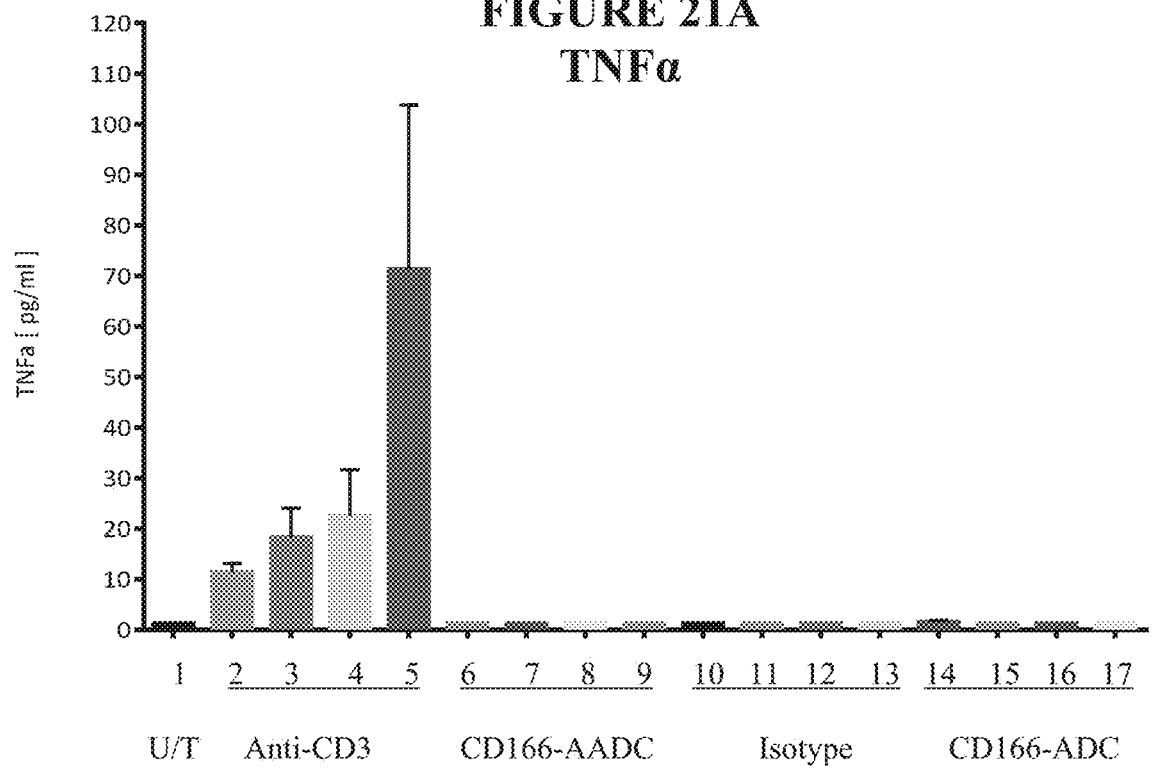
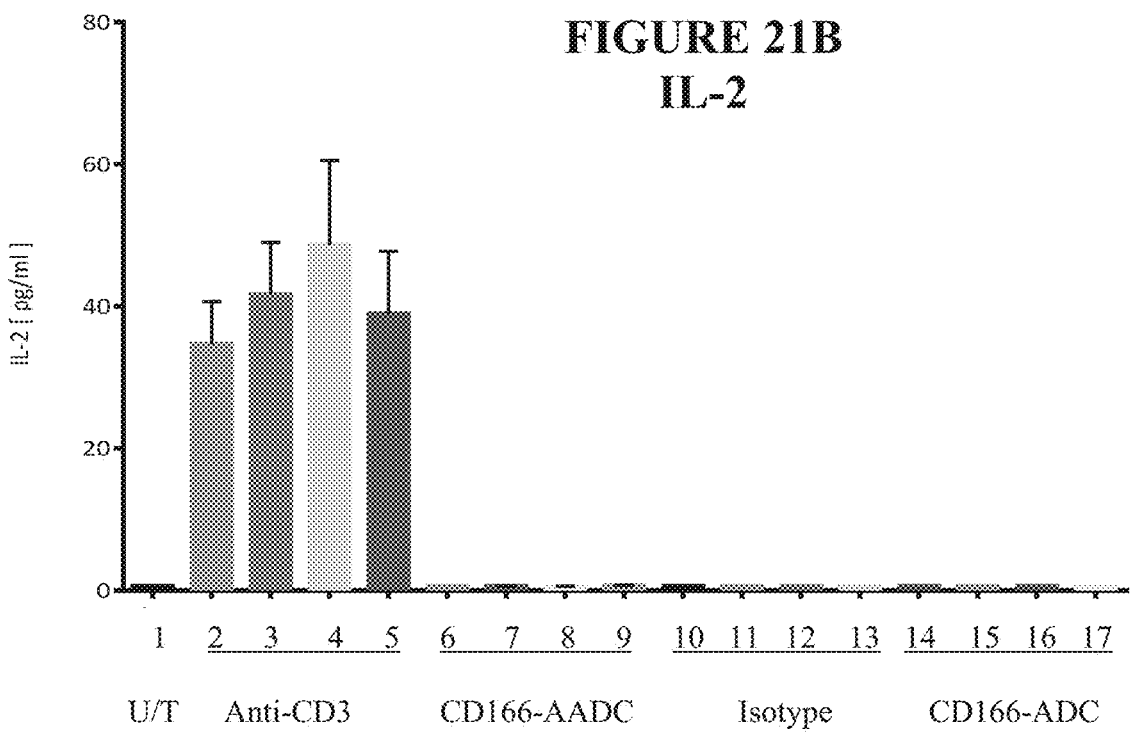

IFNγ

IL-6

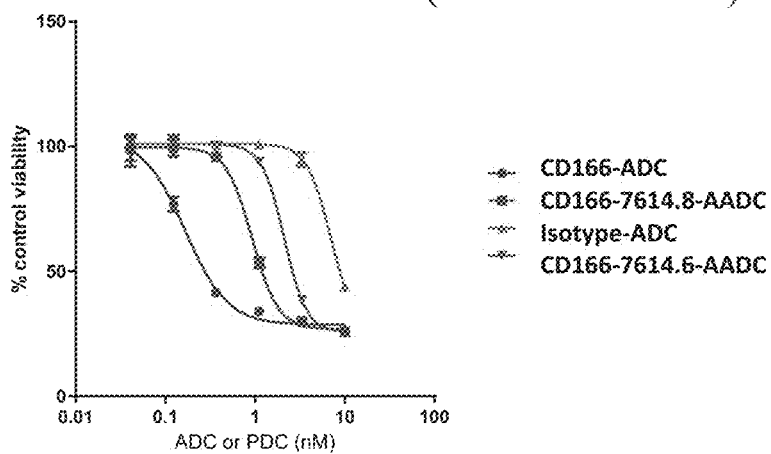
FIGURE 24A (HEC-1-A cells)
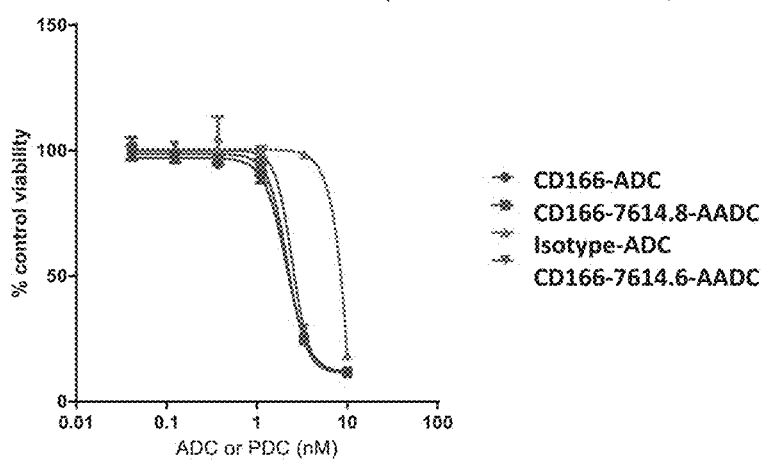
FIGURE 24B (AN3-CA cells)
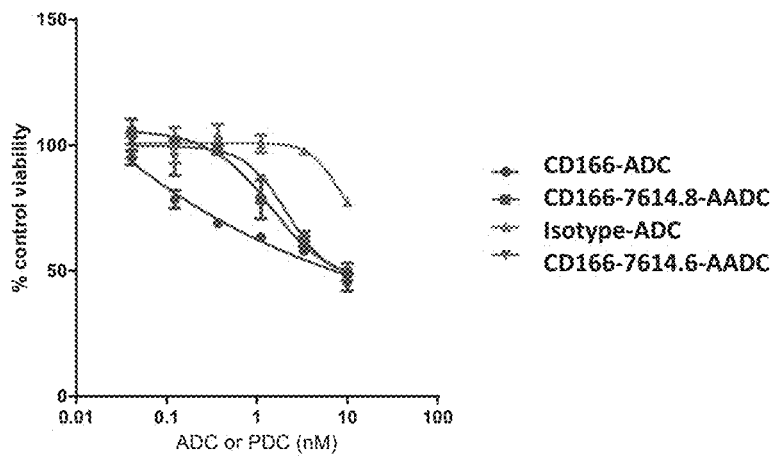
FIGURE 24C (KLE cells)

SEQUENCE LISTING

<160> NUMBER OF SEQ ID NOS: 483

<210> SEQ ID NO 1
<211> LENGTH: 5
<212> TYPE: PRT
<213> ORGANISM: Artificial Sequence
<220> FEATURE:
<223> OTHER INFORMATION: chemically synthesized

<400> SEQUENCE: 1

Gly Ser Gly Gly Ser
1               5

<210> SEQ ID NO 2
<211> LENGTH: 4
<212> TYPE: PRT
<213> ORGANISM: Artificial Sequence
<220> FEATURE:
<223> OTHER INFORMATION: chemically synthesized

<400> SEQUENCE: 2

Gly Gly Gly Ser
1

<210> SEQ ID NO 3
<211> LENGTH: 4
<212> TYPE: PRT
<213> ORGANISM: Artificial Sequence
<220> FEATURE:
<223> OTHER INFORMATION: chemically synthesized

<400> SEQUENCE: 3

Gly Gly Ser Gly
1

<210> SEQ ID NO 4
<211> LENGTH: 5
<212> TYPE: PRT
<213> ORGANISM: Artificial Sequence
<220> FEATURE:
<223> OTHER INFORMATION: chemically synthesized

<400> SEQUENCE: 4

Gly Gly Ser Gly Gly
1               5

<210> SEQ ID NO 5
<211> LENGTH: 5
<212> TYPE: PRT
<213> ORGANISM: Artificial Sequence
<220> FEATURE:
<223> OTHER INFORMATION: chemically synthesized

<400> SEQUENCE: 5

Gly Ser Gly Ser Gly
1               5

<210> SEQ ID NO 6
<211> LENGTH: 5
<212> TYPE: PRT
<213> ORGANISM: Artificial Sequence
<220> FEATURE:
<223> OTHER INFORMATION: chemically synthesized

<400> SEQUENCE: 6

Gly Ser Gly Gly Gly
1               5

```
<210> SEQ ID NO 7
<211> LENGTH: 5
<212> TYPE: PRT
<213> ORGANISM: Artificial Sequence
<220> FEATURE:
<223> OTHER INFORMATION: chemically synthesized

<400> SEQUENCE: 7

Gly Gly Gly Ser Gly
1               5

<210> SEQ ID NO 8
<211> LENGTH: 5
<212> TYPE: PRT
<213> ORGANISM: Artificial Sequence
<220> FEATURE:
<223> OTHER INFORMATION: chemically synthesized

<400> SEQUENCE: 8

Gly Ser Ser Ser Gly
1               5

<210> SEQ ID NO 9
<211> LENGTH: 13
<212> TYPE: PRT
<213> ORGANISM: Artificial Sequence
<220> FEATURE:
<223> OTHER INFORMATION: chemically synthesized

<400> SEQUENCE: 9

Gly Ser Ser Gly Gly Ser Gly Gly Ser Gly Gly Ser Gly
1               5                   10

<210> SEQ ID NO 10
<211> LENGTH: 11
<212> TYPE: PRT
<213> ORGANISM: Artificial Sequence
<220> FEATURE:
<223> OTHER INFORMATION: chemically synthesized

<400> SEQUENCE: 10

Gly Ser Ser Gly Gly Ser Gly Gly Ser Gly Gly
1               5                   10

<210> SEQ ID NO 11
<211> LENGTH: 12
<212> TYPE: PRT
<213> ORGANISM: Artificial Sequence
<220> FEATURE:
<223> OTHER INFORMATION: chemically synthesized

<400> SEQUENCE: 11

Gly Ser Ser Gly Gly Ser Gly Gly Ser Gly Gly Ser
1               5                   10

<210> SEQ ID NO 12
<211> LENGTH: 16
<212> TYPE: PRT
<213> ORGANISM: Artificial Sequence
<220> FEATURE:
<223> OTHER INFORMATION: chemically synthesized

<400> SEQUENCE: 12

Gly Ser Ser Gly Gly Ser Gly Gly Ser Gly Gly Ser Gly Gly Gly Ser
1               5                   10                  15
```

```
<210> SEQ ID NO 13
<211> LENGTH: 10
<212> TYPE: PRT
<213> ORGANISM: Artificial Sequence
<220> FEATURE:
<223> OTHER INFORMATION: chemically synthesized

<400> SEQUENCE: 13

Gly Ser Ser Gly Gly Ser Gly Gly Ser Gly
1               5                   10

<210> SEQ ID NO 14
<211> LENGTH: 11
<212> TYPE: PRT
<213> ORGANISM: Artificial Sequence
<220> FEATURE:
<223> OTHER INFORMATION: chemically synthesized

<400> SEQUENCE: 14

Gly Ser Ser Gly Gly Ser Gly Gly Ser Gly Ser
1               5                   10

<210> SEQ ID NO 15
<211> LENGTH: 4
<212> TYPE: PRT
<213> ORGANISM: Artificial Sequence
<220> FEATURE:
<223> OTHER INFORMATION: chemically synthesized

<400> SEQUENCE: 15

Gly Gly Gly Ser
1

<210> SEQ ID NO 16
<211> LENGTH: 5
<212> TYPE: PRT
<213> ORGANISM: Artificial Sequence
<220> FEATURE:
<223> OTHER INFORMATION: chemically synthesized

<400> SEQUENCE: 16

Gly Ser Ser Gly Thr
1               5

<210> SEQ ID NO 17
<211> LENGTH: 4
<212> TYPE: PRT
<213> ORGANISM: Artificial Sequence
<220> FEATURE:
<223> OTHER INFORMATION: chemically synthesized

<400> SEQUENCE: 17

Gly Ser Ser Gly
1

<210> SEQ ID NO 18
<211> LENGTH: 8
<212> TYPE: PRT
<213> ORGANISM: Artificial Sequence
<220> FEATURE:
<223> OTHER INFORMATION: chemically synthesized

<400> SEQUENCE: 18

Thr Gly Arg Gly Pro Ser Trp Val
1               5
```

```
<210> SEQ ID NO 19
<211> LENGTH: 8
<212> TYPE: PRT
<213> ORGANISM: Artificial Sequence
<220> FEATURE:
<223> OTHER INFORMATION: chemically synthesized

<400> SEQUENCE: 19

Ser Ala Arg Gly Pro Ser Arg Trp
1               5

<210> SEQ ID NO 20
<211> LENGTH: 8
<212> TYPE: PRT
<213> ORGANISM: Artificial Sequence
<220> FEATURE:
<223> OTHER INFORMATION: chemically synthesized

<400> SEQUENCE: 20

Thr Ala Arg Gly Pro Ser Phe Lys
1               5

<210> SEQ ID NO 21
<211> LENGTH: 8
<212> TYPE: PRT
<213> ORGANISM: Artificial Sequence
<220> FEATURE:
<223> OTHER INFORMATION: chemically synthesized

<400> SEQUENCE: 21

Leu Ser Gly Arg Ser Asp Asn His
1               5

<210> SEQ ID NO 22
<211> LENGTH: 8
<212> TYPE: PRT
<213> ORGANISM: Artificial Sequence
<220> FEATURE:
<223> OTHER INFORMATION: chemically synthesized

<400> SEQUENCE: 22

Gly Gly Trp His Thr Gly Arg Asn
1               5

<210> SEQ ID NO 23
<211> LENGTH: 8
<212> TYPE: PRT
<213> ORGANISM: Artificial Sequence
<220> FEATURE:
<223> OTHER INFORMATION: chemically synthesized

<400> SEQUENCE: 23

His Thr Gly Arg Ser Gly Ala Leu
1               5

<210> SEQ ID NO 24
<211> LENGTH: 8
<212> TYPE: PRT
<213> ORGANISM: Artificial Sequence
<220> FEATURE:
<223> OTHER INFORMATION: chemically synthesized

<400> SEQUENCE: 24

Pro Leu Thr Gly Arg Ser Gly Gly
1               5

<210> SEQ ID NO 25
```

```
<211> LENGTH: 8
<212> TYPE: PRT
<213> ORGANISM: Artificial Sequence
<220> FEATURE:
<223> OTHER INFORMATION: chemically synthesized

<400> SEQUENCE: 25

Ala Ala Arg Gly Pro Ala Ile His
1               5

<210> SEQ ID NO 26
<211> LENGTH: 8
<212> TYPE: PRT
<213> ORGANISM: Artificial Sequence
<220> FEATURE:
<223> OTHER INFORMATION: chemically synthesized

<400> SEQUENCE: 26

Arg Gly Pro Ala Phe Asn Pro Met
1               5

<210> SEQ ID NO 27
<211> LENGTH: 8
<212> TYPE: PRT
<213> ORGANISM: Artificial Sequence
<220> FEATURE:
<223> OTHER INFORMATION: chemically synthesized

<400> SEQUENCE: 27

Ser Ser Arg Gly Pro Ala Tyr Leu
1               5

<210> SEQ ID NO 28
<211> LENGTH: 8
<212> TYPE: PRT
<213> ORGANISM: Artificial Sequence
<220> FEATURE:
<223> OTHER INFORMATION: chemically synthesized

<400> SEQUENCE: 28

Arg Gly Pro Ala Thr Pro Ile Met
1               5

<210> SEQ ID NO 29
<211> LENGTH: 4
<212> TYPE: PRT
<213> ORGANISM: Artificial Sequence
<220> FEATURE:
<223> OTHER INFORMATION: chemically synthesized

<400> SEQUENCE: 29

Arg Gly Pro Ala
1

<210> SEQ ID NO 30
<211> LENGTH: 10
<212> TYPE: PRT
<213> ORGANISM: Artificial Sequence
<220> FEATURE:
<223> OTHER INFORMATION: chemically synthesized

<400> SEQUENCE: 30

Gly Gly Gln Pro Ser Gly Met Trp Gly Trp
1               5                   10

<210> SEQ ID NO 31
<211> LENGTH: 10
```

```
<212> TYPE: PRT
<213> ORGANISM: Artificial Sequence
<220> FEATURE:
<223> OTHER INFORMATION: chemically synthesized

<400> SEQUENCE: 31

Phe Pro Arg Pro Leu Gly Ile Thr Gly Leu
1               5                   10

<210> SEQ ID NO 32
<211> LENGTH: 10
<212> TYPE: PRT
<213> ORGANISM: Artificial Sequence
<220> FEATURE:
<223> OTHER INFORMATION: chemically synthesized

<400> SEQUENCE: 32

Val His Met Pro Leu Gly Phe Leu Gly Pro
1               5                   10

<210> SEQ ID NO 33
<211> LENGTH: 8
<212> TYPE: PRT
<213> ORGANISM: Artificial Sequence
<220> FEATURE:
<223> OTHER INFORMATION: chemically synthesized

<400> SEQUENCE: 33

Ser Pro Leu Thr Gly Arg Ser Gly
1               5

<210> SEQ ID NO 34
<211> LENGTH: 8
<212> TYPE: PRT
<213> ORGANISM: Artificial Sequence
<220> FEATURE:
<223> OTHER INFORMATION: chemically synthesized

<400> SEQUENCE: 34

Ser Ala Gly Phe Ser Leu Pro Ala
1               5

<210> SEQ ID NO 35
<211> LENGTH: 9
<212> TYPE: PRT
<213> ORGANISM: Artificial Sequence
<220> FEATURE:
<223> OTHER INFORMATION: chemically synthesized

<400> SEQUENCE: 35

Leu Ala Pro Leu Gly Leu Gln Arg Arg
1               5

<210> SEQ ID NO 36
<211> LENGTH: 8
<212> TYPE: PRT
<213> ORGANISM: Artificial Sequence
<220> FEATURE:
<223> OTHER INFORMATION: chemically synthesized

<400> SEQUENCE: 36

Ser Gly Gly Pro Leu Gly Val Arg
1               5

<210> SEQ ID NO 37
<211> LENGTH: 4
<212> TYPE: PRT
```

```
<213> ORGANISM: Artificial Sequence
<220> FEATURE:
<223> OTHER INFORMATION: chemically synthesized

<400> SEQUENCE: 37

Pro Leu Gly Leu
1

<210> SEQ ID NO 38
<211> LENGTH: 7
<212> TYPE: PRT
<213> ORGANISM: Artificial Sequence
<220> FEATURE:
<223> OTHER INFORMATION: chemically synthesized

<400> SEQUENCE: 38

Ile Ser Ser Gly Leu Ser Ser
1               5

<210> SEQ ID NO 39
<211> LENGTH: 8
<212> TYPE: PRT
<213> ORGANISM: Artificial Sequence
<220> FEATURE:
<223> OTHER INFORMATION: chemically synthesized

<400> SEQUENCE: 39

Gln Asn Gln Ala Leu Arg Met Ala
1               5

<210> SEQ ID NO 40
<211> LENGTH: 8
<212> TYPE: PRT
<213> ORGANISM: Artificial Sequence
<220> FEATURE:
<223> OTHER INFORMATION: chemically synthesized

<400> SEQUENCE: 40

Ala Gln Asn Leu Leu Gly Met Val
1               5

<210> SEQ ID NO 41
<211> LENGTH: 8
<212> TYPE: PRT
<213> ORGANISM: Artificial Sequence
<220> FEATURE:
<223> OTHER INFORMATION: chemically synthesized

<400> SEQUENCE: 41

Ser Thr Phe Pro Phe Gly Met Phe
1               5

<210> SEQ ID NO 42
<211> LENGTH: 8
<212> TYPE: PRT
<213> ORGANISM: Artificial Sequence
<220> FEATURE:
<223> OTHER INFORMATION: chemically synthesized

<400> SEQUENCE: 42

Pro Val Gly Tyr Thr Ser Ser Leu
1               5

<210> SEQ ID NO 43
<211> LENGTH: 8
<212> TYPE: PRT
<213> ORGANISM: Artificial Sequence
```

```
<220> FEATURE:
<223> OTHER INFORMATION: chemically synthesized

<400> SEQUENCE: 43

Asp Trp Leu Tyr Trp Pro Gly Ile
1               5

<210> SEQ ID NO 44
<211> LENGTH: 8
<212> TYPE: PRT
<213> ORGANISM: Artificial Sequence
<220> FEATURE:
<223> OTHER INFORMATION: chemically synthesized

<400> SEQUENCE: 44

Ile Ser Ser Gly Leu Leu Ser Ser
1               5

<210> SEQ ID NO 45
<211> LENGTH: 8
<212> TYPE: PRT
<213> ORGANISM: Artificial Sequence
<220> FEATURE:
<223> OTHER INFORMATION: chemically synthesized

<400> SEQUENCE: 45

Leu Lys Ala Ala Pro Arg Trp Ala
1               5

<210> SEQ ID NO 46
<211> LENGTH: 8
<212> TYPE: PRT
<213> ORGANISM: Artificial Sequence
<220> FEATURE:
<223> OTHER INFORMATION: chemically synthesized

<400> SEQUENCE: 46

Gly Pro Ser His Leu Val Leu Thr
1               5

<210> SEQ ID NO 47
<211> LENGTH: 8
<212> TYPE: PRT
<213> ORGANISM: Artificial Sequence
<220> FEATURE:
<223> OTHER INFORMATION: chemically synthesized

<400> SEQUENCE: 47

Leu Pro Gly Gly Leu Ser Pro Trp
1               5

<210> SEQ ID NO 48
<211> LENGTH: 8
<212> TYPE: PRT
<213> ORGANISM: Artificial Sequence
<220> FEATURE:
<223> OTHER INFORMATION: chemically synthesized

<400> SEQUENCE: 48

Met Gly Leu Phe Ser Glu Ala Gly
1               5

<210> SEQ ID NO 49
<211> LENGTH: 8
<212> TYPE: PRT
<213> ORGANISM: Artificial Sequence
<220> FEATURE:
```

```
<223> OTHER INFORMATION: chemically synthesized

<400> SEQUENCE: 49

Ser Pro Leu Pro Leu Arg Val Pro
1               5

<210> SEQ ID NO 50
<211> LENGTH: 8
<212> TYPE: PRT
<213> ORGANISM: Artificial Sequence
<220> FEATURE:
<223> OTHER INFORMATION: chemically synthesized

<400> SEQUENCE: 50

Arg Met His Leu Arg Ser Leu Gly
1               5

<210> SEQ ID NO 51
<211> LENGTH: 8
<212> TYPE: PRT
<213> ORGANISM: Artificial Sequence
<220> FEATURE:
<223> OTHER INFORMATION: chemically synthesized

<400> SEQUENCE: 51

Leu Ala Ala Pro Leu Gly Leu Leu
1               5

<210> SEQ ID NO 52
<211> LENGTH: 8
<212> TYPE: PRT
<213> ORGANISM: Artificial Sequence
<220> FEATURE:
<223> OTHER INFORMATION: chemically synthesized

<400> SEQUENCE: 52

Ala Val Gly Leu Leu Ala Pro Pro
1               5

<210> SEQ ID NO 53
<211> LENGTH: 8
<212> TYPE: PRT
<213> ORGANISM: Artificial Sequence
<220> FEATURE:
<223> OTHER INFORMATION: chemically synthesized

<400> SEQUENCE: 53

Leu Leu Ala Pro Ser His Arg Ala
1               5

<210> SEQ ID NO 54
<211> LENGTH: 8
<212> TYPE: PRT
<213> ORGANISM: Artificial Sequence
<220> FEATURE:
<223> OTHER INFORMATION: chemically synthesized

<400> SEQUENCE: 54

Pro Ala Gly Leu Trp Leu Asp Pro
1               5

<210> SEQ ID NO 55
<211> LENGTH: 7
<212> TYPE: PRT
<213> ORGANISM: Artificial Sequence
<220> FEATURE:
<223> OTHER INFORMATION: chemically synthesized
```

<400> SEQUENCE: 55

Gly Pro Arg Ser Phe Gly Leu
1               5

<210> SEQ ID NO 56
<211> LENGTH: 6
<212> TYPE: PRT
<213> ORGANISM: Artificial Sequence
<220> FEATURE:
<223> OTHER INFORMATION: chemically synthesized

<400> SEQUENCE: 56

Gly Pro Arg Ser Phe Gly
1               5

<210> SEQ ID NO 57
<211> LENGTH: 7
<212> TYPE: PRT
<213> ORGANISM: Artificial Sequence
<220> FEATURE:
<223> OTHER INFORMATION: chemically synthesized

<400> SEQUENCE: 57

Gly Pro Arg Ser Phe Gly Leu
1               5

<210> SEQ ID NO 58
<211> LENGTH: 6
<212> TYPE: PRT
<213> ORGANISM: Artificial Sequence
<220> FEATURE:
<223> OTHER INFORMATION: chemically synthesized

<400> SEQUENCE: 58

Gly Pro Arg Ser Phe Gly
1               5

<210> SEQ ID NO 59
<211> LENGTH: 12
<212> TYPE: PRT
<213> ORGANISM: Artificial Sequence
<220> FEATURE:
<223> OTHER INFORMATION: chemically synthesized

<400> SEQUENCE: 59

Asn Thr Leu Ser Gly Arg Ser Glu Asn His Ser Gly
1               5                   10

<210> SEQ ID NO 60
<211> LENGTH: 12
<212> TYPE: PRT
<213> ORGANISM: Artificial Sequence
<220> FEATURE:
<223> OTHER INFORMATION: chemically synthesized

<400> SEQUENCE: 60

Asn Thr Leu Ser Gly Arg Ser Gly Asn His Gly Ser
1               5                   10

<210> SEQ ID NO 61
<211> LENGTH: 12
<212> TYPE: PRT
<213> ORGANISM: Artificial Sequence
<220> FEATURE:
<223> OTHER INFORMATION: chemically synthesized

```
<400> SEQUENCE: 61

Thr Ser Thr Ser Gly Arg Ser Ala Asn Pro Arg Gly
1               5                   10

<210> SEQ ID NO 62
<211> LENGTH: 8
<212> TYPE: PRT
<213> ORGANISM: Artificial Sequence
<220> FEATURE:
<223> OTHER INFORMATION: chemically synthesized

<400> SEQUENCE: 62

Thr Ser Gly Arg Ser Ala Asn Pro
1               5

<210> SEQ ID NO 63
<211> LENGTH: 8
<212> TYPE: PRT
<213> ORGANISM: Artificial Sequence
<220> FEATURE:
<223> OTHER INFORMATION: chemically synthesized

<400> SEQUENCE: 63

Val Ala Gly Arg Ser Met Arg Pro
1               5

<210> SEQ ID NO 64
<211> LENGTH: 8
<212> TYPE: PRT
<213> ORGANISM: Artificial Sequence
<220> FEATURE:
<223> OTHER INFORMATION: chemically synthesized

<400> SEQUENCE: 64

Val Val Pro Glu Gly Arg Arg Ser
1               5

<210> SEQ ID NO 65
<211> LENGTH: 8
<212> TYPE: PRT
<213> ORGANISM: Artificial Sequence
<220> FEATURE:
<223> OTHER INFORMATION: chemically synthesized

<400> SEQUENCE: 65

Ile Leu Pro Arg Ser Pro Ala Phe
1               5

<210> SEQ ID NO 66
<211> LENGTH: 8
<212> TYPE: PRT
<213> ORGANISM: Artificial Sequence
<220> FEATURE:
<223> OTHER INFORMATION: chemically synthesized

<400> SEQUENCE: 66

Met Val Leu Gly Arg Ser Leu Leu
1               5

<210> SEQ ID NO 67
<211> LENGTH: 8
<212> TYPE: PRT
<213> ORGANISM: Artificial Sequence
<220> FEATURE:
<223> OTHER INFORMATION: chemically synthesized

<400> SEQUENCE: 67
```

```
Gln Gly Arg Ala Ile Thr Phe Ile
1               5
```

<210> SEQ ID NO 68
<211> LENGTH: 8
<212> TYPE: PRT
<213> ORGANISM: Artificial Sequence
<220> FEATURE:
<223> OTHER INFORMATION: chemically synthesized

<400> SEQUENCE: 68

```
Ser Pro Arg Ser Ile Met Leu Ala
1               5
```

<210> SEQ ID NO 69
<211> LENGTH: 8
<212> TYPE: PRT
<213> ORGANISM: Artificial Sequence
<220> FEATURE:
<223> OTHER INFORMATION: chemically synthesized

<400> SEQUENCE: 69

```
Ser Met Leu Arg Ser Met Pro Leu
1               5
```

<210> SEQ ID NO 70
<211> LENGTH: 13
<212> TYPE: PRT
<213> ORGANISM: Artificial Sequence
<220> FEATURE:
<223> OTHER INFORMATION: chemically synthesized

<400> SEQUENCE: 70

```
Ile Ser Ser Gly Leu Leu Ser Gly Arg Ser Asp Asn His
1               5                   10
```

<210> SEQ ID NO 71
<211> LENGTH: 22
<212> TYPE: PRT
<213> ORGANISM: Artificial Sequence
<220> FEATURE:
<223> OTHER INFORMATION: chemically synthesized

<400> SEQUENCE: 71

```
Ile Ser Ser Gly Leu Leu Ser Ser Gly Gly Ser Gly Gly Ser Leu Ser
1               5                   10                  15

Gly Arg Ser Asp Asn His
            20
```

<210> SEQ ID NO 72
<211> LENGTH: 22
<212> TYPE: PRT
<213> ORGANISM: Artificial Sequence
<220> FEATURE:
<223> OTHER INFORMATION: chemically synthesized

<400> SEQUENCE: 72

```
Ala Val Gly Leu Leu Ala Pro Pro Gly Gly Thr Ser Thr Ser Gly Arg
1               5                   10                  15

Ser Ala Asn Pro Arg Gly
            20
```

<210> SEQ ID NO 73
<211> LENGTH: 22
<212> TYPE: PRT

```
<213> ORGANISM: Artificial Sequence
<220> FEATURE:
<223> OTHER INFORMATION: chemically synthesized

<400> SEQUENCE: 73

Thr Ser Thr Ser Gly Arg Ser Ala Asn Pro Arg Gly Gly Gly Ala Val
1               5                   10                  15

Gly Leu Leu Ala Pro Pro
            20

<210> SEQ ID NO 74
<211> LENGTH: 24
<212> TYPE: PRT
<213> ORGANISM: Artificial Sequence
<220> FEATURE:
<223> OTHER INFORMATION: chemically synthesized

<400> SEQUENCE: 74

Val His Met Pro Leu Gly Phe Leu Gly Pro Gly Gly Thr Ser Thr Ser
1               5                   10                  15

Gly Arg Ser Ala Asn Pro Arg Gly
            20

<210> SEQ ID NO 75
<211> LENGTH: 24
<212> TYPE: PRT
<213> ORGANISM: Artificial Sequence
<220> FEATURE:
<223> OTHER INFORMATION: chemically synthesized

<400> SEQUENCE: 75

Thr Ser Thr Ser Gly Arg Ser Ala Asn Pro Arg Gly Gly Gly Val His
1               5                   10                  15

Met Pro Leu Gly Phe Leu Gly Pro
            20

<210> SEQ ID NO 76
<211> LENGTH: 18
<212> TYPE: PRT
<213> ORGANISM: Artificial Sequence
<220> FEATURE:
<223> OTHER INFORMATION: chemically synthesized

<400> SEQUENCE: 76

Ala Val Gly Leu Leu Ala Pro Pro Gly Gly Leu Ser Gly Arg Ser Asp
1               5                   10                  15

Asn His

<210> SEQ ID NO 77
<211> LENGTH: 18
<212> TYPE: PRT
<213> ORGANISM: Artificial Sequence
<220> FEATURE:
<223> OTHER INFORMATION: chemically synthesized

<400> SEQUENCE: 77

Leu Ser Gly Arg Ser Asp Asn His Gly Gly Ala Val Gly Leu Leu Ala
1               5                   10                  15

Pro Pro

<210> SEQ ID NO 78
<211> LENGTH: 20
<212> TYPE: PRT
<213> ORGANISM: Artificial Sequence
```

<220> FEATURE:
<223> OTHER INFORMATION: chemically synthesized

<400> SEQUENCE: 78

Val His Met Pro Leu Gly Phe Leu Gly Pro Gly Gly Leu Ser Gly Arg
1               5                   10                  15

Ser Asp Asn His
            20

<210> SEQ ID NO 79
<211> LENGTH: 20
<212> TYPE: PRT
<213> ORGANISM: Artificial Sequence
<220> FEATURE:
<223> OTHER INFORMATION: chemically synthesized

<400> SEQUENCE: 79

Leu Ser Gly Arg Ser Asp Asn His Gly Val His Met Pro Leu Gly
1               5                   10                  15

Phe Leu Gly Pro
            20

<210> SEQ ID NO 80
<211> LENGTH: 22
<212> TYPE: PRT
<213> ORGANISM: Artificial Sequence
<220> FEATURE:
<223> OTHER INFORMATION: chemically synthesized

<400> SEQUENCE: 80

Leu Ser Gly Arg Ser Asp Asn His Gly Gly Ser Gly Gly Ser Ile Ser
1               5                   10                  15

Ser Gly Leu Leu Ser Ser
            20

<210> SEQ ID NO 81
<211> LENGTH: 22
<212> TYPE: PRT
<213> ORGANISM: Artificial Sequence
<220> FEATURE:
<223> OTHER INFORMATION: chemically synthesized

<400> SEQUENCE: 81

Leu Ser Gly Arg Ser Gly Asn His Gly Gly Ser Gly Gly Ser Ile Ser
1               5                   10                  15

Ser Gly Leu Leu Ser Ser
            20

<210> SEQ ID NO 82
<211> LENGTH: 22
<212> TYPE: PRT
<213> ORGANISM: Artificial Sequence
<220> FEATURE:
<223> OTHER INFORMATION: chemically synthesized

<400> SEQUENCE: 82

Ile Ser Ser Gly Leu Leu Ser Ser Gly Gly Ser Gly Gly Ser Leu Ser
1               5                   10                  15

Gly Arg Ser Gly Asn His
            20

<210> SEQ ID NO 83
<211> LENGTH: 22
<212> TYPE: PRT

<213> ORGANISM: Artificial Sequence
<220> FEATURE:
<223> OTHER INFORMATION: chemically synthesized

<400> SEQUENCE: 83

Leu Ser Gly Arg Ser Asp Asn His Gly Gly Ser Gly Gly Ser Gln Asn
1               5                   10                  15

Gln Ala Leu Arg Met Ala
            20

<210> SEQ ID NO 84
<211> LENGTH: 22
<212> TYPE: PRT
<213> ORGANISM: Artificial Sequence
<220> FEATURE:
<223> OTHER INFORMATION: chemically synthesized

<400> SEQUENCE: 84

Gln Asn Gln Ala Leu Arg Met Ala Gly Gly Ser Gly Gly Ser Leu Ser
1               5                   10                  15

Gly Arg Ser Asp Asn His
            20

<210> SEQ ID NO 85
<211> LENGTH: 22
<212> TYPE: PRT
<213> ORGANISM: Artificial Sequence
<220> FEATURE:
<223> OTHER INFORMATION: chemically synthesized

<400> SEQUENCE: 85

Leu Ser Gly Arg Ser Gly Asn His Gly Gly Ser Gly Gly Ser Gln Asn
1               5                   10                  15

Gln Ala Leu Arg Met Ala
            20

<210> SEQ ID NO 86
<211> LENGTH: 22
<212> TYPE: PRT
<213> ORGANISM: Artificial Sequence
<220> FEATURE:
<223> OTHER INFORMATION: chemically synthesized

<400> SEQUENCE: 86

Gln Asn Gln Ala Leu Arg Met Ala Gly Gly Ser Gly Gly Ser Leu Ser
1               5                   10                  15

Gly Arg Ser Gly Asn His
            20

<210> SEQ ID NO 87
<211> LENGTH: 13
<212> TYPE: PRT
<213> ORGANISM: Artificial Sequence
<220> FEATURE:
<223> OTHER INFORMATION: chemically synthesized

<400> SEQUENCE: 87

Ile Ser Ser Gly Leu Leu Ser Gly Arg Ser Gly Asn His
1               5                   10

<210> SEQ ID NO 88
<211> LENGTH: 6
<212> TYPE: PRT
<213> ORGANISM: Artificial Sequence
<220> FEATURE:

<223> OTHER INFORMATION: chemically synthesized

<400> SEQUENCE: 88

Gln Gly Gln Ser Gly Gln
1               5

<210> SEQ ID NO 89
<211> LENGTH: 8
<212> TYPE: PRT
<213> ORGANISM: Artificial Sequence
<220> FEATURE:
<223> OTHER INFORMATION: chemically synthesized

<400> SEQUENCE: 89

Pro Arg Phe Lys Ile Ile Gly Gly
1               5

<210> SEQ ID NO 90
<211> LENGTH: 8
<212> TYPE: PRT
<213> ORGANISM: Artificial Sequence
<220> FEATURE:
<223> OTHER INFORMATION: chemically synthesized

<400> SEQUENCE: 90

Pro Arg Phe Arg Ile Ile Gly Gly
1               5

<210> SEQ ID NO 91
<211> LENGTH: 9
<212> TYPE: PRT
<213> ORGANISM: Artificial Sequence
<220> FEATURE:
<223> OTHER INFORMATION: chemically synthesized

<400> SEQUENCE: 91

Ser Ser Arg His Arg Arg Ala Leu Asp
1               5

<210> SEQ ID NO 92
<211> LENGTH: 14
<212> TYPE: PRT
<213> ORGANISM: Artificial Sequence
<220> FEATURE:
<223> OTHER INFORMATION: chemically synthesized

<400> SEQUENCE: 92

Arg Lys Ser Ser Ile Ile Ile Arg Met Arg Asp Val Val Leu
1               5                   10

<210> SEQ ID NO 93
<211> LENGTH: 15
<212> TYPE: PRT
<213> ORGANISM: Artificial Sequence
<220> FEATURE:
<223> OTHER INFORMATION: chemically synthesized

<400> SEQUENCE: 93

Ser Ser Ser Phe Asp Lys Gly Lys Tyr Lys Lys Gly Asp Asp Ala
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: chemically synthesized

<400> SEQUENCE: 94

Ser Ser Ser Phe Asp Lys Gly Lys Tyr Lys Arg Gly Asp Asp Ala
1               5                   10                  15

<210> SEQ ID NO 95
<211> LENGTH: 4
<212> TYPE: PRT
<213> ORGANISM: Artificial Sequence
<220> FEATURE:
<223> OTHER INFORMATION: chemically synthesized

<400> SEQUENCE: 95

Ile Glu Gly Arg
1

<210> SEQ ID NO 96
<211> LENGTH: 4
<212> TYPE: PRT
<213> ORGANISM: Artificial Sequence
<220> FEATURE:
<223> OTHER INFORMATION: chemically synthesized

<400> SEQUENCE: 96

Ile Asp Gly Arg
1

<210> SEQ ID NO 97
<211> LENGTH: 7
<212> TYPE: PRT
<213> ORGANISM: Artificial Sequence
<220> FEATURE:
<223> OTHER INFORMATION: chemically synthesized

<400> SEQUENCE: 97

Gly Gly Ser Ile Asp Gly Arg
1               5

<210> SEQ ID NO 98
<211> LENGTH: 6
<212> TYPE: PRT
<213> ORGANISM: Artificial Sequence
<220> FEATURE:
<223> OTHER INFORMATION: chemically synthesized

<400> SEQUENCE: 98

Pro Leu Gly Leu Trp Ala
1               5

<210> SEQ ID NO 99
<211> LENGTH: 8
<212> TYPE: PRT
<213> ORGANISM: Artificial Sequence
<220> FEATURE:
<223> OTHER INFORMATION: chemically synthesized

<400> SEQUENCE: 99

Gly Pro Gln Gly Ile Ala Gly Gln
1               5

<210> SEQ ID NO 100
<211> LENGTH: 8
<212> TYPE: PRT
<213> ORGANISM: Artificial Sequence
<220> FEATURE:
<223> OTHER INFORMATION: chemically synthesized

```
<400> SEQUENCE: 100

Gly Pro Gln Gly Leu Leu Gly Ala
1               5

<210> SEQ ID NO 101
<211> LENGTH: 5
<212> TYPE: PRT
<213> ORGANISM: Artificial Sequence
<220> FEATURE:
<223> OTHER INFORMATION: chemically synthesized

<400> SEQUENCE: 101

Gly Ile Ala Gly Gln
1               5

<210> SEQ ID NO 102
<211> LENGTH: 8
<212> TYPE: PRT
<213> ORGANISM: Artificial Sequence
<220> FEATURE:
<223> OTHER INFORMATION: chemically synthesized

<400> SEQUENCE: 102

Gly Pro Leu Gly Ile Ala Gly Ile
1               5

<210> SEQ ID NO 103
<211> LENGTH: 8
<212> TYPE: PRT
<213> ORGANISM: Artificial Sequence
<220> FEATURE:
<223> OTHER INFORMATION: chemically synthesized

<400> SEQUENCE: 103

Gly Pro Glu Gly Leu Arg Val Gly
1               5

<210> SEQ ID NO 104
<211> LENGTH: 8
<212> TYPE: PRT
<213> ORGANISM: Artificial Sequence
<220> FEATURE:
<223> OTHER INFORMATION: chemically synthesized

<400> SEQUENCE: 104

Tyr Gly Ala Gly Leu Gly Val Val
1               5

<210> SEQ ID NO 105
<211> LENGTH: 8
<212> TYPE: PRT
<213> ORGANISM: Artificial Sequence
<220> FEATURE:
<223> OTHER INFORMATION: chemically synthesized

<400> SEQUENCE: 105

Ala Gly Leu Gly Val Val Glu Arg
1               5

<210> SEQ ID NO 106
<211> LENGTH: 8
<212> TYPE: PRT
<213> ORGANISM: Artificial Sequence
<220> FEATURE:
<223> OTHER INFORMATION: chemically synthesized

<400> SEQUENCE: 106
```

Ala Gly Leu Gly Ile Ser Ser Thr
1               5

<210> SEQ ID NO 107
<211> LENGTH: 8
<212> TYPE: PRT
<213> ORGANISM: Artificial Sequence
<220> FEATURE:
<223> OTHER INFORMATION: chemically synthesized

<400> SEQUENCE: 107

Glu Pro Gln Ala Leu Ala Met Ser
1               5

<210> SEQ ID NO 108
<211> LENGTH: 8
<212> TYPE: PRT
<213> ORGANISM: Artificial Sequence
<220> FEATURE:
<223> OTHER INFORMATION: chemically synthesized

<400> SEQUENCE: 108

Gln Ala Leu Ala Met Ser Ala Ile
1               5

<210> SEQ ID NO 109
<211> LENGTH: 8
<212> TYPE: PRT
<213> ORGANISM: Artificial Sequence
<220> FEATURE:
<223> OTHER INFORMATION: chemically synthesized

<400> SEQUENCE: 109

Ala Ala Tyr His Leu Val Ser Gln
1               5

<210> SEQ ID NO 110
<211> LENGTH: 8
<212> TYPE: PRT
<213> ORGANISM: Artificial Sequence
<220> FEATURE:
<223> OTHER INFORMATION: chemically synthesized

<400> SEQUENCE: 110

Met Asp Ala Phe Leu Glu Ser Ser
1               5

<210> SEQ ID NO 111
<211> LENGTH: 8
<212> TYPE: PRT
<213> ORGANISM: Artificial Sequence
<220> FEATURE:
<223> OTHER INFORMATION: chemically synthesized

<400> SEQUENCE: 111

Glu Ser Leu Pro Val Val Ala Val
1               5

<210> SEQ ID NO 112
<211> LENGTH: 8
<212> TYPE: PRT
<213> ORGANISM: Artificial Sequence
<220> FEATURE:
<223> OTHER INFORMATION: chemically synthesized

<400> SEQUENCE: 112

```
Ser Ala Pro Ala Val Glu Ser Glu
1               5

<210> SEQ ID NO 113
<211> LENGTH: 8
<212> TYPE: PRT
<213> ORGANISM: Artificial Sequence
<220> FEATURE:
<223> OTHER INFORMATION: chemically synthesized

<400> SEQUENCE: 113

Asp Val Ala Gln Phe Val Leu Thr
1               5

<210> SEQ ID NO 114
<211> LENGTH: 8
<212> TYPE: PRT
<213> ORGANISM: Artificial Sequence
<220> FEATURE:
<223> OTHER INFORMATION: chemically synthesized

<400> SEQUENCE: 114

Val Ala Gln Phe Val Leu Thr Glu
1               5

<210> SEQ ID NO 115
<211> LENGTH: 8
<212> TYPE: PRT
<213> ORGANISM: Artificial Sequence
<220> FEATURE:
<223> OTHER INFORMATION: chemically synthesized

<400> SEQUENCE: 115

Ala Gln Phe Val Leu Thr Glu Gly
1               5

<210> SEQ ID NO 116
<211> LENGTH: 8
<212> TYPE: PRT
<213> ORGANISM: Artificial Sequence
<220> FEATURE:
<223> OTHER INFORMATION: chemically synthesized

<400> SEQUENCE: 116

Pro Val Gln Pro Ile Gly Pro Gln
1               5

<210> SEQ ID NO 117
<211> LENGTH: 273
<212> TYPE: PRT
<213> ORGANISM: Artificial Sequence
<220> FEATURE:
<223> OTHER INFORMATION: chemically synthesized

<400> SEQUENCE: 117

Gly Gly Gly Ser Gly Gly Gly Ser Gly Ser Gly Gly Ser Gly
1               5                   10                  15

Gly Gly Ser Gly Gly Gly Glu Ile Val Leu Thr Gln Ser Pro Gly
                20                  25                  30

Thr Leu Ser Leu Ser Pro Gly Glu Arg Ala Thr Leu Ser Cys Arg Ala
            35                  40                  45

Ser Gln Ser Val Ser Ser Ser Tyr Leu Ala Trp Tyr Gln Gln Lys Pro
        50                  55                  60

Gly Gln Ala Pro Arg Leu Leu Ile Tyr Gly Ala Ser Ser Arg Ala Thr
65                  70                  75                  80
```

Gly Ile Pro Asp Arg Phe Ser Gly Ser Gly Thr Asp Phe Thr
            85                  90                  95

Leu Thr Ile Ser Arg Leu Glu Pro Glu Asp Phe Ala Val Tyr Tyr Cys
            100                 105                 110

Gln Gln Tyr Gly Ser Ser Pro Leu Thr Phe Gly Gly Gly Thr Lys Val
            115                 120                 125

Glu Ile Lys Arg Ser Gly Gly Ser Thr Ile Thr Ser Tyr Asn Val Tyr
            130                 135                 140

Tyr Thr Lys Leu Ser Ser Ser Gly Thr Gln Val Gln Leu Val Gln Thr
145                 150                 155                 160

Gly Gly Gly Val Val Gln Pro Gly Arg Ser Leu Arg Leu Ser Cys Ala
                165                 170                 175

Ala Ser Gly Ser Thr Phe Ser Ser Tyr Ala Met Ser Trp Val Arg Gln
                180                 185                 190

Ala Pro Gly Lys Gly Leu Glu Trp Val Ser Ala Ile Ser Gly Ser Gly
                195                 200                 205

Gly Ser Thr Tyr Tyr Ala Asp Ser Val Lys Gly Arg Phe Thr Ile Ser
            210                 215                 220

Arg Asp Asn Ser Lys Asn Thr Leu Tyr Leu Gln Met Asn Ser Leu Arg
225                 230                 235                 240

Ala Glu Asp Thr Ala Val Tyr Tyr Cys Ala Thr Asn Ser Leu Tyr Trp
                245                 250                 255

Tyr Phe Asp Leu Trp Gly Arg Gly Thr Leu Val Thr Val Ser Ser Ala
                260                 265                 270

Ser

<210> SEQ ID NO 118
<211> LENGTH: 264
<212> TYPE: PRT
<213> ORGANISM: Artificial Sequence
<220> FEATURE:
<223> OTHER INFORMATION: chemically synthesized

<400> SEQUENCE: 118

Gly Gly Gly Ser Gly Gly Gly Ser Gly Ser Gly Gly Gly Ser Gly
1               5                   10                  15

Gly Gly Gly Ser Gly Gly Gly Gln Val Gln Leu Gln Gln Ser Gly Ala
            20                  25                  30

Glu Leu Ala Arg Pro Gly Ala Ser Val Lys Met Ser Cys Lys Ala Ser
            35                  40                  45

Gly Tyr Thr Phe Thr Arg Tyr Thr Met His Trp Val Lys Gln Arg Pro
50                  55                  60

Gly Gln Gly Leu Glu Trp Ile Gly Tyr Ile Asn Pro Ser Arg Gly Tyr
65                  70                  75                  80

Thr Asn Tyr Asn Gln Lys Phe Lys Asp Lys Ala Thr Leu Thr Thr Asp
            85                  90                  95

Lys Ser Ser Ser Thr Ala Tyr Met Gln Leu Ser Ser Leu Thr Ser Glu
            100                 105                 110

Asp Ser Ala Val Tyr Tyr Cys Ala Arg Tyr Tyr Asp Asp His Tyr Cys
            115                 120                 125

Leu Asp Tyr Trp Gly Gln Gly Thr Thr Leu Thr Val Ser Ser Gly Gly
            130                 135                 140

Gly Gly Ser Gly Gly Gly Gly Ser Gly Gly Gly Gly Ser Gln Ile Val
145                 150                 155                 160

```
Leu Thr Gln Ser Pro Ala Ile Met Ser Ala Ser Pro Gly Glu Lys Val
            165                 170                 175

Thr Met Thr Cys Ser Ala Ser Ser Val Ser Tyr Met Asn Trp Tyr
        180                 185                 190

Gln Gln Lys Ser Gly Thr Ser Pro Lys Arg Trp Ile Tyr Asp Thr Ser
            195                 200                 205

Lys Leu Ala Ser Gly Val Pro Ala His Phe Arg Gly Ser Gly Ser Gly
        210                 215                 220

Thr Ser Tyr Ser Leu Thr Ile Ser Gly Met Glu Ala Glu Asp Ala Ala
225                 230                 235                 240

Thr Tyr Tyr Cys Gln Gln Trp Ser Ser Asn Pro Phe Thr Phe Gly Ser
            245                 250                 255

Gly Thr Lys Leu Glu Ile Asn Arg
            260
```

<210> SEQ ID NO 119
<211> LENGTH: 121
<212> TYPE: PRT
<213> ORGANISM: Artificial Sequence
<220> FEATURE:
<223> OTHER INFORMATION: chemically synthesized

<400> SEQUENCE: 119

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asn Ile Trp Trp Ser Glu Asp Lys His Tyr Asn Ser Ala
    50                  55                  60

Leu Lys Ser Arg Leu Thr Ile Ser Lys Asp Thr Ser Asn Asn Gln Val
65                  70                  75                  80

Phe Leu Lys Ile Ser Ser Val Asp Thr Ala Asp Thr Ala Thr Tyr Tyr
                85                  90                  95

Cys Val Gln Ile Asp Tyr Gly Asn Asp Tyr Ala Phe Thr Tyr Trp Gly
            100                 105                 110

Gln Gly Thr Leu Val Thr Val Ser Ala
        115                 120
```

<210> SEQ ID NO 120
<211> LENGTH: 113
<212> TYPE: PRT
<213> ORGANISM: Artificial Sequence
<220> FEATURE:
<223> OTHER INFORMATION: chemically synthesized

<400> SEQUENCE: 120

```
Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80
```

```
Ser Arg Val Glu Ala Glu Asp Val Gly Val Tyr Tyr Cys Ala Gln Asn
            85                  90                  95

Leu Glu Leu Pro Tyr Thr Phe Gly Gly Thr Lys Leu Glu Ile Lys
            100                 105                 110

Arg

<210> SEQ ID NO 121
<211> LENGTH: 121
<212> TYPE: PRT
<213> ORGANISM: Artificial Sequence
<220> FEATURE:
<223> OTHER INFORMATION: chemically synthesized

<400> SEQUENCE: 121

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asn Ile Trp Trp Ser Glu Asp Lys His Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Val Gln Ile Asp Tyr Gly Asn Asp Tyr Ala Phe Thr Tyr Trp Gly
            100                 105                 110

Gln Gly Thr Leu Val Thr Val Ser Ser
        115                 120

<210> SEQ ID NO 122
<211> LENGTH: 121
<212> TYPE: PRT
<213> ORGANISM: Artificial Sequence
<220> FEATURE:
<223> OTHER INFORMATION: chemically synthesized

<400> SEQUENCE: 122

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asn Ile Trp Trp Ser Glu Asp Lys His Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Ile Thr Asn Val Asp Pro Val Asp Thr Ala Thr Tyr Tyr
            85                  90                  95

Cys Val Gln Ile Asp Tyr Gly Asn Asp Tyr Ala Phe Thr Tyr Trp Gly
            100                 105                 110

Gln Gly Thr Leu Val Thr Val Ser Ser
        115                 120

<210> SEQ ID NO 123
```

```
<211> LENGTH: 112
<212> TYPE: PRT
<213> ORGANISM: Artificial Sequence
<220> FEATURE:
<223> OTHER INFORMATION: chemically synthesized

<400> SEQUENCE: 123

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gln Gly Thr Lys Leu Glu Ile Lys
            100                 105                 110

<210> SEQ ID NO 124
<211> LENGTH: 112
<212> TYPE: PRT
<213> ORGANISM: Artificial Sequence
<220> FEATURE:
<223> OTHER INFORMATION: chemically synthesized

<400> SEQUENCE: 124

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gln Gly Thr Lys Leu Glu Ile Lys
            100                 105                 110

<210> SEQ ID NO 125
<211> LENGTH: 112
<212> TYPE: PRT
<213> ORGANISM: Artificial Sequence
<220> FEATURE:
<223> OTHER INFORMATION: chemically synthesized

<400> SEQUENCE: 125

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Ile Thr Tyr Leu Tyr Trp Tyr Leu Gln Lys Pro Gly Gln Ser
        35                  40                  45
```

```
Pro Gln Leu Leu Ile Tyr Gln Met Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gln Gly Thr Lys Leu Glu Ile Lys
                100                 105                 110
```

<210> SEQ ID NO 126
<211> LENGTH: 112
<212> TYPE: PRT
<213> ORGANISM: Artificial Sequence
<220> FEATURE:
<223> OTHER INFORMATION: chemically synthesized

<400> SEQUENCE: 126

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Arg Ala Ser Gly Val Pro
        50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gln Gly Thr Lys Leu Glu Ile Lys
                100                 105                 110
```

<210> SEQ ID NO 127
<211> LENGTH: 12
<212> TYPE: PRT
<213> ORGANISM: Artificial Sequence
<220> FEATURE:
<223> OTHER INFORMATION: chemically synthesized

<400> SEQUENCE: 127

```
Gly Phe Ser Leu Ser Thr Tyr Gly Met Gly Val Gly
1               5                   10
```

<210> SEQ ID NO 128
<211> LENGTH: 9
<212> TYPE: PRT
<213> ORGANISM: Artificial Sequence
<220> FEATURE:
<223> OTHER INFORMATION: chemically synthesized

<400> SEQUENCE: 128

```
Asn Ile Trp Trp Ser Glu Asp Lys His
1               5
```

<210> SEQ ID NO 129
<211> LENGTH: 11
<212> TYPE: PRT
<213> ORGANISM: Artificial Sequence
<220> FEATURE:
<223> OTHER INFORMATION: chemically synthesized

<400> SEQUENCE: 129

```
Ile Asp Tyr Gly Asn Asp Tyr Ala Phe Thr Tyr
1               5                   10
```

<210> SEQ ID NO 130
<211> LENGTH: 16
<212> TYPE: PRT
<213> ORGANISM: Artificial Sequence
<220> FEATURE:
<223> OTHER INFORMATION: chemically synthesized

<400> SEQUENCE: 130

```
Arg Ser Ser Lys Ser Leu Leu His Ser Asn Gly Ile Thr Tyr Leu Tyr
1               5                   10                  15
```

<210> SEQ ID NO 131
<211> LENGTH: 16
<212> TYPE: PRT
<213> ORGANISM: Artificial Sequence
<220> FEATURE:
<223> OTHER INFORMATION: chemically synthesized

<400> SEQUENCE: 131

```
Arg Ser Ser Gln Ser Leu Leu His Ser Asn Gly Ile Thr Tyr Leu Tyr
1               5                   10                  15
```

<210> SEQ ID NO 132
<211> LENGTH: 7
<212> TYPE: PRT
<213> ORGANISM: Artificial Sequence
<220> FEATURE:
<223> OTHER INFORMATION: chemically synthesized

<400> SEQUENCE: 132

```
Gln Met Ser Asn Leu Ala Ser
1               5
```

<210> SEQ ID NO 133
<211> LENGTH: 7
<212> TYPE: PRT
<213> ORGANISM: Artificial Sequence
<220> FEATURE:
<223> OTHER INFORMATION: chemically synthesized

<400> SEQUENCE: 133

```
Gln Met Ser Asn Arg Ala Ser
1               5
```

<210> SEQ ID NO 134
<211> LENGTH: 9
<212> TYPE: PRT
<213> ORGANISM: Artificial Sequence
<220> FEATURE:
<223> OTHER INFORMATION: chemically synthesized

<400> SEQUENCE: 134

```
Ala Gln Asn Leu Glu Leu Pro Tyr Thr
1               5
```

<210> SEQ ID NO 135
<211> LENGTH: 15
<212> TYPE: PRT
<213> ORGANISM: Artificial Sequence
<220> FEATURE:
<223> OTHER INFORMATION: chemically synthesized

<400> SEQUENCE: 135

```
Tyr Leu Cys Gln Arg His Pro Leu Ala Leu Lys Tyr Cys Thr Asn
```

-continued

```
<210> SEQ ID NO 136
<211> LENGTH: 15
<212> TYPE: PRT
<213> ORGANISM: Artificial Sequence
<220> FEATURE:
<223> OTHER INFORMATION: chemically synthesized

<400> SEQUENCE: 136

Pro Leu Cys Val Pro Thr Gln Leu Leu Arg Ser Cys Tyr Asn Tyr
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: chemically synthesized

<400> SEQUENCE: 137

Ala Val Cys His Pro Leu Ala Asn Val Glu Thr Gln Cys Leu Asp
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: chemically synthesized

<400> SEQUENCE: 138

Pro His Cys His Pro Leu Phe Asn Asn Thr Tyr Cys Tyr Arg His
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: chemically synthesized

<400> SEQUENCE: 139

Pro Leu Cys Arg Pro Ile Glu Leu Leu Ala Ser Cys Pro Met Lys
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: chemically synthesized

<400> SEQUENCE: 140

Gly Ala Ala Cys Val Ser Ala Trp Gly Phe Phe Cys Glu Cys Cys
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: chemically synthesized

<400> SEQUENCE: 141

Asp Cys Ala Lys Asp Ile Leu His Leu Met Pro His Cys Ser Met
1               5                   10                  15
```

<210> SEQ ID NO 142
<211> LENGTH: 15
<212> TYPE: PRT
<213> ORGANISM: Artificial Sequence
<220> FEATURE:
<223> OTHER INFORMATION: chemically synthesized

<400> SEQUENCE: 142

Asn Thr Cys Met His Pro Leu Leu Leu Gln Gly Cys Lys Thr Tyr
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: chemically synthesized

<400> SEQUENCE: 143

Tyr Leu Gly Cys Leu Leu Tyr Ala Gly Pro Gly Cys Glu Gly Gly
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: chemically synthesized

<400> SEQUENCE: 144

Ala Arg Cys Pro His Pro Leu Leu Leu Ser Ile Cys Glu Asn Asn
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: chemically synthesized

<400> SEQUENCE: 145

Glu Leu Cys Pro His Pro Leu Pro Phe Gly Phe Cys Asn Asn Tyr
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: chemically synthesized

<400> SEQUENCE: 146

Ala Leu Tyr Cys His Pro Pro Tyr Ile Arg Cys Glu Glu Met Thr
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: chemically synthesized

<400> SEQUENCE: 147

Thr Ser Leu Cys His Pro Val Met Ile Met Tyr Cys Lys Thr Gly
1               5                   10                  15

```
<210> SEQ ID NO 148
<211> LENGTH: 15
<212> TYPE: PRT
<213> ORGANISM: Artificial Sequence
<220> FEATURE:
<223> OTHER INFORMATION: chemically synthesized

<400> SEQUENCE: 148

Pro Leu Cys His Pro Leu Glu Gln Ala Ser Trp Cys Asn Met Asp
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: chemically synthesized

<400> SEQUENCE: 149

Pro His Pro Cys Pro Arg Thr Gly Ser Arg Met Cys His Phe Ser
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: chemically synthesized

<400> SEQUENCE: 150

Ser Gly Cys Arg His Pro Leu Pro Leu Lys Ala Cys Gly Thr Asn
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: chemically synthesized

<400> SEQUENCE: 151

Gly Leu Cys His Pro Ile Arg Leu His Asn Thr Gln Cys Thr Ile
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: chemically synthesized

<400> SEQUENCE: 152

Lys Cys Met His Pro Leu Asn Leu His Asn Ile Asn Cys Asn His
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: chemically synthesized

<400> SEQUENCE: 153

Pro Ile Cys His Pro Leu Arg Glu Phe Met Asn Thr Cys Phe Lys
1               5                   10                  15
```

<210> SEQ ID NO 154
<211> LENGTH: 15
<212> TYPE: PRT
<213> ORGANISM: Artificial Sequence
<220> FEATURE:
<223> OTHER INFORMATION: chemically synthesized

<400> SEQUENCE: 154

```
Asn Cys His Pro Leu Asp Val Val Gly Trp Leu Gly Cys Met Lys
1               5                   10                  15
```

<210> SEQ ID NO 155
<211> LENGTH: 15
<212> TYPE: PRT
<213> ORGANISM: Artificial Sequence
<220> FEATURE:
<223> OTHER INFORMATION: chemically synthesized

<400> SEQUENCE: 155

```
Tyr Asn Asn Val Cys His Pro Leu Phe Cys Ser Gln His Thr Tyr
1               5                   10                  15
```

<210> SEQ ID NO 156
<211> LENGTH: 15
<212> TYPE: PRT
<213> ORGANISM: Artificial Sequence
<220> FEATURE:
<223> OTHER INFORMATION: chemically synthesized

<400> SEQUENCE: 156

```
Thr Phe Cys His Pro Leu Phe Ser Leu Asn Tyr Cys Gly His Lys
1               5                   10                  15
```

<210> SEQ ID NO 157
<211> LENGTH: 15
<212> TYPE: PRT
<213> ORGANISM: Artificial Sequence
<220> FEATURE:
<223> OTHER INFORMATION: chemically synthesized

<400> SEQUENCE: 157

```
Phe Cys His Pro Leu Thr Leu Ser Asn Asn Lys Gln Cys Asn Arg
1               5                   10                  15
```

<210> SEQ ID NO 158
<211> LENGTH: 15
<212> TYPE: PRT
<213> ORGANISM: Artificial Sequence
<220> FEATURE:
<223> OTHER INFORMATION: chemically synthesized

<400> SEQUENCE: 158

```
Leu Ser His Cys Ala Val Leu Leu Leu Arg Val Cys Ser Gly Ser
1               5                   10                  15
```

<210> SEQ ID NO 159
<211> LENGTH: 15
<212> TYPE: PRT
<213> ORGANISM: Artificial Sequence
<220> FEATURE:
<223> OTHER INFORMATION: chemically synthesized

<400> SEQUENCE: 159

```
Lys Ile His Cys His Pro Leu Arg Leu Gly Thr Cys Leu Val Gly
1               5                   10                  15
```

<210> SEQ ID NO 160

```
<211> LENGTH: 15
<212> TYPE: PRT
<213> ORGANISM: Artificial Sequence
<220> FEATURE:
<223> OTHER INFORMATION: chemically synthesized

<400> SEQUENCE: 160

Glu Thr Cys Ala His Pro Leu Asp Met Arg Met Cys Arg His Asn
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: chemically synthesized

<400> SEQUENCE: 161

Pro Leu Cys Tyr Pro Leu Ile Leu Met Ser Ser Cys Trp Leu Gly
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: chemically synthesized

<400> SEQUENCE: 162

Tyr Gly Ile Cys His Pro Ala Pro Asp Leu Pro Cys Met Gln Ile
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: chemically synthesized

<400> SEQUENCE: 163

Thr Ala Cys His Pro Leu Tyr Asn Val Glu His Leu Cys Glu Ile
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: chemically synthesized

<400> SEQUENCE: 164

Thr Ala Cys Asn Lys Ser Val Cys Val Ala Gly Cys Cys Leu Leu
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: chemically synthesized

<400> SEQUENCE: 165

Leu His Pro Leu Cys Ser Tyr Met Lys Ser Cys Met Lys Asn Asn
1               5                   10                  15

<210> SEQ ID NO 166
<211> LENGTH: 15
```

```
<212> TYPE: PRT
<213> ORGANISM: Artificial Sequence
<220> FEATURE:
<223> OTHER INFORMATION: chemically synthesized

<400> SEQUENCE: 166

Thr His Cys His Cys Met Val Tyr Phe Cys Pro Cys Arg Trp Ser
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: chemically synthesized

<400> SEQUENCE: 167

Pro Lys Cys Pro His Pro Leu His Leu Ala Asn Cys Tyr Ala Ser
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: chemically synthesized
<220> FEATURE:
<221> NAME/KEY: misc_feature
<222> LOCATION: (12)..(12)
<223> OTHER INFORMATION: Xaa can be any naturally occurring amino acid

<400> SEQUENCE: 168

Lys Thr Cys Tyr His Pro Thr Pro Val Ile Ala Xaa Asn Ser Tyr
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: chemically synthesized

<400> SEQUENCE: 169

Ala Lys Cys Leu Pro Pro Leu Ile Gln Tyr Cys Arg Cys Ile Lys
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: chemically synthesized

<400> SEQUENCE: 170

His Ala Cys Gln His Pro Leu Gln Leu His Thr Cys Lys His Asn
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: chemically synthesized

<400> SEQUENCE: 171

Leu Cys His Pro Leu Val Leu Ser Ala Trp Glu Ser Cys Ser Asn
1               5                   10                  15
```

<210> SEQ ID NO 172
<211> LENGTH: 15
<212> TYPE: PRT
<213> ORGANISM: Artificial Sequence
<220> FEATURE:
<223> OTHER INFORMATION: chemically synthesized

<400> SEQUENCE: 172

Trp Pro Leu Cys Ser Phe Gly Lys Ser Phe Cys Ala Gln Asn Ala
1               5                   10                  15

<210> SEQ ID NO 173
<211> LENGTH: 15
<212> TYPE: PRT
<213> ORGANISM: Artificial Sequence
<220> FEATURE:
<223> OTHER INFORMATION: chemically synthesized

<400> SEQUENCE: 173

Glu Cys Gln Ser Phe Glu His Phe Leu Thr Asn Asn Cys His Ser
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: chemically synthesized

<400> SEQUENCE: 174

Ser Cys Lys His Pro Leu Val Met Pro Asn Leu Lys Cys Thr Arg
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: chemically synthesized

<400> SEQUENCE: 175

Tyr Pro Cys His Pro Leu Gln Leu Ser Ile Pro His Cys Thr Lys
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: chemically synthesized

<400> SEQUENCE: 176

Ile Cys His Pro Leu Thr His Thr Met Glu Tyr Met Cys Met Asn
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: chemically synthesized

<400> SEQUENCE: 177

Thr Leu Cys His Pro Leu Thr Phe Ser Val Pro Thr Cys Thr Asn
1               5                   10                  15

```
<210> SEQ ID NO 178
<211> LENGTH: 15
<212> TYPE: PRT
<213> ORGANISM: Artificial Sequence
<220> FEATURE:
<223> OTHER INFORMATION: chemically synthesized

<400> SEQUENCE: 178

Pro Leu Cys Gln Pro Asn Arg Leu Leu Gln Ala Cys Gly Asn Thr
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: chemically synthesized

<400> SEQUENCE: 179

Thr Leu Cys Arg His Pro Leu Ala Leu Asp Gly Cys Gln Asn Asn
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: chemically synthesized

<400> SEQUENCE: 180

Gln Pro Met Cys Tyr Gln Pro Ala His Pro Leu Cys Asn Thr Ile
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: chemically synthesized

<400> SEQUENCE: 181

Ser Asn Cys His Pro Leu Leu Phe Gln His Tyr His Cys Met Leu
1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: chemically synthesized

<400> SEQUENCE: 182

Glu Lys Cys Tyr His Pro Leu Thr Leu Ala His Cys Gln Asn His
1               5                   10                  15

<210> SEQ ID NO 183
<211> LENGTH: 15
<212> TYPE: PRT
<213> ORGANISM: Artificial Sequence
<220> FEATURE:
<223> OTHER INFORMATION: chemically synthesized

<400> SEQUENCE: 183

Asn Lys Cys Phe Val His Pro Leu Ala Met Pro Asn Cys Asn Ser
1               5                   10                  15

<210> SEQ ID NO 184
```

```
<211> LENGTH: 15
<212> TYPE: PRT
<213> ORGANISM: Artificial Sequence
<220> FEATURE:
<223> OTHER INFORMATION: chemically synthesized

<400> SEQUENCE: 184

Val Asn Asn Cys Leu Leu Met Thr Arg Ala His Cys Thr Ser Tyr
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: chemically synthesized

<400> SEQUENCE: 185

Leu Pro Cys Trp Ala Phe Ala Val Asn Pro Leu His Cys Gly Asp
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: chemically synthesized

<400> SEQUENCE: 186

Val Asn Asn Cys Leu Leu Met Thr Arg Ala His Cys Thr Ser Tyr
1               5                   10                  15

<210> SEQ ID NO 187
<211> LENGTH: 15
<212> TYPE: PRT
<213> ORGANISM: Artificial Sequence
<220> FEATURE:
<223> OTHER INFORMATION: chemically synthesized

<400> SEQUENCE: 187

Ser Ser Cys Pro His Pro Leu Gly Leu Thr Gly Cys Asn Asp Lys
1               5                   10                  15

<210> SEQ ID NO 188
<211> LENGTH: 15
<212> TYPE: PRT
<213> ORGANISM: Artificial Sequence
<220> FEATURE:
<223> OTHER INFORMATION: chemically synthesized

<400> SEQUENCE: 188

Asn Lys Cys Phe Val His Pro Leu Ala Met Pro Asn Cys Asn Ser
1               5                   10                  15

<210> SEQ ID NO 189
<211> LENGTH: 15
<212> TYPE: PRT
<213> ORGANISM: Artificial Sequence
<220> FEATURE:
<223> OTHER INFORMATION: chemically synthesized

<400> SEQUENCE: 189

Phe Val Gly Cys His Ser Val Tyr Val Ser Gly Cys Leu Arg Ala
1               5                   10                  15

<210> SEQ ID NO 190
<211> LENGTH: 15
```

```
<212> TYPE: PRT
<213> ORGANISM: Artificial Sequence
<220> FEATURE:
<223> OTHER INFORMATION: chemically synthesized

<400> SEQUENCE: 190

Asn Met Cys His Pro Pro His Asn Ile Tyr Ser Ile Cys Asn Met
1               5                   10                  15

<210> SEQ ID NO 191
<211> LENGTH: 14
<212> TYPE: PRT
<213> ORGANISM: Artificial Sequence
<220> FEATURE:
<223> OTHER INFORMATION: chemically synthesized

<400> SEQUENCE: 191

Leu Thr Cys His Leu Leu Pro Gly Leu Thr Leu His Thr Lys
1               5                   10

<210> SEQ ID NO 192
<211> LENGTH: 15
<212> TYPE: PRT
<213> ORGANISM: Artificial Sequence
<220> FEATURE:
<223> OTHER INFORMATION: chemically synthesized

<400> SEQUENCE: 192

Arg Thr Cys His Pro Leu Pro Gly Leu Thr Leu His Cys Thr Lys
1               5                   10                  15

<210> SEQ ID NO 193
<211> LENGTH: 15
<212> TYPE: PRT
<213> ORGANISM: Artificial Sequence
<220> FEATURE:
<223> OTHER INFORMATION: chemically synthesized

<400> SEQUENCE: 193

His Pro Leu Cys Phe Glu Ser Met Lys Asn Cys Phe Pro Asn Tyr
1               5                   10                  15

<210> SEQ ID NO 194
<211> LENGTH: 15
<212> TYPE: PRT
<213> ORGANISM: Artificial Sequence
<220> FEATURE:
<223> OTHER INFORMATION: chemically synthesized

<400> SEQUENCE: 194

Thr Thr Cys His Pro Leu Ser Phe Thr His Asn Tyr Cys Ile Thr
1               5                   10                  15

<210> SEQ ID NO 195
<211> LENGTH: 15
<212> TYPE: PRT
<213> ORGANISM: Artificial Sequence
<220> FEATURE:
<223> OTHER INFORMATION: chemically synthesized

<400> SEQUENCE: 195

Arg Asp Cys Gly Phe Asp Ala Val Arg Ala Asp Cys Leu Phe Gly
1               5                   10                  15

<210> SEQ ID NO 196
<211> LENGTH: 15
<212> TYPE: PRT
```

<213> ORGANISM: Artificial Sequence
<220> FEATURE:
<223> OTHER INFORMATION: chemically synthesized

<400> SEQUENCE: 196

Arg Thr Cys Ser Thr His Pro Leu Thr Met Pro Gln Cys Asn Tyr
1               5                   10                  15

<210> SEQ ID NO 197
<211> LENGTH: 15
<212> TYPE: PRT
<213> ORGANISM: Artificial Sequence
<220> FEATURE:
<223> OTHER INFORMATION: chemically synthesized

<400> SEQUENCE: 197

Met Lys Cys His Pro Leu Gln Leu Thr Gly Asn Thr Cys Ser Met
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: chemically synthesized

<400> SEQUENCE: 198

Ser Gly Cys Pro His Pro Leu Gln Leu Ile Thr Cys Ser Thr Ala
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: chemically synthesized

<400> SEQUENCE: 199

Lys Cys Phe Pro Ala Phe His Asp Gly Pro Leu Ala Cys Ala Ser
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: chemically synthesized

<400> SEQUENCE: 200

Leu Lys Cys Gln His Pro Leu Pro Met Ser His Cys Gln Pro Gln
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: chemically synthesized

<400> SEQUENCE: 201

Ala Phe Cys Gly Phe Ser Val Ile His Pro Leu Cys Ser Gly Ala
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: chemically synthesized

<400> SEQUENCE: 202

Ser Val His Cys Ala Val Leu Lys Leu Asp Gly Cys Leu Gly Trp
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: chemically synthesized

<400> SEQUENCE: 203

Thr Leu Pro Cys His Pro Ile Met Val Leu Gly Cys Thr Pro Met
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: chemically synthesized

<400> SEQUENCE: 204

His Tyr Pro Cys Met Lys Tyr Asn Pro Leu Asn Cys Ser Met Ser
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: chemically synthesized

<400> SEQUENCE: 205

Leu Lys Cys Pro His Pro Leu Ser Leu Asn Gly Cys Thr Leu Lys
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: chemically synthesized

<400> SEQUENCE: 206

Val Tyr Ser Cys Met Ala Asn Asn Pro Leu Asp Cys Phe Thr Gln
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: chemically synthesized

<400> SEQUENCE: 207

Pro Ile Cys His Pro Leu Val Thr Leu Met Ser Tyr Cys Asn Lys
1               5                   10                  15

<210> SEQ ID NO 208
<211> LENGTH: 15
<212> TYPE: PRT
<213> ORGANISM: Artificial Sequence
<220> FEATURE:

<223> OTHER INFORMATION: chemically synthesized

<400> SEQUENCE: 208

Asp Trp Cys Ser Phe Trp Ala Gly Gln Ser Val Trp Cys Thr Ser
1               5                   10                  15

<210> SEQ ID NO 209
<211> LENGTH: 15
<212> TYPE: PRT
<213> ORGANISM: Artificial Sequence
<220> FEATURE:
<223> OTHER INFORMATION: chemically synthesized

<400> SEQUENCE: 209

Ser Thr Cys His Pro Leu Thr Pro Phe His Asp Lys Cys Arg Tyr
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: chemically synthesized

<400> SEQUENCE: 210

Pro Val Cys Pro Pro Leu Val Thr Leu Met Ser Tyr Cys Asn Lys
1               5                   10                  15

<210> SEQ ID NO 211
<211> LENGTH: 15
<212> TYPE: PRT
<213> ORGANISM: Artificial Sequence
<220> FEATURE:
<223> OTHER INFORMATION: chemically synthesized

<400> SEQUENCE: 211

Ser Thr Cys His Pro Leu Pro Thr Leu Met Pro Tyr Cys Asn Ser
1               5                   10                  15

<210> SEQ ID NO 212
<211> LENGTH: 15
<212> TYPE: PRT
<213> ORGANISM: Artificial Sequence
<220> FEATURE:
<223> OTHER INFORMATION: chemically synthesized

<400> SEQUENCE: 212

Phe Pro Leu Cys Gly Ile Gly Pro Ala Phe Cys Asp Thr Thr Val
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: chemically synthesized

<400> SEQUENCE: 213

Pro Thr Cys His Pro Leu Val Leu Ser Val Pro Cys Pro Lys Ile
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: chemically synthesized

```
<400> SEQUENCE: 214

Gly Pro Leu Cys Asp Tyr Phe Val Phe Tyr Ser Cys Arg Gly Ser
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: chemically synthesized

<400> SEQUENCE: 215

His Thr Cys Tyr His Pro Leu Lys Leu Gly Gln Cys Glu Met Phe
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: chemically synthesized

<400> SEQUENCE: 216

Arg Thr Cys Ile His Pro Leu Pro Leu His Gln Cys His Lys Pro
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: chemically synthesized

<400> SEQUENCE: 217

Ala Cys His Pro Ile Asn Phe Asn Ser Ile Val Tyr Cys Asn Asn
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: chemically synthesized

<400> SEQUENCE: 218

Ser His Pro Cys Ser Val Val Asn Leu Pro Gly Cys Glu Pro Asp
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: chemically synthesized

<400> SEQUENCE: 219

Leu Cys His Pro Leu Val Leu Ser Ala Trp Glu Ser Cys Ser Ser
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: chemically synthesized
```

```
<400> SEQUENCE: 220

Leu Cys Ala Pro Leu Val Leu Ser Ala Trp Glu Ser Cys Ser Ser
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: chemically synthesized

<400> SEQUENCE: 221

Leu Cys His Ala Leu Val Leu Ser Ala Trp Glu Ser Cys Ser Ser
1               5                   10                  15

<210> SEQ ID NO 222
<211> LENGTH: 15
<212> TYPE: PRT
<213> ORGANISM: Artificial Sequence
<220> FEATURE:
<223> OTHER INFORMATION: chemically synthesized

<400> SEQUENCE: 222

Leu Cys His Pro Ala Val Leu Ser Ala Trp Glu Ser Cys Ser Ser
1               5                   10                  15

<210> SEQ ID NO 223
<211> LENGTH: 15
<212> TYPE: PRT
<213> ORGANISM: Artificial Sequence
<220> FEATURE:
<223> OTHER INFORMATION: chemically synthesized

<400> SEQUENCE: 223

Leu Cys His Pro Leu Ala Leu Ser Ala Trp Glu Ser Cys Ser Ser
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: chemically synthesized

<400> SEQUENCE: 224

Leu Cys His Pro Leu Val Ala Ser Ala Trp Glu Ser Cys Ser Ser
1               5                   10                  15

<210> SEQ ID NO 225
<211> LENGTH: 15
<212> TYPE: PRT
<213> ORGANISM: Artificial Sequence
<220> FEATURE:
<223> OTHER INFORMATION: chemically synthesized

<400> SEQUENCE: 225

Leu Cys His Pro Leu Val Leu Ser Ala Ala Glu Ser Cys Ser Ser
1               5                   10                  15

<210> SEQ ID NO 226
<211> LENGTH: 15
<212> TYPE: PRT
<213> ORGANISM: Artificial Sequence
<220> FEATURE:
<223> OTHER INFORMATION: chemically synthesized

<400> SEQUENCE: 226
```

```
Leu Cys His Pro Leu Val Leu Ser Ala Trp Ala Ser Cys Ser Ser
1               5                   10                  15
```

<210> SEQ ID NO 227
<211> LENGTH: 12
<212> TYPE: PRT
<213> ORGANISM: Artificial Sequence
<220> FEATURE:
<223> OTHER INFORMATION: chemically synthesized

<400> SEQUENCE: 227

```
Cys His Pro Leu Val Leu Ser Ala Trp Glu Ser Cys
1               5                   10
```

<210> SEQ ID NO 228
<211> LENGTH: 5
<212> TYPE: PRT
<213> ORGANISM: Artificial Sequence
<220> FEATURE:
<223> OTHER INFORMATION: chemically synthesized

<400> SEQUENCE: 228

```
His Pro Leu Val Leu
1               5
```

<210> SEQ ID NO 229
<211> LENGTH: 3
<212> TYPE: PRT
<213> ORGANISM: Artificial Sequence
<220> FEATURE:
<223> OTHER INFORMATION: chemically synthesized

<400> SEQUENCE: 229

```
His Pro Leu
1
```

<210> SEQ ID NO 230
<211> LENGTH: 15
<212> TYPE: PRT
<213> ORGANISM: Artificial Sequence
<220> FEATURE:
<223> OTHER INFORMATION: chemically synthesized

<400> SEQUENCE: 230

```
Leu Glu Gly Trp Cys Leu His Pro Leu Cys Leu Trp Gly Ala Gly
1               5                   10                  15
```

<210> SEQ ID NO 231
<211> LENGTH: 15
<212> TYPE: PRT
<213> ORGANISM: Artificial Sequence
<220> FEATURE:
<223> OTHER INFORMATION: chemically synthesized

<400> SEQUENCE: 231

```
Leu Glu Gly Ala Cys Leu His Pro Leu Cys Leu Trp Gly Ala Gly
1               5                   10                  15
```

<210> SEQ ID NO 232
<211> LENGTH: 15
<212> TYPE: PRT
<213> ORGANISM: Artificial Sequence
<220> FEATURE:
<223> OTHER INFORMATION: chemically synthesized

<400> SEQUENCE: 232

Leu Glu Gly Trp Cys Ala His Pro Leu Cys Leu Trp Gly Ala Gly
1               5                   10                  15

<210> SEQ ID NO 233
<211> LENGTH: 15
<212> TYPE: PRT
<213> ORGANISM: Artificial Sequence
<220> FEATURE:
<223> OTHER INFORMATION: chemically synthesized

<400> SEQUENCE: 233

Leu Glu Gly Trp Cys Leu Ala Pro Leu Cys Leu Trp Gly Ala Gly
1               5                   10                  15

<210> SEQ ID NO 234
<211> LENGTH: 15
<212> TYPE: PRT
<213> ORGANISM: Artificial Sequence
<220> FEATURE:
<223> OTHER INFORMATION: chemically synthesized

<400> SEQUENCE: 234

Leu Glu Gly Trp Cys Leu His Ala Leu Cys Leu Trp Gly Ala Gly
1               5                   10                  15

<210> SEQ ID NO 235
<211> LENGTH: 15
<212> TYPE: PRT
<213> ORGANISM: Artificial Sequence
<220> FEATURE:
<223> OTHER INFORMATION: chemically synthesized

<400> SEQUENCE: 235

Leu Glu Gly Trp Cys Leu His Pro Ala Cys Leu Trp Gly Ala Gly
1               5                   10                  15

<210> SEQ ID NO 236
<211> LENGTH: 15
<212> TYPE: PRT
<213> ORGANISM: Artificial Sequence
<220> FEATURE:
<223> OTHER INFORMATION: chemically synthesized

<400> SEQUENCE: 236

Leu Glu Gly Trp Cys Leu His Pro Leu Cys Ala Trp Gly Ala Gly
1               5                   10                  15

<210> SEQ ID NO 237
<211> LENGTH: 15
<212> TYPE: PRT
<213> ORGANISM: Artificial Sequence
<220> FEATURE:
<223> OTHER INFORMATION: chemically synthesized

<400> SEQUENCE: 237

Leu Glu Gly Trp Cys Leu His Pro Leu Cys Leu Ala Gly Ala Gly
1               5                   10                  15

<210> SEQ ID NO 238
<211> LENGTH: 6
<212> TYPE: PRT
<213> ORGANISM: Artificial Sequence
<220> FEATURE:
<223> OTHER INFORMATION: chemically synthesized

<400> SEQUENCE: 238

Cys Leu His Pro Leu Cys
1               5

-continued

<210> SEQ ID NO 239
<211> LENGTH: 451
<212> TYPE: PRT
<213> ORGANISM: Artificial Sequence
<220> FEATURE:
<223> OTHER INFORMATION: chemically synthesized

<400> SEQUENCE: 239

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asn Ile Trp Trp Ser Glu Asp Lys His Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Ile Thr Asn Val Asp Pro Val Asp Thr Ala Thr Tyr Tyr
                85                  90                  95

Cys Val Gln Ile Asp Tyr Gly Asn Asp Tyr Ala Phe Thr Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser

```
                355                 360                 365
Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 240
<211> LENGTH: 219
<212> TYPE: PRT
<213> ORGANISM: Artificial Sequence
<220> FEATURE:
<223> OTHER INFORMATION: chemically synthesized

<400> SEQUENCE: 240

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 241
<211> LENGTH: 1353
<212> TYPE: DNA
<213> ORGANISM: Artificial Sequence
<220> FEATURE:
<223> OTHER INFORMATION: chemically synthesized
```

<400> SEQUENCE: 241

```
cagatcaccc tgaaagagtc cggccccacc ctggtgaaac ccacccagac cctgaccctg      60
acatgcacct tctccggctt cagcctgtcc acctacggca tgggcgtggg ctggatcagg     120
cagcctcctg gcaaggccct ggaatggctg gccaacatct ggtggtccga ggacaagcac     180
tactccccca gcctgaagtc ccggctgacc atcaccaagg acacctccaa gaaccaggtg     240
gtgctgacaa tcacaaacgt ggaccccgtg acaccgcca cctactactg cgtgcagatc      300
gactacggca acgactacgc cttcacctac tggggccagg gcacactggt gacagtgtcc     360
tccgcctcca ccaagggccc ctccgtgttc cctctggccc cttccagcaa gtccacctct     420
ggcggcacag ctgccctggg ctgcctggtg aaagactact cccccgagcc cgtgaccgtg     480
tcctggaact ctggcgccct gaccagcgga gtgcacacct ccctgccgt gctgcagtcc      540
tccggcctgt actccctgtc ctccgtggtg accgtgccct ccagctctct gggcacccag     600
acctacatct gcaacgtgaa ccacaagccc tccaacacca aggtggacaa gaaggtggaa     660
cccaagtcct gcgacaagac ccacacctgt ccccctgcc ctgcccctga actgctgggc      720
ggaccttccg tgtttctgtt ccccccaaag cctaaggaca ccctgatgat ctccggacc      780
cccgaagtga cctgcgtggt ggtggacgtg tcccacgagg accctgaagt gaagttcaat     840
tggtacgtgg acggcgtgga agtgcacaac gccaagacca gcccagaga ggaacagtac      900
aactccacct accgggtggt gtctgtgctg accgtgctgc accaggactg gctgaacggc     960
aaagagtaca agtgcaaggt gtccaacaag gccctgcctg cccccatcga aaagaccatc    1020
tccaaggcca agggccagcc ccgcgagcct caggtgtaca cactgccccc tagccgggaa    1080
gagatgacca gaatcaggt gtccctgacc tgtctggtga aaggcttcta cccctccgat     1140
atcgccgtgg aatgggagtc caacggccag cccgagaaca actacaagac cacccccct     1200
gtgctggact ccgacggctc attcttcctg tactccaagc tgaccgtgga caagtcccgg    1260
tggcagcagg gcaacgtgtt ctcctgcagc gtgatgcacg aggccctgca caaccactac    1320
acccagaagt ccctgtccct gagccccggc aag                                 1353
```

<210> SEQ ID NO 242
<211> LENGTH: 266
<212> TYPE: PRT
<213> ORGANISM: Artificial Sequence
<220> FEATURE:
<223> OTHER INFORMATION: chemically synthesized

<400> SEQUENCE: 242

```
Gln Gly Gln Ser Gly Gln Gly Leu Cys His Pro Ala Val Leu Ser Ala
1               5                   10                  15

Trp Glu Ser Cys Ser Ser Gly Gly Ser Ser Gly Gly Ser Ile Ser
                20                  25                  30

Ser Gly Leu Leu Ser Gly Arg Ser Asp Asn His Gly Gly Ser Asp
            35                  40                  45

Ile Val Met Thr Gln Ser Pro Leu Ser Leu Pro Val Thr Pro Gly Glu
        50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
            100                 105                 110
```

Arg Phe Ser Gly Ser Gly Ser Gly Thr Asp Phe Thr Leu Lys Ile Ser
            115                 120                 125

Arg Val Glu Ala Glu Asp Val Gly Val Tyr Tyr Cys Ala Gln Asn Leu
        130                 135                 140

Glu Leu Pro Tyr Thr Phe Gly Gln Gly Thr Lys Leu Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265

<210> SEQ ID NO 243
<211> LENGTH: 798
<212> TYPE: DNA
<213> ORGANISM: Artificial Sequence
<220> FEATURE:
<223> OTHER INFORMATION: chemically synthesized

<400> SEQUENCE: 243
cagggccagt ctggacaggg cctgtgtcac cctgccgtgc tgtctgcctg ggagtcctgt     60
tcctccggcg gtggctcctc tggcggctcc atctcctctg cctgctgtc cggcagatcc    120
gacaaccacg gcggaggcag cgacatcgtg atgacccagt ccccctgtc cctgccgtg    180
acacctggcg agcctgcctc catcagctgc cggtcctcca gtccctgct gcactccaac    240
ggcatcacct acctgtactg gtatctgcag aagcccggcc agtcccctca gctgctgatc    300
taccagatgt ccaacctggc ctccggcgtg cccgacagat ctccggctc tggctccggc    360
accgacttca ccctgaagat ctcccgggtg aagccgagg acgtgggcgt gtactactgc    420
gcccagaacc tggaactgcc ctacaccttc ggccagggca ccaagctgga aatcaagcgg    480
accgtggccg ctccctccgt gttcatcttc caccctccg acgagcagct gaagtccggc    540
accgcctccg tcgtgtgcct gctgaacaac ttctaccctc gcgaggccaa ggtgcagtgg    600
aaggtggaca cgccctgca gtccggcaac tcccaggaat ccgtcaccga gcaggactcc    660
aaggacagca cctactccct gtcctccacc ctgaccctgt ccaaggccga ctacgagaag    720
cacaaggtgt acgcctgcga agtgacccac cagggcctga gcagcccgt gaccaagtcc    780
ttcaaccgcg gcgagtgc                                                  798

<210> SEQ ID NO 244
<211> LENGTH: 266
<212> TYPE: PRT
<213> ORGANISM: Artificial Sequence
<220> FEATURE:
<223> OTHER INFORMATION: chemically synthesized

<400> SEQUENCE: 244

```
Gln Gly Gln Ser Gly Gln Gly Leu Cys His Pro Leu Val Ala Ser Ala
1               5                   10                  15

Trp Glu Ser Cys Ser Ser Gly Gly Ser Ser Gly Gly Ser Ile Ser
            20                  25                  30

Ser Gly Leu Leu Ser Gly Arg Ser Asp Asn His Gly Gly Gly Ser Asp
            35                  40                  45

Ile Val Met Thr Gln Ser Pro Leu Ser Leu Pro Val Thr Pro Gly Glu
            50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
                100                 105                 110

Arg Phe Ser Gly Ser Gly Ser Gly Thr Asp Phe Thr Leu Lys Ile Ser
            115                 120                 125

Arg Val Glu Ala Glu Asp Val Gly Val Tyr Tyr Cys Ala Gln Asn Leu
            130                 135                 140

Glu Leu Pro Tyr Thr Phe Gly Gln Gly Thr Lys Leu Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
            195                 200                 205

Gly Asn Ser Gln Glu Ser Val Thr Glu Gln Asp Ser Lys Asp Ser Thr
210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265
```

<210> SEQ ID NO 245
<211> LENGTH: 798
<212> TYPE: DNA
<213> ORGANISM: Artificial Sequence
<220> FEATURE:
<223> OTHER INFORMATION: chemically synthesized

<400> SEQUENCE: 245

```
cagggccagt ctggacaggg cctgtgtcac cctctggtgg cctctgcctg ggagtcctgt      60
tcctccggcg gtggctcctc tggcggctcc atctcctctg gcctgctgtc cggcagatcc     120
gacaaccacg gcggaggcag cgacatcgtg atgacccagt cccccctgtc cctgccggtg     180
acacctggcg agcctgcctc catcagctgc cggtcctcca gtccctgct gcactccaac     240
ggcatcacct acctgtactg gtatctgcag aagcccggcc agtcccctca gctgctgatc     300
taccagatgt ccaacctggc ctccggcgtg cccgacagat ctccggctc tggctccggc     360
accgacttca ccctgaagat ctcccgcgtg gaagccgagg acgtgggcgt gtactactgc     420
gcccagaacc tggaactgcc ctacaccttc ggcagggca ccaagctgga aatcaagcgg     480
accgtggccg ctcccctccgt gttcatcttc ccacctccg acgagcagct gaagtccggc     540
```

```
accgcctccg tcgtgtgcct gctgaacaac ttctacccc gcgaggccaa ggtgcagtgg    600
aaggtggaca cgccctgca gtccggcaac tcccaggaat ccgtcaccga gcaggactcc    660
aaggacagca cctactccct gtcctccacc ctgaccctgt ccaaggccga ctacgagaag    720
cacaaggtgt acgcctgcga agtgacccac cagggcctga gcagcccgt gaccaagtcc    780 ttcaaccgcg cgagtgc                                                  798
```

<210> SEQ ID NO 246
<211> LENGTH: 270
<212> TYPE: PRT
<213> ORGANISM: Artificial Sequence
<220> FEATURE:
<223> OTHER INFORMATION: chemically synthesized

<400> SEQUENCE: 246

```
Gln Gly Gln Ser Gly Gln Gly Leu Cys His Pro Ala Val Leu Ser Ala
1               5                   10                  15

Trp Glu Ser Cys Ser Ser Gly Gly Ser Gly Gly Ser Ala Val
            20                  25                  30

Gly Leu Leu Ala Pro Pro Gly Gly Leu Ser Gly Arg Ser Asp Asn His
        35                  40                  45

Gly Gly Ser Asp Ile Val Met Thr Gln Ser Pro Leu Ser Leu Pro Val
    50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
        115                 120                 125

Leu Lys Ile Ser Arg Val Glu Ala Glu Asp Val Gly Val Tyr Tyr Cys
    130                 135                 140

Ala Gln Asn Leu Glu Leu Pro Tyr Thr Phe Gly Gln Gly Thr Lys Leu
145                 150                 155                 160

Glu Ile Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
            180                 185                 190

Asn Asn Phe Tyr Pro Arg Glu Ala Lys Val Gln Trp Lys Val Asp Asn
        195                 200                 205

Ala Leu Gln Ser Gly Asn Ser Gln Glu Ser Val Thr Glu Gln Asp Ser
    210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
            260                 265                 270
```

<210> SEQ ID NO 247
<211> LENGTH: 810
<212> TYPE: DNA
<213> ORGANISM: Artificial Sequence
<220> FEATURE:
<223> OTHER INFORMATION: chemically synthesized

<400> SEQUENCE: 247

```
cagggacagt ctggccaggg cctgtgtcac cctgctgtgc tgtctgcctg ggagtcctgt    60
tccagcggcg gaggctcctc tggcggctct gctgtgggcc tgctggctcc acctggcggc   120
ctgtccggca gatctgacaa ccacggcggc tccgacatcg tgatgaccca gtccccctg    180
tccctgcccg tgactcctgg cgagcctgcc tccatctcct gccggtcctc caagtccctg   240
ctgcactcca acggcatcac ctacctgtac tggtatctgc agaagcccgg ccagtcccct   300
cagctgctga tctaccagat gtccaacctg gcctccggcg tgcccgacag attctccggc   360
tctggctccg gcaccgactt caccctgaag atctcccggg tggaagccga ggacgtgggc   420
gtgtactact gcgcccagaa cctggaactg ccctacacct tcggccaggg caccaagctg   480
gaaatcaagc ggaccgtggc cgctccctcc gtgttcatct cccaccctc cgacgagcag   540
ctgaagtccg gcaccgcctc cgtggtctgc ctgctgaaca acttctaccc ccgcgaggcc   600
aaggtgcagt ggaaggtgga caacgccctg cagtccggca actcccagga atccgtcacc   660
gagcaggact ccaaggacag cacctactcc ctgtcctcca ccctgaccct gtccaaggcc   720
gactacgaga agcacaaggt gtacgcctgc gaagtgaccc accagggact gagcagcccc   780
gtgaccaagt ccttcaaccg gggcgagtgc                                    810
```

<210> SEQ ID NO 248
<211> LENGTH: 265
<212> TYPE: PRT
<213> ORGANISM: Artificial Sequence
<220> FEATURE:
<223> OTHER INFORMATION: chemically synthesized

<400> SEQUENCE: 248

```
Gln Gly Leu Cys His Pro Leu Val Ala Ser Ala Trp Glu Ser Cys Ser
 1               5                  10                  15
Ser Gly Gly Gly Ser Ser Gly Gly Ser Ala Val Gly Leu Leu Ala Pro
            20                  25                  30
Pro Gly Gly Leu Ser Gly Arg Ser Asp Asn His Gly Gly Ser Asp Ile
        35                  40                  45
Val Met Thr Gln Ser Pro Leu Ser Leu Pro Val Thr Pro Gly Glu Pro
    50                  55                  60
Ala Ser Ile Ser Cys Arg Ser Ser Lys Ser Leu Leu His Ser Asn Gly
65                  70                  75                  80
Ile Thr Tyr Leu Tyr Trp Tyr Leu Gln Lys Pro Gly Gln Ser Pro Gln
                85                  90                  95
Leu Leu Ile Tyr Gln Met Ser Asn Leu Ala Ser Gly Val Pro Asp Arg
            100                 105                 110
Phe Ser Gly Ser Gly Ser Gly Thr Asp Phe Thr Leu Lys Ile Ser Arg
        115                 120                 125
Val Glu Ala Glu Asp Val Gly Val Tyr Tyr Cys Ala Gln Asn Leu Glu
    130                 135                 140
Leu Pro Tyr Thr Phe Gly Gln Gly Thr Lys Leu Glu Ile Lys Arg Thr
145                 150                 155                 160
Val Ala Ala Pro Ser Val Phe Ile Phe Pro Pro Ser Asp Glu Gln Leu
                165                 170                 175
Lys Ser Gly Thr Ala Ser Val Val Cys Leu Leu Asn Asn Phe Tyr Pro
            180                 185                 190
Arg Glu Ala Lys Val Gln Trp Lys Val Asp Asn Ala Leu Gln Ser Gly
        195                 200                 205
```

```
Asn Ser Gln Glu Ser Val Thr Glu Gln Asp Ser Lys Asp Ser Thr Tyr
        210                 215                 220
Ser Leu Ser Ser Thr Leu Thr Leu Ser Lys Ala Asp Tyr Glu Lys His
225                 230                 235                 240
Lys Val Tyr Ala Cys Glu Val Thr His Gln Gly Leu Ser Ser Pro Val
                245                 250                 255
Thr Lys Ser Phe Asn Arg Gly Glu Cys
            260                 265

<210> SEQ ID NO 249
<211> LENGTH: 115
<212> TYPE: PRT
<213> ORGANISM: Artificial Sequence
<220> FEATURE:
<223> OTHER INFORMATION: chemically synthesized

<400> SEQUENCE: 249

Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asp Thr Leu Tyr
65                  70                  75                  80
Leu Gln Met Asn Ser Leu Arg Ala Glu Asp Thr Ala Val Tyr Tyr Cys
                85                  90                  95
Ala Ser Arg Ser Leu Leu Asp Tyr Trp Gly Gln Gly Thr Leu Val Thr
            100                 105                 110
Val Ser Ser
        115

<210> SEQ ID NO 250
<211> LENGTH: 115
<212> TYPE: PRT
<213> ORGANISM: Artificial Sequence
<220> FEATURE:
<223> OTHER INFORMATION: chemically synthesized

<400> SEQUENCE: 250

Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Gly Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asp Thr Leu Tyr
65                  70                  75                  80
Leu Gln Met Asn Ser Leu Arg Ala Glu Asp Thr Ala Val Tyr Tyr Cys
                85                  90                  95
Ala Ser Arg Ser Leu Leu Asp Tyr Trp Gly Gln Gly Thr Leu Val Thr
            100                 105                 110
Val Ser Ser
        115
```

<210> SEQ ID NO 251
<211> LENGTH: 107
<212> TYPE: PRT
<213> ORGANISM: Artificial Sequence
<220> FEATURE:
<223> OTHER INFORMATION: chemically synthesized

<400> SEQUENCE: 251

Asn Phe Met Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Leu Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Pro
                85                  90                  95

Val Phe Gly Gly Gly Thr Lys Val Thr Val Leu
            100                 105

<210> SEQ ID NO 252
<211> LENGTH: 116
<212> TYPE: PRT
<213> ORGANISM: Artificial Sequence
<220> FEATURE:
<223> OTHER INFORMATION: chemically synthesized

<400> SEQUENCE: 252

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Val Val Glu Phe Trp Gly Gln Gly Thr Leu Val
            100                 105                 110

Thr Val Ser Ser
        115

<210> SEQ ID NO 253
<211> LENGTH: 108
<212> TYPE: PRT
<213> ORGANISM: Artificial Sequence
<220> FEATURE:
<223> OTHER INFORMATION: chemically synthesized

<400> SEQUENCE: 253

Asp Ile Arg Met Thr Gln Ser Pro Ser Phe Leu Ser Ala Ser Val Gly
1               5                   10                  15

Asp Arg Val Thr Ile Thr Cys Arg Ala Ser Gln Asp Ile Ser Ser Tyr
            20                  25                  30

Phe Ala Trp Tyr Gln Gln Lys Pro Gly Lys Ala Pro Lys Leu Leu Ile
        35                  40                  45

Tyr Ala Ala Ser Thr Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Ile Thr Phe Gly Gln Gly Thr Arg Leu Glu Ile Lys
            100                 105

<210> SEQ ID NO 254
<211> LENGTH: 115
<212> TYPE: PRT
<213> ORGANISM: Artificial Sequence
<220> FEATURE:
<223> OTHER INFORMATION: chemically synthesized

<400> SEQUENCE: 254

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ile Val Ala Thr Ser Trp Gly Gln Gly Thr Leu Val Thr
            100                 105                 110

Val Ser Arg
        115

<210> SEQ ID NO 255
<211> LENGTH: 114
<212> TYPE: PRT
<213> ORGANISM: Artificial Sequence
<220> FEATURE:
<223> OTHER INFORMATION: chemically synthesized

<400> SEQUENCE: 255

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Asn Phe Asp Val Tyr
            20                  25                  30

Gly Met Asn Trp Val Arg Gln Val Pro Gly Lys Gly Leu Glu Trp Val
        35                  40                  45

Ser Leu Ile Asn Gly Asp Gly Leu Arg Tyr Tyr Ala Asp Ser Val
 50                  55                  60

Lys Gly Arg Phe Thr Val Ser Arg Asp Asn Ser Arg Asn Ser Leu Tyr
65                  70                  75                  80

Leu Gln Met Asn Ser Leu Arg Ser Glu Asp Thr Ala Leu Tyr Tyr Cys
                85                  90                  95

```
Val Lys Gly Asn Phe Gln Gln Trp Gly Gln Gly Thr Leu Val Thr Val
            100                 105                 110
Ser Arg

<210> SEQ ID NO 256
<211> LENGTH: 115
<212> TYPE: PRT
<213> ORGANISM: Artificial Sequence
<220> FEATURE:
<223> OTHER INFORMATION: chemically synthesized

<400> SEQUENCE: 256

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Leu Ile Ser Gly Asp Gly Gly Ser Thr Tyr Tyr Ala Asp Ser Val
    50                  55                  60

Lys Asp Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asn Tyr Phe Asp Tyr Trp Gly Gln Gly Thr Leu Val Thr
            100                 105                 110

Val Ser Arg
        115

<210> SEQ ID NO 257
<211> LENGTH: 122
<212> TYPE: PRT
<213> ORGANISM: Artificial Sequence
<220> FEATURE:
<223> OTHER INFORMATION: chemically synthesized

<400> SEQUENCE: 257

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Val Met Pro Ser Tyr Tyr Tyr Tyr Gly Met Asp Val Trp
            100                 105                 110

Gly Gln Gly Thr Thr Val Thr Val Ser Arg
        115                 120

<210> SEQ ID NO 258
<211> LENGTH: 114
<212> TYPE: PRT
<213> ORGANISM: Artificial Sequence
```

```
<220> FEATURE:
<223> OTHER INFORMATION: chemically synthesized

<400> SEQUENCE: 258

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asp Tyr Gly Met Asp Val Trp Gly Gln Gly Thr Thr Val Thr Val
            100                 105                 110

Ser Arg

<210> SEQ ID NO 259
<211> LENGTH: 108
<212> TYPE: PRT
<213> ORGANISM: Artificial Sequence
<220> FEATURE:
<223> OTHER INFORMATION: chemically synthesized

<400> SEQUENCE: 259

Ser Tyr Glu Leu Thr Gln Pro Pro Ser Val Ser Val Ala Pro Gly Gln
1               5                   10                  15

Thr Ala Arg Ile Thr Cys Gly Gly Asn Lys Ile Gly Ser Lys Ser Val
            20                  25                  30

His Trp Tyr Gln Gln Lys Gln Gly Gln Ala Pro Val Leu Val Ile Tyr
        35                  40                  45

Leu Asp Arg Asp Arg Pro Ser Gly Ile Pro Glu Arg Phe Ser Gly Ser
    50                  55                  60

Asn Ser Gly Asn Thr Ala Thr Leu Thr Ile Thr Arg Val Glu Ala Glu
65                  70                  75                  80

Asp Glu Ala Asp Tyr Tyr Cys His Leu Trp Asp Ser Gly Ser Asp Gln
                85                  90                  95

Val Phe Gly Gly Gly Thr Lys Leu Thr Val Leu Gly
            100                 105

<210> SEQ ID NO 260
<211> LENGTH: 109
<212> TYPE: PRT
<213> ORGANISM: Artificial Sequence
<220> FEATURE:
<223> OTHER INFORMATION: chemically synthesized

<400> SEQUENCE: 260

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
```

```
                50                  55                  60
Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                 85                  90                  95

Val Val Phe Gly Gly Gly Thr Lys Leu Thr Val Leu Gly
            100                 105

<210> SEQ ID NO 261
<211> LENGTH: 106
<212> TYPE: PRT
<213> ORGANISM: Artificial Sequence
<220> FEATURE:
<223> OTHER INFORMATION: chemically synthesized

<400> SEQUENCE: 261

Ser Tyr Glu Leu Thr Gln Pro Leu Ser Val Ser Val Ala Leu Gly Gln
  1               5                  10                  15

Thr Ala Arg Ile Thr Cys Gly Gly Asn Asn Ile Gly Ser Lys Asn Val
             20                  25                  30

His Trp Tyr Gln Gln Lys Pro Gly Gln Ala Pro Val Leu Val Ile Tyr
         35                  40                  45

Arg Asp Ser Asn Arg Pro Ser Gly Ile Pro Glu Arg Phe Ser Gly Ser
     50                  55                  60

Asn Ser Gly Asn Thr Ala Thr Leu Thr Ile Ser Arg Ala Gln Ala Gly
 65                  70                  75                  80

Asp Glu Ala Asp Tyr Tyr Cys Gln Val Trp Asp Ser Ser Val Val Phe
                 85                  90                  95

Gly Gly Gly Thr Lys Leu Thr Val Leu Gly
            100                 105

<210> SEQ ID NO 262
<211> LENGTH: 111
<212> TYPE: PRT
<213> ORGANISM: Artificial Sequence
<220> FEATURE:
<223> OTHER INFORMATION: chemically synthesized

<400> SEQUENCE: 262

Asn Phe Met Leu Thr Gln Pro His Ser Val Ser Glu Ser Pro Gly Lys
  1               5                  10                  15

Thr Val Thr Ile Ser Cys Thr Gly Ser Ser Gly Ser Ile Ala Ser Asn
             20                  25                  30

Tyr Val Gln Trp Tyr Gln Gln Arg Pro Gly Ser Ala Pro Thr Thr Val
         35                  40                  45

Ile Tyr Glu Asp Ser Glu Arg Pro Ser Gly Val Pro Asp Arg Phe Ser
     50                  55                  60

Gly Ser Ile Asp Ser Ser Asn Ser Ala Ser Leu Thr Ile Ser Gly
 65                  70                  75                  80

Leu Lys Thr Gln Asp Glu Ala Asp Tyr Tyr Cys Gln Ser Tyr Asp Gly
                 85                  90                  95

Val Asn Trp Val Phe Gly Gly Gly Thr Lys Leu Thr Val Leu Gly
            100                 105                 110

<210> SEQ ID NO 263
<211> LENGTH: 107
<212> TYPE: PRT
<213> ORGANISM: Artificial Sequence
<220> FEATURE:
```

<223> OTHER INFORMATION: chemically synthesized

<400> SEQUENCE: 263

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Val
                85                  90                  95

Thr Phe Gly Gln Gly Thr Lys Val Glu Ile Lys
            100                 105

<210> SEQ ID NO 264
<211> LENGTH: 11
<212> TYPE: PRT
<213> ORGANISM: Artificial Sequence
<220> FEATURE:
<223> OTHER INFORMATION: chemically synthesized

<400> SEQUENCE: 264

Gln Gly Asp Ser Leu Arg Ser Tyr Tyr Ala Ser
1               5                   10

<210> SEQ ID NO 265
<211> LENGTH: 8
<212> TYPE: PRT
<213> ORGANISM: Artificial Sequence
<220> FEATURE:
<223> OTHER INFORMATION: chemically synthesized

<400> SEQUENCE: 265

Tyr Gly Lys Asn Asn Arg Pro Ser
1               5

<210> SEQ ID NO 266
<211> LENGTH: 10
<212> TYPE: PRT
<213> ORGANISM: Artificial Sequence
<220> FEATURE:
<223> OTHER INFORMATION: chemically synthesized

<400> SEQUENCE: 266

Asn Ser Arg Asp Ser Ser Gly Asn Pro Val
1               5                   10

<210> SEQ ID NO 267
<211> LENGTH: 5
<212> TYPE: PRT
<213> ORGANISM: Artificial Sequence
<220> FEATURE:
<223> OTHER INFORMATION: chemically synthesized

<400> SEQUENCE: 267

Ser Tyr Ala Met Ser
1               5

<210> SEQ ID NO 268

```
<211> LENGTH: 17
<212> TYPE: PRT
<213> ORGANISM: Artificial Sequence
<220> FEATURE:
<223> OTHER INFORMATION: chemically synthesized

<400> SEQUENCE: 268

Ala Ile Ser Gly Ser Gly Gly Ser Thr Tyr Tyr Ala Asp Ser Val Lys
1               5                   10                  15
Gly

<210> SEQ ID NO 269
<211> LENGTH: 6
<212> TYPE: PRT
<213> ORGANISM: Artificial Sequence
<220> FEATURE:
<223> OTHER INFORMATION: chemically synthesized

<400> SEQUENCE: 269

Arg Ser Leu Leu Asp Tyr
1               5

<210> SEQ ID NO 270
<211> LENGTH: 11
<212> TYPE: PRT
<213> ORGANISM: Artificial Sequence
<220> FEATURE:
<223> OTHER INFORMATION: chemically synthesized

<400> SEQUENCE: 270

Arg Ala Ser Gln Asp Ile Ser Ser Tyr Phe Ala
1               5                   10

<210> SEQ ID NO 271
<211> LENGTH: 7
<212> TYPE: PRT
<213> ORGANISM: Artificial Sequence
<220> FEATURE:
<223> OTHER INFORMATION: chemically synthesized

<400> SEQUENCE: 271

Ala Ala Ser Thr Leu Arg Ser
1               5

<210> SEQ ID NO 272
<211> LENGTH: 10
<212> TYPE: PRT
<213> ORGANISM: Artificial Sequence
<220> FEATURE:
<223> OTHER INFORMATION: chemically synthesized

<400> SEQUENCE: 272

Gln Gln Ser Tyr Ser Thr Pro Arg Ile Thr
1               5                   10

<210> SEQ ID NO 273
<211> LENGTH: 7
<212> TYPE: PRT
<213> ORGANISM: Artificial Sequence
<220> FEATURE:
<223> OTHER INFORMATION: chemically synthesized

<400> SEQUENCE: 273

Gly Gly Gly Val Val Glu Phe
1               5
```

```
<210> SEQ ID NO 274
<211> LENGTH: 11
<212> TYPE: PRT
<213> ORGANISM: Artificial Sequence
<220> FEATURE:
<223> OTHER INFORMATION: chemically synthesized

<400> SEQUENCE: 274

Gly Gly Asn Lys Ile Gly Ser Lys Ser Val His
1               5                   10

<210> SEQ ID NO 275
<211> LENGTH: 7
<212> TYPE: PRT
<213> ORGANISM: Artificial Sequence
<220> FEATURE:
<223> OTHER INFORMATION: chemically synthesized

<400> SEQUENCE: 275

Leu Asp Arg Asp Arg Pro Ser
1               5

<210> SEQ ID NO 276
<211> LENGTH: 8
<212> TYPE: PRT
<213> ORGANISM: Artificial Sequence
<220> FEATURE:
<223> OTHER INFORMATION: chemically synthesized

<400> SEQUENCE: 276

His Leu Trp Asp Ser Gly Ser Asp
1               5

<210> SEQ ID NO 277
<211> LENGTH: 17
<212> TYPE: PRT
<213> ORGANISM: Artificial Sequence
<220> FEATURE:
<223> OTHER INFORMATION: chemically synthesized

<400> SEQUENCE: 277

Thr Ile Ser Gly Ser Gly Gly Ser Thr Tyr Tyr Ala Asp Ser Val Lys
1               5                   10                  15

Gly

<210> SEQ ID NO 278
<211> LENGTH: 6
<212> TYPE: PRT
<213> ORGANISM: Artificial Sequence
<220> FEATURE:
<223> OTHER INFORMATION: chemically synthesized

<400> SEQUENCE: 278

Gly Ile Val Ala Thr Ser
1               5

<210> SEQ ID NO 279
<211> LENGTH: 11
<212> TYPE: PRT
<213> ORGANISM: Artificial Sequence
<220> FEATURE:
<223> OTHER INFORMATION: chemically synthesized

<400> SEQUENCE: 279

Gly Gly Asn Asn Ile Gly Ser Lys Ser Val His
1               5                   10
```

<210> SEQ ID NO 280
<211> LENGTH: 7
<212> TYPE: PRT
<213> ORGANISM: Artificial Sequence
<220> FEATURE:
<223> OTHER INFORMATION: chemically synthesized

<400> SEQUENCE: 280

Tyr Asp Ser Asp Arg Pro Ser
1               5

<210> SEQ ID NO 281
<211> LENGTH: 9
<212> TYPE: PRT
<213> ORGANISM: Artificial Sequence
<220> FEATURE:
<223> OTHER INFORMATION: chemically synthesized

<400> SEQUENCE: 281

Gln Val Trp Asp Ser Ser Ser Asp His
1               5

<210> SEQ ID NO 282
<211> LENGTH: 5
<212> TYPE: PRT
<213> ORGANISM: Artificial Sequence
<220> FEATURE:
<223> OTHER INFORMATION: chemically synthesized

<400> SEQUENCE: 282

Val Tyr Gly Met Asn
1               5

<210> SEQ ID NO 283
<211> LENGTH: 17
<212> TYPE: PRT
<213> ORGANISM: Artificial Sequence
<220> FEATURE:
<223> OTHER INFORMATION: chemically synthesized

<400> SEQUENCE: 283

Leu Ile Asn Gly Asp Gly Gly Leu Arg Tyr Tyr Ala Asp Ser Val Lys
1               5                   10                  15

Gly

<210> SEQ ID NO 284
<211> LENGTH: 5
<212> TYPE: PRT
<213> ORGANISM: Artificial Sequence
<220> FEATURE:
<223> OTHER INFORMATION: chemically synthesized

<400> SEQUENCE: 284

Gly Asn Phe Gln Gln
1               5

<210> SEQ ID NO 285
<211> LENGTH: 11
<212> TYPE: PRT
<213> ORGANISM: Artificial Sequence
<220> FEATURE:
<223> OTHER INFORMATION: chemically synthesized

<400> SEQUENCE: 285

Gly Gly Asn Asn Ile Gly Ser Lys Asn Val His
1               5                   10

<210> SEQ ID NO 286
<211> LENGTH: 7
<212> TYPE: PRT
<213> ORGANISM: Artificial Sequence
<220> FEATURE:
<223> OTHER INFORMATION: chemically synthesized

<400> SEQUENCE: 286

Arg Asp Ser Asn Arg Pro Ser
1               5

<210> SEQ ID NO 287
<211> LENGTH: 6
<212> TYPE: PRT
<213> ORGANISM: Artificial Sequence
<220> FEATURE:
<223> OTHER INFORMATION: chemically synthesized

<400> SEQUENCE: 287

Gln Val Trp Asp Ser Ser
1               5

<210> SEQ ID NO 288
<211> LENGTH: 5
<212> TYPE: PRT
<213> ORGANISM: Artificial Sequence
<220> FEATURE:
<223> OTHER INFORMATION: chemically synthesized

<400> SEQUENCE: 288

Asp Tyr Ala Met His
1               5

<210> SEQ ID NO 289
<211> LENGTH: 17
<212> TYPE: PRT
<213> ORGANISM: Artificial Sequence
<220> FEATURE:
<223> OTHER INFORMATION: chemically synthesized

<400> SEQUENCE: 289

Leu Ile Ser Gly Asp Gly Gly Ser Thr Tyr Tyr Ala Asp Ser Val Lys
1               5                   10                  15

Asp

<210> SEQ ID NO 290
<211> LENGTH: 6
<212> TYPE: PRT
<213> ORGANISM: Artificial Sequence
<220> FEATURE:
<223> OTHER INFORMATION: chemically synthesized

<400> SEQUENCE: 290

Gly Asn Tyr Phe Asp Tyr
1               5

<210> SEQ ID NO 291
<211> LENGTH: 13
<212> TYPE: PRT
<213> ORGANISM: Artificial Sequence
<220> FEATURE:
<223> OTHER INFORMATION: chemically synthesized

<400> SEQUENCE: 291

Thr Gly Ser Ser Gly Ser Ile Ala Ser Asn Tyr Val Gln

```
1               5               10

<210> SEQ ID NO 292
<211> LENGTH: 7
<212> TYPE: PRT
<213> ORGANISM: Artificial Sequence
<220> FEATURE:
<223> OTHER INFORMATION: chemically synthesized

<400> SEQUENCE: 292

Glu Asp Ser Glu Arg Pro Ser
1               5

<210> SEQ ID NO 293
<211> LENGTH: 7
<212> TYPE: PRT
<213> ORGANISM: Artificial Sequence
<220> FEATURE:
<223> OTHER INFORMATION: chemically synthesized

<400> SEQUENCE: 293

Gln Ser Tyr Asp Gly Val Asn
1               5

<210> SEQ ID NO 294
<211> LENGTH: 5
<212> TYPE: PRT
<213> ORGANISM: Artificial Sequence
<220> FEATURE:
<223> OTHER INFORMATION: chemically synthesized

<400> SEQUENCE: 294

Ser Tyr Ser Met Asn
1               5

<210> SEQ ID NO 295
<211> LENGTH: 17
<212> TYPE: PRT
<213> ORGANISM: Artificial Sequence
<220> FEATURE:
<223> OTHER INFORMATION: chemically synthesized

<400> SEQUENCE: 295

Tyr Ile Ser Ser Ser Ser Ser Thr Ile Tyr Tyr Ala Asp Ser Val Lys
1               5                   10                  15

Gly

<210> SEQ ID NO 296
<211> LENGTH: 13
<212> TYPE: PRT
<213> ORGANISM: Artificial Sequence
<220> FEATURE:
<223> OTHER INFORMATION: chemically synthesized

<400> SEQUENCE: 296

Val Met Pro Ser Tyr Tyr Tyr Tyr Gly Met Asp Val
1               5                   10

<210> SEQ ID NO 297
<211> LENGTH: 11
<212> TYPE: PRT
<213> ORGANISM: Artificial Sequence
<220> FEATURE:
<223> OTHER INFORMATION: chemically synthesized

<400> SEQUENCE: 297
```

Arg Ala Ser Gln Ser Ile Ser Ser Tyr Leu Asn
1               5                   10

<210> SEQ ID NO 298
<211> LENGTH: 7
<212> TYPE: PRT
<213> ORGANISM: Artificial Sequence
<220> FEATURE:
<223> OTHER INFORMATION: chemically synthesized

<400> SEQUENCE: 298

Ala Ala Ser Ser Leu Gln Ser
1               5

<210> SEQ ID NO 299
<211> LENGTH: 7
<212> TYPE: PRT
<213> ORGANISM: Artificial Sequence
<220> FEATURE:
<223> OTHER INFORMATION: chemically synthesized

<400> SEQUENCE: 299

Gln Gln Ser Tyr Ser Thr Pro
1               5

<210> SEQ ID NO 300
<211> LENGTH: 5
<212> TYPE: PRT
<213> ORGANISM: Artificial Sequence
<220> FEATURE:
<223> OTHER INFORMATION: chemically synthesized

<400> SEQUENCE: 300

Ser Tyr Gly Met His
1               5

<210> SEQ ID NO 301
<211> LENGTH: 17
<212> TYPE: PRT
<213> ORGANISM: Artificial Sequence
<220> FEATURE:
<223> OTHER INFORMATION: chemically synthesized

<400> SEQUENCE: 301

Val Ile Ser Tyr Asp Gly Ser Asn Lys Tyr Tyr Ala Asp Ser Val Lys
1               5                   10                  15

Gly

<210> SEQ ID NO 302
<211> LENGTH: 5
<212> TYPE: PRT
<213> ORGANISM: Artificial Sequence
<220> FEATURE:
<223> OTHER INFORMATION: chemically synthesized

<400> SEQUENCE: 302

Tyr Gly Met Asp Val
1               5

<210> SEQ ID NO 303
<211> LENGTH: 270
<212> TYPE: PRT
<213> ORGANISM: Artificial Sequence
<220> FEATURE:
<223> OTHER INFORMATION: chemically synthesized

<400> SEQUENCE: 303

Gln Gly Gln Ser Gly Gln Gly Leu Cys His Pro Leu Val Ala Ser Ala
1               5                   10                  15

Trp Glu Ser Cys Ser Ser Gly Gly Ser Ser Gly Gly Ser Ala Val
            20                  25                  30

Gly Leu Leu Ala Pro Pro Gly Gly Leu Ser Gly Arg Ser Asp Asn His
            35                  40                  45

Gly Gly Ser Asp Ile Val Met Thr Gln Ser Pro Leu Ser Leu Pro Val
50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
            115                 120                 125

Leu Lys Ile Ser Arg Val Glu Ala Glu Asp Val Gly Val Tyr Tyr Cys
        130                 135                 140

Ala Gln Asn Leu Glu Leu Pro Tyr Thr Phe Gly Gln Gly Thr Lys Leu
145                 150                 155                 160

Glu Ile Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
            180                 185                 190

Asn Asn Phe Tyr Pro Arg Glu Ala Lys Val Gln Trp Lys Val Asp Asn
            195                 200                 205

Ala Leu Gln Ser Gly Asn Ser Gln Glu Ser Val Thr Glu Gln Asp Ser
210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
            260                 265                 270

<210> SEQ ID NO 304
<211> LENGTH: 810
<212> TYPE: DNA
<213> ORGANISM: Artificial Sequence
<220> FEATURE:
<223> OTHER INFORMATION: chemically synthesized

<400> SEQUENCE: 304
cagggccagt ctggccaggg cctgtgtcac cctctggtgg cctctgcctg ggagtcctgt        60
tcctccggcg gaggctcctc tggcggctct gctgtgggcc tgctggctcc acctggcggc       120
ctgtccggca gatctgacaa ccacggcggc tccgacatcg tgatgaccca gtccccctg        180 tccctgcccg tgactcctgg cgagcctgcc tccatctcct gccggtcctc caagtccctg       240
ctgcactcca acggcatcac ctacctgtac tggtatctgc agaagcccgg ccagtcccct       300
cagctgctga tctaccagat gtccaacctg gcctccggcg tgcccgacag attctccggc       360
tctggctccg gcaccgactt caccctgaag atctcccggg tggaagccga ggacgtgggc       420
gtgtactact gcgcccagaa cctggaactg ccctacacct tcggccaggg caccaagctg       480
gaaatcaagc ggaccgtggc cgctcccctc cgtgttcatc tcccacccte cgacgagcag       540

```
ctgaagtccg gcaccgcctc cgtcgtgtgc ctgctgaaca acttctaccc ccgcgaggcc    600
aaggtgcagt ggaaggtgga caacgccctg cagtccggca actcccagga atccgtgacc    660
gagcaggact ccaaggacag cacctactcc ctgtcctcca ccctgaccct gtccaaggcc    720
gactacgaga agcacaaggt gtacgcctgc gaagtgaccc accagggcct gagcagcccc    780
gtgaccaagt ccttcaaccg gggcgagtgc                                     810
```

```
<210> SEQ ID NO 305
<211> LENGTH: 7
<212> TYPE: PRT
<213> ORGANISM: Artificial Sequence
<220> FEATURE:
<223> OTHER INFORMATION: chemically synthesized

<400> SEQUENCE: 305

Gln Gly Gln Ser Gly Gln Gly
1               5

<210> SEQ ID NO 306
<211> LENGTH: 5
<212> TYPE: PRT
<213> ORGANISM: Artificial Sequence
<220> FEATURE:
<223> OTHER INFORMATION: chemically synthesized

<400> SEQUENCE: 306

Gln Gly Gln Ser Gly
1               5

<210> SEQ ID NO 307
<211> LENGTH: 4
<212> TYPE: PRT
<213> ORGANISM: Artificial Sequence
<220> FEATURE:
<223> OTHER INFORMATION: chemically synthesized

<400> SEQUENCE: 307

Gln Gly Gln Ser
1

<210> SEQ ID NO 308
<211> LENGTH: 3
<212> TYPE: PRT
<213> ORGANISM: Artificial Sequence
<220> FEATURE:
<223> OTHER INFORMATION: chemically synthesized

<400> SEQUENCE: 308

Gln Gly Gln
1

<210> SEQ ID NO 309
<211> LENGTH: 2
<212> TYPE: PRT
<213> ORGANISM: Artificial Sequence
<220> FEATURE:
<223> OTHER INFORMATION: chemically synthesized

<400> SEQUENCE: 309

Gln Gly
1

<210> SEQ ID NO 310
<211> LENGTH: 259
```

```
<212> TYPE: PRT
<213> ORGANISM: Artificial Sequence
<220> FEATURE:
<223> OTHER INFORMATION: chemically synthesized

<400> SEQUENCE: 310

Leu Cys His Pro Ala Val Leu Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Asp Asn His Gly Gly Ser Asp Ile Val Met Thr Gln Ser Pro
            35                  40                  45

Leu Ser Leu Pro Val Thr Pro Gly Glu Pro Ala Ser Ile Ser Cys Arg
50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
            115                 120                 125

Gly Val Tyr Tyr Cys Ala Gln Asn Leu Glu Leu Pro Tyr Thr Phe Gly
130                 135                 140

Gln Gly Thr Lys Leu Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
            195                 200                 205

Thr Glu Gln Asp Ser Lys Asp Ser Thr Tyr Ser Leu Ser Ser Thr Leu
210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 311
<211> LENGTH: 777
<212> TYPE: DNA
<213> ORGANISM: Artificial Sequence
<220> FEATURE:
<223> OTHER INFORMATION: chemically synthesized

<400> SEQUENCE: 311
ctgtgtcacc ctgccgtgct gtctgcctgg gagtcctgtt cctccggcgg tggctcctct      60
ggcggctcca tctcctctgg cctgctgtcc ggcagatccg acaaccacgg cggaggcagc     120
gacatcgtga tgacccagtc ccccctgtcc ctgcccgtga cacctggcga gcctgcctcc     180
atcagctgcc ggtcctccaa gtccctgctg cactccaacg gcatcaccta cctgtactgg     240
tatctgcaga agcccggcca gtcccctcag ctgctgatct accagatgtc caacctggcc     300
tccggcgtgc ccgacagatt ctccggctct ggctccggca ccgacttcac cctgaagatc     360
```

```
tcccgggtgg aagccgagga cgtgggcgtg tactactgcg cccagaacct ggaactgccc    420
tacaccttcg gccagggcac caagctggaa atcaagcgga ccgtggccgc tccctccgtg    480
ttcatcttcc cacccteega cgagcagctg aagtccggca ccgctccgt cgtgtgcctg    540 ctgaacaact tctaccctcg cgaggccaag gtgcagtgga aggtggacaa cgccctgcag    600
tccggcaact cccaggaatc cgtcaccgag caggactcca aggacagcac ctactccctg    660
tcctccaccc tgaccctgtc caaggccgac tacgagaagc acaaggtgta cgcctgcgaa    720
gtgacccacc agggcctgag cagccccgtg accaagtcct tcaaccgcgg cgagtgc    777
```

<210> SEQ ID NO 312
<211> LENGTH: 259
<212> TYPE: PRT
<213> ORGANISM: Artificial Sequence
<220> FEATURE:
<223> OTHER INFORMATION: chemically synthesized

<400> SEQUENCE: 312

```
Leu Cys His Pro Leu Val Ala Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Asp Asn His Gly Gly Gly Ser Asp Ile Val Met Thr Gln Ser Pro
        35                  40                  45

Leu Ser Leu Pro Val Thr Pro Gly Glu Pro Ala Ser Ile Ser Cys Arg
    50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
        115                 120                 125

Gly Val Tyr Tyr Cys Ala Gln Asn Leu Glu Leu Pro Tyr Thr Phe Gly
    130                 135                 140

Gln Gly Thr Lys Leu Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys
```

<210> SEQ ID NO 313
<211> LENGTH: 777
<212> TYPE: DNA
<213> ORGANISM: Artificial Sequence

```
<220> FEATURE:
<223> OTHER INFORMATION: chemically synthesized

<400> SEQUENCE: 313
ctgtgtcacc ctctggtggc ctctgcctgg gagtcctgtt cctccggcgg tggctcctct      60
ggcggctcca tctcctctgg cctgctgtcc ggcagatccg acaaccacgg cggaggcagc     120
gacatcgtga tgacccagtc ccccctgtcc ctgcccgtga cacctggcga gcctgcctcc     180
atcagctgcc ggtcctccaa gtccctgctg cactccaacg gcatcaccta cctgtactgg     240
tatctgcaga agcccggcca gtcccctcag ctgctgatct accagatgtc caacctggcc     300
tccggcgtgc ccgacagatt ctccggctct ggctccggca ccgacttcac cctgaagatc     360
tcccgcgtgg aagccgagga cgtgggcgtg tactactgcg cccagaacct ggaactgccc     420
tacaccttcg gccagggcac caagctggaa atcaagcgga ccgtggccgc tcccctccgtg     480
ttcatcttcc caccctccga cgagcagctg aagtccggca ccgcctccgt cgtgtgcctg     540
ctgaacaact tctaccccag cgaggccaag gtgcagtgga aggtggacaa cgccctgcag     600
tccggcaact cccaggaatc cgtcaccgag caggactcca aggacagcac ctactccctg     660
tcctccaccc tgaccctgtc caaggccgac tacgagaagc acaaggtgta cgcctgcgaa     720
gtgacccacc agggcctgag cagccccgtg accaagtcct tcaaccgcgg cgagtgc       777

<210> SEQ ID NO 314
<211> LENGTH: 263
<212> TYPE: PRT
<213> ORGANISM: Artificial Sequence
<220> FEATURE:
<223> OTHER INFORMATION: chemically synthesized

<400> SEQUENCE: 314

Leu Cys His Pro Ala Val Leu Ser Ala Trp Glu Ser Cys Ser Ser Gly
1               5                   10                  15

Gly Gly Ser Ser Gly Gly Ser Ala Val Gly Leu Leu Ala Pro Pro Gly
                20                  25                  30

Gly Leu Ser Gly Arg Ser Asp Asn His Gly Gly Ser Asp Ile Val Met
            35                  40                  45

Thr Gln Ser Pro Leu Ser Leu Pro Val Thr Pro Gly Glu Pro Ala Ser
        50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
    130                 135                 140

Tyr Thr Phe Gly Gln Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205
```

```
Gln Glu Ser Val Thr Glu Gln Asp Ser Lys Asp Ser Thr Tyr Ser Leu
    210                 215                 220
Ser Ser Thr Leu Thr Leu Ser Lys Ala Asp Tyr Glu Lys His Lys Val
225                 230                 235                 240
Tyr Ala Cys Glu Val Thr His Gln Gly Leu Ser Ser Pro Val Thr Lys
                245                 250                 255
Ser Phe Asn Arg Gly Glu Cys
            260
```

<210> SEQ ID NO 315
<211> LENGTH: 789
<212> TYPE: DNA
<213> ORGANISM: Artificial Sequence
<220> FEATURE:
<223> OTHER INFORMATION: chemically synthesized

<400> SEQUENCE: 315

```
ctgtgtcacc ctgctgtgct gtctgcctgg gagtcctgtt ccagcggcgg aggctcctct      60
ggcggctctg ctgtgggcct gctggctcca cctggcggcc tgtccggcag atctgacaac     120
cacggcggct ccgacatcgt gatgacccag tcccccctgt ccctgcccgt gactcctggc     180
gagcctgcct ccatctcctg ccggtcctcc aagtccctgc tgcactccaa cggcatcacc     240
tacctgtact ggtatctgca gaagcccggc cagtcccctc agctgctgat ctaccagatg     300
tccaacctgg cctccggcgt gcccgacaga ttctccggct ctggctccgg caccgacttc     360
accctgaaga tctcccgggt ggaagccgag gacgtgggcg tgtactactg cgcccagaac     420
ctggaactgc cctacacctt cggccagggc accaagctgg aaatcaagcg gaccgtggcc     480
gctcccccg tgttcatctt cccacccctcc gacgagcagc tgaagtccgg caccgcctcc     540
gtggtctgcc tgctgaacaa cttctacccc cgcgaggcca aggtgcagtg gaaggtggac     600
aacgccctgc agtccggcaa ctcccaggaa tccgtcaccg agcaggactc caaggacagc     660
acctactccc tgtcctccac cctgaccctg tccaaggccg actacgagaa gcacaaggtg     720
tacgcctgcg aagtgaccca ccagggactg agcagccccg tgaccaagtc cttcaaccgg     780
ggcgagtgc                                                              789
```

<210> SEQ ID NO 316
<211> LENGTH: 263
<212> TYPE: PRT
<213> ORGANISM: Artificial Sequence
<220> FEATURE:
<223> OTHER INFORMATION: chemically synthesized

<400> SEQUENCE: 316

```
Leu Cys His Pro Leu Val Ala Ser Ala Trp Glu Ser Cys Ser Ser Gly
1               5                   10                  15
Gly Gly Ser Ser Gly Gly Ser Ala Val Gly Leu Leu Ala Pro Pro Gly
            20                  25                  30
Gly Leu Ser Gly Arg Ser Asp Asn His Gly Gly Ser Asp Ile Val Met
        35                  40                  45
Thr Gln Ser Pro Leu Ser Leu Pro Val Thr Pro Gly Glu Pro Ala Ser
    50                  55                  60
Ile Ser Cys Arg Ser Ser Lys Ser Leu Leu His Ser Asn Gly Ile Thr
65                  70                  75                  80
Tyr Leu Tyr Trp Tyr Leu Gln Lys Pro Gly Gln Ser Pro Gln Leu Leu
                85                  90                  95
```

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
    130                 135                 140

Tyr Thr Phe Gly Gln Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 317
<211> LENGTH: 788
<212> TYPE: DNA
<213> ORGANISM: Artificial Sequence
<220> FEATURE:
<223> OTHER INFORMATION: chemically synthesized

<400> SEQUENCE: 317
tgtgtcaccc tctggtggcc tctgcctggg agtcctgttc ctccggcgga ggctcctctg      60
gcggctctgc tgtgggcctg ctggctccac ctggcggcct gtccggcaga tctgacaacc     120
acggcggctc cgacatcgtg atgacccagt cccccctgtc cctgcccgtg actcctggcg     180
agcctgcctc catctcctgc cggtcctcca gtcccctgct gcactccaac ggcatcacct     240
acctgtactg gtatctgcag aagcccggcc agtcccctca gctgctgatc taccagatgt     300
ccaacctggc ctccggcgtg cccgacagat tctccggctc tggctccggc accgacttca     360
ccctgaagat ctcccgggtg gaagccgagg acgtgggcgt gtactactgc gcccagaacc     420
tggaactgcc ctacaccttc ggccagggca ccaagctgga aatcaagcgg accgtggccg     480
ctccctccgt gttcatcttc ccaccctccg acgagcagct gaagtccggc accgcctccg     540
tcgtgtgcct gctgaacaac ttctaccccc gcgaggccaa ggtgcagtgg aaggtggaca     600
acgccctgca gtccggcaac tcccaggaat ccgtgaccga gcaggactcc aaggacagca     660
cctactccct gtcctccacc ctgaccctgt ccaaggccga ctacgagaag cacaaggtgt     720
acgcctgcga agtgacccac cagggcctga gcagccccgt gaccaagtcc ttcaaccggg     780
gcgagtgc                                                             788

<210> SEQ ID NO 318
<211> LENGTH: 8
<212> TYPE: PRT
<213> ORGANISM: Artificial Sequence
<220> FEATURE:
<223> OTHER INFORMATION: chemically synthesized

```
<400> SEQUENCE: 318

Leu Ser Gly Arg Ser Gly Asn His
1               5

<210> SEQ ID NO 319
<211> LENGTH: 9
<212> TYPE: PRT
<213> ORGANISM: Artificial Sequence
<220> FEATURE:
<223> OTHER INFORMATION: chemically synthesized

<400> SEQUENCE: 319

Ser Gly Arg Ser Ala Asn Pro Arg Gly
1               5

<210> SEQ ID NO 320
<211> LENGTH: 8
<212> TYPE: PRT
<213> ORGANISM: Artificial Sequence
<220> FEATURE:
<223> OTHER INFORMATION: chemically synthesized

<400> SEQUENCE: 320

Leu Ser Gly Arg Ser Asp Asp His
1               5

<210> SEQ ID NO 321
<211> LENGTH: 8
<212> TYPE: PRT
<213> ORGANISM: Artificial Sequence
<220> FEATURE:
<223> OTHER INFORMATION: chemically synthesized

<400> SEQUENCE: 321

Leu Ser Gly Arg Ser Asp Ile His
1               5

<210> SEQ ID NO 322
<211> LENGTH: 8
<212> TYPE: PRT
<213> ORGANISM: Artificial Sequence
<220> FEATURE:
<223> OTHER INFORMATION: chemically synthesized

<400> SEQUENCE: 322

Leu Ser Gly Arg Ser Asp Gln His
1               5

<210> SEQ ID NO 323
<211> LENGTH: 8
<212> TYPE: PRT
<213> ORGANISM: Artificial Sequence
<220> FEATURE:
<223> OTHER INFORMATION: chemically synthesized

<400> SEQUENCE: 323

Leu Ser Gly Arg Ser Asp Thr His
1               5

<210> SEQ ID NO 324
<211> LENGTH: 8
<212> TYPE: PRT
<213> ORGANISM: Artificial Sequence
<220> FEATURE:
<223> OTHER INFORMATION: chemically synthesized

<400> SEQUENCE: 324
```

```
Leu Ser Gly Arg Ser Asp Tyr His
1               5

<210> SEQ ID NO 325
<211> LENGTH: 8
<212> TYPE: PRT
<213> ORGANISM: Artificial Sequence
<220> FEATURE:
<223> OTHER INFORMATION: chemically synthesized

<400> SEQUENCE: 325

Leu Ser Gly Arg Ser Asp Asn Pro
1               5

<210> SEQ ID NO 326
<211> LENGTH: 8
<212> TYPE: PRT
<213> ORGANISM: Artificial Sequence
<220> FEATURE:
<223> OTHER INFORMATION: chemically synthesized

<400> SEQUENCE: 326

Leu Ser Gly Arg Ser Ala Asn Pro
1               5

<210> SEQ ID NO 327
<211> LENGTH: 8
<212> TYPE: PRT
<213> ORGANISM: Artificial Sequence
<220> FEATURE:
<223> OTHER INFORMATION: chemically synthesized

<400> SEQUENCE: 327

Leu Ser Gly Arg Ser Ala Asn Ile
1               5

<210> SEQ ID NO 328
<211> LENGTH: 8
<212> TYPE: PRT
<213> ORGANISM: Artificial Sequence
<220> FEATURE:
<223> OTHER INFORMATION: chemically synthesized

<400> SEQUENCE: 328

Leu Ser Gly Arg Ser Asp Asn Ile
1               5

<210> SEQ ID NO 329
<211> LENGTH: 8
<212> TYPE: PRT
<213> ORGANISM: Artificial Sequence
<220> FEATURE:
<223> OTHER INFORMATION: chemically synthesized

<400> SEQUENCE: 329

Met Ile Ala Pro Val Ala Tyr Arg
1               5

<210> SEQ ID NO 330
<211> LENGTH: 8
<212> TYPE: PRT
<213> ORGANISM: Artificial Sequence
<220> FEATURE:
<223> OTHER INFORMATION: chemically synthesized

<400> SEQUENCE: 330
```

```
Arg Pro Ser Pro Met Trp Ala Tyr
1               5

<210> SEQ ID NO 331
<211> LENGTH: 8
<212> TYPE: PRT
<213> ORGANISM: Artificial Sequence
<220> FEATURE:
<223> OTHER INFORMATION: chemically synthesized

<400> SEQUENCE: 331

Trp Ala Thr Pro Arg Pro Met Arg
1               5

<210> SEQ ID NO 332
<211> LENGTH: 8
<212> TYPE: PRT
<213> ORGANISM: Artificial Sequence
<220> FEATURE:
<223> OTHER INFORMATION: chemically synthesized

<400> SEQUENCE: 332

Phe Arg Leu Leu Asp Trp Gln Trp
1               5

<210> SEQ ID NO 333
<211> LENGTH: 5
<212> TYPE: PRT
<213> ORGANISM: Artificial Sequence
<220> FEATURE:
<223> OTHER INFORMATION: chemically synthesized

<400> SEQUENCE: 333

Ile Ser Ser Gly Leu
1               5

<210> SEQ ID NO 334
<211> LENGTH: 7
<212> TYPE: PRT
<213> ORGANISM: Artificial Sequence
<220> FEATURE:
<223> OTHER INFORMATION: chemically synthesized

<400> SEQUENCE: 334

Ile Ser Ser Gly Leu Leu Ser
1               5

<210> SEQ ID NO 335
<211> LENGTH: 6
<212> TYPE: PRT
<213> ORGANISM: Artificial Sequence
<220> FEATURE:
<223> OTHER INFORMATION: chemically synthesized

<400> SEQUENCE: 335

Ile Ser Ser Gly Leu Leu
1               5

<210> SEQ ID NO 336
<211> LENGTH: 19
<212> TYPE: PRT
<213> ORGANISM: Artificial Sequence
<220> FEATURE:
<223> OTHER INFORMATION: chemically synthesized

<400> SEQUENCE: 336

Gly Leu Ser Gly Arg Ser Asp Asn His Gly Gly Ala Val Gly Leu Leu
```

```
1               5                   10                  15

Ala Pro Pro

<210> SEQ ID NO 337
<211> LENGTH: 21
<212> TYPE: PRT
<213> ORGANISM: Artificial Sequence
<220> FEATURE:
<223> OTHER INFORMATION: chemically synthesized

<400> SEQUENCE: 337

Gly Leu Ser Gly Arg Ser Asp Asn His Gly Gly Val His Met Pro Leu
1               5                   10                  15

Gly Phe Leu Gly Pro
            20

<210> SEQ ID NO 338
<211> LENGTH: 15
<212> TYPE: PRT
<213> ORGANISM: Artificial Sequence
<220> FEATURE:
<223> OTHER INFORMATION: chemically synthesized

<400> SEQUENCE: 338

Ile Ser Ser Gly Leu Leu Ser Gly Arg Ser Ala Asn Pro Arg Gly
1               5                   10                  15

<210> SEQ ID NO 339
<211> LENGTH: 18
<212> TYPE: PRT
<213> ORGANISM: Artificial Sequence
<220> FEATURE:
<223> OTHER INFORMATION: chemically synthesized

<400> SEQUENCE: 339

Ala Val Gly Leu Leu Ala Pro Pro Thr Ser Gly Arg Ser Ala Asn Pro
1               5                   10                  15

Arg Gly

<210> SEQ ID NO 340
<211> LENGTH: 17
<212> TYPE: PRT
<213> ORGANISM: Artificial Sequence
<220> FEATURE:
<223> OTHER INFORMATION: chemically synthesized

<400> SEQUENCE: 340

Ala Val Gly Leu Leu Ala Pro Pro Ser Gly Arg Ser Ala Asn Pro Arg
1               5                   10                  15

Gly

<210> SEQ ID NO 341
<211> LENGTH: 13
<212> TYPE: PRT
<213> ORGANISM: Artificial Sequence
<220> FEATURE:
<223> OTHER INFORMATION: chemically synthesized

<400> SEQUENCE: 341

Ile Ser Ser Gly Leu Leu Ser Gly Arg Ser Asp Asp His
1               5                   10

<210> SEQ ID NO 342
<211> LENGTH: 13
```

```
<212> TYPE: PRT
<213> ORGANISM: Artificial Sequence
<220> FEATURE:
<223> OTHER INFORMATION: chemically synthesized

<400> SEQUENCE: 342

Ile Ser Ser Gly Leu Leu Ser Gly Arg Ser Asp Ile His
1               5                   10

<210> SEQ ID NO 343
<211> LENGTH: 13
<212> TYPE: PRT
<213> ORGANISM: Artificial Sequence
<220> FEATURE:
<223> OTHER INFORMATION: chemically synthesized

<400> SEQUENCE: 343

Ile Ser Ser Gly Leu Leu Ser Gly Arg Ser Asp Gln His
1               5                   10

<210> SEQ ID NO 344
<211> LENGTH: 13
<212> TYPE: PRT
<213> ORGANISM: Artificial Sequence
<220> FEATURE:
<223> OTHER INFORMATION: chemically synthesized

<400> SEQUENCE: 344

Ile Ser Ser Gly Leu Leu Ser Gly Arg Ser Asp Thr His
1               5                   10

<210> SEQ ID NO 345
<211> LENGTH: 13
<212> TYPE: PRT
<213> ORGANISM: Artificial Sequence
<220> FEATURE:
<223> OTHER INFORMATION: chemically synthesized

<400> SEQUENCE: 345

Ile Ser Ser Gly Leu Leu Ser Gly Arg Ser Asp Tyr His
1               5                   10

<210> SEQ ID NO 346
<211> LENGTH: 13
<212> TYPE: PRT
<213> ORGANISM: Artificial Sequence
<220> FEATURE:
<223> OTHER INFORMATION: chemically synthesized

<400> SEQUENCE: 346

Ile Ser Ser Gly Leu Leu Ser Gly Arg Ser Asp Asn Pro
1               5                   10

<210> SEQ ID NO 347
<211> LENGTH: 13
<212> TYPE: PRT
<213> ORGANISM: Artificial Sequence
<220> FEATURE:
<223> OTHER INFORMATION: chemically synthesized

<400> SEQUENCE: 347

Ile Ser Ser Gly Leu Leu Ser Gly Arg Ser Ala Asn Pro
1               5                   10

<210> SEQ ID NO 348
<211> LENGTH: 13
<212> TYPE: PRT
```

```
<213> ORGANISM: Artificial Sequence
<220> FEATURE:
<223> OTHER INFORMATION: chemically synthesized

<400> SEQUENCE: 348

Ile Ser Ser Gly Leu Leu Ser Gly Arg Ser Ala Asn Ile
1               5                   10

<210> SEQ ID NO 349
<211> LENGTH: 18
<212> TYPE: PRT
<213> ORGANISM: Artificial Sequence
<220> FEATURE:
<223> OTHER INFORMATION: chemically synthesized

<400> SEQUENCE: 349

Ala Val Gly Leu Leu Ala Pro Pro Gly Gly Leu Ser Gly Arg Ser Asp
1               5                   10                  15

Asp His

<210> SEQ ID NO 350
<211> LENGTH: 18
<212> TYPE: PRT
<213> ORGANISM: Artificial Sequence
<220> FEATURE:
<223> OTHER INFORMATION: chemically synthesized

<400> SEQUENCE: 350

Ala Val Gly Leu Leu Ala Pro Pro Gly Gly Leu Ser Gly Arg Ser Asp
1               5                   10                  15

Ile His

<210> SEQ ID NO 351
<211> LENGTH: 18
<212> TYPE: PRT
<213> ORGANISM: Artificial Sequence
<220> FEATURE:
<223> OTHER INFORMATION: chemically synthesized

<400> SEQUENCE: 351

Ala Val Gly Leu Leu Ala Pro Pro Gly Gly Leu Ser Gly Arg Ser Asp
1               5                   10                  15

Gln His

<210> SEQ ID NO 352
<211> LENGTH: 18
<212> TYPE: PRT
<213> ORGANISM: Artificial Sequence
<220> FEATURE:
<223> OTHER INFORMATION: chemically synthesized

<400> SEQUENCE: 352

Ala Val Gly Leu Leu Ala Pro Pro Gly Gly Leu Ser Gly Arg Ser Asp
1               5                   10                  15

Thr His

<210> SEQ ID NO 353
<211> LENGTH: 18
<212> TYPE: PRT
<213> ORGANISM: Artificial Sequence
<220> FEATURE:
<223> OTHER INFORMATION: chemically synthesized

<400> SEQUENCE: 353
```

Ala Val Gly Leu Leu Ala Pro Pro Gly Gly Leu Ser Gly Arg Ser Asp
1               5                   10                  15

Tyr His

<210> SEQ ID NO 354
<211> LENGTH: 18
<212> TYPE: PRT
<213> ORGANISM: Artificial Sequence
<220> FEATURE:
<223> OTHER INFORMATION: chemically synthesized

<400> SEQUENCE: 354

Ala Val Gly Leu Leu Ala Pro Pro Gly Gly Leu Ser Gly Arg Ser Asp
1               5                   10                  15

Asn Pro

<210> SEQ ID NO 355
<211> LENGTH: 18
<212> TYPE: PRT
<213> ORGANISM: Artificial Sequence
<220> FEATURE:
<223> OTHER INFORMATION: chemically synthesized

<400> SEQUENCE: 355

Ala Val Gly Leu Leu Ala Pro Pro Gly Gly Leu Ser Gly Arg Ser Ala
1               5                   10                  15

Asn Pro

<210> SEQ ID NO 356
<211> LENGTH: 18
<212> TYPE: PRT
<213> ORGANISM: Artificial Sequence
<220> FEATURE:
<223> OTHER INFORMATION: chemically synthesized

<400> SEQUENCE: 356

Ala Val Gly Leu Leu Ala Pro Pro Gly Gly Leu Ser Gly Arg Ser Ala
1               5                   10                  15

Asn Ile

<210> SEQ ID NO 357
<211> LENGTH: 13
<212> TYPE: PRT
<213> ORGANISM: Artificial Sequence
<220> FEATURE:
<223> OTHER INFORMATION: chemically synthesized

<400> SEQUENCE: 357

Ile Ser Ser Gly Leu Leu Ser Gly Arg Ser Asp Asn Ile
1               5                   10

<210> SEQ ID NO 358
<211> LENGTH: 18
<212> TYPE: PRT
<213> ORGANISM: Artificial Sequence
<220> FEATURE:
<223> OTHER INFORMATION: chemically synthesized

<400> SEQUENCE: 358

Ala Val Gly Leu Leu Ala Pro Pro Gly Gly Leu Ser Gly Arg Ser Asp
1               5                   10                  15

Asn Ile

```
<210> SEQ ID NO 359
<211> LENGTH: 6
<212> TYPE: PRT
<213> ORGANISM: Artificial Sequence
<220> FEATURE:
<223> OTHER INFORMATION: chemically synthesized

<400> SEQUENCE: 359

Gly Gln Ser Gly Gln Gly
1               5

<210> SEQ ID NO 360
<211> LENGTH: 5
<212> TYPE: PRT
<213> ORGANISM: Artificial Sequence
<220> FEATURE:
<223> OTHER INFORMATION: chemically synthesized

<400> SEQUENCE: 360

Gln Ser Gly Gln Gly
1               5

<210> SEQ ID NO 361
<211> LENGTH: 4
<212> TYPE: PRT
<213> ORGANISM: Artificial Sequence
<220> FEATURE:
<223> OTHER INFORMATION: chemically synthesized

<400> SEQUENCE: 361

Ser Gly Gln Gly
1

<210> SEQ ID NO 362
<211> LENGTH: 3
<212> TYPE: PRT
<213> ORGANISM: Artificial Sequence
<220> FEATURE:
<223> OTHER INFORMATION: chemically synthesized

<400> SEQUENCE: 362

Gly Gln Gly
1

<210> SEQ ID NO 363
<211> LENGTH: 159
<212> TYPE: PRT
<213> ORGANISM: Artificial Sequence
<220> FEATURE:
<223> OTHER INFORMATION: chemically synthesized

<400> SEQUENCE: 363

Gln Gly Gln Ser Gly Gln Gly Leu Cys His Pro Ala Val Leu Ser Ala
1               5                   10                  15

Trp Glu Ser Cys Ser Ser Gly Gly Ser Ser Gly Gly Ser Ile Ser
            20                  25                  30

Ser Gly Leu Leu Ser Gly Arg Ser Asp Asn His Gly Gly Ser Asp
        35                  40                  45

Ile Val Met Thr Gln Ser Pro Leu Ser Leu Pro Val Thr Pro Gly Glu
    50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95
```

```
Gln Leu Leu Ile Tyr Gln Met Ser Asn Leu Ala Ser Gly Val Pro Asp
                100                 105                 110

Arg Phe Ser Gly Ser Gly Ser Gly Thr Asp Phe Thr Leu Lys Ile Ser
            115                 120                 125

Arg Val Glu Ala Glu Asp Val Gly Val Tyr Tyr Cys Ala Gln Asn Leu
        130                 135                 140

Glu Leu Pro Tyr Thr Phe Gly Gln Gly Thr Lys Leu Glu Ile Lys
145                 150                 155
```

<210> SEQ ID NO 364
<211> LENGTH: 152
<212> TYPE: PRT
<213> ORGANISM: Artificial Sequence
<220> FEATURE:
<223> OTHER INFORMATION: chemically synthesized

<400> SEQUENCE: 364

```
Leu Cys His Pro Ala Val Leu Ser Ala Trp Glu Ser Cys Ser Ser Gly
1               5                   10                  15

Gly Gly Ser Gly Gly Ser Ile Ser Ser Gly Leu Leu Ser Gly Arg
            20                  25                  30

Ser Asp Asn His Gly Gly Gly Ser Asp Ile Val Met Thr Gln Ser Pro
            35                  40                  45

Leu Ser Leu Pro Val Thr Pro Gly Glu Pro Ala Ser Ile Ser Cys Arg
50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
                100                 105                 110

Gly Thr Asp Phe Thr Leu Lys Ile Ser Arg Val Glu Ala Glu Asp Val
            115                 120                 125

Gly Val Tyr Tyr Cys Ala Gln Asn Leu Glu Leu Pro Tyr Thr Phe Gly
        130                 135                 140

Gln Gly Thr Lys Leu Glu Ile Lys
145                 150
```

<210> SEQ ID NO 365
<211> LENGTH: 159
<212> TYPE: PRT
<213> ORGANISM: Artificial Sequence
<220> FEATURE:
<223> OTHER INFORMATION: chemically synthesized

<400> SEQUENCE: 365

```
Gln Gly Gln Ser Gly Gln Gly Leu Cys His Pro Leu Val Ala Ser Ala
1               5                   10                  15

Trp Glu Ser Cys Ser Ser Gly Gly Gly Ser Gly Gly Ser Ile Ser
            20                  25                  30

Ser Gly Leu Leu Ser Gly Arg Ser Asp Asn His Gly Gly Gly Ser Asp
            35                  40                  45

Ile Val Met Thr Gln Ser Pro Leu Ser Leu Pro Val Thr Pro Gly Glu
        50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95
```

```
Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Ala Gln Asn Leu
130                 135                 140

Glu Leu Pro Tyr Thr Phe Gly Gln Gly Thr Lys Leu Glu Ile Lys
145                 150                 155

<210> SEQ ID NO 366
<211> LENGTH: 152
<212> TYPE: PRT
<213> ORGANISM: Artificial Sequence
<220> FEATURE:
<223> OTHER INFORMATION: chemically synthesized

<400> SEQUENCE: 366

Leu Cys His Pro Leu Val Ala Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Asp Asn His Gly Gly Ser Asp Ile Val Met Thr Gln Ser Pro
        35                  40                  45

Leu Ser Leu Pro Val Thr Pro Gly Glu Pro Ala Ser Ile Ser Cys Arg
50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
        115                 120                 125

Gly Val Tyr Tyr Cys Ala Gln Asn Leu Glu Leu Pro Tyr Thr Phe Gly
    130                 135                 140

Gln Gly Thr Lys Leu Glu Ile Lys
145                 150

<210> SEQ ID NO 367
<211> LENGTH: 163
<212> TYPE: PRT
<213> ORGANISM: Artificial Sequence
<220> FEATURE:
<223> OTHER INFORMATION: chemically synthesized

<400> SEQUENCE: 367

Gln Gly Gln Ser Gly Gln Gly Leu Cys His Pro Ala Val Leu Ser Ala
1               5                   10                  15

Trp Glu Ser Cys Ser Ser Gly Gly Ser Ser Gly Gly Ser Ala Val
            20                  25                  30

Gly Leu Leu Ala Pro Pro Gly Gly Leu Ser Gly Arg Ser Asp Asn His
            35                  40                  45

Gly Gly Ser Asp Ile Val Met Thr Gln Ser Pro Leu Ser Leu Pro Val
        50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
```

```
                    85                  90                  95
Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
            115                 120                 125

Leu Lys Ile Ser Arg Val Glu Ala Glu Asp Val Gly Val Tyr Tyr Cys
            130                 135                 140

Ala Gln Asn Leu Glu Leu Pro Tyr Thr Phe Gly Gln Gly Thr Lys Leu
145                 150                 155                 160

Glu Ile Lys

<210> SEQ ID NO 368
<211> LENGTH: 156
<212> TYPE: PRT
<213> ORGANISM: Artificial Sequence
<220> FEATURE:
<223> OTHER INFORMATION: chemically synthesized

<400> SEQUENCE: 368

Leu Cys His Pro Ala Val Leu Ser Ala Trp Glu Ser Cys Ser Ser Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Asn His Gly Gly Ser Asp Ile Val Met
            35                  40                  45

Thr Gln Ser Pro Leu Ser Leu Pro Val Thr Pro Gly Glu Pro Ala Ser
            50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
            115                 120                 125

Ala Glu Asp Val Gly Val Tyr Tyr Cys Ala Gln Asn Leu Glu Leu Pro
            130                 135                 140

Tyr Thr Phe Gly Gln Gly Thr Lys Leu Glu Ile Lys
145                 150                 155

<210> SEQ ID NO 369
<211> LENGTH: 163
<212> TYPE: PRT
<213> ORGANISM: Artificial Sequence
<220> FEATURE:
<223> OTHER INFORMATION: chemically synthesized

<400> SEQUENCE: 369

Gln Gly Gln Ser Gly Gln Gly Leu Cys His Pro Leu Val Ala Ser Ala
1               5                   10                  15

Trp Glu Ser Cys Ser Ser Gly Gly Gly Ser Ser Gly Gly Ser Ala Val
            20                  25                  30

Gly Leu Leu Ala Pro Pro Gly Gly Leu Ser Gly Arg Ser Asp Asn His
            35                  40                  45

Gly Gly Ser Asp Ile Val Met Thr Gln Ser Pro Leu Ser Leu Pro Val
            50                  55                  60

Thr Pro Gly Glu Pro Ala Ser Ile Ser Cys Arg Ser Ser Lys Ser Leu
```

```
                65                  70                  75                  80
Leu His Ser Asn Gly Ile Thr Tyr Leu Tyr Trp Tyr Leu Gln Lys Pro
                    85                  90                  95

Gly Gln Ser Pro Gln Leu Leu Ile Tyr Gln Met Ser Asn Leu Ala Ser
                    100                 105                 110

Gly Val Pro Asp Arg Phe Ser Gly Ser Gly Ser Gly Thr Asp Phe Thr
                    115                 120                 125

Leu Lys Ile Ser Arg Val Glu Ala Glu Asp Val Gly Val Tyr Tyr Cys
        130                 135                 140

Ala Gln Asn Leu Glu Leu Pro Tyr Thr Phe Gly Gln Gly Thr Lys Leu
145                 150                 155                 160

Glu Ile Lys

<210> SEQ ID NO 370
<211> LENGTH: 156
<212> TYPE: PRT
<213> ORGANISM: Artificial Sequence
<220> FEATURE:
<223> OTHER INFORMATION: chemically synthesized

<400> SEQUENCE: 370

Leu Cys His Pro Leu Val Ala Ser Ala Trp Glu Ser Cys Ser Ser Gly
1               5                   10                  15

Gly Gly Ser Ser Gly Gly Ser Ala Val Gly Leu Leu Ala Pro Pro Gly
                    20                  25                  30

Gly Leu Ser Gly Arg Ser Asp Asn His Gly Gly Ser Asp Ile Val Met
                    35                  40                  45

Thr Gln Ser Pro Leu Ser Leu Pro Val Thr Pro Gly Glu Pro Ala Ser
        50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                    85                  90                  95

Ile Tyr Gln Met Ser Asn Leu Ala Ser Gly Val Pro Asp Arg Phe Ser
                    100                 105                 110

Gly Ser Gly Ser Gly Thr Asp Phe Thr Leu Lys Ile Ser Arg Val Glu
                    115                 120                 125

Ala Glu Asp Val Gly Val Tyr Tyr Cys Ala Gln Asn Leu Glu Leu Pro
        130                 135                 140

Tyr Thr Phe Gly Gln Gly Thr Lys Leu Glu Ile Lys
145                 150                 155

<210> SEQ ID NO 371
<211> LENGTH: 266
<212> TYPE: PRT
<213> ORGANISM: Artificial Sequence
<220> FEATURE:
<223> OTHER INFORMATION: chemically synthesized

<400> SEQUENCE: 371

Gln Gly Gln Ser Gly Gln Gly Leu Cys His Pro Ala Val Leu Ser Ala
1               5                   10                  15

Trp Glu Ser Cys Ser Ser Gly Gly Gly Ser Ser Gly Ser Ile Ser
                    20                  25                  30

Ser Gly Leu Leu Ser Gly Arg Ser Asp Ile His Gly Gly Ser Asp
                    35                  40                  45

Ile Val Met Thr Gln Ser Pro Leu Ser Leu Pro Val Thr Pro Gly Glu
```

```
            50                  55                  60
Pro Ala Ser Ile Ser Cys Arg Ser Ser Lys Ser Leu Leu His Ser Asn
 65                  70                  75                  80

Gly Ile Thr Tyr Leu Tyr Trp Tyr Leu Gln Lys Pro Gly Gln Ser Pro
                 85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Ala Gln Asn Leu
    130                 135                 140

Glu Leu Pro Tyr Thr Phe Gly Gln Gly Thr Lys Leu Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265

<210> SEQ ID NO 372
<211> LENGTH: 259
<212> TYPE: PRT
<213> ORGANISM: Artificial Sequence
<220> FEATURE:
<223> OTHER INFORMATION: chemically synthesized

<400> SEQUENCE: 372

Leu Cys His Pro Ala Val Leu Ser Ala Trp Glu Ser Cys Ser Ser Gly
  1               5                  10                  15

Gly Gly Ser Ser Gly Gly Ser Ile Ser Ser Gly Leu Leu Ser Gly Arg
                 20                  25                  30

Ser Asp Ile His Gly Gly Ser Asp Ile Val Met Thr Gln Ser Pro
         35                  40                  45

Leu Ser Leu Pro Val Thr Pro Gly Glu Pro Ala Ser Ile Ser Cys Arg
         50                  55                  60

Ser Ser Lys Ser Leu Leu His Ser Asn Gly Ile Thr Tyr Leu Tyr Trp
 65                  70                  75                  80

Tyr Leu Gln Lys Pro Gly Gln Ser Pro Gln Leu Leu Ile Tyr Gln Met
                 85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
        115                 120                 125

Gly Val Tyr Tyr Cys Ala Gln Asn Leu Glu Leu Pro Tyr Thr Phe Gly
    130                 135                 140

Gln Gly Thr Lys Leu Glu Ile Lys Arg Thr Val Ala Ala Pro Ser Val
```

```
145                 150                 155                 160
Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
                180                 185                 190

Trp Lys Val Asp Asn Ala Leu Gln Ser Gly Asn Ser Gln Glu Ser Val
                195                 200                 205

Thr Glu Gln Asp Ser Lys Asp Ser Thr Tyr Ser Leu Ser Ser Thr Leu
                210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 373
<211> LENGTH: 159
<212> TYPE: PRT
<213> ORGANISM: Artificial Sequence
<220> FEATURE:
<223> OTHER INFORMATION: chemically synthesized

<400> SEQUENCE: 373

Gln Gly Gln Ser Gly Gln Gly Leu Cys His Pro Ala Val Leu Ser Ala
1               5                   10                  15

Trp Glu Ser Cys Ser Ser Gly Gly Ser Ser Gly Gly Ser Ile Ser
                20                  25                  30

Ser Gly Leu Leu Ser Gly Arg Ser Asp Ile His Gly Gly Gly Ser Asp
            35                  40                  45

Ile Val Met Thr Gln Ser Pro Leu Ser Leu Pro Val Thr Pro Gly Glu
        50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
                100                 105                 110

Arg Phe Ser Gly Ser Gly Ser Gly Thr Asp Phe Thr Leu Lys Ile Ser
                115                 120                 125

Arg Val Glu Ala Glu Asp Val Gly Val Tyr Tyr Cys Ala Gln Asn Leu
                130                 135                 140

Glu Leu Pro Tyr Thr Phe Gly Gln Gly Thr Lys Leu Glu Ile Lys
145                 150                 155

<210> SEQ ID NO 374
<211> LENGTH: 152
<212> TYPE: PRT
<213> ORGANISM: Artificial Sequence
<220> FEATURE:
<223> OTHER INFORMATION: chemically synthesized

<400> SEQUENCE: 374

Leu Cys His Pro Ala Val Leu Ser Ala Trp Glu Ser Cys Ser Ser Gly
1               5                   10                  15

Gly Gly Ser Ser Gly Gly Ser Ile Ser Ser Gly Leu Leu Ser Gly Arg
                20                  25                  30

Ser Asp Ile His Gly Gly Gly Ser Asp Ile Val Met Thr Gln Ser Pro
```

```
            35                  40                  45
Leu Ser Leu Pro Val Thr Pro Gly Glu Pro Ala Ser Ile Ser Cys Arg
 50                  55                  60

Ser Ser Lys Ser Leu Leu His Ser Asn Gly Ile Thr Tyr Leu Tyr Trp
 65                  70                  75                  80

Tyr Leu Gln Lys Pro Gly Gln Ser Pro Gln Leu Leu Ile Tyr Gln Met
                 85                  90                  95

Ser Asn Leu Ala Ser Gly Val Pro Asp Arg Phe Ser Gly Ser Gly Ser
                100                 105                 110

Gly Thr Asp Phe Thr Leu Lys Ile Ser Arg Val Glu Ala Glu Asp Val
                115                 120                 125

Gly Val Tyr Tyr Cys Ala Gln Asn Leu Glu Leu Pro Tyr Thr Phe Gly
            130                 135                 140

Gln Gly Thr Lys Leu Glu Ile Lys
145                 150

<210> SEQ ID NO 375
<211> LENGTH: 270
<212> TYPE: PRT
<213> ORGANISM: Artificial Sequence
<220> FEATURE:
<223> OTHER INFORMATION: chemically synthesized

<400> SEQUENCE: 375

Gln Gly Gln Ser Gly Gln Gly Leu Cys His Pro Ala Val Leu Ser Ala
 1               5                  10                  15

Trp Glu Ser Cys Ser Ser Gly Gly Ser Ser Gly Ser Ala Val
                 20                  25                  30

Gly Leu Leu Ala Pro Pro Gly Gly Leu Ser Gly Arg Ser Asp Ile His
             35                  40                  45

Gly Gly Ser Asp Ile Val Met Thr Gln Ser Pro Leu Ser Leu Pro Val
         50                  55                  60

Thr Pro Gly Glu Pro Ala Ser Ile Ser Cys Arg Ser Ser Lys Ser Leu
 65                  70                  75                  80

Leu His Ser Asn Gly Ile Thr Tyr Leu Tyr Trp Tyr Leu Gln Lys Pro
                 85                  90                  95

Gly Gln Ser Pro Gln Leu Leu Ile Tyr Gln Met Ser Asn Leu Ala Ser
                100                 105                 110

Gly Val Pro Asp Arg Phe Ser Gly Ser Gly Ser Gly Thr Asp Phe Thr
            115                 120                 125

Leu Lys Ile Ser Arg Val Glu Ala Glu Asp Val Gly Val Tyr Tyr Cys
        130                 135                 140

Ala Gln Asn Leu Glu Leu Pro Tyr Thr Phe Gly Gln Gly Thr Lys Leu
145                 150                 155                 160

Glu Ile Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
            180                 185                 190

Asn Asn Phe Tyr Pro Arg Glu Ala Lys Val Gln Trp Lys Val Asp Asn
        195                 200                 205

Ala Leu Gln Ser Gly Asn Ser Gln Glu Ser Val Thr Glu Gln Asp Ser
    210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
```

245                 250                 255
Leu Ser Ser Pro Val Thr Lys Ser Phe Asn Arg Gly Glu Cys
            260                 265                 270

<210> SEQ ID NO 376
<211> LENGTH: 263
<212> TYPE: PRT
<213> ORGANISM: Artificial Sequence
<220> FEATURE:
<223> OTHER INFORMATION: chemically synthesized

<400> SEQUENCE: 376

Leu Cys His Pro Ala Val Leu Ser Ala Trp Glu Ser Cys Ser Ser Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Ile His Gly Gly Ser Asp Ile Val Met
        35                  40                  45

Thr Gln Ser Pro Leu Ser Leu Pro Val Thr Pro Gly Glu Pro Ala Ser
    50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
    130                 135                 140

Tyr Thr Phe Gly Gln Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 377
<211> LENGTH: 163
<212> TYPE: PRT
<213> ORGANISM: Artificial Sequence
<220> FEATURE:
<223> OTHER INFORMATION: chemically synthesized

<400> SEQUENCE: 377

Gln Gly Gln Ser Gly Gln Gly Leu Cys His Pro Ala Val Leu Ser Ala
1               5                   10                  15

```
Trp Glu Ser Cys Ser Ser Gly Gly Ser Ser Gly Ser Ala Val
             20                  25                  30

Gly Leu Leu Ala Pro Pro Gly Gly Leu Ser Gly Arg Ser Asp Ile His
         35                  40                  45

Gly Gly Ser Asp Ile Val Met Thr Gln Ser Pro Leu Ser Leu Pro Val
 50                  55                  60

Thr Pro Gly Glu Pro Ala Ser Ile Ser Cys Arg Ser Ser Lys Ser Leu
 65                  70                  75                  80

Leu His Ser Asn Gly Ile Thr Tyr Leu Tyr Trp Tyr Leu Gln Lys Pro
                 85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
        115                 120                 125

Leu Lys Ile Ser Arg Val Glu Ala Glu Asp Val Gly Val Tyr Tyr Cys
130                 135                 140

Ala Gln Asn Leu Glu Leu Pro Tyr Thr Phe Gly Gln Gly Thr Lys Leu
145                 150                 155                 160

Glu Ile Lys
```

<210> SEQ ID NO 378
<211> LENGTH: 156
<212> TYPE: PRT
<213> ORGANISM: Artificial Sequence
<220> FEATURE:
<223> OTHER INFORMATION: chemically synthesized

<400> SEQUENCE: 378

```
Leu Cys His Pro Ala Val Leu Ser Ala Trp Glu Ser Cys Ser Ser Gly
 1               5                  10                  15

Gly Gly Ser Ser Gly Gly Ser Ala Val Gly Leu Leu Ala Pro Pro Gly
             20                  25                  30

Gly Leu Ser Gly Arg Ser Asp Ile His Gly Gly Ser Asp Ile Val Met
         35                  40                  45

Thr Gln Ser Pro Leu Ser Leu Pro Val Thr Pro Gly Glu Pro Ala Ser
 50                  55                  60

Ile Ser Cys Arg Ser Ser Lys Ser Leu Leu His Ser Asn Gly Ile Thr
 65                  70                  75                  80

Tyr Leu Tyr Trp Tyr Leu Gln Lys Pro Gly Gln Ser Pro Gln Leu Leu
                 85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
130                 135                 140

Tyr Thr Phe Gly Gln Gly Thr Lys Leu Glu Ile Lys
145                 150                 155
```

<210> SEQ ID NO 379
<211> LENGTH: 266
<212> TYPE: PRT
<213> ORGANISM: Artificial Sequence
<220> FEATURE:
<223> OTHER INFORMATION: chemically synthesized

<400> SEQUENCE: 379

Gln Gly Gln Ser Gly Gln Gly Leu Cys His Pro Ala Val Leu Ser Ala
1               5                   10                  15

Trp Glu Ser Cys Ser Ser Gly Gly Ser Ser Gly Ser Ile Ser
            20                  25                  30

Ser Gly Leu Leu Ser Gly Arg Ser Asp Gln His Gly Gly Gly Ser Asp
        35                  40                  45

Ile Val Met Thr Gln Ser Pro Leu Ser Leu Pro Val Thr Pro Gly Glu
50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
            115                 120                 125

Arg Val Glu Ala Glu Asp Val Gly Val Tyr Tyr Cys Ala Gln Asn Leu
        130                 135                 140

Glu Leu Pro Tyr Thr Phe Gly Gln Gly Thr Lys Leu Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265

<210> SEQ ID NO 380
<211> LENGTH: 259
<212> TYPE: PRT
<213> ORGANISM: Artificial Sequence
<220> FEATURE:
<223> OTHER INFORMATION: chemically synthesized

<400> SEQUENCE: 380

Leu Cys His Pro Ala Val Leu Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Asp Gln His Gly Gly Gly Ser Asp Ile Val Met Thr Gln Ser Pro
        35                  40                  45

Leu Ser Leu Pro Val Thr Pro Gly Glu Pro Ala Ser Ile Ser Cys Arg
50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

```
Ser Asn Leu Ala Ser Gly Val Pro Asp Arg Phe Ser Gly Ser
            100                 105                 110

Gly Thr Asp Phe Thr Leu Lys Ile Ser Arg Val Glu Ala Glu Asp Val
        115                 120                 125

Gly Val Tyr Tyr Cys Ala Gln Asn Leu Glu Leu Pro Tyr Thr Phe Gly
    130                 135                 140

Gln Gly Thr Lys Leu Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 381
<211> LENGTH: 159
<212> TYPE: PRT
<213> ORGANISM: Artificial Sequence
<220> FEATURE:
<223> OTHER INFORMATION: chemically synthesized

<400> SEQUENCE: 381

Gln Gly Gln Ser Gly Gln Gly Leu Cys His Pro Ala Val Leu Ser Ala
1               5                   10                  15

Trp Glu Ser Cys Ser Ser Gly Gly Ser Ser Gly Gly Ser Ile Ser
            20                  25                  30

Ser Gly Leu Leu Ser Gly Arg Ser Asp Gln His Gly Gly Ser Asp
        35                  40                  45

Ile Val Met Thr Gln Ser Pro Leu Ser Leu Pro Val Thr Pro Gly Glu
50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Ala Gln Asn Leu
    130                 135                 140

Glu Leu Pro Tyr Thr Phe Gly Gln Gly Thr Lys Leu Glu Ile Lys
145                 150                 155

<210> SEQ ID NO 382
<211> LENGTH: 152
<212> TYPE: PRT
<213> ORGANISM: Artificial Sequence
<220> FEATURE:
<223> OTHER INFORMATION: chemically synthesized
```

<400> SEQUENCE: 382

Leu Cys His Pro Ala Val Leu Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Asp Gln His Gly Gly Gly Ser Asp Ile Val Met Thr Gln Ser Pro
        35                  40                  45

Leu Ser Leu Pro Val Thr Pro Gly Glu Pro Ala Ser Ile Ser Cys Arg
    50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
        115                 120                 125

Gly Val Tyr Tyr Cys Ala Gln Asn Leu Glu Leu Pro Tyr Thr Phe Gly
    130                 135                 140

Gln Gly Thr Lys Leu Glu Ile Lys
145                 150

<210> SEQ ID NO 383
<211> LENGTH: 270
<212> TYPE: PRT
<213> ORGANISM: Artificial Sequence
<220> FEATURE:
<223> OTHER INFORMATION: chemically synthesized

<400> SEQUENCE: 383

Gln Gly Gln Ser Gly Gln Gly Leu Cys His Pro Ala Val Leu Ser Ala
1               5                   10                  15

Trp Glu Ser Cys Ser Ser Gly Gly Ser Ser Gly Gly Ser Ala Val
            20                  25                  30

Gly Leu Leu Ala Pro Pro Gly Gly Leu Ser Gly Arg Ser Asp Gln His
        35                  40                  45

Gly Gly Ser Asp Ile Val Met Thr Gln Ser Pro Leu Ser Leu Pro Val
    50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
        115                 120                 125

Leu Lys Ile Ser Arg Val Glu Ala Glu Asp Val Gly Val Tyr Tyr Cys
    130                 135                 140

Ala Gln Asn Leu Glu Leu Pro Tyr Thr Phe Gly Gln Gly Thr Lys Leu
145                 150                 155                 160

Glu Ile Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
            180                 185                 190

```
Asn Asn Phe Tyr Pro Arg Glu Ala Lys Val Gln Trp Lys Val Asp Asn
            195                 200                 205

Ala Leu Gln Ser Gly Asn Ser Gln Glu Ser Val Thr Glu Gln Asp Ser
        210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
            260                 265                 270

<210> SEQ ID NO 384
<211> LENGTH: 263
<212> TYPE: PRT
<213> ORGANISM: Artificial Sequence
<220> FEATURE:
<223> OTHER INFORMATION: chemically synthesized

<400> SEQUENCE: 384

Leu Cys His Pro Ala Val Leu Ser Ala Trp Glu Ser Cys Ser Ser Gly
1               5                   10                  15

Gly Gly Ser Ser Gly Ser Ala Val Gly Leu Leu Ala Pro Pro Gly
            20                  25                  30

Gly Leu Ser Gly Arg Ser Asp Gln His Gly Gly Ser Asp Ile Val Met
        35                  40                  45

Thr Gln Ser Pro Leu Ser Leu Pro Val Thr Pro Gly Glu Pro Ala Ser
    50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
    130                 135                 140

Tyr Thr Phe Gly Gln Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 385
<211> LENGTH: 163
```

```
<212> TYPE: PRT
<213> ORGANISM: Artificial Sequence
<220> FEATURE:
<223> OTHER INFORMATION: chemically synthesized

<400> SEQUENCE: 385

Gln Gly Gln Ser Gly Gln Gly Leu Cys His Pro Ala Val Leu Ser Ala
1               5                   10                  15

Trp Glu Ser Cys Ser Ser Gly Gly Ser Gly Gly Ser Ala Val
            20                  25                  30

Gly Leu Leu Ala Pro Pro Gly Gly Leu Ser Gly Arg Ser Asp Gln His
            35                  40                  45

Gly Gly Ser Asp Ile Val Met Thr Gln Ser Pro Leu Ser Leu Pro Val
    50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
        115                 120                 125

Leu Lys Ile Ser Arg Val Glu Ala Glu Asp Val Gly Val Tyr Tyr Cys
130                 135                 140

Ala Gln Asn Leu Glu Leu Pro Tyr Thr Phe Gly Gln Gly Thr Lys Leu
145                 150                 155                 160

Glu Ile Lys

<210> SEQ ID NO 386
<211> LENGTH: 156
<212> TYPE: PRT
<213> ORGANISM: Artificial Sequence
<220> FEATURE:
<223> OTHER INFORMATION: chemically synthesized

<400> SEQUENCE: 386

Leu Cys His Pro Ala Val Leu Ser Ala Trp Glu Ser Cys Ser Ser Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Gln His Gly Gly Ser Asp Ile Val Met
            35                  40                  45

Thr Gln Ser Pro Leu Ser Leu Pro Val Thr Pro Gly Glu Pro Ala Ser
    50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
130                 135                 140

Tyr Thr Phe Gly Gln Gly Thr Lys Leu Glu Ile Lys
145                 150                 155
```

<210> SEQ ID NO 387
<211> LENGTH: 266
<212> TYPE: PRT
<213> ORGANISM: Artificial Sequence
<220> FEATURE:
<223> OTHER INFORMATION: chemically synthesized

<400> SEQUENCE: 387

```
Gln Gly Gln Ser Gly Gln Gly Leu Cys His Pro Ala Val Leu Ser Ala
1               5                   10                  15

Trp Glu Ser Cys Ser Ser Gly Gly Ser Ser Gly Gly Ser Ile Ser
            20                  25                  30

Ser Gly Leu Leu Ser Gly Arg Ser Asp Asn Pro Gly Gly Gly Ser Asp
        35                  40                  45

Ile Val Met Thr Gln Ser Pro Leu Ser Leu Pro Val Thr Pro Gly Glu
    50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Ala Gln Asn Leu
    130                 135                 140

Glu Leu Pro Tyr Thr Phe Gly Gln Gly Thr Lys Leu Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265
```

<210> SEQ ID NO 388
<211> LENGTH: 259
<212> TYPE: PRT
<213> ORGANISM: Artificial Sequence
<220> FEATURE:
<223> OTHER INFORMATION: chemically synthesized

<400> SEQUENCE: 388

```
Leu Cys His Pro Ala Val Leu Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Asp Ile Val Met Thr Gln Ser Pro
        35                  40                  45
```

Leu Ser Leu Pro Val Thr Pro Gly Glu Pro Ala Ser Ile Ser Cys Arg
 50                  55                  60

Ser Ser Lys Ser Leu Leu His Ser Asn Gly Ile Thr Tyr Leu Tyr Trp
 65                  70                  75                  80

Tyr Leu Gln Lys Pro Gly Gln Ser Pro Gln Leu Leu Ile Tyr Gln Met
                 85                  90                  95

Ser Asn Leu Ala Ser Gly Val Pro Asp Arg Phe Ser Gly Ser Gly Ser
             100                 105                 110

Gly Thr Asp Phe Thr Leu Lys Ile Ser Arg Val Glu Ala Glu Asp Val
         115                 120                 125

Gly Val Tyr Tyr Cys Ala Gln Asn Leu Glu Leu Pro Tyr Thr Phe Gly
     130                 135                 140

Gln Gly Thr Lys Leu Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 389
<211> LENGTH: 159
<212> TYPE: PRT
<213> ORGANISM: Artificial Sequence
<220> FEATURE:
<223> OTHER INFORMATION: chemically synthesized

<400> SEQUENCE: 389

Gln Gly Gln Ser Gly Gln Gly Leu Cys His Pro Ala Val Leu Ser Ala
1               5                   10                  15

Trp Glu Ser Cys Ser Ser Gly Gly Ser Ser Gly Gly Ser Ile Ser
            20                  25                  30

Ser Gly Leu Leu Ser Gly Arg Ser Asp Asn Pro Gly Gly Ser Asp
        35                  40                  45

Ile Val Met Thr Gln Ser Pro Leu Ser Leu Pro Val Thr Pro Gly Glu
 50                  55                  60

Pro Ala Ser Ile Ser Cys Arg Ser Ser Lys Ser Leu Leu His Ser Asn
 65                  70                  75                  80

Gly Ile Thr Tyr Leu Tyr Trp Tyr Leu Gln Lys Pro Gly Gln Ser Pro
                 85                  90                  95

Gln Leu Leu Ile Tyr Gln Met Ser Asn Leu Ala Ser Gly Val Pro Asp
             100                 105                 110

Arg Phe Ser Gly Ser Gly Ser Gly Thr Asp Phe Thr Leu Lys Ile Ser
         115                 120                 125

Arg Val Glu Ala Glu Asp Val Gly Val Tyr Tyr Cys Ala Gln Asn Leu
     130                 135                 140

Glu Leu Pro Tyr Thr Phe Gly Gln Gly Thr Lys Leu Glu Ile Lys
145                 150                 155

<210> SEQ ID NO 390
<211> LENGTH: 152
<212> TYPE: PRT
<213> ORGANISM: Artificial Sequence
<220> FEATURE:
<223> OTHER INFORMATION: chemically synthesized

<400> SEQUENCE: 390

Leu Cys His Pro Ala Val Leu Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Asp Ile Val Met Thr Gln Ser Pro
        35                  40                  45

Leu Ser Leu Pro Val Thr Pro Gly Glu Pro Ala Ser Ile Ser Cys Arg
    50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
        115                 120                 125

Gly Val Tyr Tyr Cys Ala Gln Asn Leu Glu Leu Pro Tyr Thr Phe Gly
    130                 135                 140

Gln Gly Thr Lys Leu Glu Ile Lys
145                 150

<210> SEQ ID NO 391
<211> LENGTH: 270
<212> TYPE: PRT
<213> ORGANISM: Artificial Sequence
<220> FEATURE:
<223> OTHER INFORMATION: chemically synthesized

<400> SEQUENCE: 391

Gln Gly Gln Ser Gly Gln Gly Leu Cys His Pro Ala Val Leu Ser Ala
1               5                   10                  15

Trp Glu Ser Cys Ser Ser Gly Gly Ser Gly Gly Ser Ala Val
            20                  25                  30

Gly Leu Leu Ala Pro Pro Gly Gly Leu Ser Gly Arg Ser Asp Asn Pro
            35                  40                  45

Gly Gly Ser Asp Ile Val Met Thr Gln Ser Pro Leu Ser Leu Pro Val
        50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
        115                 120                 125

Leu Lys Ile Ser Arg Val Glu Ala Glu Asp Val Gly Val Tyr Tyr Cys
    130                 135                 140

```
Ala Gln Asn Leu Glu Leu Pro Tyr Thr Phe Gly Gln Gly Thr Lys Leu
145                 150                 155                 160

Glu Ile Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
            180                 185                 190

Asn Asn Phe Tyr Pro Arg Glu Ala Lys Val Gln Trp Lys Val Asp Asn
        195                 200                 205

Ala Leu Gln Ser Gly Asn Ser Gln Glu Ser Val Thr Glu Gln Asp Ser
210                 215                 220

Lys Asp Ser Thr Tyr Ser Leu Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
            260                 265                 270

<210> SEQ ID NO 392
<211> LENGTH: 263
<212> TYPE: PRT
<213> ORGANISM: Artificial Sequence
<220> FEATURE:
<223> OTHER INFORMATION: chemically synthesized

<400> SEQUENCE: 392

Leu Cys His Pro Ala Val Leu Ser Ala Trp Glu Ser Cys Ser Ser Gly
1               5                   10                  15

Gly Gly Ser Ser Gly Gly Ser Ala Val Gly Leu Leu Ala Pro Pro Gly
                20                  25                  30

Gly Leu Ser Gly Arg Ser Asp Asn Pro Gly Gly Ser Asp Ile Val Met
            35                  40                  45

Thr Gln Ser Pro Leu Ser Leu Pro Val Thr Pro Gly Glu Pro Ala Ser
        50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
130                 135                 140

Tyr Thr Phe Gly Gln Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240
```

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 393
<211> LENGTH: 163
<212> TYPE: PRT
<213> ORGANISM: Artificial Sequence
<220> FEATURE:
<223> OTHER INFORMATION: chemically synthesized

<400> SEQUENCE: 393

Gln Gly Gln Ser Gly Gln Gly Leu Cys His Pro Ala Val Leu Ser Ala
1               5                   10                  15

Trp Glu Ser Cys Ser Ser Gly Gly Ser Gly Gly Ser Ala Val
                20                  25                  30

Gly Leu Leu Ala Pro Pro Gly Gly Leu Ser Gly Arg Ser Asp Asn Pro
            35                  40                  45

Gly Gly Ser Asp Ile Val Met Thr Gln Ser Pro Leu Ser Leu Pro Val
50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
        115                 120                 125

Leu Lys Ile Ser Arg Val Glu Ala Glu Asp Val Gly Val Tyr Tyr Cys
    130                 135                 140

Ala Gln Asn Leu Glu Leu Pro Tyr Thr Phe Gly Gln Gly Thr Lys Leu
145                 150                 155                 160

Glu Ile Lys

<210> SEQ ID NO 394
<211> LENGTH: 156
<212> TYPE: PRT
<213> ORGANISM: Artificial Sequence
<220> FEATURE:
<223> OTHER INFORMATION: chemically synthesized

<400> SEQUENCE: 394

Leu Cys His Pro Ala Val Leu Ser Ala Trp Glu Ser Cys Ser Ser Gly
1               5                   10                  15

Gly Gly Ser Ser Gly Gly Ser Ala Val Gly Leu Leu Ala Pro Pro Gly
                20                  25                  30

Gly Leu Ser Gly Arg Ser Asp Asn Pro Gly Gly Ser Asp Ile Val Met
            35                  40                  45

Thr Gln Ser Pro Leu Ser Leu Pro Val Thr Pro Gly Glu Pro Ala Ser
    50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
            115                 120                 125

Ala Glu Asp Val Gly Val Tyr Tyr Cys Ala Gln Asn Leu Glu Leu Pro
        130                 135                 140

Tyr Thr Phe Gly Gln Gly Thr Lys Leu Glu Ile Lys
145                 150                 155

<210> SEQ ID NO 395
<211> LENGTH: 266
<212> TYPE: PRT
<213> ORGANISM: Artificial Sequence
<220> FEATURE:
<223> OTHER INFORMATION: chemically synthesized

<400> SEQUENCE: 395

Gln Gly Gln Ser Gly Gln Gly Leu Cys His Pro Ala Val Leu Ser Ala
1               5                   10                  15

Trp Glu Ser Cys Ser Ser Gly Gly Ser Ser Gly Gly Ser Ile Ser
            20                  25                  30

Ser Gly Leu Leu Ser Gly Arg Ser Ala Asn Pro Gly Gly Gly Ser Asp
        35                  40                  45

Ile Val Met Thr Gln Ser Pro Leu Ser Leu Pro Val Thr Pro Gly Glu
    50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Ala Gln Asn Leu
    130                 135                 140

Glu Leu Pro Tyr Thr Phe Gly Gln Gly Thr Lys Leu Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265

<210> SEQ ID NO 396
<211> LENGTH: 259
<212> TYPE: PRT
<213> ORGANISM: Artificial Sequence
<220> FEATURE:
<223> OTHER INFORMATION: chemically synthesized

<400> SEQUENCE: 396

```
Leu Cys His Pro Ala Val Leu Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Ala Asn Pro Gly Gly Gly Ser Asp Ile Val Met Thr Gln Ser Pro
        35                  40                  45

Leu Ser Leu Pro Val Thr Pro Gly Glu Pro Ala Ser Ile Ser Cys Arg
    50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
        115                 120                 125

Gly Val Tyr Tyr Cys Ala Gln Asn Leu Glu Leu Pro Tyr Thr Phe Gly
130                 135                 140

Gln Gly Thr Lys Leu Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys
```

<210> SEQ ID NO 397
<211> LENGTH: 159
<212> TYPE: PRT
<213> ORGANISM: Artificial Sequence
<220> FEATURE:
<223> OTHER INFORMATION: chemically synthesized

<400> SEQUENCE: 397

```
Gln Gly Gln Ser Gly Gln Gly Leu Cys His Pro Ala Val Leu Ser Ala
1               5                   10                  15

Trp Glu Ser Cys Ser Ser Gly Gly Ser Gly Gly Ser Ile Ser
            20                  25                  30

Ser Gly Leu Leu Ser Gly Arg Ser Ala Asn Pro Gly Gly Gly Ser Asp
        35                  40                  45

Ile Val Met Thr Gln Ser Pro Leu Ser Leu Pro Val Thr Pro Gly Glu
    50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95
```

```
Gln Leu Leu Ile Tyr Gln Met Ser Asn Leu Ala Ser Gly Val Pro Asp
                100                 105                 110

Arg Phe Ser Gly Ser Gly Ser Gly Thr Asp Phe Thr Leu Lys Ile Ser
            115                 120                 125

Arg Val Glu Ala Glu Asp Val Gly Val Tyr Tyr Cys Ala Gln Asn Leu
130                 135                 140

Glu Leu Pro Tyr Thr Phe Gly Gln Gly Thr Lys Leu Glu Ile Lys
145                 150                 155

<210> SEQ ID NO 398
<211> LENGTH: 152
<212> TYPE: PRT
<213> ORGANISM: Artificial Sequence
<220> FEATURE:
<223> OTHER INFORMATION: chemically synthesized

<400> SEQUENCE: 398

Leu Cys His Pro Ala Val Leu Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Ala Asn Pro Gly Gly Ser Asp Ile Val Met Thr Gln Ser Pro
        35                  40                  45

Leu Ser Leu Pro Val Thr Pro Gly Glu Pro Ala Ser Ile Ser Cys Arg
50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
                100                 105                 110

Gly Thr Asp Phe Thr Leu Lys Ile Ser Arg Val Glu Ala Glu Asp Val
            115                 120                 125

Gly Val Tyr Tyr Cys Ala Gln Asn Leu Glu Leu Pro Tyr Thr Phe Gly
130                 135                 140

Gln Gly Thr Lys Leu Glu Ile Lys
145                 150

<210> SEQ ID NO 399
<211> LENGTH: 270
<212> TYPE: PRT
<213> ORGANISM: Artificial Sequence
<220> FEATURE:
<223> OTHER INFORMATION: chemically synthesized

<400> SEQUENCE: 399

Gln Gly Gln Ser Gly Gln Gly Leu Cys His Pro Ala Val Leu Ser Ala
1               5                   10                  15

Trp Glu Ser Cys Ser Ser Gly Gly Ser Ser Gly Gly Ser Ala Val
            20                  25                  30

Gly Leu Leu Ala Pro Pro Gly Gly Leu Ser Gly Arg Ser Ala Asn Pro
        35                  40                  45

Gly Gly Ser Asp Ile Val Met Thr Gln Ser Pro Leu Ser Leu Pro Val
            50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
```

```
                 85                  90                  95
Gly Gln Ser Pro Gln Leu Leu Ile Tyr Gln Met Ser Asn Leu Ala Ser
                100                 105                 110

Gly Val Pro Asp Arg Phe Ser Gly Ser Gly Ser Gly Thr Asp Phe Thr
            115                 120                 125

Leu Lys Ile Ser Arg Val Glu Ala Glu Asp Val Gly Val Tyr Tyr Cys
        130                 135                 140

Ala Gln Asn Leu Glu Leu Pro Tyr Thr Phe Gly Gln Gly Thr Lys Leu
145                 150                 155                 160

Glu Ile Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
                180                 185                 190

Asn Asn Phe Tyr Pro Arg Glu Ala Lys Val Gln Trp Lys Val Asp Asn
                195                 200                 205

Ala Leu Gln Ser Gly Asn Ser Gln Glu Ser Val Thr Glu Gln Asp Ser
            210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
                260                 265                 270

<210> SEQ ID NO 400
<211> LENGTH: 263
<212> TYPE: PRT
<213> ORGANISM: Artificial Sequence
<220> FEATURE:
<223> OTHER INFORMATION: chemically synthesized

<400> SEQUENCE: 400

Leu Cys His Pro Ala Val Leu Ser Ala Trp Glu Ser Cys Ser Ser Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Ala Asn Pro Gly Gly Ser Asp Ile Val Met
        35                  40                  45

Thr Gln Ser Pro Leu Ser Leu Pro Val Thr Pro Gly Glu Pro Ala Ser
    50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
                100                 105                 110

Gly Ser Gly Ser Gly Thr Asp Phe Thr Leu Lys Ile Ser Arg Val Glu
            115                 120                 125

Ala Glu Asp Val Gly Val Tyr Tyr Cys Ala Gln Asn Leu Glu Leu Pro
        130                 135                 140

Tyr Thr Phe Gly Gln Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
```

```
                180                 185                 190
Ala Lys Val Gln Trp Lys Val Asp Asn Ala Leu Gln Ser Gly Asn Ser
                195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
                260

<210> SEQ ID NO 401
<211> LENGTH: 163
<212> TYPE: PRT
<213> ORGANISM: Artificial Sequence
<220> FEATURE:
<223> OTHER INFORMATION: chemically synthesized

<400> SEQUENCE: 401

Gln Gly Gln Ser Gly Gln Gly Leu Cys His Pro Ala Val Leu Ser Ala
1               5                   10                  15

Trp Glu Ser Cys Ser Ser Gly Gly Ser Ser Gly Gly Ser Ala Val
            20                  25                  30

Gly Leu Leu Ala Pro Pro Gly Leu Ser Gly Arg Ser Ala Asn Pro
            35                  40                  45

Gly Gly Ser Asp Ile Val Met Thr Gln Ser Pro Leu Ser Leu Pro Val
    50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
            115                 120                 125

Leu Lys Ile Ser Arg Val Glu Ala Glu Asp Val Gly Val Tyr Tyr Cys
    130                 135                 140

Ala Gln Asn Leu Glu Leu Pro Tyr Thr Phe Gly Gln Gly Thr Lys Leu
145                 150                 155                 160

Glu Ile Lys

<210> SEQ ID NO 402
<211> LENGTH: 156
<212> TYPE: PRT
<213> ORGANISM: Artificial Sequence
<220> FEATURE:
<223> OTHER INFORMATION: chemically synthesized

<400> SEQUENCE: 402

Leu Cys His Pro Ala Val Leu Ser Ala Trp Glu Ser Cys Ser Ser Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Ala Asn Pro Gly Gly Ser Asp Ile Val Met
            35                  40                  45

Thr Gln Ser Pro Leu Ser Leu Pro Val Thr Pro Gly Glu Pro Ala Ser
```

```
            50                  55                  60
Ile Ser Cys Arg Ser Ser Lys Ser Leu Leu His Ser Asn Gly Ile Thr
 65                  70                  75                  80

Tyr Leu Tyr Trp Tyr Leu Gln Lys Pro Gly Gln Ser Pro Gln Leu Leu
                 85                  90                  95

Ile Tyr Gln Met Ser Asn Leu Ala Ser Gly Val Pro Asp Arg Phe Ser
                100                 105                 110

Gly Ser Gly Ser Gly Thr Asp Phe Thr Leu Lys Ile Ser Arg Val Glu
            115                 120                 125

Ala Glu Asp Val Gly Val Tyr Tyr Cys Ala Gln Asn Leu Glu Leu Pro
        130                 135                 140

Tyr Thr Phe Gly Gln Gly Thr Lys Leu Glu Ile Lys
145                 150                 155

<210> SEQ ID NO 403
<211> LENGTH: 266
<212> TYPE: PRT
<213> ORGANISM: Artificial Sequence
<220> FEATURE:
<223> OTHER INFORMATION: chemically synthesized

<400> SEQUENCE: 403

Gln Gly Gln Ser Gly Gln Gly Leu Cys His Pro Ala Val Leu Ser Ala
 1               5                  10                  15

Trp Glu Ser Cys Ser Ser Gly Gly Ser Ser Gly Gly Ser Ile Ser
                 20                  25                  30

Ser Gly Leu Leu Ser Gly Arg Ser Ala Asn Ile Gly Gly Gly Ser Asp
             35                  40                  45

Ile Val Met Thr Gln Ser Pro Leu Ser Leu Pro Val Thr Pro Gly Glu
         50                  55                  60

Pro Ala Ser Ile Ser Cys Arg Ser Ser Lys Ser Leu Leu His Ser Asn
 65                  70                  75                  80

Gly Ile Thr Tyr Leu Tyr Trp Tyr Leu Gln Lys Pro Gly Gln Ser Pro
                 85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Ala Gln Asn Leu
130                 135                 140

Glu Leu Pro Tyr Thr Phe Gly Gln Gly Thr Lys Leu Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
```

```
<210> SEQ ID NO 404
<211> LENGTH: 259
<212> TYPE: PRT
<213> ORGANISM: Artificial Sequence
<220> FEATURE:
<223> OTHER INFORMATION: chemically synthesized

<400> SEQUENCE: 404

Leu Cys His Pro Ala Val Leu Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Ala Asn Ile Gly Gly Ser Asp Ile Val Met Thr Gln Ser Pro
        35                  40                  45

Leu Ser Leu Pro Val Thr Pro Gly Glu Pro Ala Ser Ile Ser Cys Arg
50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
        115                 120                 125

Gly Val Tyr Tyr Cys Ala Gln Asn Leu Glu Leu Pro Tyr Thr Phe Gly
130                 135                 140

Gln Gly Thr Lys Leu Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 405
<211> LENGTH: 159
<212> TYPE: PRT
<213> ORGANISM: Artificial Sequence
<220> FEATURE:
<223> OTHER INFORMATION: chemically synthesized

<400> SEQUENCE: 405

Gln Gly Gln Ser Gly Gln Gly Leu Cys His Pro Ala Val Leu Ser Ala
1               5                   10                  15

Trp Glu Ser Cys Ser Ser Gly Gly Ser Gly Gly Ser Ile Ser
            20                  25                  30

Ser Gly Leu Leu Ser Gly Arg Ser Ala Asn Ile Gly Gly Gly Ser Asp
```

```
                    35                  40                  45
Ile Val Met Thr Gln Ser Pro Leu Ser Leu Pro Val Thr Pro Gly Glu
         50                  55                  60
Pro Ala Ser Ile Ser Cys Arg Ser Ser Lys Ser Leu Leu His Ser Asn
 65                  70                  75                  80
Gly Ile Thr Tyr Leu Tyr Trp Tyr Leu Gln Lys Pro Gly Gln Ser Pro
                 85                  90                  95
Gln Leu Leu Ile Tyr Gln Met Ser Asn Leu Ala Ser Gly Val Pro Asp
            100                 105                 110
Arg Phe Ser Gly Ser Gly Ser Gly Thr Asp Phe Thr Leu Lys Ile Ser
        115                 120                 125
Arg Val Glu Ala Glu Asp Val Gly Val Tyr Tyr Cys Ala Gln Asn Leu
    130                 135                 140
Glu Leu Pro Tyr Thr Phe Gly Gln Gly Thr Lys Leu Glu Ile Lys
145                 150                 155

<210> SEQ ID NO 406
<211> LENGTH: 152
<212> TYPE: PRT
<213> ORGANISM: Artificial Sequence
<220> FEATURE:
<223> OTHER INFORMATION: chemically synthesized

<400> SEQUENCE: 406

Leu Cys His Pro Ala Val Leu Ser Ala Trp Glu Ser Cys Ser Ser Gly
 1               5                  10                  15
Gly Gly Ser Ser Gly Gly Ser Ile Ser Ser Gly Leu Leu Ser Gly Arg
                20                  25                  30
Ser Ala Asn Ile Gly Gly Gly Ser Asp Ile Val Met Thr Gln Ser Pro
            35                  40                  45
Leu Ser Leu Pro Val Thr Pro Gly Glu Pro Ala Ser Ile Ser Cys Arg
 50                  55                  60
Ser Ser Lys Ser Leu Leu His Ser Asn Gly Ile Thr Tyr Leu Tyr Trp
 65                  70                  75                  80
Tyr Leu Gln Lys Pro Gly Gln Ser Pro Gln Leu Leu Ile Tyr Gln Met
                 85                  90                  95
Ser Asn Leu Ala Ser Gly Val Pro Asp Arg Phe Ser Gly Ser Gly Ser
            100                 105                 110
Gly Thr Asp Phe Thr Leu Lys Ile Ser Arg Val Glu Ala Glu Asp Val
        115                 120                 125
Gly Val Tyr Tyr Cys Ala Gln Asn Leu Glu Leu Pro Tyr Thr Phe Gly
    130                 135                 140
Gln Gly Thr Lys Leu Glu Ile Lys
145                 150

<210> SEQ ID NO 407
<211> LENGTH: 270
<212> TYPE: PRT
<213> ORGANISM: Artificial Sequence
<220> FEATURE:
<223> OTHER INFORMATION: chemically synthesized

<400> SEQUENCE: 407

Gln Gly Gln Ser Gly Gln Gly Leu Cys His Pro Ala Val Leu Ser Ala
 1               5                  10                  15
Trp Glu Ser Cys Ser Ser Gly Gly Gly Ser Ser Gly Gly Ser Ala Val
                20                  25                  30
```

```
Gly Leu Leu Ala Pro Pro Gly Leu Ser Gly Arg Ser Ala Asn Ile
            35                  40                  45

Gly Gly Ser Asp Ile Val Met Thr Gln Ser Pro Leu Ser Leu Pro Val
 50                  55                  60

Thr Pro Gly Glu Pro Ala Ser Ile Ser Cys Arg Ser Ser Lys Ser Leu
 65                  70                  75                  80

Leu His Ser Asn Gly Ile Thr Tyr Leu Tyr Trp Tyr Leu Gln Lys Pro
                 85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
            115                 120                 125

Leu Lys Ile Ser Arg Val Glu Ala Glu Asp Val Gly Val Tyr Tyr Cys
130                 135                 140

Ala Gln Asn Leu Glu Leu Pro Tyr Thr Phe Gly Gln Gly Thr Lys Leu
145                 150                 155                 160

Glu Ile Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
            180                 185                 190

Asn Asn Phe Tyr Pro Arg Glu Ala Lys Val Gln Trp Lys Val Asp Asn
            195                 200                 205

Ala Leu Gln Ser Gly Asn Ser Gln Glu Ser Val Thr Glu Gln Asp Ser
210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
            260                 265                 270

<210> SEQ ID NO 408
<211> LENGTH: 263
<212> TYPE: PRT
<213> ORGANISM: Artificial Sequence
<220> FEATURE:
<223> OTHER INFORMATION: chemically synthesized

<400> SEQUENCE: 408

Leu Cys His Pro Ala Val Leu Ser Ala Trp Glu Ser Cys Ser Ser Gly
 1               5                  10                  15

Gly Gly Ser Ser Gly Gly Ser Ala Val Gly Leu Leu Ala Pro Pro Gly
            20                  25                  30

Gly Leu Ser Gly Arg Ser Ala Asn Ile Gly Gly Ser Asp Ile Val Met
            35                  40                  45

Thr Gln Ser Pro Leu Ser Leu Pro Val Thr Pro Gly Glu Pro Ala Ser
 50                  55                  60

Ile Ser Cys Arg Ser Ser Lys Ser Leu Leu His Ser Asn Gly Ile Thr
 65                  70                  75                  80

Tyr Leu Tyr Trp Tyr Leu Gln Lys Pro Gly Gln Ser Pro Gln Leu Leu
                 85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
            115                 120                 125
```

```
Ala Glu Asp Val Gly Val Tyr Tyr Cys Ala Gln Asn Leu Glu Leu Pro
    130                 135                 140

Tyr Thr Phe Gly Gln Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 409
<211> LENGTH: 163
<212> TYPE: PRT
<213> ORGANISM: Artificial Sequence
<220> FEATURE:
<223> OTHER INFORMATION: chemically synthesized

<400> SEQUENCE: 409

Gln Gly Gln Ser Gly Gln Gly Leu Cys His Pro Ala Val Leu Ser Ala
1               5                   10                  15

Trp Glu Ser Cys Ser Ser Gly Gly Ser Ser Gly Gly Ser Ala Val
                20                  25                  30

Gly Leu Leu Ala Pro Pro Gly Gly Leu Ser Gly Arg Ser Ala Asn Ile
            35                  40                  45

Gly Gly Ser Asp Ile Val Met Thr Gln Ser Pro Leu Ser Leu Pro Val
        50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
                100                 105                 110

Gly Val Pro Asp Arg Phe Ser Gly Ser Gly Ser Gly Thr Asp Phe Thr
            115                 120                 125

Leu Lys Ile Ser Arg Val Glu Ala Glu Asp Val Gly Val Tyr Tyr Cys
        130                 135                 140

Ala Gln Asn Leu Glu Leu Pro Tyr Thr Phe Gly Gln Gly Thr Lys Leu
145                 150                 155                 160

Glu Ile Lys

<210> SEQ ID NO 410
<211> LENGTH: 156
<212> TYPE: PRT
<213> ORGANISM: Artificial Sequence
<220> FEATURE:
<223> OTHER INFORMATION: chemically synthesized

<400> SEQUENCE: 410
```

```
Leu Cys His Pro Ala Val Leu Ser Ala Trp Glu Ser Cys Ser Ser Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Ala Asn Ile Gly Gly Ser Asp Ile Val Met
        35                  40                  45

Thr Gln Ser Pro Leu Ser Leu Pro Val Thr Pro Gly Glu Pro Ala Ser
50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
130                 135                 140

Tyr Thr Phe Gly Gln Gly Thr Lys Leu Glu Ile Lys
145                 150                 155
```

<210> SEQ ID NO 411
<211> LENGTH: 266
<212> TYPE: PRT
<213> ORGANISM: Artificial Sequence
<220> FEATURE:
<223> OTHER INFORMATION: chemically synthesized

<400> SEQUENCE: 411

```
Gln Gly Gln Ser Gly Gln Gly Leu Cys His Pro Leu Val Ala Ser Ala
1               5                   10                  15

Trp Glu Ser Cys Ser Ser Gly Gly Ser Gly Gly Ser Ile Ser
            20                  25                  30

Ser Gly Leu Leu Ser Gly Arg Ser Asp Ile His Gly Gly Ser Asp
        35                  40                  45

Ile Val Met Thr Gln Ser Pro Leu Ser Leu Pro Val Thr Pro Gly Glu
50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Ala Gln Asn Leu
130                 135                 140

Glu Leu Pro Tyr Thr Phe Gly Gln Gly Thr Lys Leu Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205
```

```
Gly Asn Ser Gln Glu Ser Val Thr Glu Gln Asp Ser Lys Asp Ser Thr
            210                 215                 220
Tyr Ser Leu Ser Ser Thr Leu Thr Leu Ser Lys Ala Asp Tyr Glu Lys
225                 230                 235                 240
His Lys Val Tyr Ala Cys Glu Val Thr His Gln Gly Leu Ser Ser Pro
                245                 250                 255
Val Thr Lys Ser Phe Asn Arg Gly Glu Cys
                260                 265
```

<210> SEQ ID NO 412
<211> LENGTH: 259
<212> TYPE: PRT
<213> ORGANISM: Artificial Sequence
<220> FEATURE:
<223> OTHER INFORMATION: chemically synthesized

<400> SEQUENCE: 412

```
Leu Cys His Pro Leu Val Ala Ser Ala Trp Glu Ser Cys Ser Ser Gly
1               5                   10                  15
Gly Gly Ser Ser Gly Gly Ser Ile Ser Ser Gly Leu Leu Ser Gly Arg
                20                  25                  30
Ser Asp Ile His Gly Gly Gly Ser Asp Ile Val Met Thr Gln Ser Pro
                35                  40                  45
Leu Ser Leu Pro Val Thr Pro Gly Glu Pro Ala Ser Ile Ser Cys Arg
50                  55                  60
Ser Ser Lys Ser Leu Leu His Ser Asn Gly Ile Thr Tyr Leu Tyr Trp
65                  70                  75                  80
Tyr Leu Gln Lys Pro Gly Gln Ser Pro Gln Leu Leu Ile Tyr Gln Met
                85                  90                  95
Ser Asn Leu Ala Ser Gly Val Pro Asp Arg Phe Ser Gly Ser Gly Ser
                100                 105                 110
Gly Thr Asp Phe Thr Leu Lys Ile Ser Arg Val Glu Ala Glu Asp Val
                115                 120                 125
Gly Val Tyr Tyr Cys Ala Gln Asn Leu Glu Leu Pro Tyr Thr Phe Gly
130                 135                 140
Gln Gly Thr Lys Leu Glu Ile Lys Arg Thr Val Ala Ala Pro Ser Val
145                 150                 155                 160
Phe Ile Phe Pro Pro Ser Asp Glu Gln Leu Lys Ser Gly Thr Ala Ser
                165                 170                 175
Val Val Cys Leu Leu Asn Asn Phe Tyr Pro Arg Glu Ala Lys Val Gln
                180                 185                 190
Trp Lys Val Asp Asn Ala Leu Gln Ser Gly Asn Ser Gln Glu Ser Val
                195                 200                 205
Thr Glu Gln Asp Ser Lys Asp Ser Thr Tyr Ser Leu Ser Ser Thr Leu
            210                 215                 220
Thr Leu Ser Lys Ala Asp Tyr Glu Lys His Lys Val Tyr Ala Cys Glu
225                 230                 235                 240
Val Thr His Gln Gly Leu Ser Ser Pro Val Thr Lys Ser Phe Asn Arg
                245                 250                 255
Gly Glu Cys
```

<210> SEQ ID NO 413
<211> LENGTH: 159
<212> TYPE: PRT
<213> ORGANISM: Artificial Sequence
<220> FEATURE:
<223> OTHER INFORMATION: chemically synthesized

<400> SEQUENCE: 413

Gln Gly Gln Ser Gly Gln Gly Leu Cys His Pro Leu Val Ala Ser Ala
1               5                   10                  15

Trp Glu Ser Cys Ser Ser Gly Gly Ser Gly Gly Ser Ile Ser
            20                  25                  30

Ser Gly Leu Leu Ser Gly Arg Ser Asp Ile His Gly Gly Gly Ser Asp
        35                  40                  45

Ile Val Met Thr Gln Ser Pro Leu Ser Leu Pro Val Thr Pro Gly Glu
    50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Ala Gln Asn Leu
    130                 135                 140

Glu Leu Pro Tyr Thr Phe Gly Gln Gly Thr Lys Leu Glu Ile Lys
145                 150                 155

<210> SEQ ID NO 414
<211> LENGTH: 152
<212> TYPE: PRT
<213> ORGANISM: Artificial Sequence
<220> FEATURE:
<223> OTHER INFORMATION: chemically synthesized

<400> SEQUENCE: 414

Leu Cys His Pro Leu Val Ala Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Asp Ile His Gly Gly Ser Asp Ile Val Met Thr Gln Ser Pro
        35                  40                  45

Leu Ser Leu Pro Val Thr Pro Gly Glu Pro Ala Ser Ile Ser Cys Arg
    50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
        115                 120                 125

Gly Val Tyr Tyr Cys Ala Gln Asn Leu Glu Leu Pro Tyr Thr Phe Gly
    130                 135                 140

Gln Gly Thr Lys Leu Glu Ile Lys
145                 150

<210> SEQ ID NO 415
<211> LENGTH: 270
<212> TYPE: PRT
<213> ORGANISM: Artificial Sequence
<220> FEATURE:

<223> OTHER INFORMATION: chemically synthesized

<400> SEQUENCE: 415

Gln Gly Gln Ser Gly Gln Gly Leu Cys His Pro Leu Val Ala Ser Ala
1               5                   10                  15

Trp Glu Ser Cys Ser Ser Gly Gly Ser Ser Gly Gly Ser Ala Val
            20                  25                  30

Gly Leu Leu Ala Pro Pro Gly Gly Leu Ser Gly Arg Ser Asp Ile His
        35                  40                  45

Gly Gly Ser Asp Ile Val Met Thr Gln Ser Pro Leu Ser Leu Pro Val
    50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
        115                 120                 125

Leu Lys Ile Ser Arg Val Glu Ala Glu Asp Val Gly Val Tyr Tyr Cys
    130                 135                 140

Ala Gln Asn Leu Glu Leu Pro Tyr Thr Phe Gly Gln Gly Thr Lys Leu
145                 150                 155                 160

Glu Ile Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
            180                 185                 190

Asn Asn Phe Tyr Pro Arg Glu Ala Lys Val Gln Trp Lys Val Asp Asn
        195                 200                 205

Ala Leu Gln Ser Gly Asn Ser Gln Glu Ser Val Thr Glu Gln Asp Ser
    210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
            260                 265                 270

<210> SEQ ID NO 416
<211> LENGTH: 263
<212> TYPE: PRT
<213> ORGANISM: Artificial Sequence
<220> FEATURE:
<223> OTHER INFORMATION: chemically synthesized

<400> SEQUENCE: 416

Leu Cys His Pro Leu Val Ala Ser Ala Trp Glu Ser Cys Ser Ser Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Ile His Gly Gly Ser Asp Ile Val Met
        35                  40                  45

Thr Gln Ser Pro Leu Ser Leu Pro Val Thr Pro Gly Glu Pro Ala Ser
    50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
130                 135                 140

Tyr Thr Phe Gly Gln Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
                260

<210> SEQ ID NO 417
<211> LENGTH: 163
<212> TYPE: PRT
<213> ORGANISM: Artificial Sequence
<220> FEATURE:
<223> OTHER INFORMATION: chemically synthesized

<400> SEQUENCE: 417

Gln Gly Gln Ser Gly Gln Gly Leu Cys His Pro Leu Val Ala Ser Ala
1               5                   10                  15

Trp Glu Ser Cys Ser Ser Gly Gly Ser Ser Gly Gly Ser Ala Val
                20                  25                  30

Gly Leu Leu Ala Pro Pro Gly Gly Leu Ser Gly Arg Ser Asp Ile His
            35                  40                  45

Gly Gly Ser Asp Ile Val Met Thr Gln Ser Pro Leu Ser Leu Pro Val
        50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
        115                 120                 125

Leu Lys Ile Ser Arg Val Glu Ala Glu Asp Val Gly Val Tyr Tyr Cys
    130                 135                 140

Ala Gln Asn Leu Glu Leu Pro Tyr Thr Phe Gly Gln Gly Thr Lys Leu
145                 150                 155                 160

Glu Ile Lys

```
<210> SEQ ID NO 418
<211> LENGTH: 156
<212> TYPE: PRT
<213> ORGANISM: Artificial Sequence
<220> FEATURE:
<223> OTHER INFORMATION: chemically synthesized

<400> SEQUENCE: 418

Leu Cys His Pro Leu Val Ala Ser Ala Trp Glu Ser Cys Ser Ser Gly
1               5                   10                  15

Gly Gly Ser Ser Gly Gly Ser Ala Val Gly Leu Leu Ala Pro Pro Gly
                20                  25                  30

Gly Leu Ser Gly Arg Ser Asp Ile His Gly Gly Ser Asp Ile Val Met
            35                  40                  45

Thr Gln Ser Pro Leu Ser Leu Pro Val Thr Pro Gly Glu Pro Ala Ser
        50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
    130                 135                 140

Tyr Thr Phe Gly Gln Gly Thr Lys Leu Glu Ile Lys
145                 150                 155

<210> SEQ ID NO 419
<211> LENGTH: 266
<212> TYPE: PRT
<213> ORGANISM: Artificial Sequence
<220> FEATURE:
<223> OTHER INFORMATION: chemically synthesized

<400> SEQUENCE: 419

Gln Gly Gln Ser Gly Gln Gly Leu Cys His Pro Leu Val Ala Ser Ala
1               5                   10                  15

Trp Glu Ser Cys Ser Ser Gly Gly Gly Ser Gly Gly Ser Ile Ser
                20                  25                  30

Ser Gly Leu Leu Ser Gly Arg Ser Asp Gln His Gly Gly Ser Asp
            35                  40                  45

Ile Val Met Thr Gln Ser Pro Leu Ser Leu Pro Val Thr Pro Gly Glu
        50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Ala Gln Asn Leu
    130                 135                 140

Glu Leu Pro Tyr Thr Phe Gly Gln Gly Thr Lys Leu Glu Ile Lys Arg
145                 150                 155                 160
```

```
Thr Val Ala Ala Pro Ser Val Phe Ile Phe Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
                260                 265

<210> SEQ ID NO 420
<211> LENGTH: 259
<212> TYPE: PRT
<213> ORGANISM: Artificial Sequence
<220> FEATURE:
<223> OTHER INFORMATION: chemically synthesized

<400> SEQUENCE: 420

Leu Cys His Pro Leu Val Ala Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Asp Gln His Gly Gly Ser Asp Ile Val Met Thr Gln Ser Pro
        35                  40                  45

Leu Ser Leu Pro Val Thr Pro Gly Glu Pro Ala Ser Ile Ser Cys Arg
    50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
        115                 120                 125

Gly Val Tyr Tyr Cys Ala Gln Asn Leu Glu Leu Pro Tyr Thr Phe Gly
    130                 135                 140

Gln Gly Thr Lys Leu Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255
```

Gly Glu Cys

<210> SEQ ID NO 421
<211> LENGTH: 159
<212> TYPE: PRT
<213> ORGANISM: Artificial Sequence
<220> FEATURE:
<223> OTHER INFORMATION: chemically synthesized

<400> SEQUENCE: 421

Gln Gly Gln Ser Gly Gln Gly Leu Cys His Pro Leu Val Ala Ser Ala
1               5                   10                  15

Trp Glu Ser Cys Ser Ser Gly Gly Ser Ser Gly Gly Ser Ile Ser
                20                  25                  30

Ser Gly Leu Leu Ser Gly Arg Ser Asp Gln His Gly Gly Ser Asp
            35                  40                  45

Ile Val Met Thr Gln Ser Pro Leu Ser Leu Pro Val Thr Pro Gly Glu
    50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Ala Gln Asn Leu
    130                 135                 140

Glu Leu Pro Tyr Thr Phe Gly Gln Gly Thr Lys Leu Glu Ile Lys
145                 150                 155

<210> SEQ ID NO 422
<211> LENGTH: 152
<212> TYPE: PRT
<213> ORGANISM: Artificial Sequence
<220> FEATURE:
<223> OTHER INFORMATION: chemically synthesized

<400> SEQUENCE: 422

Leu Cys His Pro Leu Val Ala Ser Ala Trp Glu Ser Cys Ser Ser Gly
1               5                   10                  15

Gly Gly Ser Ser Gly Gly Ser Ile Ser Ser Gly Leu Leu Ser Gly Arg
                20                  25                  30

Ser Asp Gln His Gly Gly Gly Ser Asp Ile Val Met Thr Gln Ser Pro
            35                  40                  45

Leu Ser Leu Pro Val Thr Pro Gly Glu Pro Ala Ser Ile Ser Cys Arg
    50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
        115                 120                 125

Gly Val Tyr Tyr Cys Ala Gln Asn Leu Glu Leu Pro Tyr Thr Phe Gly
    130                 135                 140

```
Gln Gly Thr Lys Leu Glu Ile Lys
145                 150

<210> SEQ ID NO 423
<211> LENGTH: 270
<212> TYPE: PRT
<213> ORGANISM: Artificial Sequence
<220> FEATURE:
<223> OTHER INFORMATION: chemically synthesized

<400> SEQUENCE: 423

Gln Gly Gln Ser Gly Gln Gly Leu Cys His Pro Leu Val Ala Ser Ala
1               5                   10                  15

Trp Glu Ser Cys Ser Ser Gly Gly Ser Ser Gly Gly Ser Ala Val
            20                  25                  30

Gly Leu Leu Ala Pro Pro Gly Gly Leu Ser Gly Arg Ser Asp Gln His
            35                  40                  45

Gly Gly Ser Asp Ile Val Met Thr Gln Ser Pro Leu Ser Leu Pro Val
    50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
        115                 120                 125

Leu Lys Ile Ser Arg Val Glu Ala Glu Asp Val Gly Val Tyr Tyr Cys
    130                 135                 140

Ala Gln Asn Leu Glu Leu Pro Tyr Thr Phe Gly Gln Gly Thr Lys Leu
145                 150                 155                 160

Glu Ile Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
            180                 185                 190

Asn Asn Phe Tyr Pro Arg Glu Ala Lys Val Gln Trp Lys Val Asp Asn
        195                 200                 205

Ala Leu Gln Ser Gly Asn Ser Gln Glu Ser Val Thr Glu Gln Asp Ser
    210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
            260                 265                 270

<210> SEQ ID NO 424
<211> LENGTH: 263
<212> TYPE: PRT
<213> ORGANISM: Artificial Sequence
<220> FEATURE:
<223> OTHER INFORMATION: chemically synthesized

<400> SEQUENCE: 424

Leu Cys His Pro Leu Val Ala Ser Ala Trp Glu Ser Cys Ser Ser Gly
1               5                   10                  15

Gly Gly Ser Ser Gly Gly Ser Ala Val Gly Leu Leu Ala Pro Pro Gly
```

```
            20                  25                  30
Gly Leu Ser Gly Arg Ser Asp Gln His Gly Gly Ser Asp Ile Val Met
        35                  40                  45

Thr Gln Ser Pro Leu Ser Leu Pro Val Thr Pro Gly Glu Pro Ala Ser
 50                  55                  60

Ile Ser Cys Arg Ser Ser Lys Ser Leu Leu His Ser Asn Gly Ile Thr
 65                  70                  75                  80

Tyr Leu Tyr Trp Tyr Leu Gln Lys Pro Gly Gln Ser Pro Gln Leu Leu
                 85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
130                 135                 140

Tyr Thr Phe Gly Gln Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 425
<211> LENGTH: 163
<212> TYPE: PRT
<213> ORGANISM: Artificial Sequence
<220> FEATURE:
<223> OTHER INFORMATION: chemically synthesized

<400> SEQUENCE: 425

Gln Gly Gln Ser Gly Gln Gly Leu Cys His Pro Leu Val Ala Ser Ala
 1               5                  10                  15

Trp Glu Ser Cys Ser Ser Gly Gly Ser Ser Gly Gly Ser Ala Val
                20                  25                  30

Gly Leu Leu Ala Pro Gly Gly Leu Ser Gly Arg Ser Asp Gln His
        35                  40                  45

Gly Gly Ser Asp Ile Val Met Thr Gln Ser Pro Leu Ser Leu Pro Val
     50                  55                  60

Thr Pro Gly Glu Pro Ala Ser Ile Ser Cys Arg Ser Ser Lys Ser Leu
 65                  70                  75                  80

Leu His Ser Asn Gly Ile Thr Tyr Leu Tyr Trp Tyr Leu Gln Lys Pro
                 85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
```

```
                115                 120                 125
Leu Lys Ile Ser Arg Val Glu Ala Glu Asp Val Gly Val Tyr Tyr Cys
    130                 135                 140

Ala Gln Asn Leu Glu Leu Pro Tyr Thr Phe Gly Gln Gly Thr Lys Leu
145                 150                 155                 160

Glu Ile Lys

<210> SEQ ID NO 426
<211> LENGTH: 156
<212> TYPE: PRT
<213> ORGANISM: Artificial Sequence
<220> FEATURE:
<223> OTHER INFORMATION: chemically synthesized

<400> SEQUENCE: 426

Leu Cys His Pro Leu Val Ala Ser Ala Trp Glu Ser Cys Ser Ser Gly
1               5                   10                  15

Gly Gly Ser Ser Gly Gly Ser Ala Val Gly Leu Leu Ala Pro Pro Gly
                20                  25                  30

Gly Leu Ser Gly Arg Ser Asp Gln His Gly Gly Ser Asp Ile Val Met
            35                  40                  45

Thr Gln Ser Pro Leu Ser Leu Pro Val Thr Pro Gly Glu Pro Ala Ser
        50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
    130                 135                 140

Tyr Thr Phe Gly Gln Gly Thr Lys Leu Glu Ile Lys
145                 150                 155

<210> SEQ ID NO 427
<211> LENGTH: 266
<212> TYPE: PRT
<213> ORGANISM: Artificial Sequence
<220> FEATURE:
<223> OTHER INFORMATION: chemically synthesized

<400> SEQUENCE: 427

Gln Gly Gln Ser Gly Gln Gly Leu Cys His Pro Leu Val Ala Ser Ala
1               5                   10                  15

Trp Glu Ser Cys Ser Ser Gly Gly Gly Ser Ser Gly Gly Ser Ile Ser
                20                  25                  30

Ser Gly Leu Leu Ser Gly Arg Ser Asp Asn Pro Gly Gly Gly Ser Asp
            35                  40                  45

Ile Val Met Thr Gln Ser Pro Leu Ser Leu Pro Val Thr Pro Gly Glu
        50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
```

```
                100             105             110
Arg Phe Ser Gly Ser Gly Ser Gly Thr Asp Phe Thr Leu Lys Ile Ser
            115                 120                 125

Arg Val Glu Ala Glu Asp Val Gly Val Tyr Tyr Cys Ala Gln Asn Leu
130                 135                 140

Glu Leu Pro Tyr Thr Phe Gly Gln Gly Thr Lys Leu Glu Ile Lys Arg
145                 150                 155                 160

Thr Val Ala Ala Pro Ser Val Phe Ile Phe Pro Pro Ser Asp Glu Gln
            165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
            195                 200                 205

Gly Asn Ser Gln Glu Ser Val Thr Glu Gln Asp Ser Lys Asp Ser Thr
            210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
            245                 250                 255

Val Thr Lys Ser Phe Asn Arg Gly Glu Cys
            260                 265
```

<210> SEQ ID NO 428
<211> LENGTH: 259
<212> TYPE: PRT
<213> ORGANISM: Artificial Sequence
<220> FEATURE:
<223> OTHER INFORMATION: chemically synthesized

<400> SEQUENCE: 428

```
Leu Cys His Pro Leu Val Ala Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Asp Ile Val Met Thr Gln Ser Pro
            35                  40                  45

Leu Ser Leu Pro Val Thr Pro Gly Glu Pro Ala Ser Ile Ser Cys Arg
50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
            85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
            115                 120                 125

Gly Val Tyr Tyr Cys Ala Gln Asn Leu Glu Leu Pro Tyr Thr Phe Gly
            130                 135                 140

Gln Gly Thr Lys Leu Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
            165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
```

```
                195                 200                 205
Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 429
<211> LENGTH: 159
<212> TYPE: PRT
<213> ORGANISM: Artificial Sequence
<220> FEATURE:
<223> OTHER INFORMATION: chemically synthesized

<400> SEQUENCE: 429

Gln Gly Gln Ser Gly Gln Gly Leu Cys His Pro Leu Val Ala Ser Ala
1               5                   10                  15

Trp Glu Ser Cys Ser Ser Gly Gly Ser Ser Gly Gly Ser Ile Ser
            20                  25                  30

Ser Gly Leu Leu Ser Gly Arg Ser Asp Asn Pro Gly Gly Ser Asp
        35                  40                  45

Ile Val Met Thr Gln Ser Pro Leu Ser Leu Pro Val Thr Pro Gly Glu
    50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Ala Gln Asn Leu
    130                 135                 140

Glu Leu Pro Tyr Thr Phe Gly Gln Gly Thr Lys Leu Glu Ile Lys
145                 150                 155

<210> SEQ ID NO 430
<211> LENGTH: 152
<212> TYPE: PRT
<213> ORGANISM: Artificial Sequence
<220> FEATURE:
<223> OTHER INFORMATION: chemically synthesized

<400> SEQUENCE: 430

Leu Cys His Pro Leu Val Ala Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Asp Ile Val Met Thr Gln Ser Pro
        35                  40                  45

Leu Ser Leu Pro Val Thr Pro Gly Glu Pro Ala Ser Ile Ser Cys Arg
    50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
```

```
                    85                  90                  95
Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
            115                 120                 125

Gly Val Tyr Tyr Cys Ala Gln Asn Leu Glu Leu Pro Tyr Thr Phe Gly
            130                 135                 140

Gln Gly Thr Lys Leu Glu Ile Lys
145                 150

<210> SEQ ID NO 431
<211> LENGTH: 270
<212> TYPE: PRT
<213> ORGANISM: Artificial Sequence
<220> FEATURE:
<223> OTHER INFORMATION: chemically synthesized

<400> SEQUENCE: 431

Gln Gly Gln Ser Gly Gln Gly Leu Cys His Pro Leu Val Ala Ser Ala
1               5                   10                  15

Trp Glu Ser Cys Ser Ser Gly Gly Ser Ser Gly Gly Ser Ala Val
            20                  25                  30

Gly Leu Leu Ala Pro Pro Gly Gly Leu Ser Gly Arg Ser Asp Asn Pro
        35                  40                  45

Gly Gly Ser Asp Ile Val Met Thr Gln Ser Pro Leu Ser Leu Pro Val
    50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
            115                 120                 125

Leu Lys Ile Ser Arg Val Glu Ala Glu Asp Val Gly Val Tyr Tyr Cys
        130                 135                 140

Ala Gln Asn Leu Glu Leu Pro Tyr Thr Phe Gly Gln Gly Thr Lys Leu
145                 150                 155                 160

Glu Ile Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
            180                 185                 190

Asn Asn Phe Tyr Pro Arg Glu Ala Lys Val Gln Trp Lys Val Asp Asn
        195                 200                 205

Ala Leu Gln Ser Gly Asn Ser Gln Glu Ser Val Thr Glu Gln Asp Ser
    210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
            260                 265                 270

<210> SEQ ID NO 432
<211> LENGTH: 263
<212> TYPE: PRT
```

<213> ORGANISM: Artificial Sequence
<220> FEATURE:
<223> OTHER INFORMATION: chemically synthesized

<400> SEQUENCE: 432

Leu Cys His Pro Leu Val Ala Ser Ala Trp Glu Ser Cys Ser Ser Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Asn Pro Gly Gly Ser Asp Ile Val Met
        35                  40                  45

Thr Gln Ser Pro Leu Ser Leu Pro Val Thr Pro Gly Glu Pro Ala Ser
50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
130                 135                 140

Tyr Thr Phe Gly Gln Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
                260

<210> SEQ ID NO 433
<211> LENGTH: 163
<212> TYPE: PRT
<213> ORGANISM: Artificial Sequence
<220> FEATURE:
<223> OTHER INFORMATION: chemically synthesized

<400> SEQUENCE: 433

Gln Gly Gln Ser Gly Gln Gly Leu Cys His Pro Leu Val Ala Ser Ala
1               5                   10                  15

Trp Glu Ser Cys Ser Ser Gly Gly Gly Ser Gly Gly Ser Ala Val
            20                  25                  30

Gly Leu Leu Ala Pro Pro Gly Gly Leu Ser Gly Arg Ser Asp Asn Pro
        35                  40                  45

Gly Gly Ser Asp Ile Val Met Thr Gln Ser Pro Leu Ser Leu Pro Val
50                  55                  60

Thr Pro Gly Glu Pro Ala Ser Ile Ser Cys Arg Ser Ser Lys Ser Leu
 65                  70                  75                  80

Leu His Ser Asn Gly Ile Thr Tyr Leu Tyr Trp Tyr Leu Gln Lys Pro
                 85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
        115                 120                 125

Leu Lys Ile Ser Arg Val Glu Ala Glu Asp Val Gly Val Tyr Tyr Cys
    130                 135                 140

Ala Gln Asn Leu Glu Leu Pro Tyr Thr Phe Gly Gln Gly Thr Lys Leu
145                 150                 155                 160

Glu Ile Lys

<210> SEQ ID NO 434
<211> LENGTH: 156
<212> TYPE: PRT
<213> ORGANISM: Artificial Sequence
<220> FEATURE:
<223> OTHER INFORMATION: chemically synthesized

<400> SEQUENCE: 434

Leu Cys His Pro Leu Val Ala Ser Ala Trp Glu Ser Cys Ser Ser Gly
1               5                   10                  15

Gly Gly Ser Gly Gly Ser Ala Val Gly Leu Leu Ala Pro Pro Gly
            20                  25                  30

Gly Leu Ser Gly Arg Ser Asp Asn Pro Gly Gly Ser Asp Ile Val Met
        35                  40                  45

Thr Gln Ser Pro Leu Ser Leu Pro Val Thr Pro Gly Glu Pro Ala Ser
    50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
    130                 135                 140

Tyr Thr Phe Gly Gln Gly Thr Lys Leu Glu Ile Lys
145                 150                 155

<210> SEQ ID NO 435
<211> LENGTH: 266
<212> TYPE: PRT
<213> ORGANISM: Artificial Sequence
<220> FEATURE:
<223> OTHER INFORMATION: chemically synthesized

<400> SEQUENCE: 435

Gln Gly Gln Ser Gly Gln Gly Leu Cys His Pro Leu Val Ala Ser Ala
1               5                   10                  15

Trp Glu Ser Cys Ser Ser Gly Gly Ser Ser Gly Gly Ser Ile Ser
            20                  25                  30

Ser Gly Leu Leu Ser Gly Arg Ser Ala Asn Pro Gly Gly Gly Ser Asp
        35                  40                  45

```
Ile Val Met Thr Gln Ser Pro Leu Ser Leu Pro Val Thr Pro Gly Glu
    50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
                100                 105                 110

Arg Phe Ser Gly Ser Gly Ser Gly Thr Asp Phe Thr Leu Lys Ile Ser
            115                 120                 125

Arg Val Glu Ala Glu Asp Val Gly Val Tyr Tyr Cys Ala Gln Asn Leu
130                 135                 140

Glu Leu Pro Tyr Thr Phe Gly Gln Gly Thr Lys Leu Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
                260                 265

<210> SEQ ID NO 436
<211> LENGTH: 259
<212> TYPE: PRT
<213> ORGANISM: Artificial Sequence
<220> FEATURE:
<223> OTHER INFORMATION: chemically synthesized

<400> SEQUENCE: 436

Leu Cys His Pro Leu Val Ala Ser Ala Trp Glu Ser Cys Ser Ser Gly
1               5                   10                  15

Gly Gly Ser Ser Gly Gly Ser Ile Ser Ser Gly Leu Leu Ser Gly Arg
                20                  25                  30

Ser Ala Asn Pro Gly Gly Gly Ser Asp Ile Val Met Thr Gln Ser Pro
            35                  40                  45

Leu Ser Leu Pro Val Thr Pro Gly Glu Pro Ala Ser Ile Ser Cys Arg
    50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
        115                 120                 125

Gly Val Tyr Tyr Cys Ala Gln Asn Leu Glu Leu Pro Tyr Thr Phe Gly
130                 135                 140
```

Gln Gly Thr Lys Leu Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 437
<211> LENGTH: 159
<212> TYPE: PRT
<213> ORGANISM: Artificial Sequence
<220> FEATURE:
<223> OTHER INFORMATION: chemically synthesized

<400> SEQUENCE: 437

Gln Gly Gln Ser Gly Gln Gly Leu Cys His Pro Leu Val Ala Ser Ala
1               5                   10                  15

Trp Glu Ser Cys Ser Ser Gly Gly Gly Ser Gly Gly Ser Ile Ser
            20                  25                  30

Ser Gly Leu Leu Ser Gly Arg Ser Ala Asn Pro Gly Gly Gly Ser Asp
            35                  40                  45

Ile Val Met Thr Gln Ser Pro Leu Ser Leu Pro Val Thr Pro Gly Glu
    50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Ala Gln Asn Leu
    130                 135                 140

Glu Leu Pro Tyr Thr Phe Gly Gln Gly Thr Lys Leu Glu Ile Lys
145                 150                 155

<210> SEQ ID NO 438
<211> LENGTH: 152
<212> TYPE: PRT
<213> ORGANISM: Artificial Sequence
<220> FEATURE:
<223> OTHER INFORMATION: chemically synthesized

<400> SEQUENCE: 438

Leu Cys His Pro Leu Val Ala Ser Ala Trp Glu Ser Cys Ser Ser Gly
1               5                   10                  15

Gly Gly Ser Gly Gly Ser Ile Ser Ser Gly Leu Leu Ser Gly Arg
            20                  25                  30

Ser Ala Asn Pro Gly Gly Gly Ser Asp Ile Val Met Thr Gln Ser Pro
            35                  40                  45

Leu Ser Leu Pro Val Thr Pro Gly Glu Pro Ala Ser Ile Ser Cys Arg
 50                  55                  60

Ser Ser Lys Ser Leu Leu His Ser Asn Gly Ile Thr Tyr Leu Tyr Trp
 65                  70                  75                  80

Tyr Leu Gln Lys Pro Gly Gln Ser Pro Gln Leu Leu Ile Tyr Gln Met
                 85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
            115                 120                 125

Gly Val Tyr Tyr Cys Ala Gln Asn Leu Glu Leu Pro Tyr Thr Phe Gly
130                 135                 140

Gln Gly Thr Lys Leu Glu Ile Lys
145                 150

<210> SEQ ID NO 439
<211> LENGTH: 270
<212> TYPE: PRT
<213> ORGANISM: Artificial Sequence
<220> FEATURE:
<223> OTHER INFORMATION: chemically synthesized

<400> SEQUENCE: 439

Gln Gly Gln Ser Gly Gln Gly Leu Cys His Pro Leu Val Ala Ser Ala
1               5                   10                  15

Trp Glu Ser Cys Ser Ser Gly Gly Ser Ser Gly Gly Ser Ala Val
                20                  25                  30

Gly Leu Leu Ala Pro Pro Gly Gly Leu Ser Gly Arg Ser Ala Asn Pro
            35                  40                  45

Gly Gly Ser Asp Ile Val Met Thr Gln Ser Pro Leu Ser Leu Pro Val
 50                  55                  60

Thr Pro Gly Glu Pro Ala Ser Ile Ser Cys Arg Ser Ser Lys Ser Leu
 65                  70                  75                  80

Leu His Ser Asn Gly Ile Thr Tyr Leu Tyr Trp Tyr Leu Gln Lys Pro
                 85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
            115                 120                 125

Leu Lys Ile Ser Arg Val Glu Ala Glu Asp Val Gly Val Tyr Tyr Cys
        130                 135                 140

Ala Gln Asn Leu Glu Leu Pro Tyr Thr Phe Gly Gln Gly Thr Lys Leu
145                 150                 155                 160

Glu Ile Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
            180                 185                 190

Asn Asn Phe Tyr Pro Arg Glu Ala Lys Val Gln Trp Lys Val Asp Asn
        195                 200                 205

Ala Leu Gln Ser Gly Asn Ser Gln Glu Ser Val Thr Glu Gln Asp Ser
    210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
            245                 250                 255

Leu Ser Ser Pro Val Thr Lys Ser Phe Asn Arg Gly Glu Cys
        260                 265                 270

<210> SEQ ID NO 440
<211> LENGTH: 263
<212> TYPE: PRT
<213> ORGANISM: Artificial Sequence
<220> FEATURE:
<223> OTHER INFORMATION: chemically synthesized

<400> SEQUENCE: 440

Leu Cys His Pro Leu Val Ala Ser Ala Trp Glu Ser Cys Ser Ser Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Ala Asn Pro Gly Gly Ser Asp Ile Val Met
        35                  40                  45

Thr Gln Ser Pro Leu Ser Leu Pro Val Thr Pro Gly Glu Pro Ala Ser
    50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
    130                 135                 140

Tyr Thr Phe Gly Gln Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 441
<211> LENGTH: 163
<212> TYPE: PRT
<213> ORGANISM: Artificial Sequence
<220> FEATURE:
<223> OTHER INFORMATION: chemically synthesized

<400> SEQUENCE: 441

Gln Gly Gln Ser Gly Gln Gly Leu Cys His Pro Leu Val Ala Ser Ala
1               5                   10                  15

Trp Glu Ser Cys Ser Ser Gly Gly Ser Gly Ser Ala Val
            20                  25                  30

Gly Leu Leu Ala Pro Pro Gly Leu Ser Gly Arg Ser Ala Asn Pro
        35                  40                  45

Gly Gly Ser Asp Ile Val Met Thr Gln Ser Pro Leu Ser Leu Pro Val
50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
        115                 120                 125

Leu Lys Ile Ser Arg Val Glu Ala Glu Asp Val Gly Val Tyr Tyr Cys
130                 135                 140

Ala Gln Asn Leu Glu Leu Pro Tyr Thr Phe Gly Gln Gly Thr Lys Leu
145                 150                 155                 160

Glu Ile Lys

<210> SEQ ID NO 442
<211> LENGTH: 156
<212> TYPE: PRT
<213> ORGANISM: Artificial Sequence
<220> FEATURE:
<223> OTHER INFORMATION: chemically synthesized

<400> SEQUENCE: 442

Leu Cys His Pro Leu Val Ala Ser Ala Trp Glu Ser Cys Ser Ser Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Ala Asn Pro Gly Gly Ser Asp Ile Val Met
        35                  40                  45

Thr Gln Ser Pro Leu Ser Leu Pro Val Thr Pro Gly Glu Pro Ala Ser
    50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
130                 135                 140

Tyr Thr Phe Gly Gln Gly Thr Lys Leu Glu Ile Lys
145                 150                 155

<210> SEQ ID NO 443
<211> LENGTH: 266
<212> TYPE: PRT
<213> ORGANISM: Artificial Sequence
<220> FEATURE:
<223> OTHER INFORMATION: chemically synthesized

<400> SEQUENCE: 443

Gln Gly Gln Ser Gly Gln Gly Leu Cys His Pro Leu Val Ala Ser Ala
1               5                   10                  15

Trp Glu Ser Cys Ser Ser Gly Gly Ser Ser Gly Gly Ser Ile Ser
            20                  25                  30

Ser Gly Leu Leu Ser Gly Arg Ser Ala Asn Ile Gly Gly Ser Asp
        35                  40                  45

Ile Val Met Thr Gln Ser Pro Leu Ser Leu Pro Val Thr Pro Gly Glu
50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Ala Gln Asn Leu
130                 135                 140

Glu Leu Pro Tyr Thr Phe Gly Gln Gly Thr Lys Leu Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265

<210> SEQ ID NO 444
<211> LENGTH: 259
<212> TYPE: PRT
<213> ORGANISM: Artificial Sequence
<220> FEATURE:
<223> OTHER INFORMATION: chemically synthesized

<400> SEQUENCE: 444

Leu Cys His Pro Leu Val Ala Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Ala Asn Ile Gly Gly Ser Asp Ile Val Met Thr Gln Ser Pro
        35                  40                  45

Leu Ser Leu Pro Val Thr Pro Gly Glu Pro Ala Ser Ile Ser Cys Arg
50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

```
Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
        115                 120                 125

Gly Val Tyr Tyr Cys Ala Gln Asn Leu Glu Leu Pro Tyr Thr Phe Gly
    130                 135                 140

Gln Gly Thr Lys Leu Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 445
<211> LENGTH: 159
<212> TYPE: PRT
<213> ORGANISM: Artificial Sequence
<220> FEATURE:
<223> OTHER INFORMATION: chemically synthesized

<400> SEQUENCE: 445

Gln Gly Gln Ser Gly Gln Gly Leu Cys His Pro Leu Val Ala Ser Ala
1               5                   10                  15

Trp Glu Ser Cys Ser Ser Gly Gly Ser Ser Gly Gly Ser Ile Ser
            20                  25                  30

Ser Gly Leu Leu Ser Gly Arg Ser Ala Asn Ile Gly Gly Gly Ser Asp
        35                  40                  45

Ile Val Met Thr Gln Ser Pro Leu Ser Leu Pro Val Thr Pro Gly Glu
    50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Ala Gln Asn Leu
    130                 135                 140

Glu Leu Pro Tyr Thr Phe Gly Gln Gly Thr Lys Leu Glu Ile Lys
145                 150                 155

<210> SEQ ID NO 446
<211> LENGTH: 152
<212> TYPE: PRT
<213> ORGANISM: Artificial Sequence
<220> FEATURE:
```

<223> OTHER INFORMATION: chemically synthesized

<400> SEQUENCE: 446

Leu Cys His Pro Leu Val Ala Ser Ala Trp Glu Ser Cys Ser Ser Gly
1               5                   10                  15
Gly Gly Ser Ser Gly Gly Ser Ile Ser Ser Gly Leu Leu Ser Gly Arg
            20                  25                  30
Ser Ala Asn Ile Gly Gly Ser Asp Ile Val Met Thr Gln Ser Pro
        35                  40                  45
Leu Ser Leu Pro Val Thr Pro Gly Glu Pro Ala Ser Ile Ser Cys Arg
    50                  55                  60
Ser Ser Lys Ser Leu Leu His Ser Asn Gly Ile Thr Tyr Leu Tyr Trp
65                  70                  75                  80
Tyr Leu Gln Lys Pro Gly Gln Ser Pro Gln Leu Leu Ile Tyr Gln Met
                85                  90                  95
Ser Asn Leu Ala Ser Gly Val Pro Asp Arg Phe Ser Gly Ser Gly Ser
            100                 105                 110
Gly Thr Asp Phe Thr Leu Lys Ile Ser Arg Val Glu Ala Glu Asp Val
        115                 120                 125
Gly Val Tyr Tyr Cys Ala Gln Asn Leu Glu Leu Pro Tyr Thr Phe Gly
    130                 135                 140
Gln Gly Thr Lys Leu Glu Ile Lys
145                 150

<210> SEQ ID NO 447
<211> LENGTH: 270
<212> TYPE: PRT
<213> ORGANISM: Artificial Sequence
<220> FEATURE:
<223> OTHER INFORMATION: chemically synthesized

<400> SEQUENCE: 447

Gln Gly Gln Ser Gly Gln Gly Leu Cys His Pro Leu Val Ala Ser Ala
1               5                   10                  15
Trp Glu Ser Cys Ser Ser Gly Gly Ser Gly Gly Ser Ala Val
            20                  25                  30
Gly Leu Leu Ala Pro Pro Gly Gly Leu Ser Gly Arg Ser Ala Asn Ile
        35                  40                  45
Gly Gly Ser Asp Ile Val Met Thr Gln Ser Pro Leu Ser Leu Pro Val
    50                  55                  60
Thr Pro Gly Glu Pro Ala Ser Ile Ser Cys Arg Ser Ser Lys Ser Leu
65                  70                  75                  80
Leu His Ser Asn Gly Ile Thr Tyr Leu Tyr Trp Tyr Leu Gln Lys Pro
                85                  90                  95
Gly Gln Ser Pro Gln Leu Leu Ile Tyr Gln Met Ser Asn Leu Ala Ser
            100                 105                 110
Gly Val Pro Asp Arg Phe Ser Gly Ser Gly Ser Gly Thr Asp Phe Thr
        115                 120                 125
Leu Lys Ile Ser Arg Val Glu Ala Glu Asp Val Gly Val Tyr Tyr Cys
    130                 135                 140
Ala Gln Asn Leu Glu Leu Pro Tyr Thr Phe Gly Gln Gly Thr Lys Leu
145                 150                 155                 160
Glu Ile Lys Arg Thr Val Ala Ala Pro Ser Val Phe Ile Phe Pro Pro
                165                 170                 175
Ser Asp Glu Gln Leu Lys Ser Gly Thr Ala Ser Val Val Cys Leu Leu
            180                 185                 190

```
Asn Asn Phe Tyr Pro Arg Glu Ala Lys Val Gln Trp Lys Val Asp Asn
        195                 200                 205

Ala Leu Gln Ser Gly Asn Ser Gln Glu Ser Val Thr Glu Gln Asp Ser
    210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
            260                 265                 270

<210> SEQ ID NO 448
<211> LENGTH: 263
<212> TYPE: PRT
<213> ORGANISM: Artificial Sequence
<220> FEATURE:
<223> OTHER INFORMATION: chemically synthesized

<400> SEQUENCE: 448

Leu Cys His Pro Leu Val Ala Ser Ala Trp Glu Ser Cys Ser Ser Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Ala Asn Ile Gly Gly Ser Asp Ile Val Met
        35                  40                  45

Thr Gln Ser Pro Leu Ser Leu Pro Val Thr Pro Gly Glu Pro Ala Ser
    50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
    130                 135                 140

Tyr Thr Phe Gly Gln Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 449
```

```
<211> LENGTH: 163
<212> TYPE: PRT
<213> ORGANISM: Artificial Sequence
<220> FEATURE:
<223> OTHER INFORMATION: chemically synthesized

<400> SEQUENCE: 449

Gln Gly Gln Ser Gly Gln Gly Leu Cys His Pro Leu Val Ala Ser Ala
1               5                   10                  15

Trp Glu Ser Cys Ser Ser Gly Gly Ser Gly Ser Ala Val
            20                  25                  30

Gly Leu Leu Ala Pro Pro Gly Gly Leu Ser Gly Arg Ser Ala Asn Ile
            35                  40                  45

Gly Gly Ser Asp Ile Val Met Thr Gln Ser Pro Leu Ser Leu Pro Val
        50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
        115                 120                 125

Leu Lys Ile Ser Arg Val Glu Ala Glu Asp Val Gly Val Tyr Tyr Cys
130                 135                 140

Ala Gln Asn Leu Glu Leu Pro Tyr Thr Phe Gly Gln Gly Thr Lys Leu
145                 150                 155                 160

Glu Ile Lys

<210> SEQ ID NO 450
<211> LENGTH: 156
<212> TYPE: PRT
<213> ORGANISM: Artificial Sequence
<220> FEATURE:
<223> OTHER INFORMATION: chemically synthesized

<400> SEQUENCE: 450

Leu Cys His Pro Leu Val Ala Ser Ala Trp Glu Ser Cys Ser Ser Gly
1               5                   10                  15

Gly Gly Ser Gly Gly Ser Ala Val Gly Leu Leu Ala Pro Pro Gly
            20                  25                  30

Gly Leu Ser Gly Arg Ser Ala Asn Ile Gly Gly Ser Asp Ile Val Met
            35                  40                  45

Thr Gln Ser Pro Leu Ser Leu Pro Val Thr Pro Gly Glu Pro Ala Ser
        50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
130                 135                 140

Tyr Thr Phe Gly Gln Gly Thr Lys Leu Glu Ile Lys
145                 150                 155
```

<210> SEQ ID NO 451
<211> LENGTH: 266
<212> TYPE: PRT
<213> ORGANISM: Artificial Sequence
<220> FEATURE:
<223> OTHER INFORMATION: chemically synthesized

<400> SEQUENCE: 451

Gln Gly Gln Ser Gly Gln Gly Leu Cys His Pro Leu Val Leu Ser Ala
1               5                   10                  15

Trp Glu Ser Cys Ser Ser Gly Gly Ser Gly Gly Ser Ile Ser
            20                  25                  30

Ser Gly Leu Leu Ser Gly Arg Ser Asp Asn His Gly Gly Gly Ser Asp
        35                  40                  45

Ile Val Met Thr Gln Ser Pro Leu Ser Leu Pro Val Thr Pro Gly Glu
    50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Ala Gln Asn Leu
    130                 135                 140

Glu Leu Pro Tyr Thr Phe Gly Gln Gly Thr Lys Leu Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265

<210> SEQ ID NO 452
<211> LENGTH: 259
<212> TYPE: PRT
<213> ORGANISM: Artificial Sequence
<220> FEATURE:
<223> OTHER INFORMATION: chemically synthesized

<400> SEQUENCE: 452

Leu Cys His Pro Leu Val Leu Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Asp Asn His Gly Gly Gly Ser Asp Ile Val Met Thr Gln Ser Pro

```
            35                  40                  45
Leu Ser Leu Pro Val Thr Pro Gly Glu Pro Ala Ser Ile Ser Cys Arg
 50                  55                  60

Ser Ser Lys Ser Leu Leu His Ser Asn Gly Ile Thr Tyr Leu Tyr Trp
 65                  70                  75                  80

Tyr Leu Gln Lys Pro Gly Gln Ser Pro Gln Leu Leu Ile Tyr Gln Met
                 85                  90                  95

Ser Asn Leu Ala Ser Gly Val Pro Asp Arg Phe Ser Gly Ser Gly Ser
                100                 105                 110

Gly Thr Asp Phe Thr Leu Lys Ile Ser Arg Val Glu Ala Glu Asp Val
                115                 120                 125

Gly Val Tyr Tyr Cys Ala Gln Asn Leu Glu Leu Pro Tyr Thr Phe Gly
            130                 135                 140

Gln Gly Thr Lys Leu Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
                180                 185                 190

Trp Lys Val Asp Asn Ala Leu Gln Ser Gly Asn Ser Gln Glu Ser Val
                195                 200                 205

Thr Glu Gln Asp Ser Lys Asp Ser Thr Tyr Ser Leu Ser Ser Thr Leu
            210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 453
<211> LENGTH: 159
<212> TYPE: PRT
<213> ORGANISM: Artificial Sequence
<220> FEATURE:
<223> OTHER INFORMATION: chemically synthesized

<400> SEQUENCE: 453

Gln Gly Gln Ser Gly Gln Gly Leu Cys His Pro Leu Val Leu Ser Ala
  1               5                  10                  15

Trp Glu Ser Cys Ser Ser Gly Gly Ser Gly Gly Ser Ile Ser
                 20                  25                  30

Ser Gly Leu Leu Ser Gly Arg Ser Asp Asn His Gly Gly Gly Ser Asp
                 35                  40                  45

Ile Val Met Thr Gln Ser Pro Leu Ser Leu Pro Val Thr Pro Gly Glu
 50                  55                  60

Pro Ala Ser Ile Ser Cys Arg Ser Ser Lys Ser Leu Leu His Ser Asn
 65                  70                  75                  80

Gly Ile Thr Tyr Leu Tyr Trp Tyr Leu Gln Lys Pro Gly Gln Ser Pro
                 85                  90                  95

Gln Leu Leu Ile Tyr Gln Met Ser Asn Leu Ala Ser Gly Val Pro Asp
                100                 105                 110

Arg Phe Ser Gly Ser Gly Ser Gly Thr Asp Phe Thr Leu Lys Ile Ser
            115                 120                 125

Arg Val Glu Ala Glu Asp Val Gly Val Tyr Tyr Cys Ala Gln Asn Leu
            130                 135                 140
```

```
Glu Leu Pro Tyr Thr Phe Gly Gln Gly Thr Lys Leu Glu Ile Lys
145                 150                 155
```

<210> SEQ ID NO 454
<211> LENGTH: 152
<212> TYPE: PRT
<213> ORGANISM: Artificial Sequence
<220> FEATURE:
<223> OTHER INFORMATION: chemically synthesized

<400> SEQUENCE: 454

```
Leu Cys His Pro Leu Val Leu Ser Ala Trp Glu Ser Cys Ser Ser Gly
1               5                   10                  15

Gly Gly Ser Ser Gly Gly Ser Ile Ser Ser Gly Leu Leu Ser Gly Arg
                20                  25                  30

Ser Asp Asn His Gly Gly Gly Ser Asp Ile Val Met Thr Gln Ser Pro
            35                  40                  45

Leu Ser Leu Pro Val Thr Pro Gly Glu Pro Ala Ser Ile Ser Cys Arg
50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
        115                 120                 125

Gly Val Tyr Tyr Cys Ala Gln Asn Leu Glu Leu Pro Tyr Thr Phe Gly
130                 135                 140

Gln Gly Thr Lys Leu Glu Ile Lys
145                 150
```

<210> SEQ ID NO 455
<211> LENGTH: 270
<212> TYPE: PRT
<213> ORGANISM: Artificial Sequence
<220> FEATURE:
<223> OTHER INFORMATION: chemically synthesized

<400> SEQUENCE: 455

```
Gln Gly Gln Ser Gly Gln Gly Leu Cys His Pro Leu Val Leu Ser Ala
1               5                   10                  15

Trp Glu Ser Cys Ser Ser Gly Gly Ser Ser Gly Gly Ser Ala Val
                20                  25                  30

Gly Leu Leu Ala Pro Pro Gly Gly Leu Ser Gly Arg Ser Asp Asn His
            35                  40                  45

Gly Gly Ser Asp Ile Val Met Thr Gln Ser Pro Leu Ser Leu Pro Val
50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
        115                 120                 125

Leu Lys Ile Ser Arg Val Glu Ala Glu Asp Val Gly Val Tyr Tyr Cys
```

```
            130                 135                 140
Ala Gln Asn Leu Glu Leu Pro Tyr Thr Phe Gly Gln Gly Thr Lys Leu
145                 150                 155                 160

Glu Ile Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
            180                 185                 190

Asn Asn Phe Tyr Pro Arg Glu Ala Lys Val Gln Trp Lys Val Asp Asn
        195                 200                 205

Ala Leu Gln Ser Gly Asn Ser Gln Glu Ser Val Thr Glu Gln Asp Ser
    210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
            260                 265                 270

<210> SEQ ID NO 456
<211> LENGTH: 263
<212> TYPE: PRT
<213> ORGANISM: Artificial Sequence
<220> FEATURE:
<223> OTHER INFORMATION: chemically synthesized

<400> SEQUENCE: 456

Leu Cys His Pro Leu Val Leu Ser Ala Trp Glu Ser Cys Ser Ser Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Asn His Gly Gly Ser Asp Ile Val Met
        35                  40                  45

Thr Gln Ser Pro Leu Ser Leu Pro Val Thr Pro Gly Glu Pro Ala Ser
    50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
    130                 135                 140

Tyr Thr Phe Gly Gln Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
```

```
                225                 230                 235                 240
Tyr Ala Cys Glu Val Thr His Gln Gly Leu Ser Ser Pro Val Thr Lys
                    245                 250                 255

Ser Phe Asn Arg Gly Glu Cys
            260

<210> SEQ ID NO 457
<211> LENGTH: 163
<212> TYPE: PRT
<213> ORGANISM: Artificial Sequence
<220> FEATURE:
<223> OTHER INFORMATION: chemically synthesized

<400> SEQUENCE: 457

Gln Gly Gln Ser Gly Gln Gly Leu Cys His Pro Leu Val Leu Ser Ala
1               5                   10                  15

Trp Glu Ser Cys Ser Ser Gly Gly Ser Ser Gly Gly Ser Ala Val
                20                  25                  30

Gly Leu Leu Ala Pro Pro Gly Gly Leu Ser Gly Arg Ser Asp Asn His
            35                  40                  45

Gly Gly Ser Asp Ile Val Met Thr Gln Ser Pro Leu Ser Leu Pro Val
50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
        115                 120                 125

Leu Lys Ile Ser Arg Val Glu Ala Glu Asp Val Gly Val Tyr Tyr Cys
130                 135                 140

Ala Gln Asn Leu Glu Leu Pro Tyr Thr Phe Gly Gln Gly Thr Lys Leu
145                 150                 155                 160

Glu Ile Lys

<210> SEQ ID NO 458
<211> LENGTH: 156
<212> TYPE: PRT
<213> ORGANISM: Artificial Sequence
<220> FEATURE:
<223> OTHER INFORMATION: chemically synthesized

<400> SEQUENCE: 458

Leu Cys His Pro Leu Val Leu Ser Ala Trp Glu Ser Cys Ser Ser Gly
1               5                   10                  15

Gly Gly Ser Ser Gly Gly Ser Ala Val Gly Leu Leu Ala Pro Pro Gly
                20                  25                  30

Gly Leu Ser Gly Arg Ser Asp Asn His Gly Gly Ser Asp Ile Val Met
            35                  40                  45

Thr Gln Ser Pro Leu Ser Leu Pro Val Thr Pro Gly Glu Pro Ala Ser
        50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
```

```
                100                 105                 110
Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
        130                 135                 140

Tyr Thr Phe Gly Gln Gly Thr Lys Leu Glu Ile Lys
145                 150                 155
```

<210> SEQ ID NO 459
<211> LENGTH: 266
<212> TYPE: PRT
<213> ORGANISM: Artificial Sequence
<220> FEATURE:
<223> OTHER INFORMATION: chemically synthesized

<400> SEQUENCE: 459

```
Gln Gly Gln Ser Gly Gln Gly Leu Cys His Pro Leu Val Leu Ser Ala
1               5                   10                  15

Trp Glu Ser Cys Ser Ser Gly Gly Ser Ser Gly Gly Ser Ile Ser
            20                  25                  30

Ser Gly Leu Leu Ser Gly Arg Ser Asp Asn Pro Gly Gly Gly Ser Asp
        35                  40                  45

Ile Val Met Thr Gln Ser Pro Leu Ser Leu Pro Val Thr Pro Gly Glu
50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
                85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Ala Gln Asn Leu
    130                 135                 140

Glu Leu Pro Tyr Thr Phe Gly Gln Gly Thr Lys Leu Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265
```

<210> SEQ ID NO 460
<211> LENGTH: 259
<212> TYPE: PRT
<213> ORGANISM: Artificial Sequence
<220> FEATURE:
<223> OTHER INFORMATION: chemically synthesized

```
<400> SEQUENCE: 460

Leu Cys His Pro Leu Val Leu Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Asp Ile Val Met Thr Gln Ser Pro
        35                  40                  45

Leu Ser Leu Pro Val Thr Pro Gly Glu Pro Ala Ser Ile Ser Cys Arg
50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
        115                 120                 125

Gly Val Tyr Tyr Cys Ala Gln Asn Leu Glu Leu Pro Tyr Thr Phe Gly
130                 135                 140

Gln Gly Thr Lys Leu Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 461
<211> LENGTH: 159
<212> TYPE: PRT
<213> ORGANISM: Artificial Sequence
<220> FEATURE:
<223> OTHER INFORMATION: chemically synthesized

<400> SEQUENCE: 461

Gln Gly Gln Ser Gly Gln Gly Leu Cys His Pro Leu Val Leu Ser Ala
1               5                   10                  15

Trp Glu Ser Cys Ser Ser Gly Gly Ser Ser Gly Gly Ser Ile Ser
            20                  25                  30

Ser Gly Leu Leu Ser Gly Arg Ser Asp Asn Pro Gly Gly Gly Ser Asp
        35                  40                  45

Ile Val Met Thr Gln Ser Pro Leu Ser Leu Pro Val Thr Pro Gly Glu
50                  55                  60

Pro Ala Ser Ile Ser Cys Arg Ser Ser Lys Ser Leu Leu His Ser Asn
65                  70                  75                  80

Gly Ile Thr Tyr Leu Tyr Trp Tyr Leu Gln Lys Pro Gly Gln Ser Pro
```

```
                    85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
            115                 120                 125

Arg Val Glu Ala Glu Asp Val Gly Val Tyr Tyr Cys Ala Gln Asn Leu
130                 135                 140

Glu Leu Pro Tyr Thr Phe Gly Gln Gly Thr Lys Leu Glu Ile Lys
145                 150                 155

<210> SEQ ID NO 462
<211> LENGTH: 152
<212> TYPE: PRT
<213> ORGANISM: Artificial Sequence
<220> FEATURE:
<223> OTHER INFORMATION: chemically synthesized

<400> SEQUENCE: 462

Leu Cys His Pro Leu Val Leu Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Asp Ile Val Met Thr Gln Ser Pro
        35                  40                  45

Leu Ser Leu Pro Val Thr Pro Gly Glu Pro Ala Ser Ile Ser Cys Arg
    50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
        115                 120                 125

Gly Val Tyr Tyr Cys Ala Gln Asn Leu Glu Leu Pro Tyr Thr Phe Gly
    130                 135                 140

Gln Gly Thr Lys Leu Glu Ile Lys
145                 150

<210> SEQ ID NO 463
<211> LENGTH: 270
<212> TYPE: PRT
<213> ORGANISM: Artificial Sequence
<220> FEATURE:
<223> OTHER INFORMATION: chemically synthesized

<400> SEQUENCE: 463

Gln Gly Gln Ser Gly Gln Gly Leu Cys His Pro Leu Val Leu Ser Ala
1               5                   10                  15

Trp Glu Ser Cys Ser Ser Gly Gly Gly Ser Ser Gly Gly Ser Ala Val
            20                  25                  30

Gly Leu Leu Ala Pro Pro Gly Gly Leu Ser Gly Arg Ser Asp Asn Pro
        35                  40                  45

Gly Gly Ser Asp Ile Val Met Thr Gln Ser Pro Leu Ser Leu Pro Val
    50                  55                  60

Thr Pro Gly Glu Pro Ala Ser Ile Ser Cys Arg Ser Ser Lys Ser Leu
65                  70                  75                  80
```

Leu His Ser Asn Gly Ile Thr Tyr Leu Tyr Trp Tyr Leu Gln Lys Pro
            85                  90                  95

Gly Gln Ser Pro Gln Leu Leu Ile Tyr Gln Met Ser Asn Leu Ala Ser
        100                 105                 110

Gly Val Pro Asp Arg Phe Ser Gly Ser Gly Ser Gly Thr Asp Phe Thr
        115                 120                 125

Leu Lys Ile Ser Arg Val Glu Ala Glu Asp Val Gly Val Tyr Tyr Cys
    130                 135                 140

Ala Gln Asn Leu Glu Leu Pro Tyr Thr Phe Gly Gln Gly Thr Lys Leu
145                 150                 155                 160

Glu Ile Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
        180                 185                 190

Asn Asn Phe Tyr Pro Arg Glu Ala Lys Val Gln Trp Lys Val Asp Asn
        195                 200                 205

Ala Leu Gln Ser Gly Asn Ser Gln Glu Ser Val Thr Glu Gln Asp Ser
    210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
        260                 265                 270

<210> SEQ ID NO 464
<211> LENGTH: 263
<212> TYPE: PRT
<213> ORGANISM: Artificial Sequence
<220> FEATURE:
<223> OTHER INFORMATION: chemically synthesized

<400> SEQUENCE: 464

Leu Cys His Pro Leu Val Leu Ser Ala Trp Glu Ser Cys Ser Ser Gly
1               5                   10                  15

Gly Gly Ser Ser Gly Ser Ala Val Gly Leu Leu Ala Pro Pro Gly
            20                  25                  30

Gly Leu Ser Gly Arg Ser Asp Asn Pro Gly Gly Ser Asp Ile Val Met
        35                  40                  45

Thr Gln Ser Pro Leu Ser Leu Pro Val Thr Pro Gly Glu Pro Ala Ser
    50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
    130                 135                 140

Tyr Thr Phe Gly Gln Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
            195                 200                 205

Gln Glu Ser Val Thr Glu Gln Asp Ser Lys Asp Ser Thr Tyr Ser Leu
            210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
            245                 250                 255

Ser Phe Asn Arg Gly Glu Cys
            260

<210> SEQ ID NO 465
<211> LENGTH: 163
<212> TYPE: PRT
<213> ORGANISM: Artificial Sequence
<220> FEATURE:
<223> OTHER INFORMATION: chemically synthesized

<400> SEQUENCE: 465

Gln Gly Gln Ser Gly Gln Gly Leu Cys His Pro Leu Val Leu Ser Ala
1               5                   10                  15

Trp Glu Ser Cys Ser Ser Gly Gly Ser Ser Gly Gly Ser Ala Val
            20                  25                  30

Gly Leu Leu Ala Pro Pro Gly Gly Leu Ser Gly Arg Ser Asp Asn Pro
            35                  40                  45

Gly Gly Ser Asp Ile Val Met Thr Gln Ser Pro Leu Ser Leu Pro Val
        50                  55                  60

Thr Pro Gly Glu Pro Ala Ser Ile Ser Cys Arg Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
            115                 120                 125

Leu Lys Ile Ser Arg Val Glu Ala Glu Asp Val Gly Val Tyr Tyr Cys
        130                 135                 140

Ala Gln Asn Leu Glu Leu Pro Tyr Thr Phe Gly Gln Gly Thr Lys Leu
145                 150                 155                 160

Glu Ile Lys

<210> SEQ ID NO 466
<211> LENGTH: 156
<212> TYPE: PRT
<213> ORGANISM: Artificial Sequence
<220> FEATURE:
<223> OTHER INFORMATION: chemically synthesized

<400> SEQUENCE: 466

Leu Cys His Pro Leu Val Leu Ser Ala Trp Glu Ser Cys Ser Ser Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Asn Pro Gly Gly Ser Asp Ile Val Met
            35                  40                  45

```
Thr Gln Ser Pro Leu Ser Leu Pro Val Thr Pro Gly Glu Pro Ala Ser
 50              55                  60
Ile Ser Cys Arg Ser Ser Lys Ser Leu Leu His Ser Asn Gly Ile Thr
 65                  70                  75                  80
Tyr Leu Tyr Trp Tyr Leu Gln Lys Pro Gly Gln Ser Pro Gln Leu Leu
                 85                  90                  95
Ile Tyr Gln Met Ser Asn Leu Ala Ser Gly Val Pro Asp Arg Phe Ser
            100                 105                 110
Gly Ser Gly Ser Gly Thr Asp Phe Thr Leu Lys Ile Ser Arg Val Glu
            115                 120                 125
Ala Glu Asp Val Gly Val Tyr Tyr Cys Ala Gln Asn Leu Glu Leu Pro
130                 135                 140
Tyr Thr Phe Gly Gln Gly Thr Lys Leu Glu Ile Lys
145                 150                 155
```

<210> SEQ ID NO 467
<211> LENGTH: 266
<212> TYPE: PRT
<213> ORGANISM: Artificial Sequence
<220> FEATURE:
<223> OTHER INFORMATION: chemically synthesized

<400> SEQUENCE: 467

```
Gln Gly Gln Ser Gly Gln Gly Leu Cys His Pro Leu Val Leu Ser Ala
 1               5                  10                  15
Trp Glu Ser Cys Ser Ser Gly Gly Ser Gly Gly Ser Ile Ser
                 20                  25                  30
Ser Gly Leu Leu Ser Gly Arg Ser Ala Asn Pro Gly Gly Ser Asp
             35                  40                  45
Ile Val Met Thr Gln Ser Pro Leu Ser Leu Pro Val Thr Pro Gly Glu
 50                  55                  60
Pro Ala Ser Ile Ser Cys Arg Ser Ser Lys Ser Leu Leu His Ser Asn
 65                  70                  75                  80
Gly Ile Thr Tyr Leu Tyr Trp Tyr Leu Gln Lys Pro Gly Gln Ser Pro
                 85                  90                  95
Gln Leu Leu Ile Tyr Gln Met Ser Asn Leu Ala Ser Gly Val Pro Asp
            100                 105                 110
Arg Phe Ser Gly Ser Gly Ser Gly Thr Asp Phe Thr Leu Lys Ile Ser
            115                 120                 125
Arg Val Glu Ala Glu Asp Val Gly Val Tyr Tyr Cys Ala Gln Asn Leu
130                 135                 140
Glu Leu Pro Tyr Thr Phe Gly Gln Gly Thr Lys Leu Glu Ile Lys Arg
145                 150                 155                 160
Thr Val Ala Ala Pro Ser Val Phe Ile Phe Pro Pro Ser Asp Glu Gln
                165                 170                 175
Leu Lys Ser Gly Thr Ala Ser Val Val Cys Leu Leu Asn Asn Phe Tyr
            180                 185                 190
Pro Arg Glu Ala Lys Val Gln Trp Lys Val Asp Asn Ala Leu Gln Ser
        195                 200                 205
Gly Asn Ser Gln Glu Ser Val Thr Glu Gln Asp Ser Lys Asp Ser Thr
    210                 215                 220
Tyr Ser Leu Ser Ser Thr Leu Thr Leu Ser Lys Ala Asp Tyr Glu Lys
225                 230                 235                 240
His Lys Val Tyr Ala Cys Glu Val Thr His Gln Gly Leu Ser Ser Pro
                245                 250                 255
```

```
Val Thr Lys Ser Phe Asn Arg Gly Glu Cys
        260                 265
```

<210> SEQ ID NO 468
<211> LENGTH: 259
<212> TYPE: PRT
<213> ORGANISM: Artificial Sequence
<220> FEATURE:
<223> OTHER INFORMATION: chemically synthesized

<400> SEQUENCE: 468

```
Leu Cys His Pro Leu Val Leu Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Ala Asn Pro Gly Gly Gly Ser Asp Ile Val Met Thr Gln Ser Pro
        35                  40                  45

Leu Ser Leu Pro Val Thr Pro Gly Glu Pro Ala Ser Ile Ser Cys Arg
50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
        115                 120                 125

Gly Val Tyr Tyr Cys Ala Gln Asn Leu Glu Leu Pro Tyr Thr Phe Gly
130                 135                 140

Gln Gly Thr Lys Leu Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys
```

<210> SEQ ID NO 469
<211> LENGTH: 159
<212> TYPE: PRT
<213> ORGANISM: Artificial Sequence
<220> FEATURE:
<223> OTHER INFORMATION: chemically synthesized

<400> SEQUENCE: 469

```
Gln Gly Gln Ser Gly Gln Gly Leu Cys His Pro Leu Val Leu Ser Ala
1               5                   10                  15

Trp Glu Ser Cys Ser Ser Gly Gly Ser Ser Gly Gly Ser Ile Ser
            20                  25                  30
```

Ser Gly Leu Leu Ser Gly Arg Ser Ala Asn Pro Gly Gly Ser Asp
          35                  40                  45

Ile Val Met Thr Gln Ser Pro Leu Ser Leu Pro Val Thr Pro Gly Glu
 50                  55                  60

Pro Ala Ser Ile Ser Cys Arg Ser Ser Lys Ser Leu Leu His Ser Asn
 65                  70                  75                  80

Gly Ile Thr Tyr Leu Tyr Trp Tyr Leu Gln Lys Pro Gly Gln Ser Pro
                 85                  90                  95

Gln Leu Leu Ile Tyr Gln Met Ser Asn Leu Ala Ser Gly Val Pro Asp
            100                 105                 110

Arg Phe Ser Gly Ser Gly Ser Gly Thr Asp Phe Thr Leu Lys Ile Ser
            115                 120                 125

Arg Val Glu Ala Glu Asp Val Gly Val Tyr Tyr Cys Ala Gln Asn Leu
        130                 135                 140

Glu Leu Pro Tyr Thr Phe Gly Gln Gly Thr Lys Leu Glu Ile Lys
145                 150                 155

<210> SEQ ID NO 470
<211> LENGTH: 152
<212> TYPE: PRT
<213> ORGANISM: Artificial Sequence
<220> FEATURE:
<223> OTHER INFORMATION: chemically synthesized

<400> SEQUENCE: 470

Leu Cys His Pro Leu Val Leu Ser Ala Trp Glu Ser Cys Ser Ser Gly
1               5                   10                  15

Gly Gly Ser Ser Gly Gly Ser Ile Ser Ser Gly Leu Leu Ser Gly Arg
            20                  25                  30

Ser Ala Asn Pro Gly Gly Ser Asp Ile Val Met Thr Gln Ser Pro
            35                  40                  45

Leu Ser Leu Pro Val Thr Pro Gly Glu Pro Ala Ser Ile Ser Cys Arg
 50                  55                  60

Ser Ser Lys Ser Leu Leu His Ser Asn Gly Ile Thr Tyr Leu Tyr Trp
65                  70                  75                  80

Tyr Leu Gln Lys Pro Gly Gln Ser Pro Gln Leu Leu Ile Tyr Gln Met
                85                  90                  95

Ser Asn Leu Ala Ser Gly Val Pro Asp Arg Phe Ser Gly Ser Gly Ser
            100                 105                 110

Gly Thr Asp Phe Thr Leu Lys Ile Ser Arg Val Glu Ala Glu Asp Val
            115                 120                 125

Gly Val Tyr Tyr Cys Ala Gln Asn Leu Glu Leu Pro Tyr Thr Phe Gly
        130                 135                 140

Gln Gly Thr Lys Leu Glu Ile Lys
145                 150

<210> SEQ ID NO 471
<211> LENGTH: 270
<212> TYPE: PRT
<213> ORGANISM: Artificial Sequence
<220> FEATURE:
<223> OTHER INFORMATION: chemically synthesized

<400> SEQUENCE: 471

Gln Gly Gln Ser Gly Gln Gly Leu Cys His Pro Leu Val Leu Ser Ala
1               5                   10                  15

Trp Glu Ser Cys Ser Ser Gly Gly Gly Ser Ser Gly Gly Ser Ala Val
            20                  25                  30

Gly Leu Leu Ala Pro Pro Gly Leu Ser Gly Arg Ser Ala Asn Pro
            35                  40                  45

Gly Gly Ser Asp Ile Val Met Thr Gln Ser Pro Leu Ser Leu Pro Val
 50                  55                  60

Thr Pro Gly Glu Pro Ala Ser Ile Ser Cys Arg Ser Ser Lys Ser Leu
 65                  70                  75                  80

Leu His Ser Asn Gly Ile Thr Tyr Leu Tyr Trp Tyr Leu Gln Lys Pro
                 85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
            115                 120                 125

Leu Lys Ile Ser Arg Val Glu Ala Glu Asp Val Gly Val Tyr Tyr Cys
130                 135                 140

Ala Gln Asn Leu Glu Leu Pro Tyr Thr Phe Gly Gln Gly Thr Lys Leu
145                 150                 155                 160

Glu Ile Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
            180                 185                 190

Asn Asn Phe Tyr Pro Arg Glu Ala Lys Val Gln Trp Lys Val Asp Asn
            195                 200                 205

Ala Leu Gln Ser Gly Asn Ser Gln Glu Ser Val Thr Glu Gln Asp Ser
210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
            260                 265                 270

<210> SEQ ID NO 472
<211> LENGTH: 263
<212> TYPE: PRT
<213> ORGANISM: Artificial Sequence
<220> FEATURE:
<223> OTHER INFORMATION: chemically synthesized

<400> SEQUENCE: 472

Leu Cys His Pro Leu Val Leu Ser Ala Trp Glu Ser Cys Ser Ser Gly
 1               5                  10                  15

Gly Gly Ser Ser Gly Gly Ser Ala Val Gly Leu Leu Ala Pro Pro Gly
            20                  25                  30

Gly Leu Ser Gly Arg Ser Ala Asn Pro Gly Gly Ser Asp Ile Val Met
            35                  40                  45

Thr Gln Ser Pro Leu Ser Leu Pro Val Thr Pro Gly Glu Pro Ala Ser
 50                  55                  60

Ile Ser Cys Arg Ser Ser Lys Ser Leu Leu His Ser Asn Gly Ile Thr
 65                  70                  75                  80

Tyr Leu Tyr Trp Tyr Leu Gln Lys Pro Gly Gln Ser Pro Gln Leu Leu
                 85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
            115                 120                 125

Ala Glu Asp Val Gly Val Tyr Tyr Cys Ala Gln Asn Leu Glu Leu Pro
130                 135                 140

Tyr Thr Phe Gly Gln Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 473
<211> LENGTH: 163
<212> TYPE: PRT
<213> ORGANISM: Artificial Sequence
<220> FEATURE:
<223> OTHER INFORMATION: chemically synthesized

<400> SEQUENCE: 473

Gln Gly Gln Ser Gly Gln Gly Leu Cys His Pro Leu Val Leu Ser Ala
1               5                   10                  15

Trp Glu Ser Cys Ser Ser Gly Gly Ser Ser Gly Ser Ala Val
                20                  25                  30

Gly Leu Leu Ala Pro Pro Gly Gly Leu Ser Gly Arg Ser Ala Asn Pro
            35                  40                  45

Gly Gly Ser Asp Ile Val Met Thr Gln Ser Pro Leu Ser Leu Pro Val
        50                  55                  60

Thr Pro Gly Glu Pro Ala Ser Ile Ser Cys Arg Ser Ser Lys Ser Leu
65                  70                  75                  80

Leu His Ser Asn Gly Ile Thr Tyr Leu Tyr Trp Tyr Leu Gln Lys Pro
                85                  90                  95

Gly Gln Ser Pro Gln Leu Leu Ile Tyr Gln Met Ser Asn Leu Ala Ser
            100                 105                 110

Gly Val Pro Asp Arg Phe Ser Gly Ser Gly Ser Gly Thr Asp Phe Thr
        115                 120                 125

Leu Lys Ile Ser Arg Val Glu Ala Glu Asp Val Gly Val Tyr Tyr Cys
    130                 135                 140

Ala Gln Asn Leu Glu Leu Pro Tyr Thr Phe Gly Gln Gly Thr Lys Leu
145                 150                 155                 160

Glu Ile Lys

<210> SEQ ID NO 474
<211> LENGTH: 156
<212> TYPE: PRT
<213> ORGANISM: Artificial Sequence
<220> FEATURE:
<223> OTHER INFORMATION: chemically synthesized

<400> SEQUENCE: 474

```
Leu Cys His Pro Leu Val Leu Ser Ala Trp Glu Ser Cys Ser Ser Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Ala Asn Pro Gly Gly Ser Asp Ile Val Met
        35                  40                  45

Thr Gln Ser Pro Leu Ser Leu Pro Val Thr Pro Gly Glu Pro Ala Ser
    50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
                100                 105                 110

Gly Ser Gly Ser Gly Thr Asp Phe Thr Leu Lys Ile Ser Arg Val Glu
            115                 120                 125

Ala Glu Asp Val Gly Val Tyr Tyr Cys Ala Gln Asn Leu Glu Leu Pro
        130                 135                 140

Tyr Thr Phe Gly Gln Gly Thr Lys Leu Glu Ile Lys
145                 150                 155
```

<210> SEQ ID NO 475
<211> LENGTH: 237
<212> TYPE: PRT
<213> ORGANISM: Artificial Sequence
<220> FEATURE:
<223> OTHER INFORMATION: chemically synthesized

<400> SEQUENCE: 475

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Ser Arg Ser Leu Leu Asp Tyr Trp Gly Gln Gly Thr Leu Val Thr
                100                 105                 110

Val Ser Ser Gly Gly Gly Gly Ser Gly Gly Gly Ser Gly Gly Gly
            115                 120                 125

Gly Ser Asn Phe Met Leu Thr Gln Asp Pro Ala Val Ser Val Ala Leu
        130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Leu Leu Val
                165                 170                 175

Ile Tyr Gly Lys Asn Asn Arg Pro Ser Gly Ile Pro Asp Arg Phe Ser
                180                 185                 190

Gly Ser Ser Ser Gly Asn Thr Ala Ser Leu Thr Ile Thr Gly Ala Gln
            195                 200                 205
```

Ala Glu Asp Glu Ala Asp Tyr Tyr Cys Asn Ser Arg Asp Ser Ser Gly
            210                 215                 220

Asn Pro Val Phe Gly Gly Gly Thr Lys Val Thr Val Leu
225                 230                 235

<210> SEQ ID NO 476
<211> LENGTH: 237
<212> TYPE: PRT
<213> ORGANISM: Artificial Sequence
<220> FEATURE:
<223> OTHER INFORMATION: chemically synthesized

<400> SEQUENCE: 476

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Ser Arg Ser Leu Leu Asp Tyr Trp Gly Gln Gly Thr Leu Val Thr
            100                 105                 110

Val Ser Ser Gly Gly Gly Gly Ser Gly Gly Gly Ser Gly Gly Gly
        115                 120                 125

Gly Ser Asn Phe Met Leu Thr Gln Asp Pro Ala Val Ser Val Ala Leu
    130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Leu Leu Val
                165                 170                 175

Ile Tyr Gly Lys Asn Asn Arg Pro Ser Gly Ile Pro Asp Arg Phe Ser
            180                 185                 190

Gly Ser Ser Ser Gly Asn Thr Ala Ser Leu Thr Ile Thr Gly Ala Gln
        195                 200                 205

Ala Glu Asp Glu Ala Asp Tyr Tyr Cys Asn Ser Arg Asp Ser Ser Gly
    210                 215                 220

Asn Pro Val Phe Gly Gly Gly Thr Lys Val Thr Val Leu
225                 230                 235

<210> SEQ ID NO 477
<211> LENGTH: 5
<212> TYPE: PRT
<213> ORGANISM: Artificial Sequence
<220> FEATURE:
<223> OTHER INFORMATION: chemically synthesized

<400> SEQUENCE: 477

Ser Tyr Ala Met Gly
1               5

<210> SEQ ID NO 478
<211> LENGTH: 795
<212> TYPE: DNA

<213> ORGANISM: Artificial Sequence
<220> FEATURE:
<223> OTHER INFORMATION: chemically synthesized

<400> SEQUENCE: 478

```
cagggcctgt gtcaccctct ggtggcctct gcctgggagt cctgttcctc cggcggaggc    60
tcctctggcg gctctgctgt gggcctgctg gctccacctg gcggcctgtc cggcagatct   120
gacaaccacg gcggctccga catcgtgatg acccagtccc ccctgtccct gcccgtgact   180
cctggcgagc ctgcctccat ctcctgccgg tcctccaagt ccctgctgca ctccaacggc   240
atcacctacc tgtactggta tctgcagaag cccggccagt cccctcagct gctgatctac   300
cagatgtcca acctggcctc cggcgtgccc gacagattct ccggctctgg ctccggcacc   360
gacttcaccc tgaagatctc ccgggtggaa gccgaggacg tgggcgtgta ctactgcgcc   420
cagaacctgg aactgcccta ccttcggc cagggcacca agctggaaat caagcggacc   480
gtggccgctc cctccgtgtt catcttccca ccctccgacg agcagctgaa gtccggcacc   540
gcctccgtcg tgtgcctgct gaacaacttc taccccgcg aggccaaggt gcagtggaag   600
gtggacaacg ccctgcagtc cggcaactcc caggaatccg tgaccgagca ggactccaag   660
gacagcacct actccctgtc ctccaccctg accctgtcca aggccgacta cgagaagcac   720
aaggtgtacg cctgcgaagt gacccaccag ggcctgagca gccccgtgac caagtccttc   780
aaccggggcg agtgc   795
```

<210> SEQ ID NO 479
<211> LENGTH: 789
<212> TYPE: DNA
<213> ORGANISM: Artificial Sequence
<220> FEATURE:
<223> OTHER INFORMATION: chemically synthesized

<400> SEQUENCE: 479

```
ctgtgtcacc ctctggtggc ctctgcctgg gagtcctgtt cctccggcgg aggctcctct    60
ggcggctctg ctgtgggcct gctggctcca cctggcggcc tgtccggcag atctgacaac   120
cacgcggct ccgacatcgt gatgacccag tccccctgt ccctgcccgt gactcctggc   180
gagcctgcct ccatctcctg ccggtcctcc aagtccctgc tgcactccaa cggcatcacc   240
tacctgtact ggtatctgca gaagcccggc cagtcccctc agctgctgat ctaccagatg   300
tccaacctgg cctccggcgt gcccgacaga ttctccggct ctggctccgg caccgacttc   360
accctgaaga tctcccgggt ggaagccgag gacgtgggcg tgtactactg cgcccagaac   420
ctggaactgc cctacacctt cggccagggc accaagctgg aaatcaagcg gaccgtggcc   480
gctcctccg tgttcatctt cccacccctcc gacgagcagc tgaagtccgg caccgcctcc   540
gtcgtgtgcc tgctgaacaa cttctacccc gcgaggcca aggtgcagtg gaaggtggac   600
aacgccctgc agtccggcaa ctcccaggaa tccgtgaccg agcaggactc caaggacagc   660
acctactccc tgtcctccac cctgaccctg tccaaggccg actacgagaa gcacaaggtg   720
tacgcctgcg aagtgaccca ccagggcctg agcagccccg tgaccaagtc cttcaaccgg   780
ggcgagtgc   789
```

<210> SEQ ID NO 480
<211> LENGTH: 21
<212> TYPE: DNA
<213> ORGANISM: Artificial Sequence
<220> FEATURE:
<223> OTHER INFORMATION: chemically synthesized

```
<400> SEQUENCE: 480
cagggccagt ctggacaggg c                                             21

<210> SEQ ID NO 481
<211> LENGTH: 21
<212> TYPE: DNA
<213> ORGANISM: Artificial Sequence
<220> FEATURE:
<223> OTHER INFORMATION: chemically synthesized

<400> SEQUENCE: 481
cagggacagt ctggccaggg c                                             21

<210> SEQ ID NO 482
<211> LENGTH: 21
<212> TYPE: DNA
<213> ORGANISM: Artificial Sequence
<220> FEATURE:
<223> OTHER INFORMATION: chemically synthesized

<400> SEQUENCE: 482
cagggccagt ctggccaggg c                                             21

<210> SEQ ID NO 483
<211> LENGTH: 7
<212> TYPE: DNA
<213> ORGANISM: Artificial Sequence
<220> FEATURE:
<223> OTHER INFORMATION: chemically synthesized

<400> SEQUENCE: 483 cagggcc                                                             7
```

ANTI-CD166 ANTIBODIES, ACTIVATABLE ANTI-CD166 ANTIBODIES, AND METHODS OF USE THEREOF

RELATED APPLICATIONS

This application claims the benefit of U.S. Provisional Application Nos. 62/156,835, filed May 4, 2015; and 62/220,805, filed Sep. 18, 2015, the contents of each of which are incorporated herein by reference in their entirety.

The contents of the text file named "CYTM039001US_ST25.txt", which was created on Aug. 16, 2016 and is 347 KB in size, are hereby incorporated by reference in their entirety.

FIELD OF THE INVENTION

The invention relates generally to antibodies that bind CD166, activatable antibodies that specifically bind to CD166 and methods of making and using these anti-CD166 antibodies and anti-CD166 activatable antibodies in a variety of therapeutic, diagnostic and prophylactic indications.

BACKGROUND OF THE INVENTION

Antibody-based therapies have proven effective treatments for several diseases but in some cases, toxicities due to broad target expression have limited their therapeutic effectiveness. In addition, antibody-based therapeutics have exhibited other limitations such as rapid clearance from the circulation following administration.

In the realm of small molecule therapeutics, strategies have been developed to provide prodrugs of an active chemical entity. Such prodrugs are administered in a relatively inactive (or significantly less active) form. Once administered, the prodrug is metabolized in vivo into the active compound. Such prodrug strategies can provide for increased selectivity of the drug for its intended target and for a reduction of adverse effects.

Accordingly, there is a continued need in the field of antibody-based therapeutics for antibodies that mimic the desirable characteristics of the small molecule prodrug.

SUMMARY OF THE INVENTION

The disclosure provides antibodies or antigen-binding fragments thereof that specifically bind CD166, also known as cluster of differentiation 166, activated leukocyte cell adhesion molecule (ALCAM), and/or MEMD. The use of the term "CD166" is intended to cover any variation thereof, such as, by way of non-limiting example, CD-166 and/or CD166, and all variations are used herein interchangeably.

In some embodiments, the antibody includes an antibody or antigen-binding fragment thereof that specifically binds CD166. In some embodiments, the antibody or antigen-binding fragment thereof that binds CD166 is a monoclonal antibody, domain antibody, single chain, Fab fragment, a F(ab')₂ fragment, a scFv, a scAb, a dAb, a single domain heavy chain antibody, or a single domain light chain antibody. In some embodiments, such an antibody or antigen-binding fragment thereof that binds CD166 is a mouse, other rodent, chimeric, humanized or fully human monoclonal antibody.

In some embodiments, the antibody or antigen-binding fragment thereof comprises a heavy chain variable region amino acid sequence selected from the group consisting of SEQ ID NO: 119, 121, and 122. In some embodiments, the antibody or antigen-binding fragment thereof comprises a heavy chain variable region amino acid sequence comprising SEQ ID NO: 121 or SEQ ID NO: 122. In some embodiments, the antibody or antigen-binding fragment thereof comprises a heavy chain variable region amino acid sequence comprising SEQ ID NO: 121. In some embodiments, the antibody or antigen-binding fragment thereof comprises a heavy chain variable region amino acid sequence comprising SEQ ID NO: 122.

In some embodiments, the antibody or antigen-binding fragment thereof comprises a light chain variable region amino acid sequence selected from the group consisting of SEQ ID NO: 120 and 123-126. In some embodiments, the antibody or antigen-binding fragment thereof comprises a light chain variable region amino acid sequence selected from the group consisting of SEQ ID NO: 123-126. In some embodiments, the antibody or antigen-binding fragment thereof comprises a light chain variable region amino acid sequence comprising SEQ ID NO: 123.

In some embodiments, the antibody or antigen-binding fragment thereof comprises a heavy chain variable region amino acid sequence selected from the group consisting of SEQ ID NO: 119, 121, and 122, and a light chain variable region amino acid sequence selected from the group consisting of SEQ ID NO: 120 and 123-126.

In some embodiments, the antibody or antigen-binding fragment thereof comprises a heavy chain variable region amino acid sequence selected from the group consisting of SEQ ID NO: 121 or SEQ ID NO: 122, and a light chain variable region amino acid sequence selected from the group consisting of SEQ ID NO: 123-126. In some embodiments, the antibody or antigen-binding fragment thereof comprises a heavy chain variable region amino acid sequence selected from the group consisting of SEQ ID NO: 121, and a light chain variable region amino acid sequence selected from the group consisting of SEQ ID NO: 123. In some embodiments, the antibody or antigen-binding fragment thereof comprises a heavy chain variable region amino acid sequence selected from the group consisting of SEQ ID NO: 122, and a light chain variable region amino acid sequence selected from the group consisting of SEQ ID NO: 123.

In some embodiments, the antibody or antigen-binding fragment thereof comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 119, 121, and 122. In some embodiments, the antibody or antigen-binding fragment thereof comprises a heavy chain variable region amino acid sequence that is at least 90%, 91%, 92%, 93%, 94%, 95%, 96%, 97%, 98% or 99% identical to an amino acid sequence comprising SEQ ID NO: 121 or SEQ ID NO: 122. In some embodiments, the antibody or antigen-binding fragment thereof comprises a heavy chain variable region amino acid sequence that is at least 90%, 91%, 92%, 93%, 94%, 95%, 96%, 97%, 98% or 99% identical to an amino acid sequence comprising SEQ ID NO: 122. In some embodiments, the antibody or antigen-binding fragment thereof comprises a heavy chain variable region amino acid sequence that is at least 90%, 91%, 92%, 93%, 94%, 95%, 96%, 97%, 98% or 99% identical to an amino acid sequence comprising SEQ ID NO: 121.

In some embodiments, the antibody or antigen-binding fragment thereof comprises a light chain variable region amino acid sequence that is at least 90%, 91%, 92%, 93%, 94%, 95%, 96%, 97%, 98% or 99% identical to an amino acid sequence selected from the group consisting of SEQ ID NO: 120 and 123-126. In some embodiments, the antibody or antigen-binding fragment thereof comprises a light chain variable region amino acid sequence that is at least 90%, 91%, 92%, 93%, 94%, 95%, 96%, 97%, 98% or 99% identical to an amino acid sequence selected from the group consisting of SEQ ID NO: 123-126. In some embodiments, the antibody or antigen-binding fragment thereof comprises a light chain variable region amino acid sequence that is at least 90%, 91%, 92%, 93%, 94%, 95%, 96%, 97%, 98% or 99% identical to the amino acid sequence SEQ ID NO: 123.

In some embodiments, the antibody or antigen-binding fragment thereof comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 119, 121, and 122, and a light chain variable region amino acid sequence that is at least 90%, 91%, 92%, 93%, 94%, 95%, 96%, 97%, 98% or 99% identical to an amino acid sequence selected from the group consisting of SEQ ID NO: 120 and 123-126.

In some embodiments, the antibody or antigen-binding fragment thereof comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 121 or SEQ ID NO: 122, and a light chain variable region amino acid sequence that is at least 90%, 91%, 92%, 93%, 94%, 95%, 96%, 97%, 98% or 99% identical to an amino acid sequence selected from the group consisting of SEQ ID NO: 123-126. In some embodiments, the antibody or antigen-binding fragment thereof comprises a heavy chain variable region amino acid sequence that is at least 90%, 91%, 92%, 93%, 94%, 95%, 96%, 97%, 98% or 99% identical to the amino acid sequence selected SEQ ID NO: 122, and a light chain variable region amino acid sequence that is at least 90%, 91%, 92%, 93%, 94%, 95%, 96%, 97%, 98% or 99% identical to the amino acid sequence SEQ ID NO: 123. In some embodiments, the antibody or antigen-binding fragment thereof comprises a heavy chain variable region amino acid sequence that is at least 90%, 91%, 92%, 93%, 94%, 95%, 96%, 97%, 98% or 99% identical to the amino acid sequence selected SEQ ID NO: 121, and a light chain variable region amino acid sequence that is at least 90%, 91%, 92%, 93%, 94%, 95%, 96%, 97%, 98% or 99% identical to the amino acid sequence SEQ ID NO: 123.

In some embodiments, the antibody or antigen-binding fragment thereof comprises a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one complementarity determining region (CDR) sequence is selected from the group consisting of a VH CDR1 sequence comprising the amino acid sequence GFSLSTYGMGVG (SEQ ID NO: 127); a VH CDR2 sequence comprising the amino acid sequence NIWWSEDKH (SEQ ID NO: 128); a VH CDR3 sequence comprising the amino acid sequence IDYGNDYAFTY (SEQ ID NO: 129); a VL CDR1 sequence comprising the amino acid sequence RSSKSLLHSNGITYLY (SEQ ID NO: 130) or RSSQSLLHSNGITYLY (SEQ ID NO: 131); a VL CDR2 sequence comprising the amino acid sequence QMSNLAS (SEQ ID NO: 132) or QMSNRAS (SEQ ID NO: 133); and a VL CDR3 sequence comprising the amino acid sequence AQNLELPYT (SEQ ID NO: 134).

In some embodiments, the antibody or antigen-binding fragment thereof comprises a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one complementarity determining region (CDR) sequence is selected from the group consisting of a VH CDR1 sequence comprising the amino acid sequence GFSLSTYGMGVG (SEQ ID NO: 127); a VH CDR2 sequence comprising the amino acid sequence NIWWSEDKH (SEQ ID NO: 128); a VH CDR3 sequence comprising the amino acid sequence IDYGNDYAFTY (SEQ ID NO: 129); a VL CDR1 sequence comprising the amino acid sequence RSSKSLLHSNGITYLY (SEQ ID NO: 130); a VL CDR2 sequence comprising the amino acid sequence QMSNLAS (SEQ ID NO: 132); and a VL CDR3 sequence comprising the amino acid sequence AQNLELPYT (SEQ ID NO: 134).

In some embodiments, the antibody or antigen-binding fragment thereof comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to a VH CDR1 sequence comprising the amino acid sequence GFSLSTYGMGVG (SEQ ID NO: 127); a VH CDR2 sequence that includes a sequence that is at least 90%, 91%, 92%, 93%, 94%, 95%, 96%, 97%, 98%, 99% or more identical to a VH CDR2 sequence comprising the amino acid sequence NIWWSEDKH (SEQ ID NO: 128); a VH CDR3 sequence that includes a sequence that is at least 90%, 91%, 92%, 93%, 94%, 95%, 96%, 97%, 98%, 99% or more identical to a VH CDR3 sequence comprising the amino acid sequence IDYGNDYAFTY (SEQ ID NO: 129); a VL CDR1 sequence that includes a sequence that is at least 90%, 91%, 92%, 93%, 94%, 95%, 96%, 97%, 98%, 99% or more identical to a VL CDR1 sequence comprising the amino acid sequence comprising the amino acid sequence RSSKSLLH-SNGITYLY (SEQ ID NO: 130) or RSSQSLLHSNGITYLY (SEQ ID NO: 131); a VL CDR2 sequence that includes a sequence that is at least 90%, 91%, 92%, 93%, 94%, 95%, 96%, 97%, 98%, 99% or more identical to a VL CDR2 sequence comprising the amino acid sequence QMSNLAS (SEQ ID NO: 132) or QMSNRAS (SEQ ID NO: 133); and a VL CDR3 sequence that includes a sequence that is at least 90%, 91%, 92%, 93%, 94%, 95%, 96%, 97%, 98%, 99% or more identical to a VL CDR3 sequence comprising the amino acid sequence AQNLELPYT (SEQ ID NO: 134).

In some embodiments, the antibody or antigen-binding fragment thereof comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to a VH CDR1 sequence comprising the amino acid sequence GFSLSTYGMGVG (SEQ ID NO: 127); a VH CDR2 sequence that includes a sequence that is at least 90%, 91%, 92%, 93%, 94%, 95%, 96%, 97%, 98%, 99% or more identical to a VH CDR2 sequence comprising the amino acid sequence NIWWSEDKH (SEQ ID NO: 128); a VH CDR3 sequence that includes a sequence that is at least 90%, 91%, 92%, 93%, 94%, 95%, 96%, 97%, 98%, 99% or more identical to a VH CDR3 sequence comprising the amino acid sequence IDYGNDYAFTY (SEQ ID NO: 129); a VL CDR1 sequence that includes a sequence that is at least 90%, 91%, 92%, 93%, 94%, 95%, 96%, 97%, 98%, 99% or more identical to a VL CDR1 sequence comprising the amino acid sequence comprising the amino acid sequence RSSKSLLHSNGITYLY (SEQ ID NO: 130); a VL CDR2 sequence that includes a sequence that is at least 90%, 91%, 92% 93%, 94%, 95%, 96%, 97%, 98%, 99% or more identical to a VL CDR2 sequence comprising the amino acid sequence QMSNLAS (SEQ ID NO: 132); and a VL CDR3 sequence that includes a sequence that is at least 90%, 91%, 92%, 93%, 94%, 95%, 96%, 97%, 98%, 99% or more identical to a VL CDR3 sequence comprising the amino acid sequence AQNLELPYT (SEQ ID NO: 134).

In some embodiments, the antibody or antigen-binding fragment thereof comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises the amino acid sequence GFSLSTYGMGVG (SEQ ID NO: 127); the VH CDR2 sequence comprises the amino acid sequence NIWWSEDKH (SEQ ID NO: 128); the VH CDR3 sequence comprises the amino acid sequence IDYGNDYAFTY (SEQ ID NO: 129); the VL CDR1 sequence comprises the amino acid sequence RSSKSLLHSNGITYLY (SEQ ID NO: 130) or RSSQSLLHSNGITYLY (SEQ ID NO: 131); the VL CDR2 sequence comprises the amino acid sequence QMSNLAS (SEQ ID NO: 132) or QMSNRAS (SEQ ID NO: 133); and the VL CDR3 sequence comprises the amino acid sequence AQNLELPYT (SEQ ID NO: 134).

In some embodiments, the antibody or antigen-binding fragment thereof comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises the amino acid sequence GFSLSTYGMGVG (SEQ ID NO: 127); the VH CDR2 sequence comprises the amino acid sequence NIWWSEDKH (SEQ ID NO: 128); the VH CDR3 sequence comprises the amino acid sequence IDYGNDYAFTY (SEQ ID NO: 129); the VL CDR1 sequence comprises the amino acid sequence RSSKSLLHSNGITYLY (SEQ ID NO: 130); the VL CDR2 sequence comprises the amino acid sequence QMSNLAS (SEQ ID NO: 132); and the VL CDR3 sequence comprises the amino acid sequence AQNLELPYT (SEQ ID NO: 134).

In some embodiments, the antibody or antigen-binding fragment thereof comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises a sequence that is at least 90%, 91%, 92%, 93%, 94%, 95%, 96%, 97%, 98%, 99% or more identical to the amino acid sequence GFSLSTYGMGVG (SEQ ID NO: 127); the VH CDR2 sequence comprises a sequence that is at least 90%, 91%, 92%, 93%, 94%, 95%, 96%, 97%, 98%, 99% or more identical to the amino acid sequence NIWWSEDKH (SEQ ID NO: 128); the VH CDR3 sequence comprises a sequence that is at least 90%, 91%, 92%, 93%, 94%, 95%, 96%, 97%, 98%, 99% or more identical to the amino acid sequence IDYGNDYAFTY (SEQ ID NO: 129); the VL CDR1 sequence comprises a sequence that is at least 90%, 91%, 92%, 93%, 94%, 95%, 96%, 97%, 98%, 99% or more identical to the amino acid sequence RSSKSLLHSNGITYLY (SEQ ID NO: 130) or RSSQSLLHSNGITYLY (SEQ ID NO: 131); the VL CDR2 sequence comprises a sequence that is at least 90%, 91%, 92%, 93%, 94%, 95%, 96%, 97%, 98%, 99% or more identical to the amino acid sequence QMSNLAS (SEQ ID NO: 132) or QMSNRAS (SEQ ID NO: 133); and the VL CDR3 sequence a sequence that is at least 90%, 91%, 92%, 93%, 94%, 95%, 96%, 97%, 98%, 99% or more identical to comprises the amino acid sequence AQNLELPYT (SEQ ID NO: 134).

In some embodiments, the antibody or antigen-binding fragment thereof comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises a sequence that is at least 90%, 91%, 92%, 93%, 94%, 95%, 96%, 97%, 98%, 99% or more identical to the amino acid sequence GFSLSTYGMGVG (SEQ ID NO: 127); the VH CDR2 sequence comprises a sequence that is at least 90%, 91%, 92%, 93%, 94%, 95%, 96%, 97%, 98%, 99% or more identical to the amino acid sequence NIWWSEDKH (SEQ ID NO: 128); the VH CDR3 sequence comprises a sequence that is at least 90%, 91%, 92%, 93%, 94%, 95%, 96%, 97%, 98%, 99% or more identical to the amino acid sequence IDYGNDYAFTY (SEQ ID NO: 129); the VL CDR1 sequence comprises a sequence that is at least 90%, 91%, 92%, 93%, 94%, 95%, 96%, 97%, 98%, 99% or more identical to the amino acid sequence RSSKSLLHSNGITYLY (SEQ ID NO: 130); the VL CDR2 sequence comprises a sequence that is at least 90%, 91%, 92%, 93%, 94%, 95%, 96%, 97%, 98%, 99% or more identical to the amino acid sequence QMSNLAS (SEQ ID NO: 132); and the VL CDR3 sequence a sequence that is at least 90%, 91%, 92%, 93%, 94%, 95%, 96%, 97%, 98%, 99% or more identical to comprises the amino acid sequence AQNLELPYT (SEQ ID NO: 134).

In some embodiments, the antibody or antigen-binding fragment thereof is encoded by a nucleic acid sequence that comprises a nucleic acid sequence encoding a heavy chain amino acid sequence comprising an amino acid sequence selected from the group consisting of SEQ ID NO: 119, 121, and 122. In some embodiments, the antibody or antigen-binding fragment thereof is encoded by a nucleic acid sequence that comprises a nucleic acid sequence encoding a heavy chain amino acid sequence comprising an amino acid sequence selected from the group consisting of: SEQ ID NO: 121 or SEQ ID NO: 122. In some embodiments, the antibody or antigen-binding fragment thereof is encoded by a nucleic acid sequence that comprises a nucleic acid sequence encoding a heavy chain amino acid sequence comprising the amino acid sequence selected SEQ ID NO: 122. In some embodiments, the antibody or antigen-binding fragment thereof is encoded by a nucleic acid sequence that comprises a nucleic acid sequence encoding a heavy chain amino acid sequence comprising the amino acid sequence selected SEQ ID NO: 121.

In some embodiments, the antibody or antigen-binding fragment thereof is encoded by a nucleic acid sequence that comprises a nucleic acid sequence encoding a light chain amino acid sequence comprising an amino acid sequence selected from the group consisting of SEQ ID NO: 120 and 123-126. In some embodiments, the antibody or antigen-binding fragment thereof is encoded by a nucleic acid sequence that comprises a nucleic acid sequence encoding a light chain amino acid sequence comprising an amino acid sequence selected from the group consisting of SEQ ID NO: 123-126. In some embodiments, the antibody or antigen-binding fragment thereof is encoded by a nucleic acid sequence that comprises a nucleic acid sequence encoding a light chain amino acid sequence comprising the amino acid sequence SEQ ID NO: 123.

In some embodiments, the antibody or antigen-binding fragment thereof is encoded by a nucleic acid sequence that comprises a nucleic acid sequence encoding a heavy chain amino acid sequence comprising an amino acid sequence selected from the group consisting of SEQ ID NO: 119, 121, and 122, and a nucleic acid sequence encoding a light chain amino acid sequence comprising an amino acid sequence selected from the group consisting of SEQ ID NO: 120 and 123-126.

In some embodiments, the antibody or antigen-binding fragment thereof is encoded by a nucleic acid sequence that comprises a nucleic acid sequence encoding a heavy chain amino acid sequence comprising an amino acid sequence selected from the group consisting of SEQ ID NO: 121, and 122, and a nucleic acid sequence encoding a light chain amino acid sequence comprising an amino acid sequence selected from the group consisting of SEQ ID NO: 123-126.

In some embodiments, the antibody or antigen-binding fragment thereof is encoded by a nucleic acid sequence that comprises a nucleic acid sequence encoding a heavy chain amino acid sequence comprising the amino acid sequence of SEQ ID NO: 122, and a nucleic acid sequence encoding a light chain amino acid sequence comprising the amino acid sequence SEQ ID NO: 123. In some embodiments, the antibody or antigen-binding fragment thereof is encoded by a nucleic acid sequence that comprises a nucleic acid sequence encoding a heavy chain amino acid sequence comprising the amino acid sequence of SEQ ID NO: 121, and a nucleic acid sequence encoding a light chain amino acid sequence comprising the amino acid sequence SEQ ID NO: 123.

In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain amino acid sequence comprising an amino acid sequence selected from the group consisting of SEQ ID NO: 121 or SEQ ID NO: 122. In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain amino acid sequence comprising an amino acid sequence selected from the group consisting of SEQ ID NO: 121 or SEQ ID NO: 122. In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain amino acid sequence comprising the amino acid sequence of SEQ ID NO: 122. In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain amino acid sequence comprising the amino acid sequence of SEQ ID NO: 121.

In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a light chain amino acid sequence comprising an amino acid sequence selected from the group consisting of SEQ ID NO: 120 and 123-126. In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a light chain amino acid sequence comprising an amino acid sequence selected from the group consisting of SEQ ID NO: 123-126. In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a light chain amino acid sequence comprising the amino acid sequence of SEQ ID NO: 123.

In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain amino acid sequence comprising an amino acid sequence selected from the group consisting of SEQ ID NO: 119, 121, and 122, and a nucleic acid sequence that is at least 90%, 91%, 92%, 93%, 94%, 95%, 96%, 97%, 98% or 99% identical to a nucleic acid sequence encoding a light chain amino acid sequence comprising an amino acid sequence selected from the group consisting of SEQ ID NO: 120 and 123-126.

In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain amino acid sequence comprising an amino acid sequence selected from the group consisting of SEQ ID NO: 121 or SEQ ID NO: 122, and a nucleic acid sequence that is at least 90%, 91%, 92%, 93%, 94%, 95%, 96%, 97%, 98% or 99% identical to a nucleic acid sequence encoding a light chain amino acid sequence comprising an amino acid sequence selected from the group consisting of SEQ ID NO: 123-126. In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain amino acid sequence comprising the amino acid sequence of SEQ ID NO: 122, and a nucleic acid sequence that is at least 90%, 91%, 92%, 93%, 94%, 95%, 96%, 97%, 98% or 99% identical to a nucleic acid sequence encoding a light chain amino acid sequence comprising the amino acid sequence of SEQ ID NO: 123. In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain amino acid sequence comprising the amino acid sequence of SEQ ID NO: 121, and a nucleic acid sequence that is at least 90%, 91%, 92%, 93%, 94%, 95%, 96%, 97%, 98% or 99% identical to a nucleic acid sequence encoding a light chain amino acid sequence comprising the amino acid sequence of SEQ ID NO: 123.

In some embodiments, the antibody or antigen-binding fragment thereof is incorporated in a multispecific antibody or antigen-binding fragment thereof, where at least one arm of the multispecific antibody or antigen-binding fragment thereof specifically binds CD166. In some embodiments, the antibody or antigen-binding fragment thereof is incorporated in a bispecific antibody or antigen-binding fragment thereof, where at least one arm of the bispecific antibody or antigen-binding fragment thereof specifically binds CD166.

In some embodiments, at least one arm of the multispecific antibody or antigen-binding fragment thereof, e.g., a bispecific antibody or antigen-binding fragment thereof, comprises a heavy chain variable region amino acid sequence selected from the group consisting of SEQ ID NO: 119, 121, and 122. In some embodiments, at least one arm of the multispecific antibody or antigen-binding fragment thereof, e.g., a bispecific antibody or antigen-binding fragment thereof, comprises a heavy chain variable region amino acid sequence comprising an amino acid sequence selected from the group consisting of SEQ ID NO: 121 or SEQ ID NO: 122. In some embodiments, at least one arm of the multispecific antibody or antigen-binding fragment thereof, e.g., a bispecific antibody or antigen-binding fragment thereof, comprises a heavy chain variable region amino acid sequence comprising the amino acid sequence of SEQ ID NO: 122. In some embodiments, at least one arm of the multispecific antibody or antigen-binding fragment thereof, e.g., a bispecific antibody or antigen-binding fragment thereof, comprises a heavy chain variable region amino acid sequence comprising the amino acid sequence of SEQ ID NO: 121.

In some embodiments, at least one arm of the multispecific antibody or antigen-binding fragment thereof, e.g., a bispecific antibody or antigen-binding fragment thereof, comprises a light chain variable region amino acid sequence comprising an amino acid sequence selected from the group consisting of SEQ ID NO: 120 and 123-126. In some embodiments, at least one arm of the multispecific antibody or antigen-binding fragment thereof, e.g., a bispecific antibody or antigen-binding fragment thereof, comprises a light chain variable region amino acid sequence comprising an amino acid sequence selected from the group consisting of SEQ ID NO: 123-126. In some embodiments, at least one arm of the multispecific antibody or antigen-binding fragment thereof, e.g., a bispecific antibody or antigen-binding fragment thereof, comprises a light chain variable region amino acid sequence comprising the amino acid sequence of SEQ ID NO: 123.

In some embodiments, at least one arm of the multispecific antibody or antigen-binding fragment thereof, e.g., a bispecific antibody or antigen-binding fragment thereof, comprises a heavy chain variable region amino acid sequence comprising an amino acid sequence selected from the group consisting of SEQ ID NO: 119, 121, and 122, and a light chain variable region amino acid sequence comprising an amino acid sequence selected from the group consisting of SEQ ID NO: 120 and 123-126.

In some embodiments, at least one arm of the multispecific antibody or antigen-binding fragment thereof, e.g., a bispecific antibody or antigen-binding fragment thereof, comprises a heavy chain variable region amino acid sequence comprising an amino acid sequence selected from the group consisting of SEQ ID NO: 121 or SEQ ID NO: 122, and a light chain variable region amino acid sequence comprising an amino acid sequence selected from the group consisting of SEQ ID NO: 123-126. In some embodiments, at least one arm of the multispecific antibody or antigen-binding fragment thereof, e.g., a bispecific antibody or antigen-binding fragment thereof, comprises a heavy chain variable region amino acid sequence comprising the amino acid sequence of SEQ ID NO: SEQ ID NO: 122, and a light chain variable region amino acid sequence comprising the amino acid sequence of SEQ ID NO: 123, a bispecific antibody or antigen-binding fragment thereof, comprises a heavy chain variable region amino acid sequence comprising the amino acid sequence of SEQ ID NO: SEQ ID NO: 121, and a light chain variable region amino acid sequence comprising the amino acid sequence of SEQ ID NO: 123.

In some embodiments, at least one arm of the multispecific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99% identical to an amino acid sequence comprising an amino acid sequence selected from the group consisting of SEQ ID NO: 119, 121, and 122. In some embodiments, at least one arm of the multispecific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99% identical to an amino acid sequence comprising an amino acid sequence selected from the group consisting of SEQ ID NO: 121 or SEQ ID NO: 122. In some embodiments, at least one arm of the multispecific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99% identical to an amino acid sequence comprising the amino acid sequence of SEQ ID NO: 122. In some embodiments, at least one arm of the multi specific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99%, identical to an amino acid sequence comprising the amino acid sequence of SEQ ID NO: 121.

In some embodiments, at least one arm of the multispecific antibody or antigen-binding fragment thereof, e.g., a bispecific antibody or antigen-binding fragment thereof, comprises a light chain variable region amino acid sequence that is at least 90%, 91%, 92%, 93%, 94%, 95%, 96%, 97%, 98% or 990 identical to an amino acid sequence comprising an amino acid sequence selected from the group consisting of SEQ ID NO: 120 and 123-126. In some embodiments, at least one arm of the multispecific antibody or antigen-binding fragment thereof, e.g., a bispecific antibody or antigen-binding fragment thereof, comprises a light chain variable region amino acid sequence that is at least 90%, 91%, 92%, 93%, 94%/o, 95%, 96%, 97%, 98% or 99% identical to an amino acid sequence comprising an amino acid sequence selected from the group consisting of SEQ ID NO: 123-126. In some embodiments, at least one arm of the multispecific antibody or antigen-binding fragment thereof, e.g., a bispecific antibody or antigen-binding fragment thereof, comprises a light chain variable region amino acid sequence that is at least 90%, 91%, 92%, 93%, 94%, 95%, 96%, 97%, 98% or 99% identical to an amino acid sequence comprising the amino acid sequence of SEQ ID NO: 123.

In some embodiments, at least one arm of the multispecific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99% identical to an amino acid sequence comprising an amino acid sequence selected from the group consisting of SEQ ID NO: 119, 121, and 122, and a light chain variable region amino acid sequence that is at least 90%, 91%, 92%, 93%, 94%, 95%, 96%, 97%, 98% or 99% identical to an amino acid sequence comprising an amino acid sequence selected from the group consisting of SEQ ID NO: 120 and 123-126.

In some embodiments, at least one arm of the multispecific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99% identical to an amino acid sequence comprising an amino acid sequence selected from the group consisting of SEQ ID NO: 121 or SEQ ID NO: 122, and a light chain variable region amino acid sequence that is at least 90%, 91%, 92%, 93%, 94%, 95%, 96%, 97%, 98% or 99% identical to an amino acid sequence comprising an amino acid sequence selected from the group consisting of SEQ ID NO: 123-126.

In some embodiments, at least one arm of the multispecific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99% identical to an amino acid sequence comprising the amino acid sequence of SEQ ID NO: 122, and a light chain variable region amino acid sequence that is at least 90%, 91%, 92%, 93%, 94%, 95%, 96%, 97%, 98% or 99% identical to an amino acid sequence comprising the amino acid sequence of SEQ ID NO: 123.

In some embodiments, at least one arm of the multispecific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99% identical to an amino acid sequence comprising the amino acid sequence of SEQ ID NO: 121, and a light chain variable region amino acid sequence that is at least 90%, 91%, 92%, 93%, 94%, 95%, 96%, 97%, 98% or 99% identical to an amino acid sequence comprising the amino acid sequence of SEQ ID NO: 123.

In some embodiments, at least one arm of the multispecific antibody or antigen-binding fragment thereof, e.g., a bispecific antibody or antigen-binding fragment thereof, comprises a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one CDR sequence is selected from the group consisting of a VH CDR1 sequence comprising the amino acid sequence GFSLSTYGMGVG (SEQ ID NO: 127); a VH CDR2 sequence comprising the amino acid sequence NIWWSEDKH (SEQ ID NO: 128); a VH CDR3 sequence comprising the amino acid sequence IDYGNDYAFTY (SEQ ID NO: 129); a VL CDR1 sequence comprising the amino acid sequence RSSKSLLHSNGITYLY (SEQ ID NO: 130) or RSSQSLLHSNGITYLY (SEQ ID NO: 131); a VL CDR2 sequence comprising the amino acid sequence QMSNLAS (SEQ ID NO: 132) or QMSNRAS (SEQ ID NO: 133); and a VL CDR3 sequence comprising the amino acid sequence AQNLELPYT (SEQ ID NO: 134).

In some embodiments, at least one arm of the multispecific antibody or antigen-binding fragment thereof, e.g., a bispecific antibody or antigen-binding fragment thereof, comprises a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one CDR sequence is selected from the group consisting of a VH CDR1 sequence comprising the amino acid sequence GFSLSTYGMGVG (SEQ ID NO: 127); a VH CDR2 sequence comprising the amino acid sequence NIWWSEDKH (SEQ ID NO: 128); a VH CDR3 sequence comprising the amino acid sequence IDYGNDYAFTY (SEQ ID NO: 129); a VL CDR1 sequence comprising the amino acid sequence RSSKSLLHSNGITYLY (SEQ ID NO: 130); a VL CDR2 sequence comprising the amino acid sequence QMSNLAS (SEQ ID NO: 132); and a VL CDR3 sequence comprising the amino acid sequence AQNLELPYT (SEQ ID NO: 134).

In some embodiments, at least one arm of the multispecific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 906, 91%, 92%, 93%, 94%, 95%, 96%, 97%, 98%, 99% or more identical to a VH CDR1 sequence comprising the amino acid sequence GFSLSTYGMGVG (SEQ ID NO: 127); a VH CDR2 sequence that includes a sequence that is at least 90%, 91%, 92%, 93%, 94%, 95%, 96%, 97%, 98%, 99% or more identical to a VH CDR2 sequence the amino acid sequence NIWWSEDKH (SEQ ID NO: 128); a VH CDR3 sequence that includes a sequence that is at least 90%, 91%, 92%, 93%, 94%, 95%, 96%, 97%, 98%, 99% or more identical to a VH CDR3 sequence IDYGNDYAFTY (SEQ ID NO: 129); a VL CDR1 sequence that includes a sequence that is at least 90%, 91%, 92%, 93%, 94%, 95%, 96%, 97%, 98%, 99% or more identical to a VL CDR1 sequence comprising the amino acid sequence comprising the amino acid sequence RSSKSLLHSNGITYLY (SEQ ID NO: 130) or RSSQSLLHSNGITYLY (SEQ ID NO: 131); a VL CDR2 sequence that includes a sequence that is at least 90%, 91%, 92%, 93%, 94%, 95%, 96%, 97%, 98%, 99% or more identical to a VL CDR2 sequence comprising the amino acid sequence QMSNLAS (SEQ ID NO: 132) or QMSNRAS (SEQ ID NO: 133); and a VL CDR3 sequence that includes a sequence that is at least 90%, 91%, 92%, 93%, 94%, 95%, 96%, 97%, 98%, 99% or more identical to a VL CDR3 sequence comprising the amino acid sequence AQNLELPYT (SEQ ID NO: 134).

In some embodiments, at least one arm of the multispecific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 990 or more identical to a VH CDR1 sequence comprising the amino acid sequence GFSLSTYGMGVG (SEQ ID NO: 127); a VH CDR2 sequence that includes a sequence that is at least 90%, 91%, 92%, 93%, 94%, 95%, 96%, 97%, 98%, 99% or more identical to a VH CDR2 sequence the amino acid sequence NIWWSEDKH (SEQ ID NO: 128); a VH CDR3 sequence that includes a sequence that is at least 90%, 91%, 92%, 93%, 94%, 95%, 96%, 97%, 98%, 99% or more identical to a VH CDR3 sequence IDYGNDYAFTY (SEQ ID NO: 129); a VL CDR1 sequence that includes a sequence that is at least 90%, 91%, 92%, 93%, 94%, 95%, 96%, 97%, 98%, 99% or more identical to a VL CDR1 sequence comprising the amino acid sequence comprising the amino acid sequence RSSKSLLHSNGITYLY (SEQ ID NO: 130); a VL CDR2 sequence that includes a sequence that is at least 90%, 91%, 92%, 93%, 94%, 95%, 96%, 97%, 98%, 99% or more identical to a VL CDR2 sequence comprising the amino acid sequence QMSNLAS (SEQ ID NO: 132); and a VL CDR3 sequence that includes a sequence that is at least 90%, 91%, 92%, 93%, 94%, 95%, 96%, 97%, 98%, 99% or more identical to a VL CDR3 sequence comprising the amino acid sequence AQNLELPYT (SEQ ID NO: 134)

In some embodiments, at least one arm of the multispecific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises the amino acid sequence GFSLSTYGMGVG (SEQ ID NO: 127); the VH CDR2 sequence comprises the amino acid sequence NIWWSEDKH (SEQ ID NO: 128); the VH CDR3 sequence comprises the amino acid sequence IDYGNDYAFTY (SEQ ID NO: 129); the VL CDR1 sequence comprises the amino acid sequence RSSKSLLHSNGITYLY (SEQ ID NO: 130) or RSSQSLLHSNGITYLY (SEQ ID NO: 131); the VL CDR2 sequence comprises the amino acid sequence QMSNLAS (SEQ ID NO: 132) or QMSNRAS (SEQ ID NO: 133); and the VL CDR3 sequence comprises the amino acid sequence AQNLELPYT (SEQ ID NO: 134).

In some embodiments, at least one arm of the multispecific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises the amino acid sequence GFSLSTYGMGVG (SEQ ID NO: 127); the VH CDR2 sequence comprises the amino acid sequence NIWWSEDKH (SEQ ID NO: 128); the VH CDR3 sequence comprises the amino acid sequence IDYGNDYAFTY (SEQ ID NO: 129); the VL CDR1 sequence comprises the amino acid sequence RSSKSLLHSNGITYLY (SEQ ID NO: 130); the VL CDR2 sequence comprises the amino acid sequence QMSNLAS (SEQ ID NO: 132); and the VL CDR3 sequence comprises the amino acid sequence AQNLELPYT (SEQ ID NO: 134).

In some embodiments, at least one arm of the multispecific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises a sequence that is at least 90%, 91%, 92%, 93%, 94%, 95%, 96%, 97%, 98%, 99% or more identical to the amino acid sequence GFSLSTYGMGVG (SEQ ID NO: 127); the VH CDR2 sequence comprises a sequence that is at least 90%, 91%, 92%, 93%, 94%, 95%, 96%, 97%, 98%, 99% or more identical to the amino acid sequence NIWWSEDKH (SEQ ID NO: 128); the VH CDR3 sequence comprises a sequence that is at least 90%, 91%, 92%, 93%, 94%, 95%, 96%, 97%, 98%, 99% or more identical to the amino acid sequence IDYGNDYAFTY (SEQ ID NO: 129); the VL CDR1 sequence comprises a sequence that is at least 90%, 91%, 92%, 93%, 94%, 95%, 96%, 97%, 98%, 99%; or more identical to the amino acid sequence RSSKSLLHSNGITYLY (SEQ ID NO: 130) or RSSQSLLHSNGITYLY (SEQ ID NO: 131); the VL CDR2 sequence comprises a sequence that is at least 90%, 91%, 92%, 93%, 94%, 95%, 96%, 97%, 98%, 99% or more identical to the amino acid sequence QMSNLAS (SEQ ID NO: 132) or QMSNRAS (SEQ ID NO: 133); and the VL CDR3 sequence a sequence that is at least 90%, 91%, 92%, 93%, 94%, 95%, 96%, 97%, 98%, 99% or more identical to comprises the amino acid sequence AQNLELPYT (SEQ ID NO: 134).

In some embodiments, at least one arm of the multispecific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises a sequence that is at least 90%, 91%, 92%, 93%, 94%, 95%, 96%, 97%, 98%, 99% or more identical to the amino acid sequence GFSLSTYGMGVG (SEQ ID NO: 127); the VH CDR2 sequence comprises a sequence that is at least 90%, 91%, 92%, 93%, 94%, 95%, 96%, 97%, 98%, 99% or more identical to the amino acid sequence NIWWSEDKH (SEQ ID NO: 128); the VH CDR3 sequence comprises a sequence that is at least 90%, 91%, 92%, 93%, 94%, 95%, 96%, 97%, 98%, 99% or more identical to the amino acid sequence IDYGNDYAFTY (SEQ ID NO: 129); the VL CDR1 sequence comprises a sequence that is at least 90%, 91%, 92%, 93%, 94%, 95%, 96%, 97%, 98%, 99% or more identical to the amino acid sequence RSSKSLLHSNGITYLY (SEQ ID NO: 130); the VL CDR2 sequence comprises a sequence that is at least 90%, 91%, 92%, 93%, 94%, 95%, 96%, 97%, 98%, 99% or more identical to the amino acid sequence QMSNLAS (SEQ ID NO: 132); and the VL CDR3 sequence a sequence that is at least 90%, 91%, 92%, 93%, 94%, 95%, 96%, 97%, 98%, 99% or more identical to comprises the amino acid sequence AQNLELPYT (SEQ ID NO: 134).

In some embodiments, at least one arm of the multispecific antibody or antigen-binding fragment thereof, e.g., a bispecific antibody or antigen-binding fragment thereof, comprises a heavy chain or a heavy chain variable region that comprises or is derived from an amino acid sequence selected from the group consisting of the heavy chain variable region amino acid sequences shown in Table 12. In some embodiments, at least one arm of the multispecific antibody or antigen-binding fragment thereof, e.g., a bispecific antibody or antigen-binding fragment thereof, comprises a light chain or a light chain variable region that comprises or is derived from an amino acid sequence selected from the group consisting of the light chain variable region amino acid sequences shown in Table 12. In some embodiments, at least one arm of the multispecific antibody or antigen-binding fragment thereof, e.g., a bispecific antibody or antigen-binding fragment thereof, comprises a heavy chain or a heavy chain variable region that comprises or is derived from an amino acid sequence selected from the group consisting of the heavy chain variable region sequences shown in Table 12 and a light chain or a light chain variable region that comprises or is derived from an amino acid sequence selected from the group consisting of the light chain variable region amino acid sequences shown in Table 12.

In some embodiments, at least one arm of the multispecific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99% identical to an amino acid sequence selected from the group consisting of the heavy chain variable region sequences shown in Table 12. In some embodiments, at least one arm of the multispecific antibody or antigen-binding fragment thereof, e.g., a bispecific antibody or antigen-binding fragment thereof, comprises an amino acid sequence that is at least 90%, 91%, 92%, 93%, 94%, 95%, 96%, 97%, 98% or 99% identical to an amino acid sequence selected from the group consisting of the light chain variable region sequences shown in Table 12. In some embodiments, at least one arm of the multispecific antibody or antigen-binding fragment thereof, e.g., a bispecific antibody or antigen-binding fragment thereof, comprises an amino acid sequence that is at least 90%, 91%, 92%, 93%, 94%, 95%, 96%, 97%, 98% or 99% identical to an amino acid sequence selected from the group consisting of the heavy chain variable region sequences shown in Table 12 and a light chain variable region amino acid sequence that is at least 90%, 91%, 92%, 93%, 94%, 95%, 96%, 97%, 98% or 99% identical to an amino acid sequence selected from the group consisting of the light chain variable region sequences shown in Table 12.

In some embodiments, at least one arm of the multi specific antibody or antigen-binding fragment thereof, e.g., a bispecific antibody or antigen-binding fragment thereof, comprises a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one CDR sequence is selected from the group consisting of a VH CDR1 sequence shown in Table 13; a VH CDR2 sequence shown in Table 13; a VH CDR3 sequence shown in Table 13; a VL CDR1 sequence shown in Table 13; a VL CDR2 sequence shown in Table 13; and a VL CDR3 sequence shown in Table 13.

In some embodiments, at least one arm of the multispecific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to a VH CDR1 sequence shown in Table 13; a VH CD2 sequence that includes a sequence that is at least 90%, 91%, 92%, 93%, 94%, 95%, 96%, 97%, 980%, 99% or more identical to a VH CDR2 sequence shown in Table 13; a VH CDR3 sequence that includes a sequence that is at least 90%, 91%, 92%, 93%, 94%, 95%, 96%, 97%, 98%, 99% or more identical to a VH CDR3 sequence shown in Table 13; a VL CDR1 sequence that includes a sequence that is at least 90%, 91%, 92%, 93%, 94%, 95%, 96%, 97%, 98%, 99% or more identical to a VL CDR1 sequence shown in Table 13; a VL CDR2 sequence that includes a sequence that is at least 90%, 91%, 92%, 93%, 94%, 95%, 96%, 97%, 98%, 99% or more identical to a VL CDR2 sequence shown in Table 13; and a VL CDR3 sequence that includes a sequence that is at least 90%, 91%, 92%, 93%, 94%, 95%, 96%, 97%, 98%, 99% or more identical to a VL CDR3 sequence shown in Table 13.

In some embodiments at least one arm of the multispecific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein the combination is a combination of the six CDR sequences (VH CDR1, VH CDR2, VH CDR3, VL CDR1, VL CDR2, and VL CDR3) shown in a single row in Table 13.

In some embodiments, at least one arm of the multispecific antibody or antigen-binding fragment thereof, e.g., a bispecific antibody or antigen-binding fragment thereof, comprises a light chain variable region that comprise a combination of a VL CDR1 sequence, a VL CDR2 sequence, and a VL CDR3 sequence, wherein the combination is a combination of the three light chain CDR sequences (VL CDR1, VL CDR2, VL CDR3) shown in a single row in Table 13.

In some embodiments, at least one arm of the multispecific antibody or antigen-binding fragment thereof, e.g., a bispecific antibody or antigen-binding fragment thereof, comprises a heavy chain variable region that comprise a combination of a VH CDR1 sequence, a VH CDR2 sequence, and a VH CDR3 sequence, wherein the combination is a combination of the three heavy chain CDR sequences (VH CDR1, VH CDR2, VH CDR3) shown in a single row in Table 13.

In some embodiments, at least one arm of the multi specific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of the six CDR sequences (VH CDR1, VH CDR2, VH CDR3, VL CDR1, VL CDR2, and VL CDR3) shown in a single row in Table 13.

In some embodiments, at least one arm of the multispecific antibody or antigen-binding fragment thereof, e.g., a bispecific antibody or antigen-binding fragment thereof, comprises a heavy chain variable region that comprise a combination of a VH CDR1 sequence, a VH CDR2 sequence, and a VH CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of three heavy chain CDR sequences (VH CDR1, VH CDR2, VH CDR3) shown in a single row in Table 13.

In some embodiments, at least one arm of the multispecific antibody or antigen-binding fragment thereof, e.g., a bispecific antibody or antigen-binding fragment thereof, comprises a light chain variable region that comprise a combination of a VL CDR1 sequence, a VL CDR2 sequence, and a VL CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of three light chain CDR sequences (VL CDR1, VL CDR2, VL CDR3) shown in a single row in Table 13.

Suitable anti-CD166 antibodies of the disclosure also include an antibody or antigen binding fragment thereof that binds to the same epitope on human CD166 and/or cynomolgus monkey CD166 as an anti-CD166 antibody comprising a heavy chain variable region amino acid sequence selected from the group consisting of SEQ ID NO: 119, 121, and 122, and a light chain variable region amino acid sequence selected from the group consisting of SEQ ID NO: 120 and 123-126.

Suitable anti-CD166 antibodies of the disclosure also include an antibody or antigen binding fragment thereof that binds to the same epitope on human CD166 and/or cynomolgus monkey CD166 as an anti-CD166 antibody comprising the VH CDR1 sequence comprises the amino acid sequence GFSLSTYGMGVG (SEQ ID NO: 127); the VH CDR2 sequence comprises the amino acid sequence NIWWSEDKH (SEQ ID NO: 128); the VH CDR3 sequence comprises the amino acid sequence IDYGNDYAFTY (SEQ ID NO: 129); the VL CDR1 sequence comprises the amino acid sequence RSSKSLLHSNGITYLY (SEQ ID NO: 130) or RSSQSLLHSNGITYLY (SEQ ID NO: 131); the VL CDR2 sequence comprises the amino acid sequence QMSNLAS (SEQ ID NO: 132) or QMSNRAS (SEQ ID NO: 133); and the VL CDR3 sequence comprises the amino acid sequence AQNLELPYT (SEQ ID NO: 134).

Suitable anti-CD166 antibodies of the disclosure also include an antibody or antigen binding fragment thereof that binds to the same epitope on human CD166 and/or cynomolgus monkey CD166 as an anti-CD166 antibody comprising the VH CDR1 sequence comprises the amino acid sequence GFSLSTYGMGVG (SEQ ID NO: 127); the VH CDR2 sequence comprises the amino acid sequence NIWWSEDKH (SEQ ID NO: 128); the VH CDR3 sequence comprises the amino acid sequence IDYGNDYAFTY (SEQ ID NO: 129); the VL CDR1 sequence comprises the amino acid sequence RSSKSLLHSNGITYLY (SEQ ID NO: 130); the VL CDR2 sequence comprises the amino acid sequence QMSNLAS (SEQ ID NO: 132); and the VL CDR3 sequence comprises the amino acid sequence AQNLELPYT (SEQ ID NO: 134).

Suitable anti-CD166 antibodies of the disclosure also include an antibody or antigen binding fragment thereof that cross-competes for binding to human CD166 and/or cynomolgus monkey CD166 to an anti-CD166 antibody comprising a heavy chain variable region amino acid sequence selected from the group consisting of SEQ ID NO: 119, 121, and 122, and a light chain variable region amino acid sequence selected from the group consisting of SEQ ID NO: 120 and 123-126.

Suitable anti-CD166 antibodies of the disclosure also include an antibody or antigen binding fragment thereof that cross-competes for binding to human CD166 and/or cynomolgus monkey CD166 to an anti-CD166 antibody comprising a heavy chain variable region amino acid sequence comprising SEQ ID NO: 122, and a light chain variable region amino acid sequence comprising SEQ ID NO: 123.

Suitable anti-CD166 antibodies of the disclosure also include an antibody or antigen binding fragment thereof that cross-competes for binding to human CD166 and/or cynomolgus monkey CD166 to an anti-CD166 antibody comprising a heavy chain variable region amino acid sequence comprising SEQ ID NO: 121, and a light chain variable region amino acid sequence comprising SEQ ID NO: 123.

Suitable anti-CD166 antibodies of the disclosure also include an antibody or antigen binding fragment thereof that cross-competes for binding to human CD166 and/or cynomolgus monkey CD166 to an anti-CD166 antibody comprising the VH CDR1 sequence comprises the amino acid sequence GFSLSTYGMGVG (SEQ ID NO: 127); the VH CDR2 sequence comprises the amino acid sequence NIWWSEDKH (SEQ ID NO: 128); the VH CDR3 sequence comprises the amino acid sequence IDYGNDYAFTY (SEQ ID NO: 129); the VL CDR1 sequence comprises the amino acid sequence RSSKSLLHSNGITYLY (SEQ ID NO: 130) or RSSQSLLHSNGITYLY (SEQ ID NO: 131); the VL CDR2 sequence comprises the amino acid sequence QMSNLAS (SEQ ID NO: 132) or QMSNRAS (SEQ ID NO: 133); and the VL CDR3 sequence comprises the amino acid sequence AQNLELPYT (SEQ ID NO: 134).

Suitable anti-CD166 antibodies of the disclosure also include an antibody or antigen binding fragment thereof that cross-competes for binding to human CD166 and/or cynomolgus monkey CD166 to an anti-CD166 antibody comprising the VH CDR1 sequence comprises the amino acid sequence GFSLSTYGMGVG (SEQ ID NO: 127); the VH CDR2 sequence comprises the amino acid sequence NIWWSEDKH (SEQ ID NO: 128); the VH CDR3 sequence comprises the amino acid sequence IDYGNDYAFTY (SEQ ID NO: 129); the VL CDR1 sequence comprises the amino acid sequence RSSKSLLHSNGITYLY (SEQ ID NO: 130); the VL CDR2 sequence comprises the amino acid sequence QMSNLAS (SEQ ID NO: 132); and the VL CDR3 sequence comprises the amino acid sequence AQNLELPYT (SEQ ID NO: 134).

The disclosure also provides activatable antibodies that include an antibody or antigen-binding fragment thereof that specifically binds CD166 coupled to a masking moiety (MM), such that coupling of the MM reduces the ability of the antibody or antigen-binding fragment thereof to bind CD166. In some embodiments, the MM is coupled via a sequence that includes a substrate for a protease, for example, a protease that is active in diseased tissue and/or a protease that is co-localized with CD166 at a treatment site in a subject. The activatable anti-CD166 antibodies provided herein, also referred to herein interchangeably as anti-CD166 activatable antibodies or CD166 activatable antibodies, are stable in circulation, activated at intended sites of therapy and/or diagnosis but not in normal, e.g., healthy tissue or other tissue not targeted for treatment and/or diagnosis, and, when activated, exhibit binding to CD166 that is at least comparable to the corresponding, unmodified antibody, also referred to herein as the parental antibody.

The invention also provides methods of treating, preventing and/or delaying the onset or progression of, or alleviating a symptom associated with aberrant expression and/or activity of CD166 in a subject using activatable antibodies that bind CD166, particularly activatable antibodies that bind and neutralize or otherwise inhibit at least one biological activity of CD166 and/or CD166-mediated signaling.

The invention also provides methods of treating, preventing and/or delaying the onset or progression of, or alleviating a symptom associated with the presence, growth, proliferation, metastasis, and/or activity of cells which are expressing CD166 or aberrantly expressing CD166 in a subject using activatable antibodies that bind CD166, particularly activatable antibodies that bind, target, neutralize, kill, or otherwise inhibit at least one biological activity of cells which are expressing or aberrantly expressing CD166.

The invention also provides methods of treating, preventing and/or delaying the onset or progression of, or alleviating a symptom associated with the presence, growth, proliferation, metastasis, and/or activity of cells which are expressing CD166 in a subject using activatable antibodies that bind CD166, particularly activatable antibodies that bind, target, neutralize, kill, or otherwise inhibit at least one biological activity of cells which are expressing CD166.

The invention also provides methods of treating, preventing and/or delaying the onset or progression of, or alleviating a symptom associated with the presence, growth, proliferation, metastasis, and/or activity of cells which are aberrantly expressing CD166 in a subject using activatable antibodies that bind CD166, particularly activatable antibodies that bind, target, neutralize, kill, or otherwise inhibit at least one biological activity of cells which are aberrantly expressing CD166.

The activatable antibodies in an activated state bind CD166 and include (i) an antibody or an antigen binding fragment thereof (AB) that specifically binds to CD166; (ii) a masking moiety (MM) that, when the activatable antibody is in an uncleaved state, inhibits the binding of the AB to CD166; and (c) a cleavable moiety (CM) coupled to the AB, wherein the CM is a polypeptide that functions as a substrate for a protease.

In some embodiments, the activatable antibody in the uncleaved state has the structural arrangement from N-terminus to C-terminus as follows: MM-CM-AB or AB-CM-MM.

In some embodiments, the activatable antibody comprises a linking peptide between the MM and the CM.

In some embodiments, the activatable antibody comprises a linking peptide between the CM and the AB.

In some embodiments, the activatable antibody comprises a first linking peptide (LP1) and a second linking peptide (LP2), and wherein the activatable antibody in the uncleaved state has the structural arrangement from N-terminus to C-terminus as follows: MM-LP1-CM-LP2-AB or AB-LP2-CM-LP1-MM. In some embodiments, the two linking peptides need not be identical to each other.

In some embodiments, at least one of LP1 or LP2 comprises an amino acid sequence selected from the group consisting of $(GS)_n$, $(GGS)_n$, (GSGGS) (SEQ ID NO: 1) and $(GGGS)_n$ (SEQ ID NO: 2), where n is an integer of at least one.

In some embodiments, at least one of LP1 or LP2 comprises an amino acid sequence selected from the group consisting of GGSG (SEQ ID NO: 3), GGSGG (SEQ ID NO: 4), GSGSG (SEQ ID NO: 5), GSGGG (SEQ ID NO: 6), GGGSG (SEQ ID NO: 7), and GSSSG (SEQ ID NO: 8).

In some embodiments, LP1 comprises the amino acid sequence GSSGGSGGSGGSG (SEQ ID NO: 9), GSSGGSGGSGG (SEQ ID NO: 10), GSSGGSGGSGGS (SEQ ID NO: 11), GSSGGSGGSGGSGGGS (SEQ ID NO: 12), GSSGGSGGSG (SEQ ID NO: 13), or GSSGGSGGSGS (SEQ ID NO: 14).

In some embodiments, LP2 comprises the amino acid sequence GSS, GGS, GGGS (SEQ ID NO: 15), GSSGT (SEQ ID NO: 16) or GSSG (SEQ ID NO: 17).

In some embodiments, the AB has a dissociation constant of about 100 nM or less for binding to CD166.

In some embodiments, the AB has a dissociation constant of about 100 nM or less for binding to mammalian CD166. In some embodiments, the AB has a dissociation constant of about 10 nM or less for binding to mammalian CD166. In some embodiments, the AB has a dissociation constant of about 5 nM or less for binding to CD166. In some embodiments, the AB has a dissociation constant of about 1 nM or less for binding to CD166. In some embodiments, the AB has a dissociation constant of about 0.5 nM or less for binding to CD166. In some embodiments, the AB has a dissociation constant of about 0.1 nM or less for binding to CD166. In some embodiments, the AB has a dissociation constant of 0.01 nM to 100 nM, 0.01 nM to 10 nM, 0.01 nM to 5 nM, 0.01 nM to 1 nM, 0.01 to 0.5 nM, 0.01 nm to 0.1 nM, 0.01 nm to 0.05 nM, 0.05 nM to 100 nM, 0.05 nM to 10 nM, 0.05 nM to 5 nM, 0.05 nM to 1 nM, 0.05 to 0.5 nM, 0.05 nm to 0.1 nM, 0.1 nM to 100 nM, 0.1 nM to 10 nM, 0.1 nM to 5 nM, 0.1 nM to 1 nM, 0.1 to 0.5 nM, 0.5 nM to 100 nM, 0.5 nM to 10 nM, 0.5 nM to 5 nM, 0.5 nM to 1 nM, 1 nM to 100 nM, 1 nM to 10 nM, 1 nM to 5 nM, 5 nM to 100 nM, 5 nM to 10 nM, or 10 nM to 100 nM, for binding to mammalian CD166.

In some embodiments, the activatable antibody includes an antibody or antigen-binding fragment thereof (AB) that specifically binds CD166. In some embodiments, the antibody or antigen-binding fragment thereof that binds CD166 is a monoclonal antibody, domain antibody, single chain, Fab fragment, a F(ab')₂ fragment, a scFv, a scAb, a dAb, a single domain heavy chain antibody, or a single domain light chain antibody. In some embodiments, such an antibody or antigen-binding fragment thereof that binds CD166 is a mouse, other rodent, chimeric, humanized or fully human monoclonal antibody.

In some embodiments, the activatable antibody in an uncleaved state specifically binds to mammalian CD166 with a dissociation constant less than or equal to 1 nM, less than or equal to 5 nM, less than or equal to 10 nM, less than or equal to 15 nM, less than or equal to 20 nM, less than or equal to 25 nM, less than or equal to 50 nM, less than or equal to 100 nM, less than or equal to 150 nM, less than or equal to 250 nM, less than or equal to 500 nM, less than or equal to 750 nM, less than or equal to 1000 nM, and 122./or less than or equal to 2000 nM.

In some embodiments, the activatable antibody in an uncleaved state specifically binds to mammalian CD166 with a dissociation constant greater than or equal to 1 nM, greater than or equal to 5 nM, greater than or equal to 10 nM, greater than or equal to 15 nM, greater than or equal to 20 nM, greater than or equal to 25 nM, greater than or equal to 50 nM, greater than or equal to 100 nM, greater than or equal to 150 nM, greater than or equal to 250 nM, greater than or equal to 500 nM, greater than or equal to 750 nM, greater than or equal to 1000 nM, and 122./or greater than or equal to 2000 nM.

In some embodiments, the activatable antibody in an uncleaved state specifically binds to the mammalian CD166 with a dissociation constant in the range of 1 nM to 2000 nM, 1 nM to 1000 nM, 1 nM to 750 nM, 1 nM to 500 nM, 1 nM to 250 nM, 1 nM to 150 nM, 1 nM to 100 nM, 1 nM to 50 nM, 1 nM to 25 nM, 1 nM to 15 nM, 1 nM to 10 nM, 1 nM to 5 nM, 5 nM to 2000 nM, 5 nM to 1000 nM, 5 nM to 750 nM, 5 nM to 500 nM, 5 nM to 250 nM, 5 nM to 150 nM, 5 nM to 100 nM, 5 nM to 50 nM, 5 nM to 25 nM, 5 nM to 15 nM, 5 nM to 10 nM, 10 nM to 2000 nM, 10 nM to 1000 nM, 10 nM to 750 nM, 10 nM to 500 nM, 10 nM to 250 nM, 10 nM to 150 nM, 10 nM to 100 nM, 10 nM to 50 nM, 10 nM to 25 nM, 10 nM to 15 nM, 15 nM to 2000 nM, 15 nM to 1000 nM, 15 nM to 750 nM, 15 nM to 500 nM, 15 nM to 250 nM, 15 nM to 150 nM, 15 nM to 100 nM, 15 nM to 50 nM, 15 nM to 25 nM, 25 nM to 2000 nM, 25 nM to 1000 nM, 25 nM to 750 nM, 25 nM to 500 nM, 25 nM to 250 nM, 25 nM to 150 nM, 25 nM to 100 nM, 25 nM to 50 nM, 50 nM to 2000 nM, 50 nM to 1000 nM, 50 nM to 750 nM, 50 nM to 500 nM, 50 nM to 250 nM, 50 nM to 150 nM, 50 nM to 100 nM, 100 nM to 2000 nM, 100 nM to 1000 nM, 100 nM to 750 nM, 100 nM to 500 nM, 100 nM to 250 nM, 100 nM to 150 nM, 150 nM to 2000 nM, 150 nM to 1000 nM, 150 nM to 750 nM, 150 nM to 500 nM, 150 nM to 250 nM, 250 nM to 2000 nM, 250 nM to 1000 nM, 250 nM to 750 nM, 250 nM to 500 nM, 500 nM to 2000 nM, 500 nM to 1000 nM, 500 nM to 750 nM, 500 nM to 500 nM, 500 nM to 250 nM, 500 nM to 150 nM, 500 nM to 100 nM, 500 nM to 50 nM, 750 nM to 2000 nM, 750 nM to 1000 nM, or 1000 nM to 2000 nM.

In some embodiments, the activatable antibody in an activated state specifically binds to mammalian CD166 with a dissociation constant is less than or equal to 0.01 nM, 0.05 nM, 0.1 nM, 0.5 nM, 1 nM, 5 nM., or 10 nM.

In some embodiments, the activatable antibody in an activated state specifically binds to mammalian CD166 with a dissociation constant is greater than or equal to 0.01 nM, 0.05 nM, 0.1 nM, 0.5 nM, 1 riM, 5 nM, or 10 nM.

In some embodiments, the activatable antibody in an activated state specifically binds to the mammalian CD166 with a dissociation constant in the range of 0.01 nM to 100 nM, 0.01 nM to 10 nM, 0.01 nM to 5 nM, 0.01 nM to 1 nM, 0.01 to 0.5 nM, 0.01 nm to 0.1 nM, 0.01 nm to 0.05 nM, 0.05 nM to 100 nM, 0.05 nM to 10 nM, 0.05 nM to 5 nM, 0.05 nM to 1 nM, 0.05 nM to 0.5 nM, 0.05 nm to 0.1 nM, 0.1 nM to 100 nM, 0.1 nM to 10 nM, 0.1 nM to 5 nM, 0.1 nM to 1 nM, 0.1 to 0.5 nM, 0.5 nM to 100 nM, 0.5 nM to 10 nM, 0.5 nM to 5 nM, 0.5 nM to 1 nM, 1 nM to 100 nM, 1 nM to 10 nM, 1 nM to 5 nM, 5 nM to 100 nM, 5 nM to 10 nM, or 10 nM to 100 nM.

In some embodiments, the mammalian CD166 is selected from the group consisting of a human CD166 and a cynomolgus monkey CD166. In some embodiments, the AB specifically binds to human CD166 or cynomolgus monkey CD166 with a dissociation constant of less than 1 nM. In some embodiments, the mammalian CD166 is a human CD166. In some embodiments, the mammalian CD166 is a cynomolgus CD166.

In some embodiments, the AB has one or more of the following characteristics: (a) the AB specifically binds to human CD166; and (b) the AB specifically binds to human CD166 and cynomolgus monkey CD166.

In some embodiments, the AB has one or more of the following characteristics: (a) the AB specifically binds human CD166 and cynomolgus monkey CD166; (b) the AB inhibits binding of mammalian CD6 to mammalian CD166; (c) the AB inhibits binding of human CD6 to human CD166; and (d) the AB inhibits binding of cynomolgus monkey CD6 to cynomolgus monkey CD166.

In some embodiments, the AB blocks the ability of a natural ligand or receptor to bind to the mammalian CD166 with an EC50 less than or equal to 5 nM, less than or equal to 10 nM, less than or equal to 50 nM, less than or equal to 100 nM, less than or equal to 500 nM, and/or less than or equal to 1000 nM. In some embodiments, the AB blocks the ability of mammalian CD6 to bind to the mammalian CD166 with an EC50 less than or equal to 5 nM, less than or equal to 10 nM, less than or equal to 50 nM, less than or equal to 100 nM, less than or equal to 500 nM, and/or less than or equal to 1000 nM. In some embodiments, the natural ligand or receptor of CD166 is CD6.

In some embodiments, the AB blocks the ability of a natural ligand to bind to the mammalian CD166 with an EC50 of 5 nM to 1000 nM, 5 nM to 500 nM, 5 nM to 100 nM 5 nM to 50 nM, 5 nM to 10 nM, 10 nM to 1000 nM, 10 nM to 500 nM, 10 nM to 100 nM 10 nM to 50 nM, 50 nM to 1000 nM, 50 nM to 500 nM, 50 nM to 100 nM, 100 nM to 1000 nM, 100 nM to 500 nM, 500 nM to 1000 nM. In some embodiments, the AB blocks the ability of mammalian CD6 to bind to the mammalian CD166 with an EC50 of 5 nM to 1000 nM, 5 nM to 500 nM, 5 nM to 100 nM 5 nM to 50 nM, 5 nM to 10 nM, 10 nM to 1000 nM, 10 nM to 500 nM, 10 nM to 100 nM 10 nM to 50 nM, 50 nM to 1000 nM, 50 nM to 500 nM, 50 nM to 100 nM, 100 nM to 1000 nM, 50 nM to 500 nM, 50 nM to 100 nM, 100 nM to 1000 nM, 100 nM to 500 nM, 500 nM to 1000 nM. In some embodiments, the natural ligand or receptor of CD166 is CD6.

In some embodiments, the AB of the present disclosure inhibits or reduces the growth, proliferation, and/or metastasis of cells expressing mammalian CD166. Without intending to be bound by any theory, the AB of the present disclosure may inhibit or reduce the growth, proliferation, and/or metastasis of cells expressing mammalian CD166 by specifically binding to CD166 and inhibiting, blocking, and/or preventing the binding of a natural ligand or receptor to mammalian CD166. In some embodiments, the natural ligand or receptor of mammalian CD166 is mammalian CD6.

In some embodiments, the activatable antibody comprises a heavy chain variable region amino acid sequence selected from the group consisting of SEQ ID NO: 119, 121, and 122. In some embodiments, the activatable antibody comprises a heavy chain variable region amino acid sequence comprising SEQ ID NO: 121 or SEQ ID NO: 122.

In some embodiments, the activatable antibody comprises a light chain variable region amino acid sequence selected from the group consisting of SEQ ID NO: 120 and 123-126. In some embodiments, the activatable antibody comprises a light chain variable region amino acid sequence selected from the group consisting of SEQ ID NO: 123-126.

In some embodiments, the activatable antibody comprises a heavy chain variable region amino acid sequence selected from the group consisting of SEQ ID NO: 119, 121, and 122, and a light chain variable region amino acid sequence selected from the group consisting of SEQ ID NO: 120 and 123-126.

In some embodiments, the activatable antibody comprises a heavy chain variable region amino acid sequence comprising SEQ ID NO: 121 or SEQ ID NO: 122, and a light chain variable region amino acid sequence selected from the group consisting of SEQ ID NO: 123-126.

In some embodiments, the activatable antibody comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 119, 121, and 122. In some embodiments, the activatable antibody comprises a heavy chain variable region amino acid sequence that is at least 90%, 91%, 92%, 93%, 94%, 95%, 96%, 97%, 98% or 99%/i identical to an amino acid sequence comprising SEQ ID NO: 121 or SEQ ID NO: 122.

In some embodiments, the activatable antibody comprises a light chain variable region amino acid sequence that is at least 90%, 91%, 92%, 93%, 94%, 95%, 96%, 97%, 98% or 99% identical to an amino acid sequence selected from the group consisting of SEQ ID NO: 120 and 123-126. In some embodiments, the activatable antibody comprises a light chain variable region amino acid sequence that is at least 90%, 91%, 92%, 93%, 94%, 95%, 96%, 97%, 98% or 99% identical to an amino acid sequence selected from the group consisting of SEQ ID NO: 123-126.

In some embodiments, the activatable antibody comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 119, 121, and 122, and a light chain variable region amino acid sequence that is at least 90%, 91%, 92%, 93%, 94%, 95%, 96%, 97%, 98% or 99% identical to an amino acid sequence selected from the group consisting of SEQ ID NO: 120 and 123-126.

In some embodiments, the activatable antibody comprises a heavy chain variable region amino acid sequence that is at least 90%, 91%, 92%, 93%, 94%, 95%, 96%, 97%, 98% or 99% identical to an amino acid sequence comprising SEQ ID NO: 121 or SEQ ID NO: 122, and a light chain variable region amino acid sequence that is at least 90%, 91%, 92%, 93%, 94%, 95%, 96%, 97%, 98% or 99% identical to an amino acid sequence selected from the group consisting of SEQ ID NO: 123-126.

In some embodiments, the activatable antibody comprises a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one CDR sequence is selected from the group consisting of a VH CDR1 sequence comprising the amino acid sequence GFSLSTYGMGVG (SEQ ID NO: 127); a VH CDR2 sequence comprising the amino acid sequence NIWWSEDKH (SEQ ID NO: 128); a VH CDR3 sequence comprising the amino acid sequence IDYGNDYAFTY (SEQ ID NO: 129); a VL CDR1 sequence comprising the amino acid sequence RSSKSLLHSNGITYLY (SEQ ID NO: 130) or RSSQSLLHSNGITYLY (SEQ ID NO: 131); a VL CDR2 sequence comprising the amino acid sequence QMSNLAS (SEQ ID NO: 132) or QMSNRAS (SEQ ID NO: 133); and a VL CDR3 sequence comprising the amino acid sequence AQNLELPYT (SEQ ID NO: 134).

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to a VH CDR1 sequence comprising the amino acid sequence GFSLSTYGMGVG (SEQ ID NO: 127); a VH CDR2 sequence that includes a sequence that is at least 90%, 91%, 92%, 93%, 94%, 95%, 96%, 97%, 98%, 99% or more identical to a VH CDR2 sequence the amino acid sequence NIWWSEDKH (SEQ ID NO: 128); a VH CDR3 sequence that includes a sequence that is at least 90%, 91%, 92%, 93%, 94%, 95%, 96%, 97%, 98%, 99% or more identical to a VH CDR3 sequence IDYGNDYAFTY (SEQ ID NO: 129); a VL CDR1 sequence that includes a sequence that is at least 90%, 91%, 92%, 93%, 94%, 95%, 96%, 97%, 98%, 99% or more identical to a VL CDR1 sequence comprising the amino acid sequence comprising the amino acid sequence RSSKSLLHSNGITYLY (SEQ ID NO: 130) or RSSQSLLHSNGITYLY (SEQ ID NO: 131); a VL CDR2 sequence that includes a sequence that is at least 90%, 91%, 92%, 93%, 94%, 95%, 96%, 97%, 98%, 99% or more identical to a VL CDR2 sequence comprising the amino acid sequence QMSNLAS (SEQ ID NO: 132) or QMSNRAS (SEQ ID NO: 133); and a VL CDR3 sequence that includes a sequence that is at least 90%, 91%, 92%, 93%, 94%, 95%, 96%, 97%, 98%, 99% or more identical to a VL CDR3 sequence comprising the amino acid sequence AQNLELPYT (SEQ ID NO: 134).

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises the amino acid sequence GFSLSTYGMGVG (SEQ ID NO: 127); the VH CDR2 sequence comprises the amino acid sequence NIWWSEDKH (SEQ ID NO: 128); the VH CDR3 sequence comprises the amino acid sequence IDYGNDYAFTY (SEQ ID NO: 129); the VL CDR1 sequence comprises the amino acid sequence RSSKSLLHSNGITYLY (SEQ ID NO: 130) or RSSQSLLHSNGITYLY (SEQ ID NO: 131); the VL CDR2 sequence comprises the amino acid sequence QMSNLAS (SEQ ID NO: 132) or QMSNRAS (SEQ ID NO: 133); and the VL CDR3 sequence comprises the amino acid sequence AQNLELPYT (SEQ ID NO: 134).

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises a sequence that is at least 90%, 91%, 92%, 93%, 94%, 95%, 96%, 97%, 98%, 99% or more identical to the amino acid sequence GFSLSTYGMGVG (SEQ ID NO: 127); the VH CDR2 sequence comprises a sequence that is at least 90%, 91%, 92%, 93%, 94%, 95%, 96%, 97%, 98%, 99% or more identical to the amino acid sequence NIWWSEDKH (SEQ ID NO: 128); the VH CDR3 sequence comprises a sequence that is at least 90%, 91%, 92%, 93%, 94%, 95%, 96%, 97%, 98%, 99% or more identical to the amino acid sequence IDYGNDYAFTY (SEQ ID NO: 129); the VL CDR1 sequence comprises a sequence that is at least 90%, 91%, 92%, 93%, 94%, 95%, 96%, 97%, 98%, 99% or more identical to the amino acid sequence RSSKSLLHSNGITYLY (SEQ ID NO: 130) or RSSQSLLHSNGITYLY (SEQ ID NO: 131); the VL CDR2 sequence comprises a sequence that is at least 90%, 91%, 92%, 93%, 94%, 95%, 96%, 97%, 98%, 99% or more identical to the amino acid sequence QMSNLAS (SEQ ID NO: 132) or QMSNRAS (SEQ ID NO: 133); and the VL CDR3 sequence a sequence that is at least 90%, 91%, 92%, 93%, 94%, 95%, 96%, 97%, 98%, 99% or more identical to comprises the amino acid sequence AQNLELPYT (SEQ ID NO: 134).

In some embodiments, the AB of the activatable anti-CD166 antibody comprises a heavy chain variable region amino acid sequence selected from the group consisting of the heavy chain variable region sequences shown in Table 12. In some embodiments, the AB of the activatable anti-CD166 antibody comprises a light chain variable region amino acid sequence selected from the group consisting of the light chain variable region sequences shown in Table 12. In some embodiments, the AB of the activatable anti-CD166 antibody comprises a heavy chain variable region amino acid sequence selected from the group consisting of the heavy chain variable region sequences shown in Table 12 and a light chain variable region amino acid sequence selected from the group consisting of the light chain variable region sequences shown in Table 12.

In some embodiments, the AB of the activatable anti-CD166 antibody comprises a heavy chain variable region amino acid sequence that is at least 90%, 91%, 92%, 93%, 94%, 95%, 96%, 97%, 98% or 99% identical to an amino acid sequence selected from the group consisting of the heavy chain variable region sequences shown in Table 12. In some embodiments, the AB of the activatable anti-CD166 antibody comprises a light chain variable region amino acid sequence that is at least 90%, 91%, 92%, 93%, 94%, 95%, 96%, 97%, 98% or 99% identical to an amino acid sequence selected from the group consisting of the light chain variable region sequences shown in Table 12. In some embodiments, the AB of the activatable anti-CD166 antibody comprises a heavy chain variable region amino acid sequence that is at least 90%, 91%, 92%, 93%, 94%, 95%, 96%, 97%, 98% or 99% identical to an amino acid sequence selected from the group consisting of the heavy chain variable region sequences shown in Table 12 and a light chain variable region amino acid sequence that is at least 90%, 91%, 92%, 93%, 94%, 95%, 96%, 97%, 98% or 99% identical to an amino acid sequence selected from the group consisting of the light chain variable region sequences shown in Table 12.

In some embodiments, the activatable antibody comprises a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one CDR sequence is selected from the group consisting of a VH CDR1 sequence shown in Table 13; a VH CDR2 sequence shown in Table 13; a VH CDR3 sequence shown in Table 13; a VL CDR1 sequence shown in Table 13; a VL CDR2 sequence shown in Table 13; and a VL CDR3 sequence shown in Table 13.

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 930%, 94%, 95%, 96%, 97%, 98%, 99% or more identical to a VH CDR1 sequence shown in Table 13; a VH CDR2 sequence that includes a sequence that is at least 90%, 91%, 92%, 93%, 94%, 95%, 96%, 97%, 98%, 99% or more identical to a VH CDR2 sequence shown in Table 13; a VH CDR3 sequence that includes a sequence that is at least 90%, 91%, 92%, 93%, 94%, 95%, 96%, 97%, 98%, 99% or more identical to a VH CDR3 sequence shown in Table 13; a VL CDR1 sequence that includes a sequence that is at least 90%, 91%, 92%, 93%, 94%, 95%, 96%, 97%, 98%, 99% or more identical to a VL CDR1 sequence shown in Table 13; a VL CDR2 sequence that includes a sequence that is at least 90%, 91%, 92%, 93%, 94%, 95%, 96%, 97%, 98%, 99% or more identical to a VL CDR2 sequence shown in Table 13; and a VL CDR3 sequence that includes a sequence that is at least 90%, 91%, 92%, 93%, 94%, 95%, 96%, 97%, 98%, 99% or more identical to a VL CDR3 sequence shown in Table 13.

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the combination is a combination of the six CDR sequences (VH CDR1, VH CDR2, VH CDR3, VL CDR1, VL CDR2, and VL CDR3) shown in a single row in Table 13.

In some embodiments, the activatable antibody comprises a heavy chain variable region that comprise a combination of a VH CDR11 sequence, a VH CDR2 sequence, and a VH CDR3 sequence, wherein the combination is a combination of the three heavy chain CDR sequences (VH CDR1, VH CDR2, VH CDR3) shown in a single row in Table 13.

In some embodiments, the activatable antibody comprises a light chain variable region that comprise a combination of a VL CDR1 sequence, a VL CDR2 sequence, and a VL CDR3 sequence, wherein the combination is a combination of the three light chain CDR sequences (VL CDR1, VL CDR2, VL CDR3) shown in a single row in Table 13.

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of the six CDR sequences (VH CDR1, VH CDR2, VH CDR3, VL CDR1, VL CDR2, and VL CDR3) shown in a single row in Table 13.

In some embodiments, the activatable antibody comprises a heavy chain variable region that comprise a combination of a VH CDR1 sequence, a VH CDR2 sequence, and a VH CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of three heavy chain CDR sequences (VH CDR1, VH CDR2. VH CDR3) shown in a single row in Table 13.

In some embodiments, the activatable antibody comprises a light chain variable region that comprise a combination of a VL CDR1 sequence, a VL CDR2 sequence, and a VL CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of three light chain CDR sequences (VL CDR1, VL CDR2, VL CDR3) shown in a single row in Table 13.

In some embodiments, the activatable antibody includes may include one or more polypeptides that include the combination of sequences in a given row of Table A or any combination of a mask sequence (MM), a substrate sequence (CM), a light chain variable domain sequence or light chain variable domain CDR sequences, and a heavy chain variable domain sequence or heavy chain variable domain CDR sequences of Table B.

In some embodiments, the antibody drug conjugates (ADCs) and activatable antibody drug conjugates (AADCs) can include one or more polypeptides that include the combination of a light chain sequence or a light chain variable domain sequence, and a heavy chain sequence or a heavy chain variable domain sequences, a linker, and a toxin in a given row of Table C or any combination of a light chain sequence or a light chain variable domain sequence, and a heavy chain sequence or a heavy chain variable domain sequence, a linker, and a toxin of Table C.

In some embodiments, the MM has a dissociation constant for binding to the AB which is greater than the dissociation constant of the AB to CD166.

In some embodiments, the MM has a dissociation constant for binding to the AB which is no more than the dissociation constant of the AB to CD166.

In some embodiments, the MM has a dissociation constant for binding to the AB which is less than the dissociation constant of the AB to CD166.

In some embodiments, the dissociation constant ($K_d$) of the MM towards the AB is no more than 2, 3, 4, 5, 10, 25, 50, 100, 250, 500, 1,000, 2,500, 5,000, 10,000, 50,000, 100,000, 500,000, 1,000,000, 5,000,000, 10,000,000, 50,000,000 times or greater, or between 1-5, 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times or greater than the dissociation constant of the AB towards the target.

In some embodiments, the MM does not interfere or compete with the AB for binding to CD166 when the activatable antibody is in a cleaved state.

In some embodiments, the MM is a polypeptide of about 2 to 40 amino acids in length. In some embodiments, the MM is a polypeptide of up to about 40 amino acids in length.

In some embodiments, the MM polypeptide sequence is different from that of CD166. In some embodiments, the MM polypeptide sequence is no more than 50% identical to any natural binding partner of the AB. In some embodiments, the MM polypeptide sequence is different from that of CD166 and is no more than 40%, 30%, 25%, 20%, 15%, or 10% identical to any natural binding partner of the AB.

In some embodiments, the coupling of the MM to the AB reduces the ability of the AB to bind CD166 such that the dissociation constant ($K_d$) of the AB when coupled to the MM towards CD166 is at least two times greater than the $K_d$ of the AB when not coupled to the MM towards CD166.

In some embodiments, the coupling of the MM to the AB reduces the ability of the AB to bind CD166 such that the dissociation constant ($K_d$) of the AB when coupled to the MM towards CD166 is at least five times greater than the $K_d$ of the AB when not coupled to the MM towards CD166.

In some embodiments, the coupling of the MM to the AB reduces the ability of the AB to bind CD166 such that the dissociation constant ($K_d$) of the AB when coupled to the MM towards CD166 is at least 10 times greater than the $K_d$ of the AB when not coupled to the MM towards CD166.

In some embodiments, the coupling of the MM to the AB reduces the ability of the AB to bind CD166 such that the dissociation constant ($K_d$) of the AB when coupled to the MM towards CD166 is at least 20 times greater than the $K_d$ of the AB when not coupled to the MM towards CD166.

In some embodiments, the coupling of the MM to the AB reduces the ability of the AB to bind CD166 such that the dissociation constant ($K_d$) of the AB when coupled to the MM towards CD166 is at least 40 times greater than the $K_d$ of the AB when not coupled to the MM towards CD166.

In some embodiments, the coupling of the MM to the AB reduces the ability of the AB to bind CD166 such that the dissociation constant ($K_d$) of the AB when coupled to the MM towards CD166 is at least 100 times greater than the $K_d$ of the AB when not coupled to the MM towards CD166.

In some embodiments, the coupling of the MM to the AB reduces the ability of the AB to bind CD166 such that the dissociation constant ($K_d$) of the AB when coupled to the MM towards CD166 is at least 1000 times greater than the $K_d$ of the AB when not coupled to the MM towards CD166.

In some embodiments, the coupling of the MM to the AB reduces the ability of the AB to bind CD166 such that the dissociation constant ($K_d$) of the AB when coupled to the MM towards CD166 is at least 10,000 times greater than the $K_d$ of the AB when not coupled to the MM towards CD166.

In some embodiments, in the presence of CD166, the MM reduces the ability of the AB to bind CD166 by at least 90% when the CM is uncleaved, as compared to when the CM is cleaved when assayed in vitro using a target displacement assay such as, for example, the assay described in PCT Publication No. WO2010/081173, the contents of which are hereby incorporated by reference in their entirety.

In some embodiments, MM comprises an amino acid sequence selected from the group consisting of SEQ ID NO: 135-238.

In some embodiments, the protease that cleaves the CM is active, e.g., up-regulated or otherwise unregulated, in diseased tissue, and the protease cleaves the CM in the activatable antibody when the activatable antibody is exposed to the protease.

In some embodiments, the protease is co-localized with CD166 in a tissue, and the protease cleaves the CM in the activatable antibody when the activatable antibody is exposed to the protease.

In some embodiments, the CM is positioned in the activatable antibody such that when the activatable antibody is in the uncleaved state, binding of the activatable antibody to CD166 is reduced to occur with a dissociation constant that is at least twofold greater than the dissociation constant of an unmodified AB binding to CD166, whereas in the cleaved state (i.e., when the activatable antibody is in the cleaved state), the AB binds CD166.

In some embodiments, the CM is positioned in the activatable antibody such that when the activatable antibody is in the uncleaved state, binding of the activatable antibody to CD166 is reduced to occur with a dissociation constant that is at least fivefold greater than the dissociation constant of an unmodified AB binding to CD166, whereas in the cleaved state (i.e., when the activatable antibody is in the cleaved state), the AB binds CD166.

In some embodiments, the CM is positioned in the activatable antibody such that when the activatable antibody is in the uncleaved state, binding of the activatable antibody to CD166 is reduced to occur with a dissociation constant that is at least 10-fold greater than the dissociation constant of an unmodified AB binding to CD166, whereas in the cleaved state (i.e., when the activatable antibody is in the cleaved state), the AB binds CD166.

In some embodiments, the CM is positioned in the activatable antibody such that when the activatable antibody is in the uncleaved state, binding of the activatable antibody to CD166 is reduced to occur with a dissociation constant that is at least 20-fold greater than the dissociation constant of an unmodified AB binding to CD166, whereas in the cleaved state (i.e., when the activatable antibody is in the cleaved state), the AB binds CD166.

In some embodiments, the CM is positioned in the activatable antibody such that when the activatable antibody is in the uncleaved state, binding of the activatable antibody to CD166 is reduced to occur with a dissociation constant that is at least 40-fold greater than the dissociation constant of an unmodified AB binding to CD166, whereas in the cleaved state, the AB binds CD166.

In some embodiments, the CM is positioned in the activatable antibody such that when the activatable antibody is in the uncleaved state, binding of the activatable antibody to CD166 is reduced to occur with a dissociation constant that is at least 50-fold greater than the dissociation constant of an unmodified AB binding to CD166, whereas in the cleaved state, the AB binds CD166.

In some embodiments, the CM is positioned in the activatable antibody such that when the activatable antibody is in the uncleaved state, binding of the activatable antibody to CD166 is reduced to occur with a dissociation constant that is at least 100-fold greater than the dissociation constant of an unmodified AB binding to CD166, whereas in the cleaved state, the AB binds CD166.

In some embodiments, the CM is positioned in the activatable antibody such that when the activatable antibody is in the uncleaved state, binding of the activatable antibody to CD166 is reduced to occur with a dissociation constant that is at least 200-fold greater than the dissociation constant of an unmodified AB binding to CD166, whereas in the cleaved state, the AB binds CD166.

In some embodiments, the CM is a polypeptide of up to 15 amino acids in length.

In some embodiments, the CM is a polypeptide that includes a first cleavable moiety (CM1) that is a substrate for at least one matrix metalloprotease (MMP) and a second cleavable moiety (CM2) that is a substrate for at least one serine protease (SP). In some embodiments, each of the CM1 substrate sequence and the CM2 substrate sequence of the CM1-CM2 substrate is independently a polypeptide of up to 15 amino acids in length.

In some embodiments, the CM is a substrate for at least one protease that is or is believed to be up-regulated or otherwise unregulated in cancer. In some embodiments, the CM is a substrate for at least one protease that is or is believed to be up-regulated in inflammation. In some embodiments, the CM is a substrate for at least one protease that is or is believed to be up-regulated or otherwise unregulated in autoimmunity.

In some embodiments, the CM is a substrate for at least one protease selected from the group consisting of a matrix metalloprotease (MMP), thrombin, a neutrophil elastase, a cysteine protease, legumain, and a serine protease, such as matriptase (MT-SP1), and urokinase (uPA). Without being bound by theory, it is believed that these proteases are up-regulated or otherwise unregulated in at least one of cancer, inflammation, and/or autoimmunity.

Exemplary substrates include but are not limited to substrates cleavable by one or more of the following enzymes or proteases listed in Table 4.

In some embodiments, the CM is selected for use with a specific protease, for example a protease that is known to be co-localized with the target of the activatable antibody.

In some embodiments, the CM is a substrate for at least one MMP. Examples of MMPs include the MMPs listed in the Table 4. In some embodiments, the CM is a substrate for a protease selected from the group consisting of MMP9, MMP14, MMP1, MMP3, MMP13, MMP17, MMP11, and MMP19. In some embodiments the CM is a substrate for MMP9. In some embodiments, the CM is a substrate for MMP14.

In some embodiments, the CM is a substrate that includes the sequence TGRGPSWV (SEQ ID NO: 18); SARGPSRW (SEQ ID NO: 19); TARGPSFK (SEQ ID NO: 20); LSGRSDNH (SEQ ID NO: 21); GGWHTGRN (SEQ ID NO: 22); HTGRSGAL (SEQ ID NO: 23); PLTGRSGG (SEQ ID NO: 24); AARGPAIH (SEQ ID NO: 25); RGPAFNPM (SEQ ID NO: 26); SSRGPAYL (SEQ ID NO: 27); RGPATPIM (SEQ ID NO: 28); RGPA (SEQ ID NO: 29); GGQPSGMWGW (SEQ ID NO: 30); FPRPLGITGL (SEQ ID NO: 31); VHMPLGFLGP (SEQ ID NO: 32); SPLTGRSG (SEQ ID NO: 33); SAGFSLPA (SEQ ID NO: 34); LAPLGLQRR (SEQ ID NO: 35); SGGPLGVR (SEQ ID NO: 36); PLGL (SEQ ID NO: 37); LSGRSGNH (SEQ ID NO: 318); SGRSANPRG (SEQ ID NO: 319); LSGRSDDH (SEQ ID NO: 320); LSGRSDIH (SEQ ID NO: 321); LSGRSDQH (SEQ ID NO: 322); LSGRSDTH (SEQ ID NO: 323); LSGRSDYH (SEQ ID NO: 324); LSGRSDNP (SEQ ID NO: 325); LSGRSANP (SEQ ID NO: 326); LSGRSANI (SEQ ID NO: 327); LSGRSDNI (SEQ ID NO: 328); MIAPVAYR (SEQ ID NO: 329); RPSPMWAY (SEQ ID NO: 330); WATPRPMR (SEQ ID NO: 331); FRLLDWQW (SEQ ID NO: 332); ISSGL (SEQ ID NO: 333); ISSGLLS (SEQ ID NO: 334); and/or ISSGLL (SEQ ID NO: 335).

In some embodiments, the CM comprises the amino acid sequence LSGRSDNH (SEQ ID NO: 21). In some embodiments, the CM comprises the amino acid sequence TGRGPSWV (SEQ ID NO: 18). In some embodiments, the CM comprises the amino acid sequence PLTGRSGG (SEQ ID NO: 24). In some embodiments, the CM comprises the amino acid sequence GGQPSGMWGW (SEQ ID NO: 30). In some embodiments, the CM comprises the amino acid sequence FPRPLGITGL (SEQ ID NO: 31). In some embodiments, the CM comprises the amino acid sequence VHMPLGFLGP (SEQ ID NO: 32). In some embodiments, the CM comprises the amino acid sequence PLGL (SEQ ID NO: 37). In some embodiments, the CM comprises the amino acid sequence SARGPSRW (SEQ ID NO: 19). In some embodiments, the CM comprises the amino acid sequence TARGPSFK (SEQ ID NO: 20). In some embodiments, the CM comprises the amino acid sequence GGWHTGRN (SEQ ID NO: 22). In some embodiments, the CM comprises the amino acid sequence HTGRSGAL (SEQ ID NO: 23). In some embodiments, the CM comprises the amino acid sequence AARGPAIH (SEQ ID NO: 25). In some embodiments, the CM comprises the amino acid sequence RGPAFNPM (SEQ ID NO: 26). In some embodiments, the CM comprises the amino acid sequence SSRGPAYL (SEQ ID NO: 27). In some embodiments, the CM comprises the amino acid sequence RGPATPIM (SEQ ID NO: 28). In some embodiments, the CM comprises the amino acid sequence RGPA (SEQ ID NO: 29). In some embodiments, the CM comprises the amino acid sequence LSGRSGNH (SEQ ID NO: 315). In some embodiments, the CM comprises the amino acid sequence SGRSANPRG (SEQ ID NO: 319). In some embodiments, the CM comprises the amino acid sequence LSGRSDDH (SEQ ID NO: 320). In some embodiments, the CM comprises the amino acid sequence LSGRSDIH (SEQ ID NO: 321). In some embodiments, the CM comprises the amino acid sequence LSGRSDQH (SEQ ID NO: 322). In some embodiments, the CM comprises the amino acid sequence LSGRSDTH (SEQ ID NO: 323). In some embodiments, the CM comprises the amino acid sequence LSGRSDYH (SEQ ID NO: 324). In some embodiments, the CM comprises the amino acid sequence LSGRSDNP (SEQ ID NO: 325). In some embodiments, the CM comprises the amino acid sequence LSGRSANP (SEQ ID NO: 326). In some embodiments, the CM comprises the amino acid sequence LSGRSANI (SEQ ID NO: 327). In some embodiments, the CM comprises the amino acid sequence LSGRSDNI (SEQ ID NO: 328). In some embodiments, the CM comprises the amino acid sequence MIAPVAYR (SEQ ID NO: 329). In some embodiments, the CM comprises the amino acid sequence RPSPMWAY (SEQ ID NO: 330). In some embodiments, the CM comprises the amino acid sequence WATPRPMR (SEQ ID NO: 331). In some embodiments, the CM comprises the amino acid sequence FRLLDWQW (SEQ ID NO: 332). In some embodiments, the CM comprises the amino acid sequence ISSGL (SEQ ID NO: 333). In some embodiments, the CM comprises the amino acid sequence ISSGLLS (SEQ ID NO: 334). In some embodiments, the CM comprises the amino acid sequence and/or ISSGLL (SEQ ID NO: 335).

In some embodiments, the CM is a substrate for an MMP and includes the sequence ISSGLSS (SEQ ID NO: 38); QNQALRMA (SEQ ID NO: 39); AQNLLGMV (SEQ ID NO: 40); STFPFGMF (SEQ ID NO: 41); PVGYTSSL (SEQ ID NO: 42); DWLYWPGI (SEQ ID NO: 43), ISSGLLSS (SEQ ID NO: 44), LKAAPRWA (SEQ ID NO: 45); GPSHLVLT (SEQ ID NO: 46); LPGGLSPW (SEQ ID NO: 47); MGLFSEAG (SEQ ID NO: 48); SPLPLRVP (SEQ ID NO: 49); RMHLRSLG (SEQ ID NO: 50); LAAPLGLL (SEQ ID NO: 51); AVGLLAPP (SEQ ID NO: 52); LLAPSHRA (SEQ ID NO: 53); and/or PAGLWLDP (SEQ ID NO: 54).

In some embodiments, the CM comprises the amino acid sequence ISSGLSS (SEQ ID NO: 38). In some embodiments, the CM comprises the amino acid sequence QNQALRMA (SEQ ID NO: 39). In some embodiments, the CM comprises the amino acid sequence AQNLLGMV (SEQ ID NO: 40). In some embodiments, the CM comprises the amino acid sequence STFPFGMF (SEQ ID NO: 41). In some embodiments, the CM comprises the amino acid sequence PVGYTSSL (SEQ ID NO: 42). In some embodiments, the CM comprises the amino acid sequence DWLYWPGI (SEQ ID NO: 43). In some embodiments, the CM comprises the amino acid sequence ISSGLLSS (SEQ ID NO: 44). In some embodiments, the CM comprises the amino acid sequence LKAAPRWA (SEQ ID NO: 45). In some embodiments, the CM comprises the amino acid sequence GPSHLVLT (SEQ ID NO: 46). In some embodiments, the CM comprises the amino acid sequence LPGGLSPW (SEQ ID NO: 47). In some embodiments, the CM comprises the amino acid sequence MGLFSEAG (SEQ ID NO: 48). In some embodiments, the CM comprises the amino acid sequence SPLPLRVP (SEQ ID NO: 49). In some embodiments, the CM comprises the amino acid sequence RMHLRSLG (SEQ ID NO: 50). In some embodiments, the CM comprises the amino acid sequence LAAPLGLL (SEQ ID NO: 51). In some embodiments, the CM comprises the amino acid sequence AVGLLAPP (SEQ ID NO: 52). In some embodiments, the CM comprises the amino acid sequence LLAPSHRA (SEQ ID NO: 53). In some embodiments, the CM comprises the amino acid sequence PAGLWLDP (SEQ ID NO: 54).

In some embodiments, the CM is a substrate for thrombin. In some embodiments, the CM is a substrate for thrombin and includes the sequence GPRSFGL (SEQ ID NO: 55) or GPRSFG (SEQ ID NO: 56). In some embodiments, the CM comprises the amino acid sequence GPRSFGL (SEQ ID NO: 57). In some embodiments, the CM comprises the amino acid sequence GPRSFG (SEQ ID NO: 58).

In some embodiments, the CM comprises an amino acid sequence selected from the group consisting of NTLSGRSENHSG (SEQ ID NO: 59); NTLSGRSGNHGS (SEQ ID NO: 60); TSTSGRSANPRG (SEQ ID NO: 61); TSGRSANP (SEQ ID NO: 62); VAGRSMRP (SEQ ID NO: 63); VVPEGRRS (SEQ ID NO: 64); ILPRSPAF (SEQ ID NO: 65); MVLGRSLL (SEQ ID NO: 66); QGRAITFI (SEQ ID NO: 67); SPRSIMLA (SEQ ID NO: 68); and SMLRSMPL (SEQ ID NO: 69).

In some embodiments, the CM comprises the amino acid sequence NTLSGRSENHSG (SEQ ID NO: 59). In some embodiments, the CM comprises the amino acid sequence NTLSGRSGNHGS (SEQ ID NO: 60). In some embodiments, the CM comprises the amino acid sequence TSTSGRSANPRG (SEQ ID NO: 61). In some embodiments, the CM comprises the amino acid sequence TSGRSANP (SEQ ID NO: 62). In some embodiments, the CM comprises the amino acid sequence VAGRSMRP (SEQ ID NO: 63). In some embodiments, the CM comprises the amino acid sequence VVPEGRRS (SEQ ID NO: 64). In some embodiments, the CM comprises the amino acid sequence ILPRSPAF (SEQ ID NO: 65). In some embodiments, the CM comprises the amino acid sequence MVLGRSLL (SEQ ID NO: 66). In some embodiments, the CM comprises the amino acid sequence QGRAITFI (SEQ ID NO: 67). In some embodiments, the CM comprises the amino acid sequence SPRSIMLA (SEQ ID NO: 68). In some embodiments, the CM comprises the amino acid sequence SMLRSMPL (SEQ ID NO: 69).

In some embodiments, the CM is a substrate for a neutrophil elastase. In some embodiments, the CM is a substrate for a serine protease. In some embodiments, the CM is a substrate for uPA. In some embodiments, the CM is a substrate for legumain. In some embodiments, the CM is a substrate for matriptase. In some embodiments, the CM is a substrate for a cysteine protease. In some embodiments, the CM is a substrate for a cysteine protease, such as a cathepsin.

In some embodiments, the CM is a CM1-CM2 substrate and includes the sequence ISSGLLSGRSDNH (SEQ ID NO: 70), which is also referred to herein as substrate 2001; ISSGLLSSGGSGGSLSGRSDNH (SEQ ID NO: 71); AVGLLAPPGGTSTSGRSANPRG (SEQ ID NO: 72); TSTSGRSANPRGGGAVGLLAPP (SEQ ID NO: 73); VHMPLGFLGPGGTSTSGRSANPRG (SEQ ID NO: 74); TSTSGRSANPRGGGVHMPLGFLGP (SEQ ID NO: 75); AVGLLAPPGGLSGRSDNH (SEQ ID NO: 76), which is also referred to herein as substrate 3001; LSGRSDNHGGAVGLLAPP (SEQ ID NO: 77); VHMPLGFLGPGGLSGRSDNH (SEQ ID NO: 78); LSGRSDNHGGVHMPLGFLGP (SEQ ID NO: 79); LSGRSDNHGGSGGSISSGLLSS (SEQ ID NO: 80); LSGRSGNHGGSGGSISSGLLSS (SEQ ID NO: 81); ISSGLLSSGGSGGSLSGRSGNH (SEQ ID NO: 82); LSGRSDNHGGSGGSQNQALRMA (SEQ ID NO: 83); QNQALRMAGGSGGSLSGRSDNH (SEQ ID NO: 84); LSGRSGNHGGSGGSQNQALRMA (SEQ ID NO: 85); QNQALRMAGGSGGSLSGRSGNH (SEQ ID NO: 86); ISSGLLSGRSGNH (SEQ ID NO: 87); GLSGRSDNHGGAVGLLAPP (SEQ ID NO: 336); GLSGRSDNHGGVHMPLGFLGP (SEQ ID NO: 337); ISSGLLSGRSANPRG (SEQ ID NO: 338), which is also referred to herein as substrate 2003; AVGLLAPPTSGRSANPRG (SEQ ID NO: 339), which is also referred to herein as substrate 2004; AVGLLAPPSGRSANPRG (SEQ ID NO: 340), which is also referred to herein as substrate 2005; ISSGLLS- GRSDDH (SEQ ID NO: 341), which is also referred to herein as substrate 2006; ISSGLLSGRSDIH (SEQ ID NO: 342), which is also referred to herein as substrate 2007; ISSGLLSGRSDQH (SEQ ID NO: 343), which is also referred to herein as substrate 2008; ISSGLLSGRSDTH (SEQ ID NO: 344), which is also referred to herein as substrate 2009; ISSGLLSGRSDYH (SEQ ID NO: 345), which is also referred to herein as substrate 2010; ISSGLLSGRSDNP (SEQ ID NO: 346), which is also referred to herein as substrate 2011; ISSGLLSGRSANP (SEQ ID NO: 347), which is also referred to herein as substrate 2012; ISSGLLSGRSANI (SEQ ID NO: 348), which is also referred to herein as substrate 2013; AVGLLAPPGGLSGRSDDH (SEQ ID NO: 349), which is also referred to herein as substrate 3006; AVGLLAPPGGLSGRSDIH (SEQ ID NO: 350), which is also referred to herein as substrate 3007; AVGLLAPPGGLSGRSDQH (SEQ ID NO: 351), which is also referred to herein as substrate 3008; AVGLLAPPGGLSGRSDTH (SEQ ID NO: 352), which is also referred to herein as substrate 3009; AVGLLAPPGGLSGRSDYH (SEQ ID NO: 353), which is also referred to herein as substrate 3010; AVGLLAPPGGLSGRSDNP (SEQ ID NO: 354), which is also referred to herein as substrate 3011; AVGLLAPPGGLSGRSANP (SEQ ID NO: 355), which is also referred to herein as substrate 3012; AVGLLAPPGGLSGRSANI (SEQ ID NO: 356), which is also referred to herein as substrate 3013; ISSGLLSGRSDNI (SEQ ID NO: 347), which is also referred to herein as substrate 2014; and/or AVGLLAPPGGLSGRSDNI (SEQ ID NO: 358), which is also referred to herein as substrate 3014.

In some embodiments, the CM1-CM2 substrate includes the sequence ISSGLLSGRSDNH (SEQ ID NO: 70). In some embodiments, the CM1-CM2 substrate includes the sequence ISSGLLSSGGSGGSLSGRSDNH (SEQ ID NO: 71). In some embodiments, the CM1-CM2 substrate includes the sequence AVGLLAPPGGTSTSGRSANPRG (SEQ ID NO: 72). In some embodiments, the CM1-CM2 substrate includes the sequence TSTSGRSANPRGGGAVGLLAPP (SEQ ID NO: 73). In some embodiments, the CM1-CM2 substrate includes the sequence VHMPLGFLGPGGTSTSGRSANPRG (SEQ ID NO: 74). In some embodiments, the CM1-CM2 substrate includes the sequence TSTSGRSANPRGGGVHMPLGFLGP (SEQ ID NO: 75). In some embodiments, the CM1-CM2 substrate includes the sequence AVGLLAPPGGLSGRSDNH (SEQ ID NO: 76). In some embodiments, the CM1-CM2 substrate includes the sequence LSGRSDNHGGAVGLLAPP (SEQ ID NO: 77). In some embodiments, the CM1-CM2 substrate includes the sequence VHMPLGFLGPGGLSGRSDNH (SEQ ID NO: 78). In some embodiments, the CM1-CM2 substrate includes the sequence LSGRSDNHGGVHMPLGFLGP (SEQ ID NO: 79). In some embodiments, the CM1-CM2 substrate includes the sequence LSGRSDNHGGSGGSISSGLLSS (SEQ ID NO: 80). In some embodiments, the CM1-CM2 substrate includes the sequence LSGRSGNHGGSGGSISSGLLSS (SEQ ID NO: 81). In some embodiments, the CM1-CM2 substrate includes the sequence ISSGLLSSGGSGGSLSGRSGNH (SEQ ID NO: 82). In some embodiments, the CM1-CM2 substrate includes the sequence LSGRSDNHGGSGGSQNQALRMA (SEQ ID NO: 83). In some embodiments, the CM1-CM2 substrate includes the sequence QNQALRMAGGSGGSLSGRSDNH (SEQ ID NO: 84). In some embodiments, the CM1-CM2 substrate includes the sequence LSGRSGNHGGSGGSQNQALRMA (SEQ ID NO: 85). In some embodiments, the CM1-CM2 substrate includes the sequence QNQALRMAGGSGGSLSGRSGNH (SEQ ID NO: 86). In some embodiments, the CM1-CM2 substrate includes the sequence ISSGLLSGRSGNH (SEQ ID NO: 87). In some embodiments, the CM1-CM2 substrate includes the sequence GLSGRSDNHGGAVGLLAPP (SEQ ID NO: 336). In some embodiments, the CM1-CM2 substrate includes the sequence and/or GLSGRSDNHGGVHMPLGFLGP (SEQ ID NO: 337). In some embodiments, the CM1-CM2 substrate includes the sequence ISSGLLSGRSANPRG (SEQ ID NO: 338). In some embodiments, the CM1-CM2 substrate includes the sequence AVGLLAPPTSGRSANPRG (SEQ ID NO: 339). In some embodiments, the CM1-CM2 substrate includes the sequence AVGLLAPPSGRSANPRG (SEQ ID NO: 340). In some embodiments, the CM1-CM2 substrate includes the sequence ISSGLLSGRSDDH (SEQ ID NO: 341). In some embodiments, the CM1-CM2 substrate includes the sequence ISSGLLSGRSDIH (SEQ ID NO: 342). In some embodiments, the CM1-CM2 substrate includes the sequence ISSGLLSGRSDQH (SEQ ID NO: 343). In some embodiments, the CM1-CM2 substrate includes the sequence ISSGLLSGRSDTH (SEQ ID NO: 344). In some embodiments, the CM1-CM2 substrate includes the sequence ISSGLLSGRSDYH (SEQ ID NO: 345). In some embodiments, the CM1-CM2 substrate includes the sequence ISSGLLSGRSDNP (SEQ ID NO: 346). In some embodiments, the CM1-CM2 substrate includes the sequence ISSGLLSGRSANP (SEQ ID NO: 347). In some embodiments, the CM1-CM2 substrate includes the sequence ISSGLLSGRSANI (SEQ ID NO: 348). In some embodiments, the CM1-CM2 substrate includes the sequence AVGLLAPPGGLSGRSDDH (SEQ ID NO: 349). In some embodiments, the CM1-CM2 substrate includes the sequence AVGLLAPPGGLSGRSDIH (SEQ ID NO: 350). In some embodiments, the CM1-CM2 substrate includes the sequence AVGLLAPPGGLSGRSDQH (SEQ ID NO: 351). In some embodiments, the CM1-CM2 substrate includes the sequence AVGLLAPPGGLSGRSDTH (SEQ ID NO: 352). In some embodiments, the CM1-CM2 substrate includes the sequence AVGLLAPPGGLSGRSDYH (SEQ ID NO: 353). In some embodiments, the CM1-CM2 substrate includes the sequence AVGLLAPPGGLSGRSDNP (SEQ ID NO: 354). In some embodiments, the CM1-CM2 substrate includes the sequence AVGLLAPPGGLSGRSANP (SEQ ID NO: 355). In some embodiments, the CM1-CM2 substrate includes the sequence AVGLLAPPGGLSGRSANI (SEQ ID NO: 356), ISSGLLSGRSDNI (SEQ ID NO: 357). In some embodiments, the CM1-CM2 substrate includes the sequence AVGLLAPPGGLSGRSDNI (SEQ ID NO: 358).

In some embodiments, the CM is a substrate for at least two proteases. In some embodiments, each protease is selected from the group consisting of those shown in Table 4. In some embodiments, the CM is a substrate for at least two proteases, wherein one of the proteases is selected from the group consisting of a MMP, thrombin, a neutrophil elastase, a cysteine protease, uPA, legumain and matriptase and the other protease is selected from the group consisting of those shown in Table 4. In some embodiments, the CM is a substrate for at least two proteases selected from the group consisting of a MMP, thrombin, a neutrophil elastase, a cysteine protease, uPA, legumain and matriptase.

In some embodiments, the activatable antibody includes at least a first CM and a second CM. In some embodiments, the first CM and the second CM are each polypeptides of no more than 15 amino acids long. In some embodiments, the first CM and the second CM in the activatable antibody in the uncleaved state have the structural arrangement from N-terminus to C-terminus as follows: MM-CM1-CM2-AB or AB-CM2-CM1-MM. In some embodiments, at least one of the first CM and the second CM is a polypeptide that functions as a substrate for a protease selected from the group consisting of a MMP, thrombin, a neutrophil elastase, a cysteine protease, uPA, legumain, and matriptase. In some embodiments, the first CM is cleaved by a first cleaving agent selected from the group consisting of a MMP, thrombin, a neutrophil elastase, a cysteine protease, uPA, legumain, and matriptase in a target tissue and the second CM is cleaved by a second cleaving agent in a target tissue. In some embodiments, the other protease is selected from the group consisting of those shown in Table 4. In some embodiments, the first cleaving agent and the second cleaving agent are the same protease selected from the group consisting of a MMP, thrombin, a neutrophil elastase, a cysteine protease, uPA, legumain, and matriptase, and the first CM and the second CM are different substrates for the enzyme. In some embodiments, the first cleaving agent and the second cleaving agent are the same protease selected from the group consisting of those shown in Table 4. In some embodiments, the first cleaving agent and the second cleaving agent are different proteases. In some embodiments, the first cleaving agent and the second cleaving agent are co-localized in the target tissue. In some embodiments, the first CM and the second CM are cleaved by at least one cleaving agent in the target tissue.

In some embodiments, the activatable antibody is exposed to and cleaved by a protease such that, in the activated or cleaved state, the activated antibody includes a light chain amino acid sequence that includes at least a portion of LP2 and/or CM sequence after the protease has cleaved the CM.

Suitable activatable anti-CD166 antibodies of the disclosure also include an antibody or antigen binding fragment thereof that binds to the same epitope on human CD166 and/or cynomolgus monkey CD166 as an anti-CD166 antibody comprising a heavy chain variable region amino acid sequence selected from the group consisting of SEQ ID NO: 119, 121, and 122, and a light chain variable region amino acid sequence selected from the group consisting of SEQ ID NO: 120 and 123-126.

Suitable activatable anti-CD166 antibodies of the disclosure also include an antibody or antigen binding fragment thereof that binds to the same epitope on human CD166 and/or cynomolgus monkey CD166 as an anti-CD166 antibody comprising the VH CDR1 sequence comprises the amino acid sequence GFSLSTYGMGVG (SEQ ID NO: 127), the VH CDR2 sequence comprises the amino acid sequence NIWWSEDKH (SEQ ID NO: 128); the VH CDR3 sequence comprises the amino acid sequence IDYGNDYAFTY (SEQ ID NO: 129); the VL CDR1 sequence comprises the amino acid sequence RSSKSLLHSNGITYLY (SEQ ID NO: 130) or RSSQSLLHSNGITYLY (SEQ ID NO: 131); the VL CDR2 sequence comprises the amino acid sequence QMSNLAS (SEQ ID NO: 132) or QMSNRAS (SEQ ID NO: 133); and the VL CDR3 sequence comprises the amino acid sequence AQNLELPYT (SEQ ID NO: 134).

Suitable activatable anti-CD166 antibodies of the disclosure also include an antibody or antigen-binding fragment thereof that binds to the same epitope on human CD166 and/or cynomolgus monkey CD166 as an anti-CD166 antibody comprising a heavy chain variable region amino acid sequence selected from the group consisting of the heavy chain variable region sequences shown in Table 12 and a light chain variable region amino acid sequence selected from the group consisting of the light chain variable region sequences shown in Table 12.

Suitable activatable anti-CD166 antibodies of the disclosure also include an antibody or antigen-binding fragment thereof that binds to the same epitope on human CD166 and/or cynomolgus monkey CD166 as an anti-CD166 antibody comprising a combination of a VH CDR1 sequence, a VH CDR2 sequence, a VH CDR3 sequence, a VL CDR1 sequence, a VL CDR2 sequence, and a VL CDR3 sequence, wherein the combination is a combination of the six CDR sequences (VH CDR1, VH CDR2, VH CDR3, VL CDR1, VL CDR2, and VL CDR3) shown in a single row in Table 13.

Suitable activatable anti-CD166 antibodies of the disclosure also include an antibody or antigen binding fragment thereof that cross-competes for binding to human CD166 and/or cynomolgus monkey CD166 to an anti-CD166 antibody comprising a heavy chain variable region amino acid sequence selected from the group consisting of SEQ ID NO: 119, 121, and 122, and a light chain variable region amino acid sequence selected from the group consisting of SEQ ID NO: 120 and 123-126.

Suitable activatable anti-CD166 antibodies of the disclosure also include an antibody or antigen binding fragment thereof that cross-competes for binding to human CD166 and/or cynomolgus monkey CD166 to an anti-CD166 antibody comprising the VH CDR1 sequence comprises the amino acid sequence GFSLSTYGMGVG (SEQ ID NO: 127); the VH CDR2 sequence comprises the amino acid sequence NIWWSEDKH (SEQ ID NO: 128); the VH CDR3 sequence comprises the amino acid sequence IDYGNDYAFTY (SEQ ID NO: 129); the VL CDR1 sequence comprises the amino acid sequence RSSKSLLHSNGITYLY (SEQ ID NO: 130) or RSSQSLLHSNGITYLY (SEQ ID NO: 131); the VL CDR2 sequence comprises the amino acid sequence QMSNLAS (SEQ ID NO: 132) or QMSNRAS (SEQ ID NO: 133); and the VL CDR3 sequence comprises the amino acid sequence AQNLELPYT (SEQ ID NO: 134).

Suitable activatable anti-CD166 antibodies of the disclosure also include an antibody or antigen-binding fragment thereof that cross-competes for binding to human CD166 and/or cynomolgus monkey CD166 as an anti-CD166 antibody comprising a heavy chain variable region amino acid sequence selected from the group consisting of the heavy chain variable region sequences shown in Table 12 and a light chain variable region amino acid sequence selected from the group consisting of the light chain variable region sequences shown in Table 12.

Suitable activatable anti-CD166 antibodies of the disclosure also include an antibody or antigen-binding fragment thereof that cross-competes for binding to human CD166 and/or cynomolgus monkey CD166 as an anti-CD166 antibody comprising a combination of a VH CDR1 sequence, a VH CDR2 sequence, a VH CDR3 sequence, a VL CDR1 sequence, a VL CDR2 sequence, and a VL CDR3 sequence, wherein the combination is a combination of the six CDR sequences (VH CDR1, VH CDR2, VH CDR3, VL CDR1, VL CDR2, and VL CDR3) shown in a single row in Table 13.

In some embodiments, the activatable antibody also includes an agent conjugated to the AB. In some embodiments, the agent conjugated to the AB or the AB of an activatable antibody is a therapeutic agent. In some embodiments, the agent is an antineoplastic agent. In some embodiments, the agent is a toxin or fragment thereof. As used herein, a fragment of a toxin is a fragment that retains toxic activity. In some embodiments, the agent is conjugated to the AB via a cleavable linker. In some embodiments, the agent is conjugated to the AB via a linker that includes at least one CM1-CM2 substrate sequence. In some embodiments, the agent is conjugated to the AB via a noncleavable linker. In some embodiments, the agent is conjugated to the AB via a linker that is cleavable in an intracellular or lysosomal environment. In some embodiments, the agent is a microtubule inhibitor. In some embodiments, the agent is a nucleic acid damaging agent, such as a DNA alkylator, a DNA cleaving agent, a DNA cross-linker, a DNA intercalator, or other DNA damaging agent. In some embodiments, the agent is an agent selected from the group listed in Table 5. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the activatable antibody is conjugated to one or more equivalents of an agent. In some embodiments, the activatable antibody is conjugated to one equivalent of the agent. In some embodiments, the activatable antibody is conjugated to two, three, four, five, six, seven, eight, nine, ten, or greater than ten equivalents of the agent. In some embodiments, the activatable antibody is part of a mixture of activatable antibodies having a homogeneous number of equivalents of conjugated agents. In some embodiments, the activatable antibody is part of a mixture of activatable antibodies having a heterogeneous number of equivalents of conjugated agents. In some embodiments, the mixture of activatable antibodies is such that the average number of agents conjugated to each activatable antibody is between zero to one, between one to two, between two and three, between three and four, between four and five, between five and six, between six and seven, between seven and eight, between eight and nine, between nine and ten, and ten and greater. In some embodiments, the mixture of activatable antibodies is such that the average number of agents conjugated to each activatable antibody is one, two, three, four, five, six, seven, eight, nine, ten, or greater. In some embodiments, the activatable antibody comprises one or more site-specific amino acid sequence modifications such that the number of lysine and/or cysteine residues is increased or decreased with respect to the original amino acid sequence of the activatable antibody, thus in some embodiments correspondingly increasing or decreasing the number of agents that can be conjugated to the activatable antibody, or in some embodiments limiting the conjugation of the agents to the activatable antibody in a site-specific manner. In some embodiments, the modified activatable antibody is modified with one or more non-natural amino acids in a site-specific manner, thus in some embodiments limiting the conjugation of the agents to only the sites of the non-natural amino acids.

In some embodiments, the agent is an anti-inflammatory agent.

In some embodiments, the activatable antibody also includes a detectable moiety. In some embodiments, the detectable moiety is a diagnostic agent.

In some embodiments, the activatable antibody also includes a signal peptide. In some embodiments, the signal peptide is conjugated to the activatable antibody via a spacer. In some embodiments, the spacer is conjugated to the activatable antibody in the absence of a signal peptide. In some embodiments, the spacer is joined directly to the MM of the activatable antibody. In some embodiments, the spacer is joined directly to the MM of the activatable antibody in the structural arrangement from N-terminus to C-terminus of spacer-MM-CM-AB. An example of a spacer joined directly to the N-terminus of MM of the activatable antibody is QGQSGQ (SEQ ID NO: 88). Other examples of a spacer joined directly to the N-terminus of MM of the activatable antibody include QGQSGQG (SEQ ID NO: 305), QGQSG (SEQ ID NO: 306), QGQS (SEQ ID NO: 307), QGQ (SEQ ID NO: 308), QG (SEQ ID NO: 309), and Q. Other examples of a spacer joined directly to the N-terminus of MM of the activatable antibody include GQSGQG (SEQ ID NO: 359), QSGQG (SEQ ID NO: 360), SGQG (SEQ ID NO: 361), GQG (SEQ ID NO: 362), and G. In some embodiments, no spacer is joined to the N-terminus of the MM. In some embodiments, the spacer includes at least the amino acid sequence QGQSGQ (SEQ ID NO: 88). In some embodiments, the spacer includes at least the amino acid sequence QGQSGQG (SEQ ID NO: 305). In some embodiments, the spacer includes at least the amino acid sequence QGQSG (SEQ ID NO: 306). In some embodiments, the spacer includes at least the amino acid sequence QGQS (SEQ ID NO: 307). In some embodiments, the spacer includes at least the amino acid sequence QGQ (SEQ ID NO: 308). In some embodiments, the spacer includes at least the amino acid sequence QG (SEQ ID NO: 309). In some embodiments, the spacer includes at least the amino acid residue Q. In some embodiments, the spacer includes at least the amino acid sequence GQSGQG (SEQ ID NO: 359). In some embodiments, the spacer includes at least the amino acid sequence QSGQG (SEQ ID NO: 360). In some embodiments, the spacer includes at least the amino acid sequence SGQG (SEQ ID NO: 361). In some embodiments, the spacer includes at least the amino acid sequence GQG (SEQ ID NO: 362). In some embodiments, the spacer includes at least the amino acid sequence G. In some embodiments, the spacer is absent.

In some embodiments, the AB of the activatable antibody naturally contains one or more disulfide bonds. In some embodiments, the AB can be engineered to include one or more disulfide bonds.

In some embodiments, the activatable antibody is encoded by a nucleic acid sequence that comprises a nucleic acid sequence encoding a heavy chain variable region amino acid sequence selected from the group consisting of SEQ ID NO: 119, 121, and 122. In some embodiments, the activatable antibody is encoded by a nucleic acid sequence that comprises a nucleic acid sequence encoding a heavy chain variable region amino acid sequence comprising SEQ ID NO: 121 or SEQ ID NO: 122.

In some embodiments, the activatable antibody is encoded by a nucleic acid sequence that comprises a nucleic acid sequence encoding a light chain variable region amino acid sequence selected from the group consisting of SEQ ID NO: 120 and 123-126. In some embodiments, the activatable antibody is encoded by a nucleic acid sequence that comprises a nucleic acid sequence encoding a light chain variable region amino acid sequence selected from the group consisting of SEQ ID NO: 123-126.

In some embodiments, the activatable antibody is encoded by a nucleic acid sequence that comprises a nucleic acid sequence encoding a heavy chain variable region amino acid sequence selected from the group consisting of SEQ ID NO: 119, 121, and 122, and a nucleic acid sequence encoding a light chain variable region amino acid sequence selected from the group consisting of SEQ ID NO: 120 and 123-126.

In some embodiments, the activatable antibody is encoded by a nucleic acid sequence that comprises a nucleic acid sequence encoding a heavy chain variable region amino acid sequence selected from the group consisting of SEQ ID NO: 121, and 122, and a nucleic acid sequence encoding a light chain variable region amino acid sequence selected from the group consisting of SEQ ID NO: 123-126.

In some embodiments, the activatable antibody is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain variable region amino acid sequence comprising SEQ ID NO: 121 or SEQ ID NO: 122. In some embodiments, the activatable antibody is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain variable region amino acid sequence comprising SEQ ID NO: 121 or SEQ ID NO: 122.

In some embodiments, the activatable antibody is encoded by a nucleic acid sequence that comprises a nucleic acid sequence that is at least 90%, 91%, 92%, 93%, 94%, 95%, 96%, 97%, 98% or 99% identical to a nucleic acid sequence encoding a light chain variable region amino acid sequence selected from the group consisting of SEQ ID NO: 120 and 123-126. In some embodiments, the activatable antibody is encoded by a nucleic acid sequence that comprises a nucleic acid sequence that is at least 90%, 91%, 92%, 93%, 94%, 95%, 96%, 97%, 98% or 99% identical to a nucleic acid sequence encoding a light chain variable region amino acid sequence selected from the group consisting of SEQ ID NO: 123-126.

In some embodiments, the activatable antibody is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain variable region amino acid sequence selected from the group consisting of SEQ ID NO: 119, 121, and 122, and a nucleic acid sequence that is at least 90%, 91%, 92%, 93%, 94%, 95%, 96%, 97%, 98% or 99% identical to a nucleic acid sequence encoding a light chain variable region amino acid sequence selected from the group consisting of SEQ ID NO: 120 and 123-126.

In some embodiments, the activatable antibody is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain variable region amino acid sequence comprising SEQ ID NO: 121 or SEQ ID NO: 122, and a nucleic acid sequence that is at least 90%, 91%, 92%, 93%, 94%, 95%, 96%, 97%, 98% or 99% identical to a nucleic acid sequence encoding a light chain variable region amino acid sequence selected from the group consisting of SEQ ID NO: 123-126.

In some embodiments, the activatable antibody is encoded by a nucleic acid sequence that comprises a nucleic acid sequence encoding a heavy chain variable region amino acid sequence selected from the group consisting of the heavy chain variable region sequences shown in Table 12. In some embodiments, the activatable antibody is encoded by a nucleic acid sequence that comprises a nucleic acid sequence encoding a light chain variable region amino acid sequence selected from the group consisting of the light chain variable region sequences shown in Table 12. In some embodiments, the activatable antibody is encoded by a nucleic acid sequence that comprises a nucleic acid sequence encoding a heavy chain variable region amino acid sequence selected from the group consisting of the heavy chain variable region sequences shown in Table 12 and a nucleic acid sequence encoding a light chain variable region amino acid sequence selected from the group consisting of the light chain variable region sequences shown in Table 12.

In some embodiments, the activatable antibody is encoded by a nucleic acid sequence that comprises a nucleic acid sequence encoding a heavy chain variable region amino acid sequence that is at least 90%, 91%, 92%, 93%, 94%, 95%, 96%, 97%, 98% or 99% identical to an amino acid sequence selected from the group consisting of the heavy chain variable region sequences shown in Table 12. In some embodiments, the activatable antibody is encoded by a nucleic acid sequence that comprises a nucleic acid sequence encoding a light chain variable region amino acid sequence that is at least 90%, 91%, 92%, 93%, 94%, 95%, 96%, 97%, 98% or 99% identical to an amino acid sequence selected from the group consisting of the light chain variable region sequences shown in Table 12. In some embodiments, the activatable antibody is encoded by a nucleic acid sequence that comprises a nucleic acid sequence encoding a heavy chain variable region amino acid sequence that is at least 90%, 91%, 92%, 93%, 94%, 95%, 96%, 97%, 98% or 99%, identical to an amino acid sequence selected from the group consisting of the heavy chain variable region sequences shown in Table 12 and a nucleic acid sequence that comprises a nucleic acid sequence encoding a light chain variable region amino acid sequence that is at least 90%, 91%, 92%, 93%, 94%, 95%, 96%, 97%, 98% or 99% identical to an amino acid sequence selected from the group consisting of the light chain variable region sequences shown in Table 12.

In some embodiments, the activatable antibody is encoded by a nucleic acid sequence that comprises a nucleic acid sequence encoding a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one CDR sequence is selected from the group consisting of a VH CDR1 sequence shown in Table 13; a VH CDR2 sequence shown in Table 13; a VH CDR3 sequence shown in Table 13; a VL CDR1 sequence shown in Table 13; a VL CDR2 sequence shown in Table 13; and a VL CDR3 sequence shown in Table 13.

In some embodiments, the activatable antibody is encoded by a nucleic acid sequence that comprises a nucleic acid sequence encoding a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to a VH CDR1 sequence shown in Table 13; a VH CD2 sequence that includes a sequence that is at least 90%, 91%, 92%, 93%, 94%, 95%, 96%, 97%, 98%, 99% or more identical to a VH CDR2 sequence shown in Table 13; a VH CDR3 sequence that includes a sequence that is at least 90%, 91%, 92%, 93%, 94%, 95%, 96%, 97%, 98%, 99% or more identical to a VH CDR3 sequence shown in Table 13; a VL CDR1 sequence that includes a sequence that is at least 90%, 91%, 92%, 93%, 94%, 95%, 96%, 97%, 98%, 99% or more identical to a VL CDR1 sequence shown in Table 13; a VL CDR2 sequence that includes a sequence that is at least 90%, 91%, 92%, 93%, 94%, 95%, 96%, 97%, 98%, 99% or more identical to a VL CDR2 sequence shown in Table 13; and a VL CDR3 sequence that includes a sequence that is at least 90%, 91%, 92%, 93%, 94%, 95%, 96%, 97%, 98%, 99% or more identical to a VL CDR3 sequence shown in Table 13.

In some embodiments, the activatable antibody is encoded by a nucleic acid sequence that comprises a nucleic acid sequence encoding a combination of a VH CDR1 sequence, a VH CDR2 sequence, a VH CDR3 sequence, a VL CDR1 sequence, a VL CDR2 sequence, and a VL CDR3 sequence, wherein the combination is a combination of the six CDR sequences (VH CDR1, VH CDR2, VH CDR3, VL CDR1, VL CDR2, and VL CDR3) shown in a single row in Table 13.

In some embodiments, the activatable antibody is encoded by a nucleic acid sequence that comprises a nucleic acid sequence encoding a light chain variable region that comprise a combination of a VL CDR1 sequence, a VL CDR2 sequence, and a VL CDR3 sequence, wherein the combination is a combination of the three light chain CDR sequences (VL CDR1, VL CDR2, VL CDR3) shown in a single row in Table 13.

In some embodiments, the activatable antibody is encoded by a nucleic acid sequence that comprises a nucleic acid sequence encoding a heavy chain variable region that comprise a combination of a VH CDR1 sequence, a VH CDR2 sequence, and a VH CDR3 sequence, wherein the combination is a combination of the three heavy chain CDR sequences (VH CDR1, VH CDR2, VH CDR3) shown in a single row in Table 13.

In some embodiments, the activatable antibody is encoded by a nucleic acid sequence that comprises a nucleic acid sequence encoding a combination of a VH CDR1 sequence, a VH CDR2 sequence, a VH CDR3 sequence, a VL CDR1 sequence, a VL CDR2 sequence, and a VL CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of the six CDR sequences (VH CDR1, VH CDR2, VH CDR3, VL CDR1, VL CDR2, and VL CDR3) shown in a single row in Table 13.

In some embodiments, the activatable antibody is encoded by a nucleic acid sequence that comprises a nucleic acid sequence encoding a heavy chain variable region that comprise a combination of a VH CDR1 sequence, a VH CDR2 sequence, and a VH CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of three heavy chain CDR sequences (VH CDR1, VH CDR2, VH CDR3) shown in a single row in Table 13.

In some embodiments, the activatable antibody is encoded by a nucleic acid sequence that comprises a nucleic acid sequence encoding a light chain variable region that comprise a combination of a VL CDR1 sequence, a VL CDR2 sequence, and a VL CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of three light chain CDR sequences (VL CDR1, VL CDR2, VL CDR3) shown in a single row in Table 13.

In some embodiments, the activatable antibody includes one or more polypeptides that include the combination of sequences in a given row of Table A or any combination of a mask sequence (MM), a substrate sequence (CM), a light chain variable domain sequence or light chain variable domain CDR sequences, and a heavy chain variable domain sequence or heavy chain variable domain CDR sequences of Table B.

TABLE A

Anti-CD166 Activatable Antibody Combinations

| Comb. No. | Mask Sequence (MM) | Substrate Sequence (CM) | VL CDRs SEQ ID NOs | VH CDRs SEQ ID NOs |
|---|---|---|---|---|
| 1 | LCHPLVISAWESCSS (SEQ ID NO: 219) | LSGRSDNH (SEQ ID NO: 21) | 130, 132, 134 | 127, 128, 129 |
| 2 | LCHPLVLSAWESCSS (SEQ ID NO: 219) | ISSGLLSS (SEQ ID NO: 44) | 130, 132, 134 | 127, 128, 129 |
| 3 | LCHPLVLSAWESCSS (SEQ ID NO: 219) | LSGRSGNH (SEQ ID NO: 318) | 130, 132, 134 | 127, 128, 129 |
| 4 | LCHPLVLSAWESCSS (SEQ ID NO: 219) | AVGILAPP (SEQ ID NO: 52) | 130, 132, 134 | 127, 128, 129 |
| 5 | LCHPLVISAWESCSS (SEQ ID NO: 219) | VHMPLGFIGP (SEQ ID NO: 32) | 130, 132, 134 | 127, 128, 129 |
| 6 | LCPLVISAWESCSS (SEQ ID NO: 219) | TSTSGRSANPRG (SEQ ID NO: 61) | 130, 132, 134 | 127, 128, 129 |
| 7 | LCHPLVLSAWESCSS (SEQ ID NO: 219) | QNQALRMA (SEQ ID NO: 39) | 130, 132, 134 | 127, 128, 129 |

TABLE A-continued

Anti-CD166 Activatable Antibody Combinations

| Comb. No. | Mask Sequence (MM) | Substrate Sequence (CM) | VL CDRs SEQ ID NOs | VH CDRs SEQ ID NOs |
|---|---|---|---|---|
| 8 | LCHPLVLSAWESCSS (SEQ ID NO: 219) | ISSGLLSGRSDNH (SEQ ID NO: 70) | 130, 132, 134 | 127, 128, 129 |
| 9 | LCHPLVLSAWESCSS (SEQ ID NO: 219) | ISSGLLSGRSGNH (SEQ ID NO: 87) | 130, 132, 134 | 127, 128, 129 |
| 10 | LCHPLVISAWESCSS (SEQ ID NO: 219) | ISSGLLSGRSANPRG (SEQ ID NO: 338) | 130, 132, 134 | 127, 128, 129 |
| 11 | LCHPLVLSAWESCSS (SEQ ID NO: 219) | AVGLLAPPTSGRSANPRG (SEQ ID NO: 339) | 130, 132, 134 | 127, 128, 129 |
| 12 | LCHPLVLSAWESCSS (SEQ ID NO: 219) | AVGLLAPPSGRSANPRG (SEQ ID NO: 340) | 130, 132, 134 | 127, 128, 129 |
| 13 | LCHPLVLSAWESCSS (SEQ ID NO: 219) | ISSGLLSGRSDDH (SEQ ID NO: 341) | 130, 132, 134 | 127, 128, 129 |
| 14 | LCHPLVISAWESCSS (SEQ ID NO: 219) | ISSGLLSGRSDIH (SEQ ID NO: 342) | 130, 132, 134 | 127, 128, 129 |
| 15 | LCHPLVLSAWESCSS (SEQ ID NO: 219) | ISSGLLSGRSDQH (SEQ ID NO: 343) | 130, 132, 134 | 127, 128, 129 |
| 16 | LCHPLVLSAWESCSS (SEQ ID NO: 219) | ISSGLLSGRSDTH (SEQ ID NO: 344) | 130, 132, 134 | 127, 128, 129 |
| 17 | LCHPLVLSAWESCSS (SEQ ID NO: 219) | ISSGLLSGRSDYH (SEQ ID NO: 345) | 130, 132, 134 | 127, 128, 129 |
| 18 | LCHPLVLSAWESCSS (SEQ ID NO: 219) | ISSGILSGRSDNP (SEQ ID NO: 346) | 130, 132, 134 | 127, 128, 129 |
| 19 | LCHPLVLSAWESCSS (SEQ ID NO: 219) | ISSGLLSGRSANP (SEQ ID NO: 347) | 130, 132, 134 | 127, 128, 129 |
| 20 | LCHPLVLSAWESCSS (SEQ ID NO: 219) | ISSGLLSGRSANI (SEQ ID NO: 348) | 130, 132, 134 | 127, 128, 129 |
| 21 | LCHPLVLSAWESCSS (SEQ ID NO: 219) | ISSGLLSGRSDNI (SEQ ID NO: 357) | 130, 132, 134 | 127, 128, 129 |
| 22 | LCHPLVLSAWESCSS (SEQ ID NO: 219) | AVGILAPPGGISGRSDNH (SEQ ID NO: 76) | 130, 132, 134 | 127, 128, 129 |
| 23 | LCHPLVLSAWESCSS (SEQ ID NO: 219) | AVGLLAPPGGLSGRSDDH (SEQ ID NO: 349) | 130, 132, 134 | 127, 128, 129 |
| 24 | LCHPLVLSAWESCSS (SEQ ID NO: 219) | AVGLLAPPGGLSGRSDIH (SEQ ID NO: 350) | 130, 132, 134 | 127, 128, 129 |
| 25 | LCHPLVLSAWESCSS (SEQ ID NO: 219) | AVGLLAPPGGLSGRSDQH (SEQ ID NO: 351) | 130, 132, 134 | 127, 128, 129 |
| 26 | LCHPLVLSAWESCSS (SEQ ID NO: 219) | AVGILAPPGGISGRSDTH (SEQ ID NO: 352) | 130, 132, 134 | 127, 128, 129 |
| 27 | LCHPLVLSAWESCSS (SEQ ID NO: 219) | AVGLAPPGGLSGRSDYH (SEQ ID NO: 353) | 130, 132, 134 | 127, 128, 129 |
| 28 | LCHPLVLSAWESCSS (SEQ ID NO: 219) | AVGLLAPPGGLSGRSDNP (SEQ ID NO: 354) | 130, 132, 134 | 127, 128, 129 |
| 29 | LCHPLVLSAWESCSS (SEQ ID NO: 219) | AVGLLAPPGGLSGRSANP (SEQ ID NO: 355) | 130, 132, 134 | 127, 128, 129 |
| 30 | LCHPLVLSAWESCSS (SEQ ID NO: 219) | AVGLLAPPGGLSGRSANI (SEQ ID NO: 356) | 130, 132, 134 | 127, 128, 129 |
| 31 | LCHPLVLSAWESCSS (SEQ ID NO: 219) | AVGLLAPPGGLSGRSDNI (SEQ ID NO: 358) | 130, 132, 134 | 127, 128, 129 |

TABLE A-continued

Anti-CD166 Activatable Antibody Combinations

| Comb. No. | Mask Sequence (MM) | Substrate Sequence (CM) | VL CDRs SEQ ID NOs | VH CDRs SEQ ID NOs |
|---|---|---|---|---|
| 32 | LCHPLVLSAWESCSS (SEQ ID NO: 219) | ISSGLLSSGGSGGSLSGRSDNH (SEQ ID NO: 71) | 130, 132, 134 | 127, 128, 129 |
| 33 | LCHPAVLSAWESCSS (SEQ ID NO: 222) | LSGRSDNH (SEQ ID NO: 21) | 130, 132, 134 | 127, 128, 129 |
| 34 | LCHPAVLSAWESCSS (SEQ ID NO: 222) | ISSGLLSS (SEQ ID NO: 44) | 130, 132, 134 | 127, 128, 129 |
| 35 | LCHPAVLSAWESCSS (SEQ ID NO: 222) | LSGRSGNH (SEQ ID NO: 318) | 130, 132, 134 | 127, 128, 129 |
| 36 | LCHPAVLSAWESCSS (SEQ ID NO: 222) | AVGLLAPP (SEQ ID NO: 52) | 130, 132, 134 | 127, 128, 129 |
| 37 | LCHPAVLSAWESCSS (SEQ ID NO: 222) | VHMPLGFLGP (SEQ ID NO: 32) | 130, 132, 134 | 127, 128, 129 |
| 38 | LCHPAVLSAWESCSS (SEQ ID NO: 222) | TSTSGRSANPRG (SEQ ID NO: 61) | 130, 132, 134 | 127, 128, 129 |
| 39 | LCHPAVLSAWESCSS (SEQ ID NO: 222) | QNQALRMA (SEQ ID NO: 39) | 130, 132, 134 | 127, 128, 129 |
| 40 | LCHPAVLSAWESCSS (SEQ ID NO: 222) | ISSGLLSGRSDNH (SEQ ID NO: 70) | 130, 132, 134 | 127, 128, 129 |
| 41 | LCHPAVLSAWESCSS (SEQ ID NO: 222) | ISSGLLSGRSGNH (SEQ ID NO: 87) | 130, 132, 134 | 127, 128, 129 |
| 42 | LCHPAVLSAWESCSS (SEQ ID NO: 222) | ISSGLLSGRSANPRG (SEQ ID NO: 338) | 130, 132, 134 | 127, 128, 129 |
| 43 | LCHPAVLSAWESCSS (SEQ ID NO: 222) | AVGLLAPPTSGRSANPRG (SEQ ID NO: 339) | 130, 132, 134 | 127, 128, 129 |
| 44 | LCHPAVLSAWESCSS (SEQ ID NO: 222) | AVGLLAPPSGRSANPRG (SEQ ID NO: 340) | 130, 132, 134 | 127, 128, 129 |
| 45 | LCHPAVLSAWESCSS (SEQ ID NO: 222) | ISSGLLSGRSDDH (SEQ ID NO: 341) | 130, 132, 134 | 127, 128, 129 |
| 46 | LCHPAVLSAWESCSS (SEQ ID NO: 222) | ISSGLLSGRSDIH (SEQ ID NO: 342) | 130, 132, 134 | 127, 128, 129 |
| 47 | LCHPAVLSAWESCSS (SEQ ID NO: 222) | ISSGLLSGRSDQH (SEQ ID NO: 343) | 130, 132, 134 | 127, 128, 129 |
| 48 | LCHPAVLSAWESCSS (SEQ ID NO: 222) | ISSGLLSGRSDTH (SEQ ID NO: 344) | 130, 132, 134 | 127, 128, 129 |
| 49 | LCHPAVLSAWESCSS (SEQ ID NO: 222) | ISSGLLSGRSDYH (SEQ ID NO: 345) | 130, 132, 134 | 127, 128, 129 |
| 50 | LCHPAVLSAWESCSS (SEQ ID NO: 222) | ISSGLLSGRSDNP (SEQ ID NO: 346) | 130, 132, 134 | 127, 128, 129 |
| 51 | LCHPAVLSAWESCSS (SEQ ID NO: 222) | ISSGLLSGRSANP (SEQ ID NO: 347) | 130, 132, 134 | 127, 128, 129 |
| 52 | LCHPAVLSAWESCSS (SEQ ID NO: 222) | ISSGLLSGRSANI (SEQ ID NO: 348) | 130, 132, 134 | 127, 128, 129 |
| 53 | LCHPAVLSAWESCSS (SEQ ID NO: 222) | ISSGLLSGRSDNI (SEQ ID NO: 357) | 130, 132, 134 | 127, 128, 129 |
| 54 | LCHPAVLSAWESCSS (SEQ ID NO: 222) | AVGLLAPPGGLSGRSDNH (SEQ ID NO: 76) | 130, 132, 134 | 127, 128, 129 |
| 55 | LCHPAVLSAWESCSS (SEQ ID NO: 222) | AVGLLAPPGGLSGRSDDH (SEQ ID NO: 349) | 130, 132, 134 | 127, 128, 129 |

TABLE A-continued

Anti-CD166 Activatable Antibody Combinations

| Comb. No. | Mask Sequence (MM) | Substrate Sequence (CM) | VL CDRs SEQ ID NOs | VH CDRs SEQ ID NOs |
|---|---|---|---|---|
| 56 | LCHPAVLSAWESCSS (SEQ ID NO: 222) | AVGLLAPPGGLSGRSDIH (SEQ ID NO: 350) | 130, 132, 134 | 127, 128, 129 |
| 57 | LCHPAVLSAWESCSS (SEQ ID NO: 222) | AVGLLAPPGGLSGRSDQH (SEQ ID NO: 351) | 130, 132, 134 | 127, 128, 129 |
| 58 | LCHPAVLSAWESCSS (SEQ ID NO: 222) | AVGLLAPPGGLSGRSDTH (SEQ ID NO: 352) | 130, 132, 134 | 127, 128, 129 |
| 59 | LCHPAVLSAWESCSS (SEQ ID NO: 222) | AVGLLAPPGGLSGRSDYH (SEQ ID NO: 353) | 130, 132, 134 | 127, 128, 129 |
| 60 | LCHPAVLSAWESCSS (SEQ ID NO: 222) | AVGLLAPPGGLSGRSDNP (SEQ ID NO: 354) | 130, 132, 134 | 127, 128, 129 |
| 61 | LCHPAVLSAWESCSS (SEQ ID NO: 222) | AVGLLAPPGGLSGRSANP (SEQ ID NO: 355) | 130, 132, 134 | 127, 128, 129 |
| 62 | LCHPAVLSAWESCSS (SEQ ID NO: 222) | AVGLLAPPGGLAGRSANI (SEQ ID NO: 356) | 130, 132, 134 | 127, 128, 129 |
| 63 | LCHPAVLSAWESCSS (SEQ ID NO: 222) | AVGLLAPPGGLSGRSDNI (SEQ ID NO: 358) | 130, 132, 134 | 127, 128, 129 |
| 64 | LCHPAVLSAWESCSS (SEQ ID NO: 222) | ISSGLLSSGGSGGSLSGRSDNH (SEQ ID NO: 71) | 130, 132, 134 | 127, 128, 129 |
| 65 | LCHPLVASAWESCSS (SEQ ID NO: 224) | LSGRSDNH (SEQ ID NO: 21) | 130, 132, 134 | 127, 128, 129 |
| 66 | LCHPLVASAWESCSS (SEQ ID NO: 224) | ISSGLLSS (SEQ ID NO: 44) | 130, 132, 134 | 127, 128, 129 |
| 67 | LCHPLVASAWESCSS (SEQ ID NO: 224) | LSGRSGNH (SEQ ID NO: 318) | 130, 132, 134 | 127, 128, 129 |
| 68 | LCHPLVASAWESCSS (SEQ ID NO: 224) | AVGLLAPP (SEQ ID NO: 52) | 130, 132, 134 | 127, 128, 129 |
| 69 | LCHPLVASAWESCSS (SEQ ID NO: 224) | VHMPLGFLGP (SEQ ID NO: 32) | 130, 132, 134 | 127, 128, 129 |
| 70 | LCHPLVASAWESCSS (SEQ ID NO: 224) | TSTSGRSANPRG (SEQ ID NO: 61) | 130, 132, 134 | 127, 128, 129 |
| 71 | LCHPLVASAWESCSS (SEQ ID NO: 224) | QNQALRMA (SEQ ID NO: 39) | 130, 132, 134 | 127, 128, 129 |
| 72 | LCHPLVASAWESCSS (SEQ ID NO: 224) | ISSGLLSGRSDNH (SEQ ID NO: 70) | 130, 132, 134 | 127, 128, 129 |
| 73 | LCHPLVASAWESCSS (SEQ ID NO: 224) | ISSGLLSGRSGNH (SEQ ID NO: 87) | 130, 132, 134 | 127, 128, 129 |
| 74 | LCHPLVASAWESCSS (SEQ ID NO: 224) | ISSGLLSGRSANPRG (SEQ ID NO: 338) | 130, 132, 134 | 127, 128, 129 |
| 75 | LCHPLVASAWESCSS (SEQ ID NO: 224) | AVGLLAPPTSGRSANPRG (SEQ ID NO: 339) | 130, 132, 134 | 127, 128, 129 |
| 76 | LCHPLVASAWESCSS (SEQ ID NO: 224) | AVGLLAPPSGRSANPRG (SEQ ID NO: 340) | 130, 132, 134 | 127, 128, 129 |
| 77 | LCHPLVASAWESCSS (SEQ ID NO: 224) | ISSGLLSGRSDDH (SEQ ID NO: 341) | 130, 132, 134 | 127, 128, 129 |
| 78 | LCHPLVASAWESCSS (SEQ ID NO: 224) | ISSGLLSGRSDIH (SEQ ID NO: 342) | 130, 132, 134 | 127, 128, 129 |
| 79 | LCHPLVASAWESCSS (SEQ ID NO: 224) | ISSGLLSGRSDQH (SEQ ID NO: 343) | 130, 132, 134 | 127, 128, 129 |

TABLE A-continued

Anti-CD166 Activatable Antibody Combinations

| Comb. No. | Mask Sequence (MM) | Substrate Sequence (CM) | VL CDRs SEQ ID NOs | VH CDRs SEQ ID NOs |
|---|---|---|---|---|
| 80 | LCHPLVASAWESCSS (SEQ ID NO: 224) | ISSGLLSGRSDTH (SEQ ID NO: 344) | 130, 132, 134 | 127, 128, 129 |
| 81 | LCHPLVASAWESCSS (SEQ ID NO: 224) | ISSGLLSGRSDYH (SEQ ID NO: 345) | 130, 132, 134 | 127, 128, 129 |
| 82 | LCHPLVASAWESCSS (SEQ ID NO: 224) | ISSGLLSGRSDNP (SEQ ID NO: 346) | 130, 132, 134 | 127, 128, 129 |
| 83 | LCHPLVASAWESCSS (SEQ ID NO: 224) | ISSGLLSGRSANP (SEQ ID NO: 347) | 130, 132, 134 | 127, 128, 129 |
| 84 | LCHPLVASAWESCSS (SEQ ID NO: 224) | ISSGLLSGRSANI (SEQ ID NO: 348) | 130, 132, 134 | 127, 128, 129 |
| 85 | LCHPLVASAWESCSS (SEQ ID NO: 224) | ISSGLLSGRSDNI (SEQ ID NO: 357) | 130, 132, 134 | 127, 128, 129 |
| 86 | LCHPLVASAWESCSS (SEQ ID NO: 224) | AVGLLAPPGGLSGRSDNH (SEQ ID NO: 76) | 130, 132, 134 | 127, 128, 129 |
| 87 | LCHPLVASAWESCSS (SEQ ID NO: 224) | AVGLLAPPGGLSGRSDDH (SEQ ID NO: 349) | 130, 132, 134 | 127, 128, 129 |
| 88 | LCHPLVASAWESCSS (SEQ ID NO: 224) | AVGLLAPPGGLSGRSDIH (SEQ ID NO: 350) | 130, 132, 134 | 127, 128, 129 |
| 89 | LCHPLVASAWESCSS (SEQ ID NO: 224) | AVGLLAPPGGLSGRSDQH (SEQ ID NO: 351) | 130, 132, 134 | 127, 128, 129 |
| 90 | LCHPLVASAWESCSS (SEQ ID NO: 224) | AVGLLAPPGGLSGRSDTH (SEQ ID NO: 352) | 130, 132, 134 | 127, 128, 129 |
| 91 | LCHPLVASAWESCSS (SEQ ID NO: 224) | AVGLLAPPGGLSGRSDYH (SEQ ID NO: 353) | 130, 132, 134 | 127, 128, 129 |
| 92 | LCHPLVASAWESCSS (SEQ ID NO: 224) | AVGLLAPPGGLSGRSDNP (SEQ ID NO: 354) | 130, 132, 134 | 127, 128, 129 |
| 93 | LCHPLVASAWESCSS (SEQ ID NO: 224) | AVGLLAPPGGLSGRSANP (SEQ ID NO: 355) | 130, 132, 134 | 127, 128, 129 |
| 94 | LCHPLVASAWESCSS (SEQ ID NO: 224) | AVGLLAPPGGLSGRSANI (SEQ ID NO: 356) | 130, 132, 134 | 127, 128, 129 |
| 95 | LCHPLVASAWESCSS (SEQ ID NO: 224) | AVGLLAPPGGLSGRSDNI (SEQ ID NO: 358) | 130, 132, 134 | 127, 128, 129 |
| 96 | LCHPLVASAWESCSS (SEQ ID NO: 224) | ISSGLLSSGGSGGSLSGRSDNH (SEQ ID NO: 71) | 130, 132, 134 | 127, 128, 129 |
| 97 | LEGWCLHPLCLWGAG (SEQ ID NO: 230) | LSGRSDNH (SEQ ID NO: 21) | 130, 132, 134 | 127, 128, 129 |
| 98 | LEGWCLHPLCLWGAG (SEQ ID NO: 230) | ISSGLLSS (SEQ ID NO: 44) | 130, 132, 134 | 127, 128, 129 |
| 99 | LEGWCLHPLCLWGAG (SEQ ID NO: 230) | LSGRSGNH (SEQ ID NO: 318) | 130, 132, 134 | 127, 128, 129 |
| 100 | LEGWCLHPLCLWGAG (SEQ ID NO: 230) | AVGLLAPP (SEQ ID NO: 52) | 130, 132, 134 | 127, 128, 129 |
| 101 | LEGWCLHPLCLWGAG (SEQ ID NO: 230) | VHMPLGFLGP (SEQ ID NO: 32) | 130, 132, 134 | 127, 128, 129 |
| 102 | LEGWCLHPLCLWGAG (SEQ ID NO: 230) | TSTSGRSANPRG (SEQ ID NO: 61) | 130, 132, 134 | 127, 128, 129 |
| 103 | LEGWCLHPLCLWGAG (SEQ ID NO: 230) | QNQALRMA (SEQ ID NO: 39) | 130, 132, 134 | 127, 128, 129 |

TABLE A-continued

Anti-CD166 Activatable Antibody Combinations

| Comb. No. | Mask Sequence (MM) | Substrate Sequence (CM) | VL CDRs SEQ ID NOs | VH CDRs SEQ ID NOs |
|---|---|---|---|---|
| 104 | LEGWCLHPLCLWGAG (SEQ ID NO: 230) | ISSGLLSGRSDNH (SEQ ID NO: 70) | 130, 132, 134 | 127, 128, 129 |
| 105 | LEGWCLHPLCLWGAG (SEQ ID NO: 230) | ISSGLLSGRSGNH (SEQ ID NO: 87) | 130, 132, 134 | 127, 128, 129 |
| 106 | LEGWCLHPLCLWGAG (SEQ ID NO: 230) | ISSGLLSGRSANPRG (SEQ ID NO: 338) | 130, 132, 134 | 127, 128, 129 |
| 107 | LEGWCLHPLCLWGAG (SEQ ID NO: 230) | AVGLLAPPTSGRSANPRG (SEQ ID NO: 339) | 130, 132, 134 | 127, 128, 129 |
| 108 | LEGWCLHPLCLWGAG (SEQ ID NO: 230) | AVGLLAPPSGRSANPRG (SEQ ID NO: 340) | 130, 132, 134 | 127, 128, 129 |
| 109 | LEGWCLHPLCLWGAG (SEQ ID NO: 230) | ISSGLLSGRSDDH (SEQ ID NO: 341) | 130, 132, 134 | 127, 128, 129 |
| 110 | LEGWCLHPLCLWGAG (SEQ ID NO: 230) | ISSGLLSGRSDIH (SEQ ID NO: 342) | 130, 132, 134 | 127, 128, 129 |
| 111 | LEGWCLHPLCLWGAG (SEQ ID NO: 230) | ISSGLLSGRSDQH (SEQ ID NO: 343) | 130, 132, 134 | 127, 128, 129 |
| 112 | LEGWCLHPLCLWGAG (SEQ ID NO: 230) | ISSGLLSGRSDTH (SEQ ID NO: 344) | 130, 132, 134 | 127, 128, 129 |
| 113 | LEGWCLHPLCLWGAG (SEQ ID NO: 230) | ISSGLLSGRSDYH (SEQ ID NO: 345) | 130, 132, 134 | 127, 128, 129 |
| 114 | LEGWCLHPLCLWGAG (SEQ ID NO: 230) | ISSGLLSGRSDNP (SEQ ID NO: 346) | 130, 132, 134 | 127, 128, 129 |
| 115 | LEGWCLHPLCLWGAG (SEQ ID NO: 230) | ISSGLLSGRSANP (SEQ ID NO: 347) | 130, 132, 134 | 127, 128, 129 |
| 116 | LEGWCLHPLCLWGAG (SEQ ID NO: 230) | ISSGLLSGRSANI (SEQ ID NO: 348) | 130, 132, 134 | 127, 128, 129 |
| 117 | LEGWCLHPLCLWGAG (SEQ ID NO: 230) | ISSGLLSGRSDNI (SEQ ID NO: 357) | 130, 132, 134 | 127, 128, 129 |
| 118 | LEGWCLHPLCLWGAG (SEQ ID NO: 230) | AVGLLAPPGGLSGRSDNH (SEQ ID NO: 76) | 130, 132, 134 | 127, 128, 129 |
| 119 | LEGWCLHPLCLWGAG (SEQ ID NO: 230) | AVGLLAPPGGLSGRSDDH (SEQ ID NO: 349) | 130, 132, 134 | 127, 128, 129 |
| 120 | LEGWCLHPLCLWGAG (SEQ ID NO: 230) | AVGLLAPPGGLSGRSDIH (SEQ ID NO: 350) | 130, 132, 134 | 127, 128, 129 |
| 121 | LEGWCLHPLCLWGAG (SEQ ID NO: 230) | AVGLLAPPGGLSGRSDQH (SEQ ID NO: 351) | 130, 132, 134 | 127, 128, 129 |
| 122 | LEGWCLHPLCLWGAG (SEQ ID NO: 230) | AVGLLAPPGGLSGRSDTH (SEQ ID NO: 352) | 130, 132, 134 | 127, 128, 129 |
| 123 | LEGWCLHPLCLWGAG (SEQ ID NO: 230) | AVGLLAPPGGLSGRSDYH (SEQ ID NO: 353) | 130, 132, 134 | 127, 128, 129 |
| 124 | LEGWCLHPLCLWGAG (SEQ ID NO: 230) | AVGLLAPPGGLSGRSDNP (SEQ ID NO: 354) | 130, 132, 134 | 127, 128, 129 |
| 125 | LEGWCLHPLCLWGAG (SEQ ID NO: 230) | AVGLLAPPGGLSGRSANP (SEQ ID NO: 355) | 130, 132, 134 | 127, 128, 129 |
| 126 | LEGWCLHPLCLWGAG (SEQ ID NO: 230) | AVGLLAPPGGLSGRSANI (SEQ ID NO: 356) | 130, 132, 134 | 127, 128, 129 |
| 127 | LEGWCLHPLCLWGAG (SEQ ID NO: 230) | AVGLLAPPGGLSGRSDNI (SEQ ID NO: 358) | 130, 132, 134 | 127, 128, 129 |

TABLE A-continued

Anti-CD166 Activatable Antibody Combinations

| Comb. No. | Mask Sequence (MM) | Substrate Sequence (CM) | VL CDRs SEQ ID NOs | VH CDRs SEQ ID NOs |
|---|---|---|---|---|
| 128 | LEGWCLHPLCLWGAG (SEQ ID NO: 230) | ISSGLLSSGGSGGSLSGRSDNH (SEQ ID NO: 71) | 130, 132, 134 | 127, 128, 129 |

TABLE B

Anti-Cd166 Activatable Antibody Components

| Mask Sequence (MM) | Substrate Sequence (CM) | VL or VL CDRs | VH or VH CDRs |
|---|---|---|---|
| LCHPLVLSAWESCSS (SEQ ID NO: 219) | LSGRSDNH (SEQ ID NO: 21) | SEQ ID NOS: 130, 132, 134 | SEQ ID NOS: 121, 128, 129 |
| LCAPLVLSAWESCSS (SEQ ID NO: 220) | TGRGPSWV (SEQ ID NO: 18) | SEQ ID NO: 123 | SEQ ID NO: 121 |
| LCHALVLSAWESCSS (SEQ ID NO: 221) | PLTGRSGG (SEQ ID NO: 24) | SEQ ID NO: 124 | SEQ ID NO: 122 |
| LCHPAVLSAWESCSS (SEQ ID NO: 222) | TARGPSFK (SEQ ID NO: 20) | SEQ ID NO: 125 | |
| LCHPLALSAWESCSS (SEQ ID NO: 223) | NTLSGRSENHSG (SEQ ID NO: 59) | SEQ ID NO: 126 | |
| LCHPLVASAWESCSS (SEQ ID NO: 224) | NTLSGRSGNEGS (SEQ ID NO: 60) | SEQ ID NOS: 131, 133, 134 | |
| LCHPLVLSAAESCSS (SEQ ID NO: 225) | TSTSGRSANPRG (SEQ ID NO: 61) | | |
| LCHPLVLSAWASCSS (SEQ ID NO: 227) | TSGRSANP (SEQ ID NO: 62) | | |
| HPLVL (SEQ ID NO: 228) | VHMPLGFLGP (SEQ ID NO: 32) | | |
| HPL (SEQ ID NO: 229) | AVGLLAPP (SEQ ID NO: 52) | | |
| LEGWCLHPLCLWGAG (SEQ ID NO: 230) | AQNLLGMV (SEQ ID NO: 40) | | |
| LEGACLHPLCLWGAG (SEQ ID NO: 231) | QNQALRMA (SEQ ID NO: 39) | | |
| LEGWCAHPLCLINGAG (SEQ ID NO: 232) | LAAPLGLL (SEQ ID NO: 51) | | |
| LEGWCLAPLCLWGAG (SEQ ID NO: 233) | STFPFGME (SEQ ID NO: 41) | | |
| LEGWCLHACLWGAG (SEQ ID NO: 234) | ISSGLLSS (SEQ ID NO: 44) | | |
| LEGINCLHPACLWGAG (SEQ ID NO: 235) | PAGLWLDP (SEQ ID NO: 54) | | |
| LEGWCLHPLCAWGAG (SEQ ID NO: 236) | VAGRSMRP (SEQ ID NO: 63) | | |
| LEGWCLHPLCLAGAG (SEQ ID NO: 237) | VVPEGRRS (SEQ ID NO: 64) | | |
| CLHPLC (SEQ ID NO: 238) | TLPRSPAF (SEQ ID NO: 65) | | |
| | MVLGRSLL (SEQ ID NO: 66) | | |
| | QGRAITFT (SEQ ID NO: 67) | | |
| | SPRSIMLA (SEQ ID NO: 68) | | |
| | SMLRSMPL (SEQ ID NO: 69) | | |
| | ISSGLLSGRSDNH (SEQ ID NO: 70) | | |
| | AVGLLAPPGGLSGRSDNH (SEQ ID NO: 76) | | |
| | ISSGLLSSGGSGGSLSGRSDNE (SEQ ID NO: 71) | | |
| | LSGRSGNH (SEQ ID NO: 318) | | |
| | SGRSANPRG (SEQ ID NO: 319) | | |
| | LSGRSDDH (SEQ ID NO: 320) | | |
| | LSGRSDIH (SEQ ID NO: 321) | | |
| | LSGRSDQH (SEQ ID NO: 322) | | |
| | LSGRSDTH (SEQ ID NO: 323) | | |
| | LSGRSDYH (SEQ ID NO: 324) | | |
| | LSGRSDNP (SEQ ID NO: 325) | | |
| | LSGRSANP (SEQ ID NO: 326) | | |
| | LSGRSANI (SEQ ID NO: 327) | | |
| | LSGRSDNI (SEQ ID NO: 328) | | |
| | MIAPVAYR (SEQ ID NO: 329) | | |

TABLE B-continued

Anti-Cd166 Activatable Antibody Components

| Mask Sequence (MM) | Substrate Sequence (CM) | VL or VL CDRs | VH or VH CDRs |
|---|---|---|---|
| | RPSPMWAY (SEQ ID NO: 330) | | |
| | WATPRPMR (SEQ ID NO: 331) | | |
| | FRLLDWQW (SEQ ID NO: 332) | | |
| | ISSGL (SEQ ID NO: 333) | | |
| | ISSGLLS (SEQ ID NO: 334) | | |
| | ISSGLL (SEQ ID NO: 335) | | |
| | ISSGLLSGRSANPRG (SEQ ID NO: 338) | | |
| | AVGLLAPPTSGRSANPRG (SEQ ID NO: 339) | | |
| | AVGLLAPPSGRSANPRG (SEQ ID NO: 340) | | |
| | ISSGLLSGRSDDH (SEQ ID NO: 341) | | |
| | ISSGLLSGRSDIH (SEQ ID NO: 342) | | |
| | ISSGLLSGRSDQH (SEQ ID NO: 343) | | |
| | ISSGLLSGRSDTH (SEQ ID NO: 344) | | |
| | ISSGLLSGRSDYH (SEQ ID NO: 345) | | |
| | ISSGLLSGRSDNP (SEQ ID NO: 346) | | |
| | ISSGLLSGRSANP (SEQ ID NO: 347) | | |
| | ISSGLLSGRSANI (SEQ ID NO: 348) | | |
| | AVGLLAPPGGLSGRSDDH (SEQ ID NO: 349) | | |
| | AVGLLAPPGGLSGRSDIH (SEQ ID NO: 350) | | |
| | AVGLLAPPGGLSGRSDQH (SEQ ID NO: 351) | | |
| | AVGLLAPPGGLSGRSDTH (SEQ ID NO: 352) | | |
| | AVGLLAPPGGLSGRSDYH (SEQ ID NO: 353) | | |
| | AVGLLAPPGGLSGRSDNP (SEQ ID NO: 354) | | |
| | AVGLLAPPGGLSGRSANP (SEQ ID NO: 355) | | |
| | AVGLLAPPGGLSGRSANI (SEQ ID NO: 356) | | |
| | ISSGLLSGRSDNI (SEQ ID NO: 357) | | |
| | AVGLLAPPGGLSGRSDNI (SEQ ID NO: 358) | | |
| | GLSGRSDNHGGAVGLLAPP (SEQ ID NO: 336) | | |
| | GLSGRSDNHGGVHMPLGFLGP (SEQ ID NO: 337) | | |

In some embodiments, an activatable antibody of the present disclosure includes one or more polypeptides that include the combination of sequences selected from Table A or Table B, where the polypeptide includes a combination of a masking sequence selected from the column titled "Mask Sequence (MM)" of Table A or Table B, a substrate sequence from the column titled "Substrate Sequence (CM)" of Table A or Table B, a light chain variable domain or light chain CDRs from the column titled "VL or VL CDRs" or "VL CDRs SEQ ID NOs" of Table A or Table B, and a heavy chain variable domain or heavy chain CDRs from the column titled "VH or VH CDRs" or "VH CDRs SEQ ID Nos" of Table A or Table B. For example, an activatable antibody of the present disclosure includes the amino acid sequences of combination no. 54, which includes the masking sequence of SEQ ID NO: 222, the substrate sequence of SEQ ID NO: 76, a light chain variable domain that includes the VL CDR sequences of SEQ ID NOS: 130, 132, and 134, and a heavy chain variable domain that includes the VH CDR sequences of 127, 128, and 129. Therefore, an activatable antibody that includes at least the combination of sequences in any given row of Table A is described herein. Similarly, any combination of a mask sequence (MM), a substrate sequence (CM), a light chain variable domain sequence or light chain variable domain CDR sequences, and a heavy chain variable domain sequence or heavy chain variable domain CDR sequences of Table B is described herein. An activatable antibody that includes at least any combination of a masking sequence, a substrate sequence, a variable heavy chain or variable heavy chain CDRs, and a variable light chain or variable light chain CDRs selected from the corresponding columns Table A or Table B is also described herein. In some exemplary embodiments, an activatable antibody that includes at least the combination of sequences in any given row of Table A or any combination of a mask sequence (MM), a substrate sequence (CM), a light chain variable domain sequence or light chain variable domain CDR sequences, and a heavy chain variable domain sequence or heavy chain variable domain CDR sequences of Table B can be combined with one or more toxins, including a dolastatin or a derivative thereof, an auristatin or a derivative thereof, a maytansinoid or a derivative thereof, a duocarmycin or a derivative thereof, a calicheamicin or a derivative thereof, or a pyrrolobenzodiazepine or a derivative thereof. In some exemplary embodiments, an activatable antibody that includes at least the combination of sequences in any given row of Table A or any combination of a mask sequence (MM), a substrate sequence (CM), a light chain variable domain sequence or light chain variable domain CDR sequences, and a heavy chain variable domain sequence or heavy chain variable domain CDR sequences of Table B can be combined with one or more toxins, including auristatin E, monomethyl auristatin F (MMAF), monomethyl auristatin E (MMAE), monomethyl auristatin D (MMAD), maytansinoid DM4, maytansinoid DM1, a pyrrolobenzodiazepine, a pyrrolobenzodiazepine dimer, and/or a duocarmycin.

Any of the combinations in Table A or Table B as described above can be combined with human immunoglobulin constant regions to result in fully human IgGs including IgG1, IgG2, IgG4 or mutated constant regions to result in human IgGs with altered functions such as IgG1 N297A, IgG1 N297Q, or IgG4 S228P. The combinations described in Table A or Table B are not limited by the particular combinations shown in any given row, and thus may include any mask sequence from column 2 of Table A (or column 1 of Table B) combined with any substrate sequence from column 3 of Table A (or column 2 of Table B) combined with any VL sequence or set of VL CDR sequences from column 4 of Table A (or column 3 or Table B) combined with any VH sequence or set of VH CDR sequences from column 5 of Table A (or column 4 of Table B). In addition to the mask sequences disclosed in column 2 of Table A or column 1 of Table B, any mask sequence disclosed herein can be used in a combination. In addition to the substrate sequences disclosed in column 3 of Table A or column 2 of Table B, any CM disclosed herein can be used in a combination. In addition to the light chain variable region sequence or light chain CDR sequences disclosed in column 4 of Table A or column 3 of Table B, any light chain variable region sequence or light chain CDR sequences disclosed herein can be used in a combination. In addition to the heavy chain variable region sequence or heavy chain CDR sequences disclosed in column 5 of Table A or column 4 of Table B, any heavy chain variable region sequence or heavy chain CDR sequences disclosed herein can be used in a combination.

In some embodiments, the antibody drug conjugates (ADCs) and activatable antibody drug conjugates (AADCs) can include one or more polypeptides that include the combination of a light chain sequence or a light chain variable domain sequence, and a heavy chain sequence or a heavy chain variable domain sequences, a linker, and a toxin in a given row of Table C or any combination of a light chain sequence or a light chain variable domain sequence, and a heavy chain sequence or a heavy chain variable domain sequence, a linker, and a toxin of Table C.

TABLE C

Anti-CD166 ADC and Anti-CD166 Activatable ADC Combinations

| Comb. No. | Heavy Chain (HC) or HC Variable Region SEQ ID NO. | Light Chain (LC) or LC Variable Region SEQ ID NO. | Linker | Toxin |
|---|---|---|---|---|
| 1 | 122 | 123 | vc | MMAD |
| 2 | 122 | 123 | PEG2-vc | MMAD |
| 3 | 122 | 123 | vc | MMAE |
| 4 | 122 | 123 | vc | duocarmycin |
| 5 | 122 | 123 | spdb | DM4 |
| 6 | 239 | 240 | vc | MMAD |
| 7 | 239 | 240 | PEG2-vc | MMAD |
| 8 | 239 | 240 | vc | MMAE |
| 9 | 239 | 240 | vc | duocarmycin |
| 10 | 239 | 240 | spdb | DM4 |
| 11 | 239 | 242 | vc | MMAD |
| 12 | 239 | 242 | PEG2-vc | MMAD |
| 13 | 239 | 242 | vc | MMAE |
| 14 | 239 | 242 | vc | duocarmycin |
| 15 | 239 | 242 | spdb | DM4 |
| 16 | 239 | 310 | vc | MMAD |
| 17 | 239 | 310 | PEG2-vc | MMAD |
| 18 | 239 | 310 | vc | MMAE |
| 19 | 239 | 310 | vc | duocarmycin |
| 20 | 239 | 310 | spdb | DM4 |
| 21 | 122 | 363 | vc | MMAD |
| 22 | 122 | 363 | PEG2-vc | MMAD |
| 23 | 122 | 363 | vc | MMAE |
| 24 | 122 | 363 | vc | duocarmycin |
| 25 | 122 | 363 | spdb | DM4 |
| 26 | 122 | 364 | vc | MMAD |
| 27 | 122 | 364 | PEG2-vc | MMAD |
| 28 | 122 | 364 | vc | MMAE |
| 29 | 122 | 364 | vc | duocarmycin |
| 30 | 122 | 364 | spdb | DM4 |
| 31 | 239 | 244 | vc | MMAD |
| 32 | 239 | 244 | PEG2-vc | MMAD |
| 33 | 239 | 244 | vc | MMAE |
| 34 | 239 | 244 | vc | duocarmycin |
| 35 | 239 | 244 | spdb | DM4 |
| 36 | 239 | 312 | vc | MMAD |
| 37 | 239 | 312 | PEG2-vc | MMAD |
| 38 | 239 | 312 | vc | MMAE |
| 39 | 239 | 312 | vc | duocarmycin |
| 40 | 239 | 312 | spdb | DM4 |
| 41 | 122 | 365 | vc | MMAD |
| 42 | 122 | 365 | PEG2-vc | MMAD |
| 43 | 122 | 365 | vc | MMAE |
| 44 | 122 | 365 | vc | duocarmycin |
| 45 | 122 | 365 | spdb | DM4 |
| 46 | 122 | 366 | vc | MMAD |
| 47 | 122 | 366 | PEG2-vc | MMAD |
| 48 | 122 | 366 | vc | MMAE |
| 49 | 122 | 366 | vc | duocarmycin |
| 50 | 122 | 366 | spdb | DM4 |
| 51 | 239 | 246 | vc | MMAD |
| 52 | 239 | 246 | PEG2-vc | MMAD |
| 53 | 239 | 246 | vc | MMAE |
| 54 | 239 | 246 | vc | duocarmycin |
| 55 | 239 | 246 | spdb | DM4 |
| 56 | 239 | 314 | vc | MMAD |
| 57 | 239 | 314 | PEG2-vc | MMAD |
| 58 | 239 | 314 | vc | MMAE |
| 59 | 239 | 314 | vc | duocarmycin |
| 60 | 239 | 314 | spdb | DM4 |
| 61 | 122 | 367 | vc | MMAD |
| 62 | 122 | 367 | PEG2-vc | MMAD |
| 63 | 122 | 367 | vc | MMAE |
| 64 | 122 | 367 | vc | duocarmycin |
| 65 | 122 | 367 | spdb | DM4 |
| 66 | 122 | 368 | vc | MMAD |
| 67 | 122 | 368 | PEG2-vc | MMAD |
| 68 | 122 | 368 | vc | MMAE |
| 69 | 122 | 368 | vc | duocarmycin |
| 70 | 122 | 368 | spdb | DM4 |
| 71 | 239 | 303 | vc | MMAD |
| 72 | 239 | 303 | PEG2-vc | MMAD |

TABLE C-continued

Anti-CD166 ADC and Anti-CD166 Activatable ADC Combinations

| Comb. No. | Heavy Chain (HC) or HC Variable Region SEQ ID NO. | Light Chain (LC) or LC Variable Region SEQ ID NO. | Linker | Toxin |
|---|---|---|---|---|
| 73 | 239 | 303 | vc | MMAE |
| 74 | 239 | 303 | vc | duocarmycin |
| 75 | 239 | 303 | spdb | DM4 |
| 76 | 239 | 316 | vc | MMAD |
| 77 | 239 | 316 | PEG2-vc | MMAD |
| 78 | 239 | 316 | vc | MMAE |
| 79 | 239 | 316 | vc | duocarmycin |
| 80 | 239 | 316 | spdb | DM4 |
| 81 | 122 | 369 | vc | MMAD |
| 82 | 122 | 369 | PEG2-vc | MMAD |
| 83 | 122 | 369 | vc | MMAE |
| 84 | 122 | 369 | vc | duocarmycin |
| 85 | 122 | 369 | spdb | DM4 |
| 86 | 122 | 370 | vc | MMAD |
| 87 | 122 | 370 | PEG2-vc | MMAD |
| 88 | 122 | 370 | vc | MMAE |
| 89 | 122 | 370 | vc | duocarmycin |
| 90 | 122 | 370 | spdb | DM4 |
| 91 | 239 | 387 | vc | MMAD |
| 92 | 239 | 387 | PEG2-vc | MMAD |
| 93 | 239 | 387 | vc | MMAE |
| 94 | 239 | 387 | vc | duocarmycin |
| 95 | 239 | 387 | spdb | DM4 |
| 96 | 239 | 388 | vc | MMAD |
| 97 | 239 | 388 | PEG2-vc | MMAD |
| 98 | 239 | 388 | vc | MMAE |
| 99 | 239 | 388 | vc | duocarmycin |
| 100 | 239 | 388 | spdb | DM4 |
| 101 | 122 | 389 | vc | MMAD |
| 102 | 122 | 389 | PEG2-vc | MMAD |
| 103 | 122 | 389 | vc | MMAE |
| 104 | 122 | 389 | vc | duocarmycin |
| 105 | 122 | 389 | spdb | DM4 |
| 106 | 122 | 390 | vc | MMAD |
| 107 | 122 | 390 | PEG2-vc | MMAD |
| 108 | 122 | 390 | vc | MMAE |
| 109 | 122 | 390 | vc | duocarmycin |
| 110 | 122 | 390 | spdb | DM4 |
| 111 | 239 | 391 | vc | MMAD |
| 112 | 239 | 391 | PEG2-vc | MMAD |
| 113 | 239 | 391 | vc | MMAE |
| 114 | 239 | 391 | vc | duocarmycin |
| 115 | 239 | 391 | spdb | DM4 |
| 116 | 239 | 392 | vc | MMAD |
| 117 | 239 | 392 | PEG2-vc | MMAD |
| 118 | 239 | 392 | vc | MMAE |
| 119 | 239 | 392 | vc | duocarmycin |
| 120 | 239 | 392 | spdb | DM4 |
| 121 | 122 | 393 | vc | MMAD |
| 122 | 122 | 393 | PEG2-vc | MMAD |
| 123 | 122 | 393 | vc | MMAE |
| 124 | 122 | 393 | vc | duocarmycin |
| 125 | 122 | 393 | spdb | DM4 |
| 126 | 122 | 394 | vc | MMAD |
| 127 | 122 | 394 | PEG2-vc | MMAD |
| 128 | 122 | 394 | vc | MMAE |
| 129 | 122 | 394 | vc | duocarmycin |
| 130 | 122 | 394 | spdb | DM4 |
| 131 | 239 | 395 | vc | MMAD |
| 132 | 239 | 395 | PEG2-vc | MMAD |
| 133 | 239 | 395 | vc | MMAE |
| 134 | 239 | 395 | vc | duocarmycin |
| 135 | 239 | 395 | spdb | DM4 |
| 136 | 239 | 396 | vc | MMAD |
| 137 | 239 | 396 | PEG2-vc | MMAD |
| 138 | 239 | 396 | vc | MMAE |
| 139 | 239 | 396 | vc | duocarmycin |
| 140 | 239 | 396 | spdb | DM4 |
| 141 | 122 | 397 | vc | MMAD |
| 142 | 122 | 397 | PEG2-vc | MMAD |
| 143 | 122 | 397 | vc | MMAE |
| 144 | 122 | 397 | vc | duocarmycin |
| 145 | 122 | 397 | spdb | DM4 |
| 146 | 122 | 398 | vc | MMAD |
| 147 | 122 | 398 | PEG2-vc | MMAD |
| 148 | 122 | 398 | vc | MMAE |
| 149 | 122 | 398 | vc | duocarmycin |
| 150 | 122 | 398 | spdb | DM4 |
| 151 | 239 | 399 | vc | MMAD |
| 152 | 239 | 399 | PEG2-vc | MMAD |
| 153 | 239 | 399 | vc | MMAE |
| 154 | 239 | 399 | vc | duocarmycin |
| 155 | 239 | 399 | spdb | DM4 |
| 156 | 239 | 400 | vc | MMAD |
| 157 | 239 | 400 | PEG2-vc | MMAD |
| 158 | 239 | 400 | vc | MMAE |
| 159 | 239 | 400 | vc | duocarmycin |
| 160 | 239 | 400 | spdb | DM4 |
| 161 | 122 | 401 | vc | MMAD |
| 162 | 122 | 401 | PEG2-vc | MMAD |
| 163 | 122 | 401 | vc | MMAE |
| 164 | 122 | 401 | vc | duocarmycin |
| 165 | 122 | 401 | spdb | DM4 |
| 166 | 122 | 402 | vc | MMAD |
| 167 | 122 | 402 | PEG2-vc | MMAD |
| 168 | 122 | 402 | vc | MMAE |
| 169 | 122 | 402 | vc | duocarmycin |
| 170 | 122 | 402 | spdb | DM4 |
| 171 | 239 | 427 | vc | MMAD |
| 172 | 239 | 427 | PEG2-vc | MMAD |
| 173 | 239 | 427 | vc | MMAE |
| 174 | 239 | 427 | vc | duocarmycin |
| 175 | 239 | 427 | spdb | DM4 |
| 176 | 239 | 428 | vc | MMAD |
| 177 | 239 | 428 | PEG2-vc | MMAD |
| 178 | 239 | 428 | vc | MMAE |
| 179 | 239 | 428 | vc | duocarmycin |
| 180 | 239 | 428 | spdb | DM4 |
| 181 | 122 | 429 | vc | MMAD |
| 182 | 122 | 429 | PEG2-vc | MMAD |
| 183 | 122 | 429 | vc | MMAE |
| 184 | 122 | 429 | vc | duocarmycin |
| 185 | 122 | 429 | spdb | DM4 |
| 186 | 122 | 430 | vc | MMAD |
| 187 | 122 | 430 | PEG2-vc | MMAD |
| 188 | 122 | 430 | vc | MMAE |
| 189 | 122 | 430 | vc | duocarmycin |
| 190 | 122 | 430 | spdb | DM4 |
| 191 | 239 | 431 | vc | MMAD |
| 192 | 239 | 431 | PEG2-vc | MMAD |
| 193 | 239 | 431 | vc | MMAE |
| 194 | 239 | 431 | vc | duocarmycin |
| 195 | 239 | 431 | spdb | DM4 |
| 196 | 239 | 432 | vc | MMAD |
| 197 | 239 | 432 | PEG2-vc | MMAD |
| 198 | 239 | 432 | vc | MMAE |
| 199 | 239 | 432 | vc | duocarmycin |
| 200 | 239 | 432 | spdb | DM4 |
| 201 | 122 | 433 | vc | MMAD |
| 202 | 122 | 433 | PEG2-vc | MMAD |
| 203 | 122 | 433 | vc | MMAE |
| 204 | 122 | 433 | vc | duocarmycin |
| 205 | 122 | 433 | spdb | DM4 |
| 206 | 122 | 434 | vc | MMAD |
| 207 | 122 | 434 | PEG2-vc | MMAD |
| 208 | 122 | 434 | vc | MMAE |
| 209 | 122 | 434 | vc | duocarmycin |
| 210 | 122 | 434 | spdb | DM4 |
| 211 | 239 | 435 | vc | MMAD |
| 212 | 239 | 435 | PEG2-vc | MMAD |
| 213 | 239 | 435 | vc | MMAE |
| 214 | 239 | 435 | vc | duocarmycin |
| 215 | 239 | 435 | spdb | DM4 |
| 216 | 239 | 436 | vc | MMAD |

TABLE C-continued

Anti-CD166 ADC and Anti-CD166 Activatable ADC Combinations

| Comb. No. | Heavy Chain (HC) or HC Variable Region SEQ ID NO. | Light Chain (LC) or LC Variable Region SEQ ID NO. | Linker | Toxin |
|---|---|---|---|---|
| 217 | 239 | 436 | PEG2-vc | MMAD |
| 218 | 239 | 436 | vc | MMAE |
| 219 | 239 | 436 | vc | duocarmycin |
| 220 | 239 | 436 | spdb | DM4 |
| 221 | 122 | 437 | vc | MMAD |
| 222 | 122 | 437 | PEG2-vc | MMAD |
| 223 | 122 | 437 | vc | MMAE |
| 224 | 122 | 437 | vc | duocarmycin |
| 225 | 122 | 437 | spdb | DM4 |
| 226 | 122 | 438 | vc | MMAD |
| 227 | 122 | 438 | PEG2-vc | MMAD |
| 228 | 122 | 438 | vc | MMAE |
| 229 | 122 | 438 | vc | duocarmycin |
| 230 | 122 | 438 | spdb | DM4 |
| 231 | 239 | 439 | vc | MMAD |
| 232 | 239 | 439 | PEG2-vc | MMAD |
| 233 | 239 | 439 | vc | MMAE |
| 234 | 239 | 439 | vc | duocarmycin |
| 235 | 239 | 439 | spdb | DM4 |
| 236 | 239 | 440 | vc | MMAD |
| 237 | 239 | 440 | PEG2-vc | MMAD |
| 238 | 239 | 440 | vc | MMAE |
| 239 | 239 | 440 | vc | duocarmycin |
| 240 | 239 | 440 | spdb | DM4 |
| 241 | 122 | 441 | vc | MMAD |
| 242 | 122 | 441 | PEG2-vc | MMAD |
| 243 | 122 | 441 | vc | MMAE |
| 244 | 122 | 441 | vc | duocarmycin |
| 245 | 122 | 441 | spdb | DM4 |
| 246 | 122 | 442 | vc | MMAD |
| 247 | 122 | 442 | PEG2-vc | MMAD |
| 248 | 122 | 442 | vc | MMAE |
| 249 | 122 | 442 | vc | duocarmycin |
| 250 | 122 | 442 | spdb | DM4 |
| 251 | 239 | 451 | vc | MMAD |
| 252 | 239 | 451 | PEG2-vc | MMAD |
| 253 | 239 | 451 | vc | MMAE |
| 254 | 239 | 451 | vc | duocarmycin |
| 255 | 239 | 451 | spdb | DM4 |
| 256 | 239 | 452 | vc | MMAD |
| 257 | 239 | 452 | PEG2-vc | MMAD |
| 258 | 239 | 452 | vc | MMAE |
| 259 | 239 | 452 | vc | duocarmycin |
| 260 | 239 | 452 | spdb | DM4 |
| 261 | 122 | 453 | vc | MMAD |
| 262 | 122 | 453 | PEG2-vc | MMAD |
| 263 | 122 | 453 | vc | MMAE |
| 264 | 122 | 453 | vc | duocarmycin |
| 265 | 122 | 453 | spdb | DM4 |
| 266 | 122 | 454 | vc | MMAD |
| 267 | 122 | 454 | PEG2-vc | MMAD |
| 268 | 122 | 454 | vc | MMAE |
| 269 | 122 | 454 | vc | duocarmycin |
| 270 | 122 | 454 | spdb | DM4 |
| 271 | 239 | 455 | vc | MMAD |
| 272 | 239 | 455 | PEG2-vc | MMAD |
| 273 | 239 | 455 | vc | MMAE |
| 274 | 239 | 455 | vc | duocarmycin |
| 275 | 239 | 455 | spdb | DM4 |
| 276 | 239 | 456 | vc | MMAD |
| 277 | 239 | 456 | PEG2-vc | MMAD |
| 278 | 239 | 456 | vc | MMAE |
| 279 | 239 | 456 | vc | duocarmycin |
| 280 | 239 | 456 | spdb | DM4 |
| 281 | 122 | 457 | vc | MMAD |
| 282 | 122 | 457 | PEG2-vc | MMAD |
| 283 | 122 | 457 | vc | MMAE |
| 284 | 122 | 457 | vc | duocarmycin |
| 285 | 122 | 457 | spdb | DM4 |
| 286 | 122 | 458 | vc | MMAD |
| 287 | 122 | 458 | PEG2-vc | MMAD |
| 288 | 122 | 458 | vc | MMAE |
| 289 | 122 | 458 | vc | duocarmycin |
| 290 | 122 | 458 | spdb | DM4 |
| 291 | 239 | 459 | vc | MMAD |
| 292 | 239 | 459 | PEG2-vc | MMAD |
| 293 | 239 | 459 | vc | MMAE |
| 294 | 239 | 459 | vc | duocarmycin |
| 295 | 239 | 459 | spdb | DM4 |
| 296 | 239 | 460 | vc | MMAD |
| 297 | 239 | 460 | PEG2-vc | MMAD |
| 298 | 239 | 460 | vc | MMAE |
| 299 | 239 | 460 | vc | duocarmycin |
| 300 | 239 | 460 | spdb | DM4 |
| 301 | 122 | 461 | vc | MMAD |
| 302 | 122 | 461 | PEG2-vc | MMAD |
| 303 | 122 | 461 | vc | MMAE |
| 304 | 122 | 461 | vc | duocarmycin |
| 305 | 122 | 461 | spdb | DM4 |
| 306 | 122 | 462 | vc | MMAD |
| 307 | 122 | 462 | PEG2-vc | MMAD |
| 308 | 122 | 462 | vc | MMAE |
| 309 | 122 | 462 | vc | duocarmycin |
| 310 | 122 | 462 | spdb | DM4 |
| 311 | 239 | 463 | vc | MMAD |
| 312 | 239 | 463 | PEG2-vc | MMAD |
| 313 | 239 | 463 | vc | MMAE |
| 314 | 239 | 463 | vc | duocarmycin |
| 315 | 239 | 463 | spdb | DM4 |
| 316 | 239 | 464 | vc | MMAD |
| 317 | 239 | 464 | PEG2-vc | MMAD |
| 478 | 239 | 464 | vc | MMAE |
| 319 | 239 | 464 | vc | duocarmycin |
| 320 | 239 | 464 | spdb | DM4 |
| 321 | 122 | 465 | vc | MMAD |
| 322 | 122 | 465 | PEG2-vc | MMAD |
| 323 | 122 | 465 | vc | MMAE |
| 324 | 122 | 465 | vc | duocarmycin |
| 325 | 122 | 465 | spdb | DM4 |
| 326 | 122 | 466 | vc | MMAD |
| 327 | 122 | 466 | PEG2-vc | MMAD |
| 328 | 122 | 466 | vc | MMAE |
| 329 | 122 | 466 | vc | duocarmycin |
| 330 | 122 | 466 | spdb | DM4 |
| 331 | 239 | 467 | vc | MMAD |
| 332 | 239 | 467 | PEG2-vc | MMAD |
| 333 | 239 | 467 | vc | MMAE |
| 334 | 239 | 467 | vc | duocarmycin |
| 335 | 239 | 467 | spdb | DM4 |
| 336 | 239 | 468 | vc | MMAD |
| 337 | 239 | 468 | PEG2-vc | MMAD |
| 338 | 239 | 468 | vc | MMAE |
| 339 | 239 | 468 | vc | duocarmycin |
| 340 | 239 | 468 | spdb | DM4 |
| 341 | 122 | 469 | vc | MMAD |
| 342 | 122 | 469 | PEG2-vc | MMAD |
| 343 | 122 | 469 | vc | MMAE |
| 344 | 122 | 469 | vc | duocarmycin |
| 345 | 122 | 469 | spdb | DM4 |
| 346 | 122 | 470 | vc | MMAD |
| 347 | 122 | 470 | PEG2-vc | MMAD |
| 348 | 122 | 470 | vc | MMAE |
| 349 | 122 | 470 | vc | duocarmycin |
| 350 | 122 | 470 | spdb | DM4 |
| 351 | 239 | 471 | vc | MMAD |
| 352 | 239 | 471 | PEG2-vc | MMAD |
| 353 | 239 | 471 | vc | MMAE |
| 354 | 239 | 471 | vc | duocarmycin |
| 355 | 239 | 471 | spdb | DM4 |
| 356 | 239 | 472 | vc | MMAD |
| 357 | 239 | 472 | PEG2-vc | MMAD |
| 358 | 239 | 472 | vc | MMAE |
| 359 | 239 | 472 | vc | duocarmycin |
| 360 | 239 | 472 | spdb | DM4 |

TABLE C-continued

Anti-CD166 ADC and Anti-CD166 Activatable ADC Combinations

| Comb. No. | Heavy Chain (HC) or HC Variable Region SEQ ID NO. | Light Chain (LC) or LC Variable Region SEQ ID NO. | Linker | Toxin |
|---|---|---|---|---|
| 361 | 122 | 473 | vc | MMAD |
| 362 | 122 | 473 | PEG2-vc | MMAD |
| 363 | 122 | 473 | vc | MMAE |
| 364 | 122 | 473 | vc | duocarmycin |
| 365 | 122 | 473 | spdb | DM4 |
| 366 | 122 | 474 | vc | MMAD |
| 367 | 122 | 474 | PEG2-vc | MMAD |
| 368 | 122 | 474 | vc | MMAE |
| 369 | 122 | 474 | vc | duocarmycin |
| 370 | 122 | 474 | spdb | DM4 |

An antibody drug conjugate (ADC) of the present disclosure or activatable antibody drug conjugate (AADC) of the present disclosure may include one or more polypeptides that include the combination of amino acid sequences, a linker, and a toxin listed in a given row of Table C. Therefore, an activatable antibody drug conjugate (ADC) of the present disclosure or activatable antibody drug conjugate (AADC) of the present disclosure that includes the combination of amino acid sequences, a linker, and a toxin listed in a given row or provided as a specific combination is described herein. For example, an activatable antibody drug conjugate of the present disclosure may include the amino acid sequences of combination no. 55, which includes a heavy chain comprising the amino acid sequence of SEQ ID NO: 239, a light chain comprising the amino acid sequence of SEQ ID NO: 246, and a spdb-DM4 linker-toxin. In another example of the AADCs disclosed and described herein, an activatable antibody drug conjugate of the present disclosure may include the amino acid sequences of combination no. 33, which includes a heavy chain comprising the amino acid sequence of SEQ ID NO: 239, a light chain comprising the amino acid sequence of SEQ ID NO: 244, and a vc-MMAE linker-toxin.

Any of the combinations in Table C that list a heavy chain and light chain variable region can be combined with human immunoglobulin constant regions to result in fully human IgGs including IgG1, IgG2, IgG4 or mutated constant regions to result in human IgGs with altered functions such as IgG1 N297A, IgG1 N297Q, or IgG4 S228P. The combinations described in Table C are not limited by the particular combinations shown in any given row, and thus can include any heavy chain sequence or heavy chain variable region sequence from column 2 of Table C combined with any light chain sequence or light chain variable region sequence from column 3 of Table C combined with any linker from column 4 combined with any toxin from column 5. In addition to the heavy chain sequences or heavy chain variable region sequences listed in column 2, any heavy chain sequence or heavy chain variable region sequence disclosed herein can be used in a combination. In addition to the light chain sequences or light chain variable region sequences listed in column 3, any light chain sequence or light chain variable region sequence disclosed herein can be used in a combination. In addition to the linkers listed in column 4, any linker disclosed herein can be used in a combination. In addition to the toxins listed in column 5, any toxin disclosed herein can be used in a combination.

In some embodiments, the serum half-life of the activatable antibody is longer than that of the corresponding antibody; e.g., the pK of the activatable antibody is longer than that of the corresponding antibody. In some embodiments, the serum half-life of the activatable antibody is similar to that of the corresponding antibody. In some embodiments, the serum half-life of the activatable antibody is at least 15 days when administered to an organism. In some embodiments, the serum half-life of the activatable antibody is at least 12 days when administered to an organism. In some embodiments, the serum half-life of the activatable antibody is at least 11 days when administered to an organism. In some embodiments, the serum half-life of the activatable antibody is at least 10 days when administered to an organism. In some embodiments, the serum half-life of the activatable antibody is at least 9 days when administered to an organism. In some embodiments, the serum half-life of the activatable antibody is at least 8 days when administered to an organism. In some embodiments, the serum half-life of the activatable antibody is at least 7 days when administered to an organism. In some embodiments, the serum half-life of the activatable antibody is at least 6 days when administered to an organism. In some embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

In some embodiments, the activatable anti-CD166 antibody and/or conjugated activatable anti-CD166 antibody is monospecific. In some embodiments, the activatable anti-CD166 antibody and/or conjugated activatable anti-CD166 antibody is multispecific, e.g., by way of non-limiting example, bispecific or trifunctional. In some embodiments, the activatable anti-CD166 antibody and/or conjugated activatable anti-CD166 antibody is formulated as part of a pro-Bispecific T Cell Engager (BITE) molecule. In some embodiments, the activatable anti-CD166 antibody and/or conjugated activatable anti-CD166 antibody is formulated as part of a pro-Chimeric Antigen Receptor (CAR) modified T cell or other engineered receptor.

In some embodiments, the activatable antibody or antigen-binding fragment thereof is incorporated in a multispecific activatable antibody or antigen-binding fragment thereof, where at least one arm of the multispecific activatable antibody specifically binds CD166. In some embodiments, the activatable antibody or antigen-binding fragment thereof is incorporated in a bispecific antibody or antigen-binding fragment thereof, where at least one arm of the bispecific activatable antibody specifically binds CD166.

In some embodiments, the anti-CD166 antibodies, conjugated anti-CD166 antibodies, activatable anti-CD166 antibodies and/or conjugated activatable anti-CD166 antibodies described herein are used in conjunction with one or more additional agents or a combination of additional agents. Suitable additional agents include current pharmaceutical and/or surgical therapies for an intended application, such as, for example, cancer. For example, the anti-CD166 antibodies, conjugated anti-CD166 antibodies, activatable anti-CD166 antibodies and/or conjugated activatable anti-CD166 antibodies can be used in conjunction with an additional chemotherapeutic or anti-neoplastic agent.

In some embodiments, the additional agent(s) is a chemotherapeutic agent, such as a chemotherapeutic agent selected from the group consisting of docetaxel, paclitaxel, abraxane (i.e., albumin-conjugated paclitaxel), doxorubicin, oxaliplatin, carboplatin, cisplatin, irinotecan, and gemcitabine.

In some embodiments, the additional agent(s) is a checkpoint inhibitor, a kinase inhibitor, an agent targeting inhibitors in the tumor microenvironment, and/or a T cell or NK agonist. In some embodiments, the additional agent(s) is radiation therapy, alone or in combination with another additional agent(s) such as a chemotherapeutic or anti-neoplastic agent. In some embodiments, the additional agent(s) is a vaccine, an oncovirus, and/or a DC-activating agent such as, by way of non-limiting example, a toll-like receptor (TLR) agonist and/or α-CD40. In some embodiments, the additional agent(s) is a tumor-targeted antibody designed to kill the tumor via ADCC or via direct conjugation to a toxin (e.g., an antibody drug conjugate (ADC).

In some embodiments, the checkpoint inhibitor is an inhibitor of a target selected from the group consisting of CTLA-4, LAG-3, PD-1, CD166, TIGIT, TIM-3, B7H4, and Vista. In some embodiments, the kinase inhibitor is selected from the group consisting of B-RAFi, MEKi, and Btk inhibitors, such as ibrutinib. In some embodiments, the kinase inhibitor is crizotinib. In some embodiments, the tumor microenvironment inhibitor is selected from the group consisting of an IDO inhibitor, an α-CSF 1R inhibitor, an α-CCR4 inhibitor, a TGF-beta, a myeloid-derived suppressor cell, or a T-regulatory cell. In some embodiments, the agonist is selected from the group consisting of Ox40, GITR, CD137, ICOS, CD27, and HVEM.

In some embodiments, the inhibitor is a CTLA-4 inhibitor. In some embodiments, the inhibitor is a LAG-3 inhibitor. In some embodiments, the inhibitor is a PD-1 inhibitor. In some embodiments, the inhibitor is a CD166 inhibitor. In some embodiments, the inhibitor is a TIGIT inhibitor. In some embodiments, the inhibitor is a TIM-3 inhibitor. In some embodiments, the inhibitor is a B7H4 inhibitor. In some embodiments, the inhibitor is a Vista inhibitor. In some embodiments, the inhibitor is a B-RAFi inhibitor. In some embodiments, the inhibitor is a MEKi inhibitor. In some embodiments, the inhibitor is a Btk inhibitor. In some embodiments, the inhibitor is ibrutinib. In some embodiments, the inhibitor is crizotinib. In some embodiments, the inhibitor is an IDO inhibitor. In some embodiments, the inhibitor is an α-CSFIR inhibitor. In some embodiments, the inhibitor is an α-CCR4 inhibitor. In some embodiments, the inhibitor is a TGF-beta. In some embodiments, the inhibitor is a myeloid-derived suppressor cell. In some embodiments, the inhibitor is a T-regulatory cell.

In some embodiments, the agonist is Ox40. In some embodiments, the agonist is GITR. In some embodiments, the agonist is CD137. In some embodiments, the agonist is ICOS. In some embodiments, the agonist is CD27. In some embodiments, the agonist is HVEM.

In some embodiments, the anti-CD166 antibody, conjugated antibody, activatable antibody and/or conjugated activatable antibody is administered during and/or after treatment in combination with one or more additional agents such as, for example, a chemotherapeutic agent, an anti-inflammatory agent, and/or a an immunosuppressive agent. In some embodiments, the anti-CD166 antibody, conjugated anti-CD166 antibody, activatable anti-CD166 antibody and/or conjugated activatable anti-CD166 antibody and the additional agent are formulated into a single therapeutic composition, and the anti-CD166 antibody, conjugated anti-CD166 antibody, activatable anti-CD166 antibody and/or conjugated activatable anti-CD166 antibody and additional agent are administered simultaneously. Alternatively, the anti-CD166 antibody, conjugated anti-CD166 antibody, activatable anti-CD166 antibody and/or conjugated activatable anti-CD166 antibody and additional agent are separate from each other, e.g., each is formulated into a separate therapeutic composition, and the anti-CD166 antibody, conjugated anti-CD166 antibody, activatable anti-CD166 antibody and/or conjugated activatable anti-CD166 antibody and the additional agent are administered simultaneously, or the anti-CD166 antibody, conjugated anti-CD166 antibody, activatable anti-CD166 antibody and/or conjugated activatable anti-CD166 antibody and the additional agent are administered at different times during a treatment regimen. For example, the anti-CD166 antibody, conjugated anti-CD166 antibody, activatable anti-CD166 antibody and/or conjugated activatable anti-CD166 antibody is administered prior to the administration of the additional agent, the anti-CD166 antibody, conjugated anti-CD166 antibody, activatable anti-CD166 antibody and/or conjugated activatable anti-CD166 antibody is administered subsequent to the administration of the additional agent, or the anti-CD166 antibody, conjugated anti-CD166 antibody, activatable anti-CD166 antibody and/or conjugated activatable anti-CD166 antibody and the additional agent are administered in an alternating fashion. As described herein, the anti-CD166 antibody, conjugated anti-CD166 antibody, activatable anti-CD166 antibody and/or conjugated activatable anti-CD166 antibody and additional agent are administered in single doses or in multiple doses.

In some embodiments, the anti-CD166 antibody, conjugated anti-CD166 antibody, activatable anti-CD166 antibody and/or conjugated activatable anti-CD166 antibody and the additional agent(s) are administered simultaneously. For example, the anti-CD166 antibody, conjugated anti-CD166 antibody, activatable anti-CD166 antibody and/or conjugated activatable anti-CD166 antibody and the additional agent(s) can be formulated in a single composition or administered as two or more separate compositions. In some embodiments, the anti-CD166 antibody, conjugated anti-CD166 antibody, activatable anti-CD166 antibody and/or conjugated activatable anti-CD166 antibody and the additional agent(s) are administered sequentially, or the anti-CD166 antibody, conjugated anti-CD166 antibody, activatable anti-CD 166 antibody and/or conjugated activatable anti-CD166 antibody and the additional agent are administered at different times during a treatment regimen.

In some embodiments, the anti-CD166 antibody, conjugated anti-CD166 antibody, activatable anti-CD166 antibody and/or conjugated activatable anti-CD166 antibody is administered during and/or after treatment in combination with one or more additional agents such as, by way of non-limiting example, a chemotherapeutic agent, an anti-inflammatory agent, and/or an immunosuppressive agent, such as an alkylating agent, an anti-metabolite, an anti-microtubule agent, a topoisomerase inhibitor, a cytotoxic antibiotic, and/or any other nucleic acid damaging agent. In some embodiments, the additional agent is a taxane, such as paclitaxel (e.g., Abraxane®). In some embodiments, the additional agent is an anti-metabolite, such as gemcitabine. In some embodiments, the additional agent is an alkylating agent, such as platinum-based chemotherapy, such as carboplatin or cisplatin. In some embodiments, the additional agent is a targeted agent, such as a kinase inhibitor, e.g., sorafenib or erlotinib. In some embodiments, the additional agent is a targeted agent, such as another antibody, e.g., a monoclonal antibody (e.g., bevacizumab), a bispecific antibody, or a multispecific antibody. In some embodiments, the additional agent is a proteosome inhibitor, such as bortezomib or carfilzomib. In some embodiments, the additional agent is an immune modulating agent, such as lenolidominde or IL-2. In some embodiments, the additional agent is radiation. In some embodiments, the additional agent is an agent considered standard of care by those skilled in the art. In some embodiments, the additional agent is a chemotherapeutic agent well known to those skilled in the art.

In some embodiments, the additional agent is another antibody or antigen-binding fragment thereof, another conjugated antibody or antigen-binding fragment thereof, another activatable antibody or antigen-binding fragment thereof and/or another conjugated activatable antibody or antigen-binding fragment thereof. In some embodiments the additional agent is another antibody or antigen-binding fragment thereof, another conjugated antibody or antigen-binding fragment thereof, another activatable antibody or antigen-binding fragment thereof and/or another conjugated activatable antibody or antigen-binding fragment thereof against the same target as the first antibody or antigen-binding fragment thereof, the first conjugated antibody or antigen-binding fragment thereof, activatable antibody or antigen-binding fragment thereof and/or a conjugated activatable antibody or antigen-binding fragment thereof, e.g., against CD166. In some embodiments the additional agent is another antibody or antigen-binding fragment thereof, another conjugated antibody or antigen-binding fragment thereof, another activatable antibody or antigen-binding fragment thereof and/or another conjugated activatable antibody or antigen-binding fragment thereof against a target different than the target of the first antibody or antigen-binding fragment thereof, the first conjugated antibody or antigen-binding fragment thereof, activatable antibody or antigen-binding fragment thereof and/or a conjugated activatable antibody or antigen-binding fragment thereof.

As a non-limiting example, the antibody or antigen-binding fragment and/or the AB of an activatable antibody is a binding partner for any target listed in Table 1.

TABLE 1

| colspan="6" | Exemplary Targets |
|---|---|---|---|---|---|
| 1-92-LFA-3 | CD52 | DL44 | HVEM | LIF-R | STEAP1 |
| Alpha-4 integrin | CD56 | DLK1 | Hyaluronidase | Lewis X | STEAP2 |
| Alpha-V integrin | CD64 | DLL4 | ICOS | LIGHT | TAG-72 |
| alpha4beta1 integrin | CD70 | DPP-4 | IFNalpha | LRP4 | TAPA1 |
| alpha4beta7 integrin | CD71 | DSG1 | IFNbeta | LRRC26 | TGFbeta |
| AGR2 | CD74 | EGFR | IFNgamma | MCSP | TIGIT |
| Anti-Lewis-Y | | EGFRviii | IgE | Mesothelin | TIM-3 |
| Apelin J receptor | CD80 | Endothelin B receptor (ETBR) | IgE Receptor (FceRI) | MRP4 | TLR2 |
| APRIL | CD81 | ENPP3 | IGF | MUC1 | TLR4 |
| B7-H4 | CD86 | EpCAM | IGF1R | Mucin-16 (MUC16, CA-125) | TLR6 |
| BAFF | CD95 | EPHA2 | IL1B | Na/K ATPase | TLR7 |
| BTLA | CD117 | EPHB2 | IL1R | Neutrophil elastase | TLR8 |
| C5 complement | CD125 | ERBB3 | IL2 | NGF | TLR9 |
| C-242 | CD132 (IL-2RG) | F protein of RSV | IL11 | Nicastrin | TMEM31 |
| CA9 | CD133 | FAP | IL12 | Notch Receptors | TNFalpha |
| CA19-9 (Lewis a) | CD137 | FGF-2 | IL12p40 | Notch 1 | TNFR |
| Carbonic anhydrase 9 | CD138 | FGF8 | IL-12R, IL-12Rbeta1 | Notch 2 | TNFRS12A |
| CD2 | CD166 | FGFR1 | IL13 | Notch 3 | TRAIL-R1 |
| CD3 | CD172A | FGFR2 | IL13R | Notch 4 | TRAIL-R2 |
| CD6 | CD248 | FGFR3 | IL15 | NOV | Transferrin |
| CD9 | CDH6 | FGFR4 | IL17 | OSM-R | Transferrin receptor |
| CD11a | CEACAM5 (CEA) | Folate receptor | IL18 | OX-40 | TRK-A |

TABLE 1-continued

Exemplary Targets

| | | | | | |
|---|---|---|---|---|---|
| CD19 | CEACAM6 (NCA-90) | GAL3ST1 | IL21 | PAR2 | TRK-B |
| CD20 | CLAUDIN-3 | G-CSF | IL23 | PDGF-AA | uPAR |
| CD22 | CLAUDIN-4 | G-CSFR | IL23R | PDGF-BB | VAP1 |
| CD24 | cMet | GD2 | IL27/IL27R (wsx1) | PDGFRalpha | VCAM-1 |
| CD25 | Collagen | GITR | IL29 | PDGFRbeta | VEGF |
| CD27 | Cripto | GLUT1 | IL-31R | PD-1 | VEGF-A |
| CD28 | CSFR | GLUT4 | IL31/IL31R | PD-L1 | VEGF-B |
| CD30 | CSFR-1 | GM-CSF | IL2R | PD-L2 | VEGF-C |
| CD33 | CTLA-4 | GM-CSFR | IL4 | Phosphatidyl-serine | VEGF-D |
| CD38 | CTGF | GP IIb/IIIa receptors | IL4R | P1GF | VEGFR1 |
| CD40 | CXCL10 | Gp130 | IL6, IL6R | PSCA | VEGFR2 |
| CD40L | CXCL13 | GPIIB/IIIA | Insulin Receptor | PSMA | VEGFR3 |
| CD41 | CXCR1 | GPNMB | Jagged Ligands | RAAG12 | VISTA |
| CD44 | CXCR2 | GRP78 | Jagged 1 | RAGE | WISP-1 |
| CD44v6 | | HER2/neu | Jagged 2 | SLC44A4 | WISP-2 |
| CD47 | CXCR4 | HGF | LAG-3 | Sphingosine 1 Phosphate | WISP-3 |
| CD51 | CYR61 | hGH | | | |

As a non-limiting example, the antibody or antigen-binding fragment and/or the AB of an activatable antibody is or is derived from an antibody listed in Table 2.

TABLE 2

Exemplary sources for Abs

| Antibody Trade Name (antibody name) | Target |
|---|---|
| Avastin ™ (bevacizumab) | VEGF |
| Lucentis ™ (ranibizumab) | VEGF |
| Erbitux ™ (cetuximab) | EGFR |
| Vectibix ™ (panitumumab) | EGFR |
| Remicade ™ (infliximab) | TNFα |
| Humira ™ (adalimumab) | TNFα |
| Tysabri ™ (natalizumab) | Integrinα4 |
| Simulect ™ (basiliximab) | IL2R |
| Soliris ™ (eculizumab) | Complement C5 |
| Raptiva ™ (efalizumab) | CD11a |
| Bexxar ™ (tositumomab) | CD20 |
| Zevalin ™ (ibritumomab tiuxetan) | CD20 |
| Rituxan ™ (rituximab) | CD20 |
| Ocrelizumab | CD20 |
| Arzerra ™ (ofatumumab) | CD20 |
| Gazyva ™ (obinutuzumab) | CD20 |
| Zenapax ™ (daclizumab) | CD25 |
| Adcetris ™ (brentuximab vedotin) | CD30 |
| Myelotarg ™ (gemtuzumab) | CD33 |
| Mylotarg ™ (gemtuzumab ozogamicin) | CD33 |
| Campath ™ (alemtuzumab) | CD52 |
| ReoPro ™ (abiciximab) | Glycoprotein receptor IIb/IIIa |
| Xolair ™ (omalizumab) | IgE |
| Herceptin ™ (trastuzumab) | Her2 |
| Kadcyla ™ (trastuzumab emtansine) | Her2 |
| Synagis ™ (palivizumab) | F protein of RSV |
| (ipilimumab) | CTLA-4 |
| (tremelimumab) | CTLA-4 |
| Hu5c8 | CD40L |
| (pertuzumab) | Her2-neu |
| (ertumaxomab) | CD3/Her2-neu |
| Orencia ™ (abatacept) | CTLA-4 |
| (tanezumab) | NGF |
| (bavituximab) | Phosphatidylserine |
| (zalutumumab) | EGFR |
| (mapatumumab) | EGFR |
| (matuzumab) | EGFR |
| (nimotuzumab) | EGFR |
| ICR62 | EGFR |
| mAb 528 | EGFR |

TABLE 2-continued

Exemplary sources for Abs

| Antibody Trade Name (antibody name) | Target |
|---|---|
| CH806 | EGFR |
| MDX-447 | EGFR/CD64 |
| (edrecolomab) | EpCAM |
| RAV12 | RAAG12 |
| huJ591 | PSMA |
| Enbrel ™ (etanercept) | TNF-R |
| Amevive ™ (alefacept) | 1-92-LFA-3 |
| Antril ™, Kineret ™ (ankinra) | IL-1Ra |
| GC1008 | TGFbeta |
| | Notch, e.g., Notch 1 |
| | Jagged 1 or Jagged 2 |
| (adecatumumab) | EpCAM |
| (figitumumab) | IGF1R |
| (tocilizumab) | IL-6 receptor |
| Stelara ™ (ustekinumab) | IL-12/IL-23 |
| Prolia ™ (denosumab) | RANKL |

In some embodiments, the additional antibody or antigen binding fragment thereof, conjugated antibody or antigen binding fragment thereof, activatable antibody or antigen binding fragment thereof, and/or conjugated activatable antibody or antigen binding fragment thereof is a monoclonal antibody, domain antibody, single chain, Fab fragment, a F(ab')₂ fragment, a scFv, a scAb, a dAb, a single domain heavy chain antibody, or a single domain light chain antibody. In some embodiments, the additional antibody or antigen binding fragment thereof, conjugated antibody or antigen binding fragment thereof, activatable antibody or antigen binding fragment thereof, and/or conjugated activatable antibody or antigen binding fragment thereof is a mouse, other rodent, chimeric, humanized or fully human monoclonal antibody.

The disclosure also provides methods of producing an anti-CD166 antibody and/or activatable anti-CD166 antibody polypeptide by culturing a cell under conditions that lead to expression of the polypeptide, wherein the cell comprises an isolated nucleic acid molecule encoding an antibody and/or an activatable antibody described herein, and/or vectors that include these isolated nucleic acid sequences. The disclosure provides methods of producing an antibody and/or activatable antibody by culturing a cell under conditions that lead to expression of the antibody and/or activatable antibody, wherein the cell comprises an isolated nucleic acid molecule encoding an antibody and/or an activatable antibody described herein, and/or vectors that include these isolated nucleic acid sequences.

The invention also provides a method of manufacturing activatable antibodies that in an activated state binds CD166 by (a) culturing a cell comprising a nucleic acid construct that encodes the activatable antibody under conditions that lead to expression of the activatable antibody, wherein the activatable antibody comprises a masking moiety (MM), a cleavable moiety (CM), and an antibody or an antigen binding fragment thereof (AB) that specifically binds CD166, (i) wherein the CM is a polypeptide that functions as a substrate for a protease; and (ii) wherein the CM is positioned in the activatable antibody such that, when the activatable antibody is in an uncleaved state, the MM interferes with specific binding of the AB to CD166 and in a cleaved state the MM does not interfere or compete with specific binding of the AB to CD166; and (b) recovering the activatable antibody. Suitable AB, MM, and/or CM include any of the AB, MM, and/or CM disclosed herein.

In some embodiments, the activatable antibody in the uncleaved state has the structural arrangement from N-terminus to C-terminus as follows: MM-CM-AB or AB-CM-MM. In some embodiments, the activatable antibody comprises a linking peptide between the MM and the CM. In some embodiments, the activatable antibody comprises a linking peptide between the CM and the AB. In some embodiments, the activatable antibody comprises a first linking peptide (LP1) and a second linking peptide (LP2), and wherein the activatable antibody in the uncleaved state has the structural arrangement from N-terminus to C-terminus as follows: MM-LP1-CM-LP2-AB or AB-LP2-CM-LP1-MM. In some embodiments, the two linking peptides need not be identical to each other. In some embodiments, the activatable antibody in the uncleaved state has the structural arrangement from N-terminus to C-terminus as follows: spacer-MM-LP1-CM-LP2-AB or AB-LP2-CM-LP1-MM-spacer.

In some embodiments, at least one of LP1 or LP2 comprises an amino acid sequence selected from the group consisting of $(GS)_n$, $(GGS)_n$, $(GSGGS)_n$ (SEQ ID NO: 1) and $(GGGS)_n$ (SEQ ID NO: 2), where n is an integer of at least one.

In some embodiments, at least one of LP1 or LP2 comprises an amino acid sequence selected from the group consisting of GGSG (SEQ ID NO: 3), GGSGG (SEQ ID NO: 4), GSGSG (SEQ ID NO: 5), GSGGG (SEQ ID NO: 6), GGGSG (SEQ ID NO: 7), and GSSSG (SEQ ID NO: 8).

In some embodiments, LP1 comprises the amino acid sequence GSSGGSGGSGGSG (SEQ ID NO: 9), GSSGGSGGSGG (SEQ ID NO: 10), GSSGGSGGSGGS (SEQ ID NO: 11), GSSGGSGGSGGSGGS (SEQ ID NO: 12), GSSGGSGGSG (SEQ ID NO: 13), or GSSGGSGGSGS (SEQ ID NO: 14).

In some embodiments, LP2 comprises the amino acid sequence GSS, GGS, GGGS (SEQ ID NO: 15), GSSGT (SEQ ID NO: 16) or GSSG (SEQ ID NO: 17).

The invention provides methods of preventing, delaying the progression of, treating, alleviating a symptom of, or otherwise ameliorating an CD166 mediated disease in a subject by administering a therapeutically effective amount of an anti-CD166 antibody, conjugated anti-CD166 antibody, activatable anti-CD166 antibody and/or conjugated activatable anti-CD166 antibody described herein to a subject in need thereof.

The invention also provides methods of preventing, delaying the progression of, treating, alleviating a symptom of, or otherwise ameliorating cancer in a subject by administering a therapeutically effective amount of an anti-CD166 antibody, conjugated anti-CD166 antibody, activatable anti-CD166 antibody and/or conjugated activatable anti-CD166 antibody described herein to a subject in need thereof. CD166 is known to be expressed in a variety of cancers, such as, by way of non-limiting example, any epithelial or squamous cell cancer, any carcinoid, and/or a neuroendocrine cancer. Examples of cancers include, but are not limited to, adenocarcinoma, bile duct (biliary) cancer, bladder cancer, breast cancer, e.g., triple-negative breast cancer, Her2-negative breast cancer, estrogen receptor-positive breast cancer; carcinoid cancer; cervical cancer; cholangiocarcinoma; colorectal; endometrial; glioma; head and neck cancer, e.g., head and neck squamous cell cancer; leukemia; liver cancer; lung cancer, e.g., NSCLC, SCLC; lymphoma; melanoma; osopharyngeal cancer; ovarian cancer; pancreatic cancer; prostate cancer, e.g., metastatic castration-resistant prostate carcinoma; renal cancer; skin cancer; squamous cell cancer; stomach cancer; testis cancer; thyroid cancer; and urothelial cancer.

In some embodiments, the cancer is any epithelial or squamous cancer. In some embodiments, the cancer is prostate cancer, breast cancer, lung cancer, cervical cancer, oropharyngeal cancer, and/or head and neck cancer.

In some embodiments, the cancer is a bladder cancer, a bone cancer, a breast cancer, a carcinoid, a cervical cancer, a colorectal cancer, a colon cancer, an endometrial cancer, an epithelial cancer, a glioma, a head and neck cancer, a liver cancer, a lung cancer, a melanoma, an oropharyngeal cancer, an ovarian cancer, a pancreatic cancer, a prostate cancer, a renal cancer, a sarcoma, a skin cancer, a stomach cancer, a testis cancer, a thyroid cancer, a urogenital cancer, and/or a urothelial cancer.

In some embodiments, the cancer is selected from the group consisting of triple negative breast cancer (TNBC), non-small cell lung cancer (NSCLC), small cell lung cancer (SCLC), Ras mutant colorectal carcinoma, a rare epithelial cancer, oropharyngeal cancer, cervical cancer, head and neck squamous cell carcinoma (HNSCC), and/or prostate cancer. In some embodiments, the cancer is associated with a CD166-expressing tumor. In some embodiments, the cancer is due to a CD166-expressing tumor.

An anti-CD166 antibody, a conjugated anti-CD166 antibody, an activatable anti-CD 166 antibody and/or a conjugated activatable anti-CD166 antibody used in any of the embodiments of these methods and uses can be administered at any stage of the disease. For example, such an anti-CD166 antibody, conjugated anti-CD166 antibody, activatable anti-CD166 antibody and/or conjugated activatable anti-CD166 antibody can be administered to a patient suffering cancer of any stage, from early to metastatic. The terms subject and patient are used interchangeably herein.

In some embodiments, the subject is a mammal, such as a human, non-human primate, companion animal (e.g., cat, dog, horse), farm animal, work animal, or zoo animal. In some embodiments, the subject is a human. In some embodiments, the subject is a companion animal. In some embodiments, the subject is an animal in the care of a veterinarian.

The anti-CD166 antibody, conjugated anti-CD166 antibody, activatable anti-CD 166 antibody and/or conjugated activatable anti-CD166 antibody and therapeutic formulations thereof are administered to a subject suffering from or susceptible to a disease or disorder associated with aberrant CD166 expression and/or activity. A subject suffering from or susceptible to a disease or disorder associated with aberrant CD166 expression and/or activity is identified using any of a variety of methods known in the art. For example, subjects suffering from cancer or other neoplastic condition are identified using any of a variety of clinical and/or laboratory tests such as, physical examination and blood, urine and/or stool analysis to evaluate health status. For example, subjects suffering from inflammation and/or an inflammatory disorder are identified using any of a variety of clinical and/or laboratory tests such as physical examination and/or bodily fluid analysis, e.g., blood, urine and/or stool analysis, to evaluate health status.

Administration of an anti-CD166 antibody, conjugated anti-CD166 antibody, activatable anti-CD166 antibody and/or conjugated activatable anti-CD166 antibody to a patient suffering from a disease or disorder associated with aberrant CD166 expression and/or activity is considered successful if any of a variety of laboratory or clinical objectives is achieved. For example, administration of an anti-CD166 antibody, conjugated anti-CD166 antibody, activatable anti-CD166 antibody and/or conjugated activatable anti-CD166 antibody to a patient suffering from a disease or disorder associated with aberrant CD166 expression and/or activity is considered successful if one or more of the symptoms associated with the disease or disorder is alleviated, reduced, inhibited or does not progress to a further, i.e., worse, state. Administration of an anti-CD166 antibody, conjugated anti-CD166 antibody, activatable anti-CD166 antibody and/or conjugated activatable anti-CD166 antibody to a patient suffering from a disease or disorder associated with aberrant CD166 expression and/or activity is considered successful if the disease or disorder enters remission or does not progress to a further, i.e., worse, state.

In some embodiments, the anti-CD166 antibody, conjugated anti-CD166 antibody, activatable anti-CD166 antibody and/or conjugated activatable anti-CD166 antibody and therapeutic formulations thereof are administered to a subject suffering from or susceptible to a disease or disorder, such as subjects suffering from cancer or other neoplastic condition, wherein the subject's diseased cells are expressing CD166. In some embodiments, the diseased cells are associated with aberrant CD166 expression and/or activity. In some embodiments, the diseased cells are associated with normal CD166 expression and/or activity. A subject suffering from or susceptible to a disease or disorder wherein the subject's diseased cells express CD166 is identified using any of a variety of methods known in the art. For example, subjects suffering from cancer or other neoplastic condition are identified using any of a variety of clinical and/or laboratory tests such as, physical examination and blood, urine and/or stool analysis to evaluate health status. For example, subjects suffering from inflammation and/or an inflammatory disorder are identified using any of a variety of clinical and/or laboratory tests such as physical examination and/or bodily fluid analysis, e.g., blood, urine and/or stool analysis, to evaluate health status.

In some embodiments, the anti-CD166 antibody, conjugated anti-CD166 antibody, activatable anti-CD166 antibody and/or conjugated activatable anti-CD166 antibody and therapeutic formulations thereof are administered to a subject suffering from or susceptible to a disease or disorder associated with cells expressing CD166 or the presence, growth, proliferation, metastasis, and/or activity of such cells, such as subjects suffering from cancer or other neoplastic conditions. In some embodiments, the cells are associated with aberrant CD166 expression and/or activity. In some embodiments, the cells are associated with normal CD166 expression and/or activity. A subject suffering from or susceptible to a disease or disorder associated with cells that express CD166 is identified using any of a variety of methods known in the art. For example, subjects suffering from cancer or other neoplastic condition are identified using any of a variety of clinical and/or laboratory tests such as, physical examination and blood, urine and/or stool analysis to evaluate health status. For example, subjects suffering from inflammation and/or an inflammatory disorder are identified using any of a variety of clinical and/or laboratory tests such as physical examination and/or bodily fluid analysis, e.g., blood, urine and/or stool analysis, to evaluate health status.

Administration of an anti-CD166 antibody, conjugated anti-CD166 antibody, activatable anti-CD166 antibody and/or conjugated activatable anti-CD166 antibody to a patient suffering from a disease or disorder associated with cells expressing CD166 is considered successful if any of a variety of laboratory or clinical objectives is achieved. For example, administration of an anti-CD166 antibody, conjugated anti-CD166 antibody, activatable anti-CD166 antibody and/or conjugated activatable anti-CD166 antibody to a patient suffering from a disease or disorder associated with cells expressing CD166 is considered successful if one or more of the symptoms associated with the disease or disorder is alleviated, reduced, inhibited or does not progress to a further, i.e., worse, state. Administration of an anti-CD166 antibody, conjugated anti-CD166 antibody, activatable anti-CD166 antibody and/or conjugated activatable anti-CD166 antibody to a patient suffering from a disease or disorder associated with cells expressing CD166 is considered successful if the disease or disorder enters remission or does not progress to a further, i.e., worse, state.

In some embodiments, the anti-CD166 antibody, conjugated anti-CD166 antibody, activatable anti-CD166 antibody and/or conjugated activatable anti-CD166 antibody is administered during and/or after treatment in combination with one or more additional agents such as, for example, a chemotherapeutic agent, an anti-inflammatory agent, and/or an immunosuppressive agent. In some embodiments, the anti-CD166 antibody, conjugated anti-CD166 antibody, activatable anti-CD166 antibody and/or conjugated activatable anti-CD166 antibody and the additional agent(s) are administered simultaneously. For example, the anti-CD166 antibody, conjugated anti-CD166 antibody, activatable anti-CD166 antibody and/or conjugated activatable anti-CD166 antibody and the additional agent(s) can be formulated in a single composition or administered as two or more separate compositions. In some embodiments, the anti-CD166 antibody, conjugated anti-CD166 antibody, activatable anti-CD166 antibody and/or conjugated activatable anti-CD166 antibody and the additional agent(s) are administered sequentially.

The invention also provides methods and kits for using the activatable anti-CD166 antibodies and/or conjugated activatable anti-CD166 antibodies in a variety of diagnostic and/or prophylactic indications. For example, the invention provides methods and kits for detecting the presence or absence of a cleaving agent and a target of interest in a subject or a sample by (i) contacting a subject or sample with an anti-CD166 activatable antibody, wherein the anti-CD166 activatable antibody comprises a masking moiety (MM), a cleavable moiety (CM) that is cleaved by the cleaving agent, and an antigen binding domain or fragment thereof (AB) that specifically binds the target of interest, wherein the anti-CD166 activatable antibody in an uncleaved, non-activated state comprises a structural arrangement from N-terminus to C-terminus as follows: MM-CM-AB or AB-CM-MM; (a) wherein the MM is a peptide that inhibits binding of the AB to CD166, and wherein the MM does not have an amino acid sequence of a naturally occurring binding partner of the AB and is not a modified form of a natural binding partner of the AB; and (b) wherein, when the AB is in an uncleaved, non-activated state, the MM interferes with specific binding of the AB to CD166, and when the AB is in a cleaved, activated state the MM does not interfere or compete with specific binding of the AB to CD166; and (ii) measuring a level of activated anti-CD166 activatable antibody in the subject or sample, wherein a detectable level of activated anti-CD166 activatable antibody in the subject or sample indicates that the cleaving agent and CD166 are present in the subject or sample and wherein no detectable level of activated anti-CD166 activatable antibody in the subject or sample indicates that the cleaving agent, CD166 or both the cleaving agent and CD166 are absent in the subject or sample.

In some embodiments, the activatable anti-CD166 antibody is an activatable anti-CD166 antibody to which a therapeutic agent is conjugated. In some embodiments, the activatable anti-CD166 antibody is not conjugated to an agent. In some embodiments, the activatable anti-CD166 antibody comprises a detectable label. In some embodiments, the detectable label is positioned on the AB. In some embodiments, measuring the level of activatable anti-CD166 antibody in the subject or sample is accomplished using a secondary reagent that specifically binds to the activated antibody, wherein the reagent comprises a detectable label. In some embodiments, the secondary reagent is an antibody comprising a detectable label.

In some embodiments of these methods and kits, the activatable anti-CD166 antibody includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or 3-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor®680 or Alexa Fluor® 750. In some embodiments of these methods and kits, the ligand-based label comprises biotin, avidin, streptavidin or one or more haptens.

In some embodiments of these methods and kits, the subject is a mammal. In some embodiments of these methods, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods and kits, the method is an in vivo method. In some embodiments of these methods, the method is an in situ method. In some embodiments of these methods, the method is an ex vivo method. In some embodiments of these methods, the method is an in vitro method.

In some embodiments of the methods and kits, the method is used to identify or otherwise refine a patient population suitable for treatment with an anti-CD166 activatable antibody of the disclosure, followed by treatment by administering that activatable anti-CD166 antibody and/or conjugated activatable anti-CD166 antibody to a subject in need thereof. For example, patients that test positive for both the target (e.g., CD166) and a protease that cleaves the substrate in the cleavable moiety (CM) of the anti-CD166 activatable antibody being tested in these methods are identified as suitable candidates for treatment with such an anti-CD166 activatable antibody comprising such a CM, and the patient is then administered a therapeutically effective amount of the activatable anti-CD166 antibody and/or conjugated activatable anti-CD 166 antibody that was tested. Likewise, patients that test negative for either or both of the target (e.g., CD166) and the protease that cleaves the substrate in the CM in the activatable antibody being tested using these methods might be identified as suitable candidates for another form of therapy. In some embodiments, such patients can be tested with other anti-CD166 activatable antibodies until a suitable anti-CD166 activatable antibody for treatment is identified (e.g., an anti-CD166 activatable antibody comprising a CM that is cleaved by the patient at the site of disease). In some embodiments, the patient is then administered a therapeutically effective amount of the activatable anti-CD166 antibody and/or conjugated for which the patient tested positive. Suitable AB, MM, and/or CM include any of the AB, MM, and/or CM disclosed herein.

Pharmaceutical compositions according to the invention can include an antibody of the invention and a carrier. These pharmaceutical compositions can be included in kits, such as, for example, diagnostic kits.

BRIEF DESCRIPTION OF THE DRAWINGS

FIGS. 6A and 6C depict the results of IHC analysis on the tumor and healthy tissue samples, and FIGS. 6B and 6D depict the results of the in situ imaging assay on the tumor and healthy tissue samples.

FIGS. 7A and 7C depict the results of IHC analysis on the tumor and healthy tissue samples, and FIGS. 7B and 7D depict the results of the in situ imaging assay on the tumor and healthy tissue samples.

FIGS. 8A-8D are a series of images demonstrating that an activatable anti-CD166 antibody of the disclosure is not activated in healthy tissue samples. FIGS. 8A and 8C depict the results of IHC analysis on the healthy tissue samples, and FIGS. 8B and 8D depict the results of the in situ imaging assay on the healthy tissue samples.

FIGS. 21A-21D are graphs depicting the ability of the anti-CD166 activatable antibody drug conjugates of the present disclosure to induce an immunological response in cells.

FIGS. 24A to 24D are graphs depicting the cytotoxicity of the anti-CD166 activatable antibody drug conjugates of the present disclosure against multiple endometrial cancer-derived cell lines, and an assay showing the expression levels of CD166 on the endometrial cancer-derived cells.

DETAILED DESCRIPTION OF THE INVENTION

Figure 1:
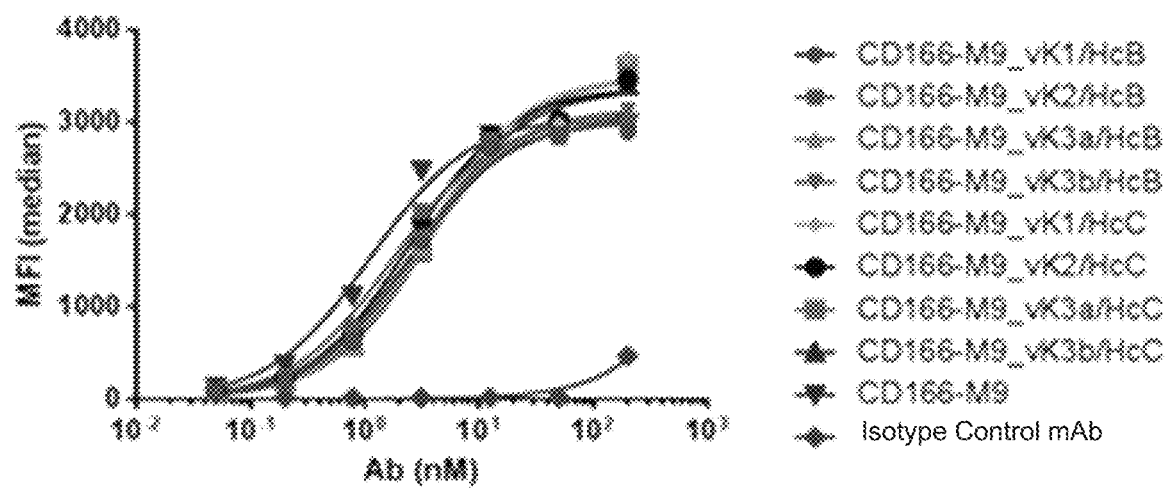
FIG. 1 is a graph depicting binding of various anti-CD166 antibodies of the present disclosure to human CD166 protein.

The present invention provides monoclonal antibodies (mAbs) and activatable monoclonal antibodies that specifically bind CD166, also known as activated leukocyte cell adhesion molecule (ALCAM). In some embodiments, the monoclonal antibodies and activatable monoclonal antibodies are internalized by CD166-containing cells. CD166 is a cell adhesion molecule that binds CD6, a cell surface receptor that belongs to the scavenger receptor cysteine-rich (SRCR) protein superfamily (SRCRSF). CD166 is known to be associated with cell-cell and cell-matrix interactions, cell adhesion, cell migration, and T-cell activation and proliferation. Aberrant expression and/or activity of CD166 and CD166-related signaling has been implicated in the pathogenesis of many diseases and disorders, such as cancer, inflammation, and autoimmunity. For example, CD166 is highly expressed in a variety of cancer types such as, for example, prostate cancer, breast cancer, lung cancer such as NSCLC and/or SCLC, oropharyngeal cancer, cervical cancer, and head and neck cancer such as HNSCC.

The disclosure provides anti-CD166 antibodies, conjugated anti-CD166 antibodies, activatable anti-CD166 antibodies, and/or conjugated activatable anti-CD166 antibodies that are useful in methods of treating, preventing, delaying the progression of, ameliorating and/or alleviating a symptom of a disease or disorder associated with aberrant CD166 expression and/or activity. For example, the activatable anti-CD166 antibodies are used in methods of treating, preventing, delaying the progression of, ameliorating and/or alleviating a symptom of a cancer or other neoplastic condition.

The disclosure provides anti-CD166 antibodies, conjugated anti-CD166 antibodies, activatable anti-CD166 antibodies, and/or conjugated activatable anti-CD166 antibodies that are useful in methods of treating, preventing, delaying the progression of, ameliorating and/or alleviating a symptom of a disease or disorder associated with cells expressing CD166. In some embodiments, the cells are associated with aberrant CD166 expression and/or activity. In some embodiments, the cells are associated with normal CD166 expression and/or activity. For example, the activatable anti-CD166 antibodies are used in methods of treating, preventing, delaying the progression of, ameliorating and/or alleviating a symptom of a cancer or other neoplastic condition.

The disclosure provides anti-CD166 antibodies, conjugated anti-CD166 antibodies, activatable anti-CD166 antibodies, and/or conjugated activatable anti-CD166 antibodies that are useful in methods of treating, preventing, delaying the progression of, ameliorating and/or alleviating a symptom of a disease or disorder in which diseased cells express CD166. In some embodiments, the diseased cells are associated with aberrant CD166 expression and/or activity. In some embodiments, the diseased cells are associated with normal CD166 expression and/or activity. For example, the activatable anti-CD166 antibodies are used in methods of treating, preventing, delaying the progression of, ameliorating and/or alleviating a symptom of a cancer or other neoplastic condition.

The activatable anti-CD166 antibodies and/or conjugated activatable anti-CD166 antibodies include an antibody or antigen-binding fragment thereof that specifically binds CD166 coupled to a masking moiety (MM), such that coupling of the MM reduces the ability of the antibody or antigen-binding fragment thereof to bind CD166. In some embodiments, the MM is coupled via a sequence that includes a substrate for a protease, for example, a protease that is co-localized with CD166 at a treatment site in a subject.

Exemplary activatable anti-CD166 antibodies of the invention include, for example, activatable antibodies that include a heavy chain and a light chain that are, or are derived from, the heavy chain variable and light chain variable sequences shown below (CDR sequences, which were defined according to the AbM definition provided in the website of Dr. Andrew C. R. Martin, available at www_bioinf_org_uk/abs/) are shown in bold and underline):

```
muM9 VH:
                                    (SEQ ID NO: 119)
QVTLKESGPGILQPSQTLSLTCSFSGFSLSTYGMVGWIRQPSGKGLE

WLANIWWSEDKHYNSALKSRLTISKDISNNQVFLKISSVDTADTATYY

CVQIDYGNDYAFTYWGQGTLVIVSA muM9 VL:
                                    (SEQ ID NO: 120)
DIVMTQAAFSNPVTLGTSASISCRSSKSLLHSNGITYLYWYLQKPGQS

PQLLIYQMSNLASGVPDRFSSSGSGTDFTLRISRVEAEDVGVYYCAQN

LELPYTFGGGTKLEIKR huM9b VH:
                                    (SEQ ID NO: 121)
QITLKESGPTLVKPTQTLTLTCTFSGFSLSTYGMVGWIRQPPGKALE

WLANIWWSEDKHYSPSLKSRLTITKDISKNQVVLTMTNMDPVDTATYY

CVQIDYGNDYAFTYWGQGTLVTVSS
```

```
huM9c VH:
                                    (SEQ ID NO: 122)
QITLKESGPILVKPTQTLTLTCTFSGFSLSTYGMVGWIRQPPGKALE

WLANIWWSEDKHYSPSLKSRLTITKDTSKNQVVLTITNVDPVDTATYY

CVQIDYGNDYAFTYWGQGTLVTVSS hM9vK-1 VL:
                                    (SEQ ID NO: 123)
DIVMTQSPLSLPVTPGEPASISCRSSKSLLHSNGITYLYWYLQKPGQS

PQLLIYQMSNLASGVPDRFSGSGSGTDFTLKISRVEAEDVGVYYCAQN

LELPYTFGQGTKLEIK hM9vK-2 VL:
                                    (SEQ ID NO: 124)
DIVMTQSPLSLPVTPGEPASISCRSSKSLLHSNGITYLYWYLQKPGQS

PQLLIYQMSNLASGVPDRESSSGSGIDETLKISRVEAEDVGVYYCAQN

LELPYTEGQGTKLEIK hM9vK-3a VL:
                                    (SEQ ID NO: 125)
DIVMTQSPLSLPVTPGEPASISCRSSQSLLHSNGITYLYWYLQKPGQS

PQLLIYQMSNRASGVPDRFSGSGSGTDFILKISRVEAEDVGVYYCAQN

LELPYTFGQGTKLEIK hM9vK-3b VL:
                                    (SEQ ID NO: 126)
DIVMTQSPLSLPVTPGEPASISCRSSQSLLHSNGITYLYWYLQKPGQS

PQLLIYQMSNRASGVPDRFSSSGSGTDFILKISRVEAEDVGVYYCAQN

LELPYTEGQGTKLEIK
```

Exemplary activatable anti-CD166 antibodies of the invention include, for example, activatable antibodies that include a heavy chain and a light chain that are, or are derived from, the heavy chain and light chain variable shown below:

```
HuCD166_HcC
Amino Acid sequence
                                    (SEQ ID NO: 239)
QITLKESGPTLVKPTQTLTLTCTFSGFSLSTYGMVGWIRQPPGKALE

WLANIWWSEDKHYSPSLKSKLTITKDTSKNQVVLTITNVDPVDTATYY

CVQIDYGNDYAFTYWGQGTLVTVSSASTKGPSVFPLAPSSKSTSGGTA

ALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPELLG

GPSVFLFPPKPKDTLMISRTPEVTCVVVDVSKEDPEVKFNWYVDGVEV

HNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVM

HEALHNHYTQKSLSLSPGK

HuCD166_Lc1
                                    (SEQ ID NO: 240)
DIVMTQSPLSLPVTPGEPASISCRSSKSLLHSNGITYLYWYLQKPGQS

PQLLIYQMSNLASGVPDRFSGSGSGTDFTLKISRVEAEDVGVYYCAQN

LELPYTFGQGTKLEIKRTVAAPSVFIFPPSDEQLKSGTASVVCLLNNF
```

-continued
YPREAKVQWKVDNALQSGNSQESVTEQDSKDSTYSLSSTLTLSKADYE

KHKVYACEVTHQGLSSPVTKSFNRGEC

Exemplary activatable anti-CD166 antibodies of the invention include, for example, activatable antibodies that include a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one CDR sequence is selected from the group consisting of a VH CDR1 sequence comprising the amino acid sequence GFSLSTYGMGVG (SEQ ID NO: 127); a VH CDR2 sequence comprising the amino acid sequence NIWWSEDKH (SEQ ID NO: 128); a VH CDR3 sequence comprising the amino acid sequence IDYGNDYAFTY (SEQ ID NO: 129); a VL CDR1 sequence comprising the amino acid sequence RSSKSLLHSNGITYLY (SEQ ID NO: 130) or RSSQSLLHSNGITYLY (SEQ ID NO: 131); a VL CDR2 sequence comprising the amino acid sequence QMSNLAS (SEQ ID NO: 132) or QMSNRAS (SEQ ID NO: 133); and a VL CDR3 sequence comprising the amino acid sequence AQNLELPYT (SEQ ID NO: 134).

In some embodiments, the activatable anti-CD166 antibody includes a heavy chain that comprises or is derived from a heavy chain amino acid sequence shown in US Patent Application Publication Nos. 20150071937, 20090070890, and/or 20090203538, the contents of each of which are hereby incorporated by reference in their entirety.

In some embodiments, the activatable anti-CD166 antibody includes a heavy chain that comprises a VH CDR1, VH CDR2, VH CDR3, VL CDR1, VL CDR2, and/or VL CDR3 sequence that comprises or is derived from a CDR acid sequence shown in US Patent Application Publication Nos. 20150071937, 20090070890, and/or 20090203538, the contents of each of which are hereby incorporated by reference in their entirety.

In some embodiments, the activatable anti-CD166 antibody includes a heavy chain that comprises or is derived from a heavy chain amino acid sequence shown in Table 12. In some embodiments, the activatable anti-CD166 antibody includes a light chain that comprises or is derived from a heavy chain amino acid sequence shown in Table 12. In some embodiments, the activatable anti-CD166 antibody includes a heavy chain that comprises or is derived from a heavy chain amino acid sequence shown in Table 12, and a light chain that comprises or is derived from a light chain amino acid sequence shown in Table 12. In some embodiments, the activatable anti-CD166 antibody includes a combination of heavy chain variable region and light chain variable region sequences from the combinations shown in Group A in Table 12. In some embodiments, the activatable anti-CD166 antibody includes the combination of heavy chain variable region and light chain variable region sequences shown in Group B in Table 12. In some embodiments, the activatable anti-CD166 antibody includes the combination of heavy chain variable region and light chain variable region sequences shown in Group C in Table 12. In some embodiments, the activatable anti-CD166 antibody includes the combination of heavy chain variable region and light chain variable region sequences shown in Group D in Table 12.

In some embodiments, the activatable anti-CD166 antibody includes a combination of the complementarity determining region (CDR) sequences of a heavy chain sequence from the heavy chain sequences shown in Group A Table 12. In some embodiments, the activatable anti-CD166 antibody includes a combination of the CDRs of a light chain sequence from the light chain sequences shown in Group A Table 12. In some embodiments, the activatable anti-CD166 antibody includes a combination of the CDRs of a heavy chain sequence from the heavy chain sequences shown in Group A Table 12 and the CDRs of a light chain sequence from the heavy chain sequences shown in Group A Table 12.

In some embodiments, the activatable anti-CD166 antibody includes a combination of CDRs of a heavy chain sequence from the heavy chain sequences shown in Group B Table 12. In some embodiments, the activatable anti-CD166 antibody includes a combination of the CDRs of a light chain sequence from the light chain sequences shown in Group B Table 12. In some embodiments, the activatable anti-CD166 antibody includes a combination of the CDRs of a heavy chain sequence from the heavy chain sequences shown in Group B Table 12 and the CDRs of a light chain sequence from the heavy chain sequences shown in Group B Table 12.

In some embodiments, the activatable anti-CD166 antibody includes a combination of the CDRs of a heavy chain sequence from the heavy chain sequences shown in Group C Table 12. In some embodiments, the activatable anti-CD166 antibody includes a combination of the CDRs of a light chain sequence from the light chain sequences shown in Group C Table 12. In some embodiments, the activatable anti-CD166 antibody includes a combination of the CDRs of a heavy chain sequence from the heavy chain sequences shown in Group C Table 12 and the CDRs of a light chain sequence from the heavy chain sequences shown in Group C Table 12.

In some embodiments, the activatable anti-CD166 antibody includes a combination of the CDRs of a heavy chain sequence from the heavy chain sequences shown in Group D Table 12. In some embodiments, the activatable anti-CD166 antibody includes a combination of the CDRs of a light chain sequence from the light chain sequences shown in Group D Table 12. In some embodiments, the activatable anti-CD166 antibody includes a combination of the CDRs of a heavy chain sequence from the heavy chain sequences shown in Group D Table 12 and the CDRs of a light chain sequence from the heavy chain sequences shown in Group D Table 12.

TABLE 12

Variable Heavy Chain Region (VH) and
Variable Light Chain Region (VL) Sequences
for Activatable Antibodies that Bind CD166

| Group a | |
|---|---|
| VH | QVQLVESGGGLVQPGGSLRLSCAASGFTFSSYAMSWVRQA<br>PGKGLEWVSAISGSGGSTYYADSVKGRFTISRDNSKDTLY<br>LQMNSLRAEDTAVYYCASRSLLDYWGQGTLVTVSS<br>(SEQ ID NO: 249) |

TABLE 12-continued

Variable Heavy Chain Region (VH) and Variable Light Chain Region (VL) Sequences for Activatable Antibodies that Bind CD166

Group A

| | |
|---|---|
| VH | QVQLVESGGGLVQPGGSLRLSCAASGFTFSSYAMGWVRQA PGKGLEWVSAISGSGGSTYYADSVKGRFTISRDNSKDTLY LQMNSLRAEDTAVYYCASRSLLDYWGQGTLVTVSS (SEQ ID NO: 250) |
| VL | NFMLTQDPAVSVALGQTVRITCQGDSLRSYYASWYQQKPG QAPLLVIYGKNNRPSGIPDRFSGSSSGNTASLTITGAQAE DEADYYCNSRDSSGNPVFGGGTKVTVL (SEQ ID NO: 251) |

Group B

| | |
|---|---|
| VH | EVQLLESGGGLVQPGGSLRLSCAASGFTFSSYAMSWVRQA PGKGLEWVSAISGSGGSTYYADSVKGRFTISRDNSKNTLY LQMNSLRAEDTAVYYCARGGGVVEFWGQGTLVTVSS (SEQ ID NO: 252) |
| VL | DIRMTQSPSFLSASVGDRVTITCRASQDISSYFAWYQQKP GKAPKLLIYAASTLRSGVPSRFSGSGSGTDFTLTISSLQP EDFATYYCQQSYSTPRITFGQGTRLEIK (SEQ ID NO: 253) |

Group C

| | |
|---|---|
| VH | EVQLVESGGGLVQPGGSLRLSCAASGFTFSSYAMSWVRQA PGKGLEWVSTISGSGGSTYYADSVKGRFTISRDNSKNTLY LQMNSLRAEDTAVYYCARGIVATSWGQGTLVTVSR (SEQ ID NO: 254) |
| VH | EVQLVESGGGVVQPGGSLRLSCAASGFNFDVYGMNWVRQV PGKGLEWVSLINGDGGLRYYADSVKGRFTVSRDNSRNSLY LQMNSLRSEDTALYYCVKGNFQQWGQGTLVTVSR (SEQ ID NO: 255) |
| VH | EVQLVESGGGLVQPGGSLRLSCAASGFTFDDYAMHWVRQA PGKGLEWVSLISGDGGSTYYADSVKDRFTISRDNSKNSLY LQMNSLRAEDTAVYYCARGNYFDYWGQGTLVTVSR (SEQ ID NO: 256) |
| VH | EVQLVESGGGLVQPGGSLRLSCAASGFTFSSYSMNWVRQA PGKGLEWVSYISSSSSTIYYADSVKGRFTISRDNAKNSLY LQMNSLRDEDTAVYYCARVMPSYYYYGMDVWGQGTTVTVSR (SEQ ID NO: 257) |
| VH | EVQLVESGGGVVQPGRSLRLSCAASGFTFSSYGMHWVRQA PGKGLEWVAVISYDGSNKYYADSVKGRFTISRDNSKNTLY LQMNSLRAEDTAVYYCADYGMDVWGQGTTVTVSR (SEQ ID NO: 258) |
| VL | SYELTQPPSVSVAPGQTARITCGGNKIGSKSVHWYQQKQG QAPVLVIYLDRDRPSGIPERFSGSNSGNTATLTITRVEAE DEADYYCHLWDSGSDQVFGGGTKLTVLG (SEQ ID NO: 259) |
| VL | SYVLTQPPSVSVAPGKTARITCGGNNIGSKSVHWYQQKPG QAPVLVIYYDSDRPSGIPERFSGSNSGNTATLTISRVEAG DEADYYCQVWDSSSDHVFGGGTKLTVLG (SEQ ID NO: 260) |
| VL | SYELTQPLSVSVALGQTARITCGGNNIGSKNVHWYQQKPG QAPVLVIYRDSNRPSGIPERFSGSNSGNTATLTISRAQAG DEADYYCQVWDSSVVFGGGTKLTVLG (SEQ ID NO: 261) |
| VL | NFMLTQPHSVSESPGKTVTISCTGSSGSIASNYVQWYQQR PGSAPTTVIYEDSERPSGVPDRFSGSIDSSSNSASLTISG LKTQDEADYYCQSYDGVNWVFGGGTKLTVLG (SEQ ID NO: 262) |
| VL | DIQMTQSPSSLSASVGDRVTITCRASQSISSYLNWYQQKP GKAPKLLIYAASSLQSGVPSRFSGSGSGTDFTLTISSLQP EDFATYYCQQSYSTPVTFGQGTKVEIK (SEQ ID NO: 263) |

Group D

| | |
|---|---|
| VH/VL | QVQLVESGGGLVQPGGSLRLSCAASGFTFSSYAMSWVRQA PGKGLEWVSAISGSGGSTYYADSVKGRFTISRDNSKDTLY LQMNSLRAEDTAVYYCASRSLLDYWGQGTLVTVSSGGGGS GGGGSGGGGSNFMLTQDPAVSVALGQTVRITCQGDSLRSY YASWYQQKPGQAPLLVIYGKNNRPSGIPDRFSGSSSGNTA SLTITGAQAEDEADYYCNSRDSGNPVFGGGTKVTVL (SEQ ID NO: 475) |
| VH/VL | QVQLVESGGGLVQPGGSLRLSCAASGFTSSSYAMGWVRQA PGKGLEWVSAISGSGGSTYYADSVKGRFTISRDNSKDTLY LQMNSLRAEDTAVYYCASRSLLDYWGQGTLVTVSSGGGGS GGGGSGGGGSNFMLTQDPAVSVALGQTVRITCQGDSLRSY YASWYQQKPGQAPLLVIYGKNNRPSGIPDRFSGSSSGNTA SLTITGAQAEDEADYYCNSRDSGNPVFGGGTKVTVL (SEQ ID NO: 476) |

In some embodiments, the activatable anti-CD166 antibody includes a CDR sequence shown in Table 13, a combination of VL CDR sequences (VL CDR1, VL CDR2, VL CDR3) selected from the group consisting of those combinations shown in a single row Table 13, a combination of VH CDR sequences (VH CDR1, VH CDR2, VH CDR3) selected from the group consisting of those combinations shown in Table 13, or a combination of VL CDR and VH CDR sequences (VL CDR1, VL CDR2, VL CDR3, VH CDR1, VH CDR2, VH CDR3) selected the group consisting of those combinations shown in Table 13.

TABLE 13

CDR Sequences for Antibodies and Activatable Antibodies that Bind CD166

| VL | | | VH | | |
|---|---|---|---|---|---|
| CDR1 (SEQ ID NO) | CDR2 (SEQ ID NO) | CDR3 (SEQ ID NO) | CDR1 (SEQ ID NO) | CDR2 (SEQ ID NO) | CDR3 (SEQ ID NO) |
| QGDSLR SYYAS (264) | YGKN NRPS (265) | NSRDS SGNPV (266) | SYAMS (267) | AISGSGGST YYADSVKG (268) | RSLLDY (269) |
| QGDSLR SYYAS (264) | YGKN NRPS (265) | NSRDS SGNPV (266) | SYAMG (477) | AISGSGGST YYADSVKG (268) | RSLLDY (269) |
| PASQDI SSYFA (270) | AAST LRS (271) | QQSYS TPRIT (272) | SYAMS (267) | AISGSGGST YYADSVKG (268) | GGGVVEF (273) |
| GGNKIG SKSVH (274) | LDRD RPS (275) | HLWDS GSD (276) | SYAMS (267) | TISGSGGST YYADSVKG (277) | GIVATS (278) |
| GGNNIG SKSVH (279) | YDSD RPS (280) | QVWDS SSDH (281) | VYGMN (282) | LINGDGGLR YYADSVKG (283) | GNFQQ (284) |
| GGNNIG SKNVH (285) | RDSN RPS (286) | QVWDS S (287) | DYAMH (288) | LISGDGGST YYADSVKD (289) | GNYFDY (290) |
| TGSSGS IASNY VQ (291) | EDSE RPS (292) | QSYDG VN (293) | SYSMN (294) | YISSSSSTI YYADSVKG (295) | VMPSYYY YGMDV (296) |
| RASQSI SSYLN (297) | AASS LQS (298) | QQSYS TP (299) | SYGMH (300) | VISYDGSNK YYADSVKG (301) | YGMDV (302) |

In some embodiments, the activatable anti-CD166 antibody comprises or is derived from an antibody that is manufactured, secreted or otherwise produced by a hybridoma, such as, for example, the hybridoma(s) disclosed in US Patent Application Publication No. 20040048319 and deposited with American Type Culture Collection (ATCC) under deposit number PTA-4478. In some embodiments, the activatable anti-CD166 antibody comprises or is derived from an antibody that is manufactured, secreted or otherwise produced by a hybridoma, such as, for example, the hybridoma(s) disclosed in U.S. Pat. No. 6,022,540 and deposited with ATCC under deposit number HB 11789.

In some embodiments, the activatable anti-CD166 antibody comprises or is derived from an antibody that is manufactured, secreted or otherwise produced by a hybridoma, such as, for example, the hybridoma(s) disclosed in U.S. Pat. No. 5,998,172 and deposited with ATCC under deposit number HB 12136, HB 12137, HB 12138, HB12139, HB 12140, and/or HB 12141.

The anti-CD166 antibodies and the ABs in the activatable antibodies of the disclosure specifically bind a CD166 target, such as, for example, mammalian CD166, and/or human CD166. Also included in the disclosure are anti-CD166 antibodies and ABs that bind to the same CD166 epitope as an antibody of the disclosure and/or an activated activatable antibody described herein. Also included in the disclosure are anti-CD166 antibodies and ABs that compete with an anti-CD166 antibody and/or an activated anti-CD166 activatable antibody described herein for binding to a CD166 target, e.g., human CD166. Also included in the disclosure are anti-CD166 antibodies and ABs that cross-compete with an anti-CD166 antibody and/or an activated anti-CD166 activatable antibody described herein for binding to a CD166 target, e.g., human CD166.

The activatable anti-CD166 antibodies provided herein include a masking moiety. In some embodiments, the masking moiety is an amino acid sequence that is coupled or otherwise attached to the anti-CD166 antibody and is positioned within the activatable anti-CD166 antibody construct such that the masking moiety reduces the ability of the anti-CD166 antibody to specifically bind CD166. Suitable masking moieties are identified using any of a variety of known techniques. For example, peptide masking moieties are identified using the methods described in PCT Publication No. WO 2009/025846 by Daugherty et al., the contents of which are hereby incorporated by reference in their entirety.

The activatable anti-CD166 antibodies provided herein include a cleavable moiety. In some embodiments, the cleavable moiety includes an amino acid sequence that is a substrate for a protease, usually an extracellular protease. Suitable substrates are identified using any of a variety of known techniques. For example, peptide substrates are identified using the methods described in U.S. Pat. No. 7,666,817 by Daugherty et al.; in U.S. Pat. No. 8,563,269 by Stagliano et al.; and in PCT Publication No. WO 2014/026136 by La Porte et al., the contents of each of which are hereby incorporated by reference in their entirety. (See also Boulware et al. "Evolutionary optimization of peptide substrates for proteases that exhibit rapid hydrolysis kinetics." Biotechnol Bioeng. 106.3 (2010): 339-46).

Exemplary substrates include but are not limited to substrates cleavable by one or more of the following enzymes or proteases listed in Table 4.

TABLE 4

| Exemplary Proteases and/or Enzymes |
|---|
| ADAMS, ADAMTS, e.g. |
| ADAM8 |
| ADAM9 |
| ADAM10 |
| ADAM12 |
| ADAM15 |
| ADAM17/TACE |
| ADAMDEC1 |
| ADAMTS1 |
| ADAMTS4 |
| ADAMTS5 |
| Aspartate proteases, e.g., |
| BACE |
| Renin |
| Aspartic cathepsins, e.g., |
| Cathepsin D |
| Cathepsin E |
| Caspases, e.g., |
| Caspase 1 |
| Caspase 2 |
| Caspase 3 |
| Caspase 4 |
| Caspase 5 |
| Caspase 6 |
| Caspase 7 |
| Caspase 8 |
| Caspase 9 |
| Caspase 10 |
| Caspase 14 |
| Cysteine cathepsins, e.g., |
| Cathepsin B |
| Cathepsin C |
| Cathepsin K |
| Cathepsin L |
| Cathepsin S |
| Cathepsin V/L2 |
| Cathepsin X/Z/P |
| Cysteine proteinases, e.g., |
| Cruzipain |
| Legumain |
| Otubain-2 |
| KLKs, e.g., |
| KLK4 |
| KLK5 |
| KLK6 |
| KLK7 |
| KLK8 |
| KLK10 |
| KLK11 |
| KLK13 |
| KLK14 |
| Metallo proteinases, e.g., |
| Meprin |
| Neprilysin |
| PSMA |
| BMP-1 |
| MMPs, e.g., |
| MMP1 |
| MMP2 |
| MMP3 |
| MMP7 |
| MMP8 |
| MMP9 |
| MMP10 |
| MMP11 |
| MMP12 |
| MMP13 |
| MMP14 |
| MMP15 |
| MMP16 |
| MMP17 |
| MMP19 |
| MMP20 |
| MMP23 |
| MMP24 |
| MMP26 |
| MMP27 |

TABLE 4-continued

Exemplary Proteases and/or Enzymes

Serine proteases, e.g.,
activated protein C
Cathepsin A
Cathepsin G
Chymase
coagulation factor proteases
(e.g., FVIIa, FIXa, FXa, FXIa,
FXIIa)
Elastase
Granzyme B
Guanidinobenzoatase
HtrA1
Human Neutrophil Elastase
Lactoferrin
Marapsin
NS3/4A
PACE4
Plasmin
PSA
tPA
Thrombin
Tryptase
uPA
Type II Transmembrane
Serine Proteases (TTSPs), e.g.,
DESC1
DPP-4
FAP
Hepsin
Matriptase-2
MT-SP1/Matriptase
TMPRSS2
TMPRSS3
TMPRSS4

The activatable anti-CD166 antibodies described herein overcome a limitation of antibody therapeutics, particularly antibody therapeutics that are known to be toxic to at least some degree in vivo. Target-mediated toxicity constitutes a major limitation for the development of therapeutic antibodies. The activatable anti-CD166 antibodies provided herein are designed to address the toxicity associated with the inhibition of the target in normal tissues by traditional therapeutic antibodies. These activatable anti-CD166 antibodies remain masked until proteolytically activated at the site of disease. Starting with an anti-CD166 antibody as a parental therapeutic antibody, the activatable anti-CD166 antibodies of the invention were engineered by coupling the antibody to an inhibitory mask through a linker that incorporates a protease substrate.

When the AB is modified with a MM and is in the presence of the target, specific binding of the AB to its target is reduced or inhibited, as compared to the specific binding of the AB not modified with an MM or the specific binding of the parental AB to the target.

The $K_d$ of the AB modified with a MM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1,000-10,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM or of the parental AB towards the target. Conversely, the binding affinity of the AB modified with a MM towards the target is at least 2, 3, 4, 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM or of the parental AB towards the target.

The dissociation constant ($K_d$) of the MM towards the AB is generally greater than the $K_d$ of the AB towards the target. The $K_d$ of the MM towards the AB can be at least 5, 10, 25, 50, 100, 250, 500, 1,000, 2,500, 5,000, 10,000, 100,000, 1,000,000 or even 10,000,000 times greater than the $K_d$ of the AB towards the target. Conversely, the binding affinity of the MM towards the AB is generally lower than the binding affinity of the AB towards the target. The binding affinity of MM towards the AB can be at least 5, 10, 25, 50, 100, 250, 500, 1,000, 2,500, 5,000, 10.000, 100,000, 1,000,000 or even 10,000,000 times lower than the binding affinity of the AB towards the target.

In some embodiments, the dissociation constant (Kd) of the MM towards the AB is approximately equal to the Kd of the AB towards the target. In some embodiments, the dissociation constant (Kd) of the MM towards the AB is no more than the dissociation constant of the AB towards the target.

In some embodiments, the dissociation constant (Kd) of the MM towards the AB is less than the dissociation constant of the AB towards the target.

In some embodiments, the dissociation constant (Kd) of the MM towards the AB is greater than the dissociation constant of the AB towards the target.

In some embodiments, the MM has a Kd for binding to the AB that is no more than the Kd for binding of the AB to the target.

In some embodiments, the MM has a Kd for binding to the AB that is no less than the Kd for binding of the AB to the target.

In some embodiments, the MM has a Kd for binding to the AB that is approximately equal to the Kd for binding of the AB to the target.

In some embodiments, the MM has a Kd for binding to the AB that is less than the Kd for binding of the AB to the target.

In some embodiments, the MM has a Kd for binding to the AB that is greater than the Kd for binding of the AB to the target.

In some embodiments, the MM has a Kd for binding to the AB that is no more than 2, 3, 4, 5, 10, 25, 50, 100, 250, 500, or 1,000 fold greater than the Kd for binding of the AB to the target. In some embodiments, the MM has a Kd for binding to the AB that is between 1-5, 2-5, 2-10, 5-10, 5-20, 5-50, 5-100, 10-100, 10-1,000, 20-100, 20-1000, or 100-1,000 fold greater than the Kd for binding of the AB to the target.

In some embodiments, the MM has an affinity for binding to the AB that is less than the affinity of binding of the AB to the target.

In some embodiments, the MM has an affinity for binding to the AB that is no more than the affinity of binding of the AB to the target.

In some embodiments, the MM has an affinity for binding to the AB that is approximately equal of the affinity of binding of the AB to the target.

In some embodiments, the MM has an affinity for binding to the AB that is no less than the affinity of binding of the AB to the target.

In some embodiments, the MM has an affinity for binding to the AB that is greater than the affinity of binding of the AB to the target.

In some embodiments, the MM has an affinity for binding to the AB that is 2, 3, 4, 5, 10, 25, 50, 100, 250, 500, or 1,000 less than the affinity of binding of the AB to the target. I In some embodiments, the MM has an affinity for binding to the AB that is between 1-5, 2-5, 2-10, 5-10, 5-20, 5-50, 5-100, 10-100, 10-1,000, 20-100, 20-1000, or 100-1,000 fold less than the affinity of binding of the AB to the target. In some embodiments, the MM has an affinity for binding to the AB that is 2 to 20 fold less than the affinity of binding of the AB to the target. In some embodiments, a MM not covalently linked to the AB and at equimolar concentration to the AB does not inhibit the binding of the AB to the target.

When the AB is modified with a MM and is in the presence of the target specific binding of the AB to its target is reduced or inhibited, as compared to the specific binding of the AB not modified with an MM or the specific binding of the parental AB to the target. When compared to the binding of the AB not modified with an MM or the binding of the parental AB to the target the AB's ability to bind the target when modified with an MM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or more when measured in vivo or in an in vitro assay.

The MM inhibits the binding of the AB to the target. The MM binds the antigen binding domain of the AB and inhibits binding of the AB to the target. The MM can sterically inhibit the binding of the AB to the target. The MM can allosterically inhibit the binding of the AB to its target. In these embodiments when the AB is modified or coupled to a MM and in the presence of target there is no binding or substantially no binding of the AB to the target, or no more than 0.001%, 0.01%, 0.1%, 1%, 20%, 3%, 4%, 5%, 6%, 7%, 8%, 9%, 10%, 15%, 20%, 25%, 30%, 35%, 40%, or 50% binding of the AB to the target, as compared to the binding of the AB not modified with an MM, the parental AB, or the AB not coupled to an MM to the target, for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

When an AB is coupled to or modified by a MM, the MM 'masks' or reduces or otherwise inhibits the specific binding of the AB to the target. When an AB is coupled to or modified by a MM, such coupling or modification can effect a structural change that reduces or inhibits the ability of the AB to specifically bind its target.

An AB coupled to or modified with an MM can be represented by the following formulae (in order from an amino (N) terminal region to carboxyl (C) terminal region:

(MM)-(AB)

(AB)-(MM)

(MM)-L-(AB)

(AB)-L-(MM)

where MM is a masking moiety, the AB is an antibody or antibody fragment thereof, and the L is a linker. In many embodiments, it may be desirable to insert one or more linkers, e.g., flexible linkers, into the composition so as to provide for flexibility.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80 similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 25% identical to any natural binding partner of the AB. In some embodiments, the MM is no more than 50% identical to any natural binding partner of the AB. In some embodiments, the MM is no more than 200% identical to any natural binding partner of the AB. In some embodiments, the MM is no more than 10% identical to any natural binding partner of the AB.

In some embodiments, the activatable antibodies include an AB that is modified by an MM and also includes one or more cleavable moieties (CM). Such activatable antibodies exhibit activatable/switchable binding, to the AB's target. Activatable antibodies generally include an antibody or antibody fragment (AB), modified by or coupled to a masking moiety (MM) and a modifiable or cleavable moiety (CM). In some embodiments, the CM contains an amino acid sequence that serves as a substrate for at least one protease.

The elements of the activatable antibodies are arranged so that the MM and CM are positioned such that in a cleaved (or relatively active) state and in the presence of a target, the AB binds a target while the activatable antibody is in an uncleaved (or relatively inactive) state in the presence of the target, specific binding of the AB to its target is reduced or inhibited. The specific binding of the AB to its target can be reduced due to the inhibition or masking of the AB's ability to specifically bind its target by the MM.

The $K_d$ of the AB modified with a MM and a CM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM and a CM or of the parental AB towards the target. Conversely, the binding affinity of the AB modified with a MM and a CM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM and a CM or of the parental AB towards the target.

When the AB is modified with a MM and a CM and is in the presence of the target but not in the presence of a modifying agent (for example at least one protease), specific binding of the AB to its target is reduced or inhibited, as compared to the specific binding of the AB not modified with an MM and a CM or of the parental AB to the target. When compared to the binding of the parental AB or the binding of an AB not modified with an MM and a CM to its target, the AB's ability to bind the target when modified with an MM and a CM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

As used herein, the term cleaved state refers to the condition of the activatable antibodies following modification of the CM by at least one protease. The term uncleaved state, as used herein, refers to the condition of the activatable antibodies in the absence of cleavage of the CM by a protease. As discussed above, the term "activatable antibodies" is used herein to refer to an activatable antibody in both its uncleaved (native) state, as well as in its cleaved state. It will be apparent to the ordinarily skilled artisan that in some embodiments a cleaved activatable antibody may lack an MM due to cleavage of the CM by protease, resulting in release of at least the MM (e.g., where the MM is not joined to the activatable antibodies by a covalent bond (e.g., a disulfide bond between cysteine residues).

By activatable or switchable is meant that the activatable antibody exhibits a first level of binding to a target when the activatable antibody is in a inhibited, masked or uncleaved state (i.e., a first conformation), and a second level of binding to the target in the uninhibited, unmasked and/or cleaved state (i.e., a second conformation), where the second level of target binding is greater than the first level of binding. In general, the access of target to the AB of the activatable antibody is greater in the presence of a cleaving agent capable of cleaving the CM, i.e., a protease, than in the absence of such a cleaving agent. Thus, when the activatable antibody is in the uncleaved state, the AB is inhibited from target binding and can be masked from target binding (i.e., the first conformation is such the AB cannot bind the target), and in the cleaved state the AB is not inhibited or is unmasked to target binding.

The CM and AB of the activatable antibodies are selected so that the AB represents a binding moiety for a given target, and the CM represents a substrate for a protease. In some embodiments, the protease is co-localized with the target at a treatment site or diagnostic site in a subject. As used herein, co-localized refers to being at the same site or relatively close nearby. In some embodiments, a protease cleaves a CM yielding an activated antibody that binds to a target located nearby the cleavage site. The activatable antibodies disclosed herein find particular use where, for example, a protease capable of cleaving a site in the CM, i.e., a protease, is present at relatively higher levels in target-containing tissue of a treatment site or diagnostic site than in tissue of non-treatment sites (for example in healthy tissue). In some embodiments, a CM of the disclosure is also cleaved by one or more other proteases. In some embodiments, it is the one or more other proteases that is co-localized with the target and that is responsible for cleavage of the CM in vivo.

In some embodiments activatable antibodies provide for reduced toxicity and/or adverse side effects that could otherwise result from binding of the AB at non-treatment sites if the AB were not masked or otherwise inhibited from binding to the target.

In general, an activatable antibody can be designed by selecting an AB of interest and constructing the remainder of the activatable antibody so that, when conformationally constrained, the MM provides for masking of the AB or reduction of binding of the AB to its target. Structural design criteria can be to be taken into account to provide for this functional feature.

Activatable antibodies exhibiting a switchable phenotype of a desired dynamic range for target binding in an inhibited versus an uninhibited conformation are provided. Dynamic range generally refers to a ratio of (a) a maximum detected level of a parameter under a first set of conditions to (b) a minimum detected value of that parameter under a second set of conditions. For example, in the context of an activatable antibody, the dynamic range refers to the ratio of (a) a maximum detected level of target protein binding to an activatable antibody in the presence of at least one protease capable of cleaving the CM of the activatable antibodies to (b) a minimum detected level of target protein binding to an activatable antibody in the absence of the protease. The dynamic range of an activatable antibody can be calculated as the ratio of the dissociation constant of an activatable antibody cleaving agent (e.g., enzyme) treatment to the dissociation constant of the activatable antibodies cleaving agent treatment. The greater the dynamic range of an activatable antibody, the better the switchable phenotype of the activatable antibody. Activatable antibodies having relatively higher dynamic range values (e.g., greater than 1) exhibit more desirable switching phenotypes such that target protein binding by the activatable antibodies occurs to a greater extent (e.g., predominantly occurs) in the presence of a cleaving agent (e.g., enzyme) capable of cleaving the CM of the activatable antibodies than in the absence of a cleaving agent.

Activatable antibodies can be provided in a variety of structural configurations. Exemplary formulae for activatable antibodies are provided below. It is specifically contemplated that the N- to C-terminal order of the AB, MM and CM may be reversed within an activatable antibody. It is also specifically contemplated that the CM and MM may overlap in amino acid sequence, e.g., such that the CM is contained within the MM.

For example, activatable antibodies can be represented by the following formula (in order from an amino (N) terminal region to carboxyl (C) terminal region:

(MM)-(CM)-(AB)

(AB)-(CM)-(MM)

where MM is a masking moiety, CM is a cleavable moiety, and AB is an antibody or fragment thereof. It should be noted that although MM and CM are indicated as distinct components in the formulae above, in all exemplary embodiments (including formulae) disclosed herein it is contemplated that the amino acid sequences of the MM and the CM could overlap, e.g., such that the CM is completely or partially contained within the MM. In addition, the formulae above provide for additional amino acid sequences that may be positioned N-terminal or C-terminal to the activatable antibodies elements.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80%, identical to any natural binding partner of the AB. In some embodiments, the MM is no more than 50% identical to any natural binding partner of the AB. In some embodiments, the MM is no more than 25% identical to any natural binding partner of the AB. In some embodiments, the MM is no more than 20% identical to any natural binding partner of the AB. In some embodiments, the MM is no more than 10% identical to any natural binding partner of the AB.

In many embodiments it may be desirable to insert one or more linkers, e.g., flexible linkers, into the activatable antibody construct so as to provide for flexibility at one or more of the MM-CM junction, the CM-AB junction, or both. For example, the AB, MM, and/or CM may not contain a sufficient number of residues (e.g., Gly, Ser, Asp, Asn, especially Gly and Ser, particularly Gly) to provide the desired flexibility. As such, the switchable phenotype of such activatable antibody constructs may benefit from introduction of one or more amino acids to provide for a flexible linker. In addition, as described below, where the activatable antibody is provided as a conformationally constrained construct, a flexible linker can be operably inserted to facilitate formation and maintenance of a cyclic structure in the uncleaved activatable antibody.

For example, in certain embodiments an activatable antibody comprises one of the following formulae (where the formula below represent an amino acid sequence in either N- to C-terminal direction or C- to N-terminal direction):

(MM)-L1-(CM)-(AB)

(MM)-(CM)-L2-(AB)

(MM)-L1-(CM)-L2-(AB)

wherein MM, CM, and AB are as defined above, wherein L1 and L2 are each independently and optionally present or absent, are the same or different flexible linkers that include at least 1 flexible amino acid (e.g., Gly). In addition, the formulae above provide for additional amino acid sequences that may be positioned N-terminal or C-terminal to the activatable antibodies elements. Examples include, but are not limited to, targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HAS)).

The CM is specifically cleaved by at least one protease at a rate of about $0.001\text{-}1500\times10^4$ $M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or $1500\times10^4$ $M^{-1}S^{-1}$. In some embodiments, the CM is specifically cleaved at a rate of about 100,000 $M^{-1}S^{-1}$. In some embodiments, the CM is specifically cleaved at a rate from about 1×10E2 to about 1×10E6 $M^{-1}S^{-1}$ (i.e., from about $1\times10^2$ to about $1\times10^6$ $M^{-1}S^{-1}$).

For specific cleavage by an enzyme, contact between the enzyme and CM is made. When the activatable antibody comprising an AB coupled to a MM and a CM is in the presence of target and sufficient enzyme activity, the CM can be cleaved. Sufficient enzyme activity can refer to the ability of the enzyme to make contact with the CM and effect cleavage. It can readily be envisioned that an enzyme may be in the vicinity of the CM but unable to cleave because of other cellular factors or protein modification of the enzyme.

Linkers suitable for use in compositions described herein are generally ones that provide flexibility of the modified AB or the activatable antibodies to facilitate the inhibition of the binding of the AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, or 20 amino acids in length.

Exemplary flexible linkers include glycine polymers (G)n, glycine-serine polymers (including, for example, (GS)n, (GSGGS)n (SEQ ID NO: 1) and (GGGS)n (SEQ ID NO: 2), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible linkers include, but are not limited to Gly-Gly-Ser-Gly (SEQ ID NO: 3), Gly-Gly-Ser-Gly-Gly (SEQ ID NO: 4), Gly-Ser-Gly-Ser-Gly (SEQ ID NO: 5), Gly-Ser-Gly-Gly-Gly (SEQ ID NO: 6), Gly-Gly-Gly-Ser-Gly (SEQ ID NO: 7), Gly-Ser-Ser-Ser-Gly (SEQ ID NO: 8), and the like. The ordinarily skilled artisan will recognize that design of an activatable antibodies can include linkers that are all or partially flexible, such that the linker can include a flexible linker as well as one or more portions that confer less flexible structure to provide for a desired activatable antibodies structure.

The disclosure also provides compositions and methods that include an activatable anti-CD166 antibody that includes an antibody or antibody fragment (AB) that specifically binds CD166, where the AB is coupled to a masking moiety (MM) that decreases the ability of the AB to bind its target. In some embodiments, the activatable anti-CD166 antibody further includes a cleavable moiety (CM) that is a substrate for a protease. The compositions and methods provided herein enable the attachment of one or more agents to one or more cysteine residues in the AB without compromising the activity (e.g., the masking, activating or binding activity) of the activatable anti-CD166 antibody. In some embodiments, the compositions and methods provided herein enable the attachment of one or more agents to one or more cysteine residues in the AB without reducing or otherwise disturbing one or more disulfide bonds within the MM. The compositions and methods provided herein produce an activatable anti-CD166 antibody that is conjugated to one or more agents, e.g., any of a variety of therapeutic, diagnostic and/or prophylactic agents, for example, in some embodiments, without any of the agent(s) being conjugated to the MM of the activatable anti-CD166 antibody. The compositions and methods provided herein produce conjugated activatable anti-CD166 antibodies in which the MM retains the ability to effectively and efficiently mask the AB of the activatable antibody in an uncleaved state. The compositions and methods provided herein produce conjugated activatable anti-CD166 antibodies in which the activatable antibody is still activated, i.e., cleaved, in the presence of a protease that can cleave the CM.

The activatable anti-CD166 antibodies have at least one point of conjugation for an agent, but in the methods and compositions provided herein less than all possible points of conjugation are available for conjugation to an agent. In some embodiments, the one or more points of conjugation are sulfur atoms involved in disulfide bonds. In some embodiments, the one or more points of conjugation are sulfur atoms involved in interchain disulfide bonds. In some embodiments, the one or more points of conjugation are sulfur atoms involved in interchain sulfide bonds, but not sulfur atoms involved in intrachain disulfide bonds. In some embodiments, the one or more points of conjugation are sulfur atoms of cysteine or other amino acid residues containing a sulfur atom. Such residues may occur naturally in the antibody structure or may be incorporated into the antibody by site-directed mutagenesis, chemical conversion, or mis-incorporation of non-natural amino acids.

Also provided are methods of preparing a conjugate of an activatable anti-CD166 antibody having one or more interchain disulfide bonds in the AB and one or more intrachain disulfide bonds in the MM, and a drug reactive with free thiols is provided. The method generally includes partially reducing interchain disulfide bonds in the activatable antibody with a reducing agent, such as, for example, TCEP; and conjugating the drug reactive with free thiols to the partially reduced activatable antibody. As used herein, the term partial reduction refers to situations where an activatable anti-CD166 antibody is contacted with a reducing agent and less than all disulfide bonds, e.g., less than all possible sites of conjugation are reduced. In some embodiments, less than 99%, 98%, 97%, 96%, 95%, 90%, 85%, 80%, 75%, 70%, 65%, 60%, 55%, 50%, 45%, 40%, 35%, 30%, 25%, 20%, 15%, 10% or less than 5% of all possible sites of conjugation are reduced.

In yet other embodiments, a method of reducing and conjugating an agent, e.g., a drug, to an activatable anti-CD166 antibody resulting in selectivity in the placement of the agent is provided. The method generally includes partially reducing the activatable anti-CD166 antibody with a reducing agent such that any conjugation sites in the masking moiety or other non-AB portion of the activatable antibody are not reduced, and conjugating the agent to interchain thiols in the AB. The conjugation site(s) are selected so as to allow desired placement of an agent to allow conjugation to occur at a desired site. The reducing agent is, for example, TCEP. The reduction reaction conditions such as, for example, the ratio of reducing agent to activatable antibody, the length of incubation, the temperature during the incubation, the pH of the reducing reaction solution, etc., are determined by identifying the conditions that produce a conjugated activatable antibody in which the MM retains the ability to effectively and efficiently mask the AB of the activatable antibody in an uncleaved state. The ratio of reduction agent to activatable anti-CD166 antibody will vary depending on the activatable antibody. In some embodiments, the ratio of reducing agent to activatable anti-CD166 antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

In some embodiments, a method of reducing interchain disulfide bonds in the AB of an activatable anti-CD166 antibody and conjugating an agent, e.g., a thiol-containing agent such as a drug, to the resulting interchain thiols to selectively locate agent(s) on the AB is provided. The method generally includes partially reducing the AB with a reducing agent to form at least two interchain thiols without forming all possible interchain thiols in the activatable antibody; and conjugating the agent to the interchain thiols of the partially reduced AB. For example, the AB of the activatable antibody is partially reduced for about 1 hour at about 37° C. at a desired ratio of reducing agent:activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

The thiol-containing reagent can be, for example, cysteine or N-acetyl cysteine. The reducing agent can be, for example, TCEP. In some embodiments, the reduced activatable antibody can be purified prior to conjugation, using for example, column chromatography, dialysis, or diafiltration. Alternatively, the reduced antibody is not purified after partial reduction and prior to conjugation.

The invention also provides partially reduced activatable anti-CD166 antibodies in which at least one interchain disulfide bond in the activatable antibody has been reduced with a reducing agent without disturbing any intrachain disulfide bonds in the activatable antibody, wherein the activatable antibody includes an antibody or an antigen binding fragment thereof (AB) that specifically binds to CD166, a masking moiety (MM) that inhibits the binding of the AB of the activatable antibody in an uncleaved state to the CD166 target, and a cleavable moiety (CM) coupled to the AB, wherein the CM is a polypeptide that functions as a substrate for a protease. In some embodiments the MM is coupled to the AB via the CM. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM-AB or AB-CM-MM. In some embodiments, reducing agent is TCEP.

The disclosure also provides partially reduced activatable antibodies in which at least one interchain disulfide bond in the activatable antibody has been reduced with a reducing agent without disturbing any intrachain disulfide bonds in the activatable antibody, wherein the activatable antibody includes an antibody or an antigen binding fragment thereof (AB) that specifically binds to the target, e.g., CD166, a masking moiety (MM) that inhibits the binding of the AB of the activatable antibody in an uncleaved state to the target, and a cleavable moiety (CM) coupled to the AB, wherein the CM is a polypeptide that functions as a substrate for at least one protease. In some embodiments, the MM is coupled to the AB via the CM. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM-AB or AB-CM-MM. In some embodiments, reducing agent is TCEP.

In yet other embodiments, a method of reducing and conjugating an agent, e.g., a drug, to an activatable anti-CD166 antibody resulting in selectivity in the placement of the agent by providing an activatable anti-CD166 antibody with a defined number and positions of lysine and/or cysteine residues. In some embodiments, the defined number of lysine and/or cysteine residues is higher or lower than the number of corresponding residues in the amino acid sequence of the parent antibody or activatable antibody. In some embodiments, the defined number of lysine and/or cysteine residues may result in a defined number of agent equivalents that can be conjugated to the anti-CD166 antibody or activatable anti-CD166 antibody. In some embodiments, the defined number of lysine and/or cysteine residues may result in a defined number of agent equivalents that can be conjugated to the anti-CD166 antibody or activatable anti-CD166 antibody in a site-specific manner. In some embodiments, the modified activatable antibody is modified with one or more non-natural amino acids in a site-specific manner, thus in some embodiments limiting the conjugation of the agents to only the sites of the non-natural amino acids. In some embodiments, the anti-CD166 antibody or activatable anti-CD166 antibody with a defined number and positions of lysine and/or cysteine residues may be partially reduced with a reducing agent as discussed herein such that any conjugation sites in the masking moiety or other non-AB portion of the activatable antibody are not reduced, and conjugating the agent to interchain thiols in the AB.

In some embodiments, the activatable antibodies described herein also include an agent conjugated to the activatable antibody. In some embodiments, the conjugated agent is a therapeutic agent, such as an anti-inflammatory and/or an antineoplastic agent. In such embodiments, the agent is conjugated to a carbohydrate moiety of the activatable antibody, for example, in some embodiments, where the carbohydrate moiety is located outside the antigen-binding region of the antibody or antigen-binding fragment in the activatable antibody. In some embodiments, the agent is conjugated to a sulfhydryl group of the antibody or antigen-binding fragment in the activatable antibody.

In some embodiments, the agent is a cytotoxic agent such as a toxin (e.g., an enzymatically active toxin of bacterial, fungal, plant, or animal origin, or fragments thereof), or a radioactive isotope (i.e., a radioconjugate).

In some embodiments, the agent is a detectable moiety such as, for example, a label or other marker. For example, the agent is or includes a radiolabeled amino acid, one or more biotinyl moieties that can be detected by marked avidin (e.g., streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties are attached by spacer molecules.

The disclosure also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents include, for example, dolastatins and derivatives thereof (e.g. auristatin E, AFP, MMAF, MMAE, MMAD, DMAF, DMAE). For example, the agent is monomethyl auristatin E (MMAE) or monomethyl auristatin D (MMAD). In some embodiments, the agent is an agent selected from the group listed in Table 5. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some embodiments, the agent is linked to the AB using a maleimide caproyl-valine-citrulline linker or a maleimide PEG-valine-citrulline linker. In some embodiments, the agent is linked to the AB using a maleimide caproyl-valine-citrulline linker. In some embodiments, the agent is linked to the AB using a maleimide PEG-valine-citrulline linker In some embodiments, the agent is monomethyl auristatin D (MMAD) linked to the AB using a maleimide PEG-valine-citrulline-para-aminobenzyloxycarbonyl linker, and this linker payload construct is referred to herein as "vc-MMAD." In some embodiments, the agent is monomethyl auristatin E (MMAE) linked to the AB using a maleimide PEG-valine-citrulline-para-aminobenzyloxycarbonyl linker, and this linker payload construct is referred to herein as "vc-MMAE." In some embodiments, the agent is linked to the AB using a maleimide PEG-valine-citrulline linker In some embodiments, the agent is monomethyl auristatin D (MMAD) linked to the AB using a maleimide bis-PEG-valine-citrulline-para-aminobenzyloxycarbonyl linker, and this linker payload construct is referred to herein as "PEG2-vc-MMAD." The structures of vc-MMAD, vc-MMAE, and PEG2-vc-MMAD are shown below:

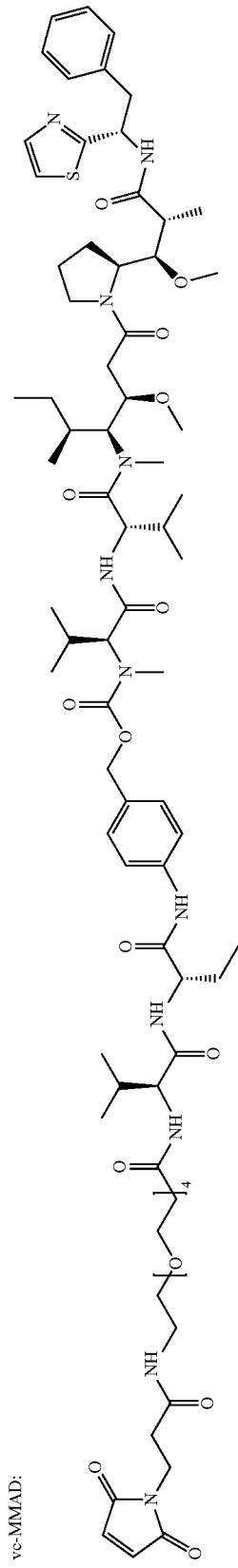
vc-MMAD:
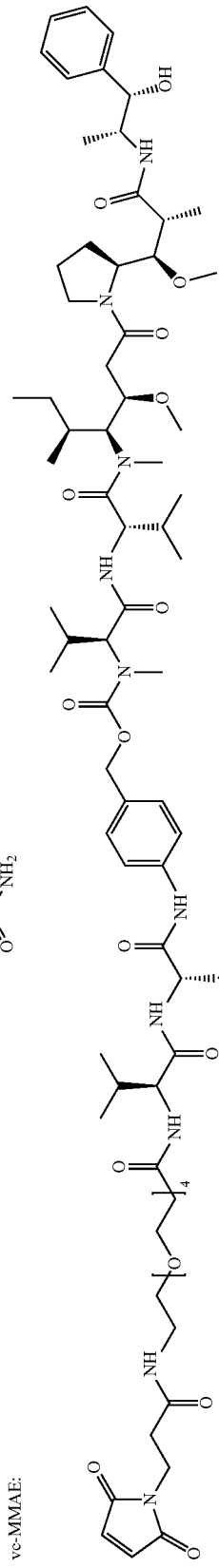
vc-MMAE:
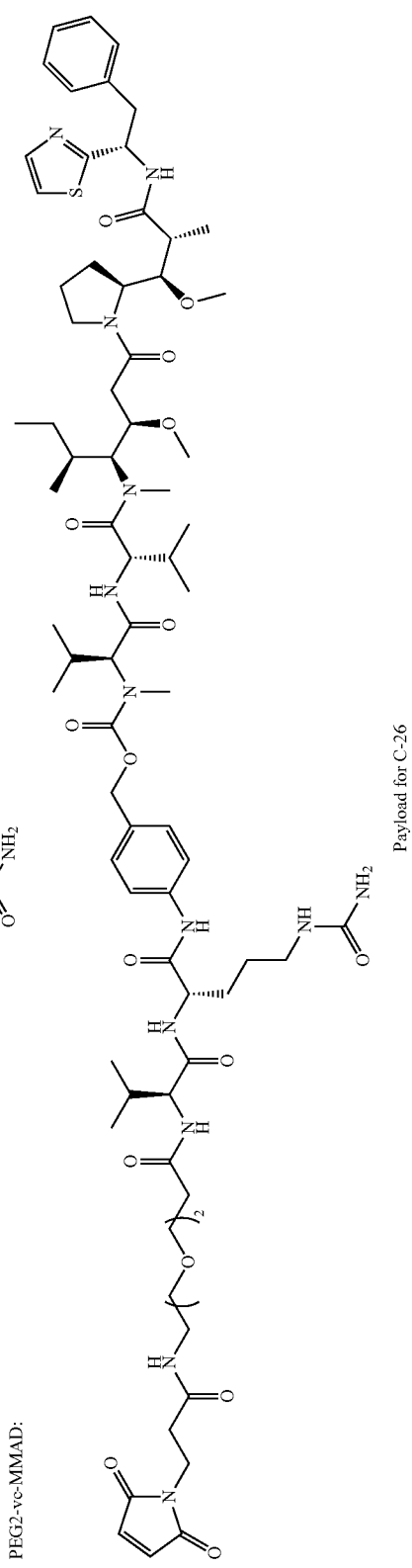
PEG2-vc-MMAD:
Payload for C-26

The disclosure also provides conjugated activatable antibodies that include an activatable antibody linked to monomethyl auristatin D (MMAD) payload, wherein the activatable antibody includes an antibody or an antigen binding fragment thereof (AB) that specifically binds to a target, a masking moiety (MM) that inhibits the binding of the AB of the activatable antibody in an uncleaved state to the target, and cleavable moiety (CM) coupled to the AB, and the CM is a polypeptide that functions as a substrate for at least one MMP protease.

In some embodiments, the MMAD-conjugated activatable antibody can be conjugated using any of several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB.

In some embodiments, the MMAD payload is conjugated to the AB via a linker. In some embodiments, the MMAD payload is conjugated to a cysteine in the AB via a linker. In some embodiments, the MMAD payload is conjugated to a lysine in the AB via a linker. In some embodiments, the MMAD payload is conjugated to another residue of the AB via a linker, such as those residues disclosed herein. In some embodiments, the linker is a thiol-containing linker. In some embodiments, the linker is a cleavable linker. In some embodiments, the linker is a non-cleavable linker. In some embodiments, the linker is selected from the group consisting of the linkers shown in Tables 6 and 7. In some embodiments, the activatable antibody and the MMAD payload are linked via a maleimide caproyl-valine-citrulline linker. In some embodiments, the activatable antibody and the MMAD payload are linked via a maleimide PEG-valine-citrulline linker. In some embodiments, the activatable antibody and the MMAD payload are linked via a maleimide caproyl-valine-citrulline-para-aminobenzyloxycarbonyl linker. In some embodiments, the activatable antibody and the MMAD payload are linked via a maleimide PEG-valine-citrulline-para-aminobenzyloxycarbonyl linker. In some embodiments, the MMAD payload is conjugated to the AB using the partial reduction and conjugation technology disclosed herein.

In some embodiments, the polyethylene glycol (PEG) component of a linker of the present disclosure is formed from 2 ethylene glycol monomers, 3 ethylene glycol monomers, 4 ethylene glycol monomers, 5 ethylene glycol monomers, 6 ethylene glycol monomers, 7 ethylene glycol monomers 8 ethylene glycol monomers, 9 ethylene glycol monomers, or at least 10 ethylene glycol monomers. In some embodiments of the present disclosure, the PEG component is a branched polymer. In some embodiments of the present disclosure, the PEG component is an unbranched polymer. In some embodiments, the PEG polymer component is functionalized with an amino group or derivative thereof, a carboxyl group or derivative thereof, or both an amino group or derivative thereof and a carboxyl group or derivative thereof.

In some embodiments, the PEG component of a linker of the present disclosure is an amino-tetra-ethylene glycol-carboxyl group or derivative thereof. In some embodiments, the PEG component of a linker of the present disclosure is an amino-tri-ethylene glycol-carboxyl group or derivative thereof. In some embodiments, the PEG component of a linker of the present disclosure is an amino-di-ethylene glycol-carboxyl group or derivative thereof. In some embodiments, an amino derivative is the formation of an amide bond between the amino group and a carboxyl group to which it is conjugated. In some embodiments, a carboxyl derivative is the formation of an amide bond between the carboxyl group and an amino group to which it is conjugated. In some embodiments, a carboxyl derivative is the formation of an ester bond between the carboxyl group and an hydroxyl group to which it is conjugated.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Table 5 lists some of the exemplary pharmaceutical agents that may be employed in the herein described disclosure but in no way is meant to be an exhaustive list.

TABLE 5

| Exemplary Pharmaceutical Agents for Conjugation |
|---|
| CYTOTOXIC AGENTS |
| Auristatins |
| Auristatin E |
| Monomethyl auristatin D (MMAD) |
| Monomethyl auristatin E (MMAE) |
| Desmethyl auristatin E (DMAE) |
| Auristatin F |
| Monomethyl auristatin F (MMAF) |
| Desmethyl auristatin F (DMAF) |
| Auristatin derivatives, e.g., amides thereof |
| Auristatin tyramine |
| Auristatin quinoline |
| Dolastatins |
| Dolastatin derivatives |
| Dolastatin 16 DmJ |
| Dolastatin 16 Dpv |
| Maytansinoids, e.g. DM-1; DM-4 |
| Maytansinoid derivatives |
| Duocarmycin |
| Duocarmycin derivatives |
| Alpha-amanitin |
| Anthracyclines |
| Doxorubicin |
| Daunorubicin |
| Bryostatins |
| Camptothecin |
| Camptothecin derivatives |
| 7-substituted Camptothecin |

TABLE 5-continued

Exemplary Pharmaceutical Agents for Conjugation 10,11-Difluoromethylenedioxycamptothecin
Combretastatins
Debromoaplysiatoxin
Kahalalide-F
Discodermolide
Ecteinascidins

ANTIVIRALS

Acyclovir
Vira A
Symmetrel

ANTIFUNGALS

Nystatin

ADDITIONAL ANTI-NEOPLASTICS

Adriamycin
Cerubidine
Bleomycin
Alkeran
Velban
Oncovin
Fluorouracil
Methotrexate
Thiotepa
Bisantrene
Novantrone
Thioguanine
Procarabizine
Cytarabine

ANTI-BACTERIALS

Aminoglycosides
Streptomycin
Neomycin
Kanamycin
Amikacin
Gentamicin
Tobramycin
Streptomycin B
Spectinomycin
Ampicillin
Sulfanilamide
Polymyxin
Chloramphenicol
Turbostatin
Phenstatins
Hydroxyphenstatin
Spongistatin 5
Spongistatin 7
Halistatin 1
Halistatin 2
Halistatin 3
Modified Bryostatins
Halocomstatins
Pyrrolobenzimidazoles (PBI)
Cibrostatin6
Doxaliform
Anthracyclins analogues
Cemadotin analogue (CemCH2-SH)
Pseudomonas toxin A (PE38) variant
Pseudomonas toxin A (ZZ-PE38) variant
ZJ-101
OSW-1
4-Nitrobenzyloxycarbonyl Derivatives of O6-Benzylguanine
Topoisomerase inhibitors
Hemiasterlin
Cephalotaxine
Homoharringtonine
Pyrrolobenzodiazepine dimers (PBDs)
Functionalized pyrrolobenzodiazepenes
Calicheamicins
Podophyllotoxins
Taxanes
Vinca alkaloids

CONJUGATABLE DETECTION REAGENTS

Fluorescein and derivatives thereof
Fluorescein isothiocyanate (FITC)

RADIOPHARMACEUTICALS $^{125}$I
$^{131}$I
$^{89}$Zr
$^{111}$In
$^{123}$I
$^{131}$I
$^{99m}$Tc
$^{201}$Tl
$^{133}$Xe
$^{11}$C
$^{62}$Cu
$^{18}$F
$^{68}$Ga
$^{13}$N
$^{15}$O
$^{38}$K
$^{82}$Rb
$^{99m}$Tc (Technetium)

HEAVY METALS

Barium
Gold
Platinum

ANTI-MYCOPLASMALS

Tylosine
Spectinomycin

Those of ordinary skill in the art will recognize that a large variety of possible moieties can be coupled to the resultant antibodies of the disclosure. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. In some embodiments, the binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present disclosure, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

In some embodiments, in addition to the compositions and methods provided herein, the conjugated activatable antibody can also be modified for site-specific conjugation through modified amino acid sequences inserted or otherwise included in the activatable antibody sequence. These modified amino acid sequences are designed to allow for controlled placement and/or dosage of the conjugated agent within a conjugated activatable antibody. For example, the activatable antibody can be engineered to include cysteine substitutions at positions on light and heavy chains that provide reactive thiol groups and do not negatively impact protein folding and assembly, nor alter antigen binding. In some embodiments, the activatable antibody can be engineered to include or otherwise introduce one or more non-natural amino acid residues within the activatable antibody to provide suitable sites for conjugation. In some embodiments, the activatable antibody can be engineered to include or otherwise introduce enzymatically activatable peptide sequences within the activatable antibody sequence.

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. In some embodiments, suitable linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC. Additional linkers include, but are not limited to, SMCC ((succinimidyl 4-(N-maleimidomethyl)cyclohexane-1-carboxylate), sulfo-SMCC (sulfosuccinimidyl 4-(N-maleimidomethyl)cyclohexane-1-carboxylate), SPDB (N-succinimidyl-4-(2-pyridyldithio) butanoate), or sulfo-SPDB (N-succinimidyl-4-(2-pyridyldithio)-2-sulfo butanoate).

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In some embodiments, the linkers are cleavable. In some embodiments, the linkers are non-cleavable. In some embodiments, two or more linkers are present. The two or more linkers are all the same, i.e., cleavable or non-cleavable, or the two or more linkers are different, i.e., at least one cleavable and at least one non-cleavable.

The present disclosure utilizes several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB. According to the disclosure, ABs may be covalently attached to an agent through an intermediate linker having at least two reactive groups, one to react with AB and one to react with the agent. The linker, which may include any compatible organic compound, can be chosen such that the reaction with AB (or agent) does not adversely affect AB reactivity and selectivity. Furthermore, the attachment of linker to agent might not destroy the activity of the agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

According to the present disclosure, suitable linkers for attachment to reduced ABs include those having certain reactive groups capable of reaction with a sulfhydryl group of a reduced antibody or fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101: 3097-3110).

According to the present disclosure, suitable linkers for attachment to neither oxidized nor reduced Abs include those having certain functional groups capable of reaction with the primary amino groups present in unmodified lysine residues in the Ab. Such reactive groups include, but are not limited to, NHS carboxylic or carbonic esters, sulfo-NHS carboxylic or carbonic esters, 4-nitrophenyl carboxylic or carbonic esters, pentafluorophenyl carboxylic or carbonic esters, acyl imidazoles, isocyanates, and isothiocyanates.

According to the present disclosure, suitable linkers for attachment to neither oxidized nor reduced Abs include those having certain functional groups capable of reaction with the carboxylic acid groups present in aspartate or glutamate residues in the Ab, which have been activated with suitable reagents. Suitable activating reagents include EDC, with or without added NHS or sulfo-NHS, and other dehydrating agents utilized for carboxamide formation. In these instances, the functional groups present in the suitable linkers would include primary and secondary amines, hydrazines, hydroxylamines, and hydrazides.

The agent may be attached to the linker before or after the linker is attached to the AB. In certain applications it may be desirable to first produce an AB-linker intermediate in which the linker is free of an associated agent. Depending upon the particular application, a specific agent may then be covalently attached to the linker. In some embodiments, the AB is first attached to the MM, CM and associated linkers and then attached to the linker for conjugation purposes.

Branched Linkers: In specific embodiments, branched linkers that have multiple sites for attachment of agents are utilized. For multiple site linkers, a single covalent attachment to an AB would result in an AB-linker intermediate capable of binding an agent at a number of sites. The sites may be aldehyde or sulfhydryl groups or any chemical site to which agents can be attached.

In some embodiments, higher specific activity (or higher ratio of agents to AB) can be achieved by attachment of a single site linker at a plurality of sites on the AB. This plurality of sites may be introduced into the AB by either of two methods. First, one may generate multiple aldehyde groups and/or sulfhydryl groups in the same AB. Second, one may attach to an aldehyde or sulfhydryl of the AB a "branched linker" having multiple functional sites for subsequent attachment to linkers. The functional sites of the branched linker or multiple site linker may be aldehyde or sulfhydryl groups, or may be any chemical site to which linkers may be attached. Still higher specific activities may be obtained by combining these two approaches, that is, attaching multiple site linkers at several sites on the AB.

Cleavable Linkers: Peptide linkers that are susceptible to cleavage by enzymes of the complement system, such as but not limited to u-plasminogen activator, tissue plasminogen activator, trypsin, plasmin, or another enzyme having proteolytic activity may be used in one embodiment of the present disclosure. According to one method of the present disclosure, an agent is attached via a linker susceptible to cleavage by complement. The antibody is selected from a class that can activate complement. The antibody-agent conjugate, thus, activates the complement cascade and releases the agent at the target site. According to another method of the present disclosure, an agent is attached via a linker susceptible to cleavage by enzymes having a proteolytic activity such as a u-plasminogen activator, a tissue plasminogen activator, plasmin, or trypsin. These cleavable linkers are useful in conjugated activatable antibodies that include an extracellular toxin, e.g., by way of non-limiting example, any of the extracellular toxins shown in Table 5.

Non-limiting examples of cleavable linker sequences are provided in Table 6.

TABLE 6

Exemplary Linker Sequences for Conjugation

| Types of Cleavable Sequences | Amino Acid Sequence |
| --- | --- |
| Plasmin cleavable sequences | |
| Pro-urokinase | PRFKIIGG (SEQ ID NO: 89) |
| | PRFRIIGG (SEQ ID NO: 90) |
| TGFβ | SSRIIRRALD (SEQ ID NO: 91) |
| Plasminogen | RKSSIIIRMRDVNTL (SEQ ID NO: 92) |
| Staphylokinase | SSSFDKGKYKKGDDA (SEQ ID NO: 93) |
| | SSSFDKGKYKRGDDA (SEQ ID NO: 94) |
| Factor Xa cleavable sequences | IEGR (SEQ ID NO: 95) |
| | IDGR (SEQ ID NO: 96) |
| | GGSIDGR (SEQ ID NO: 97) |
| MMP cleavable sequences | |
| Gelatinase A | PLGLWA (SEQ ID NO: 98) |
| Collagenase cleavable sequences | |
| Calf skin collagen (α1(I) chain) | GPQGIAGQ (SEQ ID NO: 99) |
| Calf skin collagen (α2(I) chain) | GPQGLLGA (SEQ ID NO: 100) |
| Bovine cartilage collagen (α1(II) chain) | GIAGQ (SEQ ID NO: 101) |
| Human liver collagen (α1(III) chain) | GPLGIAGI (SEQ ID NO: 102) |
| Human α₂M | GPEGLRVG (SEQ ID NO: 103) |
| Human PZP | YGAGLGVV (SEQ ID NO: 104) |
| | AGLGVVER (SEQ ID NO: 105) |
| | AGLGISST (SEQ ID NO: 106) |

TABLE 6-continued

Exemplary Linker Sequences for Conjugation

| Types of Cleavable Sequences | Amino Acid Sequence |
| --- | --- |
| Rat α₁M | EPQALAMS (SEQ ID NO: 107) |
| | QALAMSAI (SEQ ID NO: 108) |
| Rat α₂M | AAYHLVSQ (SEQ ID NO: 109) |
| | MDAFLESS (SEQ ID NO: 110) |
| Rat α₁I₃(2J) | ESLPVVAV (SEQ ID NO: 111) |
| Rat α₁I₃(27J) | SAPAVESE (SEQ ID NO: 112) |
| Human fibroblast collagenase (autolytic cleavages) | DVAQFVLT (SEQ ID NO: 113) |
| | VAQFVLTE (SEQ ID NO: 114) |
| | AQFVLTEG (SEQ ID NO: 115) |
| | PVQPIGPQ (SEQ ID NO: 116) |

In addition, agents may be attached via disulfide bonds (for example, the disulfide bonds on a cysteine molecule) to the AB. Since many tumors naturally release high levels of glutathione (a reducing agent) this can reduce the disulfide bonds with subsequent release of the agent at the site of delivery. In some embodiments, the reducing agent that would modify a CM would also modify the linker of the conjugated activatable antibody.

Spacers and Cleavable Elements: In some embodiments, it may be necessary to construct the linker in such a way as to optimize the spacing between the agent and the AB of the activatable antibody. This may be accomplished by use of a linker of the general structure:

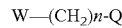

$$W-(CH_2)n-Q$$

wherein
W is either $-NH-CH_2-$ or $-CH_2-$;
Q is an amino acid, peptide; and
n is an integer from 0 to 20.

In some embodiments, the linker may comprise a spacer element and a cleavable element. The spacer element serves to position the cleavable element away from the core of the AB such that the cleavable element is more accessible to the enzyme responsible for cleavage. Certain of the branched linkers described above may serve as spacer elements.

Throughout this discussion, it should be understood that the attachment of linker to agent (or of spacer element to cleavable element, or cleavable element to agent) need not be particular mode of attachment or reaction. Any reaction providing a product of suitable stability and biological compatibility is acceptable.

Serum Complement and Selection of Linkers: According to one method of the present disclosure, when release of an agent is desired, an AB that is an antibody of a class that can activate complement is used. The resulting conjugate retains both the ability to bind antigen and activate the complement cascade. Thus, according to this embodiment of the present disclosure, an agent is joined to one end of the cleavable linker or cleavable element and the other end of the linker group is attached to a specific site on the AB. For example, if the agent has an hydroxy group or an amino group, it may be attached to the carboxy terminus of a peptide, amino acid or other suitably chosen linker via an ester or amide bond, respectively. For example, such agents may be attached to the linker peptide via a carbodimide reaction. If the agent contains functional groups that would interfere with attachment to the linker, these interfering functional groups can be blocked before attachment and deblocked once the product conjugate or intermediate is made. The opposite or amino terminus of the linker is then used either directly or after further modification for binding to an AB that is capable of activating complement.

Linkers (or spacer elements of linkers) may be of any desired length, one end of which can be covalently attached to specific sites on the AB of the activatable antibody. The other end of the linker or spacer element may be attached to an amino acid or peptide linker.

Thus when these conjugates bind to antigen in the presence of complement the amide or ester bond that attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like as presented in but not limited to those in Table 5.

Linkers for Release without Complement Activation: In yet another application of targeted delivery, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates may be prepared by attaching the agent to an AB that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

Biochemical Cross Linkers: In some embodiments, the activatable antibody may be conjugated to one or more therapeutic agents using certain biochemical cross-linkers. Cross-linking reagents form molecular bridges that tie together functional groups of two different molecules. To link two different proteins in a step-wise manner, hetero-bifunctional cross-linkers can be used that eliminate unwanted homopolymer formation.

Peptidyl linkers cleavable by lysosomal proteases are also useful, for example, Val-Cit, Val-Ala or other dipeptides. In addition, acid-labile linkers cleavable in the low-pH environment of the lysosome may be used, for example: bis-sialyl ether. Other suitable linkers include cathepsin-labile substrates, particularly those that show optimal function at an acidic pH.

Exemplary hetero-bifunctional cross-linkers are referenced in Table 7.

TABLE 7

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
|---|---|---|---|
| SMPT | Primary amines Sulfhydryls | Greater stability | 11.2 Å |
| SPDP | Primary amines Sulfhydryls | Thiolation Cleavable cross-linking | 6.8 Å |
| LC-SPDP | Primary amines Sulfhydryls | Extended spacer arm | 15.6 Å |
| Sulfo- | Primary amines | Extender spacer arm | 15.6 Å |

TABLE 7-continued

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
|---|---|---|---|
| LC-SPDP | Sulfhydryls | Water-soluble | |
| SMCC | Primary amines | Stable maleimide reactive group | 11.6 Å |
| | Sulfhydryls | Enzyme-antibody conjugation Hapten-carrier protein conjugation | |
| Sulfo-SMCC | Primary amines | Stable maleimide reactive group | 11.6 Å |
| | Sulfhydryls | Water-soluble Enzyme-antibody conjugation | |
| MBS | Primary amines Sulfhydryls | Enzyme-antibody conjugation Hapten-carrier protein conjugation | 9.9 Å |
| Sulfo-MBS | Primary amines Sulfhydryls | Water-soluble | 9.9 Å |
| SIAB | Primary amines Sulfhydryls | Enzyme-antibody conjugation | 10.6 Å |
| Sulfo-SIAB | Primary amines Sulfhydryls | Water-soluble | 10.6 Å |
| SMPB | Primary amines Sulfhydryls | Extended spacer arm Enzyme-antibody conjugation | 14.5 Å |
| Sulfo-SMPB | Primary amines Sulfhydryls | Extended spacer arm Water-soluble | 14.5 Å |
| EDE/Sulfo-NHS | Primary amines Carboxyl groups | Hapten-Carrier conjugation | 0 |
| ABH | Carbohydrates Nonselective | Reacts with sugar groups | 11.9 Å |

Non-Cleavable Linkers or Direct Attachment: In some embodiments of the disclosure, the conjugate may be designed so that the agent is delivered to the target but not released. This may be accomplished by attaching an agent to an AB either directly or via a non-cleavable linker.

These non-cleavable linkers may include amino acids, peptides, D-amino acids or other organic compounds that may be modified to include functional groups that can subsequently be utilized in attachment to ABs by the methods described herein. A-general formula for such an organic linker could be

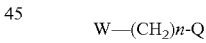

wherein
W is either —NH—CH$_2$— or —CH$_2$—;
Q is an amino acid, peptide; and
n is an integer from 0 to 20.

Non-Cleavable Conjugates: In some embodiments, a compound may be attached to ABs that do not activate complement. When using ABs that are incapable of complement activation, this attachment may be accomplished using linkers that are susceptible to cleavage by activated complement or using linkers that are not susceptible to cleavage by activated complement.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present disclosure can be conjugated to the liposomes as described in Martin et al., J. Biol. Chem., 257: 286-288 (1982) via a disulfide-interchange reaction.

Definitions

Unless otherwise defined, scientific and technical terms used in connection with the present disclosure shall have the meanings that are commonly understood by those of ordinary skill in the art. The term "a" entity or "an" entity refers to one or more of that entity. For example, a compound refers to one or more compounds. As such, the terms "a", "an", "one or more" and "at least one" can be used interchangeably. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active, e.g., antigen-binding, portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, domain antibody, single chain, Fab, and F(ab')$_2$ fragments, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as IgG$_1$, IgG$_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is ≤1 µM; in some embodiments, ≤100 nM and in some embodiments, ≤10 nM.

As used herein, the terms "specific binding," "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to the target, when the binding constant ($K_d$) is ≤1 µM, in some embodiments ≤100 nM, in some embodiments ≤10 nM, and in some embodiments ≤100 pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the disclosure include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the disclosure comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and that has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length and in some embodiments, 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the disclosure are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Green, Eds., Sinauer Associates, Sunderland, Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and that are 5' to the 5' end of the RNA transcript are referred to as "upstream sequences", sequence regions on the DNA strand having the same sequence as the RNA and that are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, in some embodiments, at least 90 percent sequence identity, in some embodiments, at least 95 percent sequence identity, and in some embodiments, at least 99 percent sequence identity.

In some embodiments, residue positions that are not identical differ by conservative amino acid substitutions.

As discussed herein, minor variations in the amino acid sequences of antibodies or immunoglobulin molecules are contemplated as being encompassed by the present disclosure, providing that the variations in the amino acid sequence maintain at least 75%, in some embodiments, at least 80%, 90%, 95%, and in some embodiments, 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Suitable amino- and carboxy-termini of fragments or analogs occur near boundaries of functional domains. Structural and functional domains can be identified by comparison of the nucleotide and/or amino acid sequence data to public or proprietary sequence databases. In some embodiments, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Suitable amino acid substitutions are those that: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various muteins of a sequence other than the naturally-occurring peptide sequence. For example, single or multiple amino acid substitutions (for example, conservative amino acid substitutions) may be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, in some embodiments, at least 14 amino acids long, in some embodiments, at least 20 amino acids long, usually at least 50 amino acids long, and in some embodiments, at least 70 amino acids long. The term "analog" as used herein refers to polypeptides that are comprised of a segment of at least 25 amino acids that has substantial identity to a portion of a deduced amino acid sequence and that has specific binding to the target, under suitable binding conditions. Typically, polypeptide analogs comprise a conservative amino acid substitution (or addition or deletion) with respect to the naturally-occurring sequence. Analogs typically are at least 20 amino acids long, in some embodiments, at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and in some embodiments, a substantially purified fraction is a composition wherein the object species comprises at least about 50 percent (on a molar basis) of all macromolecular species present.

Generally, a substantially pure composition will comprise more than about 80 percent of all macromolecular species present in the composition, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects.

Antibodies and/or activatable antibodies of the disclosure specifically bind a given target, e.g., a human target protein such as human CD166. Also included in the disclosure are antibodies and/or activatable antibodies that bind to the same epitope as the antibodies and/or activatable antibodies described herein. Also included in the disclosure are antibodies and/or antibodies activatable antibodies that compete with an anti-CD166 antibody and/or an anti-CD166 activatable antibody described herein for binding to CD166, e.g., human CD166. Also included in the disclosure are antibodies and/or antibodies activatable antibodies that cross-compete with an anti-CD166 antibody and/or an anti-CD166 activatable antibody described herein for binding to CD166, e.g., human CD166.

Those skilled in the art will recognize that it is possible to determine, without undue experimentation, if a monoclonal antibody (e.g., a murine monoclonal or humanized antibody) has the same specificity as a monoclonal antibody used in the methods described herein by ascertaining whether the former prevents the latter from binding to the target. If the monoclonal antibody being tested competes with the monoclonal antibody of the disclosure, as shown by a decrease in binding by the monoclonal antibody of the disclosure, then the two monoclonal antibodies bind to the same, or a closely related, epitope. An alternative method for determining whether a monoclonal antibody has the specificity of a monoclonal antibody of the disclosure is to pre-incubate the monoclonal antibody of the disclosure with the target and then add the monoclonal antibody being tested to determine if the monoclonal antibody being tested is inhibited in its ability to bind the target. If the monoclonal antibody being tested is inhibited then, in all likelihood, it has the same, or functionally equivalent, epitopic specificity as the monoclonal antibody of the disclosure.

Multispecific Activatable Antibodies

The disclosure also provides multispecific anti-CD166 activatable antibodies. The multispecific activatable antibodies provided herein are multispecific antibodies that recognize CD166 and at least one or more different antigens or epitopes and that include at least one masking moiety (MM) linked to at least one antigen- or epitope-binding domain of the multispecific antibody such that coupling of the MM reduces the ability of the antigen- or epitope-binding domain to bind its target. In some embodiments, the MM is coupled to the antigen- or epitope-binding domain of the multispecific antibody via a cleavable moiety (CM) that functions as a substrate for at least one protease. The activatable multispecific antibodies provided herein are stable in circulation, activated at intended sites of therapy and/or diagnosis but not in normal, i.e., healthy tissue, and, when activated, exhibit binding to a target that is at least comparable to the corresponding, unmodified multispecific antibody.

In some embodiments, the multispecific activatable antibodies are designed to engage immune effector cells, also referred to herein as immune-effector cell engaging multispecific activatable antibodies. In some embodiments, the multispecific activatable antibodies are designed to engage leukocytes, also referred to herein as leukocyte engaging multispecific activatable antibodies. In some embodiments, the multispecific activatable antibodies are designed to engage T cells, also referred to herein as T-cell engaging multispecific activatable antibodies. In some embodiments, the multispecific activatable antibodies engage a surface antigen on a leukocyte, such as on a T cell, on a natural killer (NK) cell, on a myeloid mononuclear cell, on a macrophage, and/or on another immune effector cell. In some embodiments, the immune effector cell is a leukocyte. In some embodiments, the immune effector cell is a T cell. In some embodiments, the immune effector cell is a NK cell. In some embodiments, the immune effector cell is a mononuclear cell, such as a myeloid mononuclear cell. In some embodiments, the multispecific activatable antibodies are designed to bind or otherwise interact with more than one target and/or more than one epitope, also referred to herein as multi-antigen targeting activatable antibodies. As used herein, the terms "target" and "antigen" are used interchangeably.

In some embodiments, immune effector cell engaging multispecific activatable antibodies of the disclosure include a targeting antibody or antigen-binding fragment thereof that binds CD166 and an immune effector cell engaging antibody or antigen-binding portion thereof, where at least one of the targeting antibody or antigen-binding fragment thereof and/or the immune effector cell engaging antibody or antigen-binding portion thereof is masked. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds CD166, where the AB2 is attached to a masking moiety (MM2) such that coupling of the MM2 reduces the ability of the AB2 to bind CD166. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds CD166, where the AB2 is attached to a masking moiety (MM2) such that coupling of the MM2 reduces the ability of the AB2 to bind CD166. In some embodiments, the non-immune effector cell engaging antibody is a cancer targeting antibody. In some embodiments the non-immune cell effector antibody is an IgG. In some embodiments the immune effector cell engaging antibody is a scFv. In some embodiments the CD166-targeting antibody (e.g., non-immune cell effector antibody) is an IgG and the immune effector cell engaging antibody is a scFv. In some embodiments, the immune effector cell is a leukocyte. In some embodiments, the immune effector cell is a T cell. In some embodiments, the immune effector cell is a NK cell. In some embodiments, the immune effector cell is a myeloid mononuclear cell.

In some embodiments, T-cell engaging multispecific activatable antibodies of the disclosure include a CD166-targeting antibody or antigen-binding fragment thereof and a T-cell engaging antibody or antigen-binding portion thereof, where at least one of the CD166-targeting antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds CD166, where the AB2 is attached to a masking moiety (MM2) such that coupling of the MM2 reduces the ability of the AB2 to bind CD166. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds CD166, where the AB2 is attached to a masking moiety (MM2) such that coupling of the MM2 reduces the ability of the AB2 to bind CD166.

In some embodiments of an immune effector cell engaging multispecific activatable antibody, one antigen is CD166, and another antigen is typically a stimulatory or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA. In some embodiments, the antigen is a stimulatory receptor present on the surface of a T cell or NK cell; examples of such stimulatory receptors include, but are not limited to, CD3, CD27, CD28, CD137 (also referred to as 4-1BB), GITR, HVEM, ICOS, NKG2D, and OX40. In some embodiments, the antigen is an inhibitory receptor present on the surface of a T-cell; examples of such inhibitory receptors include, but are not limited to, BTLA, CTLA-4, LAG3, PD-1, TIGIT, TIM3, and NK-expressed KIRs. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PDL1, PDL2, or TNFSF9.

In some embodiments, the T-cell engaging multispecific activatable antibody includes an anti-CD3 epsilon (CD3ε, also referred to herein as CD3e and CD3) scFv and a targeting antibody or antigen-binding fragment thereof, where at least one of the anti-CD3ε scFv and/or the targeting antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the targeting antibody or antigen-binding fragment thereof includes a second antibody or fragment thereof that includes a second antibody or antigen-binding fragment thereof (AB2) that binds CD166, where the AB2 is attached to a masking moiety (MM2) such that coupling of the MM2 reduces the ability of the AB2 to bind CD166. In some embodiments, the CD3εscFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the targeting antibody or antigen-binding fragment thereof includes a second antibody or fragment thereof that includes a second antibody or antigen-binding fragment thereof (AB2) that binds CD166, where the AB2 is attached to a masking moiety (MM2) such that coupling of the MM2 reduces the ability of the AB2 to bind CD166.

In some embodiments, the multi-antigen targeting antibodies and/or multi-antigen targeting activatable antibodies include at least a first antibody or antigen-binding fragment thereof that binds a first target and/or first epitope and a second antibody or antigen-binding fragment thereof that binds a second target and/or a second epitope. In some embodiments, the multi-antigen targeting antibodies and/or multi-antigen targeting activatable antibodies bind two or more different targets. In some embodiments, the multi-antigen targeting antibodies and/or multi-antigen targeting activatable antibodies bind two or more different epitopes on the same target. In some embodiments, the multi-antigen targeting antibodies and/or multi-antigen targeting activatable antibodies bind a combination of two or more different targets and two or more different epitopes on the same target.

In some embodiments, a multispecific activatable antibody comprising an IgG has the IgG variable domains masked. In some embodiments, a multispecific activatable antibody comprising a scFv has the scFv domains masked. In some embodiments, a multispecific activatable antibody has both IgG variable domains and scFv domains, where at least one of the IgG variable domains is coupled to a masking moiety. In some embodiments, a multispecific activatable antibody has both IgG variable domains and scFv domains, where at least one of the scFv domains is coupled to a masking moiety. In some embodiments, a multispecific activatable antibody has both IgG variable domains and scFv domains, where at least one of the IgG variable domains is coupled to a masking moiety and at least one of the scFv domains is coupled to a masking moiety. In some embodiments, a multispecific activatable antibody has both IgG variable domains and scFv domains, where each of the IgG variable domains and the scFv domains is coupled to its own masking moiety. In some embodiments, one antibody domain of a multispecific activatable antibody has specificity for a target antigen and another antibody domain has specificity for a T-cell surface antigen. In some embodiments, one antibody domain of a multispecific activatable antibody has specificity for a target antigen and another antibody domain has specificity for another target antigen. In some embodiments, one antibody domain of a multispecific activatable antibody has specificity for an epitope of a target antigen and another antibody domain has specificity for another epitope of the target antigen.

In a multispecific activatable antibody, a scFv can be fused to the carboxyl terminus of the heavy chain of an IgG activatable antibody, to the carboxyl terminus of the light chain of an IgG activatable antibody, or to the carboxyl termini of both the heavy and light chains of an IgG activatable antibody. In a multispecific activatable antibody, a scFv can be fused to the amino terminus of the heavy chain of an IgG activatable antibody, to the amino terminus of the light chain of an IgG activatable antibody, or to the amino termini of both the heavy and light chains of an IgG activatable antibody. In a multispecific activatable antibody, a scFv can be fused to any combination of one or more carboxyl termini and one or more amino termini of an IgG activatable antibody. In some embodiments, a masking moiety (MM) linked to a cleavable moiety (CM) is attached to and masks an antigen binding domain of the IgG. In some embodiments, a masking moiety (MM) linked to a cleavable moiety (CM) is attached to and masks an antigen binding domain of at least one scFv. In some embodiments, a masking moiety (MM) linked to a cleavable moiety (CM) is attached to and masks an antigen binding domain of an IgG and a masking moiety (MM) linked to a cleavable moiety (CM) is attached to and masks an antigen binding domain of at least one scFv.

The disclosure provides examples of multispecific activatable antibody structures which include, but are not limited to, the following: (VL-CL)₂:(VH-CH1-CH2-CH3-L4-VH*-L3-VL*-L2-CM-L1-MM)₂; (VL-CL)₂:(VH-CH1-CH2-CH3-L4-VL*-L3-VH*-L2-CM-L1-MM)₂; (MM-L1-CM-L2-VL-CL)₂:(VH-CH1-CH2-CH3-L4-VH*-L3-VL*)₂; (MM-L1-CM-L2-VL-CL)₂:(VH-CH1-CH2-CH3-L4-VL*-L3-VH*)₂ (VL-CL)₂:(MM-L1-CM-L2-VL*-L3-VH*-L4-VH-CH1-CH2-CH3)₂; (VL-CL)₂:(MM-L1-CM-L2-VH*-L3-VL*-L4-VH-CH1-CH2-CH3)₂; (MM-L1-CM-L2-VL-CL)₂:(VL*-L3-VH*-L4-VH-CH1-CH2-CH3)₂; (MM-L1-CM-L2-VL-CL)₂:(VH*-L3-VL*-L4-VH-CH-CH2-CH3)₂ (VL-CL-L4-VH*-L3-VL*-L2-CM-L1-MM)₂: (VH-CH1-CH2-CH3)₂; (VL-CL-L4-VL*-L3-VH*-L2-CM-L1-MM)₂:(VH-CH1-CH2-CH3)₂; (MM-L1-CM-L2-VL*-L3-VH*-L4-VL-CL)₂:(VH-CH1-CH2-CH3)₂; (MM-L1-CM-L2-VH*-L3-VL*-L4-VL-CL)₂:(VH-CH1-CH2-CH3)₂; (VL-CL-L4-VH*-L3-VL*-L2-CM-L1-MM)₂; (MM-L1-CM-L2-VL*-L3-VH*-L4-VH-CH1-CH2-CH3)₂; (VL-CL-L4-VH*-L3-VL*-L2-CM-L1-MM)₂: (MM-L1-CM-L2-VH*-L3-VL*-L4-VH-CH1-CH2-CH3)₂; (VL-CL-L4-VL*-L3-VH*-L2-CM-L1-MM)₂: (MM-L1-CM-L2-VL*-L3-VH*-L4-VH-CH1-CH2-CH3)₂; (VL-CL-L4-VL*-L3-VH*-L2-CM-L1-MM)₂: (MM-L-CM-L2-VH*-L3-VL*-L4-VH-CH1-CH2-CH3)₂; (VL-CL-L4-VL*-L3-VH*)₂: (MM-L1-CM-L2-VL*-L3-VH*-L4-VH-CH1-CH2-CH3)₂; (VL-CL-L4-VL*-L3-VH*)₂: (MM-L1-CM-L2-VH*-L3-VL*-L4-VH-CH1-CH2-CH3)₂; (VL-CL-L4-VL*-L3-VH*)₂: (MM-L-CM-L2-VL*-L3-VH*-L4-VH-CH1-CH2-CH3)₂; (VL-CL-L4-VL*-L3-VH*)₂: (MM-L1-CM-L2-VH*-L3-VL*-L4-VH-CH1-CH2-CH3)₂; (VL-CL-L4-VH*-L3-VL*-L2-CM-L1-MM)₂: (VL*-L3-VH*-L4-VH-CH1-CH2-CH3)₂; (VL-CL-L4-VH*-L3-VL*-L2-CM-L1-MM)₂: (VH*-L3-VL*-L4-VH-CH1-CH2-CH3)₂; (VL-CL-L4-VL*-L3-VH*-L2-CM-L 1-MM)₂: (VL*-L3-VH*-L4-VH-CH1-CH2-CH3)₂; or (VL-CL-L4-VL*-L3-VH*-L2-CM-L1-MM)₂: (VH*-L3-VL*-L4-VH-CH1-CH2-CH3)₂, wherein: VL and VH represent the light and heavy variable domains of the first specificity, contained in the IgG, VL* and VH* represent the variable domains of the second specificity, contained in the scFv; L1 is a linker peptide connecting the masking moiety (MM) and the cleavable moiety (CM); L2 is a linker peptide connecting the cleavable moiety (CM), and the antibody; L3 is a linker peptide connecting the variable domains of the scFv; L4 is a linker peptide connecting the antibody of the first specificity to the antibody of the second specificity; CL is the light-chain constant domain; and CH1, CH2, CH3 are the heavy chain constant domains. The first and second specificities may be toward any antigen or epitope.

In some embodiments of a T-cell engaging multispecific activatable antibody, one antigen is CD166, and another antigen is typically a stimulatory (also referred to herein as activating) or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137 (also referred to as TNFRSF9), CTLA-4, GITR, HVEM, ICOS, LAG3, NKG2D, OX40, PD-1, TIGIT, TIM3, or VISTA. The antibody domain conferring specificity to the T-cell surface antigen may also be substituted by a ligand or ligand domain that binds to a T-cell receptor, a NK-cell receptor, a macrophage receptor, and/or other immune effector cell receptor.

In some embodiments, the targeting antibody is an anti-CD166 antibody disclosed herein. In some embodiments, the targeting antibody can be in the form an activatable antibody. In some embodiments, the scFv(s) can be in the form of a Pro-scFv (see, e.g., WO 2009/025846, WO 2010/081173).

In some embodiments, the scFv is specific for binding CD3ε, and comprises or is derived from an antibody or fragment thereof that binds CD3ε, e.g., CH2527, FN18, H2C, OKT3, 2C11, UCHT1, or V9. In some embodiments, the scFv is specific for binding CTLA-4 (also referred to herein as CTLA and CTLA4).

In some embodiments, the anti-CTLA-4 scFv includes the amino acid sequence:

```
                                            (SEQ ID NO: 117)
GGGSGGGGSGSGGGSGGGGSGGGEIVLTQSPGTLSLSPGERATLSCRAS

QSVSSSYLAWYQQKPGQAPRLLIYGASSRATGIPDRFSGSGSGTDFTLT

ISRLEPEDFAVYYCQQYGSSPLTFGGGTKVEIKRSGGSTITSYNVYYTK

LSSSGTQVQLVQTGGGVVQPGRSLRLSCAASGSTFSSYAMSWVRQAPGK

GLEWVSAISGSGGSTYYADSVKGRFTISRDNSKNTLYLQMNSLRAEDTA

VYYCATNSLYWYFDLWGRGTLVTVSSAS
```

In some embodiments, the anti-CTLA-4 scFv includes the amino acid sequence that is at least 90%, 91%, 92%, 93%, 94%, 95%, 96%, 97%, 98%, 99% or more identical to the amino acid sequence of SEQ ID NO: 117.

In some embodiments, the anti-CD3ε scFv includes the amino acid sequence:

(SEQ ID NO: 118)
GGGSGGGGSGSGGGSGGGSGGGQVQLQQSGAELARPGASVKMSCKASG

YTFTRYTMHWVKQRPGQGLEWIGYINPSRGYTNYNQKFKDKATLTTDKS

SSTAYMQLSSLTSEDSAVYYCARYYDDHYCLDYWGQGTTLTVSSGGGGS

GGGGSGGGGSQIVLTQSPAIMSASPGEKVTMTCSASSSVSYMNWYQQKS

GTSPKRWIYDTSKLASGVPAHFRGSGSGTSYSLTISGMEAEDAATYYCQ

QWSSNPFTFGSGTKLEINR

In some embodiments, the anti-CD3ε scFv includes the amino acid sequence that is at least 90%, 91%, 92%, 93%, 94%, 95%, 96%, 97%, 98%, 99% or more identical to the amino acid sequence of SEQ ID NO: 118.

In some embodiments, the scFv is specific for binding one or more T-cells, one or more NK-cells and/or one or more macrophages. In some embodiments, the scFv is specific for binding a target selected from the group consisting of B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA.

In some embodiments, the multispecific activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the multispecific activatable antibody via a linker. In some embodiments, the agent is conjugated to the AB via a cleavable linker. In some embodiments, the linker is a non-cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is an agent selected from the group listed in Table 5. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the multispecific activatable antibody also includes a detectable moiety. In some embodiments, the detectable moiety is a diagnostic agent.

In some embodiments, the multispecific activatable antibody naturally contains one or more disulfide bonds. In some embodiments, the multispecific activatable antibody can be engineered to include one or more disulfide bonds.

The disclosure also provides an isolated nucleic acid molecule encoding a multispecific activatable antibody described herein, as well as vectors that include these isolated nucleic acid sequences. The disclosure provides methods of producing a multispecific activatable antibody by culturing a cell under conditions that lead to expression of the activatable antibody, wherein the cell comprises such a nucleic acid molecule. In some embodiments, the cell comprises such a vector.

The disclosure also provides a method of manufacturing multi specific activatable antibodies of the disclosure by (a) culturing a cell comprising a nucleic acid construct that encodes the multispecific activatable antibody under conditions that lead to expression of the multispecific activatable, and (b) recovering the multispecific activatable antibody. Suitable AB, MM, and/or CM include any of the AB, MM, and/or CM disclosed herein.

The disclosure also provides multispecific activatable antibodies and/or multispecific activatable antibody compositions that include at least a first antibody or antigen-binding fragment thereof (AB1) that specifically binds a first target or first epitope and a second antibody or antigen-biding fragment thereof (AB2) that binds a second target or a second epitope, where at least AB1 is coupled or otherwise attached to a masking moiety (MM1), such that coupling of the MM1 reduces the ability of AB1 to bind its target. In some embodiments, the MM1 is coupled to AB1 via a first cleavable moiety (CM1) sequence that includes a substrate for a protease, for example, a protease that is co-localized with the target of AB1 at a treatment site or a diagnostic site in a subject. The multispecific activatable antibodies provided herein are stable in circulation, activated at intended sites of therapy and/or diagnosis but not in normal, i.e., healthy tissue, and, when activated, exhibit binding to the target of AB1 that is at least comparable to the corresponding, unmodified multispecific antibody. Suitable AB, MM, and/or CM include any of the AB, MM, and/or CM disclosed herein.

The disclosure also provides compositions and methods that include a multispecific activatable antibody that includes at least a first antibody or antibody fragment (AB1) that specifically binds a target and a second antibody or antibody fragment (AB2), where at least the first AB in the multispecific activatable antibody is coupled to a masking moiety (MM1) that decreases the ability of AB1 to bind its target. In some embodiments, each AB is coupled to a MM that decreases the ability of its corresponding AB to each target. For example, in bispecific activatable antibody embodiments, AB1 is coupled to a first masking moiety (MM1) that decreases the ability of AB1 to bind its target, and AB2 is coupled to a second masking moiety (MM2) that decreases the ability of AB2 to bind its target. In some embodiments, the multispecific activatable antibody comprises more than two AB regions; in such embodiments, AB1 is coupled to a first masking moiety (MM1) that decreases the ability of AB1 to bind its target, AB2 is coupled to a second masking moiety (MM2) that decreases the ability of AB2 to bind its target, AB3 is coupled to a third masking moiety (MM3) that decreases the ability of AB3 to bind its target, and so on for each AB in the multispecific activatable antibody. Suitable AB, MM, and/or CM include any of the AB, MM, and/or CM disclosed herein.

In some embodiments, the multispecific activatable antibody further includes at least one cleavable moiety (CM) that is a substrate for a protease, where the CM links a MM to an AB. For example, in some embodiments, the multispecific activatable antibody includes at least a first antibody or antibody fragment (AB1) that specifically binds a target and a second antibody or antibody fragment (AB2), where at least the first AB in the multispecific activatable antibody is coupled via a first cleavable moiety (CM1) to a masking moiety (MM1) that decreases the ability of AB1 to bind its target. In some bispecific activatable antibody embodiments, AB1 is coupled via CM1 to MM1, and AB2 is coupled via a second cleavable moiety (CM2) to a second masking moiety (MM2) that decreases the ability of AB2 to bind its target. In some embodiments, the multispecific activatable antibody comprises more than two AB regions; in some of these embodiments, AB1 is coupled via CM1 to MM1, AB2 is coupled via CM2 to MM2, and AB3 is coupled via a third cleavable moiety (CM3) to a third masking moiety (MM3) that decreases the ability of AB3 to bind its target, and so on for each AB in the multispecific activatable antibody. Suitable AB, MM, and/or CM include any of the AB, MM, and/or CM disclosed herein.

Activatable Antibodies Having Non-Binding Steric Moieties or Binding Partners for Non-Binding Steric Moieties The disclosure also provides activatable antibodies that include non-binding steric moieties (NB) or binding partners (BP) for non-binding steric moieties, where the BP recruits or otherwise attracts the NB to the activatable antibody. The activatable antibodies provided herein include, for example, an activatable antibody that includes a non-binding steric moiety (NB), a cleavable linker (CL) and antibody or antibody fragment (AB) that binds a target; an activatable antibody that includes a binding partner for a non-binding steric moiety (BP), a CL and an AB; and an activatable antibody that includes a BP to which an NB has been recruited, a CL and an AB that binds the target. Activatable antibodies in which the NB is covalently linked to the CL and AB of the activatable antibody or is associated by interaction with a BP that is covalently linked to the CL and AB of the activatable antibody are referred to herein as "NB-containing activatable antibodies." By activatable or switchable is meant that the activatable antibody exhibits a first level of binding to a target when the activatable antibody is in an inhibited, masked or uncleaved state (i.e., a first conformation), and a second level of binding to the target when the activatable antibody is in an uninhibited, unmasked and/or cleaved state (i.e., a second conformation, i.e., activated antibody), where the second level of target binding is greater than the first level of target binding. The activatable antibody compositions can exhibit increased bioavailability and more favorable biodistribution compared to conventional antibody therapeutics.

In some embodiments, activatable antibodies provide for reduced toxicity and/or adverse side effects that could otherwise result from binding of the at non-treatment sites and/or non-diagnostic sites if the AB were not masked or otherwise inhibited from binding to such a site.

Anti-CD166 activatable antibodies that include a non-binding steric moiety (NB) can be made using the methods set forth in PCT Publication No. WO 2013/192546, the contents of which are hereby incorporated by reference in their entirety.

Use of Antibodies, Conjugated Antibodies, Activatable Antibodies, and Conjugated Activatable Antibodies It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2): 1-60 (2000), Charman WN "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the disclosure, which include an anti-CD166 antibody and/or activatable anti-CD166 antibody, such as by way of non-limiting example, an antibody, a conjugated antibody, an activatable antibody and/or a conjugated activatable antibody, are used to prevent, treat or otherwise ameliorate a disease or disorder associated with aberrant target expression and/or activity. For example, therapeutic formulations of the disclosure, which include an antibody, a conjugated antibody, an activatable antibody and/or a conjugated activatable antibody, are used to treat or otherwise ameliorate a cancer or other neoplastic condition, inflammation, an inflammatory disorder, and/or an autoimmune disease. In some embodiments, the cancer is a solid tumor or a hematologic malignancy where the target is expressed. In some embodiments, the cancer is a solid tumor where the target is expressed. In some embodiments, the cancer is a hematologic malignancy where the target is expressed. In some embodiments, the target is expressed on parenchyma (e.g., in cancer, the portion of an organ or tissue that often carries out function(s) of the organ or tissue). In some embodiments, the target is expressed on a cell, tissue, or organ. In some embodiments, the target is expressed on stroma (i.e., the connective supportive framework of a cell, tissue, or organ). In some embodiments, the target is expressed on an osteoblast. In some embodiments, the target is expressed on the endothelium (vasculature). In some embodiments, the target is expressed on a cancer stem cell. In some embodiments, the agent to which the antibody and/or the activatable antibody is conjugated is a microtubule inhibitor. In some embodiments, the agent to which the antibody and/or the activatable antibody is conjugated is a nucleic acid damaging agent.

Efficaciousness of prevention, amelioration or treatment is determined in association with any known method for diagnosing or treating the disease or disorder associated with target expression and/or activity, such as, for example, aberrant target expression and/or activity. Prolonging the survival of a subject or otherwise delaying the progression of the disease or disorder associated with target expression and/or activity, e.g., aberrant target expression and/or activity, in a subject indicates that the antibody, conjugated antibody, activatable antibody and/or conjugated activatable antibody confers a clinical benefit.

An antibody, a conjugated antibody, an activatable antibody and/or a conjugated activatable antibody can be administered in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

In some embodiments where antibody fragments are used, the smallest fragment that specifically binds to the binding domain of the target protein is selected. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compounds as necessary for the particular indication being treated, for example, in some embodiments, those with complementary activities that do not adversely affect each other. In some embodiments, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

In some embodiments, the antibody, the conjugated antibody, activatable antibody and/or conjugated activatable antibody contains a detectable label. An intact antibody, or a fragment thereof (e.g., Fab, scFv, or F(ab)$_2$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the disclosure can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, immunochemical staining, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

The antibodies, conjugated antibodies, activatable antibodies and/or conjugated activatable antibodies of the disclosure are also useful in a variety of diagnostic and prophylactic formulations. In one embodiment, an antibody, a conjugated antibody, an activatable antibody and/or a conjugated activatable antibody is administered to patients that are at risk of developing one or more of the aforementioned disorders. A patient's or organ's predisposition to one or more of the aforementioned disorders can be determined using genotypic, serological or biochemical markers.

In some embodiments of the disclosure, an antibody, a conjugated antibody, an activatable antibody and/or a conjugated activatable antibody is administered to human individuals diagnosed with a clinical indication associated with one or more of the aforementioned disorders. Upon diagnosis, an antibody, a conjugated antibody, an activatable antibody and/or a conjugated activatable antibody is administered to mitigate or reverse the effects of the clinical indication.

An antibody, a conjugated antibody, an activatable antibody, and/or a conjugated activatable antibody of the disclosure is also useful in the detection of a target in patient samples and accordingly are useful as diagnostics. For example, the antibodies and/or activatable antibodies, and conjugated versions thereof, of the disclosure are used in in vitro assays, e.g., ELISA, to detect target levels in a patient sample.

In one embodiment, an antibody, a conjugated antibody, an activatable antibody and/or a conjugated activatable antibody of the disclosure is immobilized on a solid support (e.g., the well(s) of a microtiter plate). The immobilized antibody, conjugated antibody, activatable antibody and/or conjugated activatable antibody serves as a capture antibody for any target that may be present in a test sample. Prior to contacting the immobilized antibody and/or activatable antibody, and/or conjugated versions thereof, with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen in the test sample is determined by comparison with a standard curve developed from the standard samples.

It will be appreciated that based on the results obtained using the antibodies and activatable antibodies of the disclosure, and conjugated versions thereof, in an in vitro diagnostic assay, it is possible to stage a disease in a subject based on expression levels of the target antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

An antibody, a conjugated antibody, an activatable antibody and/or a conjugated activatable antibody can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable antibodies having an enzymatically cleavable CM can be used to detect the presence or absence of an enzyme that is capable of cleaving the CM. Such activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of an activatable antibody) in a given cell or tissue of a given host organism. Such accumulation of activated antibodies indicates not only that the tissue expresses enzymatic activity (or an increased reduction potential depending on the nature of the CM) but also that the tissue expresses target to which the activated antibody binds.

For example, the CM can be selected to be substrate for at least one protease found at the site of a tumor, at the site of a viral or bacterial infection at a biologically confined site (e.g., such as in an abscess, in an organ, and the like), and the like. The AB can be one that binds a target antigen. Using methods as disclosed herein, or when appropriate, methods familiar to one skilled in the art, a detectable label (e.g., a fluorescent label or radioactive label or radiotracer) can be conjugated to an AB or other region of an antibody and/or activatable antibody. Suitable detectable labels are discussed in the context of the above screening methods and additional specific examples are provided below. Using an AB specific to a protein or peptide of the disease state, along with at least one protease whose activity is elevated in the disease tissue of interest, activatable antibodies will exhibit an increased rate of binding to disease tissue relative to tissues where the CM specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM is not present at a detectable level (or is present at lower levels in non-disease tissues or is present in inactive conformation), accumulation of activated antibodies in the disease tissue is enhanced relative to non-disease tissues.

In another example, activatable antibodies can be used to detect the presence or absence of a cleaving agent in a sample. For example, where the activatable antibodies contain a CM susceptible to cleavage by an enzyme, the activatable antibodies can be used to detect (either qualitatively or quantitatively) the presence of an enzyme in the sample. In another example, where the activatable antibodies contain a CM susceptible to cleavage by reducing agent, the activatable antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable antibody that is not released following cleavage, for example, the detectable label can be a quenched fluorescent label or other label that is not detectable until cleavage has occurred. The assay can be conducted by, for example, contacting the immobilized, detectably labeled activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable antibodies as described above, and the presence or absence of the target can be detected by detection of a target-AB complex e.g., by use of a detectably labeled anti-target antibody.

Activatable antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody is labeled with a detectable label. The detectable label may be a fluorescent dye, (e.g. a fluorophore, Fluorescein Isothiocyanate (FITC), Rhodamine Isothiocyanate (TRITC), an Alexa Fluor® label), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable antibody indicates that the sample contains the target and contains a protease that is specific for the CM of the activatable antibody. In some embodiments, the presence of the protease can be confirmed using broad spectrum protease inhibitors such as those described herein, and/or by using an agent that is specific for the protease, for example, an antibody such as A11, which is specific for the protease matriptase and inhibits the proteolytic activity of matriptase; see e.g., International Publication Number WO 2010/129609, published 11 Nov. 2010. The same approach of using broad spectrum protease inhibitors such as those described herein, and/or by using a more selective inhibitory agent can be used to identify a protease that is specific for the CM of the activatable antibody. In some embodiments, the presence of the target can be confirmed using an agent that is specific for the target, e.g., another antibody, or the detectable label can be competed with unlabeled target. In some embodiments, unlabeled activatable antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a protease that is specific for the CM of the activatable antibody.

These techniques are also useful in kits and/or as reagents for the detection, identification or characterization of protease activity in a variety of cells, tissues, and organisms based on the protease-specific CM in the activatable antibody.

The disclosure provides methods of using the antibodies and/or activatable antibodies in a variety of diagnostic and/or prophylactic indications. For example, the disclosure provides methods of detecting presence or absence of a cleaving agent and a target of interest in a subject or a sample by (i) contacting a subject or sample with an activatable antibody, wherein the activatable antibody comprises a masking moiety (MM), a cleavable moiety (CM) that is cleaved by the cleaving agent, e.g., a protease, and an antigen binding domain or fragment thereof (AB) that specifically binds the target of interest, wherein the activatable antibody in an uncleaved, non-activated state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent and the target are present in the subject or sample and wherein no detectable level of activated activatable antibody in the subject or sample indicates that the cleaving agent, the target or both the cleaving agent and the target are absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides methods of detecting presence or absence of a cleaving agent in a subject or a sample by (i) contacting a subject or sample with an activatable antibody in the presence of a target of interest, e.g., the target, wherein the activatable antibody comprises a masking moiety (MM), a cleavable moiety (CM) that is cleaved by the cleaving agent, e.g., a protease, and an antigen binding domain or fragment thereof (AB) that specifically binds the target of interest, wherein the activatable antibody in an uncleaved, non-activated state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent is present in the subject or sample and wherein no detectable level of activated activatable antibody in the subject or sample indicates that the cleaving agent is absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody comprises a masking moiety (MM), a cleavable moiety (CM) that is cleaved by the cleaving agent, e.g., a protease, and an antigen binding domain or fragment thereof (AB) that specifically binds the target of interest, wherein the activatable antibody in an uncleaved, non-activated state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB: and is not a modified form of a natural binding partner of the AB: and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent is present in the subject or sample and wherein no detectable level of activated activatable antibody in the subject or sample indicates that the cleaving agent is absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides methods of detecting presence or absence of a cleaving agent in a subject or a sample by (i) contacting a subject or sample with an activatable antibody, wherein the activatable antibody comprises a masking moiety (MM), a cleavable moiety (CM) that is cleaved by the cleaving agent, e.g., a protease, an antigen binding domain (AB) that specifically binds the target, and a detectable label, wherein the activatable antibody in an uncleaved, non-activated state comprises a structural arrangement from N-terminus to C-terminus as follows: MM-CM-AB or AB-CM-MM; wherein the MM is a peptide that inhibits binding of the AB to the target, and wherein the MM does not have an amino acid sequence of a naturally occurring binding partner of the AB and is not a modified form of a natural binding partner of the AB; wherein, in an uncleaved, non-activated state, the MM interferes with specific binding of the AB to the target, and in a cleaved, activated state the MM does not interfere or compete with specific binding of the AB to the target; and wherein the detectable label is positioned on a portion of the activatable antibody that is released following cleavage of the CM; and (ii) measuring a level of detectable label in the subject or sample, wherein a detectable level of the detectable label in the subject or sample indicates that the cleaving agent is absent and/or not sufficiently present in the subject or sample and wherein no detectable level of the detectable label in the subject or sample indicates that the cleaving agent is present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody and/or conjugated activatable antibody (e.g., an activatable antibody to which a therapeutic agent is conjugated) described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent and the target are present in the subject or biological sample and wherein no detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample.

The disclosure also provides methods of detecting presence or absence of a cleaving agent in a subject or a sample by (i) contacting a subject or biological sample with an activatable antibody in the presence of the target, and (ii) measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample. Such an activatable antibody includes a masking moiety (MM), a cleavable moiety (CM) that is cleaved by the cleaving agent, e.g., a protease, and an antigen binding domain or fragment thereof (AB) that specifically binds the target, wherein the activatable antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments all antigen binding sites are masked. In some embodiments, the measuring step includes use of a secondary reagent comprising a detectable label.

The disclosure also provides kits for use in methods of detecting presence or absence of a cleaving agent and the target in a subject or a sample, where the kits include at least an activatable antibody and/or conjugated activatable antibody described herein for use in contacting a subject or biological sample with an activatable antibody in the presence of the target, and measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample. Such an activatable antibody includes a masking moiety (MM), a cleavable moiety (CM) that is cleaved by the cleaving agent, e.g., a protease, and an antigen binding domain or fragment thereof (AB) that specifically binds the target, wherein the activatable antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments all antigen binding sites are masked. In some embodiments, the measuring step includes use of a secondary reagent comprising a detectable label.

The disclosure also provides kits for use in methods of detecting presence or absence of a cleaving agent in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM, wherein a detectable level of activated activatable antibody in the subject or biological sample indicates that the cleaving agent is absent and/or not sufficiently present in the subject or biological sample such that the target binding and/or protease cleavage of the activatable antibody cannot be detected in the subject or biological sample, and wherein no detectable level of activated activatable antibody in the subject or biological sample indicates that the cleaving agent is present in the subject or biological sample at a detectable level.

The disclosure provides methods of detecting presence or absence of a cleaving agent and the target in a subject or a sample by (i) contacting a subject or biological sample with an activatable antibody, wherein the activatable antibody includes a detectable label that is positioned on a portion of the activatable antibody that is released following cleavage of the CM and (ii) measuring a level of activated activatable antibody in the subject or biological sample, wherein a detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90°, about 95% and/or about 100%. Such an activatable antibody includes a masking moiety (MM), a cleavable moiety (CM) that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

The disclosure also provides methods of detecting presence or absence of a cleaving agent in a subject or a sample by (i) contacting a subject or biological sample with an activatable antibody, wherein the activatable antibody includes a detectable label that is positioned on a portion of the activatable antibody that is released following cleavage of the CM; and (ii) measuring a level of detectable label in the subject or biological sample, wherein a detectable level of the detectable label in the subject or biological sample indicates that the cleaving agent is absent and/or not sufficiently present in the subject or biological sample at a detectable level, such that protease cleavage of the activatable antibody cannot be detected in the subject or biological sample, and wherein a reduced detectable level of the detectable label in the subject or biological sample indicates that the cleaving agent is present in the subject or biological sample. A reduced level of detectable label is, for example, a reduction of about 5%, about 10%, about 15%, about 20%, about 25%, about 30%, about 35%, about 40%, about 45%, about 50%, about 55%, about 60, about 65%, about 70, about 75%, about 80%, about 85%, about 90%, about 95% and/or about 100%. Such an activatable antibody includes a masking moiety (MM), a cleavable moiety (CM) that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent of interest in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM, wherein a detectable level of the detectable label in the subject or biological sample indicates that the cleaving agent, the target, or both the cleaving agent and the target are absent and/or not sufficiently present in the subject or biological sample, such that the target binding and/or protease cleavage of the activatable antibody cannot be detected in the subject or biological sample, and wherein a reduced detectable level of the detectable label in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

In some embodiments of these methods and kits, the activatable antibody includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or β-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor® 680 or Alexa Fluor®750. In some embodiments of these methods and kits, the ligand-based label comprises biotin, avidin, streptavidin or one or more haptens.

In some embodiments of these methods and kits, the subject is a mammal. In some embodiments of these methods and kits, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods, the method is an in viwo method. In some embodiments of these methods, the method is an in situ method. In some embodiments of these methods, the method is an ex vivo method. In some embodiments of these methods, the method is an in vitro method.

In some embodiments, in situ imaging and/or in vivo imaging are useful in methods to identify which patients to treat. For example, in in situ imaging, the activatable antibodies are used to screen patient samples to identify those patients having the appropriate protease(s) and target(s) at the appropriate location, e.g., at a tumor site.

In some embodiments in situ imaging is used to identify or otherwise refine a patient population suitable for treatment with an activatable antibody of the disclosure. For example, patients that test positive for both the target (e.g., the target) and a protease that cleaves the substrate in the cleavable moiety (CM) of the activatable antibody being tested (e.g., accumulate activated antibodies at the disease site) are identified as suitable candidates for treatment with such an activatable antibody comprising such a CM. Likewise, patients that test negative for either or both of the target (e.g., the target) and the protease that cleaves the substrate in the CM in the activatable antibody being tested using these methods might be identified as suitable candidates for another form of therapy. In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease). In some embodiments, the patient is then administered a therapeutically effective amount of the activatable antibody for which the patient tested positive.

In some embodiments in vivo imaging is used to identify or otherwise refine a patient population suitable for treatment with an activatable antibody of the disclosure. For example, patients that test positive for both the target (e.g., the target) and a protease that cleaves the substrate in the cleavable moiety (CM) of the activatable antibody being tested (e.g., accumulate activated antibodies at the disease site) are identified as suitable candidates for treatment with such an activatable antibody comprising such a CM. Likewise, patients that test negative might be identified as suitable candidates for another form of therapy. In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease). In some embodiments, the patient is then administered a therapeutically effective amount of the activatable antibody for which the patient tested positive.

In some embodiments of the methods and kits, the method or kit is used to identify or otherwise refine a patient population suitable for treatment with an activatable antibody of the disclosure. For example, patients that test positive for both the target (e.g., the target) and a protease that cleaves the substrate in the cleavable moiety (CM) of the activatable antibody being tested in these methods are identified as suitable candidates for treatment with such an activatable antibody comprising such a CM. Likewise, patients that test negative for both of the targets (e.g., the target) and the protease that cleaves the substrate in the CM in the activatable antibody being tested using these methods might be identified as suitable candidates for another form of therapy. In some embodiments, such patients can be tested with other activatable antibodies until a suitable activatable antibody for treatment is identified (e.g., an activatable antibody comprising a CM that is cleaved by the patient at the site of disease). In some embodiments, patients that test negative for either of the target (e.g., the target) are identified as suitable candidates for treatment with such an activatable antibody comprising such a CM. In some embodiments, patients that test negative for either of the target (e.g., the target) are identified as not being suitable candidates for treatment with such an activatable antibody comprising such a CM. In some embodiments, such patients can be tested with other activatable antibodies until a suitable activatable antibody for treatment is identified (e.g., an activatable antibody comprising a CM that is cleaved by the patient at the site of disease). In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

In some embodiments, a method or kit is used to identify or otherwise refine a patient population suitable for treatment with an anti-the target activatable antibody and/or conjugated activatable antibody (e.g., activatable antibody to which a therapeutic agent is conjugated) of the disclosure, followed by treatment by administering that activatable antibody and/or conjugated activatable antibody to a subject in need thereof. For example, patients that test positive for both the targets (e.g., the target) and a protease that cleaves the substrate in the cleavable moiety (CM) of the activatable antibody and/or conjugated activatable antibody being tested in these methods are identified as suitable candidates for treatment with such antibody and/or such a conjugated activatable antibody comprising such a CM, and the patient is then administered a therapeutically effective amount of the activatable antibody and/or conjugated activatable antibody that was tested. Likewise, patients that test negative for either or both of the target (e.g., the target) and the protease that cleaves the substrate in the CM in the activatable antibody being tested using these methods might be identified as suitable candidates for another form of therapy. In some embodiments, such patients can be tested with other antibody and/or conjugated activatable antibody until a suitable antibody and/or conjugated activatable antibody for treatment is identified (e.g., an activatable antibody and/or conjugated activatable antibody comprising a CM that is cleaved by the patient at the site of disease). In some embodiments, the patient is then administered a therapeutically effective amount of the activatable antibody and/or conjugated activatable antibody for which the patient tested positive.

In some embodiments of these methods and kits, the MM is a peptide having a length from about 4 to 40 amino acids. In some embodiments of these methods and kits, the activatable antibody comprises a linker peptide, wherein the linker peptide is positioned between the MM and the CM. In some embodiments of these methods and kits, the activatable antibody comprises a linker peptide, where the linker peptide is positioned between the AB and the CM. In some embodiments of these methods and kits, the activatable antibody comprises a first linker peptide (L1) and a second linker peptide (L2), wherein the first linker peptide is positioned between the MM and the CM and the second linker peptide is positioned between the AB and the CM. In some embodiments of these methods and kits, each of L1 and L2 is a peptide of about 1 to 20 amino acids in length, and wherein each of L1 and L2 need not be the same linker. In some embodiments of these methods and kits, one or both of L1 and L2 comprises a glycine-serine polymer. In some embodiments of these methods and kits, at least one of L1 and L2 comprises an amino acid sequence selected from the group consisting of (GS)n, (GSGGS)n (SEQ ID NO: 1) and (GGGS)n (SEQ ID NO: 2), where n is an integer of at least one. In some embodiments of these methods and kits, at least one of L1 and L2 comprises an amino acid sequence having the formula (GGS)n, where n is an integer of at least one. In some embodiments of these methods and kits, at least one of L1 and L2 comprises an amino acid sequence selected from the group consisting of Gly-Gly-Ser-Gly (SEQ ID NO: 3), Gly-Gly-Ser-Gly-Gly (SEQ ID NO: 4), Gly-Ser-Gly-Ser-Gly (SEQ ID NO: 5), Gly-Ser-Gly-Gly-Gly (SEQ ID NO: 6), Gly-Gly-Gly-Ser-Gly (SEQ ID NO: 7), and Gly-Ser-Ser-Ser-Gly (SEQ ID NO: 8).

In some embodiments of these methods and kits, the AB comprises an antibody or antibody fragment sequence selected from the cross-reactive antibody sequences presented herein. In some embodiments of these methods and kits, the AB comprises a Fab fragment, a scFv or a single chain antibody (scAb).

In some embodiments of these methods and kits, the cleaving agent is a protease that is co-localized in the subject or sample with the target and the CM is a polypeptide that functions as a substrate for the protease, wherein the protease cleaves the CM in the activatable antibody when the activatable antibody is exposed to the protease. In some embodiments of these methods and kits, the CM is a polypeptide of up to 15 amino acids in length. In some embodiments of these methods and kits, the CM is coupled to the N-terminus of the AB. In some embodiments of these methods and kits, the CM is coupled to the C-terminus of the AB. In some embodiments of these methods and kits, the CM is coupled to the N-terminus of a VL chain of the AB.

The antibodies, conjugated antibodies, activatable antibodies and/or conjugated activatable antibodies of the disclosure are used in diagnostic and prophylactic formulations. In one embodiment, an activatable antibody is administered to patients that are at risk of developing one or more of the aforementioned inflammation, inflammatory disorders, cancer or other disorders.

A patient's or organ's predisposition to one or more of the aforementioned disorders can be determined using genotypic, serological or biochemical markers.

In some embodiments of the disclosure, an antibody, a conjugated antibody, an activatable antibody and/or a conjugated activatable antibody is administered to human individuals diagnosed with a clinical indication associated with one or more of the aforementioned disorders. Upon diagnosis, an antibody, a conjugated antibody, an activatable antibody and/or a conjugated activatable antibody is administered to mitigate or reverse the effects of the clinical indication.

Antibodies, conjugated antibodies, activatable antibodies and/or conjugated activatable antibodies of the disclosure are also useful in the detection of the target in patient samples and accordingly are useful as diagnostics. For example, the antibodies, conjugated antibodies, the activatable antibodies and/or conjugated activatable antibodies of the disclosure are used in in vitro assays, e.g., ELISA, to detect target levels in a patient sample.

In one embodiment, an antibody and/or activatable antibody of the disclosure is immobilized on a solid support (e.g., the well(s) of a microtiter plate). The immobilized antibody and/or activatable antibody serves as a capture antibody for any target that may be present in a test sample. Prior to contacting the immobilized antibody and/or activatable antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen in the test sample is determined by comparison with a standard curve developed from the standard samples.

It will be appreciated that based on the results obtained using the antibodies and/or activatable antibodies of the disclosure in an in vitro diagnostic assay, it is possible to stage a disease in a subject based on expression levels of the Target antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Antibodies, conjugated antibodies, activatable antibodies and/or conjugated activatable antibodies can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable antibodies having an enzymatically cleavable CM can be used to detect the presence or absence of an enzyme that is capable of cleaving the CM. Such activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of an activatable antibody) in a given cell or tissue of a given host organism. Such accumulation of activated antibodies indicates not only that the tissue expresses enzymatic activity (or an increased reduction potential depending on the nature of the CM) but also that the tissue expresses target to which the activated antibody binds.

For example, the CM can be selected to be a protease substrate for a protease found at the site of a tumor, at the site of a viral or bacterial infection at a biologically confined site (e.g., such as in an abscess, in an organ, and the like), and the like. The AB can be one that binds a target antigen. Using methods familiar to one skilled in the art, a detectable label (e.g., a fluorescent label or radioactive label or radiotracer) can be conjugated to an AB or other region of an activatable antibody. Suitable detectable labels are discussed in the context of the above screening methods and additional specific examples are provided below. Using an AB specific to a protein or peptide of the disease state, along with a protease whose activity is elevated in the disease tissue of interest, activatable antibodies will exhibit an increased rate of binding to disease tissue relative to tissues where the CM specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM is not present at a detectable level (or is present at lower levels in non-disease tissues or is present in inactive conformation), accumulation of activated antibodies in the disease tissue is enhanced relative to non-disease tissues.

In another example, activatable antibodies can be used to detect the presence or absence of a cleaving agent in a sample. For example, where the activatable antibodies contain a CM susceptible to cleavage by an enzyme, the activatable antibodies can be used to detect (either qualitatively or quantitatively) the presence of an enzyme in the sample. In another example, where the activatable antibodies contain a CM susceptible to cleavage by reducing agent, the activatable antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable antibody that is not released following cleavage, for example, the detectable label can be a quenched fluorescent label or other label that is not detectable until cleavage has occurred. The assay can be conducted by, for example, contacting the immobilized, detectably labeled activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable antibodies as described above, and the presence or absence of the target can be detected by detection of a target-AB complex e.g., by use of a detectably labeled anti-target antibody.

Activatable antibodies are also useful in in situ imaging for the validation of activatable antibody activation, e.g., by protease cleavage, and binding to a particular target. II situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody is labeled with a detectable label. The detectable label may be a fluorescent dye, (e.g. Fluorescein Isothiocyanate (FITC), Rhodamine Isothiocyanate (TRITC), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable antibody indicates that the sample contains the target and contains a protease that is specific for the CM of the activatable antibody. In some embodiments, the presence of the protease can be confirmed using broad spectrum protease inhibitors such as those described herein, and/or by using an agent that is specific for the protease, for example, an antibody such as A11, which is specific for the protease matriptase and inhibits the proteolytic activity of matriptase; see e.g., International Publication Number WO 2010/129609, published 11 Nov. 2010. The same approach of using broad spectrum protease inhibitors such as those described herein, and/or by using a more selective inhibitory agent can be used to identify a protease or class of proteases specific for the CM of the activatable antibody. In some embodiments, the presence of the target can be confirmed using an agent that is specific for the target, e.g., another antibody, or the detectable label can be competed with unlabeled target. In some embodiments, unlabeled activatable antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a protease that is specific for the CM of the activatable antibody.

These techniques are also useful in kits and/or as reagents for the detection, identification or characterization of protease activity in a variety of cells, tissues, and organisms based on the protease-specific CM in the activatable antibody.

In some embodiments, in situ imaging and/or in vivo imaging are useful in methods to identify which patients to treat. For example, in in situ imaging, the activatable antibodies are used to screen patient samples to identify those patients having the appropriate protease(s) and target(s) at the appropriate location, e.g., at a tumor site.

In some embodiments in situ imaging is used to identify or otherwise refine a patient population suitable for treatment with an activatable antibody of the disclosure. For example, patients that test positive for both the target and a protease that cleaves the substrate in the cleavable moiety (CM) of the activatable antibody being tested (e.g., accumulate activated antibodies at the disease site) are identified as suitable candidates for treatment with such an activatable antibody comprising such a CM. Likewise, patients that test negative for either or both of the target and the protease that cleaves the substrate in the CM in the activatable antibody being tested using these methods are identified as suitable candidates for another form of therapy (i.e., not suitable for treatment with the activatable antibody being tested). In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease).

In some embodiments in vivo imaging is used to identify or otherwise refine a patient population suitable for treatment with an activatable antibody of the disclosure. For example, patients that test positive for both the target and a protease that cleaves the substrate in the cleavable moiety (CM) of the activatable antibody being tested (e.g., accumulate activated antibodies at the disease site) are identified as suitable candidates for treatment with such an activatable antibody comprising such a CM. Likewise, patients that test negative are identified as suitable candidates for another form of therapy (i.e., not suitable for treatment with the activatable antibody being tested). In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease).

Pharmaceutical Compositions

The antibodies, conjugated antibodies, activatable antibodies and/or conjugated activatable antibodies of the disclosure (also referred to herein as "active compounds"), and derivatives, fragments, analogs and homologs thereof, can be incorporated into pharmaceutical compositions suitable for administration. Such compositions typically comprise the antibody, the conjugated antibody, activatable antibody and/or conjugated activatable antibody and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1

Characterization of Anti-CD166 Antibodies

The studies provided herein were designed to evaluate binding of anti-CD166 antibodies of the disclosure.

Binding of various anti-CD166 antibodies of the disclosure was confirmed by ELISA (FIG. 1). Anti-human CD166 antibodies comprising the following VH and VL sequences were tested:

| Antibody Name | VH SEQ | VL SEQ |
| --- | --- | --- |
| CD166-M9_vK1/HcB | SEQ ID NO: 121 | SEQ ID NO: 123 |
| CD166-M9_vK2/HcB | SEQ ID NO: 121 | SEQ ID NO: 124 |
| CD166-M9_vk3a/HcB | SEQ ID NO: 121 | SEQ ID NO: 125 |
| CD166-M9_vK3b/HcB | SEQ ID NO: 121 | SEQ ID NO: 126 |
| CD166-M9_vK1/HcC | SEQ ID NO: 122 | SEQ ID NO: 123 |
| CD166-M9_vK2/HcC | SEQ ID NO: 122 | SEQ ID NO: 124 |
| CD166-M9_vK3a/HcC | SEQ ID NO: 122 | SEQ ID NO: 125 |
| CD166-M9_vK3b/HcC | SEQ ID NO: 122 | SEQ ID NO: 126 |

The M9 mAb was obtained using mouse hybridoma technology, and the remaining sequences were generated by humanizing the M9 mAb sequence. Those of ordinary skill in the art will appreciate that the ability to raise anti-CD166 antibodies was hampered for a long time, because researchers could not generate hybridomas and/or antibodies in mice that were administered human CD166. In contrast, the anti-CD166 antibodies presented herein were generated against human CD166 in mice.

The antibody CD166-M9 antibody comprising VH of SEQ ID NO: 119, VL of SEQ ID NO: 120 was used a positive control, and an isotype control antibody was used a negative control.

As shown in FIG. 1, all of the humanized ant-CD166 antibodies showed comparable binding to CD166 M9. Using a standard ELISA protocol, human CD166 protein was absorbed to ELISA plates and subsequently incubated with the indicated concentration of antibody. Bound antibody was detected with an anti-human FAB-peroxidase secondary.

Example 2

Mask Discovery

The studies provided herein were designed to identify and characterize masking moieties for use in activatable anti-CD166 antibodies of the disclosure.

Figure 2:
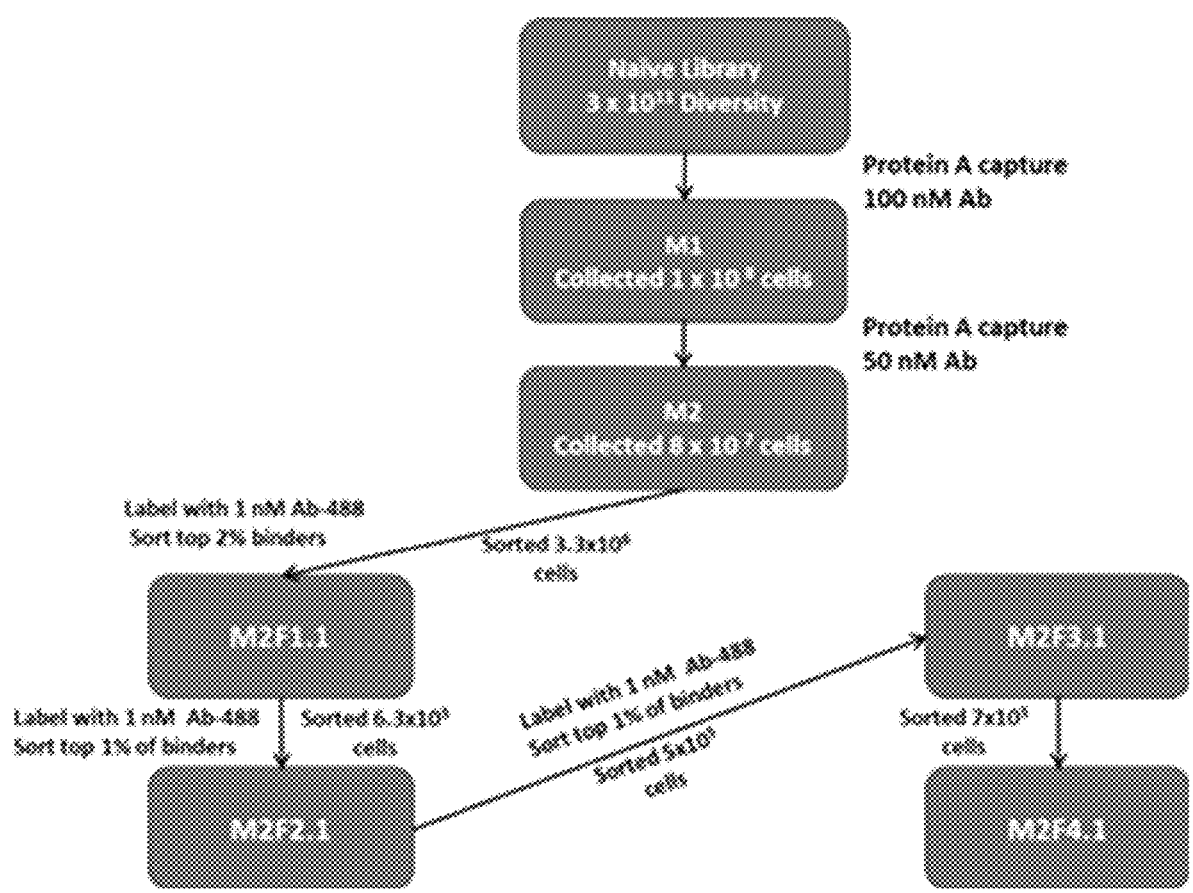
FIG. 2 is a schematic representation of the selection scheme for anti-CD166 masking peptides of the present disclosure. The boxes indicate populations with the sort parameters indicated between the boxes. All FACS sorts were conducted in 0.5% BSA with excess mouse Isotype to block non-specific binding to the Alexa Fluor 488 labeled M9 Mab (VH of SEQ ID NO: 119, VL of SEQ ID NO: 120).

The mouse anti-CD166 Mab M9 (VH of SEQ ID NO: 119, VL of SEQ ID NO: 120 was used to screen a cysteine constrained $X_{15}$ peptide library with a total diversity of $3\times10^{11}$, where X is any amino acid, using a method similar to that described in PCT International Publication Number WO 2010/081173, published 15 Jul. 2010. The screening consisted of two rounds of MACS and four rounds of FACS sorting. The sort process is outlined in FIG. 2.

Individual clones from the M2F1.1, M2F2. 1, M2F3.1, and M2F4.1 populations were sequenced and the results are shown in Table 9.

TABLE 9

Masking Peptide Sequences:

M2F1.1

| | | |
| --- | --- | --- |
| JF16490 | YICQRHPLALKYCTN | (SEQ ID NO: 135) |
| JF16492 | PLCVPTQLLRSCYNY | (SEQ ID NO: 136) |
| JF16493 | AVCHPLANVETQCLD | (SEQ ID NO: 137) |
| JF16494 | PHCHPLENNTYCYRH | (SEQ ID NO: 138) |
| JF16495 | PLCRPIELLASCPMK | (SEQ ID NO: 139) |
| JF16496 | GAACVSAWGFFCECC | (SEQ ID NO: 140) |
| JF16498 | DCAKDILHLMPHCSM | (SEQ ID NO: 141) |
| JFI6501 | NTCMHPLLMQGCKTY | (SEQ ID NO: 142) |
| JF16503 | YLGCLLYAGPGCEGG | (SEQ ID NO: 143) |
| JF16506 | ARCPHPLLLSICENN | (SEQ ID NO: 144) |
| JF16507 | ELCPHPLPFGFCNNY | (SEG ID NO: 145) |
| JF16508 | ALYCHPPYIRCEEMT | (SEQ ID NO: 146) |

M2F2.1

| | | |
| --- | --- | --- |
| JF16534 | TSLCHPVMIMYCHTG | (SEQ ID NO: 147) |
| JF16535 | PLCHPLEQASWCNMD | (SEQ ID NO: 148) |
| JF16536 | PHPCPRTGSRMCHFS | (SEG ID NO: 149) |
| JF16537 | SGCRHPLPLKACGTN | (SEQ ID NO: 150) |
| JF16538 | GICHPIRLHNTQCTI | (SEQ ID NO: 151) |
| JF16539 | KCMEPLNIHNINCNH | (SEQ ID NO: 152) |
| JF16540 | PICHPLREFMNICFK | (SEQ ID NO: 153) |
| JF16541 | NCHPLDVVGWLGCMK | (SEQ ID NO: 154) |
| JF16542 | YNNVCHPLFCSQHTY | (SEQ ID NO: 155) |
| JF16543 | TFCHPLFSLNYCGEK | (SEQ ID NO: 156) |
| JF16544 | FCHPLTLSNNKOCNR | (SEG ID NO: 157) |
| JF16545 | LSHCAVLLLRVCSGS | (SEQ ID NO: 158) |
| JF16546 | KIHCHPLRLGTCLVG | (SEQ ID NO: 159) |
| JF16547 | ETCAHPLDMRMCREN | (SEQ ID NO: 160) |
| JF16548 | PLCYPLILMSSCWLG | (SEQ ID NO: 161) |
| JF16549 | YGICHPAPDLPCMQI | (SEQ ID NO: 162) |
| JF16550 | TACHPLYNVEHLCEI | (SEQ ID NO: 163) |
| JF16551 | TACNKSVCVAGCCLL | (SEQ ID NO: 164) |

TABLE 9-continued

Masking Peptide Sequences:

| | | |
|---|---|---|
| JF16552 | LHPLCSYMKSCMKNN | (SEQ ID NO: 165) |
| JF16553 | THCHCMVYFCPCRWS | (SEQ ID NO: 166) |

M2F3.1

| | | |
|---|---|---|
| JF16554 | PKCPHPLHLANCYAS | (SEQ ID NO: 167) |
| JF16555 | KTCYHPTPVIAXNSY | (SEQ ID NO: 168) |
| JF16556 | AKCLPPLIQYCRCIK | (SEQ ID NO: 169) |
| JF16557 | HACQHPLQIHTCKHN | (SEQ ID NO: 170) |
| JF16558 | LCHPLVLSAWESCSN | (SEQ ID NO: 171) |
| JF16559 | WPLCSFGKSFCAQNA | (SEQ ID NO: 172) |
| JF16560 | ECQSFEHFLTNNCHS | (SEQ ID NO: 173) |
| JF16561 | SCKHPLVMPNLKCTR | (SEQ ID NO: 174) |
| JF16562 | YPCHPLQLSIPHCTK | (SEQ ID NO: 175) |
| JF16563 | ICHPLTHTMEYMCMN | (SEQ ID NO: 176) |
| JF16564 | TLCHPLIFSVPICTN | (SEQ ID NO: 177) |
| JF16565 | PLCOPNRLLQACGNT | (SEQ ID NO: 178) |
| JF16566 | TLCRHPLALDGCQNN | (SEQ ID NO: 179) |
| JF16567 | QPMCYQPAHPLCNTI | (SEQ ID NO: 180) |
| JF16568 | SNCHPLLFQHYECML | (SEQ ID NO: 181) |
| JF16569 | EKCYHPLTLAHCQNH | (SEQ ID NO: 182) |
| JF16571 | NKCFVHPLAMPNCNS | (SEQ ID NO: 183) |
| JF16572 | VNNCLLMTRAHCTSY | (SEQ ID NO: 184) |
| JF16573 | LPCWAFAVNPLHCGD | (SEQ ID NO: 185) |

M2F4.1

| | | |
|---|---|---|
| JS7503 | VNNCLLMTRAHCTSY | (SEQ ID NO: 186) |
| JS7504 | SSCPHPLGITGCNDK | (SEQ ID NO: 187) |
| JS7505 | NKCFVHPLAMPNCNS | (SEQ ID NO: 188) |
| JS7506 | FVGCHSVYVSGCLRA | (SEQ ID NO: 189) |
| JS7507 | NMCHPPHNIYSICNM | (SEQ ID NO: 190) |
| JS7509 | LTCHILPGLTLH-TK | (SEQ ID NO: 191) |
| JS7510 | RTCHPLPGLILHCTK | (SEQ ID NO: 192) |
| JS7511 | HPLCFESMKNCFPNY | (SEQ ID NO: 193) |
| JS7513 | ITCHPLSFIHNYCIT | (SEQ ID NO: 194) |
| JS7515 | RDCGFDAVRADCLFG | (SEQ ID NO: 195) |
| JS7516 | RTCSTHPLIMPQCNY | (SEQ ID NO: 196) |
| JS7517 | MKCHPLQLTGNTCSM | (SEQ ID NO: 197) |
| JS7518 | SGCPHPLQIITCSTA | (SEQ ID NO: 198) |
| JS7519 | KCFPATHDGPLACAS | (SEQ ID NO: 199) |
| JS7520 | LKCQHPLPMSHCQPQ | (SEQ ID NO: 200) |
| JS7521 | AFCGFSVIHPLCSGA | (SEQ ID NO: 201) |

TABLE 9-continued

Masking Peptide Sequences:

| | | |
|---|---|---|
| JS7522 | SVHCAVLKIDGCLGW | (SEQ ID NO: 202) |
| JS7523 | TLPCHPIMVLGCTPM | (SEQ ID NO: 203) |
| JS7525 | HYPCMKYNPLNCSMS | (SEQ ID NO: 204) |
| JS7526 | LKCPHTLSLNGCTLK | (SEQ ID NO: 205) |
| JS7527 | VYSCMANNTLDCFTQ | (SEQ ID NO: 206) |
| JS7528 | PICHPLVTLMSYCNK | (SEQ ID NO: 207) |
| JS7529 | DWCSFWAGQSVWCTS | (SEQ ID NO: 208) |
| JS7530 | STCHPLTPFHDKCRY | (SEQ ID NO: 209) |
| JS7531 | PVCPPLVTLMSYCNK | (SEQ ID NO: 210) |
| JS7532 | STCHTLPTLMPYCNS | (SEQ ID NO: 211) |
| JS7533 | FPLCGIGPAFCDTTV | (SEQ ID NO: 212) |
| JS7534 | PTCHPLVLSVPCPKI | (SEQ ID NO: 213) |
| JS7537 | GPLCDYFVFYSCRGS | (SEQ ID NO: 214) |
| JS7538 | HTCYHPLKLGQCEMF | (SEQ ID NO: 215) |
| JS7539 | RTCIHPLPLHQCHKP | (SEQ ID NO: 216) |
| JS7540 | ACHPINFNSIVYCNN | (SEQ ID NO: 217) |
| JS7542 | SHPCSVVNLPGCEPD | (SEQ ID NO: 218) |

Masks were truncated and alanine scanned to generate families of activatable antibodies with different masking efficiencies. The sequences are shown below in Table 10. The "a" indicates the position of the alanine incorporated as part of the scan. It is equivalent to "A".

TABLE 10

| Truncation and Alanine Scanning of Masking Peptides | | |
|---|---|---|
| 7614 | LCHPLVLSAWESCSS | (SEQ ID NO: 219) |
| 7614.4 | LCaPLVLSAWESCSS | (SEQ ID NO: 220) |
| 7614.5 | LCHaLVLSAWESCSS | (SEQ ID NO: 221) |
| 7614.6 | LCHPaVLSAWESCSS | (SEQ ID NO: 222) |
| 7614.7 | LCHPLaLSAWESCSS | (SEQ ID NO: 223) |
| 7614.8 | LCHPLVaSAWESCSS | (SEQ ID NO: 224) |
| 7614.9 | LCHPLVLSAaESCSS | (SEQ ID NO: 225) |
| 7614.10 | LCHPLVLSAWaSCSS | (SEQ ID NO: 226) |
| 7614.11 | CHPLVLSAWESC | (SEQ ID NO: 227) |
| 7614.12 | HPLVL | (SEQ ID NO: 228) |
| 7614.13 | HPL | (SEQ ID NO: 229) |
| 16522 | LEGWCLHPLCLWGAG | (SEQ ID NO: 230) |
| 16522.14 | LEGaCLHPLCLWGAG | (SEQ ID NO: 231) |
| 16522.15 | LEGWCaHPLCLWGAG | (SEQ ID NO: 232) |
| 16522.16 | LEGWCLaPLCLWGAG | (SEQ ID NO: 233) |

TABLE 10-continued

| Truncation and Alanine Scanning of Masking Peptides | | |
|---|---|---|
| 16522.17 | LECWCLHaLCLWGAG | (SEQ ID NO: 234) |
| 16522.18 | LEGWCLHPaCLWGAG | (SEQ ID NO: 235) |
| 16522.19 | LEGWCTEPLCaWGAG | (SEQ ID NO: 236) |
| 16522.20 | LEGWCLHPLCLaGAG | (SEQ ID NO: 237) |
| 16522.21 | CLHPLC | (SEQ ID NO: 238) |

These masking peptides were used to generate anti-CD166 activatable antibodies of the disclosure. The sequences for certain of these anti-CD166 activatable antibodies are shown below in Table 11. In some embodiments, these anti-CD166 activatable antibodies include cleavable moiety 2001 (ISSGLLSGRSDNH; SEQ ID NO: 70), cleavable moiety 3001 (AVGLLAPPGGLSGRSDNH; SEQ ID NO: 76), cleavable moiety 2007 (ISSGLLSGRSDIH; SEQ ID NO: 342), cleavable moiety 2008 (ISSGLLSGRSDQH; SEQ ID NO: 343), cleavable moiety 2011 (ISSGLLSGRSDNP; SEQ ID NO: 346), cleavable moiety 2012 (ISSGLLSGRSANP; SEQ ID NO: 347), cleavable moiety 2013 (ISSGLLSGRSANI; SEQ ID NO: 348), cleavable moiety 3007 (AVGLLAPPGGLSGRSDIH; SEQ ID NO: 350), cleavable moiety 3008 (AVGLLAPPGGLSGRSDQH; SEQ ID NO: 351), cleavable moiety 3011 (AVGLLAPPGGLSGRSDNP; SEQ ID NO: 354), cleavable moiety 3012 (AVGLLAPPGGLSGRSANP; SEQ ID NO: 355), or cleavable moiety 3013 (AVGLLAPPGGLSGRSANI; SEQ ID NO: 356), as indicated.

While certain sequences shown below include the spacer sequence of SEQ ID NO: 305, those of ordinary skill in the art appreciate that the activatable anti-CD166 antibodies of the disclosure can include any suitable spacer sequence, such as, for example, a spacer sequence selected from the group consisting of QGQSGQG (SEQ ID NO: 305), QGQSGQ (SEQ ID NO: 88), QGQSG (SEQ ID NO: 306), QGQS (SEQ ID NO: 307), QGQ (SEQ ID NO: 308), QG (SEQ ID NO: 309), GQSGQG (SEQ ID NO: 359), QSGQG (SEQ ID NO: 360), SGQG (SEQ ID NO: 361), GQG (SEQ ID NO: 362), G or Q. In some embodiments, the activatable anti-CD166 antibodies of the disclosure can have no spacer sequence joined to its N-terminus.

TABLE 11

| Anti-CD166 Activatable Antibody Sequences |
|---|
| Anti-CD166 Activatable Antibody Heavy Chain (HuCD166_HcC):<br>Amino Acid sequence |
| (SEQ ID NO: 239) |
| QITLKESGPTLVKPTQTLTLTCTFSGFSLSTYGMGVGWIRQPPGKALEWLANIWWSEDKHYSPSLKSRLT |
| ITKDTSKNQVVLTITNVDPVDTATYYCVQIDYGNDYAFTYWGQGTLVTVSSASTKGPSVFPLAPSSKSTS |
| GGTAALGCLVKDYFPEPVTVSWNSGALTSGVHTFPAVLQSSGLYSLSSVVTVPSSSLGTQTYICNVNHKP |
| 3NTKVDKKVEPKSCDKTHTCPPCPAPELLGGPSVFLFPPKPKDTLMISRTPEVTCVVVDVSHEDPEVKFN |
| WYVDGVEVHNAKTKPREEQYNSTYRVVSVLTVLHQDWLNGKEYKCKVSNKALPAPIEKTISKAKGQPREP |
| QVYTLPPSRSEMTKNQVSLTCLVKGFYPSDIAVEWESNGQPENNYKTTPPVLDSDGSFFLYSKLTVDKSR |
| WQQGNVFSCSVMHEALHNHYTQKSLSLSPGK |
| Nucleotide sequence |
| (SEQ ID NO: 241) |
| CAGATCACCCTGAAAGAGTCCGGCCCCACCCTGGTGAAACCCACCCAGACCCTGACCCTGACATGCACCT |
| TCTCCGGCTTCAGCCTGTCCACCTACGGCATGGGCGTGGGCTGGATCAGGCAGCCTCCTGGCAAGGCCCT |
| GGAATGGCTGGCCAACATCTGGTGGTCCGAGGACAAGCACTACTCCCCCAGCCTGAAGTCCCGGCTGACC |
| ATCACCAAGGACACCTCCAAGAACCAGGTGGTGCTGACAATCACAAACGTGGACCCCGTGGACACCGCCA |
| CCTACTACTGCGTGCAGATCGACTACGGCAACGACTACGCCTTCACCTACTGGGGCCAGGGCACACTGGT |
| GACAGTGTCCTCCGCCTCCACCAAGGGCCCCTCCGTGTTCCCTCTGGCCCCTTCCAGCAAGTCCACCTCT |
| GGCGGCACAGCTGCCCTGGGCTGCCTGGTGAAAGACTACTTCCCCGAGCCCGTGACCGTGTCCTGGAACT |
| CTGGCGCCCTGACCAGCGGAGTGCACACCTTCCCTGCCGTGCTGCAGTCCTCCGGCCTGTACTCCCTGTC |
| CTCCGTGGTGACCGTGCCCTCCAGCTCTCTGGGCACCCAGACCTACATCTGCAACGTGAACCACAAGCCC |
| TCCAACACCAAGGTGGACAAGAAGGTGGAACCCAAGTCCTGCGACAAGACCCACACCTGTCCCCCCTGCC |
| CTGCCCCTGAACTGCTGGGCGGACCTTCCGTGTTTCTGTTCCCCCCAAAGCCTAAGGACACCCTGATGAT |
| CTCCCGGACCCCCGAAGTGACCTGCGTGGTGGTGGACGTGTCCCACGAGGACCCTGAAGTGAAGTTCAAT |
| TGGTACGTGGACGGCGTGGAAGTGCACAACGCCAAGACCAAGCCCAGAGAGGAACAGTACAACTCCACCT |
| ACCGGGTGGTGTCTGTGCTGACCGTGCTGCACCAGGACTGGCTGAACGGCAAAGAGTACAAGTGCAAGGT |
| GTCCAACAAGGCCCTGCCTGCCCCCATCGAAAAGACCATCTCCAAGGCCAAGGGCCAGCCCCGCGAGCCT |

TABLE 11-continued

Anti-CD166 Activatable Antibody Sequences

CAGGTGTACACACTGCCCCCTAGCCGGGAAGAGATGACCAAGAATCAGGTGTCCCTGACCTGTCTGGTGA

AAGGCTTCTACCCCTCCGATATCGCCGTGGAATGGGAGTCCAACGGCCAGCCCGAGAACAACTACAAGAC

CACCCCCCCTGTGCTGGACTCCGACGGCTCATTCTTCCTGTACTCCAAGCTGACCGTGGACAAGTCCCGG

TGGCAGCAGGGCAACGTGTTCTCCTGCAGCGTGATGCACGAGGCCCTGCACAACCACTACACCCAGAAGT

CCCTGTCCCTGAGCCCCGGCAAG

[spacer (SEQ ID NO: 305)][HuCD166Lc1_7614.6_2001 (SEQ ID NO: 310)]
Amino Acid sequence
(SEQ ID NO: 242)
[QGQSGQG][LCHPAVLSAWESCSSGGGSSGGSISSGLLSGRSDNHGGGSDIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTFGQGTKLEIKRTVAAPSVFIFPPSDEQLKSGTASVVCLLNNFYPREAKVQWKVDNALQ

SGNSQESVTEQDSKDSTYSLSSTLTLSFCADYEKHIWYACEWHQGLSSPVTKSFNRGEC]

[spacer (SEQ ID NO: 319)][HuCD166Lc1_7614.6_2001 (SEQ ID NO: 311)]
Nucleotide Sequence
(SEQ ID NO: 243)
[CAGGGCCAGTCTGGACAGGGC][CTGTGTCACCCTGCCGTGCTGTCTGCCTGGGAGTCCTGTTCCTCCG

GCGGTGGCTCCTCTGGCGGCTCCATCTCCTCTGGCCTGCTGTCCGGCAGATCCGACAACCACGGCGGAGG

CAGCGACATCGTGATGACCCAGTCCCCCCTGTCCCTGCCCGTGACACCTGGCGAGCCTGCCTCCATCAGC

TGCCGGTCCTCCAAGTCCCTGCTGCACTCCAACGGCATCACCTACCTGTACTGGTATCTGCAGAAGCCCG

GCCAGTCCCCTCAGCTGCTGATCTACCAGATGTCCAACCTGGCCTCCGGCGTGCCCGACAGATTCTCCGG

CTCTGGCTCCGGCACCGACTTCACCCTGAAGATCTCCCGGGTGGAAGCCGAGGACGTGGGCGTGTACTAC

TGCGCCCAGAACCTGGAACTGCCCTACACCTTCGGCCAGGGCACCAAGCTGGAAATCAAGCGGACCGTGG

CCGCTCCCTCCGTGTTCATCTTCCCACCCTCCGACGAGCAGCTGAAGTCCGGCACCGCCTCCGTCGTGTG

CCTGCTGAACAACTTCTACCCTCGCGAGGCCAAGGTGCAGTGGAAGGTGGACAACGCCCTGCAGTCCGGC

AACTCCCAGGAATCCGTCACCGAGCAGGACTCCAAGGACAGCACCTACTCCCTGTCCTCCACCCTGACCC

TGTCCaAGGCCGACTACGAGAAGCACAAGGTGTACGCCTGCGAAGTGACCCACCAGGGCCTGAGCAGCCC

CGTGACCAAGTCCTTCAACCGCGGCGAGTGC]

[spacer (SEQ ID NO: 305)][HuCD166Lc1_7614.8_2001 (SEQ ID NO: 312)]
Amino Acid Sequence
(SEQ ID NO: 244)
[QGQSGQG][LCHPLVASAWESCSSGGGSSGGSISSGLLSGRSDNHGGGSDIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTFGQGTKLEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC]

[spacer (SEQ ID NO: 319)][HuCD166Lc1_7614.8_2001 (SEQ ID NO: 313)]
Nucleotide Sequence
(SEQ ID NO: 245)
[CAGGGCCAGTCTGGACAGGGC][CTGTGTCACCCTCTGGTGGCCTCTGCCTGGGAGTCCTGTTCCTCCG

GCGGTGGCTCCTCTGGCGGCTCCATCTCCTCTGGCCTGCTGTCCGGCAGATCCGACAACCACGGCGGAGG

CAGCGACATCGTGATGACCCAGTCCCCCCTGTCCCTGCCCGTGACACCTGGCGAGCCTGCCTCCATCAGC

TGCCGGTCCTCCAAGTCCCTGCTGCACTCCAACGGCATCACCTACCTGTACTGGTATCTGCAGAAGCCCG

GCCAGTCCCCTCAGCTGCTGATCTACCAGATGTCCAACCTGGCCTCCGGCGTGCCCGACAGATTCTCCGG

CTCTGGCTCCGGCACCGACTTCACCCTGAAGATCTCCCGCGTGGAAGCCGAGGACGTGGGCGTGTACTAC

TGCGCCCAGAACCTGGAACTGCCCTACACCTTCGGCCAGGGCACCAAGCTGGAAATCAAGCGGACCGTGG

CCGCTCCCTCCGTGTTCATCTTCCCACCCTCCGACGAGCAGCTGAAGTCCGGCACCGCCTCCGTCGTGTG

TABLE 11-continued

Anti-CD166 Activatable Antibody Sequences

CCTGCTGAACAACTTCTACCCCCGCGAGGCCAAGGTGCAGTGGAAGGTGGACAACGCCCTGCAGTCCGGC

AACTCCCAGGAATCCGTCACCGAGCAGGACTCCAAGGACAGCACCTACTCCCTGTCCTCCACCCTGACCC

TGTCCAAGGCCGACTACGAGAAGCACAAGGTGTACGCCTGCGAAGTGACCCACCAGGGCCTGAGCAGCCC

CGTGACCAAGTCCTTCAACCGCGGCGAGTGC]

[spacer (SEQ ID NO: 305)][HuCD166Lc1_7614.6_3001(SEQ ID NO: 314)]
Amino Acid Sequence
                                                              (SEQ ID NO: 246)
[[QGQSGQG][LCHPAVLSAWESCSSGGGSSGGSAVGLLAPPGGLSGRSDNHGGSDIVMTQSPLSLPVTP

GEPASISCRSSKSLLHSNGITYLYWYLQKPGQSPQLLIYQMSNLASGVPDRFSGSGSGTDFTLKISRVEA

EDVGVYYCAQNLELPYTFGQGTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC

[spacer (SEQ ID NO: 319)][HuCD166Lc1_7614.6_3001 (SEQ ID NO: 315)]
Nucleotide Sequence
                                                               (SEQ ID NO: 247)
[CAGGGACAGTCTGGCCAGGGC][CTGTGTCACCCTGCTGTGCTGTCTGCCTGGGAGTCCTGTTCCAGCG

GCGGAGGCTCCTCTGGCGGCTCTGCTGTGGGCCTGCTGGCTCCACCTGGCGGCCTGTCCGGCAGATCTGA

CAACCACGGCGGCTCCGACATCGTGATGACCCAGTCCCCCCTGTCCCTGCCCGTGACTCCTGGCGAGCCT

GCCTCCATCTCCTGCCGGTCCTCCAAGTCCCTGCTGCACTCCAACGGCATCACCTACCTGTACTGGTATC

TGCAGAAGCCCGGCCAGTCCCCTCAGCTGCTGATCTACCAGATGTCCAACCTGGCCTCCGGCGTGCCCGA

CAGATTCTCCGGCTCTGGCTCCGGCACCGACTTCACCCTGAAGATCTCCCGGGTGGAAGCCGAGGACGTG

GGCGTGTACTACTGCGCCCAGAACCTGGAACTGCCCTACACCTTCGGCCAGGGCACCAAGCTGGAAATCA

AGCGGACCGTGGCCGCTCCCTCCGTGTTCATCTTCCCACCCTCCGACGAGCAGCTGAAGTCCGGCACCGC

CTCCGTGGTCTGCCTGCTGAACAACTTCTACCCCCGCGAGGCCAAGGTGCAGTGGAAGGTGGACAACGCC

CTGCAGTCCGGCAACTCCCAGGAATCCGTCACCGAGCAGGACTCCAAGGACAGCACCTACTCCCTGTCCT

CCACCCTGACCCTGTCCAAGGCCGACTACGAGAAGCACAAGGTGTACGCCTGCGAAGTGACCCACCAGGG

ACTGAGCAGCCCCGTGACCAAGTCCTTCAACCGGGGCGAGTGC]

[spacer (SEQ ID NO: 309)][HuCD166Lc1_7614.8_3001 (SEQ ID NO: 316)]
Amino Acid Sequence
                                                               (SEQ ID NO: 248)
[QG][LCHPLVASAWESCSSGGGSSGGSAVGLLAPPGGLSGRSDNKGGSDIVMTQSPLSLPVTPGEPASI

SCRSSKSLLHSNGITYLYWYLQKPGQSPQLLIYQMSNLASGVPDRFSGSGSGTDFTLKISRVEAEDVGVY

YCAQNLELPYTFGQGTKLEIKRTVAAPSVTIFPPSDEQLKSGTASVVCLLNNFYPREAKVQWIWDNALQS

GNSQESVTEQDSKDSTYSLSSTLTLSKADYEKHKVYACEVTHQGLSSPVTKSFNRGEC]

[spacer (SEQ ID NO: 320)][HuCD166Lc1_7614.8_3001 (SEQ ID NO: 317)]
Nucleotide Sequence
                                                               (SEQ ID NO: 478)
[[CAGGGCC][TGTGTCACCCTCTGGTGGCCTCTGCCTGGGAGTCCTGTTCCTCCGGCGGAGGCTCCTCT

GGCGGCTCTGCTGTGGGCCTGCTGGCTCCACCTGGCGGCCTGTCCGGCAGATCTGACAACCACGGCGGCT

CCGACATCGTGATGACCCAGTCCCCCCTGTCCCTGCCCGTGACTCCTGGCGAGCCTGCCTCCATCTCCTG

CCGGTCCTCCAAGTCCCTGCTGCACTCCAACGGCATCACCTACCTGTACTGGTATCTGCAGAAGCCCGGC

CAGTCCCCTCAGCTGCTGATCTACCAGATGTCCAACCTGGCCTCCGGCGTGCCCGACAGATTCTCCGGCT

CTGGCTCCGGCACCGACTTCACCCTGAAGATCTCCCGGGTGGAAGCCGAGGACGTGGGCGTGTACTACTG

CGCCCAGAACCTGGAACTGCCCTACACCTTCGGCCAGGGCACCAAGCTGGAAATCAAGCGGACCGTGGCC

GCTCCCTCCGTGTTCATCTTCCCACCCTCCGACGAGCAGCTGAAGTCCGGCACCGCCTCCGTCGTGTGCC

TGCTGAACAACTTCTACCCCCGCGAGGCCAAGGTGCAGTGGAAGGTGGACAACGCCCTGCAGTCCGGCAA

TABLE 11-continued

Anti-CD166 Activatable Antibody Sequences

CTCCCAGGAATCCGTGACCGAGCAGGACTCCAAGGACAGCACCTACTCCCTGTCCTCCACCCTGACCCTG

TCCAAGGCCGACTACGAGAAGCACAAGGTGTACGCCTGCGAAGTGACCCACCAGGGCCTGAGCAGCCCCG

TGACCAAGTCCTTCAACCGGGGCGAGTGC]

[spacer (SEQ ID NO: 305)][HuCD166Lc1_7614.8_3001 (SEQ ID NO: 316)]
Amino Acid Sequence
(SEQ ID NO: 303)
[QGQSGQG][LCHPLVASAWESCSSGGGSSGGSAVGLLAPPGGLSGRSDNHGGSDIVMTQSPLSLPVTPG

EPASISCRSSKSLLHSNGITYLYWYLQKPGQSPQLLIYQMSNLASGVPDRFSGSGSGTDFTLKISRVEAE

DVGVYYCAQNLELPYTFGQGTKLEIKRTVAAPSVFIFPPSDEQLKSGTASVVCLLNNFYPREAKVQWKVD

NALQSGNSQESVTEQDSKDSTYSLSSTLTLSKADYEKHECVYACEVTHQGLSSPVTKSFNRGEC]

[spacer (SEQ ID NO: 319)][HuCD166Lc1_7614.8_CM2 (SEQ ID NO: 317)]
Nucleotide Sequence
(SEQ ID NO: 304)
[CAGGGCCAGTCTGGCCAGGGC][CTGTGTCACCCTCTGGTGGCCTCTGCCTGGGAGTCCTGTTCCTCCG

GCGGAGGCTCCTCTGGCGGCTCTGCTGTGGGCCTGCTGGCTCCACCTGGCGGCCTGTCCGGCAGATCTGA

CAACCACGGCGGCTCCGACATCGTGATGACCCAGTCCCCCCTGTCCCTGCCCGTGACTCCTGGCGAGCCT

GCCTCCATCTCCTGCCGGTCCTCCAAGTCCCTGCTGCACTCCAACGGCATCACCTACCTGTACTGGTATC

TGCAGAAGCCCGGCCAGTCCCCTCAGCTGCTGATCTACCAGATGTCCAACCTGGCCTCCGGCGTGCCCGA

CAGATTCTCCGGCTCTGGCTCCGGCACCGACTTCACCCTGAAGATCTCCCGGGTGGAAGCCGAGGACGTG

GGCGTGTACTACTGCGCCCAGAACCTGGAACTGCCCTACACCTTCGGCCAGGGCACCAAGCTGGAAATCA

AGCGGACCGTGGCCGCTCCCTCCGTGTTCATCTTCCCACCCTCCGACGAGCAGCTGAAGTCCGGCACCGC

CTCCGTCGTGTGCCTGCTGAACAACTTCTACCCCCGCGAGGCCAAGGTGCAGTGGAAGGTGGACAACGCC

CTGCAGTCCGGCAACTCCCAGGAATCCGTGACCGAGCAGGACTCCAAGGACAGCACCTACTCCCTGTCCT

CCACCCTGACCCTGTCCAAGGCCGACTACGAGAAGCACAAGGTGTACGCCTGCGAAGTGACCCACCAGGG

CCTGAGCAGCCCCGTGACCAAGTCCTTCAACCGGGGCGAGTGC

[Spacer (SEQ ID NO: 305)][HuCD166Lc1_7614.6_2001 VL domain
(SEQ ID NO: 364)] Amino Acid sequence
(SEQ ID NO: 363)
[QGQSGQG][LCHPAVLSAWESCSSGGGSSGGSISSGLLSGRSDNHGGSDIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTFGQGTKLEIK]

[spacer (SEQ ID NO: 305)][HuCD166Lc1_7614.8_2001 VL domain
(SEQ ID NO: 366)] Amino Acid Sequence
(SEQ ID NO: 365)
[QGQSGQG][LCHPLVASAWESCSSGGGSSGGSISSGLLSGRSDNHGGSDIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTFGQGTKLEIK]

[spacer (SEQ ID NO: 305)][HuCD166Lc1_7614.6_3001 VL domain
(SEQ ID NO: 368)] Amino Acid Sequence
(SEQ ID NO: 367)
[[QGQSGQG][LCHPAVLSAWESCSSGGGSSGGSAVGLLAPPGGLSGRSDNHGGSDIVMTQSPLSLPVTP

GEPASISCRSSKSLLHSNGITYLYWYLQKPGQSPQLLIYQMSNLASGVPDRFSGSGSGTDFTLKISRVEA

EDVGVYYCAQNLELPYTFGQGTKLEIK]

TABLE 11-continued

Anti-CD166 Activatable Antibody Sequences

[spacer (SEQ ID NO: 305)] [huCD166Lc1_7614.8_3001 VL domain
(SEQ ID NO: 370)] Amino Acid Sequence
(SEQ ID NO: 369)
[QGQSGQG][LCHPLVASAWESCSSGGGSSGGSAVGLLAPPGGLSGRSDNHGGSDIVWTQSPLSLPVTPG

EPASISCRSSKSLLKSNGITYLYWYLQKPGQSPQLLIYQMSNLASGVPDRFSGSGSGTDFTLKISRVEAE

DVGVYYCAQNLELPYTFGQGTKLEIK]

[spacer (SEQ ID NO: 305)][HuCD166Lc1_7614.6_2007 (SEQ ID NO: 372)]
Amino Acid sequence
(SEQ ID NO: 371)
[QGQSGQG][LCKPAVLSAWESCSSGGGSSGGSISSGLLSGRSDIHGCGSDIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTFGQGTKLEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC]

[spacer (SEQ ID NO: 305)][HuCD166Lc1_7614.6_2007 VL domain
(SEQ ID NO: 374)] Amino Acid sequence
(SEQ ID NO: 373)
[QGQSGQG][LCHPAVLSAWESCSSGGGSSGGSISSGLLSGRSDIKGGGSCIVMTQSPLSLPVTPGEPAS

ISCRSSKSLLHSNGITYLYWYLQKPGQSPQLLIYQMSMLASGVPDRFSGSGSGTDFTLKISRVEAEDVGV

YYCAQNLELPYTFGQGTKLEIK]

[spacer (SEQ ID NO: 305)][HuCD166Lc1_7614.6_3007 (SEQ ID NO: 376)]
Amino Acid Sequence
(SEQ ID NO: 375)
[[QGQSGQG][LCHPAVLSAWESCSSGGGSSGGSAVGLLAPPGGLSGRSDIHGGSDIVMTQSPLSLPVTP

GEPASISCRSSKSLLHSNGITYLYWYLQKPGQSPQLLIYQMSNLASGVPDRFSGSGSGTDFTLKISRVEA

EDVGVYYCAQNLELPYTFGQGTKLEIKRTVAAPSVFIFPPSDEQLKSGTASVVCLLNNFYPREAKVQWKV

DNALQSGKSQESVTEQDSKDSTYSLSSTLTLSKADYEKHKVYACEVTHQGLSSPVTKSFNRGEC]

[spacer (SEQ ID NO: 305)][HuCD166Lc1_7614.6_3007 VL domain
(SEQ ID NO: 378)] Amino Acid Sequence
(SEQ ID NO: 377)
[[QGQSGQG][LCHPAVLSAWESCSSGGGSSGGSAVGLLAPPGGLSGRSDIHGGSDIVMTQSPLSLPVTP

GEPASISCRSSKSLLHSNGITYLYWYLQKPGQSPQLLIYQMSNLASGVPDRFSGSGSGTDFTLKISRVEA

EDVGVYYCAQNLELPYTFGQGTKLEIK]

[spacer (SEQ ID NO: 305)][HuCD166Lc1_7614.6_2008 (SEQ ID NO: 380)]
Amino Acid sequence
(SEQ ID NO: 379)
[QGQSGQG][LCHPAVLSAWESCSSGGGSSGGSISSGLLSGRSDQHGGSDIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTFGQGTKLEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC]

[spacer (SEQ ID NO: 305)] |HuCD166Lc1_7614.6_2008 VL domain
(SEQ ID NO: 382)] Amino Acid sequence
(SEQ ID NO: 381)
[QGQSGQG][LCHPAVLSAWESCSSGGGSSGGSISSGLLSGRSDQHGGSCIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTFGQGTKLEIK]

[spacer (SEQ ID NO: 305)][huCD166Lc1_7614.6_3008 (SEQ ID NO: 384)]
Amino Acid Sequence
(SEQ ID NO: 383)
[[QGQSGQG][LCHPAVLSAWESCSSGGGSSGGSAVGLLAPPGGLSGRSDQHGGSDIVMTQSPLSLPVTP

GEPASISCRSSKSLLHSNGITYLYWYLQKPGQSPQLLIYQMSNLASGVPDRFSGSGSGTDFTLKISRVEA

TABLE 11-continued

Anti-CD166 Activatable Antibody Sequences

EDVGVYYCAQNLELPYTFGQGTKLEIKRTVAAPSVFIFPPSDEQLKSGTASVVCLLNNFYPREAKVQWKV

DNALQSGNSQESTOEQDSKDSTYSLSSTLTLSKADYEKHKVYACEVTHQGLSSPVTKSFNRGEC]

[spacer (SEQ ID NO: 305)][huCD166Lc1_7614.6_3008 VL domain
(SEQ ID NO: 386)] Amino Acid Sequence
(SEQ ID NO: 385)
[[QGQSGQG][LCHPAVLSAWESCSSGGGSSGGSAVGLLAPPGGLSGRSDQHGGSDIVMTQSPLSLPVTP

GEPASISCRSSKSLLHSNGITYLYWYLQKPGQSPQLLIYQMSNLASGVPDRFSGSGSGTDFTLKISRVEA

EDVGVYYCAQNLELPYTFGQGTKLEIK]

[spacer (SEQ ID NO: 305)][HuCD166Lc1_7614.6_2011 (SEQ ID NO: 388)]
Amino Acid sequence
(SEQ ID NO: 387)
[QGQSGQG][LCHPAVLSAWESCSSGGGSSGGSISSGLLSGRSDNPGGGSDIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTFGQGTKLEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC]

[spacer (SEQ ID NO: 305)][HuCD166Lc1_7614.6_2011 VL domain
(SEQ ID NO: 390)] Amino Acid sequence
(SEQ ID NO: 389)
[QGQSGQG][LCHPAVLSAWESCSSGGGSSGGSISSGLLSGRSDNPGGGSDIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTPGQGTKLEIK]

[spacer (SEQ ID NO: 305)][huCD166Lc1_7614.6_3011 (SEQ ID NO: 392)]
Amino Acid Sequence
(SEQ ID NO: 391)
[[QGQSGQG][LCKPAVLSAWESCSSGGGSSGGSAVGLLAPPGGLSGRSDNPGGGSDIVMTQSPLSLPVTP

GEPASISCRSSKSLLHSNGITYLYWYLQKPGQSPQLLIYQMSNLASGVPDRFSGSGSGTDFTLKISRVEA

EDVGVYYCAQNLELPYTFGQGTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC]

[spacer (SEQ ID NO: 305)][huCD166Lc1_7614.6_3011 VL domain
(SEQ ID NO: 394)] Amino Acid Sequence
(SEQ ID NO: 393)
[[QGQSGQG][LCKPAVLSAWESCSSGGGSSGGSAVGLLAPPGGLSGRSDNPGGGSDIVMTQSPLSLPVTP

GEPASISCRSSKSLLHSNGITYLYWYLQKPGQSPQLLIYQMSNLASGVPDRFSGSGSGTDFTLKISRVEA

EDVGVYYCAQNLELPYTFGQGTKLEIK]

[spacer (SEQ ID NO: 305)][HuCD166Lc1_7614.6_2012 (SEQ ID NO: 396)]
Amino Acid sequence
(SEQ ID NO: 395)
[QGQSGQG][LCHPAVLSAWESCSSGGGSSGGSISSGLLSGRSANPGGGSDIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTFGQGTKLEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC]

[spacer (SEQ ID NO: 305)][HuCD166Lc1_7614.6_2012 VL domain
(SEQ ID NO: 398)] Amino Acid sequence
(SEQ ID NO: 397)
[QGQSGQG][LCHPAVLSAWESCSSGGGSSGGSISSGLLSGRSANPGGGSDIVMTQSPLSLPVTPGEPAS

ISCRSSKSLLHSNGITYLYWYLQKPGQSPQLLIYQMSNLASGVPDRFSGSG5GTDFTLKISRVEAEDVGV

YYCAQNLELPYTFGQGTKLEIK]

TABLE 11-continued

Anti-CD166 Activatable Antibody Sequences

[spacer (SEQ ID NO: 305)][HuCD166Lc1_7614.6_3012 (SEQ ID NO: 400)]
Amino Acid Sequence
(SEQ ID NO: 399)
[[QGQSGQG][LCHPAVLSAWESCSSGGGSSGGSAVGLLAPPGGLSGRSANPGGSDIVMTQSPLSLPVTP
GEPASISCRSSKSLLHSNGITYLYWYLQKPGQSPQLLIYQMSNLASGVPDRFSGSGSGTDFTLKISRVEA
EDVGVYYCAQNLELPYTFGQGTKLEIKRTVAAPSVFIFPPSDEQLK5GTASVVCLLNNFYPREAKVQWKV
DNALQSGKSQESVTEQDSKDSTYSLSSTLTLSKADYEKHKVYACEVTHQGLSSPVTKSFNRGEC]

[spacer (SEQ ID NO: 305)] [huCD166Lc[_7614.6_3012 VL domain
(SEQ ID NO: 402)] Amino Acid Sequence
(SEQ ID NO: 401)
[[QGQSGQG][LCHPAVLSAWESCSSGGGSSGGSAVGLLAPPGGLSGRSANPGGSDIVMTQSPLSLPVTP
GEPASISCRSSKSLLHSNGITYLYWYLQKPGQSPQLLIYQMSNLASGVPDRFSGSGSGTDFTLKISRVEA
EDVGVYYCAQNLELPYTFGQGTKLEIK]

[spacer (SEQ ID NO: 305)][HuCD166Lc1_7614.6_2013 (SEQ ID NO: 404)]
Amino Acid sequence
(SEQ ID NO: 403)
[QGQSGQG][LCHPAVLSAWESCSSGGGSSGGSISSGLLSGRSANIGGGSDIVMTQSPLSLPVTPGEPAS
ISCRSSKSLLHSNGITYLYWYLQKPGQSPQLLIYQMSNLASGVPDRFSGSGSGTDFTLKISRVEAEDVGV
YYCAQNLELPYTFGQGTKLEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC]

[spacer (SEQ ID NO: 305)][HuCD166Lc1_7614.6_2013 VL domain
(SEQ ID NO: 406)] Amino Acid sequence
(SEQ ID NO: 405)
[QGQSGQG][LCHPAVLSAWESCSSGGGSSGGSISSGLLSGRSANIGGGSDIVMTQSPLSLPVTPGEPAS
ISCRSSKSLLHSNGITYLYWYLQKPGQSPQLLIYQMSNLASGVPDRFSGSGSGTDFTLKISRVEAEDVGV
YYCAQNLELPYTFGQGTKLEIK]

[spacer (SEQ ID NO: 305)][huCD166Lc1_7614.6_3013 (SEQ ID NO: 408)]
Amino Acid Sequence
(SEQ ID NO: 407)
[[QGQSGQG][LCHPAVLSAWESCSSGGGSSGGSAVGLLAPPGGLSGRSANIGGSDIVMTQSPLSLPVTP
GEPASISCRSSKSLLHSNGITYLYWYLQKPGQSPQLLIYQMSNLASGVPDRFSGSGSGTDFTLKISRVEA
EDVGVYYCAQNLELPYTFGQGTKLEIKRTVAAPSVFIFPPSDEQLKSGTASVVCLLNNFYPREAKVQWKV
DNALQSGNSQESTQEQDSKDSTYSLSSTLTLSKADYEKHKVYACEVTHQGLSSPVTKSFNRGEC]

[spacer (SEQ ID NO: 305)][HuCD166Lc1_7614.6_3013 VL domain
(SEQ ID NO: 410)] Amino Acid Sequence
(SEQ ID NO: 409)
[[QGQSGQG][LCHPAVLSAWESCSSGGGSSGGSAVGLLAPPGGLSGRSANIGGSDIVMTQSPLSLPVTP
GEPASISCRSSKSLLHSNGITYLYWYLQKPGQSPQLLIYQMSNLASGVPDRFSGSGSGTDFTLKISRVEA
EDVGVYYCAQNLELPYTFGQGTKLEIK]

[spacer (SEQ ID NO: 305)][HuCD166Lc1_7614.8_2007 (SEQ ID NO: 412)]
Amino Acid sequence
(SEQ ID NO: 411)
[QGQSGQG][LCHPLVASAWESCSSGGGSSGGSISSGLLSGRSDIHGGGSDIVMTQSPLSLPVTPGEPAS
ISCRSSKSLLHSNGITYLYWYLQKPGQSPQLLIYQMSNLASGVPDRFSGSGSGTDFTLKISRVEAEDVGV
YYCAQNLELPYTFGQGTKLEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC]

TABLE 11-continued

Anti-CD166 Activatable Antibody Sequences

[spacer (SEQ ID NO: 305)][HuCD166Lc1_7614.8_2007 VL domain
(SEQ ID NO: 414)] Amino Acid sequence
(SEQ ID NO: 413)
[QGQSGQG][LCHPLVASAWESCSSGGGSSGGSISSGLLSGRSDIHGGSDIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTFGQGTKLEIK]

[spacer (SEQ ID NO: 305)][HuCD166Lc1_7614.8_3007 (SEQ ID NO: 416)]
Amino Acid Sequence
(SEQ ID NO: 415)
[[QGQSGQG][LCMPLVASAWESCSSGGGSSGGSAVGLLAPPGGLSGRSDIHGGSDIVMTQSPLSLPVTP

GEPASISCRSSKSLLHSNGITYLYWYLQKPGQSPQLLIYQMSNIASGVPDRFSGSGSGTDFTLKISRVEA

EDVGVYYCAQNLELPYTFGQGTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC]

[spacer (SEQ ID NO: 305)][HuCD166Lc1_7614.8_3007 VL domain
(SEQ ID NO: 418)] Amino Acid Sequence
(SEQ ID NO: 417)
[[QGQSGQG][LCHPLVASAWESCSSGGGSSGGSAVGLLAPPGGLSGRSDIHGGSDIVMTQSPLSLPVTP

GEPASISCRSSKSLLHSNGITYLYWYLQKPGQSPQLLIYQMSNLASGVPDRFSGSGSGTDFTLKISRVEA

EDVGVYYCAQNLELPYTFGQGTKLEIK]

[spacer (SEQ ID NO: 305)][HuCD166Lc1_7614.8_2008 (SEQ ID NO: 420)]
Amino Acid sequence
(SEQ ID NO: 419)
[QGQSGQG][LCHPLVASAWESCSSGGGSSGGSISSGLLSGRSDQHGGSDIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTFGQGTKLEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC]

[spacer (SEQ ID NO: 305)][HuCD166Lc1_7614.8_2008 VL domain
(SEQ ID NO: 422)] Amino Acid sequence
(SEQ ID NO: 421)
[QGQSGQG][LCHPLVASAWESCSSGGGSSGGSISSGLLSGRSDQHGGSCIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTFGQGTKLEIK]

[spacer (SEQ ID NO: 305)][HuCD166Lc1_7614.8_3008 (SEQ ID NO: 424)]
Amino Acid Sequence
(SEQ ID NO: 423)
[[QGQSGQG][LCHPLVASAWESCSSGGGSSGGSAVGLLAPPGGLSGRSDQHGGSDIVMTQSPLSLPVTP

GEPASISCRSSKSLLHSNGITYLYWYLQKPGQSPQLLIYQMSNLASGVPDRFSGSGSGTDFTLKISRVEA

EDVGVYYCAQNLELPYTFGQGTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC]

[spacer (SEQ ID NO: 305)][HuCD166Lc1_7614.8_3008 VL domain
(SEQ ID NO: 426)] Amino Acid Sequence
(SEQ ID NO: 425)
[[QGQSGQG]]LCHPLVASAWESCSSGGGSSGGSAVGLLAPPGGLSGRSDQHGGSDIVMTQSPLSLPVTP

GEPASISCRSSKSLLHSNGITYLYWYLQKPGQSPQLLIYQMSNLASGVPDRFSG3GSGTDFTLKISRVEA

EDVGVYYCAQNLELPYTFGQGTKLEIK]

[spacer (SEQ ID NO: 305)][HuCD166Lc1_7614.8_2011 (SEQ ID NO: 428)]
Amino Acid sequence
(SEQ ID NO: 427)
[QGQSGQG][LCHPLVASAWESCSSGGGSSGGSISSGLLSGRSDMPGGSDIVMTQSPLSLPVTFGEPAS

ISCRSSKSLLHSNGITYLYWYLQKPGQSPQLLIYQMSNLASGVPDRFSGSGSGTDFTLKISRVEAEDVGV

TABLE 11-continued

Anti-CD166 Activatable Antibody Sequences

YYCAQNLELPYTFGQGTKLEIKRTVAAPSVFIFPPSDEQLKSGTASVVCLLNNFYPREAKVQWKVDNALQ

SGNSQESVTEQDSKDSTYSLSSTLTLSKADYEKHIWYACEVTHQGLSSPVTKSFNRGSC]

[spacer (SEQ ID NO: 305)][HuCD166Lc1_7614.8_2011 VL domain
(SEQ ID NO: 430)] Amino Acid sequence
(SEQ ID NO: 429)
[QGQSGQG][LCHPLVASAWESCSSGGGSSGGSISSGLLSGRSDNPGGGSDIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTPGQGTKLEIK]

[spacer (SEQ ID NO: 305)][huCD166Lc1_7614.8_3011(SEQ ID NO: 432)]
Amino Acid Sequence
(SEQ ID NO: 431)
[[QGQSGQG][LCHPLVASAWESCSSGGGSSGGSAVGLLAPPGGLSGRSDNPGGGSDIVMTQSPLSLPVTP

GEPASISCRSSKSLLHSNGITYLYWYLQKPGQSPQLLIYQMSNLASGVPDRFSGSGSGTDFTLKISRVEA

EDVGVYYCAQNLELPYTFGQGTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC]

[spacer (SEQ ID NO: 305)][HuCD166Lc1_7614.8_3011 VL domain
(SEQ ID NO: 434)] Amino Acid Sequence
(SEQ ID NO: 433)
[[QGQSGQG][LCHPLVASAWESCSSGGGSSGGSAVGLLAPPGGLSGRSDNPGGGSDIVMTQSPLSLPVTP

GEPASISCRSSKSLLHSNGITYLYWYLQKPGQSPQLLIYQMSNLASGVPDRFSGSGSGTDFTLKISRVEA

EDVGVYYCAQNLELPYTFGQGTKLEIK]

[spacer (SEQ ID NO: 305)][HuCD166Lc1_7614.8_2012 (SEQ ID NO: 436)]
Amino Acid sequence
(SEQ ID NO: 435)
[QGQSGQG][LCHPLVASAWESCSSGGGSSGGSISSGLLSGRSANPGGGSDIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTFGQGTKLEIKRTVAAPSVFIFPPSDEQLKSGTASVVCLLNNFYPREAKVQWKVDNALQ

SGNSQESVTEQDSKDSTYSLSSTLTLSKADYEKHKTQACEVTHQGLSSPVTKSFNRGEC]

[spacer (SEQ ID NO: 305)][HuCD166Lc1_7614.8_2012 VL domain
(SEQ ID NO: 438)] Amino Acid sequence
(SEQ ID NO: 437)
[QGQSGQG][LCHPLVASAWESCSSGGGSSGGSISSGLLSGRSANPGGGSDIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTFGQGTKLEIK]

[spacer (SEQ ID NO: 305)][HuCD166Lc1_7614.8_3012 (SEQ ID NO: 440)]
Amino Acid Sequence
(SEQ ID NO: 439)
[[QGQSGQG][LCHPLVASAWESCSSGGGSSGGSAVGLLAPPGGLSGRSANPGGGSDIVMTQSPLSLPVTP

GEPASISCRSSKSLLHSNGITYLYWYLQKPGQSPQLLIYQMSNLASGVPDRFSGSGSGTDFTLKISRVEA

EDVGVYYCAQNLELPYTFGQGTKLEIKRTVAAPSVFIFPPSDEQLKSGTASVVCLLNNFYPREAKVQWKV

DNALQSGKSQESVTEQDSKDSTYSLSSTLTLSKADYEKHKVYACEVTHQGLSSPVTKSFNRGEC]

[spacer (SEQ ID NO: 305)][7614.8_3012 VL domain (SEQ ID NO: 442)]
Amino Acid Sequence
(SEQ ID NO: 441)
[[QGQSGQG][LCHPLVASAWESCSSGGGSSGGSAVGLLAPPGGLSGRSANPGGGSDIVMTQSPLSLPVTP

GEPASISCRSSKSLLHSNGITYLYWYLQKPGQSPQLLIYQMSNLASGVPDRFSGSGSGTDFTLKISRVEA

EDVGVYYCAQNLELPYTFGQGTKLEIK]

TABLE 11-continued

Anti-CD166 Activatable Antibody Sequences

[spacer (SEQ ID NO: 305)][HuCD166Lc1_7614.8_2013 (SEQ ID NO: 444)]
Amino Acid sequence
(SEQ ID NO: 443)
[QGQSGQG][LCHPLVASAWESCSSGGGSSGGSISSGLLSGRSANIGGGSDIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTFGQGTKLEIKRTYAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC]

[spacer (SEQ ID NO: 305)][HuCD166Lc1_7614.8_2013 VL domain
(SEQ ID NO: 446)] Amino Acid sequence
(SEQ ID NO: 445)
[QGQSGQG][LCHPLVASAWESCSSGGGSSGGSISSGLLSGRSANIGGGSDIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTFGQGTKLEIK]

[spacer (SEQ ID NO: 305)][HuCD166Lc1_7614.8_3013 (SEQ ID NO: 448)]
Amino Acid Sequence
(SEQ ID NO: 447)
[[QGQSGQG][LCHPLVASAWESCSSGGGSSGGSAVGLLAPPGGLSGRSANIGGGSDIVMTQSPLSLPVTP

GEPASISCRSSKSLLHSNGITYLYWYLQKPGQSPQLLIYQMSNLASGVPDRFSGSGSGTDFTLKISRVEA

EDVGVYYCAQNLELPYTFGQGTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC]

[spacer (SEQ ID NO: 305)][HuCD166Lc1_7614.8_3013 VL domain
(SEQ ID NO: 450)] Amino Acid Sequence
(SEQ ID NO: 449)
[[QGQSGQG][LCHPLVASAWESCSSGGGSSGGSAVGLLAPPGGLSGRSANIGGGSDIVMTQSPLSLPVTP

GEPASISCRSSKSLLHSNGITYLYWYLQKPGQSPQLLIYQMSNLASGVPDRFSGSGSGTDFTLKISRVEA

EDVGVYYCAQNLELPYTFGQGTKLEIK]

[spacer (SEQ ID NO: 305)][HuCD166Lc1_7614_2001 (SEQ ID NO: 452)]
Amino Acid sequence
(SEQ ID NO: 451)
[QGQSGQG][LCHPLVLSAWESCSSGGGSSGGSISSGLLSGRSDNHGGGSDIVMTQSPLSLPVTPGEPAS

ISCRSSKSLLHSNGITYLYWYLQKPGQSPQLLIYQMSNLASGVPDRFSGSGSGTDFTLKISRVEAEDYGV

YYCAQNLELPYTFGQGTKLEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC]

[spacer (SEQ ID NO: 305)][HuCD166Lc1_7614_2001 VL domain
(SEQ ID NO: 454)] Amino Acid sequence
(SEQ ID NO: 453)
[QGQSGQG][LCHPLVLSAWESCSSGGGSSGGSISSGLLSGRSDNHGGGSDIVMTQSPLSLPVTPGEPAS

ISCRSSKSLLHSNGITYLYWYLQKPGQSPQLLIYQMSNLASGVPDRFSGSGSGTDFTLKISRVEAEDVGV

YYCAQNLELPYTFGQGTKLEIK]

[spacer (SEQ ID NO: 305)][HuCD166Lc1_7614_3001 (SEQ ID NO: 456)]
Amino Acid Sequence
(SEQ ID NO: 455)
[[QGQSGQG][LCHPLVLSAWESCSSGGGSSGGSAVGLLAPPGGLSGRSDNHGGGSDIVMTQSPLSLPVTP

GEPASISCRSSKSLLHSNGITYLYWYLQKPGQSPQLLIYQMSNLASGVPDRFSGSGSGTDETLKISRVEA

EDVGVYYCAQNLELPYTFGQGTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC]

TABLE 11-continued

Anti-CD166 Activatable Antibody Sequences

[spacer (SEQ ID NO: 305)][HuCD166Lc1_7614_3001 VL domain
(SEQ ID NO: 458)] Amino Acid Sequence
(SEQ ID NO: 457)
[[QCQSGQG][LCHPLVLSAWESCSSGGGSSGGSAVGLLAPPGGLSGRSDNKGGSDIWITQSPLSLPVTP
GEPASISCRSSKSLLHSNGITYLYWYLQKPGQSPQLLIYQMSNLASGVPDRFSGSGSGTDFTLKISRVEA
EDVGVYYCAQNLELPYTFGQGTKLEIK]

[spacer (SEQ ID NO: 305)][HuCD166Lc1_7614_2011 (SEQ ID NO: 460)]
Amino Acid sequence
(SEQ ID NO: 459)
[QGQSGQG][LCHPLVLSAWESCSSGGGSSGGSISSGLLSGRSDNPGGGSDIVMTQSPLSLPVTPGEPAS
ISCRSSKSLLHSNGITYLYWYLQKPGQSPQLLIYQMSNLASGVPDRFSGSGSGTDFTLKISRVEAEDVGV
YYCAQNLELPYTFGQGTKLEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC]

[spacer (SEQ ID NO: 305)][HuCD166Lc1_7614_2011 VL domain
(SEQ ID NO: 462)] Amino Acid sequence
(SEQ ID NO: 461)
[QGQSGQG][LCHPLVLSAWESCSSGGGSSGGSISSGLLSGRSDNPGGGSCIVMTQSPLSLPVTPGEPAS
ISCRSSKSLLHSNGITYLYWYLQKPGQSPQLLIYQMSNLASGVPDRFSGSGSGTDFTLKISRVEAEDVGV
YYCAQNLELPYTFGQGTKLEIK]

[spacer (SEQ ID NO: 305)][HuCD166Lc1_7614_3011 (SEQ ID NO: 464)]
Amino Acid Sequence
(SEQ ID NO: 463)
[[QGQSGQG][LCHPLVLSAWESCSSGGGSSGGSAVGLLAPPGGLSGRSDNPGGSDIVMTQSPLSLPVTP
GEPASISCRSSKSLLHSNGITYLYWYLQKPGQSPQLLIYQMSNLASGVPDRFSGSGSGTDFTLKISRVEA
EDVGVYYCAQNLELPYTFGQGTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGEC]

[spacer (SEQ ID NO: 305)][HuCD166Lc1_7614_3011 VL domain
(SEQ ID NO: 466)] Amino Acid Sequence
(SEQ ID NO: 465)
[[QGQSGQG][LCHPLVLSAWESCSSGGGSSGGSAVGLLAPPGGLSGRSDNPGGSDIVMTQSPLSLPVTP
GEPASISCRSSKSLLHSNGITYLYWYLQKPGQSPQLLIYQMSNLASGVPDRFSG3GSGTDFTLKISRVEA
EDVGVYYCAQNLELPYTFGQGTKLEIK]

[spacer (SEQ ID NO: 305)][HuCD166Lc1_7614_2012 (SEQ ID NO: 468)]
Amino Acid sequence
(SEQ ID NO: 467)
[QGQSGQG][LCHPLVLSAWESCSSGGGSSGGSISSGLLSGRSANPGGGSDIVMTQSPLSLPVTFGEPAS
ISCRSSKSLLHSNGITYLYWYLQKPGQSPQLLIYQMSNLASGVPDRFSGSGSGTDFTLKISRVEAEDVGV
YYCAQNLELPYTFGQGTKLEIKRTVAAPSVFIFPPSDEQLKSGTASVVCLLNNFYPREAKVQWIDNALQ
SGNSQESVTBQDSKDSTYSLSSTLTLSKADYEKHKVYACEVTHQGLSSPVTKSFNRGEC]

[spacer (SEQ ID NO: 305)][HuCD166Lc1_7614_2012 VL domain
(SEQ ID NO: 470)] Amino Acid sequence
(SEQ ID NO: 469)
[QGQSGQG][LCHPLVLSAWESCSSGGGSSGGSISSGLLSGRSANPGGGSDIVMTQSPLSLPVTPGEPAS
ISCRSSKSLLHSNGITYLYWYLQKPGQSPQLLIYQMSNLASGVPDRFSGSGSGTDFTLKISRVEAEDVGV
YYCAQNLELPYTPGQGTKLEIK]

[spacer (SEQ ID NO: 305)][huCD166Lc1_7614_3012 (SEQ ID NO: 472)]
Amino Acid Sequence
(SEQ ID NO: 471)
[[QGQSGQG][LCHPLVLSAWESCSSGGGSSGGSAVGLLAPPGGLSGRSANPGGSDIVMTQSPLSLPVTP
GEPASISCRSSKSLLHSNGITYLYWYLQKPGQSPQLLIYQMSNLASGVPDRFSGSGSGTDFTLKISRVEA TABLE 11-continued Anti-CD166 Activatable Antibody Sequences

EDVGVYYCAQNLELPYTFGQGTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC]

[spacer (SEQ ID NO: 305)][HuCD166Lc1_7614_3012 VL domain
(SEQ ID NO: 474)] Ammo Acid Sequence
(SEQ ID NO: 473)
[[QGQSGQG][LCHPLVLSAWESCSSGGGSSGGSAVGLLAPPGGLSGRSANPGGSDIVMTQSPLSLPVTP

GEPASISCRSSKSLLHSNGITYLYWYLQKPGQSPQLLIYQMSNLASGVPDRFSGSGSGTDFTLKISRVEA

EDVGVYYCAQNLELPYTFGQGTKLEIK]

Example 3

Generation of Activatable Anti-CD166 Antibodies

The studies provided herein were designed to generate activatable anti-CD166 antibodies of the disclosure.

Figure 3A:
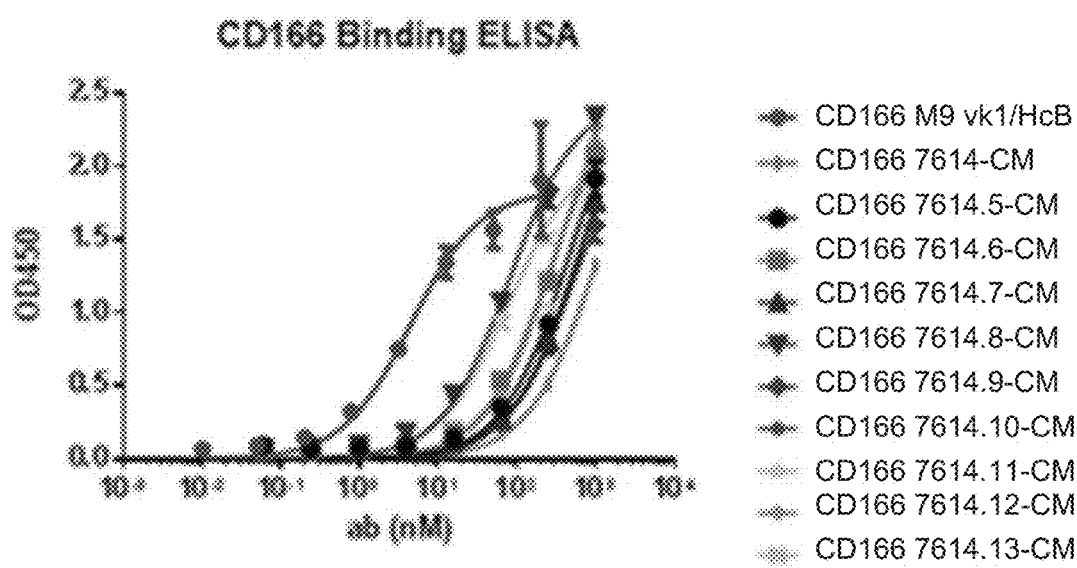
FIGS. 3A and 3B are a series of graphs depicting the ability of the anti-CD166 antibody CD166 M9 vK1/HcB (VH of SEQ ID NO: 121, VL of SEQ ID NO: 123) of the present disclosure and various anti-CD166 activatable antibodies of the present disclosure to bind human CD166.
Figure 3B:
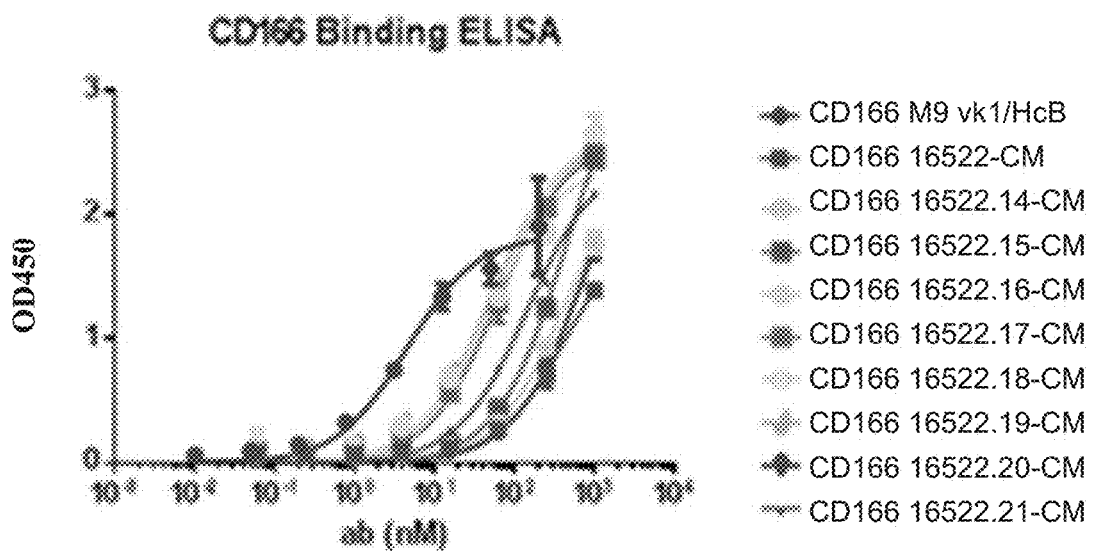

Anti-CD166 activatable antibodies were generated with different masking efficiencies (i.e., a measurement of the ability of the MM of the activatable antibody to block binding of the AB of the activatable antibody to its target). The peptides 16522 and 7614 were mutated by truncation and alanine scanning as described in Example 2, and these masking peptide variants were used to generate families of anti-CD166 activatable antibodies with a range of fold masking. The ability of the anti-CD166 antibody CD166 M9 vK1/HcB (VH of SEQ ID NO: 121, VL of SEQ ID NO: 123) and various anti-CD166 activatable antibodies to bind human CD166 was evaluated using a CD166 binding ELISA (FIG. 3A, 3B). The anti-CD166 activatable antibodies tested included the variable heavy chain sequence of SEQ ID NO: 121, the variable light chain sequence of SEQ ID NO: 123, a cleavable moiety (CM) comprising the amino acid sequence ISSGLLSGRSDNH (SEQ ID NO: 70) referred to herein as substrate 2001, and one of the masking moieties shown in Table 10. The full sequences are shown above in Table 11.

Using a standard ELISA protocol, human CD166 protein is absorbed to ELISA plates and subsequently incubated with the indicated concentration of antibody or activatable antibody. Bound antibody or activatable antibody was detected with an anti-human FAB-peroxidase secondary. A summary of the exemplary apparent iin vitro dissociation constants (Kd) of the activatable antibodies of the present invention to CD166 polypeptide as determined by ELISA is shown below in Table 17, as well as the respective increase in Kd relative to the parent anti-CD166 M9 antibody (vk-1/HcB). Except for the parental anti-CD166 M9 antibody, the mask for each activatable antibody is as indicated as described herein, and the substrate sequence was 2001 (ISSGLLSGRSDNH (SEQ ID NO: 70)).

TABLE 17

Apparent ELISA Dissociation Constants of Activatable Anti-CD166 Antibodies

| Antibody Construct | Apparent Kd (nM) | Fold Increase in Kd |
|---|---|---|
| CD166 M9 vk1/HcB | 4.4 | 1 |
| CD166-16522-2001 | 423.7 | 95 |
| CD166-7614-2001 | 998.6 | 225 |

TABLE 17-continued

Apparent ELISA Dissociation Constants of Activatable Anti-CD166 Antibodies

| Antibody Construct | Apparent Kd (nM) | Fold Increase in Kd |
|---|---|---|
| CD166-7614.5-2001 | 495.0 | 112 |
| CD166-7614.6-2001 | 265.6 | 60 |
| CD166-7614.7-2001 | 618.6 | 139 |
| CD166-7614.8-2001 | 82.2 | 19 |
| CD166-7614.9-2001 | 534.0 | 120 |
| CD166-7614.10-2001 | 685.2 | 154 |
| CD166-7614.11-2001 | 544.0 | 123 |
| CD166-7614.12-2001 | 331.9 | 75 |
| CD166-7614.13-2001 | 77.7 | 18 |
| CD166-16522.14-2001 | 422.1 | 95 |
| CD166-16522.15-2001 | 447.7 | 101 |
| CD166-16522.16-2001 | 47.4 | 11 |
| CD166-16522.17-2001 | 61.6 | 14 |
| CD166-16522.18-2001 | 57.7 | 13 |
| CD166-16522.19-2001 | 49.2 | 11 |
| CD166-16522.20-2001 | 700.3 | 158 |
| CD166-16522.21-2001 | 144.7 | 33 |

Example 4

Activation of Activatable Anti-CD166 Antibodies

The studies provided herein were designed to evaluate activation of activatable anti-CD166 antibodies.

Figure 4:
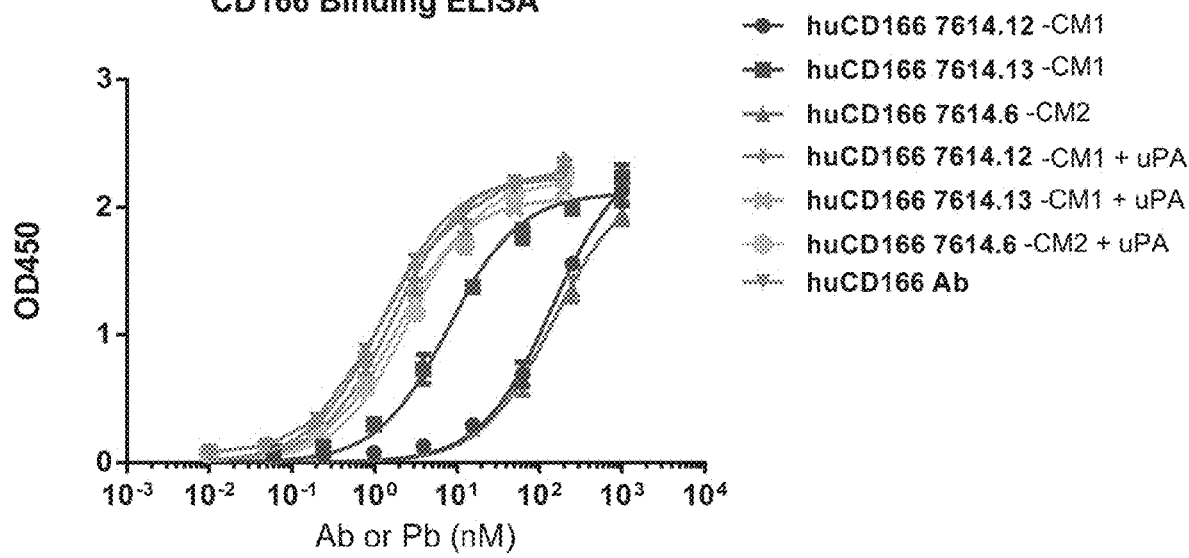
FIG. 4 is a graph depicting the ability of various anti-CD166 activatable antibodies of the disclosure to bind human CD166 when proteolytically activated.

FIG. 4 is a graph depicting the ability of various anti-CD166 activatable antibodies of the disclosure to bind human CD166 when proteolytically activated. As shown in FIG. 4, anti-CD166 activatable antibodies recover antibody binding when proteolytically activated. The binding of the anti-CD166 antibody (huM9 HcC/vk-1; VH of SEQ ID NO: 122, VL of SEQ ID NO: 123), various anti-CD166 activatable antibodies of the disclosure, and uPA activated anti-CD166 activatable antibodies was evaluated using a CD166 binding ELISA. The anti-CD166 activatable antibodies tested included the variable heavy chain sequence of SEQ ID NO: 122, the variable light chain sequence of SEQ ID NO: 123, either a cleavable moiety (CM1, substrate 2001) comprising the amino acid sequence ISSGLLSGRSDNH (SEQ ID NO: 70) or a cleavable moiety (CM2, substrate 3001) comprising the amino acid sequence AVGLLAPPG-GLSGRSDNH (SEQ ID NO: 76), and one of the masking moieties shown in Table 10. The full sequences are shown above in Table 11.

Using a standard ELISA protocol, human CD166 protein is absorbed to ELISA plates and subsequently incubated with the indicated concentration of antibody or activatable antibody. Bound antibody or activatable antibody was detected with an anti-human FAB-peroxidase secondary.

In an exemplary study, the binding affinity of anti-CD166 antibodies (anti-CD166 HcC/vk-1 of the present disclosure and anti-CD166 activatable antibodies (anti-CD166-7614.6-3001) of the present disclosure to human cells (HCC1806 human breast cancer cells) and human CD166 were determined. Under these conditions, apparent exemplary binding affinities ($K_d$) by ELISA are 96.2 nM and 1.3 nM for the anti-CD166 activatable antibody and the anti-CD166 antibody of the present disclosure, respectively. In the exemplary HCC1806 cell binding assay as measured by flow cytometry, apparent binding affinities (Kd) are 372 nM and 3.2 nM for the anti-CD166 activatable antibody and the anti-CD166 antibody of the present disclosure, respectively. These exemplary results demonstrated that the anti-CD166 activatable antibody, in an uncleaved state, demonstrated a lower binding affinity to isolated CD166 polypeptide and CD166 on cells, as compared to the anti-CD166 antibody of the present disclosure.

Figure 5:
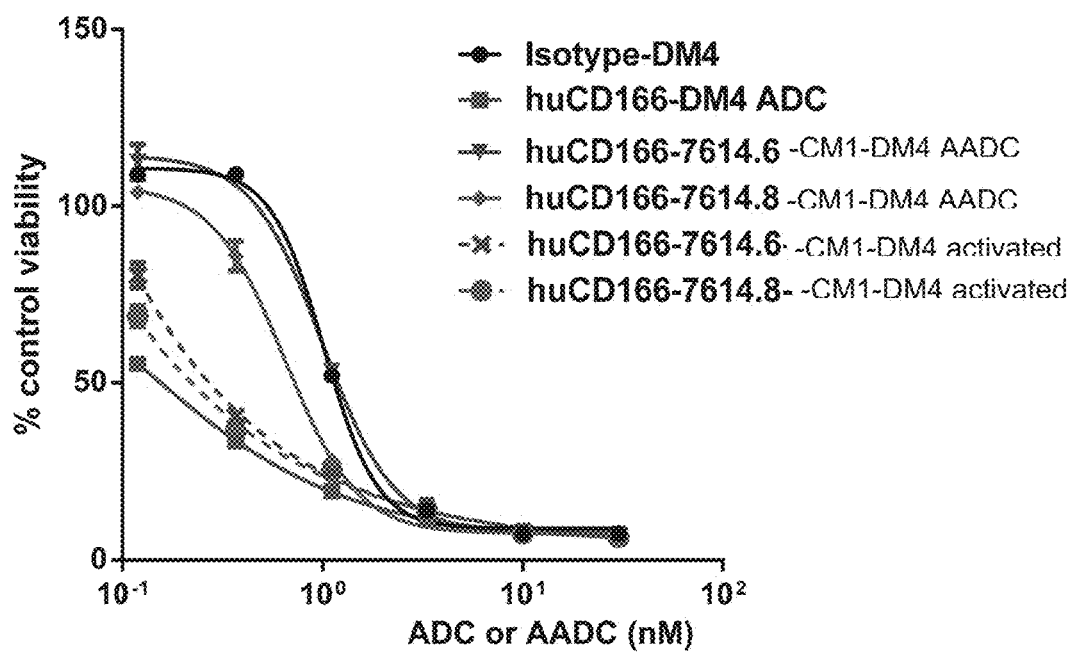
FIG. 5 is a graph depicting the ability of various conjugated anti-CD166 activatable antibodies of the disclosure to bind human CD166 when proteolytically activated.

FIG. 5 is a graph depicting the ability of various conjugated anti-CD166 activatable antibodies of the disclosure to effect cell killing of HCC1806 cells when proteolytically activated with uPA. These conjugated anti-CD166 activatable antibodies are also referred to herein as "CD166 AADC" or CD166 Activatable Antibody Drug Conjugates. The conjugated anti-CD166 activatable antibodies tested included the variable heavy chain sequence of SEQ ID NO: 122, the variable light chain sequence of SEQ ID NO: 123, a cleavable moiety (CM1, substrate 2001) comprising the amino acid sequence ISSGLLSGRSDNH (SEQ ID NO: 70), one of the masking moieties shown in Table 10, and the maytansinoid DM4 conjugated to the activatable antibody via an SPDB linker. The full sequences of the activatable antibodies are shown above in Table 11. All conjugated activatable antibodies disclosed herein were produced by TCRS (The Chemistry Research Solution).

As shown in FIG. 5, various conjugated anti-CD166 activatable antibodies of the disclosure behave like isotype-DM4 when masked, but when proteolytically activated with uPA, these conjugated anti-CD166 activatable antibodies show similar cell killing to that of the huCD166 ADC. The ability of drug conjugates to kill HCC1806 cells was evaluated by adding the indicated concentration of ADC or AADC and incubating the cells for 3 days. Cell viability was measured using the CellTiter Glo assay. Similar results were observed when an activatable antibody conjugated to a nucleic acid damaging agent was tested in such cell killing assays.

The next studies were designed to evaluate the activation and binding of anti-CD166 activatable antibodies in tumor samples upon exposure to one or more proteases.

Xenograft tumor samples and healthy tissue samples were analyzed using immunohistochemistry (IHC) analysis and an in situ imaging assay that is described in PCT Publication No. WO 2014/107599, the contents of which are hereby incorporated by reference in their entirety. Briefly, this in situ assay uses an activatable anti-CD166 antibody of the disclosure, the corresponding parental antibody, and a modified version of the activatable anti-CD166 antibody in which the CM is replaced with a non-cleavable linker, referred to herein generally as anti-CD166 NSUB modified antibody. The parental antibody is used as a positive control, while the non-cleavable version of the activatable anti-CD166 antibody is used as a negative control. Xenograft frozen tissue sections are then placed on the glass slide, rinsed two times with PBS-T followed by PBS, followed by 30 min pretreatment of tissue with broad spectrum protease inhibitors cocktail or buffer only. A detectable label such as Alexa Fluor-680® is then conjugated to each of the activatable anti-CD166 antibody and the anti-CD166 NSUB modified antibody. The detectably labeled activatable anti-CD166 antibody and the anti-CD166 NSUB modified antibody are then applied on the tissue and incubated for one hour in the dark (to prevent bleaching of fluorescence). After incubation with 1 µg/ml of the incubated tumor sections were rinsed three times with PBS-T followed by PBS and counterstained with nuclear marker DAPI for 1 minute. Fluorescence microscopy analysis is then used to detect positive staining. Positive staining of the activatable anti-CD166 antibody that is abolished by the pretreatment of the tissue sections with protease inhibitors indicates that the binding of the activatable anti-CD166 antibody to the tissue sample is a result of the proteolytic event. Positive staining of the activatable anti-CD166 antibody should also be abolished when the tissue is pretreated with an excess of unlabeled ("cold") parental antibody. Furthermore, incubation of the tumor tissue should reveal positive staining for parental antibody that is not affected by pretreatment of tissue with protease inhibitors, but is abolished when the tissue is pretreated with unlabeled parental antibody. No signal should be detected for the anti-CD166 NSUB modified antibody detected on the tissue pretreated, on the tissue not pretreated with protease inhibitors, or on the tissue pretreated with unlabeled parental antibody.

Figure 6A:
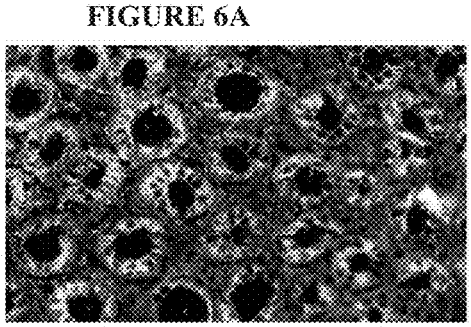
FIGS. 6A-6D are a series of images demonstrating that an activatable anti-CD166 antibody of the disclosure is activated (i.e., cleaved) in colon cancer tissue samples, and the activatable anti-CD166 antibody is not activated in healthy tissue samples.
Figure 6B:
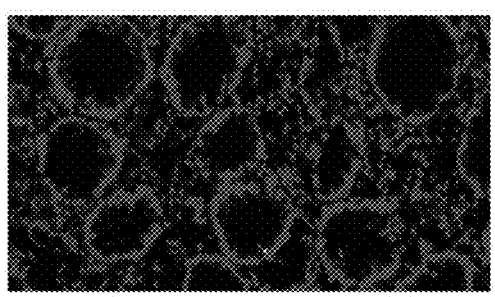
Figure 6C:
Figure 6D:
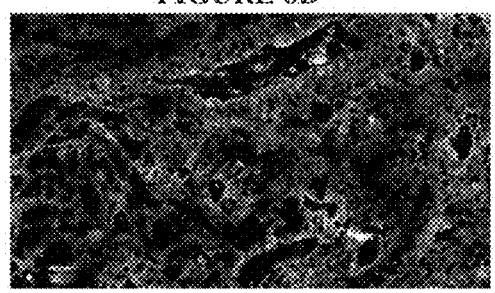

FIGS. 6A-6D are a series of images demonstrating that the activatable anti-CD166 antibody is activated (i.e., cleaved) in colon cancer tissue samples, and the activatable anti-CD166 antibody is not activated in healthy tissue samples. FIGS. 6A and 6C depict the results of IHC analysis on the tumor and healthy tissue samples, and FIGS. 6B and 6D depict the results of the in situ imaging assay on the tumor and healthy tissue samples.

Figure 7A:
FIGS. 7A-7D are a series of images demonstrating that an activatable anti-CD166 antibody of the disclosure is activated (i.e., cleaved) in lung cancer tissue samples, and the activatable anti-CD166 antibody is not activated in healthy tissue samples.
Figure 7B:
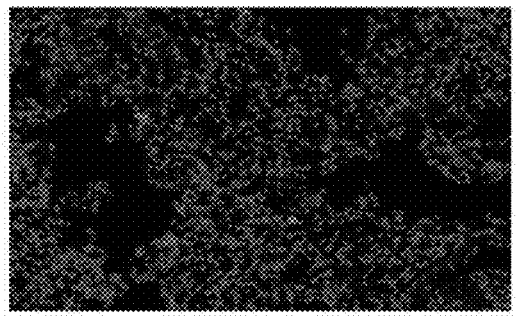
Figure 7C:
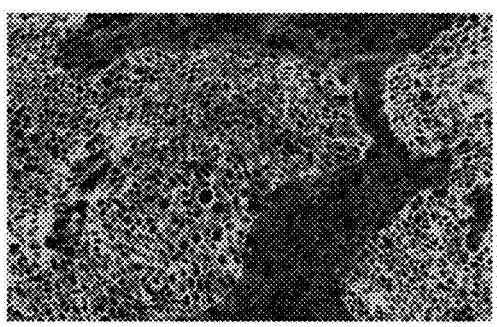
Figure 7D:

FIGS. 7A-7D are a series of images demonstrating that the activatable anti-CD166 antibody is activated (i.e., cleaved) in lung cancer tissue samples, and the activatable anti-CD166 antibody is not activated in healthy tissue samples. FIGS. 7A and 7C depict the results of IHC analysis on the tumor and healthy tissue samples, and FIGS. 7B and 7D depict the results of the in situ imaging assay on the tumor and healthy tissue samples.

FIGS. 8A-8D are a series of images demonstrating that the activatable anti-CD166 antibody is not activated in healthy tissue samples. FIGS. 8A and 8C depict the results of IHC analysis on the healthy tissue samples, and FIGS. 8B and 8D depict the results of the in situ imaging assay on the healthy tissue samples.

Example 5

Potency of Conjugated Anti-CD166 Antibodies

This example demonstrates that a conjugated anti-CD166 antibody of the disclosure ("CD166 ADC") displays in vitro killing activity as compared to a control antibody conjugate ("Control ADC").

Figure 9:
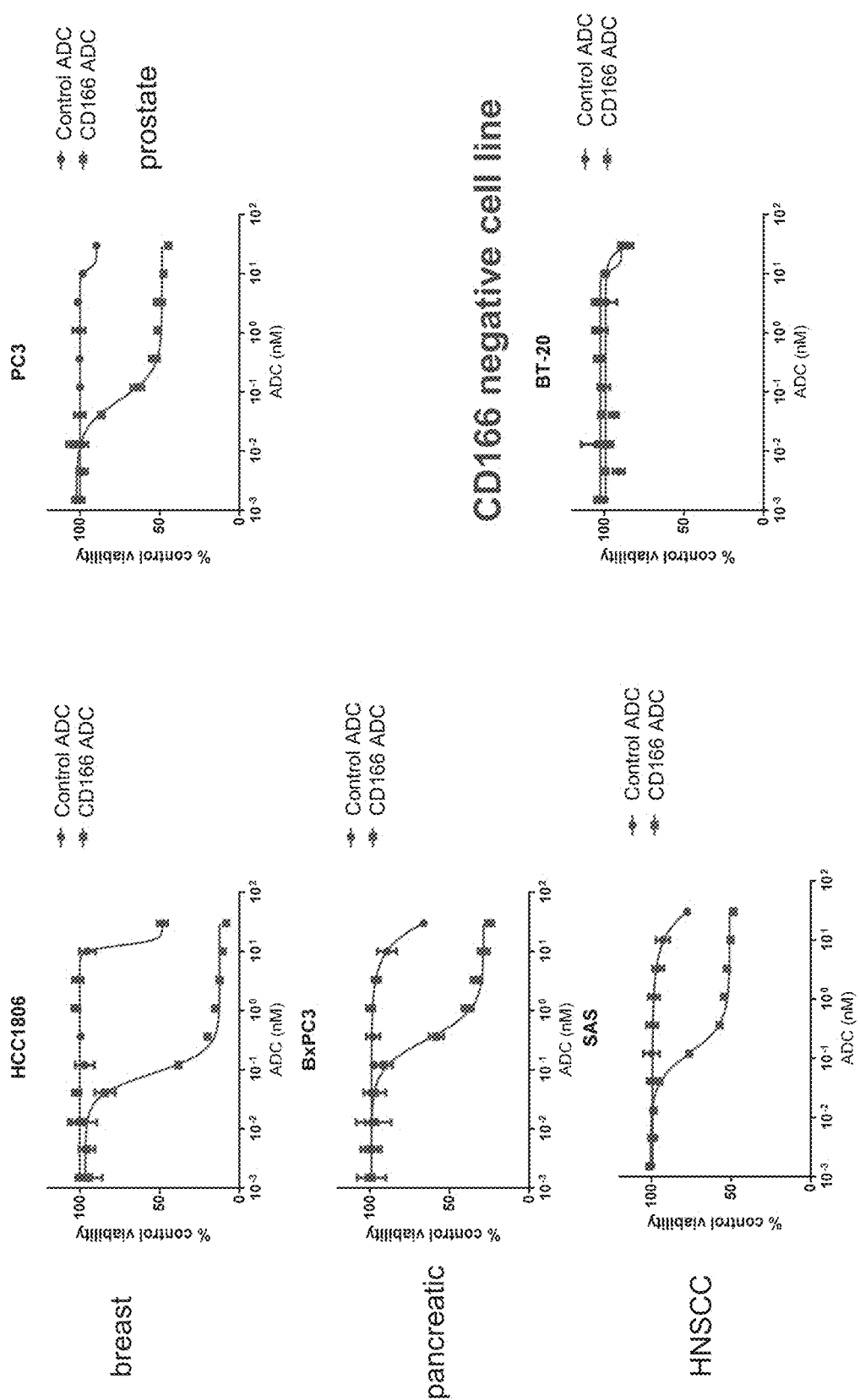
FIG. 9 is a series of graphs depicting the potency of a conjugated anti-CD166 antibody of the disclosure against a breast cancer cell line, a prostate cancer cell line, a pancreatic cancer cell line, a head and neck squamous cell cancer cell line, and a CD166 cell line as a negative control.

FIG. 9 is a series of graphs depicting the potency of a conjugated anti-CD166 antibody of the disclosure against a breast cancer cell line, a prostate cancer cell line, a pancreatic cancer cell line, a head and neck squamous cell cancer cell line, and a CD166 cell line as a negative control.

Example 6

Efficacy of Conjugated Activatable Anti-CD166 Antibodies in Tumor Models

This example demonstrates the efficacy of a conjugated activatable anti-CD166 antibody of the disclosure ("CD166 AADC" or CD166 Activatable Antibody Drug Conjugate) in various cancer models.

Figure 10:
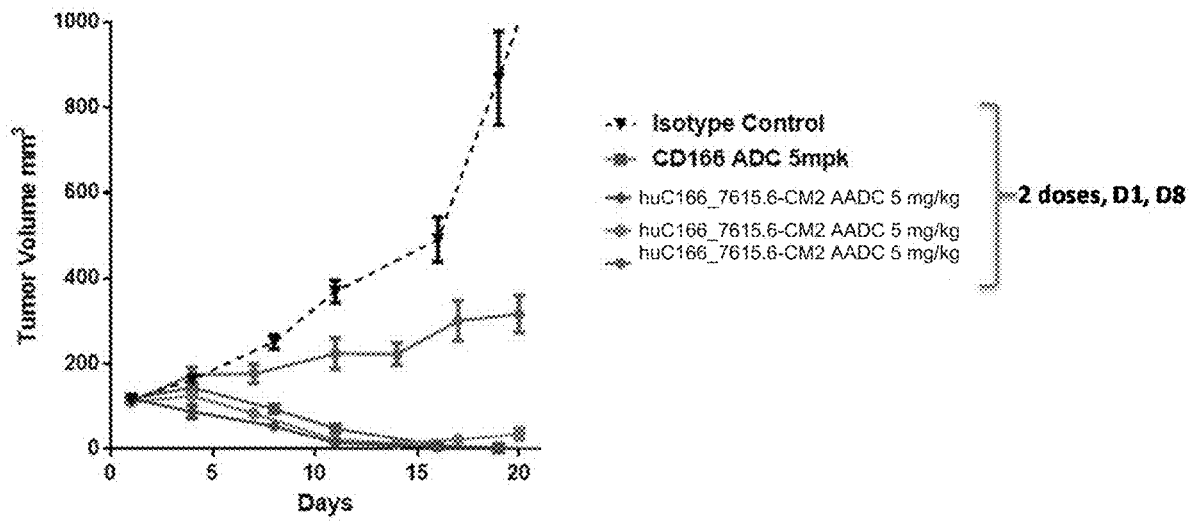
FIG. 10 is a graph depicting the efficacy of a conjugated activatable anti-CD166 antibody (AADC, Activatable Antibody Drug Complex) of the disclosure in a breast cancer model.

FIG. 10 is a graph depicting the efficacy of an AADC that includes an activatable anti-CD166 antibody of the disclosure conjugated to the maytansinoid DM4, as compared to an isotype DM4-conjugated control, and an ADC that includes a DM4-conjugated version of the parental antibody for the activatable anti-CD166 antibody. Efficacy is measured as mean tumor volume measured at various time points post administration (5 mg/kg IV on days 1 and 8) in a breast cancer model.

As shown in FIG. 10, the efficacy of the AADC is equivalent to the efficacy seen with the ADC.

Figure 11:
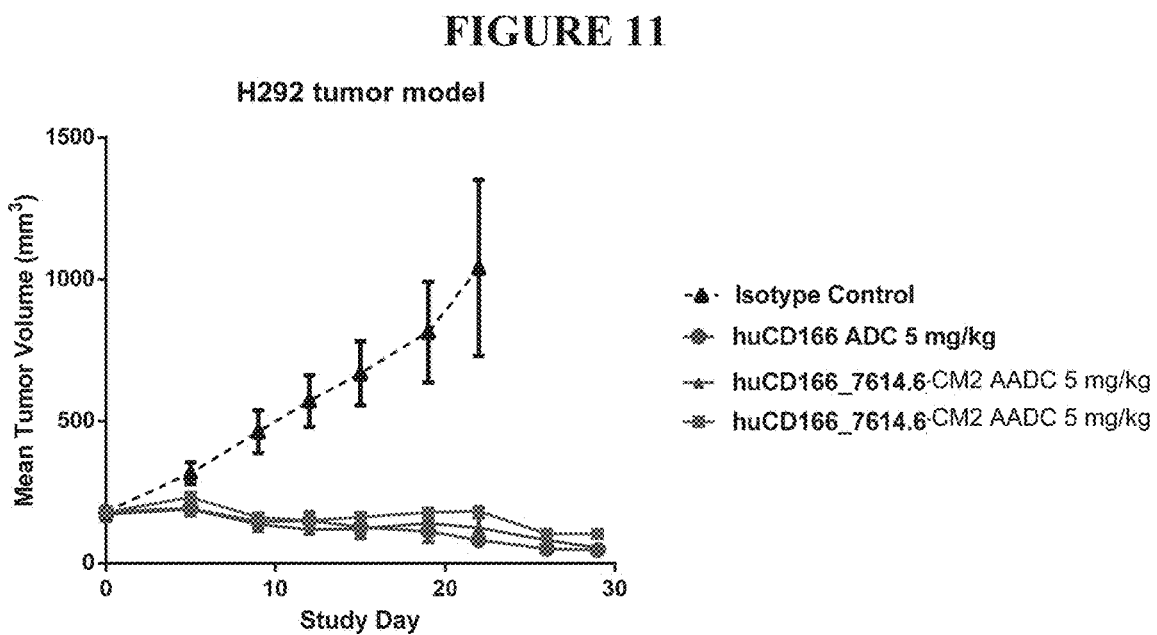
FIG. 11 is a graph depicting the efficacy of a CD166 AADC DM4 conjugate of the present disclosure (i.e., an activatable anti-CD166 antibody of the disclosure conjugated to DM4) in the H292 non-small cell lung cancer (NSCLC) model.

FIG. 11 is a graph depicting the efficacy of the CD166 activatable anti-CD166 antibodies of the disclosure, as compared to the isotype DM4-conjugated control, and the CD166 ADC DM4 conjugated parental anti-CD166 antibody. Efficacy is measured as mean tumor volume measured at various time points post administration (5 mg/kg IV on days 1 and 8) in the H292 non-small cell lung cancer (NSCLC) model.

H292 xenograft tumors were treated with isotype-DM4 control, huCD166-DM4 ADC, huCD166_7614.6_CM2-DM4 AADC, or huCD166_7614.6_CM1-DM4 ADDC, where CM1 and CM2 are the 2001 and 3001 substrates described herein, respectively. Tumors were grown to an average of 150 mm$^3$, then the mice were randomized into groups of eight and dosed on days 1 and 8 with the indicated test articles. Mean tumor volume±SEM is plotted.

As shown in FIG. 11, the efficacy of both of the AADCs tested is equivalent to the efficacy seen with the ADC.

Figure 12:
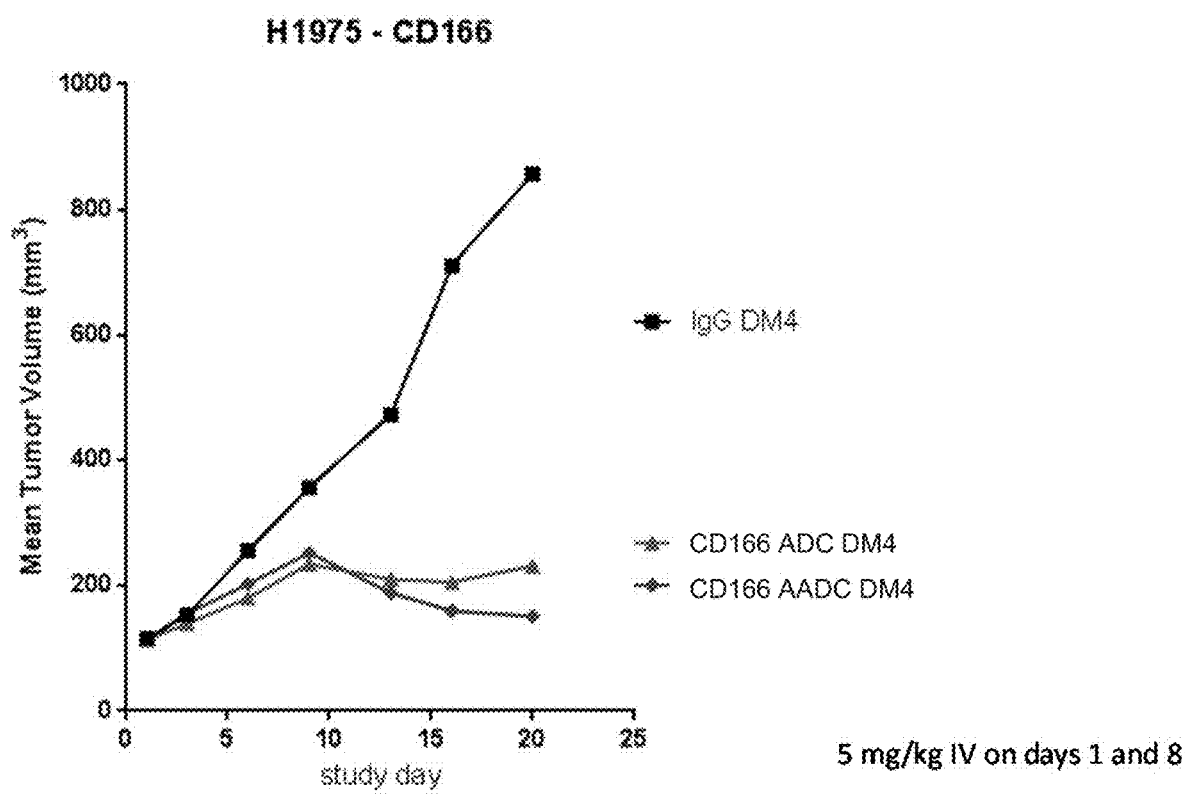
FIG. 12 is a graph depicting the efficacy of the CD166 AADC DM4 conjugate of the present disclosure in the H1975 non-small cell lung cancer (NSCLC) model.

FIG. 12 is a graph depicting the efficacy of the CD166 AADC DM4 conjugated activatable anti-CD166 antibody, also referred to herein as huCD166_7614.6_CM2-DM4 AADC (where CM2 is the 3001 substrate), as compared to the isotype DM4-conjugated control, and the CD166 ADC DM4 conjugated parental anti-CD166 antibody. Efficacy is measured as mean tumor volume measured at various time points post administration (5 mg/kg IV on days 1 and 8) in the H1975 non-small cell lung cancer (NSCLC) model.

As shown in FIG. 12, the efficacy of the AADC is equivalent to the efficacy seen with the ADC.

Example 7

Tolerability Analysis of Activatable Anti-CD166 Antibodies

Anti-CD166 antibodies of the disclosure were characterized for their species specificity towards binding to human CD166 and other closely related proteins.

Figure 13:
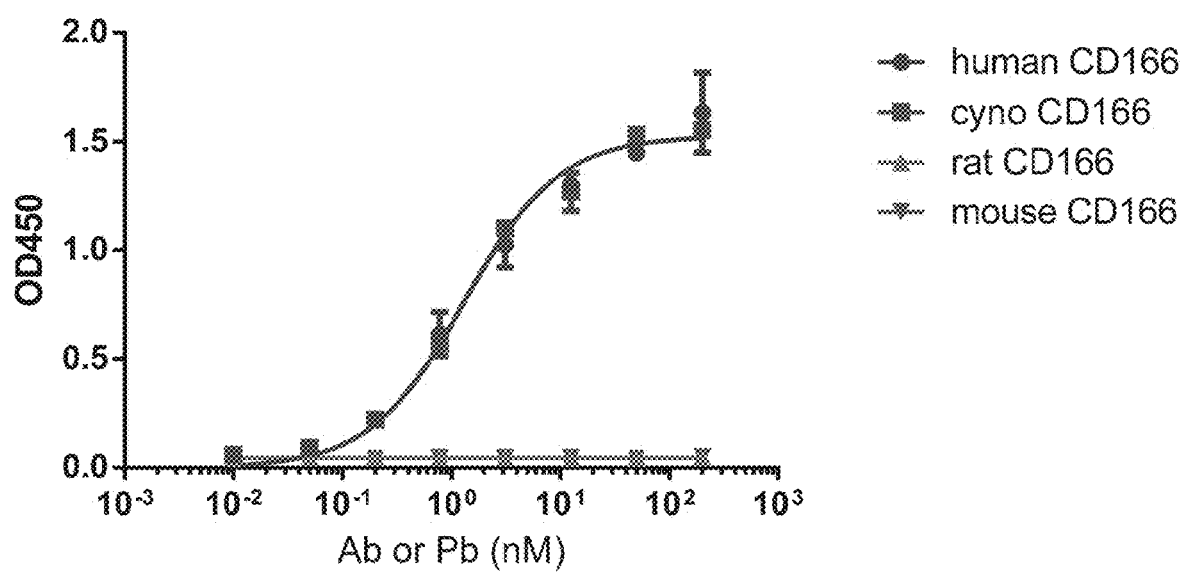
FIG. 13 is a graph depicting the ability of the anti-CD166 antibodies of the disclosure to bind human and cynomolgus monkey CD166 with equal affinity.

As shown in FIG. 13, anti-CD166 antibodies of the disclosure bind human and cynomolgus monkey CD166 with equal affinity. None of the anti-CD166 antibodies of the disclosure tested bound to rat or mouse CD166. The $K_d$ of binding of the anti-CD166 antibody to human CD166 and cynomolgus CD166 in these exemplary binding studies are 1.3 nM for both.

Next, CD166 expression levels were analyzed in various normal human and cynomolgus monkey tissue types. As shown in Table 3 below, CD166 expression levels were nearly identical the human and cynomolgus monkey tissue samples analyzed:

TABLE 3

CD166 Expression Levels in Normal Human and Cynomolgus Tissue Samples

| Tissue Type | Cynomolgus | Human |
| --- | --- | --- |
| Breast | ++ | ++ |
| Brain | − | − |
| Colon | ++ | ++ |
| Esophagus | − | − |
| Heart | − | − |
| Kidney | + | + |
| Liver | ++ | ++ |
| Lung | ++ | + |
| Nerve | − | − |
| Ovary | ++ | + |
| Pancreas | ++ | ++ |
| Prostate | +++ | +++ |
| Skin | N/A | −/+ |
| Small Intestine | ++ | ++ |
| Salivary Gland | ++ | ++ |
| Spleen | − | − |
| Stomach | +++ | +++ |
| Striated/Skeletal Muscle | − | − |
| Testis | − | − |
| Uterus | ++ | ++ |

Significant CD166 expression was detected in both human and cynomolgus liver tissue samples.

In initial pharmacokinetic studies, the conjugated anti-CD166 activatable antibodies of the disclosure were found to avoid antigen sink (i.e., rapid clearance of antibodies due to the abundance of naturally expressed CD166 antigen throughout the body).

Figure 14:
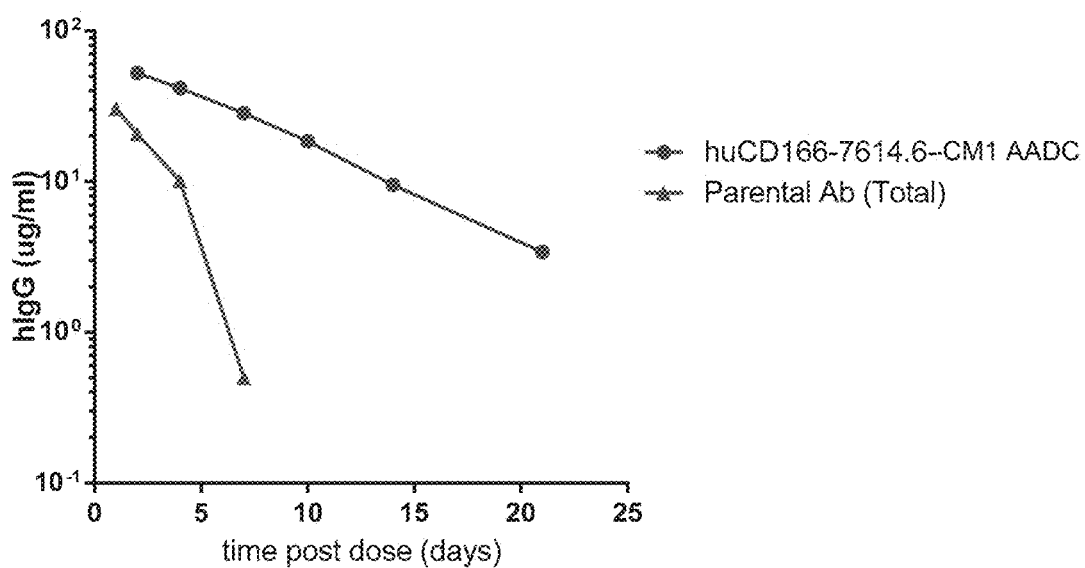
FIG. 14 is graph depicting the results of a tolerability study in cynomolgus monkeys using an activatable anti-CD166 antibody of the disclosure.

FIG. 14 demonstrates the results of a tolerability study in cynomolgus monkeys using 5 mg/kg administration of a conjugated anti-CD166 activatable antibody of the disclosure. These studies were performed using huCD166_7614.6_CM2-DM4 AADC (where CM2 is the 3001 substrate). 5 mg/kg was selected as that is the therapeutic dose used for other DM4 antibody conjugates that include a SPDB linkage.

The pharmacokinetics of the huCD166-7614.6-CM1 DM4 drug conjugate (where CM1 is the 2001 substrate) and the un-conjugated huCD166 antibody were evaluated in cynomolgus monkeys after a single 5 mg/kg or 3 mg/kg dose, respectively. Total serum levels of human IgG were measured using an anti-human IgG sandwich ELISA. Consistent with avoiding on-target sinks, the CD166 AADC showed significantly more exposure than the antibody. Monkeys treated with the huCD166-7614.6-CM1 DM4 drug conjugate had no observable toxicities. After 21 days, there were no clinical observations, no signs of on-target toxicity, and no sign of liver toxicity. As shown in FIG. 14, the clearance of a DM4 anti-CD166 antibody conjugate was compared to the parental antibody. Antigen binding was below the level of quantification.

Figure 15:
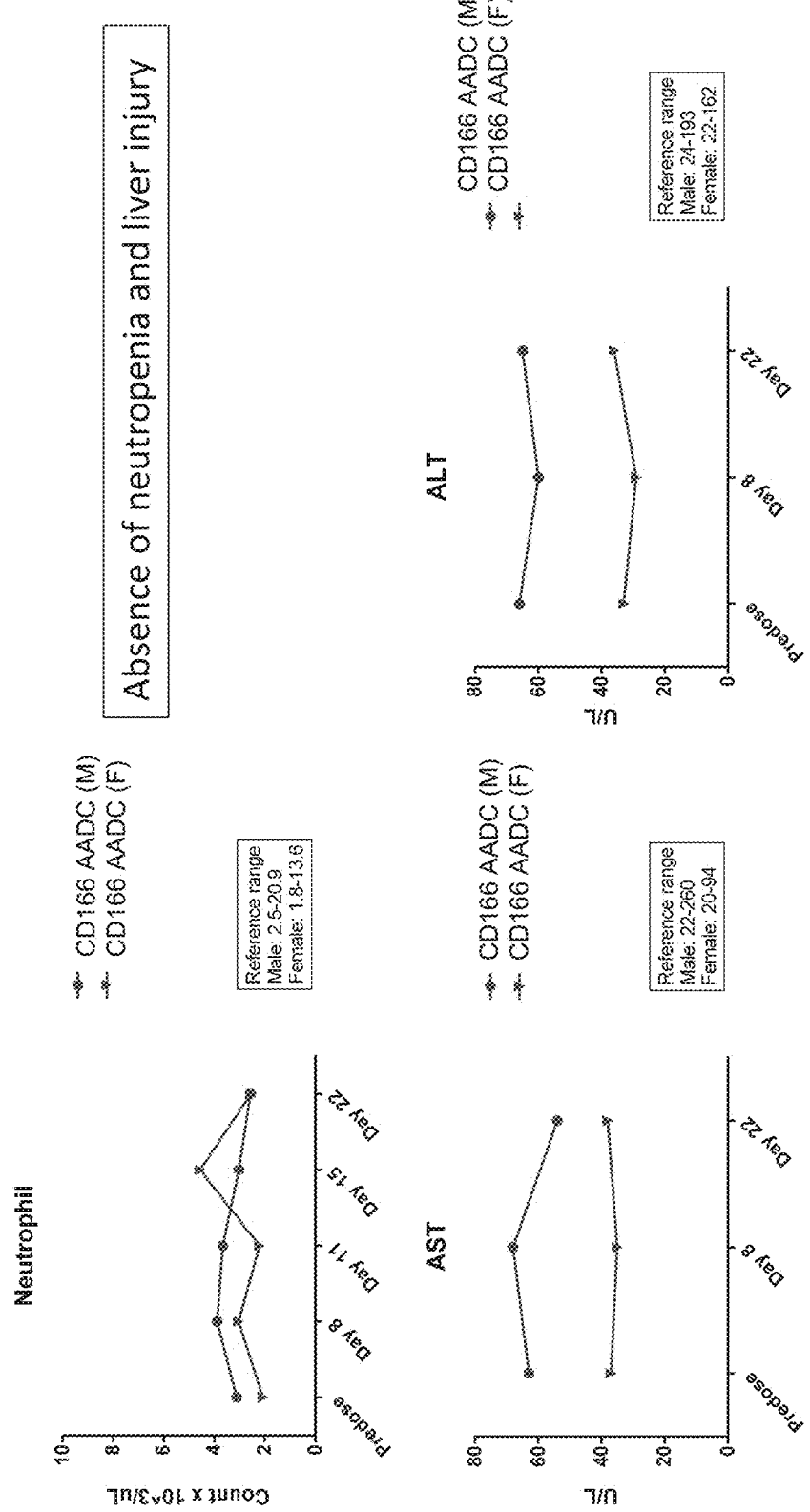
FIG. 15 is a graph that demonstrates that the conjugated anti-CD166 activatable antibody of the present disclosure is well tolerated at the projected therapeutic dosage.

FIG. 15 is a graph that demonstrates that the conjugated anti-CD166 activatable antibody is well tolerated at the projected therapeutic dosage. These studies were performed using huCD166_7614.6_CM2-DM4 AADC (where CM2 is the 3001 substrate).

Thus, unlike traditional ADC therapy, there is no evidence of liver damage in the cynomolgus monkeys following administration of a conjugated anti-CD166 activatable antibody of the disclosure.

Example 8

Protease-Dependent Activation of Anti-CD166 Activatable Antibodies

The exemplary studies provided herein were designed to evaluate the protease-dependent activation of activatable anti-CD166 activatable antibodies and conjugated activatable antibodies of the disclosure.

Figure 16A:
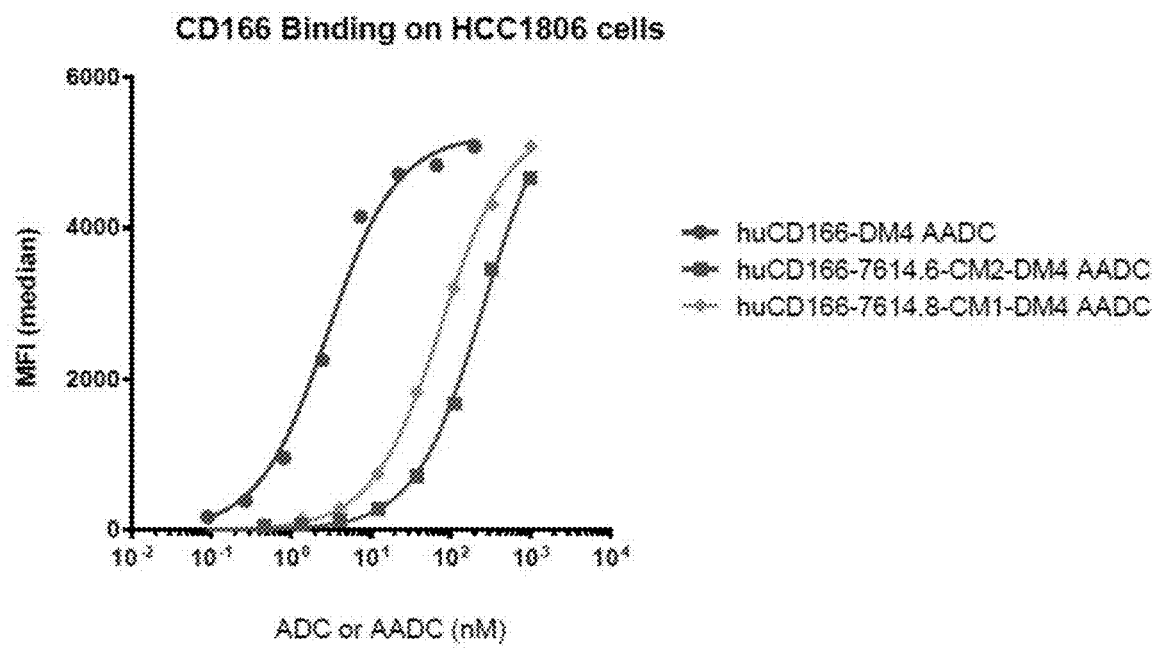
FIGS. 16A, 16B, and 16C are a series of graphs depicting the ability of various conjugated anti-CD166 activatable antibodies of the disclosure to bind human CD166 when such conjugated activatable antibodies are proteolytically activated.
Figure 16B:
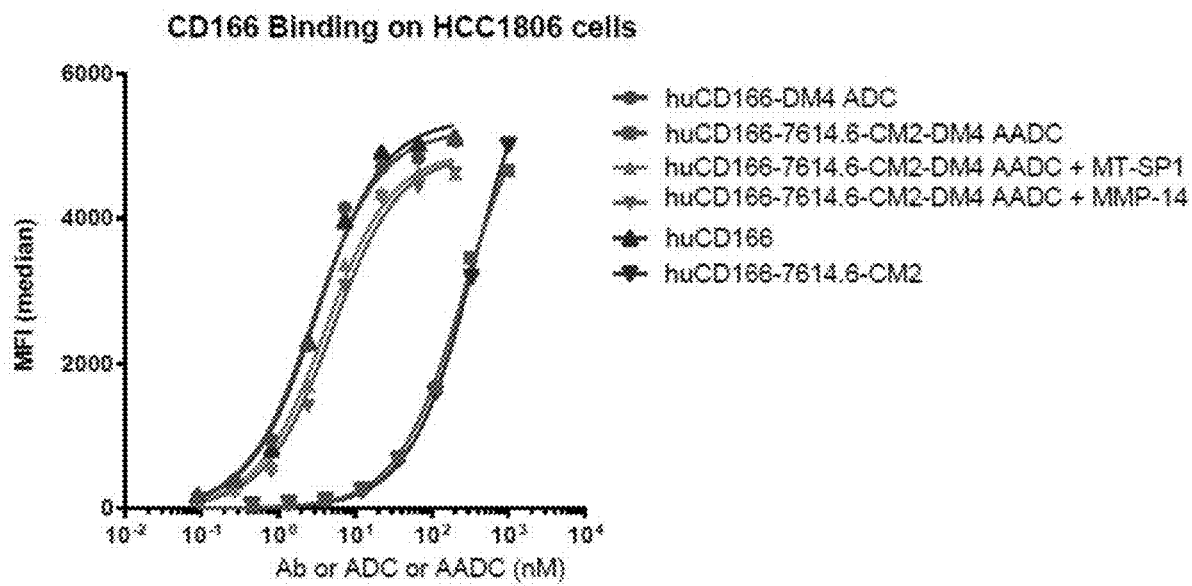
Figure 16C:
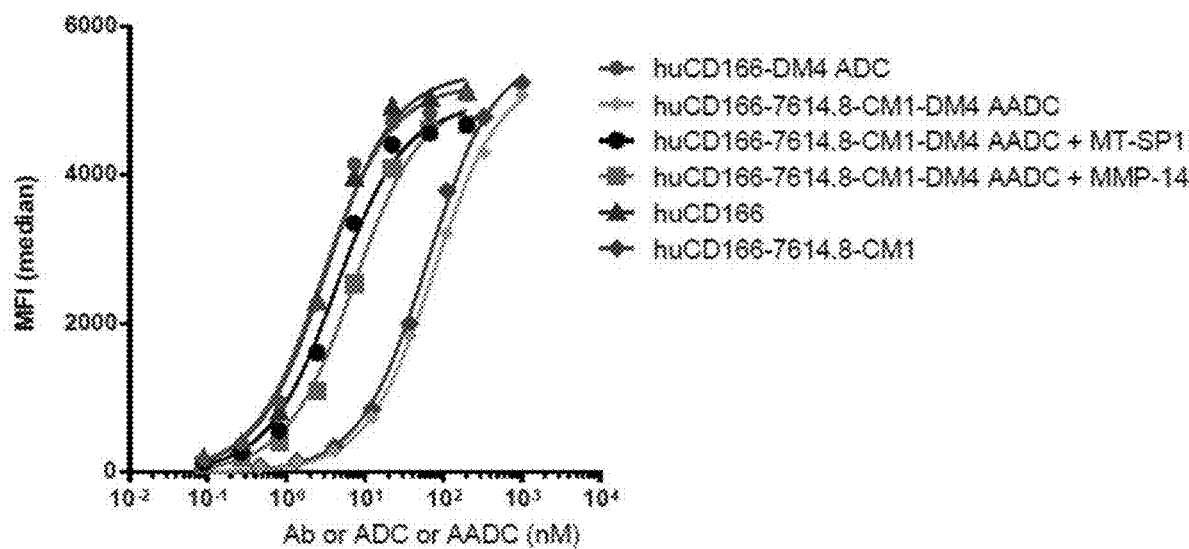

FIGS. 16A, 16B, and 16C are graphs depicting the ability of various anti-CD166 conjugated anti-CD166 activatable antibodies of the disclosure to bind human CD166 on HCC1806 cells in the presence or absence of protease-dependent activation. These conjugated anti-CD166 activatable antibodies are also referred to herein as "CD166 AADC" or "CD166 Activatable Antibody Drug Conjugates". As shown in FIG. 16A, conjugated anti-CD166 activatable antibodies are blocked from binding to CD166 on HCC1806 cells. In contrast, as shown in FIGS. 16B and 16C, conjugated anti-CD166 activatable antibodies recover antibody binding activity that is similar to the binding activity of unmasked conjugated anti-CD166 antibody and unmasked anti-CD166 antibody when the AADCs were proteolytically activated with matriptase (MT-SP1) or matrix metalloprotease 14 (MMP-14).

The binding of the anti-CD166 antibody (VH of SEQ ID NO: 122, VL of SEQ ID NO: 123), various conjugated and unconjugated anti-CD166 activatable antibodies of the disclosure, and protease-activated conjugated anti-CD166 activatable antibodies of the disclosure were evaluated using flow cytometry-based binding assay. The conjugated and unconjugated anti-CD166 activatable antibodies tested included the variable heavy chain sequence of SEQ ID NO: 122, the variable light chain sequence of SEQ ID NO: 123, either a cleavable moiety (CM1, substrate 2001) comprising the amino acid sequence ISSGLLSGRSDNH (SEQ ID NO: 70) or a cleavable moiety (CM2, substrate 3001) comprising the amino acid sequence AVGLLAPPGGLSGRSDNH (SEQ ID NO: 76), and one of the masking moieties shown in Table 10. The full sequences are shown above in Table 11. The conjugated anti-CD166 antibodies and conjugated anti-CD166 activatable antibodies included the maytansinoid DM4 conjugated to the activatable antibody via an SPDB linker. In a typical assay, HCC1806 cells were incubated with the indicated concentrations of anti-CD166 antibody, activatable antibody, conjugated antibody, or activatable antibody in PBS+2% FBS for 1 hr on ice. After washing 2× with PBS+2% FBS, cells were incubated with a goat anti-human IgG secondary antibody, conjugated to AlexaFluor 647 (Jackson ImmunoResearch), for 30-45 min on ice. Cells were then washed 2× with PBS+2% FBS and fixed with 1% formaldehyde. Bound antibody was detected using a Guava EasyCyte cytometer and the median fluorescence intensity (MFI) of the cell population was measured.

As shown in FIG. 16A, conjugated anti-CD166 activatable antibodies are blocked from binding to CD166 on HCC1806 cells. As shown in FIGS. 16B and 16C, various conjugated and unconjugated anti-CD166 activatable antibodies of the disclosure behave like each other when masked, but when the conjugated anti-CD166 activatable antibodies were proteolytically activated with a protease, they showed similar binding to that of the unmasked huCD166 parental antibody and the unmasked huCD166 ADC.

Example 9

Binding of Activatable Anti-CD166 and Antibody Drug Conjugates to Human Tissues The exemplary studies in this Example show the binding properties of anti-CD166 antibody drug conjugates (ADCs) and activatable anti-CD166 antibody drug conjugates (AADCs) of the present disclosure to human tissues.

In this study, frozen tissue sections derived from normal human prostate, ovary, breast, pancreas, and right atrium (Cat. Nos. T1234201, T1234086, T1234183, T1234188, and T1234127, respectively; BioChain, Newark, Calif.) were prepared and blocked using standard protocols, and then incubated with 0.4 µg/mL with an anti-CD166 ADC of the present disclosure (anti-CD166-spdb-DM4), an anti-CD166 AADC of the present disclosure (anti-CD166-7614.6-3001-spdb-DM4), an activated anti-CD166 AADC of the present disclosure (anti-CD166-7614.6-3001-spdb-DM4 incubated with purified uPA for 16 hours at 37° C.), or an isotype control ADC (chKTI-spdb-DM4, a chimeric human IgG1 anti-soybean trypsin inhibitor antibody, conjugated to spdb-DM4). After incubation with the test articles, sections were treated with 2.5 µg/mL mouse anti-DM4 monoclonal antibody (Immunogen). Detection of the DM4 payload was achieved by incubation with an anti-mouse antibody conjugated to an HRP polymer (Envision™+System-HRP Labeled polymer anti-mouse, Dako, K4006) followed by addition of a 3,3'-diaminobenzidine substrate (DAB Plus, Dako, K3467). Tissues were counterstained with hematoxylin and images were acquired on an Olympus VS120 Virtual Slide Scanner.

The exemplary results of this study showed that anti-CD166 AADC of the present disclosure (anti-CD166-7614.6-3001-spdb-DM4) displayed a lack of immunostaining on each of the five human tissue sections consistent with its masked state, and similar to that observed with the isotype control ADC. Activation of the anti-CD166 AADC of the present disclosure by uPA restored binding of the activated anti-CD166 AADC in two of the highest expressing tissues, prostate and breast. The staining intensity and distribution of the uPA-activated anti-CD166 AADC of the present disclosure were similar to that of the parental anti-CD166 antibody drug conjugate (anti-CD166-spdb-DM4).

Example 10

Binding of Anti-CD166 Antibodies to Human Cancers

This Example shows that CD166 is expressed in a variety of patient-derived tumors by immunohistochemical (IHC) staining using an anti-CD166 antibody.

In this study, formalin-fixed paraffin-embedded tumor samples (FFPE) in tissue microarrays (US Biomax) were prepared and blocked using standard protocols, and then incubated with 5 µg/mL anti-CD166 rabbit monoclonal antibody EPR2759[2] (Abcam, ab109215). Detection of anti-CD166 antibody was performed by incubation with 5 µg/mL biotinylated-conjugated donkey anti-rabbit IgG antibody (Jackson Immunoresearch, 711-065-152), followed by addition of the ABC-HRP Elite Standard (Vector Laboratories, PK-6100) to form the avidin-biotin-HRP complex, followed by addition of a 3,3'-diaminobenzidine substrate (DAB Plus, Dako, K3467). Tissues were counterstained with hematoxylin and images were acquired on an Olympus VS120 virtual slide scanner.

Each tissue core was assigned a IHC score of "negative" (no staining), "weak" (intensity 1+ in ≤70% tumor cells or 2+ in ≤30% tumor cells), "moderate" (intensity 1+ in >70% of tumor cells or 2+ in >30% to ≤70% tumor cells or 3+ in ≤30% tumor cells), or "strong" (intensity 2+ in >70% of tumor cells or 3+ in >30% tumor cells), and the percent of tested samples showing "moderate" or "strong" IHC staining for anti-CD166 are show in Table 4 below.

TABLE 4

HIC Assay of CD166 Expression In Patient-Derived Cancers

| Tissue (Total No. of Samples) | Cancer Type | % Samples with Moderate or Strong IHC Score |
|---|---|---|
| Prostrate (119) | Adenocarcinoma | 98.3 |
| Breast (392) | Ductal carcinoma | 87.5 |
| Lung (213) | Non-small cell lung cancer | 83.1 |
| Head & Neck (12) | Squamous cell carcinoma | 81.1 |
| Endometrial (147) | Adenocarcinoma | 75.5 |
| Ovarian (129) | Adenocarcinoma | 70.5 |
| Biliary (77) | Cholangiocarcinoma | 56.5 |

Example 11

Binding of Anti-CD166 Antibodies to Human and Cynomolgus Cells

The exemplary studies provided herein were designed to evaluate anti-CD166 activatable antibodies of the disclosure for binding to human and cynomolgus cells in a flow cytometry assay.

Figure 17:
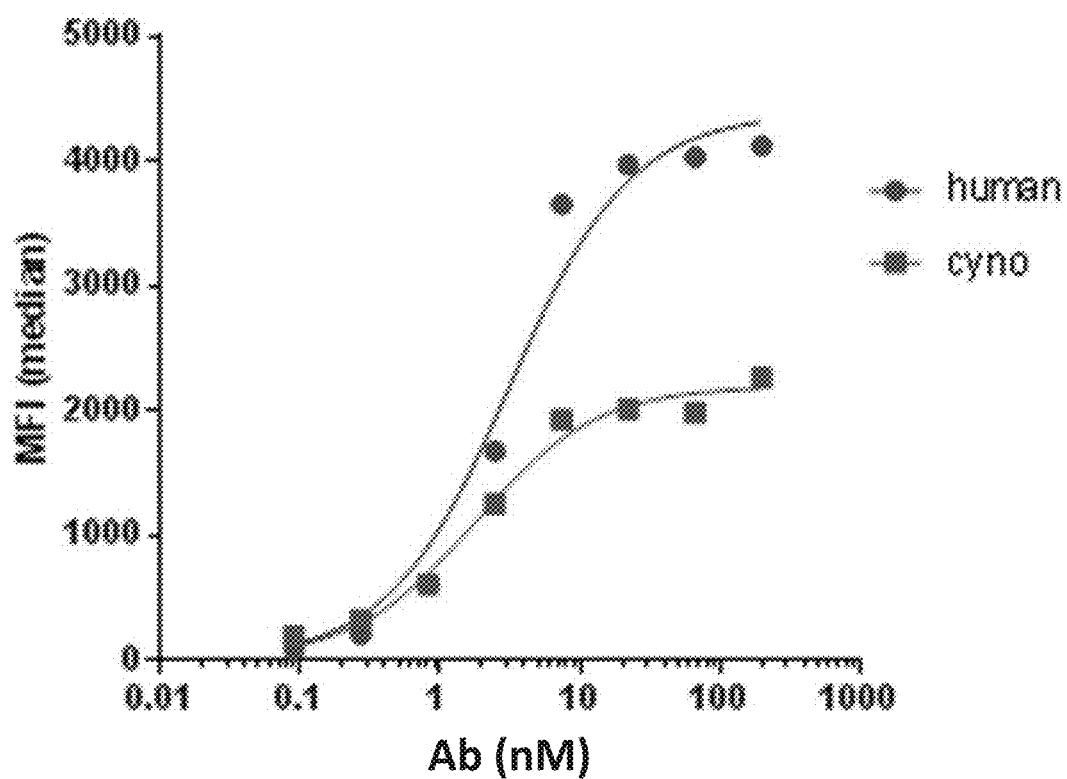
FIG. 17 is a graph depicting the ability of the anti-CD166 antibodies of the present disclosure to bind human H292 cells and cynomolgus monkey primary kidney epithelial cells with comparable affinity.

FIG. 17 is a graph depicting the ability of an anti-CD166 antibody (anti-huCD 166) of the disclosure to bind human H292 cells or cynomolgus primary kidney epithelial cells, as measured by flow cytometry. As shown in FIG. 17, anti-CD166 antibodies of the present disclosure demonstrated comparable binding affinities to CD166 on the cell surface of both human and cynomolgus cells.

The binding of the anti-CD166 antibody (huM9 vk-1/HcC; VH of SEQ ID NO: 122, VL of SEQ ID NO: 123) of the present disclosure to human H292 cells and cynomolgus primary kidney epithelial cells was evaluated using flow cytometry-based binding assay. In a typical assay, H292 cells or cynomolgus primary kidney epithelial cells were incubated with the indicated concentrations of anti-CD166 antibody in PBS+2% FBS for 1 hr on ice. After washing 2× with PBS+2% FBS, cells were incubated with a goat anti-human IgG secondary antibody, conjugated to AlexaFluor 647 (Jackson ImmunoResearch), for 30-45 min on ice. Cells were then washed 2× with PBS+2% FBS and fixed with 1% formaldehyde. Bound antibody was detected using a Guava EasyCyte cytometer and the mean fluorescence intensity (MFI) of the cell population was measured.

As shown in FIG. 17, an anti-CD166 antibody of the present disclosure bound to human and cynomolgus cells with comparable affinity ($EC_{50}$ of 3.1 nM to human cells, and $EC_{50}$ of 1.7 nM to cynomolgus cells).

Example 12

Inhibition of Cell Binding to CD6 by Anti-CD166 Antibodies

In this exemplary study, anti-CD166 antibodies of the present disclosure demonstrate the ability to block the adhesion of human lymphoma cells to immobilized CD6, the receptor for which CD166 is the ligand.

Figure 18:
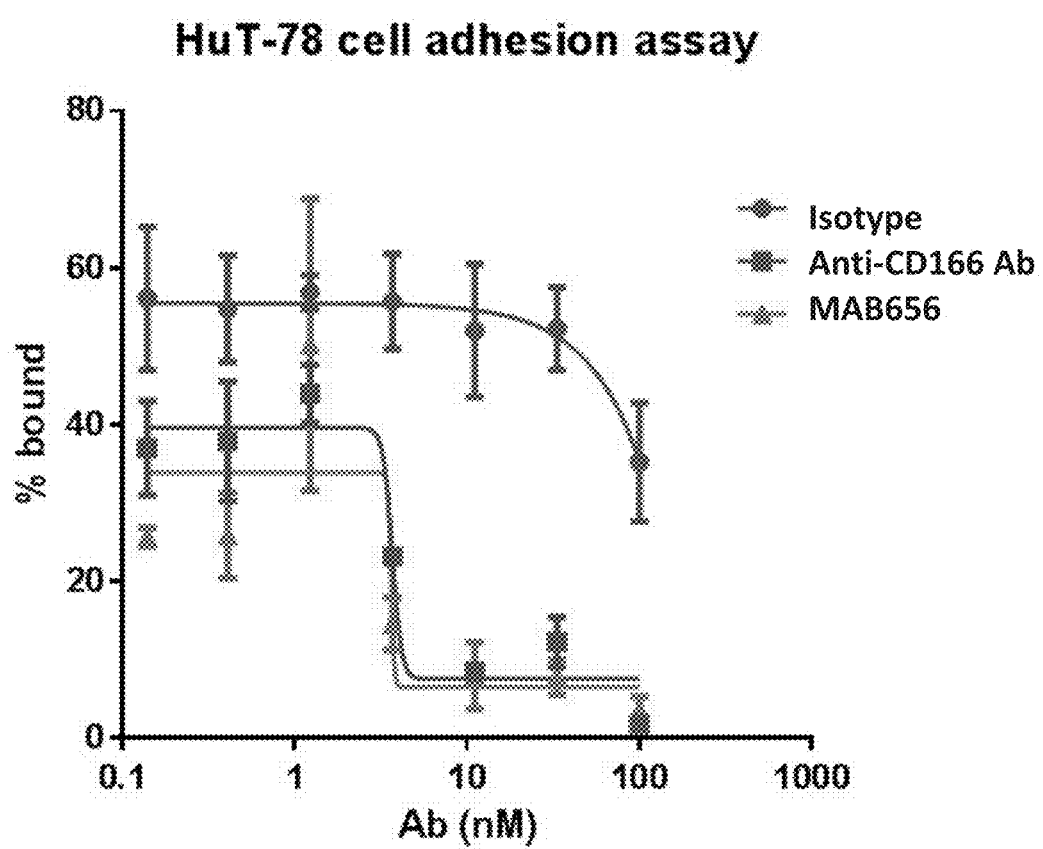
FIG. 18 is a graph depicting the ability of the anti-CD166 antibodies of the present disclosure to inhibit human HuT-78 cells from binding CD6 receptor.

FIG. 18 is a graph depicting the ability of an anti-CD166 antibody (anti-huCD166; vk-1/HcC) of the present disclosure to block the adhesion of HuT-78 human lymphoma cells to immobilized human CD166. In this assay, CD166-expressing HuT-78 cells are fluorescently labeled and incubated with recombinant CD6 protein immobilized on plastic plates. After several washes, bound HuT-78 cells are detected by measuring fluorescence and reported as a percentage of total fluorescence (before washing). MAB656 is an anti-CD166 mouse monoclonal antibody reported to inhibit cell adhesion in this assay (R&D Systems), presumably by disrupting CD166 interaction with its receptor, CD6. In this exemplary assay, the anti-CD166 antibody of the present disclosure and MAB656 showed similar levels of inhibition of cell adhesion to CD6. Both antibodies showed nearly an EC50 of approximately 3.7 nM. An isotype control antibody showed no inhibition of cell adhesion.

Example 13

Protease-Dependent Activation of Anti-CD166 Activatable Antibodies

The exemplary studies provided herein were designed to evaluate the protease-dependent activation of anti-CD166 activatable antibodies and conjugated activatable antibodies of the disclosure.

Figure 19A:
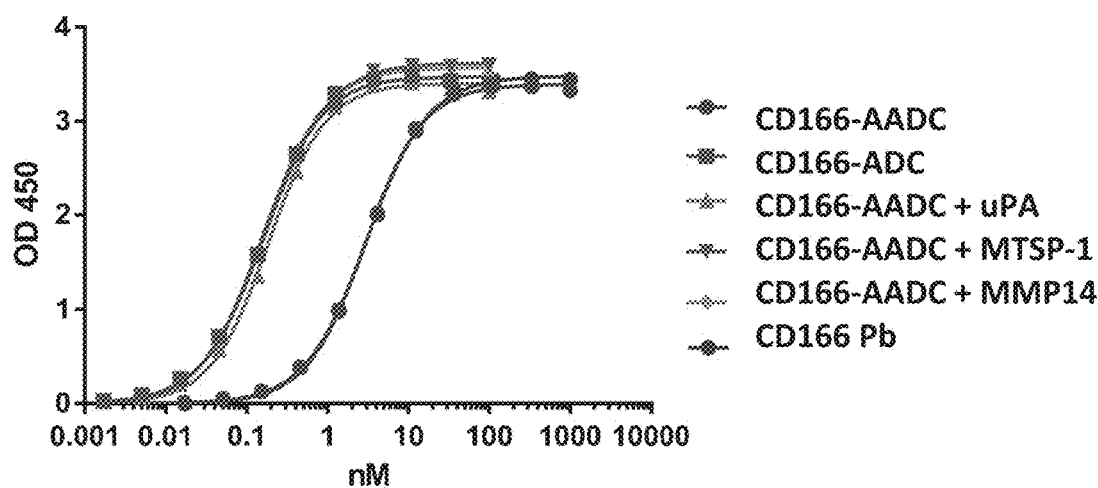
FIGS. 19A-19C are graphs depicting the ability of the anti-CD166 activatable antibody drug conjugates of the present disclosure to bind CD166 and human cells in a protease-activated (cleaved) and unactivated (cleaved) forms.

FIG. 19A is a graph depicting the in vitro binding to CD166 in an ELISA assay of an anti-CD166 antibody (anti-huCD166 HcC/vk-1, "CD166 Ab"), an anti-CD166 antibody drug conjugate (anti-CD166-spdb-DM4, "CD166-ADC"), an anti-CD166 activatable antibody (anti-CD166-7614.6-3001, "CD166 Pb"), an activatable antibody drug conjugate (anti-CD166-7614.6-3001-spdb-DM4, "CD166-AADC"). As indicated, assays were also performed with protease-activated anti-CD166 activatable antibody drug conjugate, using either urokinase (uPA), matriptase (MT-SP1), or matrix metalloprotease 14 (MMP14) as indicated. Using a standard ELISA protocol, human CD166 protein was absorbed to ELISA plates and subsequently incubated with the indicated concentration of antibody. Bound antibody was detected with a horseradish peroxidase-conjugated anti-human IgG secondary antibody.

Figure 19B:
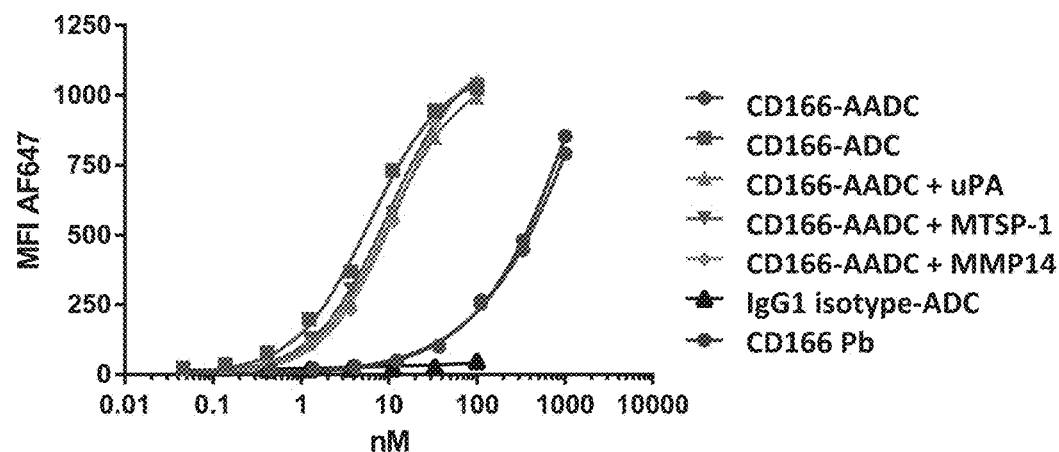
Figure 19C:
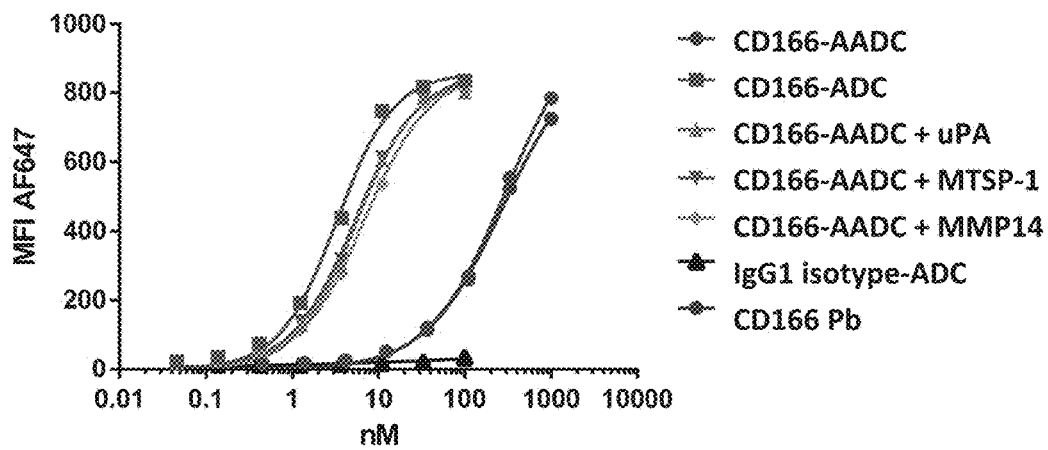

FIGS. 19B and 19C are graphs depicting the binding to human HCC1806 or H292 cells in a flow cytometry assay of an anti-CD166 antibody (anti-huCD166 HcC/vk-1, "CD166 Ab"), an anti-CD166 antibody drug conjugate (anti-CD166-spdb-DM4, "CD166-ADC"), an anti-CD166 activatable antibody (anti-CD166-7614.6-3001, "CD166 Pb"), an activatable antibody drug conjugate (anti-CD166-7614.6-3001-spdb-DM4, "CD166-AADC"). As indicated, assays were also performed with protease-activated anti-CD166 activatable antibody drug conjugate, using either urokinase (uPA), matriptase (MT-SP1), or matrix metalloprotease 14 (MMP14) as indicated. As a control, and IgG1 isotype antibody conjugated to spdb-DM4 ("IgG1 isotype-ADC") was also tested. In a typical assay, H292 cells or HCC1806 cells were incubated with the indicated concentrations of anti-CD166 antibody in PBS+2% FBS for 1 hr on ice. After washing 2× with PBS+2% FBS, cells were incubated with a goat anti-human IgG secondary antibody, conjugated to AlexaFluor 647 (Jackson ImmunoResearch), for 30-45 min on ice. Cells were then washed 2× with PBS+2% FBS and fixed with 1% formaldehyde. Bound antibody was detected using a Guava EasyCyte cytometer and the median fluorescence intensity (MFI) of the cell population was measured.

TABLE 14

Binding of Anti-CD166 Antibody Constructs to CD166 and Human Cells

| Antibody Construct | CD166 ELISA Kd (nM) | HCC1806 Flow Cytomtry Kd (nM) | H292 Flow Cytomtry Kd (nM) |
|---|---|---|---|
| CD166-AADC | 2.9 | >300 | >200 |
| CD166-AADC, uPA cleaved | 0.18 | 9.9 | 5.5 |
| CD166-AADC, matriptase cleaved | 0.17 | 9.9 | 5.3 |
| CD166-AADC, MMP-14 cleaved | 0.16 | 12 | 6.9 |
| CD166-ADC | 0.15 | 6.1 | 3.3 |
| CD166-Pb | 3.05 | >300 | >200 |

As shown by the exemplary results in Table 14, the uncleaved CD166-AADC demonstrated an increased apparent Kd as compared to the unmasked CD166-ADC in ELISA and flow cytometry assays. Activation of the CD166-AADC by all three of the proteases appeared to restore the binding affinity of the anti-CD166 activatable antibody drug conjugate to a level comparable to that the unmasked CD166-ADC.

Figure 20A:
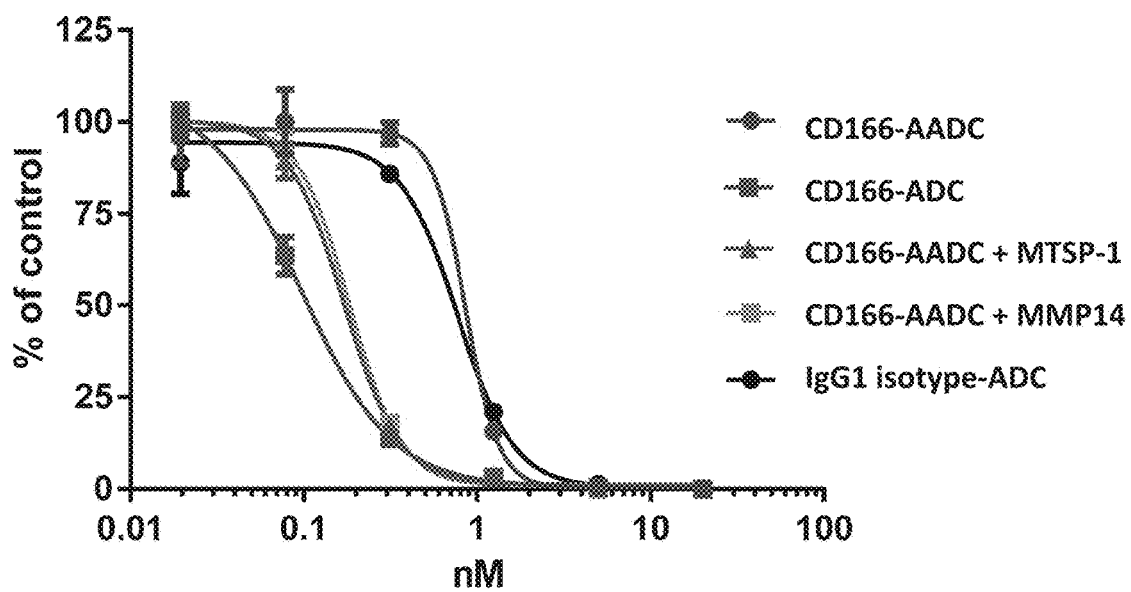
FIGS. 20A and 20B are graphs depicting an exemplary cytotoxicity assay of the anti-CD166 activatable antibody drug conjugates of the present disclosure to human H292 and HCC1806 cells.
Figure 20B:
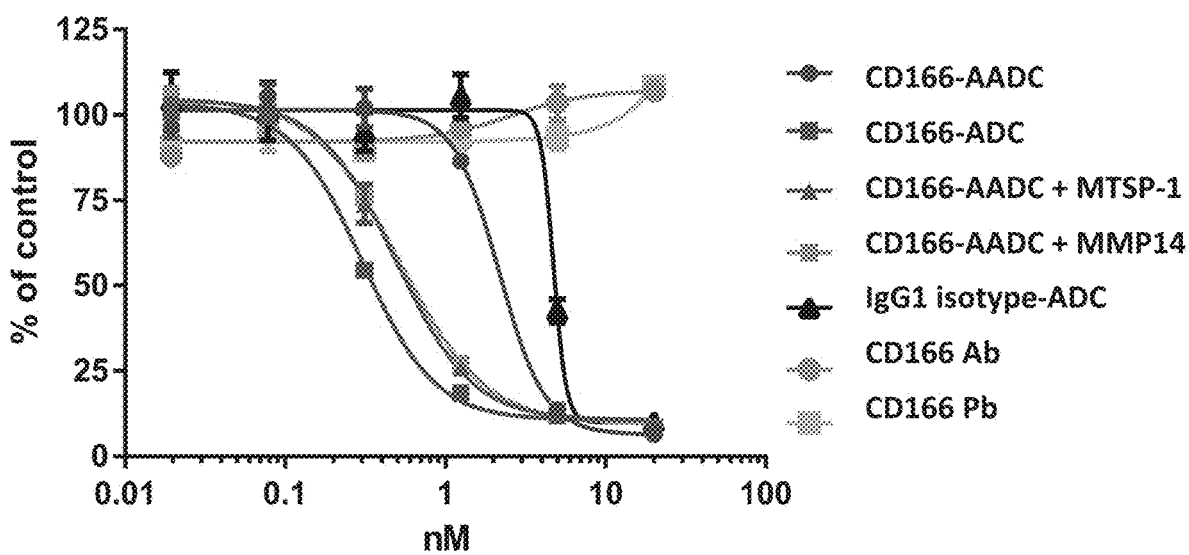
Figure 21C:
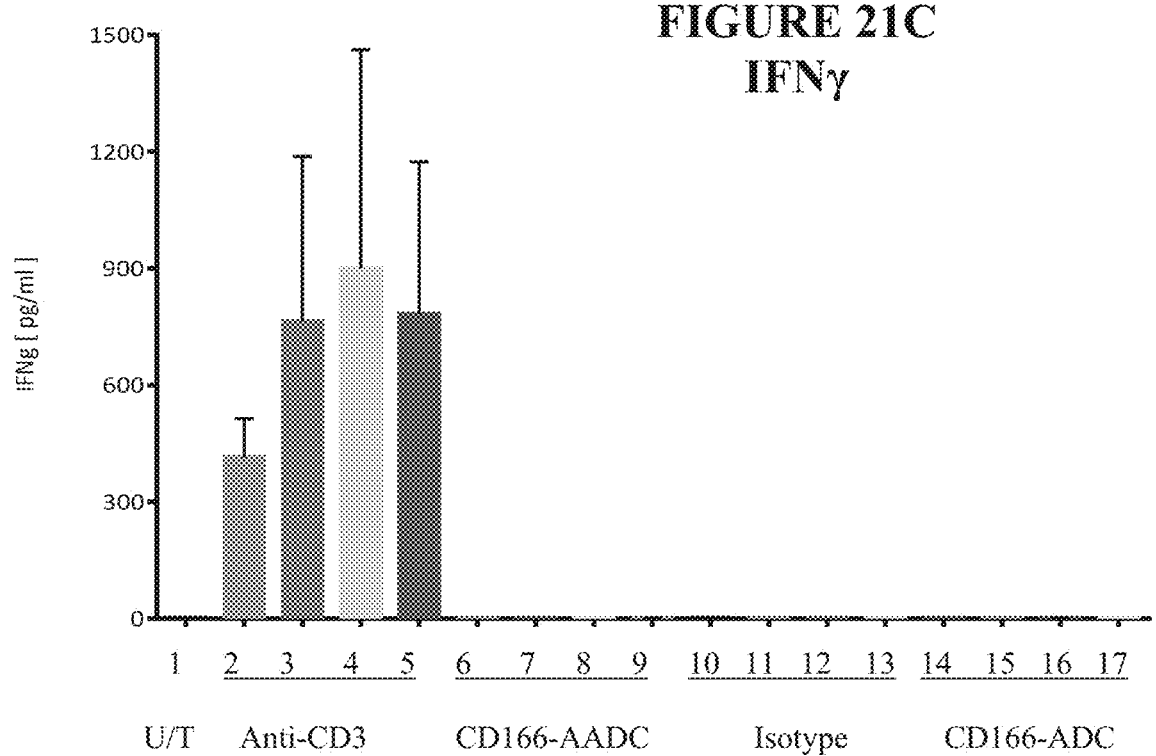
Figure 21D:
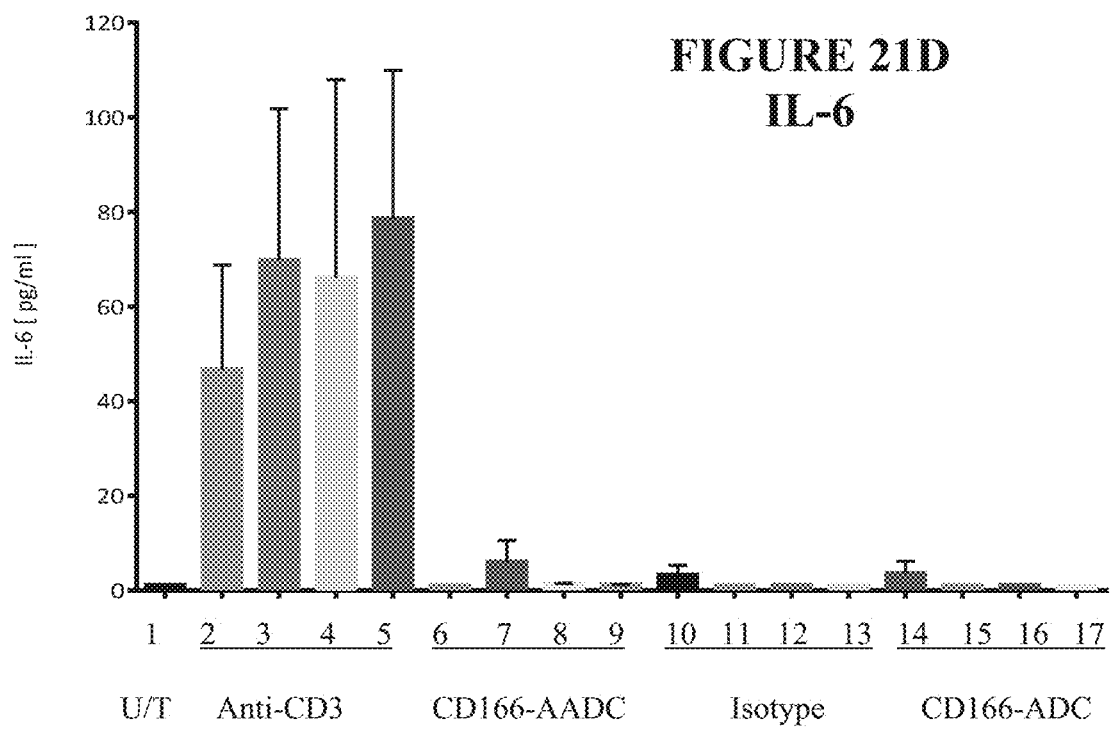

FIGS. 20A and 20B are graphs depicting the in vitro cytotoxicity to human HCC1806 or H292 cells in of an anti-CD166 antibody (anti-huCD166 HcC/vk-1, "CD166 Ab"), an anti-CD166 antibody drug conjugate (anti-CD166-spdb-DM4, "CD166-ADC"), an anti-CD166 activatable antibody (anti-CD166-7614.6-3001, "CD166 Pb"), an activatable antibody drug conjugate (anti-CD166-7614.6-3001-spdb-DM4, "CD166-AADC"). As indicated, assays were also performed with protease-activated anti-CD166 activatable antibody drug conjugate, using either urokinase (uPA), matriptase (MT-SP1), or matrix metalloprotease 14 (MMP14) as indicated. As a control, and IgG isotype antibody conjugated to spdb-DM4 ("IgG1 isotype-ADC") was also tested. In a typical assay, H292 cells or HCC1806 cells were incubated with the indicated concentrations of antibody, activatable antibody, activatable antibody drug conjugated, or activatable antibody drug conjugate treated with protease, and incubating the cells for 3 to 5 days. Cell viability was measured using the CellTiter Glo assay. The results of these cytotoxicity assays is summarized below in Table 15.

TABLE 15

In vitro Cytotoxicity of Anti-CD166 Antibody Constructs to Human Cells

| Antibody Construct | H292 EC50 (nM) | HC1806 EC50 (nM) |
|---|---|---|
| CD166-AADC | 2.2 | 0.9 |
| CD166-AADC, uPA cleaved | 0.5 | 0.3 |
| CD166-AADC, matriptase cleaved | 0.5 | 0.2 |
| CD166-AADC, MMP-14 cleaved | 0.5 | 0.2 |
| CD166-ADC | 0.3 | 0.1 |

These exemplary results of Table 15 and FIGS. 20A and 20B demonstrate that activatable anti-CD166 antibody drug conjugates (CD166-AADC) of the present disclosure that are proteolytically-activated with protease that recognize the substrate sequence (CM) show a several-fold increase in cytotoxicity to human cells as compared to the corresponding uncleaved anti-CD166 AADC. Furthermore, the activated anti-CD166 AADC demonstrate a cytotoxicity that is comparable to the unmasked anti-CD166 ADC.

Example 14

Immunological Risk Assay of Anti-CD166 Activatable Antibodies

The exemplary studies provided herein were designed to evaluate the ability of activatable anti-CD166 antibody drug conjugates (CD166-AADC) of the present disclosure to trigger an immunological response in an in vitro assay.

In these exemplary studies, human peripheral blood mononuclear cells (PBMCs) were tested in in vitro assays for cytokine release and proliferation in response to treatment with activatable anti-CD166 antibody drug conjugate (anti-CD166-7614.6-3001-spdb-DM4, "CD166-AADC"), an anti-CD166 antibody drug conjugate (anti-CD166 (vk-1/HcC)-spdb-DM4, "CD166-ADC"), an anti-CD3 positive control (OKT3 antibody), and an isotype control antibody drug conjugate ("Isotype") at the following concentrations:

| No. | Antibody (nM) |
|---|---|
| 1 | Untreated |
| 2 | Anti-CD3 (0.67 nM) |
| 3 | Anti-CD3 (6.7 nM) |
| 4 | Anti-CD3 (67 nM) |
| 5 | Anti-CD3 (670 nM) |
| 6 | CD166-AADC (0.67 nM) |
| 7 | CD166-AADC (6.7 nM) |
| 8 | CD166-AADC (67 nM) |
| 9 | CD166-AADC (670 nM) |
| 10 | Isotype (0.67 nM) |
| 11 | Isotype (6.7 nM) |
| 12 | Isotype (67 nM) |
| 13 | Isotype (670 nM) |
| 14 | CD166-ADC (0.67 nM) |
| 15 | CD166-ADC (6.7 nM) |
| 16 | CD166-ADC (67 nM) |
| 17 | CD166-ADC (670 nM) |

In this exemplary study, five normal, healthy donors in two separate formats, wet coat and soluble test article, were evaluated. A standard panel of Th1 and Th2 cytokines including IL-2, IL4, IL-6, IL-10, TNFα, and IFNγ were measured at 24 hr post-treatment. As shown in FIG. 21A-21D, dose titration of either CD166-AADC or the corresponding CD166-ADC showed no significant cytokine release from human PBMCs, as compared with a positive control (anti-CD3, OKT3) and negative (isotype ADC) control antibodies. Additionally, unlike the positive control OKT3 antibody, neither CD166-AADC nor CD166-ADC induced PBMC proliferation, assessed at day 8 post-treatment.

Example 16

Antibody-Dependent Cell Cytotoxicity of Conjugated Activatable Anti-CD166 Antibodies The exemplary studies provided herein were designed to evaluate the in vitro antibody-dependent cell cytotoxicity (ADCC) to human cells of anti-CD166 activatable antibody drug conjugates of the present disclosure.

Figure 22:
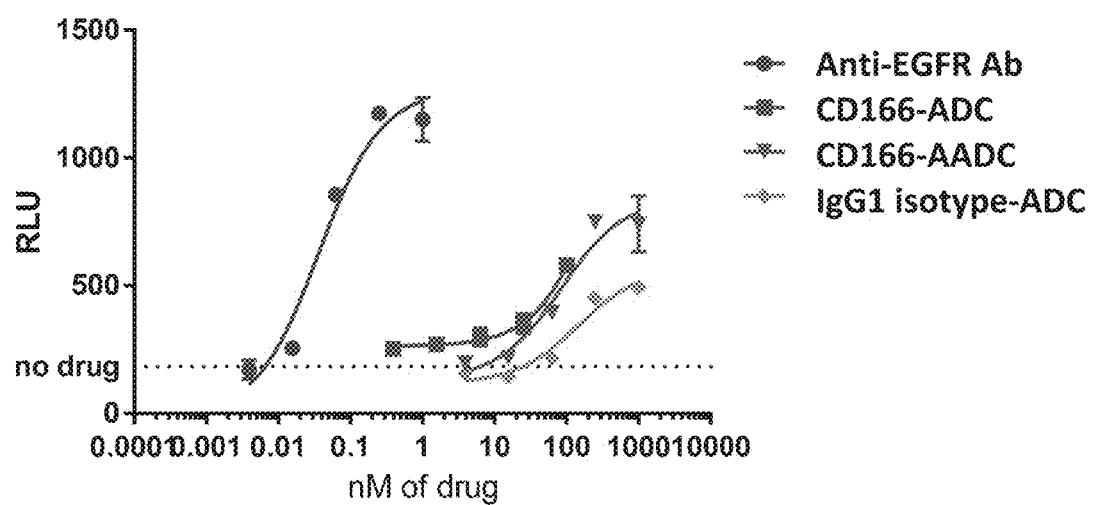
FIG. 22 is a graph depicting the ability of the anti-CD166 activatable antibody drug conjugates of the present disclosure to induce an antibody-dependent cell cytotoxicity in cells.

FIG. 22 is a graph depicting an in vitro ADCC assay on human ovarian adenocarcinoma cells (SKOV3) using an anti-CD166 activatable antibody drug conjugate of the present disclosure (anti-huCD166 (HcC/vk-1)-7614.6-3001-spdb-DM4, "CD166-AADC"), an anti-CD166 antibody drug conjugate (anti-CD166-spdb-DM4, "CD166-ADC"), an anti-EGFR positive control, and an IgG1 isotype control-spdb-DM4 ("IgG isotype-ADC")

ADCC activities in this exemplary assay were evaluated using an ADCC reporter bioassay (Promega). In this assay, Jurkat T cells stably transfected with FcRγIIIa and an NF-AT-inducible luciferase reporter were incubated with CD166-expressing SKOV3 cells in the presence of CD166-AADC or control antibodies. Luciferase activity is stimulated as a function of antibody binding to target cells, FcRγIIIa receptor engagement and downstream signaling in effector cells. In SKOV3 cells, which express high levels of CD166 and EGFR, incubation with CD166-AADC or the CD166-ADC showed similar activity to an IgG1 isotype control ADC, and lower than observed with the positive control anti-EGFR antibody. Dose titration of CD166-AADC or CD166-ADC in the assay. These data suggest that CD166-AADC, as well as CD166-ADC, have limited potential for ADCC.

Example 17

Efficacy of Conjugated Activatable Anti-CD166 Antibodies Against Cell—and Patient—Derived Xenograft Tumor Models The exemplary studies provided herein were designed to evaluate the in vivo efficacy of anti-CD166 activatable antibody drug conjugates of the present disclosure against cell- and patient-derived xenografts in a mouse tumor model.

In these exemplary studies, multiple human cell line-derived and patient-derived xenograft (PDX) models representing various cancer types were tested. Two cell line derived xenograft models (H292 non-small cell lung carcinoma (NSCLC) cells and HCC1806 triple negative breast carcinoma cells), and two patient-derived xenograft (PDX) models for ovarian carcinoma (CTG-0791) and cholangiocarcinoma (CTG-0941). For each model, tumor-bearing mice were randomized into groups and treatment begun with an anti-CD166 activatable antibody drug conjugate of the present disclosure (anti-huCD166 (HcC/vk-1)-7614.6-3001-spdb-DM4, "CD166-AADC"), an isotype control SPDB-DM4 conjugate, or vehicle control as indicated. Test articles were administered intravenously on study day 0 and 7, at 3 or 5 mg/kg as indicated.

Figure 23:
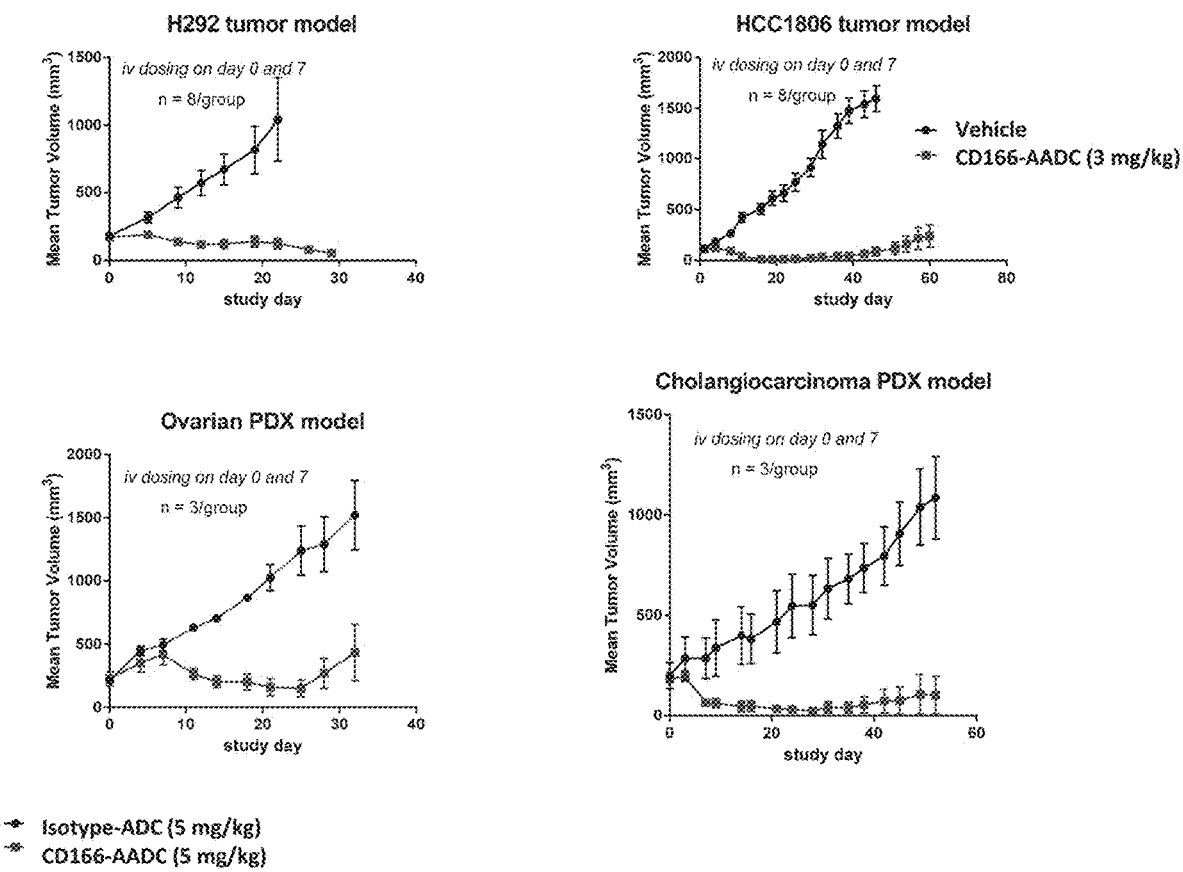
FIG. 23 are graphs depicting the efficacy of the anti-CD166 activatable antibody drug conjugates of the present disclosure against multiple cell-derived and patient-derived xenograft tumor models.

As depicted in FIG. 23, treatment with CD166-AADC, at or below the expected therapeutic dose in humans, led to tumor regressions and durable responses in the majority of mice. Other similar exemplary studies are summarized in Table 16 below.

TABLE 16

Efficacy of Anti-CD166 Activatable Antibody Drug Conjugates

| Tumor Model | Cancer Type | Anti-Tumor Response With CD166-AADC |
| --- | --- | --- |
| H292 | NSCLC | Yes |
| H1975 | NSCLC | Yes |
| CTG-0166 | NSCLC (squamous) | Yes |
| HCC1806 | Triple negative breast cancer | Yes |

TABLE 16-continued

Efficacy of Anti-CD166 Activatable Antibody Drug Conjugates

| Tumor Model | Cancer Type | Anti-Tumor Response With CD166-AADC |
| --- | --- | --- |
| CTG-0791 | Ovarian | Yes |
| CTG-0941 | Cholangiocarcinoma | Yes |

Example 18

In Vitro Cytotoxicity of Conjugated Activatable Anti-CD166 Antibodies Against Endometrial Cancer-Derived Cell Lines The exemplary studies provided herein were designed to evaluate the in vitro efficacy of anti-CD166 activatable antibody drug conjugates of the present disclosure against endometrial cancer-derived cell lines.

Figure 24D:
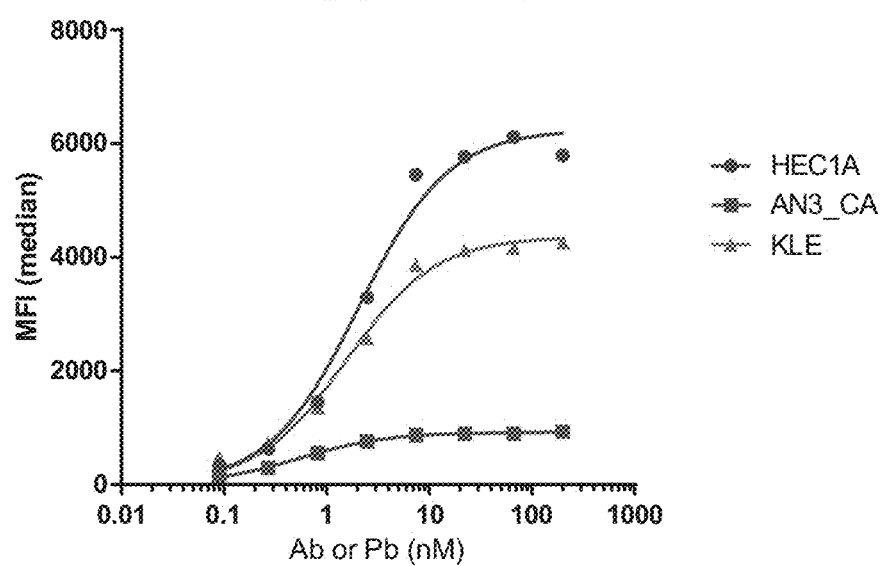

As shown in FIGS. 24A-24C, these exemplary studies showed the in vitro cytotoxicity to human uterine endometrial cancer-derived cell lines (HEC-1-A, AN3-CA, and KLE cell lines) of an anti-CD166 antibody drug conjugate (anti-CD166-spdb-DM4, "CD166-ADC"), and activatable antibody drug conjugates (anti-CD166-7614.6-3001-spdb-DM4, "CD166-7614.6-AADC"; and anti-CD166-7614.8-3001-spdb-DM4, "CD166-7614.8-AADC"). An isotype control-ADC (chKTI-spdb-DM4) was used as a control. In a typical assay, the cells were incubated with the indicated concentrations of antibody drug conjugate, or activatable antibody drug conjugate, and incubating the cells for 3 to 5 days. Cell viability was measured using the CellTiter Glo assay. These exemplary results showed that the anti-CD166-AADCs and anti-CD166-ADCs of the present disclosure demonstrated cytotoxicity against all cell lines as compared to the negative control. These exemplary results also showed that the uncleaved anti-CD166-AADCs showed a lower cytotoxicity than anti-CD166-ADCs of the present disclosure due to their lower affinity to the target due to the mask substrate. The relative susceptibility of the cell lines to the anti-CD166 articles of the present disclosure appeared to correlate to the level of CD166 expression in each cell. As shown in FIG. 24D, to determine the relative amount of surface-expressed CD166 on each endometrial cell line, a flow cytometry assay using anti-CD166 of the present disclosure was performed.

Example 18

In Vitro Cytotoxicity of Conjugated Anti-CD166 Antibody Drug Conjugates Against Various Cancer-Derived Cell Lines The exemplary studies provided herein were designed to evaluate the in vitro efficacy of anti-CD166 antibody drug conjugates of the present disclosure against endometrial cancer-derived cell lines.

In these exemplary studies, the in vitro cytotoxicity of anti-CD166 antibody drug conjugates (anti-CD166 (vk-1/HcC)-spdb-DM4, "CD166-ADC") were tested against multiple human cancer-derived cell lines. In a typical assay, the cells were incubated with concentrations of CD166-ADC for 3 to 5 days at various concentrations (from 0.1 nM to 50 nM). Cell viability was measured using the CellTiter Glo assay. The cytotoxicity of the CD166-ADC was compared to a negative isotype control (chKTI-spdb-DM4. In the case of the PC3 prostate cancer cell line and the SAS head and neck squamous cell carcinoma cell lines, the tested article was anti-CD166-vc-MMAD, and the negative control was an isotypic palivizumab-vc-MMAD. The results of these cytotoxicity assays is summarized below in Table 8.

TABLE 8

In vitro Cytotoxicity of Anti-CD166 Antibody Drug Conjugate to Human Cancer Cells

| Cell Type | Cancer Type | Cytotoxicity of CD166-ADC? |
|---|---|---|
| ZR75-1 | Human breast ductal carcinoma (estrogen receptor positive) | Yes |
| ZR75-30 | Human breast ductal carcinoma (estrogen receptor positive) | Yes |
| MDA-MB-361 | Human breast adenocarcinoma (estrogen receptor positive) | Yes |
| HCC1954 | Human breast ductal carcinoma (triple-negative) | Yes |
| HCC1143 | Human breast cancer (triple-negative) | Yes |
| PC3 | Human prostate adenocarcinoma | Yes |
| SAS | Human head & neck squamous cell carcinoma | Yes |

Example 19

In Vivo Imaging of Activatable Anti-CD166 Antibodies in a Mouse Lung Cancer Xenograft Model This Example shows that activatable anti-CD166 antibodies of the present disclosure demonstrate tumor-associated protease-dependent in vivo activation and binding to CD166 expressed in a lung cancer (NSCLC) mouse xenograft model by in vivo fluorescent imaging.

Figure 25A:
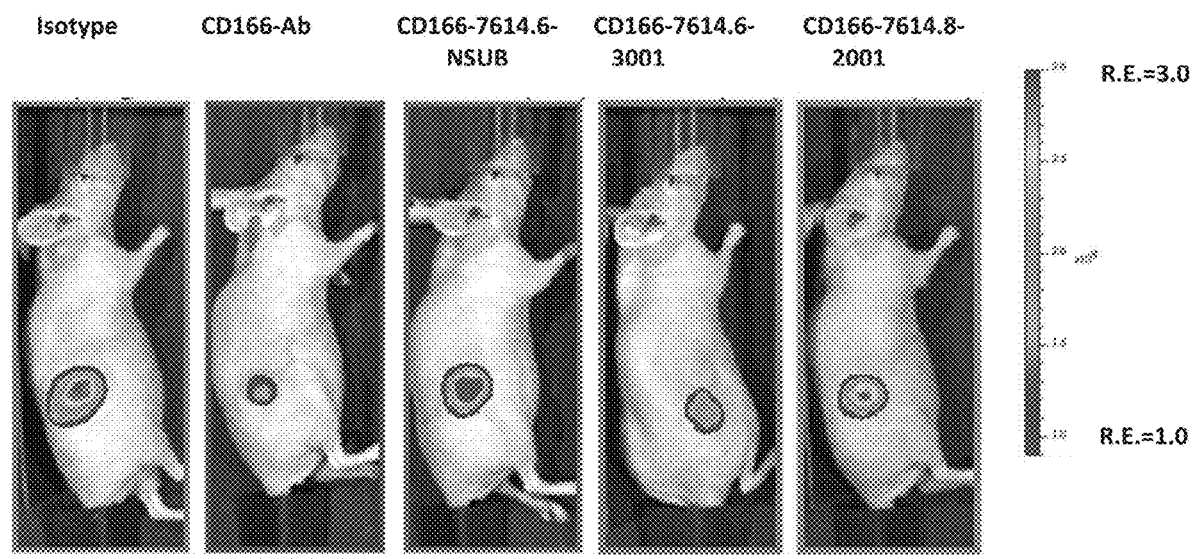
FIGS. 25A and 25B depicts exemplary studies of in situ binding of anti-CD166 antibodies of the present disclosure in a lung cancer xenograft model.
Figure 25B:
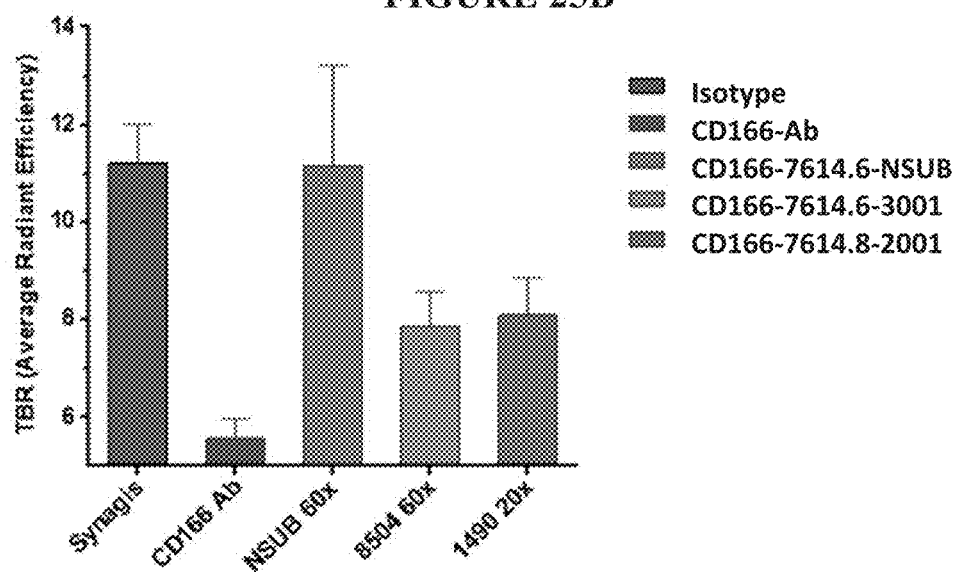

FIG. 25A shows in vivo imaging of live mice with lung tumor xenografts (H292 cells) using fluorescently-conjugated anti-CD166 and activatable anti-CD166 antibodies of the present disclosure. In this study, 7-8 week-old nu/nu female mice (n=3) were implanted subcutaneously in the right hind flank with 5×10$^6$ H292 cells, a human non-small cell lung cancer-derived cell line. After the tumors grew to 300 to 380 mm$^3$, an anti-CD166 antibody (vk-1/HcC) of the present disclosure ("CD166-Ab"), activatable anti-CD166 antibodies with differing mask sequences and substrate sequences of the present disclosure (anti-CD166-7614.6-3001, anti-CD166-7614.8-2001), or a masked anti-CD166 antibody of the present disclosure lacking a CM domain ("CD166 7614.6-NSUB") were administered as a pre-blocking reagent to each of the mice at a dose of 5 mg/kg. As a control, an isotype antibody (palivizumab) was similarly administered. About 48 hours later, the mice were injected with anti-CD166 antibody labeled with AlexaFluor 750 (anti-CD166-AF750). The mice were subjected to in vivo fluorescent imaging 24, 72, and 96 hours after administration of the anti-CD166-AF750, using a 745 nm excitation signal and detecting an 800 nm emission signal. Representative mice imaged at 96 hours are depicted. The scale shows the relative magnitude of the detected fluorescent signal. The mean tumor-to-background ratio (TBR) for each test article as measured for the mice is shown in FIG. 25B.

The results of this exemplary study showed that fluorescent signals from the unmasked anti-CD166 antibody of the present disclosure and the activatable anti-CD166 antibodies of the present disclosure were able to bind CD166 in the xenograft, thus blocking the subsequent binding of fluorescently-labeled anti-CD166. In contrast, a correspondingly masked anti-CD166 antibody but which lacked a protease cleavage site (CM) did not block subsequent binding of CD166-AF750 to an extent comparable to the isotype control. Without being bound by any particular theory, this exemplary study demonstrated that activatable anti-CD166 antibodies of the present disclosure can be activated iin vivo via tumor-associated protease cleavage, thus allowing the activated activatable anti-CD166 antibody to bind CD166 in the xenograft tumor to an extent comparable to the unmasked anti-CD166 antibody of the present disclosure. The masked anti-CD166 antibody lacking a protease cleavage domain (CM) of the present disclosure was not activatable in the same manner, and thus did not appreciably bind to the tumor xenograft.

Example 20

Efficacy of Conjugated Activatable Anti-CD166 Antibodies Against Cell-Derived Xenograft Tumor Models The exemplary studies provided herein were designed to evaluate the in vivo efficacy of anti-CD166 activatable antibody drug conjugates (AADCs) of the present disclosure against cell-derived xenografts in a mouse tumor model.

In these exemplary studies, anti-CD166 activatable antibody drug conjugates of the present disclosure were tested for efficacy against model mouse tumor xenograft model of lung cancer (H292 human non-small cell lung carcinoma (NSCLC) cells). In this study, tumor-bearing mice were treated with an anti-CD166 antibody drug conjugates and anti-CD166 activatable antibody drug conjugate (AADC) of the present disclosure, including anti-CD166-7614-2001-spdb-DM4 ("CD166-7614-2001-DM4"), anti-CD166-7614.6-2001-spdb-DM4 ("CD166-7614.6-2001-DM4"), anti-CD166-7614.8-3001-spdb-DM4 ("CD166-7614.8-3001-DM4"), anti-huCD166-spdb-DM4 ("CD166-DM4"), and an isotype control (palivizumab-spdb-DM4; "Isotype-DM4"). 5 mg/kg of test articles were administered intravenously on study days 1 and 8 to each mouse, and the mean tumor volume (MTV) of the H292 xenograft was measured on the indicated days.

Figure 26:
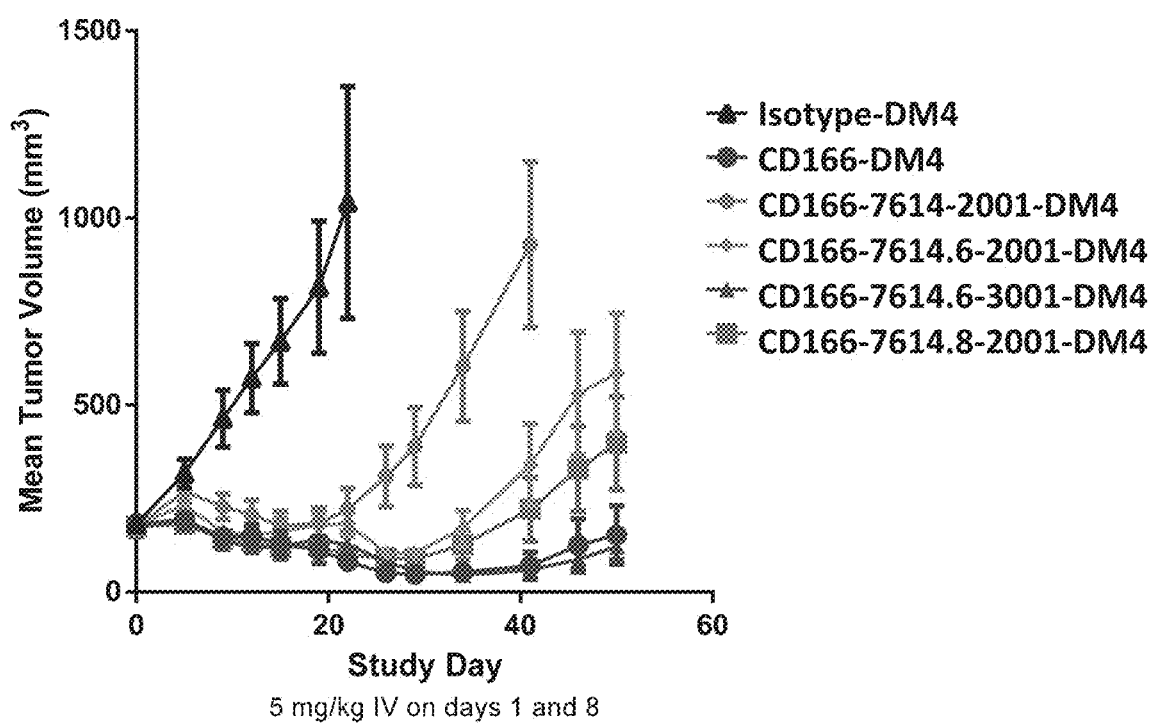
FIG. 26 is a graph depicting the efficacy of the anti-CD166 activatable antibody drug conjugates of the present disclosure against a mouse lung cancer xenograft model.

As depicted in FIG. 26, treatment with the activatable anti-CD166 antibody drug conjugates of the present disclosure resulted in a decrease in MTV over time to a degree comparable to that observed with the unmasked anti-CD166-DM4 drug conjugate. The anti-CD166-DM4 AADC having a mask with a measurably higher effect on decreasing the parental antibody binding affinity to CD166 (see, e.g., Table 17) appeared to have measurably lower efficacy than the anti-CD166 AADCs having lower masks.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed:

1. An isolated antibody or an antigen binding fragment thereof (AB) that specifically binds to mammalian CD166, wherein the AB specifically binds human CD166 and cynomolgus monkey CD166, wherein the AB comprises the VH CDR1 amino acid sequence GFSLSTYGMGVG (SEQ ID NO: 127); the VH CDR2 amino acid sequence NIWWSEDKH (SEQ ID NO: 128); the VH CDR3 amino acid sequence IDYGNDYAFTY (SEQ ID NO: 129); the VL CDR1 amino acid sequence RSSKSLLHSNGITYLY (SEQ ID NO: 130) or RSSQSLLHSNGITYLY (SEQ ID NO: 131); the VL CDR2 amino acid sequence QMSNLAS (SEQ ID NO: 132) or QMSNRAS (SEQ ID NO: 133); and the VL CDR3 amino acid sequence AQNLELPYT (SEQ ID NO: 134).

2. The AB of claim 1, wherein the AB comprises a heavy chain variable region comprising the amino acid sequence of SEQ ID NO: 121 or SEQ ID NO: 122, and a light chain variable region comprising an amino acid sequence selected from the group consisting of SEQ ID NOs: 123-126.

3. An activatable antibody that, in an activated state, binds CD166 comprising:
   an antibody or an antigen binding fragment thereof (AB) that specifically binds to mammalian CD166, wherein the AB specifically binds human CD166 and cynomolgus monkey CD166, wherein the AB comprises the VH CDR1 amino acid sequence GFSLSTYGMGVG (SEQ ID NO: 127); the VH CDR2 amino acid sequence NIWWSEDKH (SEQ ID NO: 128); the VH CDR3 amino acid sequence IDYGNDYAFTY (SEQ ID NO: 129); the VL CDR1 amino acid sequence RSSKSLLHSNGITYLY (SEQ ID NO: 130) or RSSQSLLHSNGITYLY (SEQ ID NO: 131); the VL CDR2 amino acid sequence QMSNLAS (SEQ ID NO: 132) or QMSNRAS (SEQ ID NO: 133); and the VL CDR3 amino acid sequence AQNLELPYT (SEQ ID NO: 134);
   a masking moiety (MM) coupled to the AB that inhibits the binding of the AB to CD166 when the activatable antibody is in an uncleaved state; and
   a cleavable moiety (CM) coupled to the AB, wherein the CM is a polypeptide that functions as a substrate for a protease.

4. The activatable antibody of claim 3, wherein the MM has one or more of the characteristics selected from the group consisting of:
   (i) the MM has a dissociation constant for binding to the AB that is greater than the dissociation constant of the AB to CD166;
   (ii) the MM does not interfere or compete with the AB for binding to CD166 when the activatable antibody is in a cleaved state;
   (iii) the MM is a polypeptide of no more than 40 amino acids in length;
   (iv) the MM polypeptide sequence is different from that of human CD166;
   (v) the MM polypeptide sequence is no more than 50% identical to any natural binding partner of the AB; and
   (vi) the MM comprises an amino acid sequence selected from the group consisting of SEQ ID NOs: 135-238.

5. The activatable antibody of claim 3, wherein the CM has one or more of the characteristics selected from the group consisting of:

(i) the CM is a substrate for a protease that is active in diseased tissue; and (ii) the CM comprises an amino acid sequence selected from the group consisting of SEQ ID NOs: 18-87 and 318-358.

6. The activatable antibody of claim 3, wherein the antigen binding fragment thereof is selected from the group consisting of a Fab fragment, a F(ab')₂ fragment, a scFv, a scAb, a dAb, a single domain heavy chain antibody, and a single domain light chain antibody.

7. The activatable antibody of claim 3, wherein the AB comprises a heavy chain variable region comprising the amino acid sequence of SEQ ID NO: 121 or SEQ ID NO: 122, and a light chain variable region comprising an amino acid sequence selected from the group consisting of SEQ ID NOs: 123-126.

8. The activatable antibody of claim 3, wherein the AB is linked to the CM.

9. The activatable antibody of claim 3, wherein the AB is linked directly to the CM.

10. The activatable antibody of claim 3, wherein the AB is linked to the CM via a linking peptide.

11. The activatable antibody of claim 3, wherein the MM is linked to the CM such that the activatable antibody in an uncleaved state comprises the structural arrangement from N-terminus to C-terminus as follows: MM-CM-AB or AB-CM-MM.

12. The activatable antibody of claim 3, wherein the activatable antibody comprises a linking peptide between the MM and the CM, a linking peptide between the CM and the AB, or both a linking peptide between the MM and the CM and a linking peptide between the CM and the AB.

13. The activatable antibody of claim 3, wherein the activatable antibody comprises a first linking peptide (LP1) and a second linking peptide (LP2), and wherein the activatable antibody in the uncleaved state has the structural arrangement from N-terminus to C-terminus as follows: MM-LP1-CM-LP2-AB or AB-LP2-CM-LP1-MM.

14. The activatable antibody of claim 13, wherein the two linking peptides are not identical to each other.

15. The activatable antibody of claim 13, wherein each of LP1 and LP2 is a peptide of about 1 to 20 amino acids in length.

16. The activatable antibody of claim 3, wherein the activatable antibody has one or more of the characteristics selected from the group consisting of:

(a) the activatable antibody comprises the heavy chain comprising an amino acid sequence of SEQ ID NO: 239 and a light chain comprising an amino acid sequence selected from the group consisting of SEQ ID NOs: 240, 242, 244, 246, 248, 303, 310, 312, 314, 316, 371, 372, 375, 376, 379, 380, 383, 384, 387, 388, 391, 392, 395, 396, 399, 400, 403, 404, 407, 408, 411, 412, 415, 416, 419, 420, 423, 424, 427, 428, 431, 432, 435, 436, 439, 440, 443, 444, 447, 448, 451, 452, 455, 456, 459, 460, 463, 464, 467, 468, 471, and 472;

(b) the activatable antibody comprises a combination of amino acid sequences, wherein the combination of amino acid sequences is selected from a single row in Table A, wherein for a given combination,
(i) the heavy chain of the AB comprises the amino acid sequences of the VH CDR sequences corresponding to the given combination in the single row listed in Table A,
(ii) the light chain of the AB comprises the amino acid sequences of the VL CDR sequences corresponding to the given combination in the single row listed in Table A,
(iii) the MM comprises the amino acid sequence of the mask sequence (MM) corresponding to the given combination in the single row listed in Table A, and
(iv) the CM comprises the amino acid sequence of the substrate sequence (CM) corresponding to the given combination in the single row listed in Table A;

(c) the activatable antibody comprises a combination of amino acid sequences, wherein for a given combination of amino acid sequences,
(i) the heavy chain of the AB comprises the amino acid sequences of the VH sequence or VH CDR sequences selected from the group consisting of: the VH sequence or VH CDR sequences listed in the corresponding column of Table B,
(ii) the light chain of the AB comprises the amino acid sequences of the VL sequence or VL CDR sequences selected from the group consisting of: the VL sequence or VL CDR sequences listed in the corresponding column of Table B,
(iii) the MM comprises the amino acid sequence of the mask sequence (MM) selected from the group consisting of: the MM sequences listed in the corresponding column of Table B, and
(iv) the CM comprises the amino acid sequence of the substrate sequence (CM) selected from the group consisting of: the CM sequences listed in the corresponding column of Table B; and (d) the activatable antibody comprises a heavy chain variable region comprising an amino acid sequence selected from the group consisting of SEQ ID NOs: 121 and 122, and a light chain variable region comprising an amino acid sequence selected from the group consisting of SEQ ID NOs: 123-126, 363-370, 373, 374, 377, 378, 381, 382, 385, 386, 389, 390, 393, 394, 397, 398, 401, 402, 405, 406, 409, 410, 413, 414, 417, 418, 421, 422, 425, 426, 429, 430, 433, 434, 437, 438, 441, 442, 445, 446, 449, 450, 453, 454, 457, 458, 461, 462, 465, 466, 469, 470, 473, and 474.

17. An activatable antibody comprising an antibody or an antigen binding fragment thereof (AB) that specifically binds to mammalian CD166, a masking moiety (MM), and a cleavable moiety (CM),
wherein the AB comprises the VH CDR1 amino acid sequence GFSLSTYGMGVG (SEQ ID NO: 127); the VH CDR2 amino acid sequence NIWWSEDKH (SEQ ID NO: 128); the VH CDR3 amino acid sequence IDYGNDYAFTY (SEQ ID NO: 129); the VL CDR1 amino acid sequence RSSKSLLHSNGITYLY (SEQ ID NO: 130) or RSSQSLLHSNGITYLY (SEQ ID NO: 131); the VL CDR2 amino acid sequence QMSNLAS (SEQ ID NO: 132) or QMSNRAS (SEQ ID NO: 133); and the VL CDR3 amino acid sequence AQNLELPYT (SEQ ID NO: 134); and
wherein the activatable antibody has one or more of the following characteristics selected from the group consisting of:

(i) the activatable antibody comprises a heavy chain comprising an amino acid sequence of SEQ ID NO: 239; and a light chain sequence comprising an amino acid sequence selected from the group consisting of SEQ ID Nos: 240, 242, 244, 246, 248, 303, 310, 312, 314, 316, 371, 372, 375, 376, 379, 380, 383, 384, 387, 388, 391, 392, 395, 396, 399, 400, 403, 404, 407, 408, 411, 412, 415, 416, 419, 420, 423, 424, 427, 428, 431, 432, 435, 436, 439, 440, 443, 444, 447, 448, 451, 452, 455, 456, 459, 460, 463, 464, 467, 468, 471, and 472;

(ii) the MM comprises an amino acid sequence selected from the group consisting of SEQ ID Nos: 135-238, and the CM comprises an amino acid sequence selected from the group consisting of SEQ ID Nos: 18-87 and 318-358; and (iii) the activatable antibody comprises a heavy chain variable region comprising an amino acid sequence selected from the group consisting of SEQ ID NOs: 121 and 122, and a light chain variable region comprising an amino acid sequence selected from the group consisting of SEQ ID NOs: 123-126, 363-370, 373, 374, 377, 378, 381, 382, 385, 386, 389, 390, 393, 394, 397, 398, 401, 402, 405, 406, 409, 410, 413, 414, 417, 418, 421, 422, 425, 426, 429, 430, 433, 434, 437, 438, 441, 442, 445, 446, 449, 450, 453, 454, 457, 458, 461, 462, 465, 466, 469, 470, 473, and 474.

18. A conjugated activatable antibody comprising the activatable antibody of claim 3 conjugated to an agent.

19. The conjugated activatable antibody of claim 18, wherein the agent has one or more of the characteristics selected from the group consisting of:
(a) the agent is a toxin or a fragment thereof;
(b) the agent is a microtubule inhibitor;
(c) the agent is a nucleic acid damaging agent;
(d) the agent is a dolastatin;
(e) the agent is an auristatin;
(f) the agent is a maytansinoid;
(g) the agent is a duocarmycin;
(h) the agent is a calicheamicin;
(i) the agent is a pyrrolobenzodiazepine;
(j) the agent is auristatin E;
(k) the agent is monomethyl auristatin E (MMAE);
(l) the agent is monomethyl auristatin D (MMAD);
(m) the agent is the maytansinoid DM1;
(n) the agent is the maytansinoid DM4;
(o) the agent is a detectable moiety; and
(p) the agent is a diagnostic agent.

20. The conjugated activatable antibody of claim 18, wherein the agent is conjugated to the AB via a linker.

21. The conjugated activatable antibody of claim 18, wherein the linker with which the agent is conjugated to the AB comprises an SPDB moiety, a vc moiety, or a PEG2-vc moiety.

22. The conjugated activatable antibody of claim 18, wherein the agent is a toxin conjugated to the AB via a linker, and wherein the linker and the toxin conjugated to the AB comprise a moiety selected from the group consisting of: an SPDB-DM4 moiety, a vc-MMAD moiety, a vc-MMAE moiety, a vc-duocarmycin moiety, or a PEG2-vc-MMAD moiety.

23. The conjugated activatable antibody of claim 20, wherein the linker is a cleavable linker.

24. The conjugated activatable antibody of claim 20, wherein the linker is a non-cleavable linker.

25. A conjugated activatable antibody that, in an activated state, specifically binds to mammalian CD166 comprising:
(a) an activatable antibody comprising:
(i) an antibody or an antigen binding fragment thereof (AB) that specifically binds to mammalian CD166, wherein the AB specifically binds human CD166 and cynomolgus monkey CD166, wherein the AB comprises the VH CDR1 amino acid sequence GFSLSTYGMGVG (SEQ ID NO: 127); the VH CDR2 amino acid sequence NIWWSEDKH (SEQ ID NO: 128); the VH CDR3 amino acid sequence IDYGNDYAFTY (SEQ ID NO: 129); the VL CDR1 amino acid sequence RSSKSLLHSNGITYLY (SEQ ID NO: 130) or RSSQSLLHSNGITYLY (SEQ ID NO: 131); the VL CDR2 amino acid sequence QMSNLAS (SEQ ID NO: 132) or QMSNRAS (SEQ ID NO: 133); and the VL CDR3 amino acid sequence AQNLELPYT (SEQ ID NO: 134);
(ii) a masking moiety (MM) coupled to the AB that inhibits the binding of the AB to CD166 when the activatable antibody is in an uncleaved state;
(iii) a cleavable moiety (CM) coupled to the AB, wherein the CM is a polypeptide that functions as a substrate for a protease; and
(b) an agent conjugated to the AB.

26. The conjugated activatable antibody of claim 25, wherein the agent is selected from the group consisting of a dolastatin, an auristatin, a maytansinoid, a duocarmycin, a calicheamicin, a pyrrolobenzodiazepine, auristatin E, monomethyl auristatin F (MMAF), monomethyl auristatin E (MMAE), monomethyl auristatin D (MMAD), maytansinoid DM4, maytansinoid DM1, a duocarmycin, a calicheamicin, a pyrrolobenzodiazepine, and a pyrrolobenzodiazepine dimer.

27. The conjugated activatable antibody of claim 25, wherein the agent is conjugated to the AB via a linker.

28. The conjugated activatable antibody of claim 25, wherein the linker with which the agent is conjugated to the AB comprises an SPDB moiety, a vc moiety, or a PEG2-vc moiety.

29. The conjugated antibody or conjugated activatable antibody of claim 25, wherein the agent is a toxin conjugated to the AB via a linker, and wherein the linker and the toxin conjugated to the AB comprise a moiety selected from the group consisting of: an SPDB-DM4 moiety, a vc-MMAD moiety, a vc-MMAE moiety, a vc-duocarmycin moiety, or a PEG2-vc-MMAD moiety.

30. The conjugated activatable antibody of claim 25, wherein the activatable antibody has one or more of the characteristics selected from the group consisting of:
(i) the activatable antibody comprises a heavy chain variable region comprising an amino acid sequence selected from the group consisting of SEQ ID NOs: 121 and 122, and a light chain variable region comprising an amino acid sequence selected from the group consisting of SEQ ID NOs: 123-126, 363-370, 373, 374, 377, 378, 381, 382, 385, 386, 389, 390, 393, 394, 397, 398, 401, 402, 405, 406, 409, 410, 413, 414, 417, 418, 421, 422, 425, 426, 429, 430, 433, 434, 437, 438, 441, 442, 445, 446, 449, 450, 453, 454, 457, 458, 461, 462, 465, 466, 469, 470, 473, and 474; and
(ii) the activatable antibody comprises the heavy chain comprising an amino acid sequence of SEQ ID NO: 239 and a light chain comprising an amino acid sequence selected from the group consisting of SEQ ID NOs: 240, 242, 244, 246, 248, 303, 310, 312, 314, 316, 371, 372, 375, 376, 379, 380, 383, 384, 387, 388, 391, 392, 395, 396, 399, 400, 403, 404, 407, 408, 411, 412, 415, 416, 419, 420, 423, 424, 427, 428, 431, 432, 435, 436, 439, 440, 443, 444, 447, 448, 451, 452, 455, 456, 459, 460, 463, 464, 467, 468, 471, and 472.

31. The conjugated activatable antibody of claim 25, wherein the MM comprises an amino acid sequence selected from the group consisting of SEQ ID NOs: 135-238.

32. The conjugated activatable antibody of claim 25, wherein the CM comprises an amino acid sequence selected from the group consisting of SEQ ID NOs: 18-87 and 318-358.

33. The conjugated activatable antibody of claim 25, wherein the activatable antibody has one or more of the following characteristics selected from the group consisting of:
(i) the activatable antibody comprises a combination of amino acid sequences, wherein the combination of amino acid sequences is selected from a single row in Table A, wherein for a given combination,
  (a) the heavy chain of the AB comprises the amino acid sequences of the VH CDR sequences corresponding to the given combination in the single row listed in Table A,
  (b) the light chain of the AB comprises the amino acid sequences of the VL CDR sequences corresponding to the given combination in the single row listed in Table A,
  (c) the MM comprises the amino acid sequence of the mask sequence (MM) corresponding to the given combination in the single row listed in Table A, and
  (d) the CM comprises the amino acid sequence of the substrate sequence (CM) corresponding to the given combination in the single row listed in Table A; and
(ii) the activatable antibody comprises a combination of amino acid sequences, wherein for a given combination of amino acid sequences,
  (a) the heavy chain of the AB comprises the amino acid sequences of the VH sequence or VH CDR sequences selected from the group consisting of: the VH sequence or VH CDR sequences listed in the corresponding column of Table B,
  (b) the light chain of the AB comprises the amino acid sequences of the VL sequence or VL CDR sequences selected from the group consisting of: the VL sequence or VL CDR sequences listed in the corresponding column of Table B,
  (c) the MM comprises the amino acid sequence of the mask sequence (MM) selected from the group consisting of: the MM sequences listed in the corresponding column of Table B, and
  (d) the CM comprises the amino acid sequence of the substrate sequence (CM) selected from the group consisting of: the CM sequences listed in the corresponding column of Table B.

34. A conjugated antibody comprising:
(a) an antibody or an antigen binding fragment thereof (AB) that specifically binds to mammalian CD166, wherein the AB comprises:
  (i) the VH CDR1 amino acid sequence GFSLSTYGMGVG (SEQ ID NO: 127); the VH CDR2 amino acid sequence NIWWSEDKH (SEQ ID NO: 128); the VH CDR3 amino acid sequence IDYGNDYAFTY (SEQ ID NO: 129); the VL CDR1 amino acid sequence RSSKSLLHSNGITYLY (SEQ ID NO: 130) or RSSQSLLHSNGITYLY (SEQ ID NO: 131); the VL CDR2 amino acid sequence QMSNLAS (SEQ ID NO: 132) or QMSNRAS (SEQ ID NO: 133); and the VL CDR3 amino acid sequence AQNLELPYT (SEQ ID NO: 134), or
  (ii) a heavy chain variable region comprising an amino acid sequence selected from the group consisting of SEQ ID NOs: 121 and 122, and a light chain variable region comprising an amino acid sequence selected from the group consisting of SEQ ID NOs: 123-126, 363-370, 373, 374, 377, 378, 381, 382, 385, 386, 389, 390, 393, 394, 397, 398, 401, 402, 405, 406, 409, 410, 413, 414, 417, 418, 421, 422, 425, 426, 429, 430, 433, 434, 437, 438, 441, 442, 445, 446, 449, 450, 453, 454, 457, 458, 461, 462, 465, 466, 469, 470, 473, and 474, or
  (iii) a heavy chain comprising an amino acid sequence selected from the group consisting of SEQ ID NO: 239; and a light chain sequence comprising an amino acid sequence selected from the group consisting of SEQ ID NOs: 240, 242, 244, 246, 248, 303, 310, 312, 314, 316, 371, 372, 375, 376, 379, 380, 383, 384, 387, 388, 391, 392, 395, 396, 399, 400, 403, 404, 407, 408, 411, 412, 415, 416, 419, 420, 423, 424, 427, 428, 431, 432, 435, 436, 439, 440, 443, 444, 447, 448, 451, 452, 455, 456, 459, 460, 463, 464, 467, 468, 471, and 472; and
(b) an agent conjugated to the AB, wherein the agent is selected from the group consisting of auristatin E, monomethyl auristatin F (MMAF), monomethyl auristatin E (MMAE), monomethyl auristatin D (MMAD), maytansinoid DM4, maytansinoid DM1, a calicheamicin, a pyrrolobenzodiazepine, a pyrrolobenzodiazepine dimer, and a duocarmycin.

35. A conjugated activatable antibody that, in an activated state, binds to CD166, comprising:
(a) an activatable antibody comprising:
  (i) an antibody or an antigen binding fragment thereof (AB) that specifically binds to mammalian CD166, wherein the AB specifically binds human CD166 and cynomolgus monkey CD166;
  (ii) a masking moiety (MM) coupled to the AB that inhibits the binding of the AB to CD166 when the activatable antibody is in an uncleaved state;
  (iii) a cleavable moiety (CM) coupled to the AB, wherein the CM is a polypeptide that functions as a substrate for a protease; and
(b) an agent conjugated to the AB,
wherein the activatable antibody comprises:
  (i) the VH CDR1 amino acid sequence GFSLSTYGMGVG (SEQ ID NO: 127); the VH CDR2 amino acid sequence NIWWSEDKH (SEQ ID NO: 128); the VH CDR3 amino acid sequence IDYGNDYAFTY (SEQ ID NO: 129); the VL CDR1 amino acid sequence RSSKSLLHSNGITYLY (SEQ ID NO: 130) or RSSQSLLHSNGITYLY (SEQ ID NO: 131); the VL CDR2 amino acid sequence QMSNLAS (SEQ ID NO: 132) or QMSNRAS (SEQ ID NO: 133); and the VL CDR3 amino acid sequence AQNLELPYT (SEQ ID NO: 134), or
  (ii) a heavy chain variable region comprising an amino acid sequence selected from the group consisting of SEQ ID NOs: 121 and 122, and a light chain variable region comprising an amino acid sequence selected from the group consisting of SEQ ID NOs: 123-126, 363-370, 373, 374, 377, 378, 381, 382, 385, 386, 389, 390, 393, 394, 397, 398, 401, 402, 405, 406, 409, 410, 413, 414, 417, 418, 421, 422, 425, 426, 429, 430, 433, 434, 437, 438, 441, 442, 445, 446, 449, 450, 453, 454, 457, 458, 461, 462, 465, 466, 469, 470, 473, and 474, or
  (iii) a heavy chain comprising an amino acid sequence selected from the group consisting of SEQ ID NOS: 121, 122, and 239, and a light chain comprising an amino acid sequence selected from the group consisting of SEQ ID NO: 239; and a light chain sequence comprising an amino acid sequence selected from the group consisting of SEQ ID NOs:

240, 242, 244, 246, 248, 303, 310, 312, 314, 316, 371, 372, 375, 376, 379, 380, 383, 384, 387, 388, 391, 392, 395, 396, 399, 400, 403, 404, 407, 408, 411, 412, 415, 416, 419, 420, 423, 424, 427, 428, 431, 432, 435, 436, 439, 440, 443, 444, 447, 448, 451, 452, 455, 456, 459, 460, 463, 464, 467, 468, 471, and 472; and wherein the agent is selected from the group consisting of auristatin E, monomethyl auristatin F (MMAF), monomethyl auristatin E (MMAE), monomethyl auristatin D (MMAD), maytansinoid DM4, maytansinoid DM1, a calicheamicin, a pyrrolobenzodiazepine, a pyrrolobenzodiazepine dimer, and a duocarmycin.

36. The conjugated activatable antibody of claim 35, wherein the MM comprises an amino acid sequence selected from the group consisting of SEQ ID NOs: 135-238.

37. The conjugated activatable antibody of claim 35, wherein the CM comprises an amino acid sequence selected from the group consisting of SEQ ID NOs: 18-87 and 318-358.

38. The conjugated activatable antibody of claim 35, wherein the agent is conjugated to the AB via a linker, and wherein the linker to which the agent is conjugated to the AB comprises an SPDB moiety, a vc moiety, or a PEG2-vc moiety.

39. The conjugated activatable antibody of claim 35, wherein the agent is a toxin conjugated to the AB via a linker, and wherein the linker and the toxin conjugated to the AB comprise a moiety selected from the group consisting of: an SPDB-DM4 moiety, a vc-MMAD moiety, a vc-MMAE moiety, a vc-duocarmycin moiety, or a PEG2-vc-MMAD moiety.

40. A conjugated activatable antibody or conjugated antibody comprising:
an antibody or antigen binding fragment thereof (AB) that, in an activated state, binds CD166; and
a toxin conjugated to the AB via a linker,
wherein the conjugated activatable antibody or the conjugated antibody comprises amino acid sequences, a linker, and a toxin selected from a single row in Table C, wherein for the given combination:
(a) the AB comprises a heavy chain comprising the amino acid sequence of the heavy chain sequence or heavy chain variable domain sequence corresponding to the given combination in the single row listed in Table C,
(b) the AB comprises a light chain comprising the amino acid sequence of the light chain sequence or light chain variable domain sequence corresponding to the given combination in the single row listed in Table C, and
(c) the linker and the toxin comprise the linker and the toxin corresponding to the given combination in the single row listed in Table C.

41. A pharmaceutical composition comprising the activatable antibody of claim 3 and a carrier.

42. The pharmaceutical composition of claim 41 comprising an additional agent.

43. The pharmaceutical composition of claim 42, wherein the additional agent is a therapeutic agent.

44. An isolated nucleic acid molecule encoding the activatable antibody of claim 3.

45. A vector comprising the isolated nucleic acid molecule of claim 44.

46. A method of producing an activatable antibody by culturing a cell under conditions that lead to expression of the activatable antibody, wherein the cell comprises the nucleic acid molecule of claim 44.

47. A method of manufacturing an activatable antibody that, in an activated state, binds CD166, the method comprising:
(a) culturing a cell comprising a nucleic acid construct that encodes the activatable antibody under conditions that lead to expression of the activatable antibody, wherein the activatable antibody comprises an activatable antibody of claim 3;
and
(b) recovering the activatable antibody.

48. A method of treating, alleviating a symptom of, or delaying the progression of a disorder or disease in which diseased cells express CD166 comprising administering a therapeutically effective amount of the conjugated activatable antibody of claim 18 to a subject in need thereof.

49. The method of claim 48, wherein the disorder or disease is cancer.

50. A method of treating, alleviating a symptom of, or delaying the progression of a disorder or disease associated with cells expressing CD166 comprising administering a therapeutically effective amount of the conjugated activatable antibody of claim 18 to a subject in need thereof.

51. The method of claim 50, wherein the disorder or disease associated with cells expressing CD166 is cancer.

52. The method of claim 51, wherein the cancer is an adenocarcinoma, a bile duct (biliary) cancer, a bladder cancer, a bone cancer, a breast cancer, a Her2-negative breast cancer, a triple-negative breast cancer, an endometrial cancer, an estrogen receptor-positive breast cancer, a carcinoid, a cervical cancer, a cholangiocarcinoma, a colorectal cancer, a colon cancer, a glioma, a head and neck cancer, a head and neck squamous cell cancer, a leukemia, a liver cancer, a lung cancer, a non-small cell lung cancer, a small cell lung cancer, a lymphoma, a melanoma, an oropharyngeal cancer, an ovarian cancer, a pancreatic cancer, a prostate cancer, a metastatic castration-resistant prostate carcinoma, a renal cancer, a sarcoma, a skin cancer, a squamous cell cancer, a stomach cancer, a testis cancer, a thyroid cancer, a urogenital cancer, or a urothelial cancer.

53. The method of claim 51, wherein the cancer is selected from the group consisting of a cholangiocarcinoma, an endometrial cancer, triple negative breast cancer (TNBC), an estrogen receptor-positive breast cancer, non-small cell lung cancer (NSCLC), a prostate carcinoma, small cell lung cancer (SCLC), oropharyngeal cancer, cervical cancer, an ovarian cancer, head and neck squamous cell carcinoma (HNSCC), and prostate cancer.

54. A method of inhibiting or reducing the growth, proliferation, or metastasis of cells expressing mammalian CD166 comprising administering a therapeutically effective amount of the conjugated activatable antibody of claim 18 to a subject in need thereof.

55. A method of inhibiting, blocking, or preventing the binding of a natural ligand or receptor to mammalian CD166, comprising administering a therapeutically effective amount of the antibody of conjugated activatable antibody of claim 18 to a subject in need thereof.

56. The method of claim 55, wherein the natural ligand or receptor is mammalian CD6.

57. The method of claim 54, wherein the expression and/or activity of the mammalian CD166 is aberrant.

58. The method of claim 48, wherein the method comprises administering an additional agent.

59. The method of claim 58, wherein the additional agent is a therapeutic agent.

60. A pharmaceutical composition comprising the conjugated activatable antibody of claim 18; and a carrier.

61. The pharmaceutical composition of claim 60 comprising an additional agent.

62. The method of claim 49, wherein the cancer is an adenocarcinoma, a bile duct (biliary) cancer, a bladder cancer, a bone cancer, a breast cancer, a Her2-negative breast cancer, a triple-negative breast cancer, an endometrial cancer, an estrogen receptor-positive breast cancer, a carcinoid, a cervical cancer, a cholangiocarcinoma, a colorectal cancer, a colon cancer, a glioma, a head and neck cancer, a head and neck squamous cell cancer, a leukemia, a liver cancer, a lung cancer, a non-small cell lung cancer, a small cell lung cancer, a lymphoma, a melanoma, an oropharyngeal cancer, an ovarian cancer, a pancreatic cancer, a prostate cancer, a metastatic castration-resistant prostate carcinoma, a renal cancer, a sarcoma, a skin cancer, a squamous cell cancer, a stomach cancer, a testis cancer, a thyroid cancer, a urogenital cancer, or a urothelial cancer.

63. The method of claim 49, wherein the cancer is selected from the group consisting of a cholangiocarcinoma, an endometrial cancer, triple negative breast cancer (TNBC), an estrogen receptor-positive breast cancer, non-small cell lung cancer (NSCLC), a prostate carcinoma, small cell lung cancer (SCLC), oropharyngeal cancer, cervical cancer, an ovarian cancer, head and neck squamous cell carcinoma (HNSCC), and prostate cancer.

64. The activatable antibody of claim 3, wherein the MM is linked to the CM.

65. The activatable antibody of claim 3, wherein the MM is linked directly to the CM.

66. The activatable antibody of claim 3, wherein the MM is linked to the CM via a linking peptide.

67. A conjugated activatable antibody that, in an activated state, specifically binds to mammalian CD166 comprising:
   an antibody or an antigen binding fragment thereof (AB) that specifically binds to mammalian CD166, wherein the AB specifically binds human CD166 and cynomolgus monkey CD166;
   a masking moiety (MM) coupled to the AB that inhibits the binding of the AB to CD166 when the activatable antibody is in an uncleaved state;
   a cleavable moiety (CM) coupled to the AB, wherein the CM is a polypeptide that functions as a substrate for a protease; and
   an agent conjugated to the AB via a linker,
   wherein the AB comprises the VH CDR1 amino acid sequence GFSLSTYGMGVG (SEQ ID NO: 127); the VH CDR2 amino acid sequence NIWWSEDKH (SEQ ID NO: 128); the VH CDR3 amino acid sequence IDYGNDYAFTY (SEQ ID NO: 129); the VL CDR1 amino acid sequence RSSKSLLHSNGITYLY (SEQ ID NO: 130) or RSSQSLLHSNGITYLY (SEQ ID NO: 131); the VL CDR2 amino acid sequence QMSNLAS (SEQ ID NO: 132) or QMSNRAS (SEQ ID NO: 133); and the VL CDR3 amino acid sequence AQNLELPYT (SEQ ID NO: 134);
   wherein the MM comprises the amino acid sequence of SEQ ID NO: 222,
   wherein the CM comprises the amino acid sequence of SEQ ID NO: 76,
   wherein the MM is linked to the CM such that the activatable antibody in an uncleaved state comprises the structural arrangement from N-terminus to C-terminus as follows: MM-CM-AB or AB-CM-MM, and
   wherein the linker and the agent comprises vc-MMAE.

68. The conjugated activatable antibody of claim 67, wherein the conjugated activatable antibody comprises a first linking peptide (LP1) and a second linking peptide (LP2), and wherein the conjugated activatable antibody in the uncleaved state has the structural arrangement from N-terminus to C-terminus as follows: MM-LP1-CM-LP2-AB.

69. The conjugated activatable antibody of claim 68, wherein the first linking peptide (LP1) comprises the amino acid sequence of GGGSSGGS (positions 23-30 of SEQ ID NO: 455) and a second linking peptide (LP2) comprises the amino acid sequence of GGS.

70. A conjugated activatable antibody that, in an activated state, specifically binds to mammalian CD166 comprising:
   an antibody or an antigen binding fragment thereof (AB) that specifically binds mammalian CD166, wherein the AB specifically binds human CD166 and cynomolgus monkey CD166;
   a masking moiety (MM) coupled to the AB that inhibits the binding of the AB to CD166 when the activatable antibody is in an uncleaved state;
   a cleavable moiety (CM) coupled to the AB, wherein the CM is a polypeptide that functions as a substrate for a protease; and
   an agent conjugated to the AB via a linker,
   wherein the AB comprises a heavy chain variable region comprising the amino acid sequence of SEQ ID NOs: 122, and a light chain variable region comprising the amino acid sequence of SEQ ID NOs: 123,
   wherein the MM comprises an amino acid sequence of SEQ ID NO: 222,
   wherein the CM comprises an amino acid sequence of SEQ ID NO: 76,
   wherein the MM is linked to the CM such that the activatable antibody in an uncleaved state comprises the structural arrangement from N-terminus to C-terminus as follows: MM-CM-AB or AB-CM-MM, and
   wherein the linker and the agent comprises vc-MMAE.

71. The conjugated activatable antibody of claim 70, wherein the conjugated activatable antibody comprises a first linking peptide (LP1) and a second linking peptide (LP2), and wherein the conjugated activatable antibody in the uncleaved state has the structural arrangement from N-terminus to C-terminus as follows: MM-LP1-CM-LP2-AB.

72. The conjugated activatable antibody of claim 71, wherein the first linking peptide (LP1) comprises the amino acid sequence of GGGSSGGS (positions 23-30 of SEQ ID NO: 455) and a second linking peptide (LP2) comprises the amino acid sequence of GGS.

73. A conjugated activatable antibody that, in an activated state, specifically binds to mammalian CD166 comprising:
   an antibody or an antigen binding fragment thereof (AB) that specifically binds mammalian CD166, wherein the AB specifically binds human CD166 and cynomolgus monkey CD166;
   a masking moiety (MM) coupled to the AB that inhibits the binding of the AB to CD166 when the activatable antibody is in an uncleaved state;
   a cleavable moiety (CM) coupled to the AB, wherein the CM is a polypeptide that functions as a substrate for a protease; and
   an agent conjugated to the AB via a linker,
   wherein the activatable antibody comprises a heavy chain variable region comprising the amino acid sequence of SEQ ID NOs: 122, and a light chain variable region comprising the amino acid sequence of SEQ ID NOs: 368, and
   wherein the linker and the agent comprises vc-MMAE.

74. A conjugated activatable antibody that, in an activated state, specifically binds to mammalian CD166 comprising:
an antibody or an antigen binding fragment thereof (AB) that specifically binds mammalian CD166, wherein the AB specifically binds human CD166 and cynomolgus monkey CD166;
a masking moiety (MM) coupled to the AB that inhibits the binding of the AB to CD166 when the activatable antibody is in an uncleaved state;
a cleavable moiety (CM) coupled to the AB, wherein the CM is a polypeptide that functions as a substrate for a protease; and
an agent conjugated to the AB via a linker,
wherein the activatable antibody comprises a heavy chain comprising the amino acid sequence of SEQ ID NOs: 239, and a light chain comprising the amino acid sequence of SEQ ID NOs: 240, and
wherein the MM comprises an amino acid sequence of SEQ ID NO: 222,
wherein the CM comprises an amino acid sequence of SEQ ID NO: 76,
wherein the linker and the agent comprises vc-MMAE.

75. The conjugated activatable antibody of claim 74, wherein the conjugated activatable antibody comprises a first linking peptide (LP1) and a second linking peptide (LP2), and wherein the conjugated activatable antibody in the uncleaved state has the structural arrangement from N-terminus to C-terminus as follows: MM-LP1-CM-LP2-AB.

76. The conjugated activatable antibody of claim 75, wherein the first linking peptide (LP1) comprises the amino acid sequence of GGGSSGGS (positions 23-30 of SEQ ID NO: 455) and a second linking peptide (LP2) comprises the amino acid sequence of GGS.

77. A conjugated activatable antibody that, in an activated state, specifically binds to mammalian CD166 comprising:
an antibody or an antigen binding fragment thereof (AB) that specifically binds mammalian CD166, wherein the AB specifically binds human CD166 and cynomolgus monkey CD166;
a masking moiety (MM) coupled to the AB that inhibits the binding of the AB to CD166 when the activatable antibody is in an uncleaved state;
a cleavable moiety (CM) coupled to the AB, wherein the CM is a polypeptide that functions as a substrate for a protease; and
an agent conjugated to the AB via a linker,
wherein the activatable antibody comprises a heavy chain comprising the amino acid sequence of SEQ ID NOs: 239, and a light chain comprising the amino acid sequence of SEQ ID NOs: 314, and
wherein the linker and the agent comprises vc-MMAE.

78. A conjugated activatable antibody that, in an activated state, specifically binds to mammalian CD166 comprising:
n antibody or an antigen binding fragment thereof (AB) that specifically binds to mammalian CD166, wherein the AB specifically binds human CD166 and cynomolgus monkey CD166;
masking moiety (MM) coupled to the AB that inhibits the binding of the AB to CD166when the activatable antibody is in an uncleaved state;
cleavable moiety (CM) coupled to the AB, wherein the CM is a polypeptide that functions as a substrate for a protease; and an agent conjugated to the AB via a linker, wherein the AB comprises the VH CDR1 amino acid sequence GFSLSTYGMGVG (SEQ ID NO: 127); the VH CDR2 amino acid sequence NIWWSEDKH (SEQ ID NO: 128); the VH CDR3 amino acid sequence IDYGNDYAFTY (SEQ ID NO: 129); the VL CDR1 amino acid sequence RSSKSLLHSNGITYLY (SEQ ID NO: 130) or RSSQSLLHSNGITYLY (SEQ ID NO: 131); the VL CDR2 amino acid sequence QMSNLAS (SEQ ID NO: 132) or QMSNRAS (SEQ ID NO: 133); and the VL CDR3 amino acid sequence AQNLELPYT (SEQ ID NO: 134);
wherein the MM comprises the amino acid sequence of SEQ ID NO: 222,
wherein the CM comprises the amino acid sequence of SEQ ID NO: 76,
wherein the MM is linked to the CM such that the activatable antibody in an uncleaved state comprises the structural arrangement from N-terminus to C-terminus as follows: MM-CM- AB or AB-CM-MM, and
wherein the linker and the agent comprises SPDB-DM4.

79. The conjugated activatable antibody of claim 78, wherein the conjugated activatable antibody comprises a first linking peptide (LP1) and a second linking peptide (LP2), and wherein the conjugated activatable antibody in the uncleaved state has the structural arrangement from N-terminus to C-terminus as follows: MM-LP1-CM-LP2-AB.

80. The conjugated activatable antibody of claim 79, wherein the first linking peptide (LP1) comprises the amino acid sequence of GGGSSGGS (positions 23-30 of SEQ ID NO: 455) and a second linking peptide (LP2) comprises the amino acid sequence of GGS.

81. A conjugated activatable antibody that, in an activated state, specifically binds to mammalian CD166 comprising:
an antibody or an antigen binding fragment thereof (AB) that specifically binds mammalian CD166, wherein the AB specifically binds human CD166 and cynomolgus monkey CD166;
a masking moiety (MM) coupled to the AB that inhibits the binding of the AB to CD166when the activatable antibody is in an uncleaved state;
a cleavable moiety (CM) coupled to the AB, wherein the CM is a polypeptide that functions as a substrate for a protease; and
an agent conjugated to the AB via a linker,
wherein the AB comprises a heavy chain variable region comprising the amino acid sequence of SEQ ID NOs: 122, and a light chain variable region comprising the amino acid sequence of SEQ ID NOs: 123,
wherein the MM comprises an amino acid sequence of SEQ ID NO: 222,
wherein the CM comprises an amino acid sequence of SEQ ID NO: 76,
wherein the MM is linked to the CM such that the activatable antibody in an uncleaved state comprises the structural arrangement from N-terminus to C-terminus as follows: MM-CM- AB or AB-CM-MM, and
wherein the linker and the agent comprises SPDB-DM4.

82. The conjugated activatable antibody of claim 81, wherein the conjugated activatable antibody comprises a first linking peptide (LP1) and a second linking peptide (LP2), and wherein the conjugated activatable antibody in the uncleaved state has the structural arrangement from N-terminus to C-terminus as follows: MM-LP1-CM-LP2-AB.

83. The conjugated activatable antibody of claim 82, wherein the first linking peptide (LP1) comprises the amino acid sequence of GGGSSGGS (positions 23-30 of SEQ ID NO: 455) and a second linking peptide (LP2) comprises the amino acid sequence of GGS.

84. A conjugated activatable antibody that, in an activated state, specifically binds to mammalian CD166 comprising:
an antibody or an antigen binding fragment thereof (AB) that specifically binds mammalian CD166, wherein the AB specifically binds human CD166 and cynomolgus monkey CD166;
a masking moiety (MM) coupled to the AB that inhibits the binding of the AB to CD166when the activatable antibody is in an uncleaved state;
a cleavable moiety (CM) coupled to the AB, wherein the CM is a polypeptide that functions as a substrate for a protease; and
an agent conjugated to the AB via a linker,
wherein the activatable antibody comprises a heavy chain variable region comprising the amino acid sequence of SEQ ID NOs: 122, and a light chain variable region comprising the amino acid sequence of SEQ ID NOs: 368, and
wherein the linker and the agent comprises SPDB-DM4.

85. A conjugated activatable antibody that, in an activated state, specifically binds to mammalian CD166comprising:
an antibody or an antigen binding fragment thereof (AB) that specifically binds mammalian CD166, wherein the AB specifically binds human CD166 and cynomolgus monkey CD166;
a masking moiety (MM) coupled to the AB that inhibits the binding of the AB to CD166when the activatable antibody is in an uncleaved state;
a cleavable moiety (CM) coupled to the AB, wherein the CM is a polypeptide that functions as a substrate for a protease; and
an agent conjugated to the AB via a linker,
wherein the activatable antibody comprises a heavy chain comprising the amino acid sequence of SEQ ID NOs: 239, and a light chain comprising the amino acid sequence of SEQ ID NOs: 240, and
wherein the MM comprises an amino acid sequence of SEQ ID NO: 222,
wherein the CM comprises an amino acid sequence of SEQ ID NO: 76,
wherein the linker and the agent comprises SPDB-DM4.

86. The conjugated activatable antibody of claim 85, wherein the conjugated activatable antibody comprises a first linking peptide (LP1) and a second linking peptide (LP2), and wherein the conjugated activatable antibody in the uncleaved state has the structural arrangement from N-terminus to C-terminus as follows: MM-LP1-CM-LP2-AB.

87. The conjugated activatable antibody of claim 86, wherein the first linking peptide (LP1) comprises the amino acid sequence of GGGSSGGS (positions 23-30 of SEQ ID NO: 455) and a second linking peptide (LP2) comprises the amino acid sequence of GGS.

88. A conjugated activatable antibody that, in an activated state, specifically binds to mammalian CD166 comprising:
an antibody or an antigen binding fragment thereof (AB) that specifically binds mammalian CD166, wherein the AB specifically binds human CD166 and cynomolgus monkey CD166;
a masking moiety (MM) coupled to the AB that inhibits the binding of the AB to CD166when the activatable antibody is in an uncleaved state;
a cleavable moiety (CM) coupled to the AB, wherein the CM is a polypeptide that functions as a substrate for a protease; and
an agent conjugated to the AB via a linker,
wherein the activatable antibody comprises a heavy chain comprising the amino acid sequence of SEQ ID NOs: 239, and a light chain comprising the amino acid sequence of SEQ ID NOs: 314, and
wherein the linker and the agent comprises SPDB-DM4.

* * * * *

UNITED STATES PATENT AND TRADEMARK OFFICE
CERTIFICATE OF CORRECTION

PATENT NO. : 10,745,481 B2
APPLICATION NO. : 15/146603
DATED : August 18, 2020
INVENTOR(S) : James William West et al.

Page 1 of 2

It is certified that error appears in the above-identified patent and that said Letters Patent is hereby corrected as shown below:

In the Claims

At Column 496, Claim number 29, Line number 32:
"29. The conjugated antibody or conjugated activatable"
Should read:
-- 29. The conjugated activatable --

At Column 503, Claim number 78, Line number 55:
"n antibody or an antigen binding fragment thereof (AB)"
Should read:
-- an antibody or an antigen binding fragment thereof (AB) --

At Column 503, Claim number 78, Line number 59:
"masking moiety (MM) coupled to the AB that inhibits the"
Should read:
-- a masking moiety (MM) coupled to the AB that inhibits the --

At Column 503, Claim number 78, Line number 62:
"cleavable moiety (CM) coupled to the AB, wherein the"
Should read:
-- a cleavable moiety (CM) coupled to the AB, wherein the --

At Column 505, Claim number 84, Line number 8:
"the binding of the AB to CD166when the activatable"
Should read:
-- the binding of the AB to CD166 when the activatable --

At Column 505, Claim number 85, Line number 21:
"state, specifically binds to mammalian CD166comprising:"

Signed and Sealed this
Fifth Day of January, 2021

Andrei Iancu
*Director of the United States Patent and Trademark Office*

Should read:
-- state, specifically binds to mammalian CD166 comprising: --

At Column 505, Claim number 85, Line number 27:
"the binding of the AB to CD166when the activatable"
Should read:
-- the binding of the AB to CD166 when the activatable --

At Column 506, Claim number 88, Line number 25:
"the binding of the AB to CD166when the activatable"
Should read:
-- the binding of the AB to CD166 when the activatable --